US006750228B1

(12) United States Patent
Barta et al.

(10) Patent No.: US 6,750,228 B1
(45) Date of Patent: *Jun. 15, 2004

(54) AROMATIC SULFONE HYDROXAMIC ACID METALLOPROTEASE INHIBITOR

(75) Inventors: Thomas E Barta, Evanston, IL (US); Daniel P Becker, Glenview, IL (US); Louis J Bedell, Mt. Prospect, IL (US); Terri L Boehm, Ballwin, MO (US); Jeffrey N Carroll, Collinsville, IL (US); Gary A DeCrescenzo, St. Charles, MO (US); Yvette M Fobian, Wildwood, MO (US); John N Freskos, Clayton, MO (US); Daniel P Getman, Chesterfield, MO (US); Joseph J McDonald, Ballwin, MO (US); Madeleine H Li, Vernon Hills, IL (US); Susan L Hockerman, Lincolnwood, IL (US); Susan C Howard, Fenton, MO (US); Steve A Kolodziej, Ballwin, MO (US); Deborah A Mischke, Defiance, MO (US); Joseph G Rico, Ballwin, MO (US); Nathan W Stehle, Ballwin, MO (US); Michael B Tollefson, Hainesville, IL (US); William F Vernier, St. Louis, MO (US); Clara I Villamil, Glenview, IL (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/570,731

(22) Filed: May 12, 2000

Related U.S. Application Data

(63) Continuation-in-part of application No. 09/311,837, filed on May 14, 1999, which is a continuation-in-part of application No. 09/256,948, filed on Feb. 24, 1999, now abandoned.

(60) Provisional application No. 60/101,080, filed on Sep. 18, 1998, provisional application No. 90/095,501, filed on Aug. 6, 1998, provisional application No. 60/095,347, filed on Aug. 4, 1998, and provisional application No. 60/066,007, filed on Nov. 14, 1997.

(51) Int. Cl.$^7$ .................... A61K 31/445; C07D 211/06

(52) U.S. Cl. ...................... 514/316; 514/318; 514/328; 514/330; 546/189; 546/193; 546/220; 546/225

(58) Field of Search ................................ 514/316, 328, 514/318, 330; 546/189, 193, 220, 225

(56) References Cited

U.S. PATENT DOCUMENTS

| | | | | |
|---|---|---|---|---|
| 4,595,700 A | | 6/1986 | Donald et al. | 514/516 |
| 5,932,595 A | | 8/1999 | Bender et al. | 514/317 |
| 6,013,649 A | | 1/2000 | Freskos et al. | 514/237.8 |
| 6,300,514 B1 | | 10/2001 | Takahashi et al. | 560/17 |
| 6,541,489 B1 | * | 4/2003 | Barta et al. | 514/330 |

FOREIGN PATENT DOCUMENTS

| | | | |
|---|---|---|---|
| EP | 0 266 182 | 5/1988 | C07D/307/32 |
| EP | 0 606 046 | 7/1994 | C07D/213/42 |
| EP | 0 780 386 | 6/1997 | C07D/309/08 |
| EP | 0 930 067 | 7/1999 | A61K/31/40 |
| JP | 4-338331 | 11/1992 | A61K/31/365 |
| JP | WO 97/49679 | 12/1997 | C07C/317/44 |
| WO | 90/05719 | 5/1990 | C07C/323/62 |
| WO | 93/20047 | 10/1993 | C07C/317/44 |
| WO | 94/02466 | 2/1994 | C07D/221/14 |
| WO | 94/24140 | 10/1994 | C07H/13/04 |
| WO | 95/09841 | 4/1995 | C07C/323/60 |
| WO | 95/12389 | 5/1995 | A61K/9/127 |
| WO | WO 95/13289 | 5/1995 | C07K/5/062 |
| WO | WO 95/29892 | 11/1995 | C07D/207/327 |
| WO | 96/06074 | 2/1996 | C07C/259/06 |
| WO | 96/11209 | 4/1996 | C07K/5/06 |
| WO | 97/20824 | 6/1997 | C07D/241/04 |
| WO | 97/24117 | 7/1997 | A61K/31/19 |
| WO | 98/37877 | 9/1998 | A61K/31/16 |
| WO | 98/38163 | 9/1998 | C07C/323/60 |
| WO | WO 99/09000 | 2/1999 | C07C/235/00 |
| WO | 99 25687 | 5/1999 | C07D/211/66 |
| WO | 99/42436 | 8/1999 | C07C/239/14 |
| WO | WO 00/46221 | 8/2000 | C07D/405/12 |
| WO | 00/50396 | 8/2000 | C07D/211/66 |
| WO | WO 00/59874 | 10/2000 | C07C/259/06 |
| WO | WO 00/69821 | 11/2000 | C07D/211/66 |

OTHER PUBLICATIONS

King "Bioisosters, conformational restriction . . . " Med. Chem:Principle and practice (1994)p. 206–209.*

U.S. patent application Ser. No. 10/042,737, Barta et al., filed May 10, 2002.

U.S. patent application Ser. No. 09/989,943, Barta et al., Nov. 21, 2001.

(List continued on next page.)

*Primary Examiner*—Ceila Chang
(74) *Attorney, Agent, or Firm*—Harness, Dickey & Pierce, P.L.C

(57) ABSTRACT

A treatment process is disclosed that comprises administering an effective amount of an aromatic sulfone hydroxamic acid that exhibits excellent inhibitory activity of one or more matrix metalloprotease (MMP) enzymes, such as MMP-2, MMP-9 and MMP-13, while exhibiting substantially less inhibition at least of MMP-1 to a host having a condition associated with pathological matrix metalloprotease activity. Also disclosed are metalloprotease inhibitor compounds having those selective activities, processes for manufacture of such compounds and pharmaceutical compositions using an inhibitor. A contemplated compound corresponds in structure to formula B, below,

B

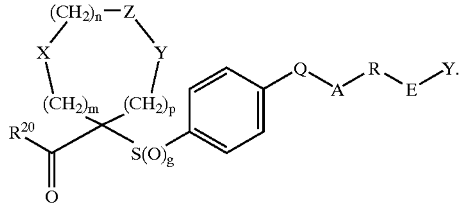

44 Claims, No Drawings

OTHER PUBLICATIONS

U.S. patent application Ser. No. 09/311,837, Barta et al., May 14, 1999.
U.S. patent application Ser. No. 09/954,451, Barta et al., Sep. 17, 2001.
U.S. patent application Ser. No. 09/554,082, Barta et al., May 12, 2000.
U.S. patent application Ser. No. 09/191,129, Barta et al., Nov. 13, 1998.
Brown, "Synthetic Inhibitors of Matrix Metalloproteinases"; *Matrix Metalloproteinases*, pp. 243–261 (Academic Press. Eds Parks, W.C., & Mecham, R.P., 1998.
Tang, *ADAMTS: a novel family of extracellular matrix proteases*, The International Journal of Biochemistry & Cell Biology 33 (2001) pp. 33–44.
Woessner, "The Matrix Metalloproteinase Family", *Matrix Metalloproteinases*, pp. 1–14 (Academic Press, Eds Parks, W.C., & Mecham, R.P., 1998).
Gearing et al. *Nature*, 376, 555–557 (1994).
McGeehan et al., *Nature* 370, 558–561 (1994).
Mitchell et al., *J. Clin. Invsest.*, 97(3) 761–768 (1996).
Reboul et al., *J. Clin Invest.*, 97(9), 2011–2019 (1996).
Schwartz et al., *Progr. Med. Chem.*, 29:271–334 (1992).
Rasmussen et al., *Pharmacol. Ther.*, 75(I): 69–75 (1997).
Denis et al., *Invest. New Drugs*, 15A, 175–185 (1997).
*A Model of Angiogenesis in the Mouse Cornea*; Kenyon, BM, et al., Investigative Ophthalmology & Visual Science, vol. 37, No. 8, (Jul. 1996).
Knight et al., *FEBS Lett.* 296(3):263 (1992).
Luckow et al., *J. Virol.*, 67:4566–4579 (1993).
McClure et al. "Matrix metalloprotease . . . " CA 131:125454 (1999).
Dack et al. "Preparation of N–hydroxytetrahydro . . . " CA 131:44740 (1999).

* cited by examiner

AROMATIC SULFONE HYDROXAMIC ACID METALLOPROTEASE INHIBITOR

CROSS-REFERENCE TO RELATED APPLICATION

This application is a continuation-in-part application of U.S. patent application Ser. No. 09/311,837 (filed May 14, 1999) and Ser. No. 09/256,948 (filed Feb. 24, 1999, now abandoned). U.S. patent application Ser. No. 09/311,837 claims priority to U.S. patent application Ser. Nos. 09/256,948, 09/191,129 (filed Nov. 13, 1998), and Ser. No. 09/186,410 (filed Nov. 5, 1998, now abandoned); and U.S. Provisional Patent Application Nos. 60/101,080 (filed Sep. 18, 1998), 60/095,501 (filed Aug. 6, 1998), 60/095,347 (filed Aug. 4, 1998), and 60/066,007 (filed Nov. 14, 1997). U.S. patent application Ser. No. 09/256,948 claims priority to U.S. patent application Ser. Nos. 09/186,410 and 09/186,410; and U.S. Provisional Patent Application Nos. 60/101,080, 60/095,501, 60/095,347, and 60/066,007. The entire text of each of the above patent applications is hereby incorporated by reference into this patent application.

TECHNICAL FIELD

This invention is directed to proteinase (protease) inhibitors, and more particularly to the use of aromatic sulfone hydroxamic acid compounds that, inter alia, are selective inhibitors of matrix metalloproteinases in a process for treating conditions associated with pathological matrix metalloproteinase activity, the selective inhibitors themselves, compositions of proteinase inhibitors, intermediates for the syntheses of proteinase inhibitors, and processes for the preparation of proteinase inhibitors.

BACKGROUND OF THE INVENTION

Connective tissue, extracellular matrix constituents and basement membranes are required components of all mammals. These components are the biological materials that provide rigidity, differentiation, attachments and, in some cases, elasticity to biological systems including human beings and other mammals. Connective tissues components include, for example, collagen, elastin, proteoglycans, fibronectin and laminin. These biochemicals makeup, or are components of structures, such as skin, bone, teeth, tendon, cartilage, basement membrane, blood vessels, cornea and vitreous humor.

Under normal conditions, connective tissue turnover and/or repair processes are controlled and in equilibrium. The loss of this balance for whatever reason leads to a number of disease states. Inhibition of the enzymes responsible loss of equilibrium provides a control mechanism for this tissue decomposition and, therefore, a treatment for these diseases.

Degradation of connective tissue or connective tissue components is carried out by the action of proteinase enzymes released from resident tissue cells and/or invading inflammatory or tumor cells. A major class of enzymes involved in this function are the zinc metalloproteinases (metalloproteases).

The metalloprotease enzymes are divided into classes with some members having several different names in common use. Examples are: collagenase I (MMP-1, fibroblast collagenase; EC 3.4.24.3); collagenase II (MMP-8, neutrophil collagenase; EC 3.4.24.34), collagenase III (MMP-13), stromelysin 1 (MMP-3; EC 3.4.24.17), stromelysin 2 (MMP-10; EC 3.4.24.22), proteoglycanase, matrilysin (MMP-7), gelatinase A (MMP-2, 72 kDa gelatinase, basement membrane collagenase; EC 3.4.24.24), gelatinase B (MMP-9, 92 kDa gelatinase; EC 3.4.24.35), stromelysin 3 (MMP-11), metalloelastase (MMP-12, HME, human macrophage elastase) and membrane MMP (MMP-14). MMP is an abbreviation or acronym representing the term Matrix Metalloprotease with the attached numerals providing differentiation between specific members of the MMP group.

The uncontrolled breakdown of connective tissue by metalloproteases is a feature of many pathological conditions. Examples include rheumatoid arthritis, osteoarthritis, septic arthritis; corneal, epidermal or gastric ulceration; tumor metastasis, invasion or angiogenesis; periodontal disease; proteinuria; Alzheimers Disease; coronary thrombosis and bone disease. Defective injury repair processes also occur. This can produce improper wound healing leading to weak repairs, adhesions and scarring. These latter defects can lead to disfigurement and/or permanent disabilities as with post-surgical adhesions.

Metalloproteases are also involved in the biosynthesis of tumor necrosis factor (TNF), and inhibition of the production or action of TNF and related compounds is an important clinical disease treatment mechanism. TNF-$\alpha$, for example, is a cytokine that at present is thought to be produced initially as a 28 kD cell-associated molecule. It is released as an active, 17 kD form that can mediate a large number of deleterious effects in vitro and in vivo. For example, TNF can cause and/or contribute to the effects of inflammation, rheumatoid arthritis, autoimmune disease, multiple sclerosis, graft rejection, fibrotic disease, cancer, infectious diseases, malaria, mycobacterial infection, meningitis, fever, psoriasis, cardiovascular/pulmonary effects such as post-ischemic reperfusion injury, congestive heart failure, hemorrhage, coagulation, hyperoxic alveolar injury, radiation damage and acute phase responses like those seen with infections and sepsis and during shock such as septic shock and hemodynamic shock. Chronic release of active TNF can cause cachexia and anorexia. TNF can be lethal, and TNF can help control the growth of tumor cells.

TNF-$\alpha$ convertase is a metalloprotease involved in the formation of soluble TNF-$\alpha$. Inhibition of TNF-$\alpha$ convertase (TACE) inhibits production of active TNF-$\alpha$. Compounds that inhibit both MMPs activity and TNF-$\alpha$ production have been disclosed in WIPO International Publication Nos. WO 94/24140, WO 94/02466 and WO 97/20824. Compounds that inhibit MMPs such as collagenase, stromelysin and gelatinase have been shown to inhibit the release of TNF (Gearing et al. *Nature* 376, 555–557 (1994), McGeehan et al., *Nature* 376, 558–561 (1994)). There remains a need for effective MMP inhibitors. There also remains a need for effective TNF-$\alpha$ convertase inhibiting agents.

MMPs are involved in other biochemical processes in mammals as well. Included is the control of ovulation, post-partum uterine involution, possibly implantation, cleavage of APP ($\beta$-Amyloid Precursor Protein) to the amyloid plaque and inactivation of $\alpha_1$-protease inhibitor ($\alpha_1$-PI). Inhibition of these metalloproteases permits the control of fertility and the treatment or prevention of Alzheimers Disease. In addition, increasing and maintaining the levels of an endogenous or administered serine protease inhibitor drug or biochemical such as $\alpha_1$-PI supports the treatment and prevention of diseases such as emphysema, pulmonary diseases, inflammatory diseases and diseases of aging such as loss of skin or organ stretch and resiliency.

Inhibition of selected MMPs can also be desirable in other instances. Treatment of cancer and/or inhibition of metastasis and/or inhibition of angiogenesis are examples of approaches to the treatment of diseases wherein the selective inhibition of stromelysin, gelatinase A or B, or collagenase III appear to be the relatively most important enzyme or enzymes to inhibit especially when compared with collagenase I (MMP-1). A drug that does not inhibit collagenase I can have a superior therapeutic profile. Osteoarthritis, another prevalent disease wherein it is believed that cartilage degradation of inflamed joints is at least partially caused by MMP-13 released from cells such as stimulated chrondrocytes, may be best treated by administration of drugs one of whose modes of action is inhibition of MMP-13. See, for example, Mitchell et al., *J. Clin. Invest.*, 97:761–768 (1996) and Reboul et al., *J. Clin. Invest.*, 97:2011–2019 (1996).

Inhibitors of metalloproteases are known. Examples include natural biochemicals such as tissue inhibitors of metalloproteinases (TIMPs), $\alpha_2$-macroglobulin and their analogs or derivatives. These endogenous inhibitors are high molecular weight protein molecules that form inactive complexes with metalloproteases. A number of smaller peptide-like compounds that inhibit metalloproteases have been described. Mercaptoamide peptidyl derivatives have shown ACE inhibition in vitro and in vivo. Angiotensin converting enzyme (ACE) aids in the production of angiotensin II, a potent pressor substance in mammals and inhibition of this enzyme leads to the lowering of blood pressure.

Thiol group-containing amide or peptidyl amide-based metalloprotease (MMP) inhibitors are known as is shown in, for example, WO95/12389, WO96/11209 and U.S. Pat. No. 4,595,700. Hydroxamate group-containing MMP inhibitors are disclosed in a number of published patent applications such as WO 95/29892, WO 97/24117, WO 97/49679 and EP 0 780 386 that disclose carbon back-boned compounds, and WO 90/05719, WO 93/20047, WO 95/09841 and WO 96/06074 that disclose hydroxamates that have a peptidyl back-bones or peptidomimetic back-bones, as does the article by Schwartz et al., *Progr. Med. Chem.*, 29:271–334 (1992) and those of Rasmussen et al., *Pharmacol. Ther.*, 75(1): 69–75 (1997) and Denis et al., *Invest. New Drugs*, 15(3): 175–185 (1997).

One possible problem associated with known MMP inhibitors is that such compounds often exhibit the same or similar inhibitory effects against each of the MMP enzymes. For example, the peptidomimetic hydroxamate known as batimastat is reported to exhibit $IC_{50}$ values of about 1 to about 20 nanomolar (nM) against each of MMP-1, MMP-2, MMP-3, MMP-7, and MMP-9. Marimastat, another peptidomimetic hydroxamate was reported to be another broad-spectrum MMP inhibitor with an enzyme inhibitory spectrum very similar to batimastat, except that marimastat exhibited an $IC_{50}$ value against MMP-3 of 230 nM. Rasmussen et al., *Pharmacol. Ther.*, 75(1): 69–75 (1997).

Meta analysis of data from Phase I/II studies using marimastat in patients with advanced, rapidly progressive, treatment-refractory solid tumor cancers (colorectal, pancreatic, ovarian, prostate) indicated a dose-related reduction in the rise of cancer-specific antigens used as surrogate markers for biological activity. Although marimastat exhibited some measure of efficacy via these markers, toxic side effects were noted. The most common drug-related toxicity of marimastat in those clinical trials was musculoskeletal pain and stiffness, often commencing in the small joints in the hands, spreading to the arms and shoulder. A short dosing holiday of 1–3 weeks followed by dosage reduction permits treatment to continue. Rasmussen et al., *Pharmacol. Ther.*, 75(1): 69–75 (1997). It is thought that the lack of specificity of inhibitory effect among the MMPs may be the cause of that effect.

International application WO 98/38163, published on Sep. 3, 1998 disclose a large group of hydroxamate inhibitors of MMPs and TACE. The compounds of WO 98/38163 contain one or two substituents adjacent to the hydroxamate functionality and a substituent that can be an aromatic sulfonyl group adjacent to those one or two substituents.

International application WO 98/37877, published on Sep. 3, 1998 discloses compounds that contain a 5- to 7-membered heterocyclic ring adjacent to the hydroxamate functionality and can contain an aromatic sulfonyl group adjacent to the heterocyclic ring.

Although many of the known MMP inhibitors such as batimastat, marimastat and the hydroxamates of WO 98/37877 and WO 98/38163 exhibit a broad spectrum of activity against MMPs, those compounds are not particularly selective in their inhibitory activity. This lack of selectivity may be the cause of the musculoskeletal pain and stiffness observed with their use. In addition, it can be therapeutically advantageous to utilize a medicament that is selective in its activity as compared to a generally active material so that treatment can be more closely tailored to the pathological condition presented by the host mammal. The disclosure that follows describes a process for treating a host mammal having a condition associated with pathological matrix metalloprotease activity that utilizes a compound that selectively inhibits one or more MMPs, while exhibiting less activity against at least MMP-1.

SUMMARY OF THE INVENTION

The present invention is directed to a treatment process that comprises administering a contemplated aromatic sulfone hydroxamic acid metalloprotease inhibitor in an effective amount to a host mammal having a condition associated with pathological metalloprotease activity. A contemplated molecule, inter alia, exhibits excellent inhibitory activity of one or more matrix metalloprotease (MMP) enzymes, such as MMP-2, MMP-9 and MMP-13, while exhibiting substantially less inhibition at least of MMP-1. By "substantially less" it is meant that a contemplated compound exhibits an $IC_{50}$ value ratio against one or more of MMP-2, MMP-9 or MMP-13 as compared to its $IC_{50}$ value against MMP-1, e.g., $IC_{50}$ MMP-2:$IC_{50}$ MMP-1, that is less than about 1:10, preferably less than about 1:100, and most preferably less than about 1:1000 in the in vitro inhibition assay utilized hereinafter. The invention also contemplates particular compounds that selectively inhibit the activity of one or more of MMP-2, MMP-9 and MMP-13, while exhibiting substantially less inhibition at least of MMP-1, as well as a composition containing such a MMP inhibitor as active ingredient. Similarly contemplated are particular compounds such as those of Examples 16, 498, 667, 672 and 684 that selectively inhibit the activity of one or more of MMP-2, MMP-9 and MMP-13, while exhibiting substantially less inhibition at least of MMP-7, as well as a composition containing such a MMP inhibitor as active ingredient. The invention further contemplates intermediates in the preparation of a contemplated aromatic sulfone hydroxamic acid molecule and a process for preparing an aromatic sulfone hydroxamic acid molecule.

Briefly, one embodiment of the present invention is directed to a treatment process that comprises administering a contemplated aromatic sulfone hydroxamic acid metalloprotease inhibitor that selectively inhibits matrix metalloprotease activity as above in an effective amount to a host mammal having a condition associated with pathological metalloprotease activity. The administered enzyme inhibitor corresponds in structure to formula I, below, or a pharmaceutically acceptable salt thereof:

I

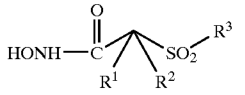

wherein $R^1$ and $R^2$ are both hydrido or $R^1$ and $R^2$ together with the atoms to which they are bonded form a 5- to 8-membered ring containing one, two or three heteroatoms in the ring that are oxygen, sulfur or nitrogen.

$R^3$ in formula I is an optionally substituted aryl or optionally substituted heteroaryl radical. When $R^3$ is a substituted aryl or heteroaryl radical, a contemplated substituent is selected from the group consisting of an aryl, heteroaryl, aralkyl, heteroaralkyl, aryloxy, arylthio, aralkoxy, heteroaralkoxy, aralkoxyalkyl, aryloxyalkyl, aralkanoylalkyl, arylcarbonylalkyl, aralkylaryl, aryloxyalkylaryl, aralkoxyaryl, arylazoaryl, arylhydrazinoaryl, alkylthioaryl, arylthioalkyl, alkylthioaralkyl, aralkylthioalkyl, an aralkylthioaryl radical, the sulfoxide or sulfone of any of the thio substituents, and a fused ring structure comprising two or more 5- or 6-membered rings selected from the group consisting of aryl, heteroaryl, carbocyclic and heterocyclic.

The substituent bonded to the aryl or heteroaryl radical of which the $R^3$ radical is comprised itself can be substituted with one or more substituents; i.e., the substituting substituent is optionally substituted. When that aryl or heteroaryl radical is substituted, and the substituting moiety (group, substituent, or radical) is itself substituted, the last-named substituent is independently selected from the group consisting of a cyano, perfluoroalkyl, trifluoromethoxy, trifluoromethylthio, haloalkyl, trifluoromethylalkyl, aralkoxycarbonyl, aryloxycarbonyl, hydroxy, halo, alkyl, alkoxy, nitro, thiol, hydroxycarbonyl, aryloxy, arylthio, aralkyl, aryl, arylcarbonylamino, heteroaryloxy, heteroarylthio, heteroaralkyl, cycloalkyl, heterocyclooxy, heterocyclothio, heterocycloamino, cycloalkyloxy, cycloalkylthio, heteroaralkoxy, heteroaralkylthio, aralkoxy, aralkylthio, aralkylamino, heterocyclo, heteroaryl, arylazo, hydroxycarbonylalkoxy, alkoxycarbonylalkoxy, alkanoyl, arylcarbonyl, aralkanoyl, alkanoyloxy, aralkanoyloxy, hydroxyalkyl, hydroxyalkoxy, alkylthio, alkoxyalkylthio, alkoxycarbonyl, aryloxyalkoxyaryl, arylthioalkylthioaryl, aryloxyalkylthioaryl, arylthioalkoxyaryl, hydroxycarbonylalkoxy, hydroxycarbonylalkylthio, alkoxycarbonylalkoxy, alkoxycarbonylalkylthio, amino, wherein the amino nitrogen is (i) unsubstituted, or (ii) substituted with one or two substituents that are independently selected from the group consisting of an alkyl, aryl, heteroaryl, aralkyl, cycloalkyl, aralkoxycarbonyl, alkoxycarbonyl, arylcarbonyl, aralkanoyl, heteroarylcarbonyl, heteroaralkanoyl and an alkanoyl group, or (iii) wherein the amino nitrogen and two substituents attached thereto form a 5- to 8-membered heterocyclo or heteroaryl ring containing zero to two additional heteroatoms that are nitrogen, oxygen or sulfur and which ring itself is (a) unsubstituted or (b) substituted with one or two groups independently selected from the group consisting of an aryl, alkyl, heteroaryl, aralkyl, heteroaralkyl, hydroxy, alkoxy, alkanoyl, cycloalkyl, heterocycloalkyl, alkoxycarbonyl, hydroxyalkyl, trifluoromethyl, benzofused heterocycloalkyl, hydroxyalkoxyalkyl, aralkoxycarbonyl, hydroxycarbonyl, aryloxycarbonyl, benzofused heterocycloalkoxy, benzofused cycloalkylcarbonyl, heterocycloalkylcarbonyl, and a cycloalkylcarbonyl group, carbonylamino wherein the carbonylamino nitrogen is (i) unsubstituted, or (ii) is the reacted amine of an amino acid, or (iii) substituted with one or two radicals selected from the group consisting of an alkyl, hydroxyalkyl, hydroxyheteroaralkyl, cycloalkyl, aralkyl, trifluoromethylalkyl, heterocycloalkyl, benzofused heterocycloalkyl, benzofused heterocycloalkyl, benzofused cycloalkyl, and an N,N-dialkylsubstituted alkylamino-alkyl group, or (iv) the carboxamido nitrogen and two substituents bonded thereto together form a 5- to 8-membered heterocyclo, heteroaryl or benzofused heterocycloalkyl ring that is itself unsubstituted or substituted with one or two radicals independently selected from the group consisting of an alkyl, alkoxycarbonyl, nitro, heterocycloalkyl, hydroxy, hydroxycarbonyl, aryl, aralkyl, heteroaralkyl and an amino group, wherein the amino nitrogen is (i) unsubstituted, or (ii) substituted with one or two substituents that are independently selected from the group consisting of alkyl, aryl, and heteroaryl, or (iii) wherein the amino nitrogen and two substituents attached thereto form a 5- to 8-membered heterocyclo or heteroaryl ring, and an aminoalkyl group wherein the aminoalkyl nitrogen is (i) unsubstituted, or (ii) substituted with one or two substituents independently selected from the group consisting of an alkyl, aryl, aralkyl, cycloalkyl, aralkoxycarbonyl, alkoxycarbonyl, and an alkanoyl group, or (iii) wherein the aminoalkyl nitrogen and two substituents attached thereto form a 5- to 8-membered heterocyclo or heteroaryl ring.

Preferably, the $R^3$ substituent is Ph—Q—A—R—E—Y wherein Ph is phenyl substituted at the 4-position relative to the depicted $SO_2$ group, and —Q—A—R—E—Y is a substituent in which Q is a 5- to 7-membered heterocyclic ring containing one or two nitrogen atoms, one of which is bonded the depicted phenyl group, and whose remaining members are defined hereinafter for the substituent G—A—R—E—Y.

A compound of formula I is a compound of more general formula A, wherein $R^3$, $R^1$ and $R^2$ are as defined before and $R^{20}$ is defined below.

A

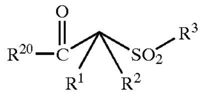

The substituent $R^{20}$ is (a) —O—$R^{21}$, where $R^{21}$ is selected from the group consisting of a hydrido, $C_1$–$C_6$-alkyl, aryl, ar-$C_1$–$C_6$-alkyl group and a pharmaceutically acceptable cation, (b) —NH—O—$R^{22}$ wherein $R^{22}$ is a selectively removable protecting group such as a 2-tetrahydropyranyl, benzyl, p-methoxybenzyl (MOZ), carbonyl-$C_1$–$C_6$-alkoxy, trisubstituted silyl group or o-nitrophenyl group, peptide synthesis resin and the like, wherein the trisubstituted silyl group is substituted with $C_1$–$C_6$-alkyl, aryl, or ar-$C_1$–$C_6$-alkyl or a mixture thereof, (c) —NH—O—$R^{14}$, where $R^{14}$ is hydrido, a pharmaceutically acceptable cation or $C(W)R^{25}$ where W is O (oxo) or S (thioxo) and $R^{25}$ is selected from the group consisting of an $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl and amino $C_1$–$C_6$-alkyl group wherein the amino $C_1$–$C_6$-alkyl nitrogen is (i) unsubstituted or (ii) substituted with one or two substituents independently selected from the group consisting of an $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and $C_1$–$C_6$-alkanoyl radical, or (iii) wherein the amino $C_1$–$C_6$-alkyl nitrogen and two substituents attached thereto form a 5- to 8-membered heterocyclo or heteroaryl ring, or (d) —$NR^{26}R^{27}$, where $R^{26}$ and $R^{27}$ are independently selected from the group consisting of a hydrido, $C_1$–$C_6$-alkyl, amino $C_1$–$C_6$-alkyl, hydroxy $C_1$–$C_6$-alkyl, aryl, ar-$C_1$–$C_6$-alkyl group, or $R^{26}$ and $R^{27}$ together with the depicted nitrogen atom form a 5- to 8-membered ring containing zero or one additional heteroatom that is oxygen, nitrogen or sulfur. When used in a contemplated process or method, $R^{20}$ is —NH—O—$R^{22}$, as defined above.

In preferred practice, $R^1$ and $R^2$ together with the atoms to which they are bonded form a 6-membered ring.

An $R^3$ radical preferably has a length that is greater than that of a pentyl group [a —$(CH_2)_4CH_3$ chain], more preferably greater than about that of a hexyl group [a —$(CH_2)_5CH_3$ chain], and most preferably greater than an octyl group [a —$(CH_2)_7CH_3$ chain]. An $R^3$ radical preferably has a length that is less than that of an icosyl group [a —$(CH_2)_{19}CH_3$ chain], and more preferably a length that is less than that of a stearyl group [a —$(CH_2)_{17}CH_3$ chain). A preferred $R^3$ group contains two or more 5- or 6-membered rings. A contemplated $R^3$ group, when rotated about an axis drawn through the $SO_2$-bonded 1-position and the substituent-bonded 4-position of a 6-membered ring or the $SO_2$-bonded 1-position and substituent-bonded 3- or 4-position of a 5-membered ring, defines a three-dimensional volume whose widest dimension has the width in a direction transverse to that axis to rotation of about one furanyl ring to about two phenyl rings.

It is also preferred that a $R^3$ radical be a single-ringed aryl or heteroaryl group that is 5- or 6-membered, and is itself substituted at its own 4-position when a 6-membered ring or at its own 3- or 4-position when a 5-membered ring with an optionally substituted substituent selected from the group consisting of one other single-ringed aryl or heteroaryl group, a $C_3$–$C_{14}$ alkyl group, a N-piperidyl group, a N-piperazyl group, a phenoxy group, a thiophenoxy group, a 4-thiopyridyl group, a phenylazo group and a benzamido group. The substituent of the 5- or 6-membered aryl or heteroaryl group can itself be substituted as discussed before.

A preferred compound for use in a contemplated process has a structure that corresponds to formula II, below, or a pharmaceutically acceptable salt thereof:

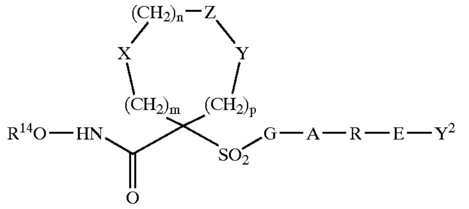

wherein $R^{14}$ is hydrido, a pharmaceutically acceptable cation or $C(W)R^{15}$ where W is O or S and $R^{15}$ is selected from the group consisting of an $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl and amino $C_1$–$C_6$-alkyl group wherein the aminoalkyl nitrogen is (i) unsubstituted or (ii) substituted with one or two substituents independently selected from the group consisting of an $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and $C_1$–$C_6$-alkanoyl radical, or (iii) wherein the amino $C_1$–$C_6$-alkyl nitrogen and two substituents attached thereto form a 5- to 8-membered heterocyclo or heteroaryl ring;

m is zero, 1 or 2;

n is zero, 1 or 2;

p is zero, 1 or 2;

the sum of m+n+p=1, 2, 3 or 4;

(a) one of X, Y and Z is selected from the group consisting of C(O), $NR^6$, O, S, S(O), $S(O)_2$ and $NS(O)_2R^7$, and the remaining two of X, Y and Z are $CR^8R^9$, and $CR^{10}R^{11}$, or (b) X and Z or Z and Y together constitute a moiety that is selected from the group consisting of $NR^6C(O)$, $NR^6S(O)$, $NR^6S(O)_2$, $NR^6S$, $NR^6O$, SS, $NR^6NR^6$ and OC(O), with the remaining one of X, Y and Z being $CR^8R^9$, or (c) n is zero and X, Y and Z together constitute a moiety selected from the group consisting of

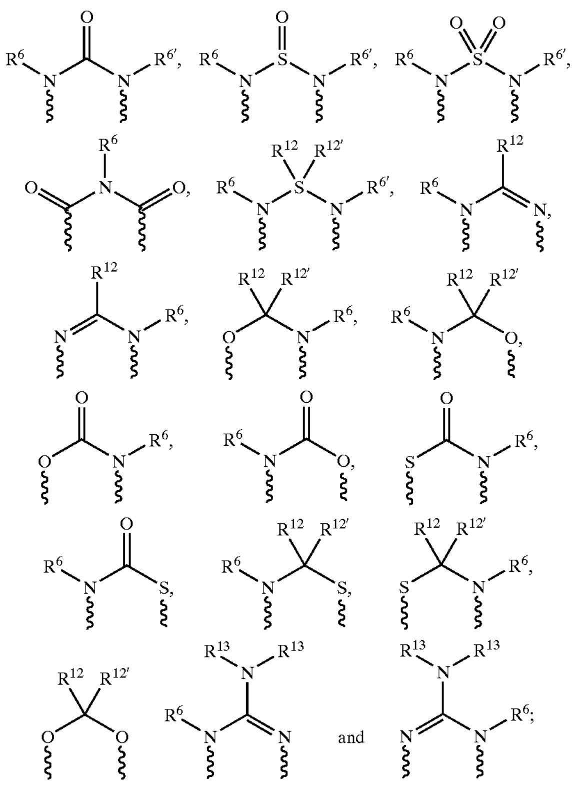

and wherein wavy lines are bonds to the atoms of the depicted ring;

$R^6$ and $R^{6'}$ are independently selected from the group consisting of hydrido, formyl, sulfonic-$C_1$–$C_6$-alkyl, $C_1$–$C_6$-alkoxycarbonyl-$C_1$–$C_6$-alkyl, hydroxycarbonyl-$C_1$–$C_6$-alkyl, $C_1$–$C_6$-alkylcarbonyl-$C_1$–$C_6$-alkyl, $R^8R^9$-aminocarbonyl- $C_1$–$C_6$-alkyl, $C_1$–$C_6$-alkoxycarbonyl-$C_1$–$C_6$-alkylcarbonyl, hydroxycarbonyl-$C_1$–$C_6$-alkylcarbonyl, $C_1$–$C_6$-alkylcarbonyl-$C_1$–$C_6$-alkylcarbonyl, $C_1$–$C_6$-alkoxycarbonylcarbonyl, hydroxycarbonylcarbonyl, $C_1$–$C_6$-alkylcarbonylcarbonyl, $R^8R^9$-aminocarbonylcarbonyl, $C_1$–$C_6$-alkanoyl, aryl-$C_1$–$C_6$-alkyl, aroyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, heteroarycarbonyl, heterocyclocarbonyl, $C_3$–$C_8$-heterocycloalkyl, $C_3$–$C_8$-heterocycloalkylcarbonyl, aryl, $C_5$–$C_6$-heterocyclo, $C_5$–$C_6$-heteroaryl, $C_3$–$C_8$-cycloalkyl-$C_1$–$C_6$-alkyl, aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, arylsulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyl($R^8$N)iminocarbonyl, aryl($R^8$N)iminocarbonyl, $C_5$–$C_6$-heterocyclo($R^8$N)iminocarbonyl, arylthio-$C_1$–$C_6$-alkyl, $C_1$–$C_6$-alkylthio-$C_1$–$C_6$-alkyl, arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—($R^8$)iminomethyl, $NR^8R^9$—$C_1$–$C_5$-alkylcarbonyl, hydroxy-$C_1$–$C_5$-alkyl, $R^8R^9$-aminocarbonyl, $R^8R^9$-aminocarbonyl-$C_1$–$C_6$-alkylcarbonyl, hydroxyaminocarbonyl, $R^8R^9$-aminosulfonyl, $R^8R^9$-aminosulfon-$C_1$–$C_6$-alkyl, $R^8R^9$-amino-$C_1$–$C_6$-alkylsulfonyl and an $R^8R^9$-amino-$C_1$–$C_6$-alkyl group;

$R^7$ is selected from the group consisting of a arylalkyl, aryl, heteroaryl, heterocyclo, $C_1$–$C_6$-alkyl, $C_3$–$C_6$-alkynyl, $C_3$–$C_6$-alkenyl, $C_1$–$C_6$-carboxyalkyl and a $C_1$–$C_6$-hydroxyalkyl group;

$R^8$ and $R^9$ and $R^{10}$ and $R^{11}$ are independently selected from the group consisting of a hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–-$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl, or wherein $R^8$ and $R^9$ or $R^{10}$ and $R^{11}$ and the carbon to which they are bonded form a carbonyl group, or wherein $R^8$ and $R^9$ or $R^{10}$ and $R^{11}$, or $R^8$ and $R^{10}$ together with the atoms to which they are bonded form a 5- to 8-membered carbocyclic ring, or a 5- to 8-membered heterocyclic or heteroaryl ring containing one or two heteroatoms that are nitrogen, oxygen, or sulfur, with the proviso that only one of $R^8$ and $R^9$ or $R^{10}$ and $R^{11}$ is hydroxy;

$R^{12}$ and $R^{12'}$ are independently selected from the group consisting of a hydrido, $C_1$–$C_6$-alkyl, aryl, ar-$C_1$–$C_6$-alkyl, heteroaryl, heteroaralkyl, $C_2$–$C_6$-alkynyl, $C_2$–$C_6$-alkenyl, thiol-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aryloxy-$C_1$–$C_6$-alkyl, amino-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, $C_1$–$C_6$-alkylthio-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl;

$R^{13}$ is selected from the group consisting of a hydrido, benzyl, phenyl, $C_1$–$C_6$-alkyl, $C_2$–$C_6$-alkynyl, $C_2$–$C_6$-alkenyl and a $C_1$–$C_6$-hydroxyalkyl group; and G—A—R—E—$Y^2$ is a substituent that preferably has a length greater than that of a pentyl group, and more preferably has a length greater than that of a hexyl group. The substituent G—A—R—E—$Y^2$ preferably has a length that is less than that of an icosyl group, and is more preferably less than that of a stearyl group. In this substituent:

G is an aryl or heteroaryl group;

A is selected from the group consisting of (1) —O—;

(2) —S—;

(3) —$NR^{17}$—;

(4) —CO—N($R^{17}$) or —N($R^{17}$)—CO—, wherein $R^{17}$ is hydrogen, $C_1$–$C_4$-alkyl, or phenyl;

(5) —CO—O— or —O—CO—;

(6) —O—CO—O—;

(7) —HC═CH—;

(8) —NH—CO—NH—;

(9) —C≡C—;

(10) —NH—CO—O— or —O—CO—NH—;

(11) —N═N—;

(12) —NH—NH—; and

(13) —CS—N($R^{18}$)— or —N($R^{18}$)—CS—, wherein $R^{18}$ is hydrogen $C_1$–$C_4$-alkyl, or phenyl; or

(14) A is absent and G is bonded directly to R;

R is a moiety selected from the group consisting of alkyl, alkoxyalkyl, aryl, heteroaryl, cycloalkyl, heterocycloalkyl, aralkyl, heteroaralkyl, heterocycloalkylalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, and a heterocycloalkylthioalkyl group wherein the aryl or heteroaryl or cycloalkyl or heterocycloalkyl substituent is (i) unsubstituted or (ii) substituted with one or two radicals selected from the group consisting of a halo, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkanoylamino, and a alkoxycarbonyl group, and R is other than alkyl or alkoxyalkyl when A is —O— or —S—;

E is selected from the group consisting of (1) —CO($R^{19}$)— or —($R^{19}$)CO—, wherein $R^{19}$ is a heterocycloalkyl, or a cycloalkyl group;

(2) —CONH— or —HNCO—; and (3) —CO—;

(4) —$SO_2$—$R^{19}$— or —$R^{19}$—$SO_2$—;

(5) —$SO_2$—;

(6) —NH—$SO_2$— or —$SO_2$—NH—;

(7) —S—;

(8) —NH—CO—O— or —O—CO—NH—; or (9) E is absent and R is bonded directly to $Y^2$; and the moiety $Y^2$ is absent or is selected from the group consisting of a hydrido, alkyl, alkoxy, haloalkyl, aryl, aralkyl, cycloalkyl, heteroaryl, hydroxy, aryloxy, aralkoxy, heteroaryloxy, heteroaralkyl, perfluoroalkoxy, perfluoroalkylthio, trifluoromethylalkyl, alkenyl, heterocycloalkyl, cycloalkyl, trifluoromethyl, alkoxycarbonyl, and a aminoalkyl group, wherein the aryl, heteroaryl, aralkyl, or heterocycloalkyl group is (i) unsubstituted or (ii) substituted with one or two radicals independently selected from the group consisting of an alkanoyl, halo, nitro, aralkyl, aryl, alkoxy, trifluoroalkyl, trifluoroalkoxy and an amino group wherein the amino nitrogen is (i) unsubstituted or (ii) substituted with one or two groups independently selected from hydrido, alkyl, and an aralkyl group.

A particularly preferred compound for use in a contemplated process corresponds in structure to formula III, below, or a pharmaceutically acceptable salt thereof:

III

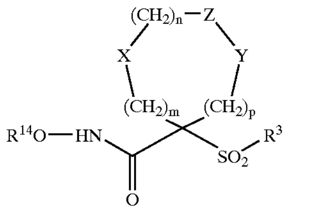

wherein m, n, p, X, Z, Y and $R^{14}$ are as defined above for formula II, and the $R^3$ radical that is defined below is a sub-set of the previously discussed G—A—R—E—$Y^2$ substituents.

Thus, $R^3$ is a radical that is comprised of a single-ringed aryl or heteroaryl group that is 5- or 6-membered, and is itself substituted at its own 4-position when a 6-membered ring and at its own 3- or 4-position when a 5-membered ring with a substituent selected from the group consisting of a thiophenoxy, 4-chlorophenoxy, 3-chlorophenoxy, 4-methoxyphenoxy, 3-benzodioxol-5-yloxy, 3,4-dimethylphenoxy, 4-fluorophenoxy, 4-fluorothiophenoxy, phenoxy, 4-trifluoromethoxyphenoxy, 4-trifluoromethylphenoxy, 4-(trifluoromethylthio)-phenoxy, 4-(trifluoromethylthio)-thiophenoxy, 4-chloro-3-fluorophenoxy, 4-isopropoxyphenoxy, 4-isopropylphenoxy, (2-methyl-1,3-benzothiazol-5-yl)oxy, 4-(1H-imidazol-1-yl)phenoxy, 4-chloro-3-methylphenoxy, 3-methylphenoxy, 4-ethoxyphenoxy, 3,4-difluorophenoxy, 4-chloro-3-methylphenoxy, 4-fluoro-3-chlorophenoxy, 4-(1H-1,2,4-triazol-1-yl)phenoxy, 3,5-difluorophenoxy, 3,4-dichlorophenoxy, 4-cyclopentylphenoxy, 4-bromo-3-methylphenoxy, 4-bromophenoxy, 4-methylthiophenoxy, 4-phenylphenoxy, 4-benzylphenoxy, 6-quinolinyloxy, 4-amino-3-methylphenoxy, 3-methoxyphenoxy, 5,6,7,8-tetrahydro-2-naphthalenyloxy, 3-hydroxymethylphenoxy, N-piperidyl, N-piperazinyl and a 4-benzyloxyphenoxy group.

A more particularly preferred compound for use in a contemplated process has a structure that corresponds to formula IV, below, or a pharmaceutically acceptable salt thereof:

IV

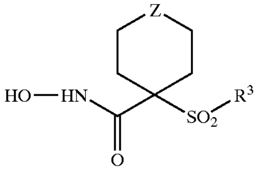

wherein $R^3$ is as defined above for formula I, more preferably as defined for formula II (wherein this $R^3$ group is the G—A—R—E—$Y^2$ substituent), and more preferably still as defined for formula III, and Z is selected group the group consisting of O, S, $NR^6$, SO, $SO_2$, and $NSO_2R^7$, wherein $R^6$ is selected from the group consisting of hydrido, $C_1$–$C_5$-alkyl, $C_1$–$C_5$-alkanoyl, benzyl, benzoyl, $C_3$–$C_5$-alkynyl, $C_3$–$C_5$-alkenyl, $C_1$–$C_3$-alkoxy-$C_1$–$C_4$-alkyl, $C_3$–$C_6$-cycloalkyl, heteroaryl-$C_1$–$C_6$-alkyl, $C_1$–$C_5$-hydroxyalkyl, $C_1$–$C_5$-carboxyalkyl, $C_1$–$C_5$-alkoxy $C_1$–$C_5$-alkylcarbonyl, and $NR^8R^9$—$C_1$–$C_5$-alkylcarbonyl or $NR^8R^9$—$C_1$–$C_5$-alkyl wherein $R^8$ and $R^9$ are independently hydrido, $C_1$–$C_5$-alkyl, $C_1$–$C_5$-alkoxycarbonyl or aryl-$C_1$–$C_5$-alkoxycarbonyl, or $NR^8R^9$ together form a heterocyclic ring containing 5- to 8-atoms in the ring; and $R^7$ is selected from the group consisting of an arylalkyl, aryl, heteroaryl, heterocyclo, $C_1$–$C_6$-alkyl, $C_3$–$C_6$-alkynyl, $C_3$–$C_6$-alkenyl, $C_1$–$C_6$-carboxyalkyl and a $C_1$–$C_6$-hydroxyalkyl group.

A still more preferred group of compounds for use in a contemplated process correspond in structure to formula V, below, or a pharmaceutically acceptable salt thereof:

V

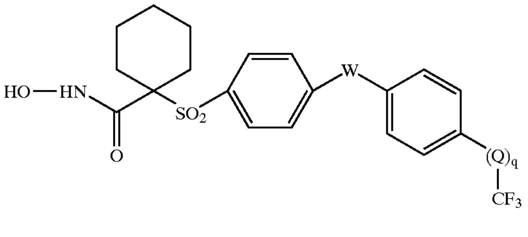

wherein

Z is as previously defined in formula IV;

W and Q are independently oxygen (O), $NR^6$ or sulfur (S), and $R^6$ is as defined in formula IV; and q is zero or one such that when q is zero, the trifluoromethyl group is bonded directly to the depicted phenyl ring.

Further compounds of formula A are also particularly preferred. One group of these compounds corresponds in structure to formula B (including formulas B, B-A, B-1, B-1A, B-2, B-2A, B-3 and B-3A), formula VIC, and more still particularly to formula VIC-1 and formula VIC-2, and formula VIII, below. In those formulas, ring structure Q is a substituent of the depicted phenyl ring and can itself be substituted. Substituent Q including the depicted nitrogen atom is a heterocyclic ring that contains 5- or 7-members, preferably 6-members, and can contain zero or one additional nitrogen atom. The substituents of Q such as A—R—E—$Y_2$, R—E—$Y^2$ and E—$Y^2$ are as defined before, and such a substituent is bonded at the 4-position relative to that depicted nitrogen atom when Q is a 6- or 7-membered ring and at the 3- or 4-position relative to that depicted nitrogen when Q is a 5-membered ring. The remaining members such a Q-bearing substituent (e.g., A—R—E—$Y^2$) are defined herein for the substituent G—A—R—E—$Y^2$. In addition, $R^{20}$, X, Y, Z, m, n, and p of the ring system and g are as before described, with Z preferably being O or $NR^6$.

B

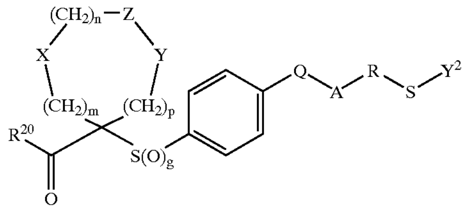

B-A

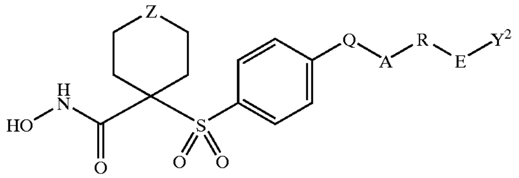

B-1

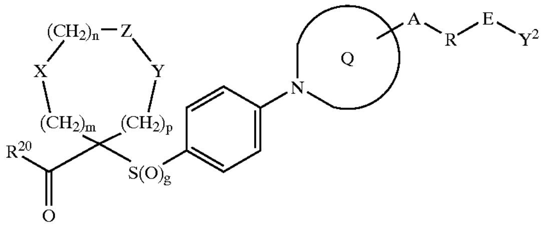

B-1A

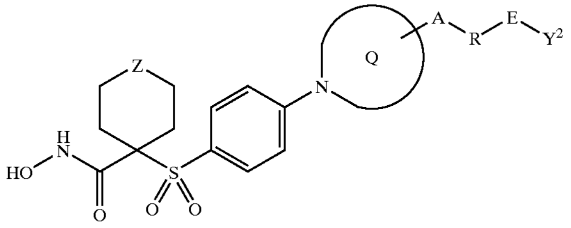

-continued

B-2

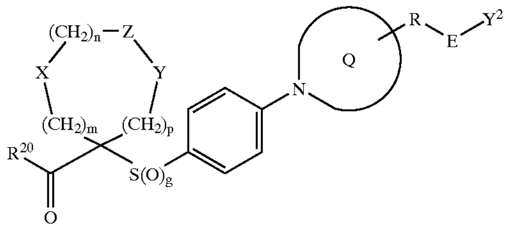

B-2A

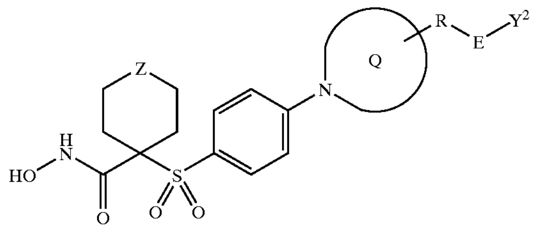

B-3

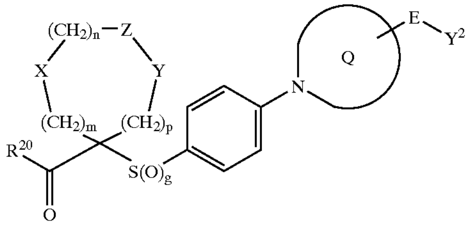

B-3A

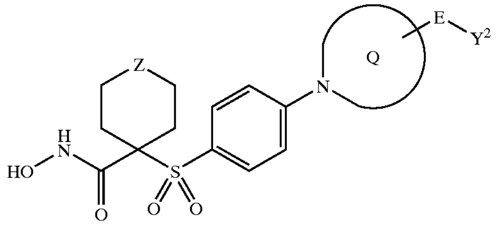

VIC

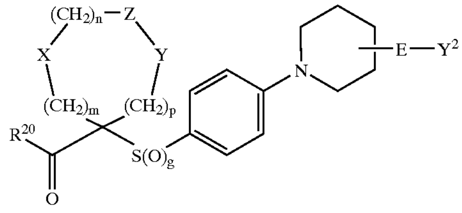

VIC-1

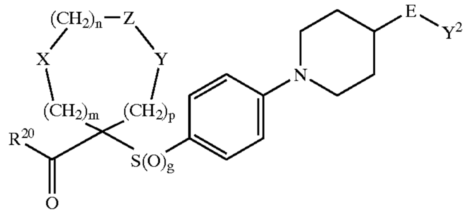

-continued

VIC-2

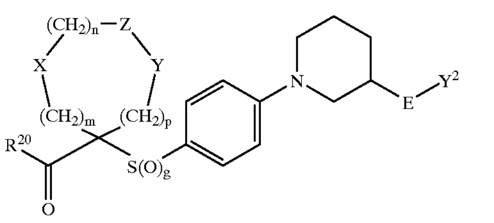

VIII

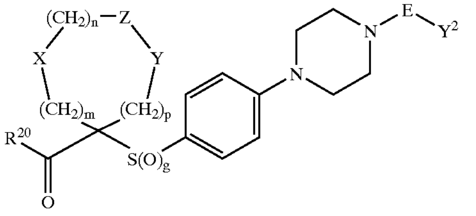

The compounds of formulas IX, IX-1, IX-2, X, XI, XI-1, XI-2 and XII, below, are more particularly preferred among the compounds of formula VIC, formula VIC-1, formula VIC-2, and formula VIII. In those latter formulas, Z is as before described, with Z preferably being O or $NR^6$, and substituent Q is a 6-membered ring, as is shown. The A moiety of the Q ring substituent —A—R—E—$Y^2$ (e.g. of formula B or B-1) is preferably absent in some embodiments, as in the compounds of formulas XI through XII, whereas both moieties A and R of that substituent group are absent in compounds of formulas IX through X. The moieties A, R, E and $Y^2$ of the substituent group —A—R—E—$Y^2$ are defined for the substituent group —G—A—R—E—$Y_2$.

IX

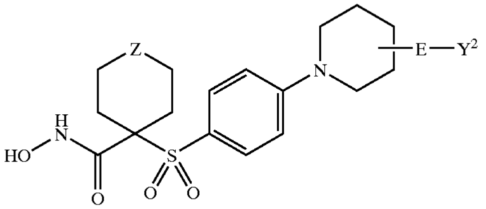

IX-1

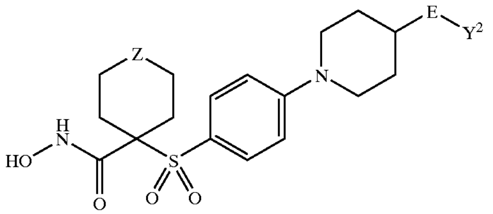

IX-2

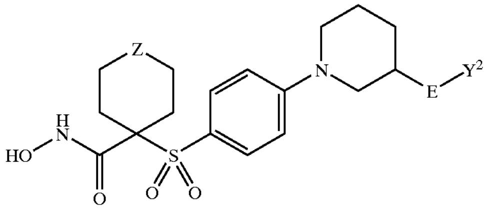

-continued

X

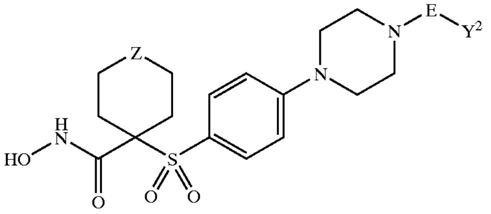

When used in a contemplated in a before-described process, a compound of formulas A, B, and I–VI, VI VIC, VIC-1, VIC-2, VIII, IX, IX-1, IX-2, X, XI, XI-1, XI-2 and XII, a $R^{20}$ group is preferably —NH—O—$R^{22}$ as defined above, and such a compound can also be present as a pharmaceutically acceptable salt. In addition, when so used, g is 2 in formulas B, VIC, VIC-1, VIC-2 and VII. The compounds of formulas A, B, and I–VI, VI VIC, VIC-1, VIC-2, VIII, IX, IX-1, IX-2, X, XI, XI-1, XI-2 and XII and their pharmaceutically acceptable salts are contemplated compounds of this invention.

The present invention also contemplates a precursor or intermediate compound that is useful in preparing a compound of formulas I–X. Such an intermediate compound corresponds in structure to formula VI, below:

VI

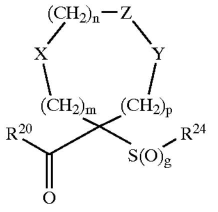

wherein m, n, p, X, Z and Y are as defined above for formula II, g is zero, 1 or 2 and $R^{24}$ is $R^3$ as defined in formulas I, III or IV, is the substituent G—A—R—E—$Y^2$ of formula II (formula VIA) or is $R^{3'}$, an aryl or heteroaryl group that is substituted with a coupling substituent reactive for coupling with another moiety (formula VIB), such as a nucleophilically displaceable leaving group, D.

VIA

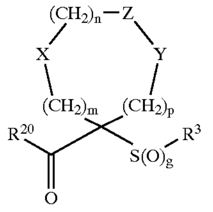

VIB

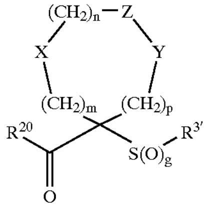

Exemplary nucleophilically displaceable leaving groups, D, include a halo (fluoro, chloro, bromo, or iodo) nitro, azido, phenylsulfoxido, aryloxy, $C_1$–$C_6$-alkoxy, a $C_1$–$C_6$-alkylsulfonate or arylsulfonate group and a trisubstituted ammonium group in which the three substituents are independently aryl, ar-$C_1$–$C_6$-alkyl or $C_1$–$C_6$-alkyl.

$R^{20}$ is (a) —O—$R^{21}$, where $R^{21}$ is selected from the group consisting of a hydrido, $C_1$–$C_6$-alkyl, aryl, ar-$C_1$–$C_6$-alkyl group and a pharmaceutically acceptable cation, (b) —NH—O—$R^{22}$ wherein $R^{22}$ is a selectively removable protecting group such as a 2-tetrahydropyranyl, benzyl, p-methoxybenzyl (MOZ), carbonyl-$C_1$–$C_6$-alkoxy, trisubstituted silyl group or o-nitrophenyl group, peptide synthesis resin and the like, wherein the trisubstituted silyl group is substituted with $C_1$–$C_6$-alkyl, aryl, or ar-$C_1$–$C_6$-alkyl or a mixture thereof, (c) —NH—O—$R^{14}$, where $R^{14}$ is hydrido, a pharmaceutically acceptable cation or C(W)$R^{25}$ where W is O (oxo) or S (thioxo) and $R^{25}$ is selected from the group consisting of an $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl and amino $C_1$–$C_6$-alkyl group wherein the amino $C_1$–$C_6$-alkyl nitrogen is (i) unsubstituted or (ii) substituted with one or two substituents independently selected from the group consisting of an $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and $C_1$–$C_6$-alkanoyl radical, or (iii) wherein the amino $C_1$–$C_6$-alkyl nitrogen and two substituents attached thereto form a 5- to 8-membered heterocyclo or heteroaryl ring, or (d) —$NR^{26}R^{27}$, where $R^{26}$ and $R^{27}$ are independently selected from the group consisting of a hydrido, $C_1$–$C_6$-alkyl, amino $C_1$–$C_6$-alkyl, hydroxy $C_1$–$C_6$-alkyl, aryl, ar-$C_1$–$C_6$-alkyl group, or $R^{26}$ and $R^{27}$ together with the depicted nitrogen atom form a 5- to 8-membered ring containing zero or one additional heteroatom that is oxygen, nitrogen or sulfur.

A particularly preferred precursor intermediate to an intermediate compound of formula VI is an intermediate compound of formula VII

VII

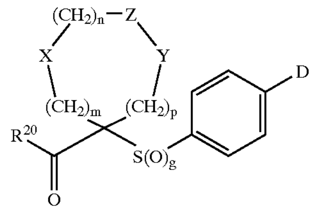

wherein m, n, p, g, X, Z, Y, D and $R^{20}$ are as defined above for formula VI.

Among the several benefits and advantages of the present invention are the provision of compounds and compositions effective as inhibitors of matrix metalloproteinase activity, the provision of such compounds and compositions that are effective for the inhibition of metalloproteinases implicated in diseases and disorders involving uncontrolled breakdown of connective tissue.

More particularly, a benefit of this invention is the provision of a compound and composition effective for selectively inhibiting certain metalloproteinases, such as one or more of MMP-2, MMP-9 and MMP-13, associated with pathological conditions such as, for example, rheumatoid arthritis, osteoarthritis, septic arthritis, corneal, epidermal or gastric ulceration, tumor metastasis, invasion or angiogenesis, periodontal disease, proteinuria, Alzheimer's Disease, coronary thrombosis and bone disease.

An advantage of the invention is the provision of compounds, compositions and methods effective for treating such pathological conditions by selective inhibition of a metalloproteinase such as MMP-2, MMP-9 or MMP-13 associated with such conditions with minimal side effects resulting from inhibition of other metalloproteinases, such as MMP-1, whose activity is necessary or desirable for normal body function.

Yet another advantage of the invention is the provision of a process for preparing such compounds.

Another benefit is the provision of a method for treating a pathological condition associated with abnormal matrix metalloproteinase activity.

A further advantage of the invention is the provision of a process for preparing such compositions.

Still further benefits and advantages of the invention will be apparent to the skilled worker from the disclosure that follows.

DETAILED DESCRIPTION OF THE INVENTION

In accordance with the present invention, it has been discovered that certain aromatic sulfone hydroxamic acids (hydroxamates) are effective for inhibition of matrix metalloproteinases ("MMPs") believed to be associated with uncontrolled or otherwise pathological breakdown of connective tissue. In particular, it has been found that these certain aromatic sulfone hydroxamates are effective for inhibition of one or more enzymes such as MMP-2, MMP-9 and MMP-13, which can be particularly destructive to tissue if present or generated in abnormal quantities or concentrations, and thus exhibit a pathological activity. Included in that pathological activity is the assistance of tumors and tumor cells in the process of penetrating basement membrane, and developing a new or improved blood supply; i.e., angiogenesis.

Moreover, it has been discovered that these aromatic sulfone hydroxamates are selective in the inhibition of one or more of MMP-2, MMP-9 and MMP-13 without excessive inhibition of other collagenases essential to normal bodily function such as tissue turnover and repair. More particularly, it has been found that a contemplated aromatic sulfone hydroxamate of the invention, or a pharmaceutically acceptable salt thereof, is particularly active in inhibiting of one or more of MMP-2, MMP-9 and MMP-13 in an in vitro assay that is predictive of in vivo activity. In addition, while being selective for one or more of MMP-2, MMP-9 and MMP-13, a contemplated aromatic sulfone hydroxamate, or its salt, has a limited or minimal in vitro inhibitory effect on MMP-1.

There is thus a substantial difference in the activity of a compound used in a contemplated process toward one or more of MMP-2, MMP-9 and MMP-13 and MMP-1. This substantial difference is assayed using the in vitro inhibition assay discussed in the examples. A substantial difference in activity corresponds to a compound exhibiting an $IC_{50}$ value against one or more of MMP-2, MMP-9 and MMP-13 that is about 0.1 times that of the compound against MMP-1, and more preferably 0.01 times that against MMP-1 and most preferably 0.001 times that against MMP-1, or more. Indeed, some compounds exhibit selectivity differences measured by $IC_{50}$ values that exceed the bounds of the assay at the number 100,000-fold. These selectivities are illustrated in the Inhibition Tables hereinafter.

Put differently, a contemplated compound can inhibit the activity of MMP-2 compared to MMP-9 or MMP-13 and MMP-1. Similarly, a contemplated compound can inhibit the activity of MMP-13 and MMP-2, while exhibiting less inhibition against MMP-1 and MMP-9. In addition, a contemplated compound can inhibit the activity of a MMP enzyme, while having less of an effect on tumor necrosis factor release.

The advantages of the selectivity of a contemplated compound can be appreciated, without wishing to be bound by theory, by considering the therapeutic uses the compounds. For example, inhibition of MMP-1 is suggested to be undesirable due to its role as a housekeeping enzyme, helping to maintain normal connective tissue turnover and repair. Inhibition of MMP-1 can lead to toxicities or side effects such as such as joint or connective tissue deterioration and pain. On the other hand, MMP-13 has been suggested to be intimately involved in the destruction of joint components in diseases such as osteoarthritis. Thus, potent and selective inhibition of MMP-13 compared with inhibition MMP-1 is highly desirable because a MMP-13 inhibitor can have a positive effect on disease progression in a patient in addition to having an anti-inflammatory effect.

Inhibition of MMP-2 and MMP-9 can be desirable for inhibition of tumor growth, metastasis, invasion and/or angiogenesis. A profile of selective inhibition of MMP-2 and MMP-9 relative to MMP-1 can provide a therapeutic advantage.

Yet another advantage of a contemplated compound is the selectivity with respect to tumor necrosis factor release and/or tumor necrosis factor receptor release that provides the physician with another factor to help select the best drug for a particular patient. While not wishing to be bound by theory, it is believed that there are several factors to this type of selectivity to be considered.

The first is that presence of tumor necrosis factor can be desirable for the control of cancer in the organism, so long as TNF is not present in a toxic excess. Thus, uncontrolled inhibition of release of TNF can be counterproductive and actually can be considered an adverse side effect even in cancer patients. In addition, selectivity with respect to inhibition of the release of the tumor necrosis factor receptor can also be desirable. The presence of that receptor can be desirable for maintaining a controlled tumor necrosis level in the mammal by binding excess TNF.

A contemplated selective MMP inhibitor compound useful in a contemplated process can be administered to by various routes and provide adequate therapeutic blood levels of enzymatically active inhibitor. A compound can be administered, for example, by the oral (IG, PO) or intravenous (IV) routes. Oral administration is advantageous if the patient is ambulatory, not hospitalized, physically able and sufficiently responsible to take drug at the required intervals. This is true even if the person is being treated with more than one drug for one or more diseases. On the other hand, IV drug administration is an advantage in a hospital setting wherein the dose and thus the blood levels can well controlled. A contemplated inhibitor can also be formulated for IM administration if desired. This route of administration can be desirable for the administration of prodrugs or regular drug delivery to patients that are either physically weak or have a poor compliance record or require constant drug blood levels.

Thus, in one embodiment, the present invention is directed to a treatment process that comprises administering a contemplated aromatic sulfone hydroxamic acid metalloprotease inhibitor, or a pharmaceutically acceptable salt thereof, in an effective amount to a host mammal having a condition associated with pathological matrix metalloprotease activity. A contemplated aromatic sulfone hydroxamate inhibitor compound useful in such a process inhibits the activity of one or more of MMP-2, MMP-9 and MMP-13, and exhibits substantially less inhibitory activity against at least MMP-1 in the in vitro assay noted above and discussed in detail hereinbelow. An aromatic sulfone hydroxamate inhibitor compound for use in a contemplated process corresponds in structure to formula I, below:

I

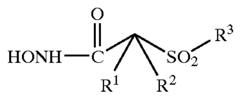

wherein

In one embodiment, $R^1$ and $R^2$ are both hydrido. In another embodiment, $R^1$ and $R^2$ together with the atoms to which they are bonded form a 5- to 8-membered ring containing one, two or three heteroatoms in the ring that are oxygen, sulfur or nitrogen.

It is preferred that $R^1$ and $R^2$ together with the atoms to which they are bonded form a five- to eight-membered ring that contains one or two heteroatoms in the ring, although $R^1$ and $R^2$ together with the atoms to which they are bonded form a 5- to 8-membered ring containing one, two or three heteroatoms. The heterocyclic ring can itself also be substituted with up to six $C_1$–$C_6$-alkyl groups or groups that comprise a another 5- to 8-membered carbocyclic or heterocyclic ring, an amino group, or contain one or two oxo (carbonyl) groups.

$R^3$ in formula I is an optionally substituted aryl or optionally substituted heteroaryl radical. That R3 radical is selected from the group consisting of an aryl, heteroaryl, aralkyl, heteroaralkyl, aralkoxy, heteroaralkoxy, aralkoxyalkyl, aryloxyalkyl, aralkanoylalkyl, arylcarbonylalkyl, aralkylaryl, aryloxyalkylaryl, aralkoxyaryl, arylazoaryl, arylhydrazinoaryl, alkylthioaryl, arylthioalkyl, alkylthioaralkyl, aralkylthioalkyl, an aralkylthioaryl radical, the sulfoxide or sulfone of any of the thio substituents, and a fused ring structure comprising two or more 5- or 6-membered rings selected from the group consisting of aryl, heteroaryl, carbocyclic and heterocyclic.

The substituent of which $R^3$ is comprised itself is unsubstituted or substituted with one or more substituents independently selected from the group consisting of a cyano, perfluoroalkyl, trifluoromethylalkyl, hydroxy, halo, alkyl, alkoxy, nitro, thiol, hydroxycarbonyl, aryloxy, arylthio, aralkyl, aryl, heteroaryloxy, heteroarylthio, heteroaralkyl, cycloalkyl, heterocyclooxy, heterocyclothio, heterocycloamino, cycloalkyloxy, cycloalkylthio, heteroaralkoxy, heteroaralkylthio, aralkoxy, aralkylthio, aralkylamino, heterocyclo, heteroaryl, arylazo, hydroxycarbonylalkoxy, alkoxycarbonylalkoxy, alkanoyl, arylcarbonyl, aralkanoyl, alkanoyloxy, aralkanoyloxy, hydroxyalkyl, hydroxyalkoxy, alkylthio, alkoxyalkylthio, alkoxycarbonyl, aryloxyalkoxyaryl, arylthioalkylthioaryl, aryloxyalkylthioaryl, arylthioalkoxyaryl, hydroxycarbonylalkoxy, hydroxycarbonylalkylthio, alkoxycarbonylalkoxy, alkoxycarbonylalkylthio, amino, wherein the amino nitrogen is (i) unsubstituted, or (ii) substituted with one or two substituents that are independently selected from the group consisting of an alkyl, aryl, heteroaryl, aralkyl, cycloalkyl, aralkoxycarbonyl, alkoxycarbonyl, arylcarbonyl, aralkanoyl, heteroarylcarbonyl, heteroaralkanoyl and an alkanoyl group, or (iii) wherein the amino nitrogen and two substituents attached thereto form a 5- to 8-membered heterocyclo or heteroaryl ring containing zero to two additional heteroatoms that are nitrogen, oxygen or sulfur and which ring itself is (a) unsubstituted or (b) substituted with one or two groups independently selected from the group consisting of an aryl, alkyl, heteroaryl, aralkyl, heteroaralkyl, hydroxy, alkoxy, alkanoyl, cycloalkyl, heterocycloalkyl, alkoxycarbonyl, hydroxyalkyl, trifluoromethyl, benzofused heterocycloalkyl, hydroxyalkoxyalkyl, aralkoxycarbonyl, hydroxycarbonyl, aryloxycarbonyl, benzofused heterocycloalkoxy, benzofused cycloalkylcarbonyl, heterocycloalkylcarbonyl, and a cycloalkylcarbonyl group, carbonylamino wherein the carboxamido nitrogen is (i) unsubstituted, or (ii) is the reacted amine of an amino acid, or (iii) substituted with one or two radicals selected from the group consisting of an alkyl, hydroxyalkyl, hydroxyheteroaralkyl, cycloalkyl, aralkyl, trifluoromethylalkyl, heterocycloalkyl, benzofused heterocycloalkyl, benzofused heterocycloalkyl, benzofused cycloalkyl, and an N,N-dialkylsubstituted alkylamino-alkyl group, or (iv) the carboxamido nitrogen and two substituents bonded thereto together form a 5- to 8-membered heterocyclo, heteroaryl or benzofused heterocycloalkyl ring that is itself unsubstituted or substituted with one or two radicals independently selected from the group consisting of an alkyl, alkoxycarbonyl, nitro, heterocycloalkyl, hydroxy, hydroxycarbonyl, aryl, aralkyl, heteroaralkyl and an amino group, wherein the amino nitrogen is (i) unsubstituted, or (ii) substituted with one or two substituents that are independently selected from the group consisting of alkyl, aryl, and heteroaryl, or (iii) wherein the amino nitrogen and two substituents attached thereto form a 5- to 8-membered heterocyclo or heteroaryl ring, and an aminoalkyl group wherein the aminoalkyl nitrogen is (i) unsubstituted, or (ii) substituted with one or two substituents independently selected from the group consisting of an alkyl, aryl, aralkyl, cycloalkyl, aralkoxycarbonyl, alkoxycarbonyl, and an alkanoyl group, or (iii) wherein the aminoalkyl nitrogen and two substituents attached thereto form a 5- to 8-membered heterocyclo or heteroaryl ring. A compound of formula I can also be used in the form of a pharmaceutically acceptable salt.

The $R^3$ radical has a length that is greater than that of a pentyl group [a $-(CH_2)_4CH_3$ chain], is more preferably greater than about the length of a hexyl group [a $-(CH_2)_5CH_3$ chain], and most preferably is greater than about the length of an octyl group [a $-(CH_2)_7CH_3$ chain]. A $R^3$ group has a length that is less than that of an icosyl group [eicosyl; a $-(CH_2)_{19}CH_3$ chain], and more preferably, a length that is less than that of a stearyl group [a $-(CH_2)_{17}CH_3$ chain). When rotated about an axis drawn through the $SO_2$-bonded 1-position and the substituent-bonded 4-position of a 6-membered ring or the $SO_2$-bonded 1-position and substituent-bonded 3- or 4-position of a 5-membered ring, a contemplated $R^3$ radical defines a three-dimensional volume whose widest dimension has the width of about one furanyl ring to about two phenyl rings in a direction transverse to that axis to rotation.

A compound of formula I is a compound of more general formula A, wherein $R^3$, $R^1$ and $R^2$ are as defined before and $R^{20}$ is defined below.

A

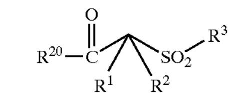

The substituent $R^{20}$ is (a) —O—$R^{21}$, where $R^{21}$ is selected from the group consisting of a hydrido, $C_1$–$C_6$-alkyl, aryl, ar-$C_1$–$C_6$-alkyl group and a pharmaceutically acceptable cation, (b) —NH—O—$R^{22}$ wherein $R^{22}$ is a selectively removable protecting group such as a 2-tetrahydropyranyl, benzyl, p-methoxybenzyl (MOZ), carbonyl-$C_1$–$C_6$-alkoxy, trisubstituted silyl group or o-nitrophenyl group, peptide synthesis resin and the like, wherein the trisubstituted silyl group is substituted with $C_1$–$C_6$-alkyl, aryl, or ar-$C_1$–$C_6$-alkyl or a mixture thereof, (c) —NH—O—$R^{14}$, where $R^{14}$ is hydrido, a pharmaceutically acceptable cation or $C(W)R^{25}$ where W is O (oxo) or S (thioxo) and $R^{25}$ is selected from the group consisting of an $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl and amino $C_1$–$C_6$-alkyl group wherein the amino $C_1$–$C_6$-alkyl nitrogen is (i) unsubstituted or (ii) substituted with one or two substituents independently selected from the group consisting of an $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and $C_1$–$C_6$-alkanoyl radical, or (iii) wherein the amino $C_1$–$C_6$-alkyl nitrogen and two substituents attached thereto form a 5- to 8-membered heterocyclo or heteroaryl ring, or (d) —$NR^{26}R^{27}$, where $R^{26}$ and $R^{27}$ are independently selected from the group consisting of a hydrido, $C_1$–$C_6$-alkyl, amino $C_1$–$C_6$-alkyl, hydroxy $C_1$–$C_6$-alkyl, aryl, ar-$C_1$–$C_6$-alkyl group, or $R^{26}$ and $R^{27}$ together with the depicted nitrogen atom form a 5- to 8-membered ring containing zero or one additional heteroatom that is oxygen, nitrogen or sulfur.

Several exemplary $R^1$ and $R^2$ groups that together form a contemplated heterocyclic ring are shown in the Tables that follow hereinafter, as well as in the descriptions of those 5- to 8-membered rings and the specific Examples, as are several contemplated aromatic sulfone hydroxamic acid compounds.

In more preferred practice, $R^1$ and $R^2$ of formula I or formula A together with the atom to which they are bonded form a 5- to 8-membered ring that contains one, two or three heteroatoms. Most preferably, that ring is a 6-membered ring that contains one heteroatom located at the 4-position relative to the position at which the $SO_2$ group is bonded. Other preferred compounds for use in a contemplated process correspond in structure to one or more of formulas II, III, IV or V, which are discussed hereinafter.

In one embodiment, a preferred compound used in a contemplated process has a structure that corresponds to formula II, below:

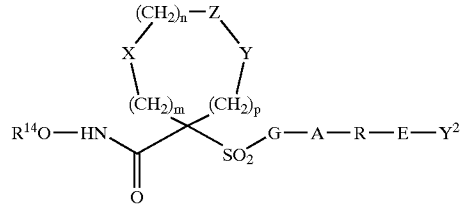

wherein $R^{14}$ is hydrido, a pharmaceutically acceptable cation or $C(W)R^{15}$ where W is O or S and $R^{15}$ is selected from the group consisting of an $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl and amino $C_1$–$C_6$-alkyl group wherein the aminoalkyl nitrogen is (i) unsubstituted or (ii) substituted with one or two substituents independently selected from the group consisting of an $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and $C_1$–$C_6$-alkanoyl radical, or (iii) wherein the amino $C_1$–$C_6$-alkyl nitrogen and two substituents attached thereto form a 5- to 8-membered heterocyclo or heteroaryl ring;

m is zero, 1 or 2;

n is zero, 1 or 2;

p is zero, 1 or 2;

the sum of m+n+p=1, 2, 3 or 4;

(a) one of X, Y and Z is selected from the group consisting of C(O), $NR^6$, O, S, S(O), $S(O)_2$ and $NS(O)_2R^7$, and the remaining two of X, Y and Z are $CR^8R^9$, and $CR^{10}R^{11}$, or (b) X and Z or Z and Y together constitute a moiety that is selected from the group consisting of $NR^6C(O)$, $NR^6S(O)$, $NR^6S(O)_2$, $NR^6S$, $NR^6O$, SS, $NR^6NR^6$ and OC(O), with the remaining one of X, Y and Z being $CR^8R^9$, or (c) n is zero and X, Y and Z together constitute a moiety selected from the group consisting of

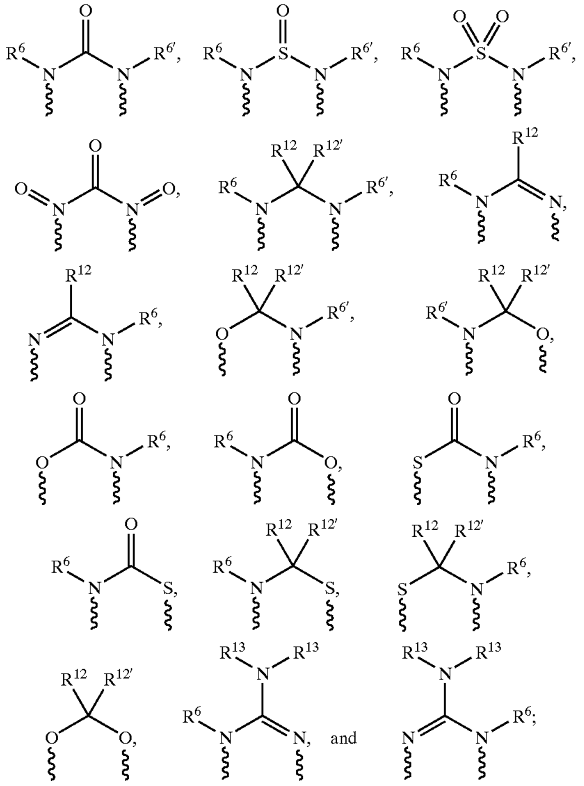

wherein wavy lines are bonds to the atoms of the depicted ring;

$R^6$ and $R^{6'}$ are independently selected from the group consisting of hydrido, formyl, sulfonic-$C_1$–$C_6$-alkyl, $C_1$–$C_6$-alkoxycarbonyl-$C_1$–$C_6$-alkyl, hydroxycarbonyl-$C_1$–$C_6$-alkyl, $C_1$–$C_6$-alkylcarbonyl-$C_1$–$C_6$-alkyl, $R^8R^9$-aminocarbonyl-$C_1$–$C_6$-alkyl, $C_1$–$C_6$-alkoxycarbonyl-$C_1$–$C_6$-alkylcarbonyl, hydroxycarbonyl-$C_1$–$C_6$-alkylcarbonyl, $C_1$–$C_6$-alkylcarbonyl-$C_1$–$C_6$-alkylcarbonyl, $C_1$–$C_6$-alkoxycarbonylcarbonyl, hydroxycarbonylcarbonyl, $C_1$–$C_6$-alkylcarbonylcarbonyl, $R^8R^9$-aminocarbonylcarbonyl, $C_1$–$C_6$-alkanoyl, aryl-$C_1$–$C_6$-alkyl, aroyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, heteroarycarbonyl, heterocyclocarbonyl, $C_3$–$C_8$-heterocycloalkyl, $C_3$–$C_8$-heterocycloalkylcarbonyl, aryl, $C_5$–$C_6$-heterocyclo, $C_5$–$C_6$-heteroaryl, $C_3$–$C_8$-cycloalkyl-$C_1$–$C_6$-alkyl, aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, arylsulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyl($R^8$N)iminocarbonyl, aryl($R^8$N)iminocarbonyl, $C_5$–$C_6$-heterocyclo($R^8$N)iminocarbonyl, arylthio-$C_1$–$C_6$-alkyl, $C_1$–$C_6$-alkylthio-$C_1$–$C_6$-alkyl, arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—($R^8$)iminomethyl, $NR^8R^9$—$C_1$–$C_5$-alkylcarbonyl, hydroxy-$C_1$–$C_5$-alkyl, $R^8R^9$-aminocarbonyl, $R^8R^9$-aminocarbonyl-$C_1$–$C_6$-alkylcarbonyl, hydroxyaminocarbonyl, $R^8R^9$-aminosulfonyl, $R^8R^9$-aminosulfon-$C_1$–$C_6$-alkyl, $R^8R^9$-amino-$C_1$–$C_6$-alkylsulfonyl and an $R^8R^9$-amino-$C_1$–$C_6$-alkyl group;

$R^7$ is selected from the group consisting of a arylalkyl, aryl, heteroaryl, heterocyclo, $C_1$–$C_6$-alkyl, $C_3$–$C_6$-alkynyl, $C_3$–$C_6$-alkenyl, $C_1$–$C_6$-carboxyalkyl and a $C_1$–$C_6$-hydroxyalkyl group;

$R^8$ and $R^9$ and $R^{10}$ and $R^{11}$ are independently selected from the group consisting of a hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl, or wherein $R^8$ and $R^9$ or $R^{10}$ and $R^{11}$ and the carbon to which they are bonded form a carbonyl group, or wherein $R^8$ and $R^9$ or $R^{10}$ and $R^{11}$, or $R^8$ and $R^{10}$ together with the atoms to which they are bonded form a 5- to 8-membered carbocyclic ring, or a 5- to 8-membered heterocyclic or heteroaryl ring containing one or two heteroatoms that are nitrogen, oxygen, or sulfur, with the proviso that only one of $R^8$ and $R^9$ or $R^{10}$ and $R^{11}$ is hydroxy;

$R^{12}$ and $R^{12'}$ are independently selected from the group consisting of a hydrido, $C_1$–$C_6$-alkyl, aryl, ar-$C_1$–$C_6$-alkyl, heteroaryl, heteroaralkyl, $C_2$–$C_6$-alkynyl, $C_2$–$C_6$-alkenyl, thiol-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aryloxy-$C_1$–$C_6$-alkyl, amino-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, $C_1$–$C_6$-alkylthio-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl;

$R^{13}$ is selected from the group consisting of a hydrido, benzyl, phenyl, $C_1$–$C_6$-alkyl, $C_2$–$C_6$-alkynyl, $C_2$–$C_6$-alkenyl and a $C_1$–$C_6$-hydroxyalkyl group; and G—A—R—E—$Y^2$ is a substituent that preferably has a length greater than that of a pentyl group, and more preferably has a length greater than that of a hexyl group. The substituent G—A—R—E—$Y^2$ preferably has a length that is less than that of an icosyl group, and is more preferably less than that of a stearyl group. In this substituent:

G is an aryl or heteroaryl group;

A is selected from the group consisting of (1) —O—;

(2) —S—;

(3) —$NR^{17}$—;

(4) —CO—N($R^{17}$) or —N($R^{17}$)—CO—, wherein $R^{17}$ is hydrogen, $C_1$–$C_4$-alkyl, or phenyl;

(5) —CO—O— or —O—CO—;

(6) —O—CO—O—;

(7) —HC=CH—;

(8) —NH—CO—NH—;

(9) —C≡C—;

(10) —NH—CO—O— or —O—CO—NH—;

(11) —N=N—;

(12) —NH—NH—; and

(13) —CS—N($R^{18}$)— or —($R^{18}$)—CS—, wherein $R^{18}$ is hydrogen $C_1$–$C_4$-alkyl, or phenyl; or

(14) A is absent and G is bonded directly to R;

R is a moiety selected from the group consisting of alkyl, alkoxyalkyl, aryl, heteroaryl, cycloalkyl, heterocycloalkyl, aralkyl, heteroaralkyl, heterocycloalkylalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, and a heterocycloalkylthioalkyl group wherein the aryl or heteroaryl or cycloalkyl or heterocycloalkyl substituent is (i) unsubstituted or (ii) substituted with one or two radicals selected from the group consisting of a halo, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkanoylamino, and a alkoxycarbonyl group, and R is other than alkyl or alkoxyalkyl when A is —O— or —S—;

E is selected from the group consisting of (1) —CO($R^{19}$)— or —($R^{19}$)CO—, wherein $R^{19}$ is a heterocycloalkyl, or a cycloalkyl group;

(2) —CONH— or —HNCO—; and (3) —CO—;

(4) —$SO_2$—$R^{19}$— or —$R^{19}$—$SO_2$—;

(5) —$SO_2$—;

(6) —NH—$SO_2$— or —$SO_2$—NH—;

(7) —S—;

(8) —NH—CO—O— or —O—CO—NH—; or (9) E is absent and R is bonded directly to $Y^2$; and the moiety $Y^2$ is absent or is selected from the group consisting of a hydrido, alkyl, alkoxy, haloalkyl, aryl, aralkyl, cycloalkyl, heteroaryl, hydroxy, aryloxy, aralkoxy, heteroaryloxy, heteroaralkyl, perfluoroalkoxy, perfluoroalkylthio, trifluoromethylalkyl, alkenyl, heterocycloalkyl, cycloalkyl, trifluoromethyl, alkoxycarbonyl, and a aminoalkyl group, wherein the aryl, heteroaryl, aralkyl, or heterocycloalkyl group is (i) unsubstituted or (ii) substituted with one or two radicals independently selected from the group consisting of an alkanoyl, halo, nitro, aralkyl, aryl, alkoxy, trifluoroalkyl, trifluoroalkoxy and an amino group wherein the amino nitrogen is (i) unsubstituted or (ii) substituted with one or two groups independently selected from hydrido, alkyl, and an aralkyl group.

The substituent —G—A—R—E—$Y^2$ preferably contains two to four carbocyclic or heterocyclic rings, including the aryl or heteroaryl group, G. More preferably, each of those rings is 6-membered. Additional separate preferences for a compound of formula II include: (a) that A is —O— or —S—, (b) R is an aryl, heteroaryl, cycloalkyl or heterocycloalkyl group, (c) E is absent, and (d) $Y^2$ is selected from the group consisting of hydrido, an alkyl, alkoxy, perfluoroalkoxy and a perfluoroalkylthio group.

A more preferred compound for use in a contemplated process has a structure that corresponds to formula III, below:

III

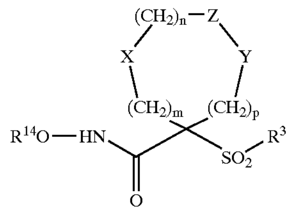

wherein $R^3$ is a single-ringed aryl or heteroaryl group that is 5- or 6-membered, and is itself substituted at its own 4-position when a 6-membered ring and at its own 3- or 4-position when a 5-membered ring with a substituent selected from the group consisting of a thiophenoxy, 4-chlorophenoxy, 3-chlorophenoxy, 4-methoxyphenoxy, 3-benzodioxol-5-yloxy, 3,4- dimethylphenoxy, 4-fluorophenoxy, 4-fluorothiophenoxy, phenoxy, 4-trifluoromethoxyphenoxy, 4-trifluoromethylphenoxy, 4-(trifluoromethylthio)phenoxy, 4-(trifluoromethylthio)thiophenoxy, 4-chloro-3-fluorophenoxy, 4-isopropoxyphenoxy, 4-isopropylphenoxy, (2-methyl-1,3-benzothiazol-5-yl)oxy, 4-(1H-imidazol-1-yl)phenoxy, 4-chloro-3-methylphenoxy, 3-methyl-phenoxy, 4-ethoxyphenoxy, 3,4-difluorophenoxy, 4-chloro-3-methylphenoxy, 4-fluoro-3-chlorophenoxy, 4-(1H-1,2,4-triazol-1-yl)phenoxy, 3,5-difluorophenoxy, 3,4-dichlorophenoxy, 4-cyclopentylphenoxy, 4-bromo-3-methylphenoxy, 4-bromophenoxy, 4-methylthiophenoxy, 4-phenylphenoxy, 4-benzylphenoxy, 6-quinolinyloxy, 4-amino-3-methylphenoxy, 3-methoxyphenoxy, 5,6,7,8-tetrahydro-2-naphthalenyloxy, 3-hydroxymethylphenoxy, and a 4-benzyloxyphenoxy group;

$R^{14}$ is hydrido, a pharmaceutically acceptable cation or $C(W)R^{15}$ where W is O or S and $R^{15}$ is selected from the group consisting of an $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl and amino $C_1$–$C_6$-alkyl group wherein the aminoalkyl nitrogen is (i) unsubstituted or (ii) substituted with one or two substituents independently selected from the group consisting of an $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and a $C_1$–$C_6$-alkanoyl radical, or (iii) wherein the amino $C_1$–$C_6$-alkyl nitrogen and two substituents attached thereto form a 5- to 8-membered heterocyclo or heteroaryl ring;

m is zero, 1 or 2;

n is zero, 1 or 2;

p is zero, 1 or 2;

the sum of m+n+p=1, 2, 3 or 4;

(a) one of X, Y and Z is selected from the group consisting of C(O), $NR^6$, O, S, S(O), $S(O)_2$ and $NS(O)_2R^7$, and the remaining two of X, Y and Z are $CR^8R^9$, and $CR^{10}R^{11}$, or (b) X and Z or Z and Y together constitute a moiety that is selected from the group consisting of $NR^6C(O)$, $NR^6S(O)$, $NR^6S(O)_2$, $NR^6S$, $NR^6O$, SS, $NR^6NR^6$ and OC(O), with the remaining one of X, Y and Z being $CR^8R^9$, or (c) n is zero and X, Y and Z together constitute a moiety selected from the group consisting of

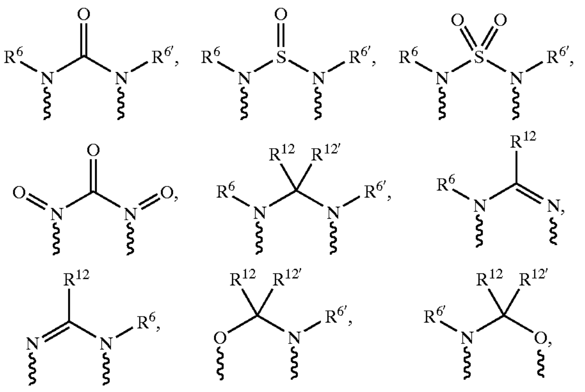

-continued

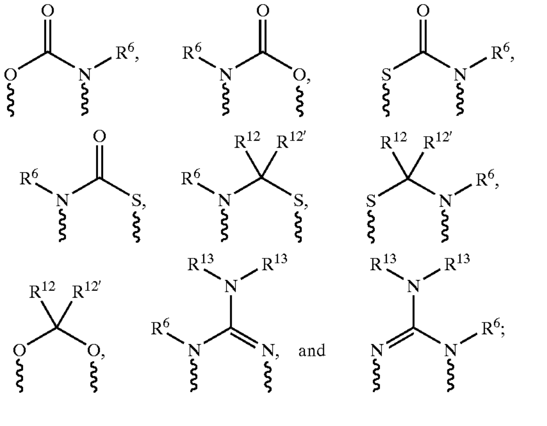

wherein wavy lines are bonds to the atoms of the depicted ring;

$R^6$ and $R^{6'}$ are independently selected from the group consisting of hydrido, formyl, sulfonic-$C_1$–$C_6$-alkyl, $C_1$–$C_6$-alkoxycarbonyl-$C_1$–$C_6$-alkyl, hydroxycarbonyl-$C_1$–$C_6$-alkyl, $C_1$–$C_6$-alkylcarbonyl-$C_1$–$C_6$-alkyl, $R^8R^9$-aminocarbonyl-$C_1$–$C_6$-alkyl, $C_1$–$C_6$-alkoxycarbonyl-$C_1$–$C_6$-alkylcarbonyl, hydroxycarbonyl-$C_1$–$C_6$-alkylcarbonyl, $C_1$–$C_6$-alkylcarbonyl-$C_1$–$C_6$-alkylcarbonyl, $C_1$–$C_6$-alkoxycarbonylcarbonyl, hydroxycarbonylcarbonyl, $C_1$–$C_6$-alkylcarbonylcarbonyl, $R^8R^9$-aminocarbonylcarbonyl, $C_1$–$C_6$-alkanoyl, aryl-$C_1$–$C_6$-alkyl, aroyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, heteroarycarbonyl, heterocyclocarbonyl, $C_3$–$C_8$-heterocycloalkyl, $C_3$–$C_8$-heterocycloalkylcarbonyl, aryl, $C_5$–$C_6$-heterocyclo, $C_5$–$C_6$-heteroaryl, $C_3$–$C_8$-cycloalkyl-$C_1$–$C_6$-alkyl, aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, arylsulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyl($R^8$N)iminocarbonyl, aryl($R^8$N)iminocarbonyl, $C_5$–$C_6$-heterocyclo($R^8$N)iminocarbonyl, arylthio-$C_1$–$C_6$-alkyl, $C_1$–$C_6$-alkylthio-$C_1$–$C_6$-alkyl, arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—($R^8$)iminomethyl, $NR^8R^9$—$C_1$–$C_5$-alkylcarbonyl, hydroxy-$C_1$–$C_5$-alkyl, $R^8R^9$-aminocarbonyl, $R^8R^9$-aminocarbonyl-$C_1$–$C_6$-alkylcarbonyl, hydroxyaminocarbonyl, $R^8R^9$-aminosulfonyl, $R^8R^9$-aminosulfon-$C_1$–$C_6$-alkyl, $R^8R^9$-amino-$C_1$–$C_6$-alkylsulfonyl and an $R^8R^9$-amino-$C_1$–$C_6$-alkyl group;

$R^7$ is selected from the group consisting of a arylalkyl, aryl, heteroaryl, heterocyclo, $C_1$–$C_6$-alkyl, $C_3$–$C_6$-alkynyl, $C_3$–$C_6$-alkenyl, $C_1$–$C_6$-carboxyalkyl and a $C_1$–$C_6$-hydroxyalkyl group;

$R^8$ and $R^9$ and $R^{10}$ and $R^{11}$ are independently selected from the group consisting of a hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl, or wherein $R^8$ and $R^9$ or $R^{10}$ and $R^{11}$ and the carbon to which they are bonded form a carbonyl group, or wherein $R^8$ and $R^9$ or $R^{10}$ and $R^{11}$, or $R^8$ and $R^{10}$ together with the atoms to which they are bonded form a 5- to 8-membered carbocyclic ring, or a 5- to 8-membered heterocyclic or heteroaryl ring containing one or two heteroatoms that are nitrogen, oxygen, or sulfur, with the proviso that only one of $R^8$ and $R^9$ or $R^{10}$ and $R^{11}$ is hydroxy;

$R^{12}$ and $R^{12'}$ are independently selected from the group consisting of a hydrido, $C_1$–$C_6$-alkyl, aryl, ar-$C_1$–$C_6$-alkyl, heteroaryl, heteroaralkyl, $C_2$–$C_6$-alkynyl, $C_2$–$C_6$-alkenyl, thiol-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aryloxy-$C_1$–$C_6$-alkyl, amino-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, $C_1$–$C_6$-alkylthio-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl; and $R^{13}$ is selected from the group consisting of a hydrido, benzyl, phenyl, $C_1$–$C_6$-alkyl, $C_2$–$C_6$-alkynyl, $C_2$–$C_6$-alkenyl and a $C_1$–$C_6$-hydroxyalkyl group. Again, the use of a compound of formula III as a pharmaceutically acceptable salt is also contemplated.

Preferences related to a compound of formula III that also apply to a compound of formula II include the following, which are independently preferred: (a) the sum of m+n+p=1 or 2, and more preferably 2; (b) Z is O, S or $NR^6$; (c) $R^6$ is selected from the group consisting of $C_3$–$C_6$-cycloalkyl, $C_1$–$C_6$-alkyl, $C_3$–$C_6$-alkenyl, $C_3$–$C_6$-alkynyl, $C_1$–$C_6$-alkoxy-$C_1$–$C_6$-alkyl, amino-$C_1$–$C_6$-alkyl, aminosulfonyl, heteroaryl-$C_1$–$C_6$-alkyl, aryloxycarbonyl, and $C_1$–$C_6$-alkoxycarbonyl; and (d) m=n=zero, p=1, and Y is $NR^6$. Another preference for a compound of both of formulas II and III is that $R^{14}$ be hydrido, or that W of the $C(W)R^{15}$ pro-drug form be O and $R^{15}$ be a $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, or aryloxy group.

A still more preferred compound for use in a contemplated process corresponds in structure to formula IV, below:

IV

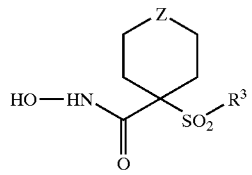

Here, $R^3$ is as defined above as to formulas I, III and more preferably as defined as to formula II (wherein the $R^3$ radical is the substituent G—A—R—E—$Y^2$). Most preferably, $R^3$ is as defined in formula III.

Z is selected group the group consisting of O, S, $NR^6$, SO, $SO_2$, and $NSO_2R^7$, wherein $R^6$ is selected from the group consisting of hydrido, $C_1$–$C_5$-alkyl, $C_1$–$C_5$-alkanoyl, benzyl, benzoyl, $C_3$–$C_5$-alkynyl, $C_3$–$C_5$-alkenyl, $C_1$–$C_3$-alkoxy-$C_1$–$C_4$-alkyl, $C_3$–$C_6$-cycloalkyl, heteroaryl-$C_1$–$C_6$-alkyl, $C_1$–$C_5$-hydroxyalkyl, $C_1$–$C_5$-carboxyalkyl, $C_1$–$C_5$-alkoxy $C_1$–$C_5$-alkylcarbonyl, and $NR^8R^9$—$C_1$–$C_5$-alkylcarbonyl or $NR^8R^9$—$C_1$–$C_5$-alkyl wherein $R^8$ and $R^9$ are independently hydrido, $C_1$–$C_5$-alkyl, $C_1$–$C_5$-alkoxycarbonyl or aryl-$C_1$–$C_5$-alkoxycarbonyl, or $NR^8R^9$ together form a heterocyclic ring containing 5- to 8-atoms in the ring; and $R^7$ is selected from the group consisting of an arylalkyl, aryl, heteroaryl, heterocyclo, $C_1$–$C_6$-alkyl, $C_3$–$C_6$-alkynyl, $C_3$–$C_6$-alkenyl, $C_1$–$C_6$-carboxyalkyl and a $C_1$–$C_6$-hydroxyalkyl group. Most preferably, Z is O or $NR^6$. Here too, the use of a compound of formula IV as a pharmaceutically acceptable salt is contemplated.

A still more preferred group of contemplated compounds for use in a contemplated process correspond in structure to formula V, below;

V

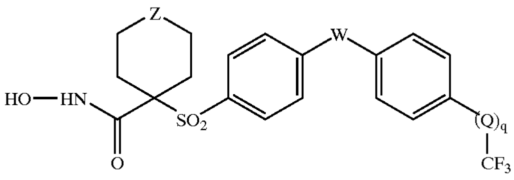

wherein

Z is as previously defined for formula IV;

W and Q are independently oxygen (O), $NR^6$ or sulfur (S), and $R^6$ is as defined in formula IV; and q is zero or one such that when q is zero, Q is absent and the trifluoromethyl group is bonded directly to the depicted phenyl ring. Here again, the use of a compound of formula IV as a pharmaceutically acceptable salt is contemplated.

Further compounds of formula A are also particularly preferred. One group of these compounds corresponds in structure to formula B, formula VIC, and more still particularly to formula VIC-1 and formula VIC-2, and formula VIII, below. In those formulas, ring structure Q including the depicted nitrogen atom is a heterocyclic ring that contains 5- or 7-members, preferably 6-members, and can contain zero or one additional nitrogen atom in addition to that depicted. The members of substituent —A—R—E—$Y^2$ (or —R—E—$Y^2$ or —E—$Y^2$) are as defined elsewhere in the definition of the members of the substituent —G—A—R—E—$Y^2$. Furthermore, substituent A—R—E—$Y^2$ (or substituent R—E—$Y^2$ or —E—$Y^2$) is bonded at the 4-position relative to that depicted nitrogen atom when Q is a 6- or 7-membered ring and at the 3- or 4-position relative to that depicted nitrogen when Q is a 5-membered ring. Still further, $R^{20}$, X, Y, Z, m, n, and p of the ring system and g are as before described.

B

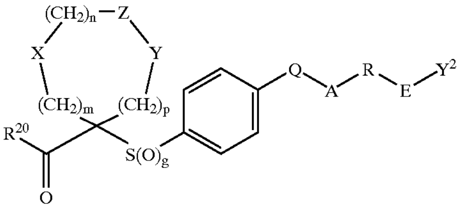

B-A

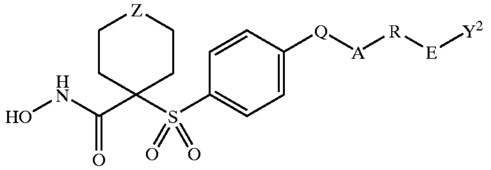

B-1

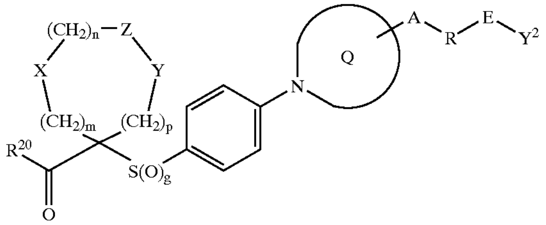

B-1A

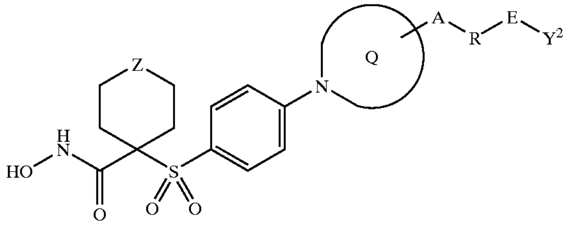

B-2

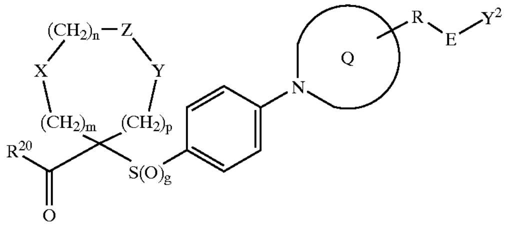

-continued

B-2A

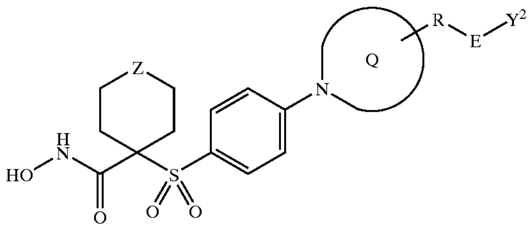

B-3

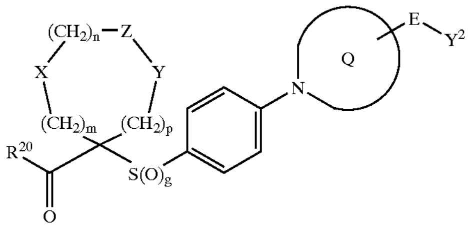

B-3A

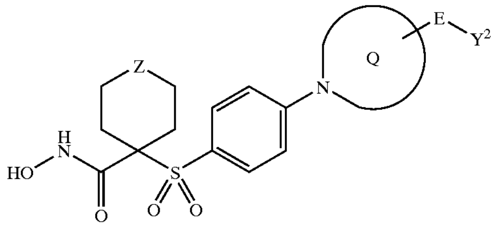

VIC

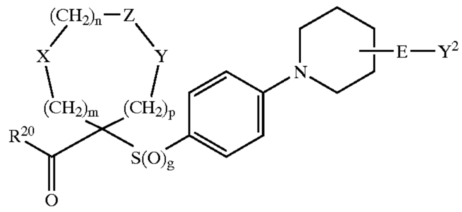

VIC-1

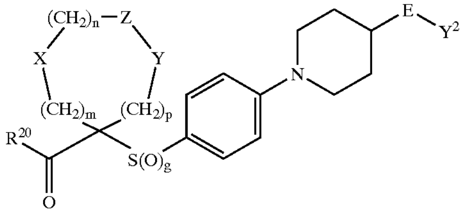

VIC-2

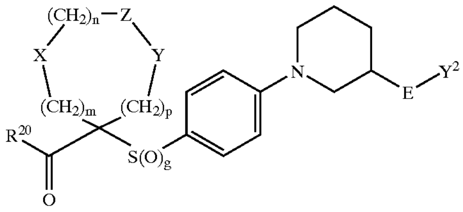

VIII

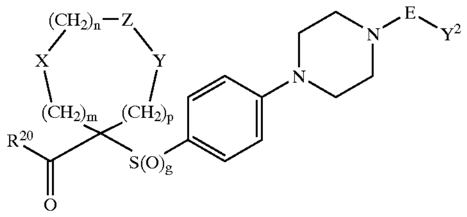

More particularly preferred among the compounds of formula VIC, formula VIC-1, formula VIC-2, and formula VIII, are the compounds of formulas IX, IX-1, IX-2, X, XI, XI-1, XI-2 and XII, below, wherein Z is as before described and the members of the substituent group —E—$Y_2$ and —R—E—$Y_2$ are defined for the substituent group —G—A—R—E—$Y^2$.

IX

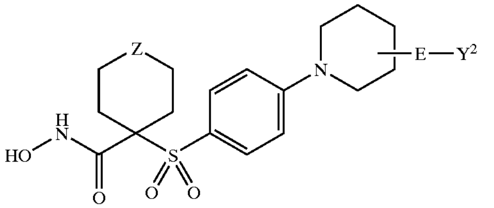

IX-1

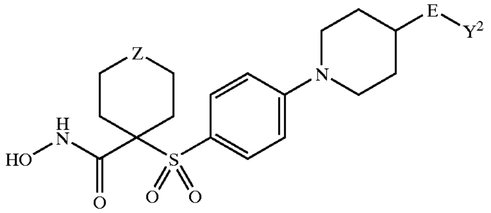

IX-2

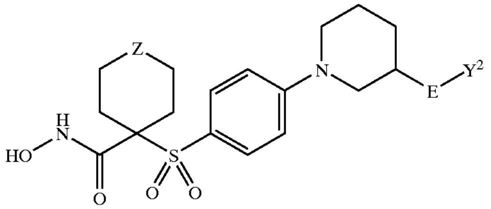

X

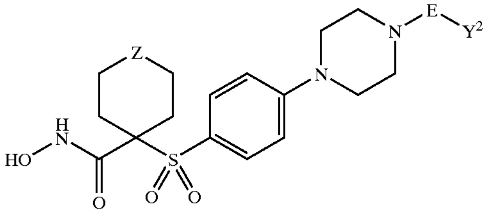

XI

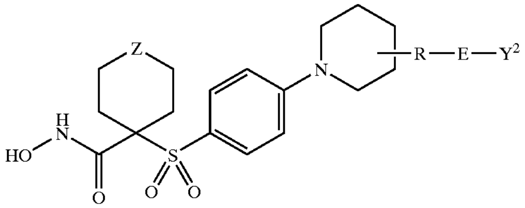

-continued

XI-1

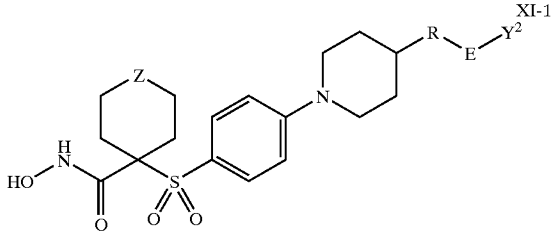

XI-2

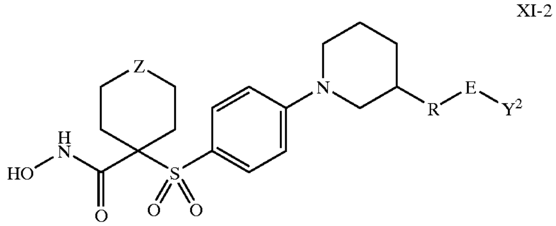

XII

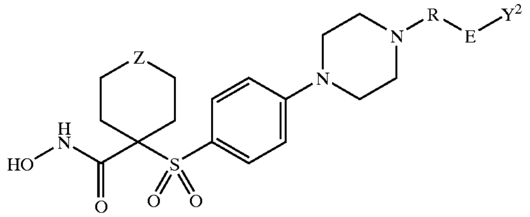

The use of a compound of formulas A and I–VI, VI VIC, VIC-1, VIC-2, VIII, IX, IX-1, IX-2 and X, or a pharmaceutically acceptable salt of one of those compounds is contemplated in a before-described process. In addition, the compounds of those formulas and their pharmaceutically acceptable salts are contemplated compounds of this invention.

Particularly preferred compounds within the group defined by formula B have the structural formulas shown below:

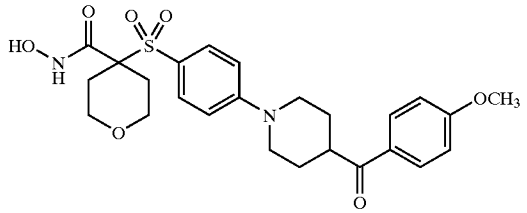

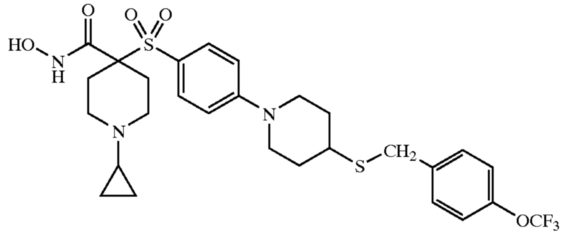

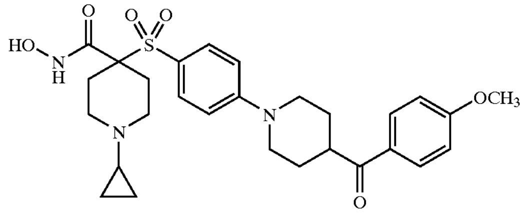

-continued

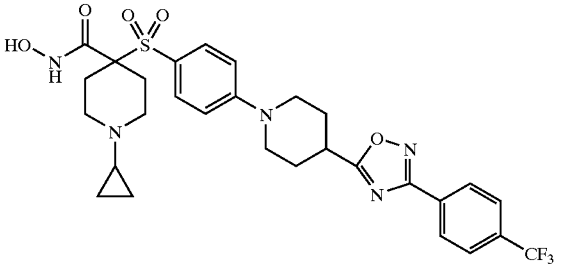

Several particularly preferred compounds whose structures correspond to formulas I through XII are illustrated in the Tables and examples provided hereinafter.

As was noted before, the compounds of formulas I–XII, and their pharmaceutically acceptable salts are themselves contemplated compounds of the invention.

In preferred practice, an $SO_2$-linked $R^3$ radical is an aryl or heteroaryl group that is a 5- or 6-membered single-ring that is itself substituted with one other single-ringed aryl or heteroaryl group or, with an alkyl or alkoxy group having a chain length of 3 to about 16 carbon atoms (and more preferably a length of up to about 14 carbon atoms), a phenoxy group, a thiophenoxy [$C_6H_5$—S—] group, a phenylazo [$C_6H_5$—$N_2$—] group, a N-piperidyl [$C_5H_{10}N$—] group, a N-piperazyl [$NC_4H_9N$—] group or a benzamido [—NHC(O)$C_6H_5$] group. The $SO_2$-linked single-ringed aryl or heteroaryl $R^3$ group here is substituted at its own 4-position when a 6-membered ring and at its own 3- or 4-position when a 5-membered ring.

The $SO_2$-linked aryl or heteroaryl group of a $R^3$ radical is preferably itself substituted at the 4-position when a 6-membered ring or the 3- or 4-position when a 5-membered ring. A particularly preferred substituent is a single-ringed aryl or heteroaryl, phenoxy, thiophenoxy, phenylazo, N-piperidyl, N-piperazyl or benzamido group that is unsubstituted or can itself be substituted.

The 4- and 3-positions of rings discussed here are numbered from the sites of substituent bonding as compared to formalized ring numbering positions used in heteroaryl nomenclature, as is discussed further hereinbelow. Here, single atoms such as halogen moieties (fluoro, chloro, bromo, or iodo) or substituents that contain one to a chain length of about five atoms other than hydrogen such as phenyl, $C_1$–$C_4$ alkyl, trifluoromethyl, trifluoromethoxy, trifluorothiomethyl or carboxyethyl groups are preferred, although longer substituents can be accommodated up to a total length of an icosyl group.

Exemplary particularly preferred substituted $SO_2$-linked $R^3$ radicals include 4-(phenyl)phenyl [biphenyl], 4-(4'-methoxyphenyl)phenyl, 4-(phenoxy)phenyl, 4-(thiophenyl) phenyl [4-(phenylthio)phenyl], 4-(azophenyl)phenyl, 4-[(4'-trifluoromethylthio)phenoxy]phenyl, 4-[(4'-trifluoromethylthio)thiophenyl]phenyl, 4-[(4'-trifluoromethyl)phenoxy]phenyl, 4-[(4'-trifluoromethyl) thiophenyl]phenyl, 4-[(4'-trifluoromethoxy)phenoxy] phenyl, 4-[(4'-trifluoromethoxy)thiophenyl]phenyl, 4-[(4'-phenyl)N-piperidyl]phenyl, 4-[(4'-acetyl)N-piperazyl] phenyl and 4-(benzamido)phenyl.

Inasmuch as a contemplated $SO_2$-linked aryl or heteroaryl radical of an $R^3$ group is itself preferably substituted with a 6-membered ring, two nomenclature systems are used together herein for ease in understanding substituent positions. The first system uses position numbers for the ring directly bonded to the $SO_2$-group, whereas the second system uses ortho, meta or para for the position of one or more substituents of a 6-membered ring bonded to a $SO_2$-linked aryl or heteroaryl radical. Although ortho, meta and para positional nomenclature is normally not used with aliphatic ring systems, it is believed more readily understood for describing the present compounds when used in conjunction with the numerical system for the first ring bonded to the $SO_2$-group. When a $R^3$ radical is other than a 6-membered ring, substituent positions are numbered from the position of linkage to the aromatic or heteroaromatic ring. Formal chemical nomenclature is used in naming particular compounds.

Thus, the 1-position of an above-discussed $SO_2$-linked aryl or heteroaryl group is the position at which the $SO_2$-group is bonded to the ring. The 4- and 3-positions of rings discussed here are numbered from the sites of substituent bonding from the $SO_2$-linkage as compared to formalized ring numbering positions used in heteroaryl nomenclature.

When examined along its longest chain of atoms, an $R^3$ radical including its own substituent has a total length that is greater than a saturated chain of five carbon atoms (a pentyl group), and preferably has a length greater than that of a saturated chain of six carbon atoms (a hexyl group); i.e., a length of about a heptyl chain or longer. An $R^3$ radical also has a length that is less than that of a saturated chain of about 20 carbon atoms [an icosyl group (icosyl was formerly spelled eicosyl)] and more preferably about 18 carbon atoms (a stearyl group). Most preferably, the length of $R^3$ is about that of an 8 to about 12 carbon atom chain, even though many more atoms may be present in ring structures or substituents. This length requirement is discussed further below.

Looked at more generally, and aside from specific moieties from which it is constructed, an $R^3$ radical (group or moiety) has a length that is greater than that of a pentyl group. Such an $R^3$ radical also has a length that is less than that of an icosyl (didecyl) group. That is to say that $R^3$ is a radical having a minimal length longer that a saturated five carbon chain, and preferably greater than a hexyl group, but is shorter than the length of a saturated twenty carbon atom chain, and preferably shorter than an eighteen carbon chain. Most preferably, $R^3$ has a length greater than that of an octyl group and less than that of a lauryl group.

More specifically, an $R^3$ group has a minimal length of a hexyl group only when that substituent is comprised of two rings that can be fused or simply covalently linked together by exocyclic bonding. When $R^3$ does not contain two linked or fused rings, e.g., where a $R^3$ radical includes an alkyl or second, third or fourth ring substituent, $R^3$ has a length that is greater than that of a hexyl group. Exemplary of such two ring $R^3$ groups are a 2-naphthyl group or a 2-quinolinyl group (each with a six carbon chain length) and 8-purinyl (with a five carbon atom chain length). Without wishing to be bound by theory, it is believed that the presence of multiple rings in $R^3$ enhances selectivity of the enzyme activity inhibitor profile.

The radical chain lengths are measured along the longest linear atom chain in the radical, following the skeletal atoms around a ring where necessary. Each atom in the chain, e.g. carbon, oxygen, sulfur or nitrogen, is presumed to be carbon for ease in calculation.

Such lengths can be readily determined by using published bond angles, bond lengths and atomic radii, as needed, to draw and measure a desired, usually staggered, chain, or by building models using commercially available kits whose bond angles, lengths and atomic radii are in accord with accepted, published values. Radical (substituent) lengths can also be determined somewhat less exactly by assuming that all atoms have bond lengths saturated carbon, that unsaturated bonds have the same lengths as saturated bonds and that bond angles for unsaturated bonds are the same as those for saturated bonds, although the above-mentioned modes of measurement are preferred. For example, a phenyl or pyridyl group has a length of a four carbon chain, as does a propoxy group, whereas a biphenyl group has a length of about an eight carbon chain using such a measurement mode.

In addition, a $R^3$ group when rotated about an axis drawn through the $SO_2$-bonded 1-position and the 4-position of a 6-membered ring or the $SO_2$-bonded position and substituent-bonded 3- or 4-position of a 5-membered ring defines a three-dimensional volume whose widest dimension has the width of about one furanyl ring to about two phenyl rings in a direction transverse to that axis to rotation.

Thus, a 2-naphthyl substituent or an 8-purinyl substituent is an appropriately sized $R^3$ group when examined using the above rotational width criterion as well as the before-discussed criterion. On the other hand, a 1-naphthyl group or a 7- or 9-purinyl group is too wide upon rotation and is excluded from being an $R^3$ group.

As a consequence of these length and width requirements, $R^3$ radicals such as 4-(phenyl)phenyl [biphenyl], 4-(4'-methoxyphenyl)-phenyl, 4-(phenoxy)phenyl, 4-(thiophenyl) phenyl [4-(phenylthio)phenyl], 4-(azophenyl)phenyl, 4-[(4'-trifluoromethylthio)phenoxy]phenyl, 4-[(4'-trifluoromethylthio)thiophenyl]phenyl, 4-[(4'-trifluoromethyl )phenoxy]phenyl, 4-[(4'-trifluoromethyl) thiophenyl]phenyl, 4-[(4'-trifluoromethoxy)phenoxy] phenyl, 4-[(4'-trifluoromethoxy)thiophenyl]phenyl, 4-[(4'-phenyl)N-piperidyl]phenyl, 4-[(4'-acetyl)N-piperazyl] phenyl and 4-(benzamido)phenyl are particularly preferred $R^3$ radicals. Those substituents can themselves also be substituted in the second ring from the $SO_2$ group at the meta- or para-position or both with a single atom or a substituent containing a longest chain length that is preferably of up to five atoms, excluding hydrogen.

Without wishing to be bound by theory, the length of a $R^3$ radical substituent bonded to the $SO_2$ group is believed to play a role in the overall activity of a contemplated inhibitor compound against MMP enzymes generally. The length of the $R^3$ radical group also appears to play a role in the selective activity of an inhibitor compound against particular MMP enzymes.

In particularly preferred practice, $R^3$ is a $PhR^{23}$ group, wherein Ph is phenyl. The phenyl ring (Ph) of a $PhR^{23}$ group is substituted at its para-position (4-position) by an $R^{23}$ group that can be another single-ringed aryl or heteroaryl group, a piperidyl group, a piperazinyl group, a phenoxy group, a thiophenoxy [$C_6H_5$—S—] group, a phenylazo [$C_6H_5$—$N_2$—] group or a benzamido [—NHC(O)$C_6H_5$] group.

In one embodiment of a particularly preferred aromatic sulfone hydroxamate inhibitor compound, an $R^{23}$ substituent is phenoxy and is itself substituted at its own para-position with a moiety that is selected from the group consisting of a halogen, a $C_1$–$C_4$ alkoxy group, a $C_1$–$C_4$ alkyl group, a dimethylamino group, a carboxyl $C_1$–$C_3$ alkylene group, a $C_1$–$C_4$ alkoxy carbonyl $C_1$–$C_3$ alkylene group, a trifluoromethylthio group, a trifluoromethoxy group, a trifluoromethyl group and a carboxamido $C_1$–$C_3$ alkylene group, or is substituted at the meta- and para-positions by a methylenedioxy group. It is to be understood that any $R^{23}$ substituent can be substituted with a moiety from the above list. Such substitution at the para-position is preferred.

The present invention also contemplates a compound that corresponds in structure to formula VI, below, that is useful in preparing a compound of formulas I–V, as well as as an active MMP-inhibiting compound and as a pro-drug form of an inhibitor.

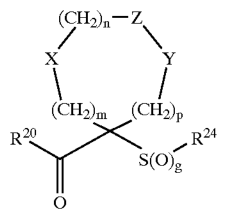

VI wherein g is zero, 1 or 2;

$R^{20}$ is (a) —O—$R^{21}$, where $R^{21}$ is selected from the group consisting of a hydrido, $C_1$–$C_6$-alkyl, aryl, ar-$C_1$–$C_6$-alkyl group and a pharmaceutically acceptable cation, (b) —NH—O—$R^{22}$ wherein $R^{22}$ is a selectively removable protecting group such as a 2-tetrahydropyranyl, benzyl, p-methoxybenzyl (MOZ), carbonyl-$C_1$–$C_6$-alkoxy, trisubstituted silyl group or o-nitrophenyl group, peptide synthesis resin and the like, wherein the trisubstituted silyl group is substituted with $C_1$–$C_6$-alkyl, aryl, or ar-$C_1$–$C_6$-alkyl or a mixture thereof, (c) —NH—O—$R^{14}$, where $R^{14}$ is hydrido, a pharmaceutically acceptable cation or C(W)$R^{25}$ where W is O (oxo) or S (thioxo) and $R^{25}$ is selected from the group consisting of an $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl and amino $C_1$–$C_6$-alkyl group wherein the amino $C_1$–$C_6$-alkyl nitrogen is (i) unsubstituted or (ii) substituted with one or two substituents independently selected from the group consisting of an $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and $C_1$–$C_6$-alkanoyl radical, or (iii) wherein the amino $C_1$–$C_6$-alkyl nitrogen and two substituents attached thereto form a 5- to 8-membered heterocyclo or heteroaryl ring, or (d) —N$R^{26}R^{27}$, where $R^{26}$ and $R^{27}$ are independently selected from the group consisting of a hydrido, $C_1$–$C_6$-alkyl, amino $C_1$–$C_6$-alkyl, hydroxy $C_1$–$C_6$-alkyl, aryl, ar-$C_1$–$C_6$-alkyl group, or $R^{26}$ and $R^{27}$ together with the depicted nitrogen atom form a 5- to 7-membered ring containing zero or one additional heteroatom that is oxygen, nitrogen or sulfur;

m is zero, 1 or 2;

n is zero, 1 or 2;

p is zero, 1 or 2;

the sum of m+n+p=1, 2, 3 or 4;

(a) one of X, Y and Z is selected from the group consisting of C(O), N$R^6$, O, S, S(O), $S(O)_2$ and $NS(O)_2R^7$, and the remaining two of X, Y and Z are $CR^8R^9$, and $CR^{10}R^{11}$, or (b) X and Z or Z and Y together constitute a moiety that is selected from the group consisting of $NR^6C(O)$, $NR^6S(O)$, $NR^6S(O)_2$, $NR^6S$, $NR^6O$, SS, $NR^6NR^6$ and OC(O), with the remaining one of X, Y and Z being $CR^8R^9$, or (c) n is zero and X, Y and Z together constitute a moiety selected from the group consisting of

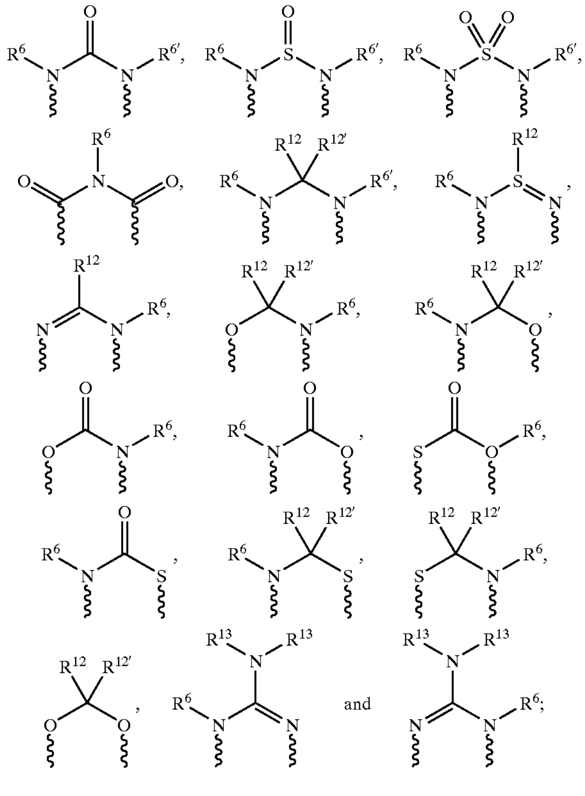

and wherein wavy lines are bonds to the atoms of the depicted ring;

$R^6$ and $R^{6'}$ are independently selected from the group consisting of hydrido, formyl, sulfonic-$C_1$–$C_6$-alkyl, $C_1$–$C_6$-alkoxycarbonyl-$C_1$–$C_6$-alkyl, hydroxycarbonyl-$C_1$–$C_6$-alkyl, $C_1$–$C_6$-alkylcarbonyl-$C_1$–$C_6$-alkyl, $R^8R^9$-aminocarbonyl-$C_1$–$C_6$-alkyl, $C_1$–$C_6$-alkoxycarbonyl-$C_1$–$C_6$-alkylcarbonyl, hydroxycarbonyl-$C_1$–$C_6$-alkylcarbonyl, $C_1$–$C_6$-alkylcarbonyl-$C_1$–$C_6$-alkylcarbonyl, $C_1$–$C_6$-alkoxycarbonylcarbonyl, hydroxycarbonylcarbonyl, $C_1$–$C_6$-alkylcarbonylcarbonyl, $R^8R^9$-aminocarbonylcarbonyl, $C_1$–$C_6$-alkanoyl, aryl-$C_1$–$C_6$-alkyl, aroyl, bis ($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, heteroarycarbonyl, heterocyclocarbonyl, $C_3$–$C_8$-heterocycloalkyl, $C_3$–$C_8$-heterocycloalkylcarbonyl, aryl, $C_5$–$C_6$-heterocyclo, $C_5$–$C_6$-heteroaryl, $C_3$–$C_8$-cycloalkyl-$C_1$–$C_6$-alkyl, aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, arylsulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyl($R^8$N)iminocarbonyl, aryl($R^8$N)iminocarbonyl, $C_5$–$C_6$-heterocyclo($R^8$N) iminocarbonyl, arylthio-$C_1$–$C_6$-alkyl, $C_1$–$C_6$-alkylthio-$C_1$–$C_6$-alkyl, arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—($R^8$)iminomethyl, $NR^8R^9$—$C_1$–$C_5$-alkylcarbonyl, hydroxy-$C_1$–$C_5$-alkyl, $R^8R^9$-aminocarbonyl, $R^8R^9$-aminocarbonyl-$C_1$–$C_6$-alkylcarbonyl, hydroxyaminocarbonyl, $R^8R^9$-aminosulfonyl, $R^8R^9$-aminosulfon-$C_1$–$C_6$-alkyl, $R^8R^9$-amino-$C_1$–$C_6$-alkylsulfonyl and an $R^8R^9$-amino-$C_1$–$C_6$-alkyl group;

$R^7$ is selected from the group consisting of a arylalkyl, aryl, heteroaryl, heterocyclo, $C_1$–$C_6$-alkyl, $C_3$–$C_6$-alkynyl, $C_3$–$C_6$-alkenyl, $C_1$–$C_6$-carboxyalkyl and a $C_1$–$C_6$-hydroxyalkyl group;

$R^8$ and $R^9$ and $R^{10}$ and $R^{11}$ are independently selected from the group consisting of a hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl, or wherein $R^8$ and $R^9$ or $R^{10}$ and $R_{11}$ and the carbon to which they are bonded form a carbonyl group, or wherein $R^8$ and $R^9$ or $R^{10}$ and $R^{11}$, or $R^8$ and $R^{10}$ together with the atoms to which they are bonded form a 5- to 8-membered carbocyclic ring, or a 5- to 8-membered heterocyclic or heteroaryl ring containing one or two heteroatoms that are nitrogen, oxygen, or sulfur, with the proviso that only one of $R^8$ and $R^9$ or $R^{10}$ and $R^{11}$ is hydroxy;

$R^{12}$ and $R^{12'}$ are independently selected from the group consisting of a hydrido, $C_1$–$C_6$-alkyl, aryl, ar-$C_1$–$C_6$-alkyl, heteroaryl, heteroaralkyl, $C_2$–$C_6$-alkynyl, $C_2$–$C_6$-alkenyl, thiol-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aryloxy-$C_1$–$C_6$-alkyl, amino-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, $C_1$–$C_6$-alkylthio-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl;

$R^{13}$ is selected from the group consisting of a hydrido, benzyl, phenyl, $C_1$–$C_6$-alkyl, $C_2$–$C_6$-alkynyl, $C_2$–$C_6$-alkenyl and a $C_1$–$C_6$-hydroxyalkyl group; and $R_{24}$ is $R_3$ as defined in formulas I, III, IV or is the substituent G—A—R—E—$Y^2$ of formula II (formula VIA). Alternatively, $R^{24}$ is $R^{3'}$, an aryl or heteroaryl group that is substituted with a coupling substituent reactive for coupling with another moiety (formula VIB), such as a nucleophilically displaceable leaving group, D.

VIA

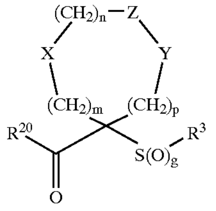

VIB

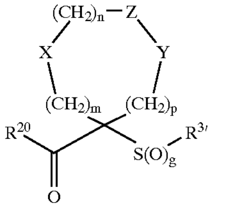

Exemplary nucleophilically displaceable leaving groups, D, include a halo (fluoro, chloro, bromo, or iodo) nitro, azido, phenylsulfoxido, aryloxy, $C_1$–$C_6$-alkoxy, a $C_1$–$C_6$-alkylsulfonate or arylsulfonate group and a trisubstituted ammonium group in which the three substituents are independently aryl, ar-$C_1$–$C_6$-alkyl or $C_1$–$C_6$-alkyl. Additional coupling substituents include, without limitation, a hydroxyl group and an amino group that can be coupled with carbonyl-containing moieties to form esters, urethanes, carbonates, amides and ureas. Similarly, a carboxyl coupling substituent can be used to form an ester, thioester or amide. Thus, a coupling substituent is useful in converting a coupling substituent-containing aryl or heteroaryl group into a substituent such as a G—A—R—E—$Y^2$ substituent discussed hereinabove by the formation of a covalent bond.

A compound of formula VI can be coupled with another moiety at the $R^{3'}$ coupling substituent to form a compound whose newly formed $R^3$ group is that of formulas I, III, IV or —G—A—R—E—$Y_2$. Exemplary of such couplings are the nucleophilic displacement to form ethers and thioethers, as well as the formation of ester, amide, urea, carbonate, urethane and the like linkages.

More particularly, where a $R^{20}$ group is —O— $R^{21}$, with $R^{21}$ being selected from the group consisting of a hydrido, $C_1$–$C_6$-alkyl, aryl, ar-$C_1$–$C_6$-alkyl group and a pharmaceutically acceptable cation, a precursor carboxylic acid or ester compound is defined that can be readily transformed into a hydroxamic acid, as is illustrated in several examples hereinafter.

Where a $R^{20}$ group is —NH—O—$R^{22}$, wherein $R^{22}$ is a selectively removable protecting group such as a 2-tetrahydropyranyl, benzyl, p-methoxybenzyl (MOZ), carbonyl-$C_1$–$C_6$-alkoxy, trisubstituted silyl group, an o-nitrophenyl group, or a peptide synthesis resin and the like, a synthetic intermediate is typically defined. In these compounds, a trisubstituted silyl group is substituted with $C_1$–$C_6$-alkyl, aryl, ar-$C_1$–$C_6$-alkyl or a mixture thereof, such as a trimethylsilyl, dimethylisopropylsilyl, triethylsilyl, triphenylsilyl, t-butyldiphenylsilyl, diphenylmethylsilyl, a tribenzylsilyl group, and the like. Exemplary trisubstituted silyl protecting groups and their uses are discussed at several places in Greene et al., *Protective Groups In Organic Synthesis*, 2nd ed., John Wiley & Sons, Inc., New York (1991).

A contemplated peptide synthesis resin is solid phase support also known as a so-called Merrifield's Peptide Resin that is adapted for synthesis and selective release of hydroxamic acid derivatives as is commercially available from Sigma Chemical Co., St. Louis, Mo. An exemplary peptide synthesis resin so adapted and its use in the synthesis of hydroxamic acid derivatives is discussed in Floyd et al., *Tetrahedron Let.*, 37(44):8048–8048(1996).

A 2-tetrahydropyranyl (THP) protecting group is a particularly preferred selectively removable protecting group. A contemplated THP-protected hydroxamate compound of formula VII can be prepared by reacting the carboxylic acid precursor compound of formula VII [where $R^{20}$ is —O—$R^{21}$ and $R^{21}$ is a hydrido group] in water with O-(tetrahydro-2H-pyran-2-yl)hydroxylamine in the presence of N-methylmorpholine, N-hydroxybenzotriazole hydrate and a water-soluble carbodiimide such as 1-(3-dimethylaminopropyl)-3-ethylcarbodiimide hydrochloride. The THP protecting group is readily removable in an aqueous acid solution such as an aqueous mixture of p-toluenesulfonic acid or HCl and acetonitrile or methanol. An illustrative THP-protected compound corresponds in structure to formula VIIB, below, wherein m, n, p, g, X, Z, Y, and D are as defined previously.

Where $R^{20}$ is —$NR^{26}R^{27}$, and $R^{26}$ and $R^{27}$ are as defined before, an amide compound is defined that can be used as a precursor intermediate and surprisingly as a MMP inhibitor compound. $R^{26}$ and $R^{27}$ are both preferably hydrido.

Where a $R^{20}$ group is —NH—O—$R^{14}$, and $R^{14}$ is hydrido, or a pharmaceutically acceptable cation, an active hydroxamic acid or hydroxamate is defined. Where a $R^{20}$ group is —NH—O—$R^{14}$ and $R^{14}$, is a $C(W)R^{25}$ group as defined before, a pro-drug form of the hydroxamic acid is defined that can form a hydroxamic acid or hydroxamate form of the inhibitor in situ.

A particularly preferred precursor intermediate to an intermediate compound of formula VI is an intermediate compound of formula VII, below

VII

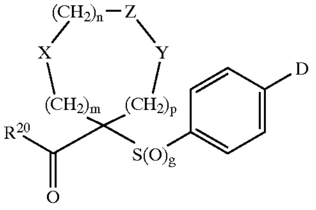

wherein m, n, p, g, X, Z, Y, D and $R^{20}$ are as defined above for formula VI.

VIIB

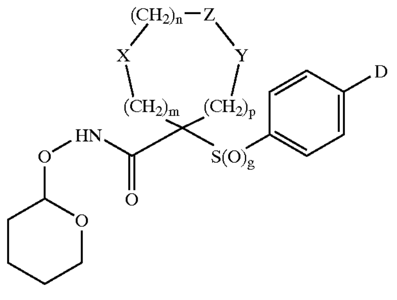

In regard to a compound of each of formulas VI and VII, the subscript letter "g" is used to show the oxidation state of the sulfur atom. Where g is zero, the sulfur is unoxidized, and the compound depicted is typically the sulfide reaction product of a sulfur-containing synthon as is illustrated in the examples hereinafter. Where g is 1, the sulfur is oxidized to a sulfoxide, whereas when g is 2, the sulfur is oxidized to a sulfone as is also illustrated hereinafter. A compound of formulas VI or VII wherein g is zero or 1 as itself typically an intermediate in the formation of a similar compound wherein g is 2 and the intermediate is a preferred sulfone.

A preferred intermediate corresponds in structure to formula VIIA, below, wherein $R^{20}$, X, Y, Z, m, n, p and D are as defined previously.

VIIA

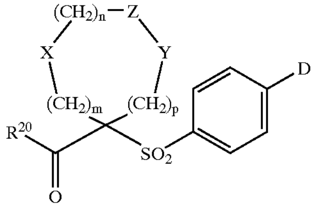

In the written descriptions of molecules and groups, molecular descriptors can be combined to produce words or phrases that describe structural groups or are combined to describe structural groups. Such descriptors are used in this document. Common illustrative examples include such terms as aralkyl (or arylalkyl), heteroaralkyl, heterocycloalkyl, cycloalkylalkyl, aralkoxyalkoxycarbonyl and the like. A specific example of a compound encompassed with the latter descriptor aralkoxyalkoxycarbonyl is $C_6H_5$—$CH_2$—$CH_2$—O—$CH_2$—O—(C═O)— wherein $C_6H_5$— is phenyl. It is also to be noted that a structural group can have more than one descriptive word or phrase in the art, for example, heteroaryloxyalkylcarbonyl can also be termed heteroaryloxyalkanoyl. Such combinations are used herein in the description of the processes, compounds and compositions of this invention and further examples are described below. The following list is not intended to be exhaustive or drawn out but provide illustrative examples of words or phrases (terms) that are used herein.

As utilized herein, the term "alkyl", alone or in combination, means a straight-chain or branched-chain alkyl radical containing 1 to about 12 carbon atoms, preferably 1 to about 10 carbon atoms, and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "alkenyl", alone or in combination, means a straight-chain or branched-chain hydrocarbon radical having one or more double bonds and containing 2 to about 12 carbon atoms preferably 2 to about 10 carbon atoms, and more preferably, 2 to about 6 carbon atoms. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like.

The term "alkynyl", alone or in combination, means a straight-chain hydrocarbon radical having one or more triple bonds and containing 2 to about 12 carbon atoms, preferably 2 to about 10 carbon atoms, and more preferably, 2 to about 6 carbon atoms. Examples of alkynyl radicals include ethynyl, 2-propynyl, 3-propynyl, decynyl, 1-butynyl, 2-butynyl, 3-butynyl, and the like.

The term "carbonyl" or "oxo", alone or in combination, means a —C(═O)— group wherein the remaining two bonds (valences) can be independently substituted. The term carbonyl is also intended to encompass a hydrated carbonyl group —$C(OH)_2$—.

The term "thiol" or "sulfhydryl", alone or in combination, means a —SH group. The term "thio" or "thia", alone or in combination, means a thiaether group; i.e., an ether group wherein the ether oxygen is replaced by a sulfur atom.

The term "amino", alone or in combination, means an amine or —$NH_2$ group whereas the term mono-substituted amino, alone or in combination, means a substituted amine —N(H)(substituent) group wherein one hydrogen atom is replaced with a substituent, and disubstituted amine means a —$N(substituent)_2$ wherein two hydrogen atoms of the amino group are replaced with independently selected substituent groups.

Amines, amino groups and amides are compounds that can be designated as primary (I°), secondary (II°) or tertiary (III°) or unsubstituted, mono-substituted or N,N-disubstituted depending on the degree of substitution of the amino nitrogen. Quaternary amine (ammonium) (IV°) means a nitrogen with four substituents [—$N^+(substituent)_4$] that is positively charged and accompanied by a counter ion, whereas N-oxide means one substituent is oxygen and the group is represented as [—$N^+(substituent)_3$—$O^-$; i.e., the charges are internally compensated.

The term "cyano", alone or in combination, means a —C-triple bond-N (—C≡N) group. The term "azido", alone or in combination, means a —N-triple bond-N (—N≡N) group. The term "hydroxyl", alone or in combination, means a —OH group. The term "nitro", alone or in combination, means a —$NO_2$ group. The term "azo", alone or in combination, means a —N═N-group wherein the bonds at the terminal positions can be independently substituted.

The term "hydrazino", alone or in combination, means a —NH—NH— group wherein the depicted remaining two bonds (valences) can be independently substituted. The hydrogen atoms of the hydrazino group can be replaced, independently, with substituents and the nitrogen atoms can form acid addition salts or be quaternized.

The term "sulfonyl", alone or in combination, means a —$SO_2$— group wherein the depicted remaining two bonds (valences) can be independently substituted. The term "sulfoxido", alone or in combination, means a —SO— group wherein the remaining two bonds (valences) can be independently substituted.

The term "sulfone", alone or in combination, means a —$SO_2$— group wherein the depicted remaining two bonds (valences) can be independently substituted. The term "sulfenamide", alone or in combination, means a —SON═ group wherein the remaining three depicted bonds (valences) can be independently substituted. The term "sulfide", alone or in combination, means a —S— group wherein the remaining two bonds (valences) can be independently substituted.

The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like.

The term "cycloalkyl", alone or in combination, means a cyclic alkyl radical that contains 3 to about 8 carbon atoms. The term "cycloalkylalkyl" means an alkyl radical as defined above that is substituted by a cycloalkyl radical containing 3 to about 8, preferably 3 to about 6, carbon atoms. Examples of such cycloalkyl radicals include cyclopropyl, cyclobutyl, cyclopentyl, cyclohexyl and the like.

A heterocyclic (heterocyclo) or heterocyclo portion of a heterocyclocarbonyl, heterocyclooxycarbonyl, heterocycloalkoxycarbonyl, or heterocycloalkyl group or the like is a saturated or partially unsaturated monocyclic, bicyclic or tricyclic heterocycle that contains one or more hetero atoms selected from nitrogen, oxygen and sulphur. Heterocyclo compounds include benzofused heterocyclic compounds such as benzo-1,4-dioxane. Such a moiety can be optionally substituted on one or more ring carbon atoms by halogen, hydroxy, hydroxycarbonyl, alkyl, alkoxy, oxo, and the like, and/or on a secondary nitrogen atom (i.e., —NH—) of the ring by alkyl, aralkoxycarbonyl, alkanoyl, aryl or arylalkyl or on a tertiary nitrogen atom (i.e., =N—) by oxido and that is attached via a carbon atom. The tertiary nitrogen atom with three substituents can also attached to form a N-oxide [=N(O)—] group.

The term "aryl", alone or in combination, means a 5- or 6-membered carbocyclic aromatic ring-containing moiety or a fused ring system containing two or three rings that have all carbon atoms in the ring; i.e., a carbocyclic aryl radical. Exemplary carbocyclic aryl radicals include phenyl, indenyl and naphthyl radicals.

The term "heteroaryl", alone or in combination means a 5- or 6-membered aromatic ring-containing moiety or a fused ring system (radical) containing two or three rings that have carbon atoms and also one or more heteroatoms in the ring(s) such as sulfur, oxygen and nitrogen. Examples of such heterocyclic or heteroaryl groups are pyrrolidinyl, piperidyl, piperazinyl, morpholinyl, thiamorpholinyl, pyrrolyl, imidazolyl (e.g., imidazol-4-yl, 1-benzyloxycarbonylimidazol-4-yl, and the like), pyrazolyl, pyridyl, pyrazinyl, pyrimidinyl, furyl, tetrahydrofuryl, thienyl, triazolyl, tetrazolyl, oxazolyl, oxadiazoyl, thiazolyl, thiadiazoyl, indolyl (e.g., 2-indolyl, and the like), quinolinyl, (e.g., 2-quinolinyl, 3-quinolinyl, 1-oxido-2-quinolinyl, and the like), isoquinolinyl (e.g., 1-isoquinolinyl, 3-isoquinolinyl, and the like), tetrahydroquinolinyl (e.g., 1,2,3,4-tetrahydro-2-quinolyl, and the like), 1,2,3,4-tetrahydroisoquinolinyl (e.g., 1,2,3,4-tetrahydro-1-oxo-isoquinolinyl, and the like), quinoxalinyl, β-carbolinyl, 2-benzofurancarbonyl, benzothiophenyl, 1-, 2-, 4- or 5-benzimidazolyl, and the like radicals.

When an aryl or heteroaryl radical is a substituting moiety (group, substituent, or radical), it can itself substituted, the last-named substituent is independently selected from the group consisting of a cyano, perfluoroalkyl, trifluoromethoxy, trifluoromethylthio, haloalkyl, trifluoromethylalkyl, aralkoxycarbonyl, aryloxycarbonyl, hydroxy, halo, alkyl, alkoxy, nitro, thiol, hydroxycarbonyl, aryloxy, arylthio, aralkyl, aryl, arylcarbonylamino, heteroaryloxy, heteroarylthio, heteroaralkyl, cycloalkyl, heterocyclooxy, heterocyclothio, heterocycloamino, cycloalkyloxy, cycloalkylthio, heteroaralkoxy, heteroaralkylthio, aralkoxy, aralkylthio, aralkylamino, heterocyclo, heteroaryl, arylazo, hydroxycarbonylalkoxy, alkoxycarbonylalkoxy, alkanoyl, arylcarbonyl, aralkanoyl, alkanoyloxy, aralkanoyloxy, hydroxyalkyl, hydroxyalkoxy, alkylthio, alkoxyalkylthio, alkoxycarbonyl, aryloxyalkoxyaryl, arylthioalkylthioaryl, aryloxyalkylthioaryl, arylthioalkoxyaryl, hydroxycarbonylalkoxy, hydroxycarbonylalkylthio, alkoxycarbonylalkoxy, alkoxycarbonylalkylthio, amino, wherein the amino nitrogen is (i) unsubstituted, or (ii) substituted with one or two substituents that are independently selected from the group consisting of an alkyl, aryl, heteroaryl, aralkyl, cycloalkyl, aralkoxycarbonyl, alkoxycarbonyl, arylcarbonyl, aralkanoyl, heteroarylcarbonyl, heteroaralkanoyl and an alkanoyl group, or (iii) wherein the amino nitrogen and two substituents attached thereto form a 5- to 8-membered heterocyclo or heteroaryl ring containing zero to two additional heteroatoms that are nitrogen, oxygen or sulfur and which ring itself is (a) unsubstituted or (b) substituted with one or two groups independently selected from the group consisting of an aryl, alkyl, heteroaryl, aralkyl, heteroaralkyl, hydroxy, alkoxy, alkanoyl, cycloalkyl, heterocycloalkyl, alkoxycarbonyl, hydroxyalkyl, trifluoromethyl, benzofused heterocycloalkyl, hydroxyalkoxyalkyl, aralkoxycarbonyl, hydroxycarbonyl, aryloxycarbonyl, benzofused heterocycloalkoxy, benzofused cycloalkylcarbonyl, heterocycloalkylcarbonyl, and a cycloalkylcarbonyl group, carbonylamino wherein the carbonylamino nitrogen is (i) unsubstituted, or (ii) is the reacted amine of an amino acid, or (iii) substituted with one or two radicals selected from the group consisting of an alkyl, hydroxyalkyl, hydroxyheteroaralkyl, cycloalkyl, aralkyl, trifluoromethylalkyl, heterocycloalkyl, benzofused heterocycloalkyl, benzofused heterocycloalkyl, benzofused cycloalkyl, and an N,N-dialkylsubstituted alkylamino-alkyl group, or (iv) the carboxamido nitrogen and two substituents bonded thereto together form a 5- to 8-membered heterocyclo, heteroaryl or benzofused heterocycloalkyl ring that is itself unsubstituted or substituted with one or two radicals independently selected from the group consisting of an alkyl, alkoxycarbonyl, nitro, heterocycloalkyl, hydroxy, hydroxycarbonyl, aryl, aralkyl, heteroaralkyl and an amino group, wherein the amino nitrogen is (i) unsubstituted, or (ii) substituted with one or two substituents that are independently selected from the group consisting of alkyl, aryl, and heteroaryl, or (iii) wherein the amino nitrogen and two substituents attached thereto form a 5- to 8-membered heterocyclo or heteroaryl ring, and an aminoalkyl group wherein the aminoalkyl nitrogen is (i) unsubstituted, or (ii) substituted with one or two substituents independently selected from the group consisting of an alkyl, aryl, aralkyl, cycloalkyl, aralkoxycarbonyl, alkoxycarbonyl, and an alkanoyl group, or (iii) wherein the aminoalkyl nitrogen and two substituents attached thereto form a 5- to 8-membered heterocyclo or heteroaryl ring.

The term "aralkyl", alone or in combination, means an alkyl radical as defined above in which one hydrogen atom is replaced by an aryl radical as defined above, such as benzyl, 2-phenylethyl and the like.

The term "aralkoxycarbonyl", alone or in combination, means a radical of the formula aralkyl-O—C(O)— in which the term "aralkyl" has the significance given above. An example of an aralkoxycarbonyl radical is benzyloxycarbonyl.

The term "aryloxy" means a radical of the formula aryl-O— in which the term aryl has the significance given above. The phenoxy radical is an exemplary aryloxy radical.

The terms "heteroaralkyl" and "heteroaryloxy" mean radicals structurally similar to aralkyl and aryloxy that are formed from heteroaryl radicals. Exemplary radicals include 4-picolinyl and 2-pyrimidinoxy, respectively.

The terms "alkanoyl" or "alkylcarbonyl", alone or in combination, means an acyl radical derived from an alkanecarboxylic acid, examples of which include formyl, acetyl, propionyl, butyryl, valeryl, 4-methylvaleryl, and the like.

The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid that is optionally substituted by, for example, alkanoylamino, such as 1,2,3,4-tetrahydro-2-naphthoyl, 2-acetamido-1,2,3,4-tetrahydro-2-naphthoyl.

The terms "aralkanoyl" or "aralkylcarbonyl" mean an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl and the like.

The terms "aroyl" or "arylcarbonyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl) benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "cycloalkylalkoxycarbonyl" means an acyl group of the formula cycloalkylalkyl-O—CO— wherein cycloalkylalkyl has the significance given above. The term "aryloxyalkanoyl" means an acyl radical of the formula aryl-O-alkanoyl wherein aryl and alkanoyl have the significance given above. The term "heterocyclooxycarbonyl" means an acyl group having the formula heterocyclo-O—CO— wherein heterocyclo is as defined above.

The term "heterocycloalkanoyl" is an acyl radical of the formula heterocyclo-substituted alkane carboxylic acid wherein heterocyclo has the significance given above. The term "heterocycloalkoxycarbonyl" means an acyl radical of the formula heterocyclo-substituted alkane-O—CO— wherein heterocyclo has the significance given above. The term "heteroaryloxycarbonyl" means an acyl radical represented by the formula heteroaryl-O—CO— wherein heteroaryl has the significance given above.

The term "aminocarbonyl" (carboxamide) alone or in combination, means an amino-substituted carbonyl (carbamoyl) group derived from an amine reacted with a carboxylic acid wherein the amino (amido nitrogen) group is unsubstituted (—$NH_2$) or a substituted primary or secondary amino group containing one or two substituents selected from the group consisting of hydrogen, alkyl, aryl, aralkyl, cycloalkyl, cycloalkylalkyl radicals and the like, as recited. A hydroxamate is a N-hydroxycarboxamide.

The term "aminoalkanoyl" means an acyl group derived from an amino-substituted alkanecarboxylic acid wherein the amino group can be a primary or secondary amino group containing substituents independently selected from hydrogen, alkyl, aryl, aralkyl, cycloalkyl, cycloalkylalkyl radicals and the like.

The term "halogen" means fluoride, chloride, bromide or iodide. The term "haloalkyl" means an alkyl radical having the significance as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl and the like.

The term "perfluoroalkyl" means an alkyl group wherein each hydrogen has been replaced by a fluorine atom. Examples of such perfluoroalkyl groups, in addition to trifluoromethyl above, are perfluorobutyl, perfluoroisopropyl, perfluorododecyl and perfluorodecyl.

The term "perfluoroalkoxy" alone or in combination, means a perfluoroalkyl ether radical wherein the term perfluoroalkyl is as defined above. Examples of such perfluoroalkoxy groups, in addition to trifluoromethoxy ($F_3C$—O—), are perfluorobutoxy, perfluoroisopropoxy, perfluorododecoxy and perfluorodecoxy.

The term "perfluoroalkylthio" alone or in combination, means a perfluoroalkyl thioether radical wherein the term perfluoroalkyl is as defined above. Examples of such perfluoroalkylthio groups, in addition to trifluoromethylthio ($F_3C$—S—), are perfluorobutylthio, perfluoroisopropylthio, perfluorododecylthio and perfluorodecylthio.

The term "aromatic ring" in combinations such as substituted-aromatic ring sulfone or substituted-aromatic ring sulfoxide means aryl or heteroaryl as defined before.

The term "pharmaceutically acceptable" is used adjectivally herein to mean that the modified noun is appropriate for use in a pharmaceutical product. Pharmaceutically acceptable cations include metallic ions and organic ions. More preferred metallic ions include, but are not limited to appropriate alkali metal (Group Ia) salts, alkaline earth metal (Group IIa) salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, benzoic acid, and the like.

"M" utilized in the reaction schemes that follow represents a leaving group such as halogen, phosphate ester or sulfate ester.

Preparation of Useful Compounds

Schemes A through C and Schemes 1 through 19 hereinbelow illustrate chemical processes and transformations that can be useful for the preparation of compounds useful in this invention; i.e., compounds of formulas I, II, III, IV and V and similar cyclic inhibitors. In addition, the preparation of compounds of formula VI and formula VII is illustrated. Compounds of formula VI and formula VII can be used as intermediates in the preparation of the compounds of formulas I, II, III, IV and V or pro-drugs or MMP inhibitors.

In Schemes A through C, the symbol J independently represents $R^{20}$ or other synthetically useful groups such as amides, acid chlorides, mixed anhydrides and the like. The n is 0, 1 or 2 and is preferred to be 1 or 2 in Scheme C. The n of these schemes corresponds to g in formulas VI and VII., and is zero, 1 or 2. The symbol m is 1 or 2. The symbol r is independently 1, 2 or 3. The symbol P represents a protecting group that can also be a member of the group $R^6$. In Scheme A, for simplicity and clarity of illustration positional isomers are illustrated with a bond through the ring in standard fashion. Later Schemes typically only show one positional isomer but positional isomers are represented by these structures and reactions in a manner consistent with Formula I, II, III, IV, V, VI, VII above. Similarly, the symbol B represents O, S, SO, $SO_2$ and $NR^6$. The symbols C and C' independently are electrophilic groups or groups capable of participating in a condensation reaction. Here to it should be noted that the six-membered ring is shown for illustrative purposes but the procedures and/or reagents are applicable to and represent combinations the permit the preparation of 5- to 8-membered rings.

The structures in Schemes 1 through 19 are also shown with compounds that represent theother compounds of this invention. The aromatic ring in Scheme C is aryl and heteroaryl. The moieties of —A—R—E—$Y^2$ are as defined before. Reactions illustrated involving a spiroheterocyclic nitrogen atom may not be applicable to those compounds with sulfur or oxygen.

Scheme A

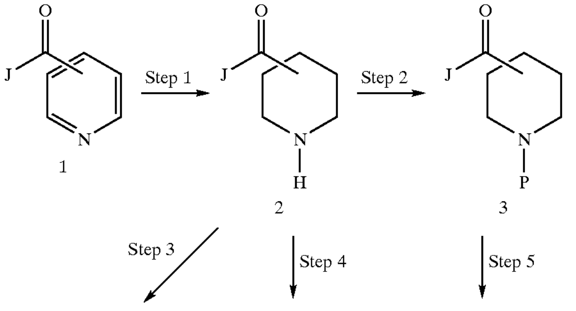

-continued

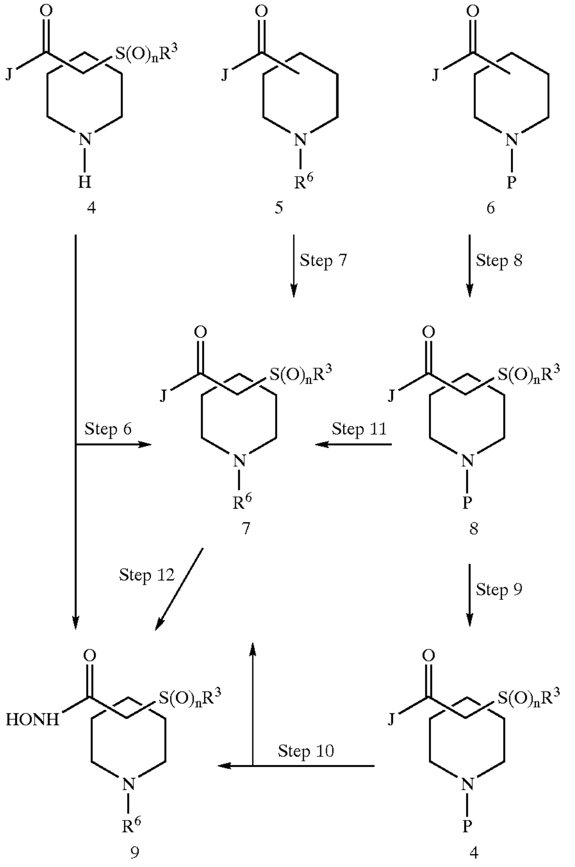

Scheme A shows in step 1 the reduction of a heteraryl compound to a carboxyl derivative. Generally, the first product is a hydrogen-containing amine heterocycle when the starting material is aromatic or an $R^6$-containing heterocycle when a partially unsaturated heterocycle is the starting material.

Compound 2 can be treated in several ways depending on the needs of the chemist. In Step 2, the nitrogen can be protected by preparing, for example, a carbobenzoxy (Z) or tert-butoxycarbonyl derivative. Such acylations can be carried out by methods well known in the art, especially the art of amino acid and peptide synthesis. The process of acylation with activated carboxyl group- or activated sulfonyl group-containing reagents to prepare contemplated compounds is carried out in the same manner. Examples of such acylating groups are carbonyl azides, halides, anhydrides, mixed anhydrides, carbodiimide derivatives or other less traditional activated ester groups such as the hydroxybenzotriazole derivative. These acylations can be run in the presence of base including mild bases such as triethylamine or N-ethylmorpholine if desired. The preparation of some activated ester reagents and their use to prepare other compounds useful in this invention is discussed below. It should be recalled that the groups constituting P and serving as a selectively removable protecting group can also be included as part of the group $R^6$.

Step 4 of Scheme A shows the alkylation or acylation of Compound 2 to produce compound 5. The process of acylation and alkylation are as discussed herein. In Step 5, the group J can be changed if desired. An example of such a change is exchange of an ester for a THP-protected hydroxamate conversion of a THP-protected hydroxamate inot a hydroxamate or conversion of an acid into a protected hydroxamate or the like.

Steps 3, 7 and 8 show the preparation of sulfur-containing derivatives of the contemplated compounds or intermediates to those compounds. The starting material for the above steps (e.g., compounds 2, 5 and 6) can be treated with a base to deprotonate the carbon alpha to the carbonyl function. This anion can be reacted with a sulfur electrophile to produce a sulfone, sulfoxide or sulfide. Such electrophiles can be of the form of, for example, $R^{24}S—SR^{24}$, $R^{24}SO_2C_1$, $R^{24}SC_1$, $R^{24}SOC_1$, $R^{24}S(O)—SR^{24}$ and the like where $R^{24}$ is as defined before or is an aryl or heteroaryl sulfur-containing material containing a coupling substituent, $R^{3'}$, that can be used to prepare one of the $R^{24}$-containing groups. Preparation of the anion requires a base and a strong base may be required such as one of the metal amides, hydrides or alkyls discussed herein. The solvents are nonprotic, and dipolar aprotic solvents are preferred along with an inert atmosphere. Subsequent schemes usually utilize $R^3$ for the $R^{24}$ group for ease of illustration.

It should be noted that these processes produce sulfides (thio ethers), sulfoxides or sulfones depending on starting material. In addition, the sulfides can be oxidized to sulfoxides or sulfones, and the sulfoxides can be oxidized to their corresponding sulfone derivatives. The choice of position in the synthetic sequence to change the oxidation state of sulfur as well as the decision to change oxidation state is under the control of the chemist skilled in the art. Methods of oxidizing sulfur are discussed hereinbelow.

Scheme A, Steps 6, 9, 10 and 12 independently illustrate the interconversion of groups within J. Examples of such interconversions include exchange of an ester for hydroxamic acid or hydroxamic acid derivative, conversion of a carboxylic acid into an activated carbonyl derivative or into a hydroxamic acid or hydroxamic acid derivative (pro-drug or protected derivative), or removal of a protecting group from a hydroxamate derivative. The preparation of activated carbonyl compounds their reaction with nucleophiles such as hydroxamic acid, protected hydroxamates or hydroxamic acid pro-drugs is discussed below as is the conversion of protected hydroxamic acid derivatives into hydroxamic acids. The preparation of, for example, hydroxybenzotriazole/carbodiimide, derived products is discussed herein. The preparation or hydrolysis of esters, amides, amide derivatives, acid chlorides, acid anhydrides, mixed anhydrides and the like are synthetic methods very well known in the art, and are not discussed in detail herein. Step 6 illustrates the conversion of compound 4 into compound 9, without first being converted into compound 7.

Scheme B

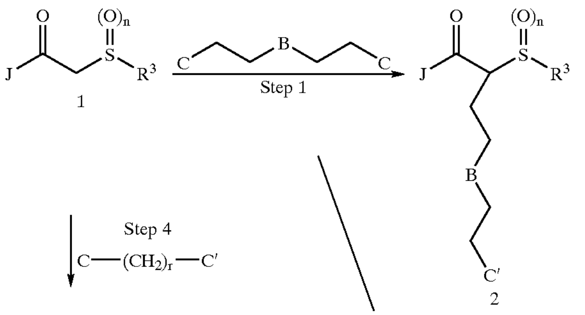

-continued

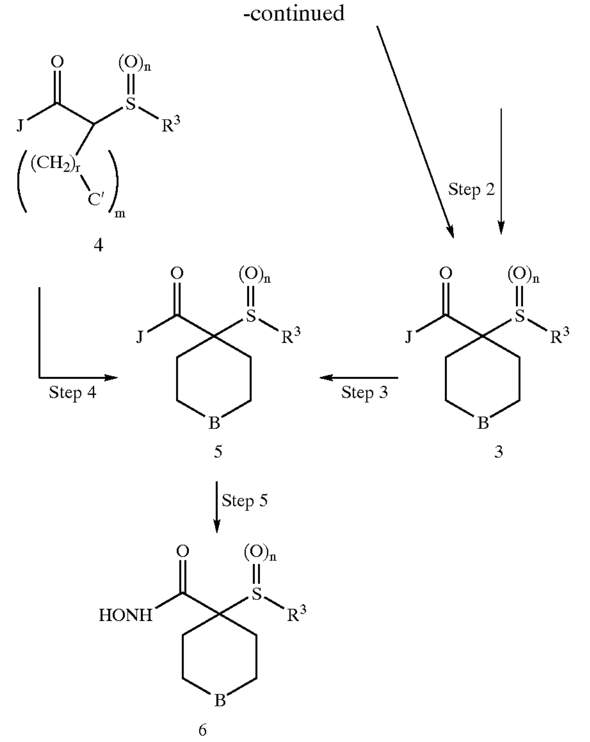

Scheme B illustrates an alternate method of preparing contemplated compounds. The reagent shown above the arrow in Step 1 is a reagent with two active groups in addition to the heteroatoms (B) noted before. Here again, the particular reagent illustrated was selected to permit a clear illustration of the reaction, but it is also intended to represent reagents that permit the preparation of the heteroatom position, and 5-, 7- and 8-membered ring size compounds. These reagents are readily selected by those skilled in the art.

C and C' in this Step 1 reagent are independently an electophile or a group convertible into an electrophile. Such groups include halides, sulfonic acid esters, epoxides, thioepoxides, hydroxyl groups, and the like. This reagent is reacted with a nucleophilic anion of a sulfur containing carbonyl compound such as compound 1. The anion is formed by deprotonation of compound 1 and examples of bases suitable for such a deprotonation are discussed below. Treatment with the above electrophilic reagent is carried out under alkylating conditions well known in the art and discussed herein. The product of this reaction can be either Compound 2 or Compound 3; i.e., the reaction can be carried out as a pot or two step process as required.

Step 3 illustrates the interconversion of J groups if desired as discussed above for Scheme A. Step 4 uses reagent where C, for example, represents a nucleophile as discussed above and C' represents an electrophile or a nucleophile such as hydroxyl, thiol or $R^6$-amino. It is noted that C' can be, independently, a nucleophile or an electrophile when m is 2; i.e., the C' groups are not required to be the same when m is 2. When m is 2, treatment with a second mole of base provides the skilled chemist an alternative preparation of Compound 5. When C' is hydroxyl, thiol, or $R^6$-amino and m is 2, the person skilled in the art can condense Compound 4 with, for example, an aldehyde or ketone, under reductive conditions or with subsequent reduction to form a contemplated compound. As above, the compound where m is 2 can be made in one step (one pot process) or two steps, thus permitting the chemist the choice of having the reagent(s) be the same (one pot) or different (two step).

Scheme B also illustrates the interconversions of the groups within J, the oxidation state of the sulfur and groups on nitrogen; i.e., $R^6$ groups, to provide the contemplated compounds. These methods and processes are discussed above for the reactions of Scheme A.

Scheme C

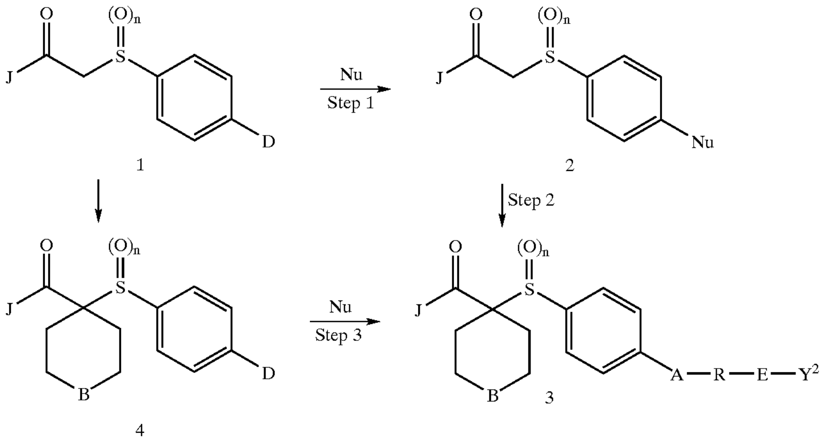

Scheme C illustrates the nucleophilic displacement of a group D as defined herein. This reaction is carried out in a similar manner to the displacement reactions discussed herein. The choice of oxidation state of the sulfur is made by the person skilled in the art, but sulfoxide or sulfone groups are preferred, and the sulfone is most preferred. The displacement can be carried out either before or after the methylene next to the carbonyl group is reacted to form a spiro heterocyclic group.

Steps 1, 2 and 3 also illustrate that although the nucleophilic displacement can be carried out with one nucleophile (Nu), the product of this reaction can be modified by methods well known in the art and as shown herein to provide the group —A—R—E—$Y^2$ as defined hereinbefore.

A non-limiting illustration of such a process is provided when D is fluoride. The fluoride leaving group can be directly displaced with the anion of 4-trifluoromethylphenol, 4-trifluoromethoxyphenol, 4-trifluoromethylthiophenol and the like to provide a contemplated compound. This is a one pot process from Compound 4. Other compounds included in —A—R—E—$Y^2$ can be prepared by displacing the fluoride leaving group with ammonia to provide an amine, which can then be acylated by methods discussed wherein with, for example, 4-trifluoromethylbenzoyl chloride, to form another contemplated product compound.

The $R^6$ function can be changed and/or further modified in compounds or at steps in the Schemes as desired or required by the person skilled in the art to prepare the contemplated compounds. Interconversion of dual purpose functional groups such as short or long term protecting groups into other $R^6$ groups has been mentioned. Many other routine and/or useful conversions, including the preparation of synthetic intermediates, are very well known in the art. A few non-limiting examples of such conversions or reactions include: reductions; nucleophilic displacement/substitution reactions; exchange or preparation of carboxylic or sulfonic acids, amides, esters, acid halides, mixed anhydrides and the like; electrophilic displacement/substitution reactions; oxidations; ring/chain conversions, ring opening reactions, condensation reactions including those involving sulfonyl or carbonyl groups and/or carbon-hydrogen bonds influenced by either or both of those groups. The selection of preparative methods or conversion methods of the contemplated compounds and the order of the reaction(s) is made by the skilled person. It is expected that should a particular sequence or method prove to be undesirable that an alternative will be selected and used. Included is the choice of preparing/adding the groups in a single step using a convergent inhibitor strategy or preparing the final $R^6$ group following a stepwise strategy.

Thus, in general, the choices of starting material and reaction conditions can vary as is well known to those skilled in the art. Usually, no single set of conditions is limiting because variations can be applied as required. Conditions are also selected as desired to suit a specific purpose such as small scale preparations or large scale preparations. In either case, the use of less safe or less environmentally sound materials or reagents is usually be minimized. Examples of such materials are diazomethane, diethyl ether, heavy metal salts, dimethyl sulfide, chloroform, benzene and the like.

These reactions can be carried out under a dry inert atmosphere such a nitrogen or argon if desired. Selected reactions known to those skilled in the art, can be carried out under a dry atmosphere such as dry air whereas other synthetic steps, for example, aqueous acid or base ester or amide hydrolysis, can be carried out under laboratory air. In addition, some processes of these syntheses can be carried out in a pressure apparatus at pressures above, equal to or below atmospheric pressure. The use of such an apparatus aids in the control of gaseous reagents such as hydrogen, ammonia, trimethylamine, methylamine, oxygen and the like, and can also help prevent the leakage of air or humidity into a reaction in progress. This discussion is not intended to be exhaustive as it is readily noted that additional or alternative methods, conditions, reactions or systems can be identified and used by a chemist of ordinary skill.

The illustrated reactions are usually carried out at a temperature of between −25° C. to solvent reflux under an inert atmosphere such as nitrogen or argon. The solvent or solvent mixture can vary widely depending upon reagents and other conditions and can include polar or dipolar aprotic solvents as listed or mixtures of these solvents. Reactions can be carried out at lower temperatures such as dry ice/acetone or liquid nitrogen temperature if desired to carry out such reactions as metalations or anion formations using strong bases.

In some cases, amines such as triethylamine, pyridine or other non-reactive bases can serve as reagents and/or solvents and/or co-solvents. In some instances, in these reactions and other reactions in these Schemes, protecting groups can be used to maintain or retain groups in other parts of a molecule(s) at locations that is(are) not desired reactive centers. Examples of such groups that the skilled person can maintain or retain include, amines, other hydroxyls, thiols, acids and the like. Such protecting groups can include acyl groups, arylalkyl groups, carbamoyl groups, ethers, alkoxyalkyl ethers, cycloalkyloxy ethers, arylalkyl groups, silyl groups including trisubstituted silyl groups, ester groups and the like. Examples of such protecting groups include acetyl, trifluoroacetyl, tetrahydropyran (THP), benzyl, tert-butoxy carbonyl (BOC or TBOC), benzyloxycarbonyl (Z or CBZ), tert-butyldimethylsilyl (TBDMS) or methoxyethoxymethylene (MEM) groups. The preparation of such protected compounds as well as their removal is well known in the art. The protecting groups can also be used as substituents in the contemplated compounds whose utility is as a drug rather than as a synthetic intermediate.

Many reactions or processes involve bases that can act as reactants, reagents, deprotonating agents, acid scavengers, salt forming reagents, solvents, co-solvents and the like. Bases that can be used include, for example, metal hydroxides such as sodium, potassium, lithium, cesium or magnesium hydroxide, oxides such as those of sodium, potassium, lithium, calcium or magnesium, metal carbonates such as those of sodium, potassium, lithium, cesium, calcium or magnesium, metal bicarbonates such as sodium bicarbonate or potassium bicarbonate, primary (I°), secondary (II°) or tertiary (III°) organic amines such as alkyl amines, arylalkyl amines, alkylarylalkyl amines, heterocyclic amines or heteroaryl amines, ammonium hydroxides or quaternary ammonium hydroxides. As non-limiting examples, such amines can include triethylamine, trimethylamine, diisopropylamine, methyldiisopropylamine, diazabicyclononane, tribenzylamine, dimethylbenzylamine, morpholine, N-methylmorpholine, N,N'-dimethylpiperazine, N-ethylpiperidine, 1,1,5,5-tetramethylpiperidine, dimethylaminopyridine, pyridine, quinoline, tetramethylethylenediamine, and the like. Non-limiting examples of ammonium hydroxides, usually made from amines and water, can include ammonium hydroxide, triethylammonium hydroxide, trimethylammonium hydroxide, methyldiiospropylammonium hydroxide, tribenzylammonium hydroxide, dimethylbenzylammonium hydroxide, morpholinium hydroxide, N-methylmorpholinium hydroxide, N,N'-dimethylpiperazinium hydroxide, N-ethylpiperidinium hydroxide, and the like. As non-limiting examples, quaternary ammonium hydroxides can include tetraethylammonium hydroxide, tetramethylammonium hydroxide, dimethyldiiospropyl-ammonium hydroxide, benzylmethyldiisopropylammonium hydroxide, methyldiazabicyclononylammonium hydroxide, methyltribenzylammonium hydroxide, N,N-dimethylmorpholiniumhydroxide, N,N,N',N'-tetramethylpiperazinium hydroxide, and N-ethyl-N'-hexylpiperidinium hydroxide and the like.

Metal hydrides, amides or alcoholates such as calcium hydride, sodium hydride, potassium hydride, lithium hydride, aluminum hydride, diisobutylaluminum hydride (DIBAL) sodium methoxide, potassium tert-butoxide, calcium ethoxide, magnesium ethoxide, sodium amide, potassium diisopropyl amide and the like can also be suitable reagents. Organometallic deprotonating agents such as alkyl or aryl lithium reagents such as methyl lithium, phenyl lithium, tert-butyl lithium, lithium acetylide or butyl lithium, Grignard reagents such as methylmagnesium bromide or methymagnesium chloride, organocadmium reagents such as dimethylcadmium and the like can also serve as bases for causing salt formation or catalyzing the reaction. Quaternary ammonium hydroxides or mixed salts are also useful for aiding phase transfer couplings or serving as phase transfer reagents. Pharmaceutically acceptable bases can be reacted with acids to form contemplated pharmaceutically acceptable salts. It should also be noted that optically active bases can be used to make optically active salts which can be used for optical resolutions.

Generally, reaction media can comprise a single solvent, mixed solvents of the same or different classes or serve as a reagent in a single or mixed solvent system. The solvents can be protic, non-protic or dipolar aprotic. Non-limiting examples of protic solvents include water, methanol (MeOH), denatured or pure 95% or absolute ethanol, isopropanol and the like. Typical non-protic solvents include acetone, tetrahydrofuran (THF), dioxane, diethyl ether, tert-butylmethyl ether (TBME), aromatics such as xylene, toluene, or benzene, ethyl acetate, methyl acetate, butyl acetate, trichloroethane, methylene chloride, ethylenedichloride (EDC), hexane, heptane, isooctane, cyclohexane and the like. Dipolar aprotic solvents include compounds such as dimethylformamide (DMF), dimethylacetamide (DMAc), acetonitrile, DMSO, hexamethylphosphorus triamide (HMPA), nitromethane, tetramethylurea, N-methylpyrrolidone and the like. Non-limiting examples of reagents that can be used as solvents or as part of a mixed solvent system include organic or inorganic mono- or multi-protic acids or bases such as hydrochloric acid, phosphoric acid, sulfuric acid, acetic acid, formic acid, citric acid, succinic acid, triethylamine, morpholine, N-methylmorpholine, piperidine, pyrazine, piperazine, pyridine, potassium hydroxide, sodium hydroxide, alcohols or amines for making esters or amides or thiols for making contemplated products and the like.

The preparation of compounds contemplated herein can require the oxidation of nitrogen or sulfur to N-oxide derivatives or sulfoxides or sulfones. Reagents for this process can include, in a non-limiting example, peroxymonosulfate (OXONE®), hydrogen peroxide, meta-chloroperbenzoic acid, perbenzoic acid, peracetic acid, perlactic acid, tert-butyl peroxide, tert-butyl hypochlorite, sodium hydpochlorite, hypochlorous acid, sodium meta-periodate, periodic acid and the like with the weaker agents being most useful for the preparation of sulfones and sulfoxides. Protic, non-protic, dipolar aprotic solvents, either pure or mixed, can be chosen, for example, methanol/water.

The oxidation can be carried out at temperature of about −78° to about 50° degrees Centigrade, and normally selected from a range −10° C. to about 40° C. Sulfoxides are best prepared using one equivalent of oxidizing agent. It can be desirable in the case of more active oxidizing agents, but not required, that the reactions be carried out under an inert gas atmosphere with or without degassed solvents. It should be noted that the oxidation of sulfides to sulfones can be carried out in one step or two steps via the sulfoxide as desired by the chemist.

Reduction is a well known process in the art with a useful method being hydrogenation. In such cases (catalytic reduction), there can be a metal catalyst such as Rh, Pd, Pt, Ni or the like with or without an additional support such as carbon, barium carbonate and the like. Solvents can be protic or non-protic pure solvents or mixed solvents as required. The reductions can be carried out at atmospheric pressure to a pressure of multiple atmospheres with atmospheric pressure to about 40 pounds per square inch (psi) preferred or very high pressures in special hydrogenation equipment well known in the art.

Reductive alkylation of amines or active methylene compounds is also a useful method of preparing compounds. Such alkylations can be carried out under reductive hydrogenation conditions as presented above using, for example, aldehydes or ketones. Hydride transfer reagents such as sodium cyanoborohydride, aluminum hydride, lithium aluminumhydride, borane, sodium borohydride, di-isobutylaluminum hydride and the like are also useful as reagents for reductive alkylation. Acyl groups can be reduced in a similar manner to produce substituted amines.

Alternative methods of alkylating carbon or nitrogen are direct alkylation. Such an alkylation, as is well known in the art, can be carried by treatment of an activated carbon containing at least one hydrogen with base to form the corresponding anion, adding an electrophilic reagent and permitting the SN2 reaction to proceed. An amine to be alkylated is treated similarly except that deprotonation may not be required. Electrophiles include halogen derivatives, sulfonate esters, epoxides and the like.

Bases and solvents for alkylation reactions are those discussed above. Preferred are bases that are hindered such that competition with the electrophile is minimized. Additional preferred bases are metal hydrides, amide anions or organometallic bases such as n-butyl lithium. The solvents, solvent mixtures or solvent/reagent mixtures discussed are satisfactory but non-protic or dipolar aprotic solvents such as acetone, acetonitrile, DMF and the like are examples of preferred classes.

Acids are used in many reactions during various syntheses. For example, removal of the THP protecting group to produce the hydroxamic acid. The acid can be a mono-, di- or tri-protic organic or inorganic acid. Examples of acids include hydrochloric acid, phosphoric acid, sulfuric acid, acetic acid, formic acid, citric acid, succinic acid, hydrobromic acid, hydrofluoric acid, carbonic acid, phosphorus acid, p-toluene sulfonic acid, trifluoromethane sulfonic acid, trifluoroacetic acid, difluoroacetic acid, benzoic acid, methane sulfonic acid, benzene sulfonic acid, 2,6-dimethylbenzene sulfonic acid, trichloroacetic acid, nitrobenzoic acid, dinitrobenzoic acid, trinitrobenzoic acid, and the like. They can also be Lewis acids such as aluminum chloride, borontrifluoride, antimony pentafluoride and the like. Acids in a protic can also be used to hydrolyze esters, amides and the like as well as catalyze exchange reactions.

Conversion of a carboxylic acid protected as an ester or amide into a hydroxamic acid or hydroxamic acid derivative such as an O-arylalkylether or O-cycloalkoxyalkylether group is useful. In the case where hydroxylamine is used, treatment of an ester or amide with one or more equivalents of hydroxylamine hydrochloride at room temperature or above in a solvent or solvents, usually protic or partially protic, such as those listed above can provide a hydroxamic acid directly. This exchange process can be further catalyzed by the addition of additional acid. Alternatively, a base such as a salt of an alcohol used as a solvent, for example, sodium methoxide in methanol, can be used to form hydroxylamine from hydroxylamine hydrochloride in situ which can exchange with an ester or amide. As mentioned above, exchange can be carried out with a protected hydroxyl amine such as tetrahydropyranylhydroxyamine ($THPONH_2$), benzylhydroxylamine ($BnONH_2$), and the like in which case compounds such as shown in Schemes A, B and C that are tetrahydropyranyl (THP) or benzyl (Bn) hydroxamic acid derivatives are the products. Removal of the protecting groups when desired, for example, following further transformations in another part of the molecule or following storage, is accomplished by standard methods well known in the art such as acid hydrolysis of the THP group as discussed above or reductive removal of the benzyl group with hydrogen and a metal catalyst such as palladium, platinum, palladium on carbon or nickel.

In the case where $R^{20}$ is hydroxyl; i.e., where the intermediate is a carboxylic acid, standard coupling reactions can be used. For example, the acid can be converted into an acid chloride, mixed anhydride or activated ester such as hydroxybenzotriazole and treated with hydroxylamine or a protected hydroxylamine in the presence of a non-competitive base to the nitrogen acylated compound. This is the same product as discussed above. Couplings of this nature are well known in the art and especially the art related to peptide and amino acid chemistry.

An amide of this invention, whether used as a drug or as a protecting group, is prepared by treatment of an acid halide, anhydride, mixed anhydride or active ester with a primary amine, secondary amine or ammonia, or their equivalent. These standard coupling reactions are well known in the art and are discussed elsewhere herein. An alternative method of preparation of amides is by the exchange of, for example, an alkoxycarbonyl (ester) or aminecarbonyl (amide) group for an amine or different amine as required. Ester exchange processes are especially useful when less hindered amines, including ammonia, are used to make the corresponding amides of this invention.

Further, amides can be prepared from hydroxamic acids or protected hydroxamic acid compounds by catalytic reductions or in vivo or in vitro enzymatic processes. For example, catalytic reduction of O-benzylhydroxamic acid compounds is known to produce varying ratios of amide and hydroxamic acid depending upon the catalyst used as well as other reaction conditions such as solvent, temperature, hydrogen gas pressure and the like.

Compounds contemplated herein can possess one or more asymmetric carbon atoms and are thus capable of existing in the form of optical isomers, enantiomers, diastereoisomers, as well as in the form of racemic or nonracemic mixtures. A compound can also exist in other isomeric forms such as ortho, meta and para isomers, cis and trans isomers, syn and anti isomers, E and Z isomers, tautomeric isomers, alpha and beta isomers, axial and equatorial isomers and isomers due to hindered rotation. An isomer can exist in equilibrium with another isomer in a mammal or a test system. Such a compound can also exist as an isomeric equilibrium system with a solvent or water, for example, as a hydrated ketone or aldehyde, as is well known in the art. All isomers are included as compounds of this invention.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, are applicable to the preparation of the corresponding compounds that are contemplated.

Scheme 1
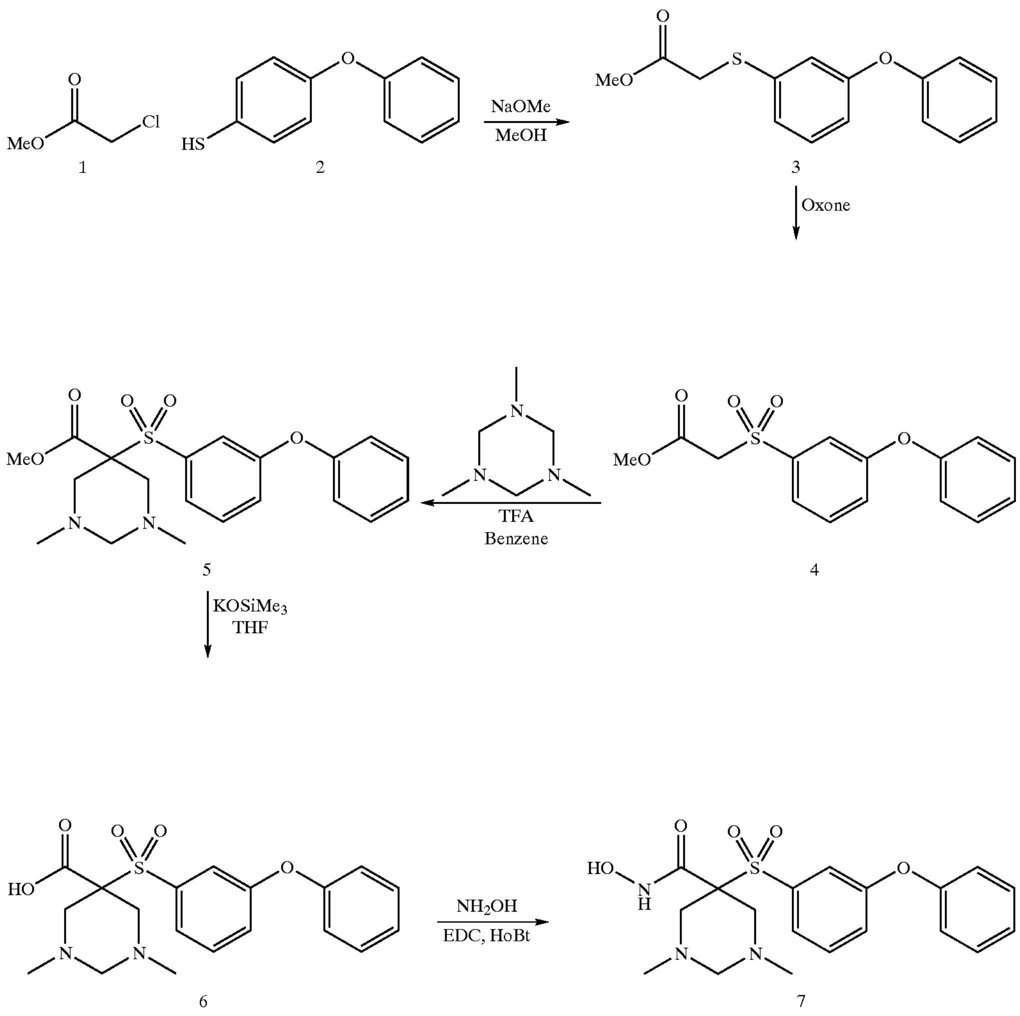
Scheme 2
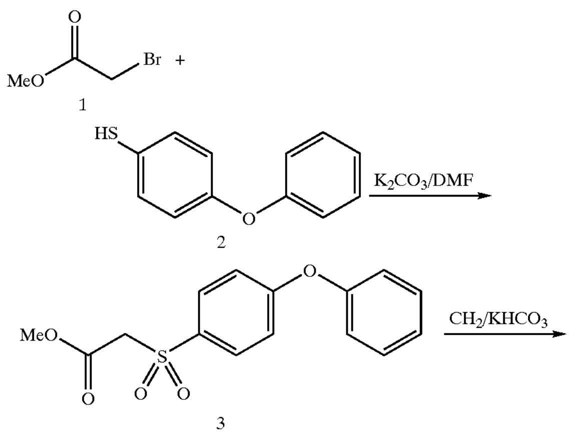
-continued
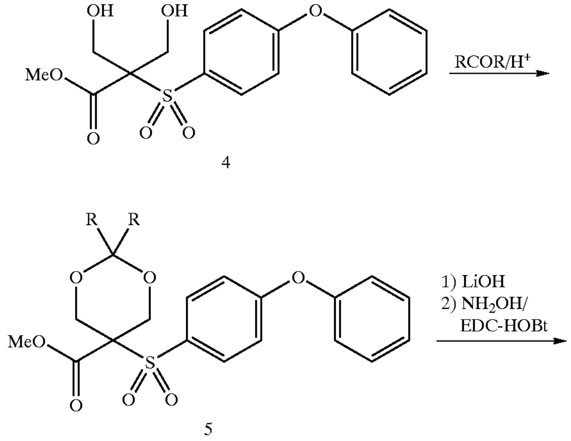

-continued
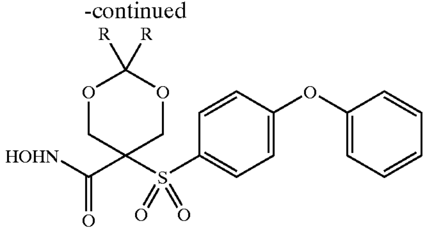
6
-continued
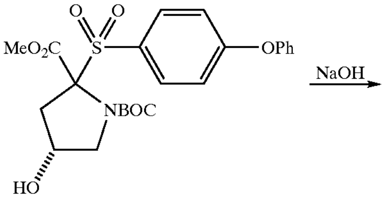
3
Scheme 3
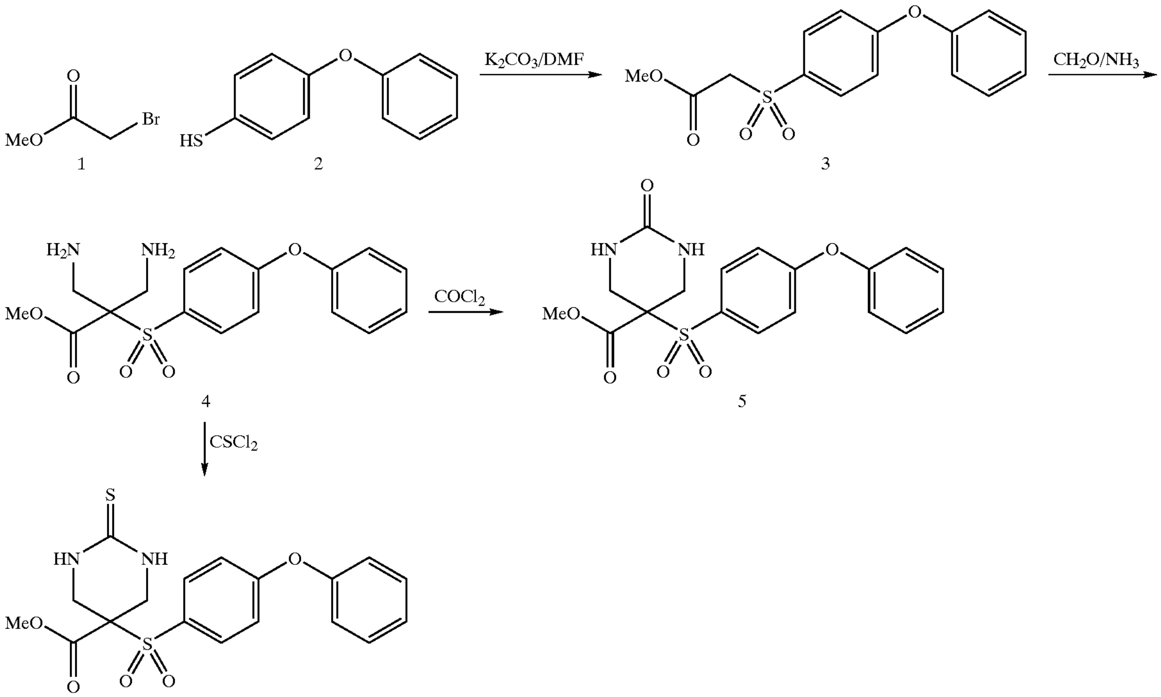
1 2 3 4 5 6
Scheme 4
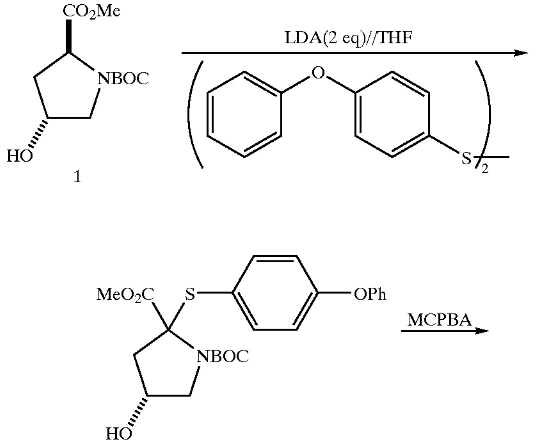
1 2
-continued
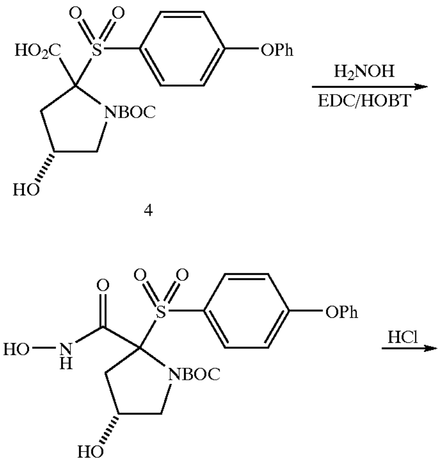
4 5

-continued
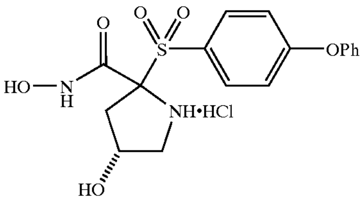
6
Scheme 5
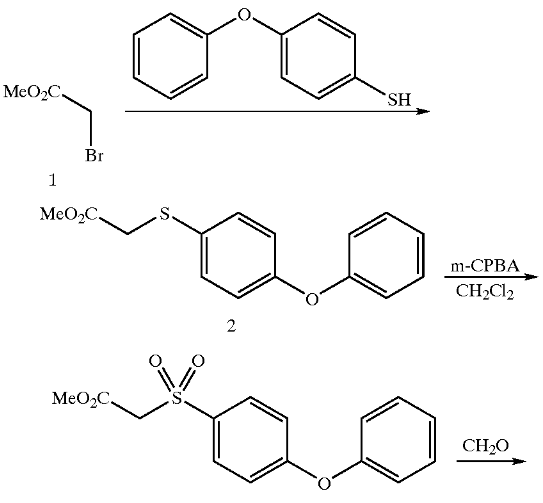
1
2
3
-continued
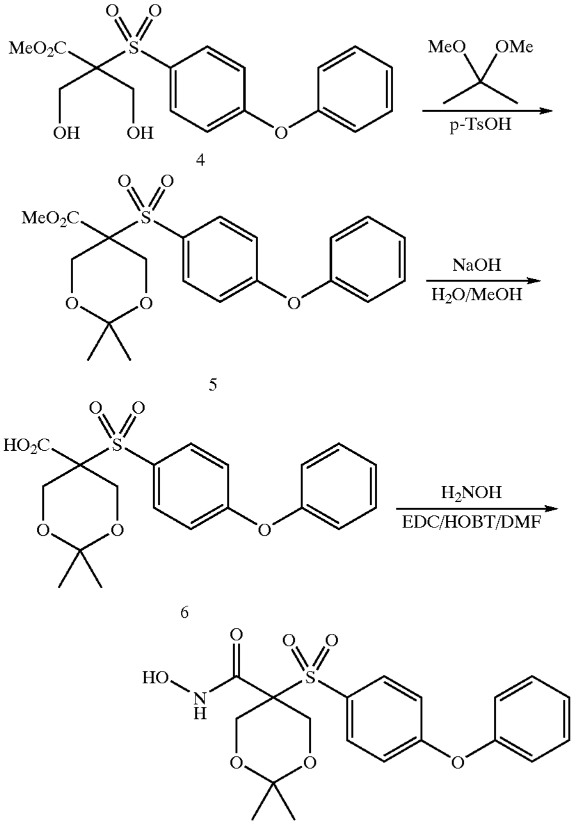
4
5
6
7
Scheme 6
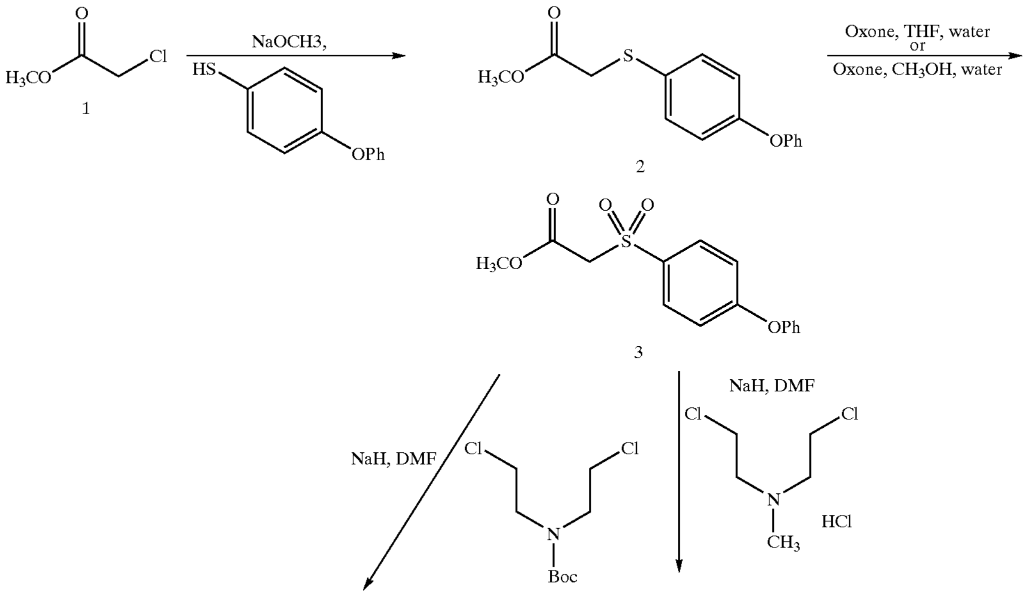
1
2
3

-continued
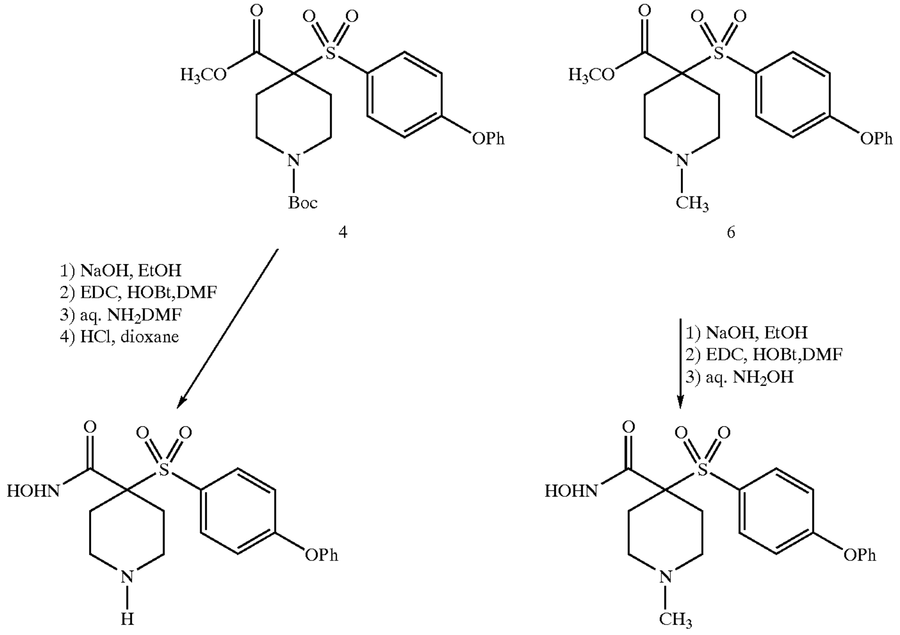
4 6 5 7
Scheme 7
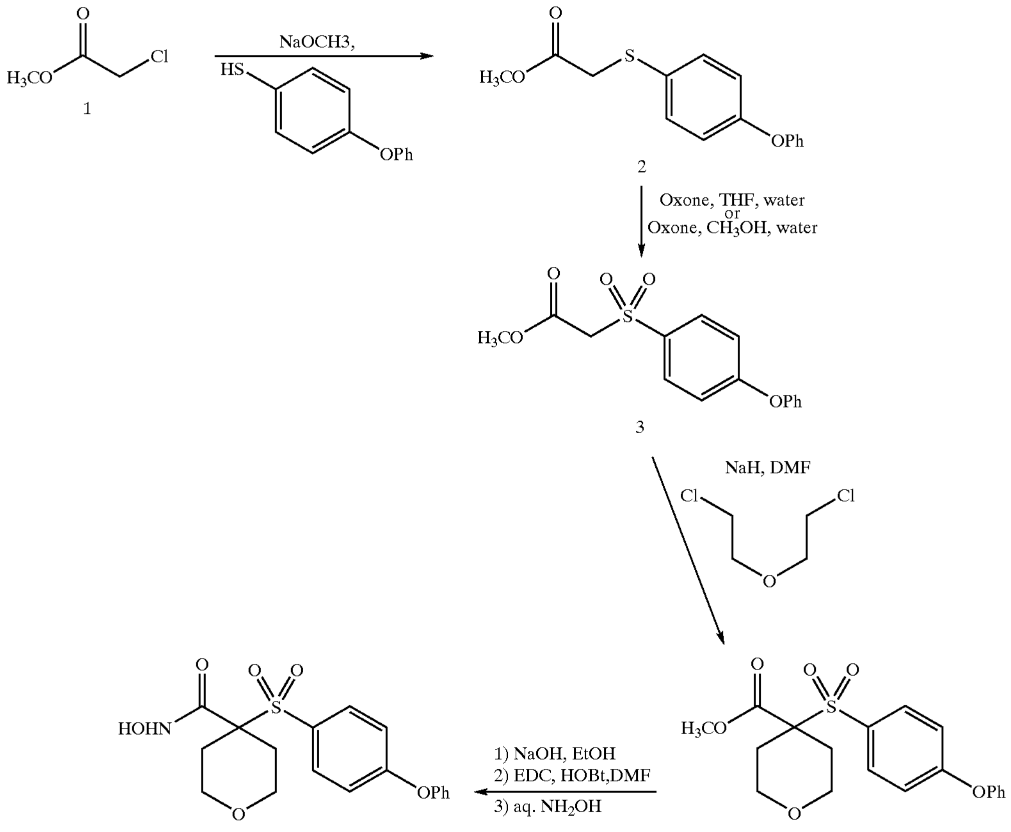
1 2 3 4 5

Scheme 8
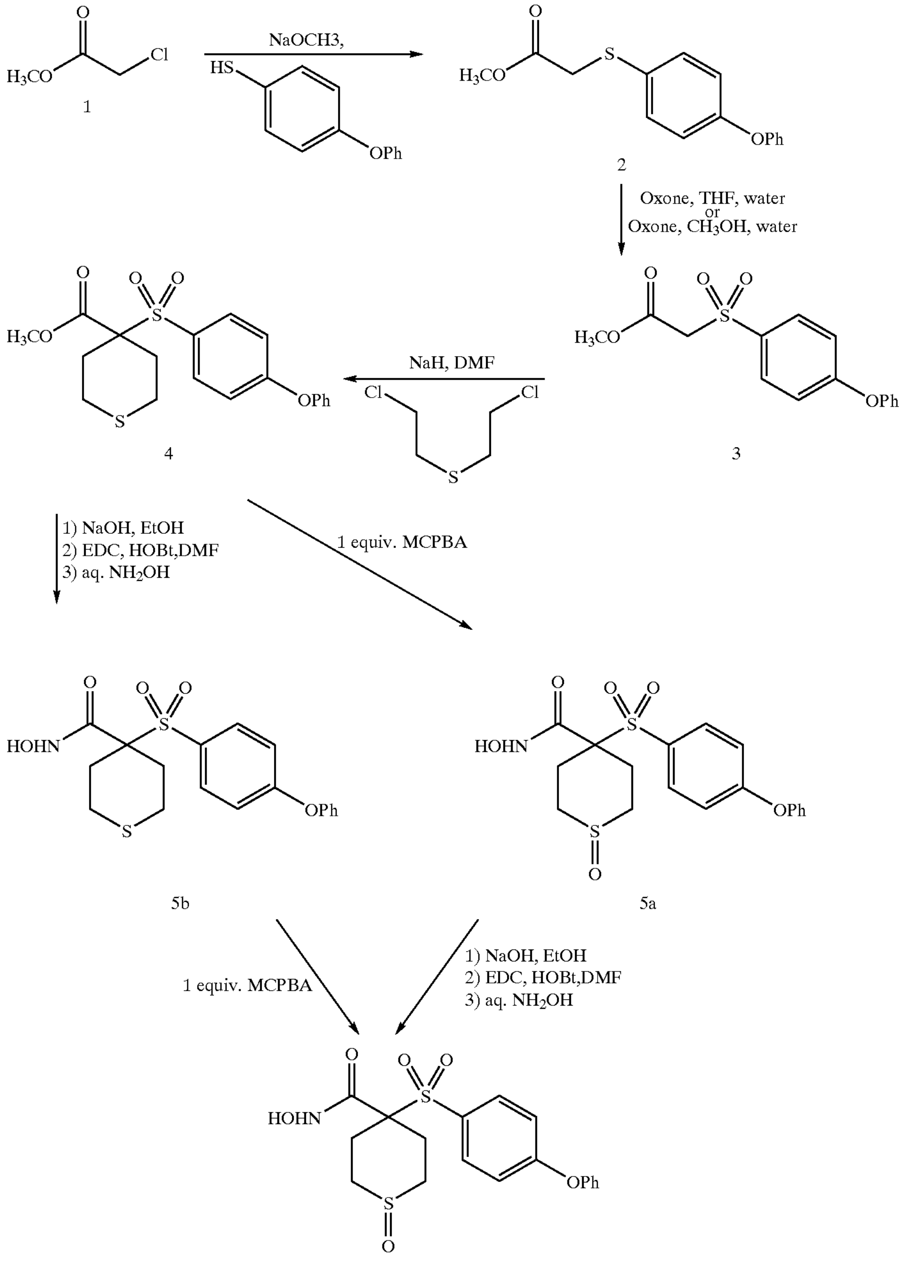
6
-continued
Scheme 9
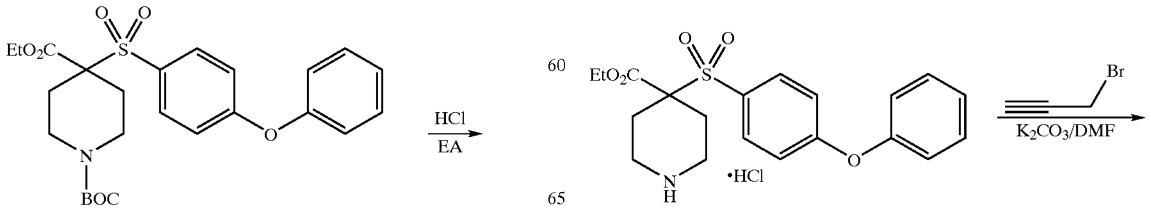
1 2

-continued
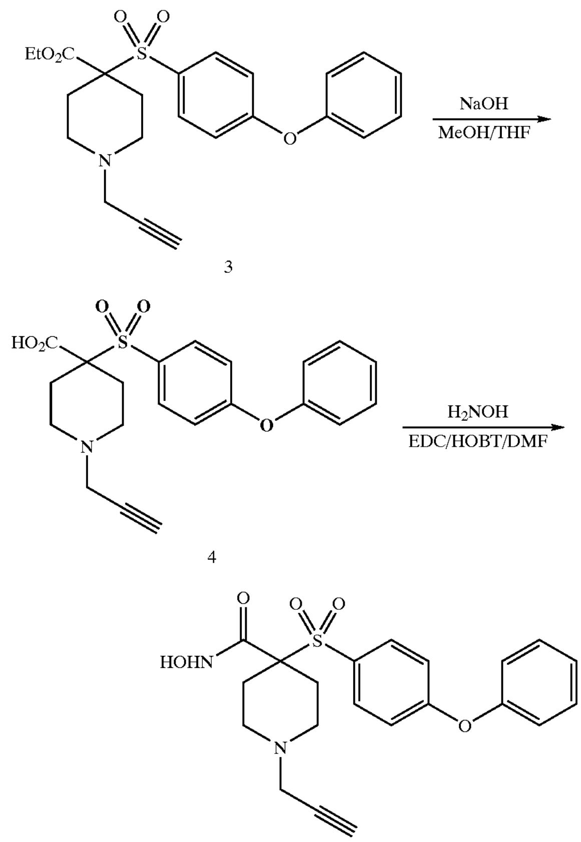
3
4
5
Scheme 10
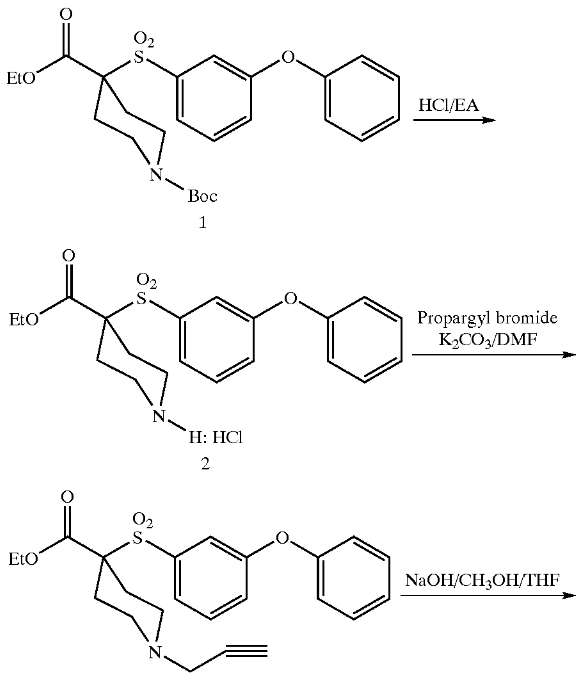
1
2
3
-continued
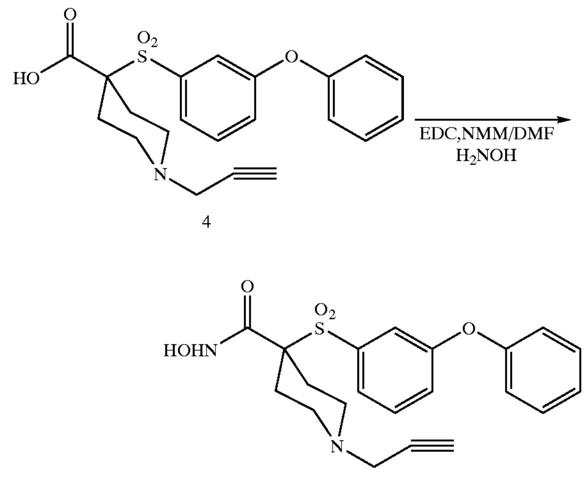
4
5
Scheme 11
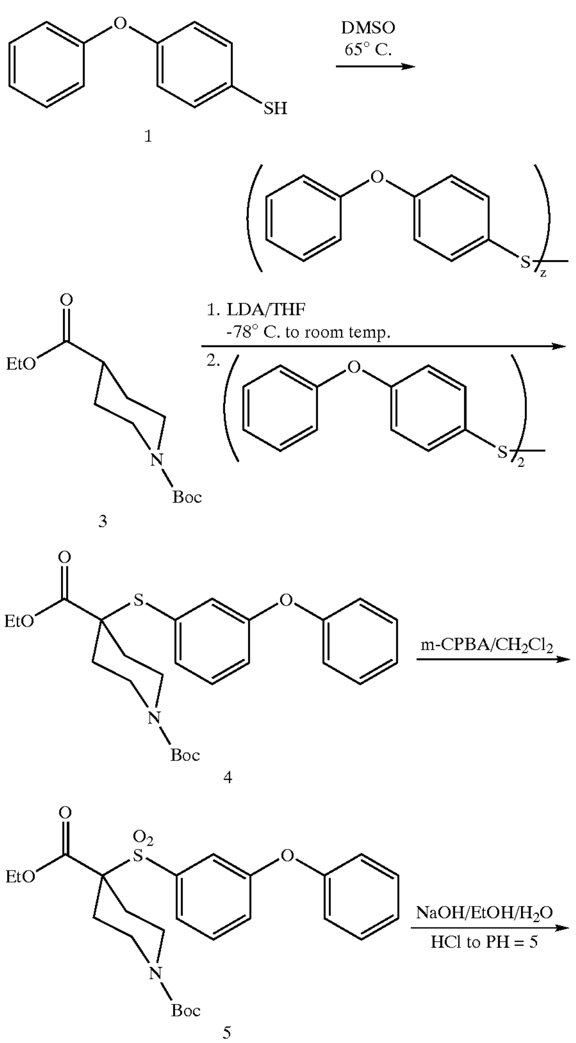
1
3
4
5

-continued
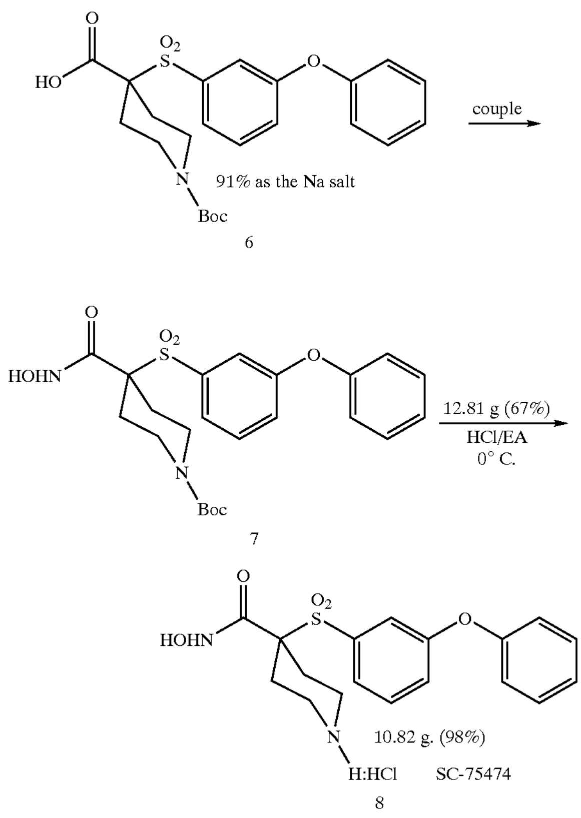
Scheme 12
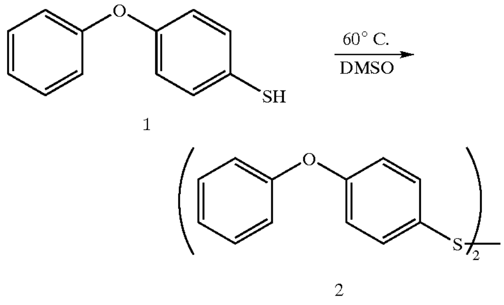
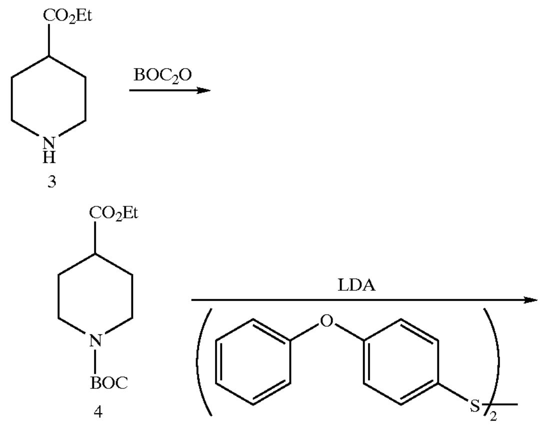
-continued
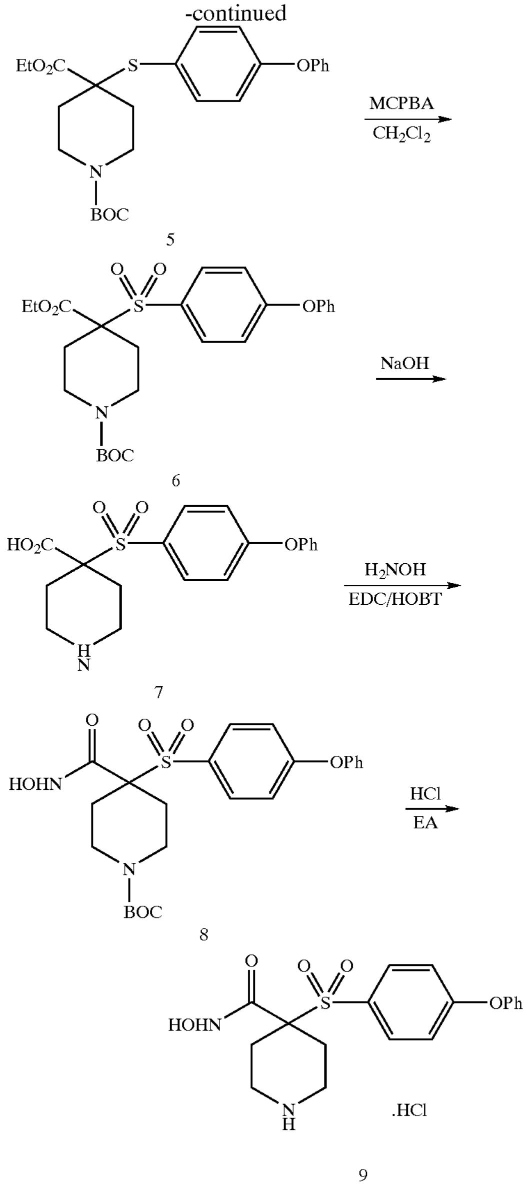
Scheme 13
In a similar manner, the following analogs can be made.
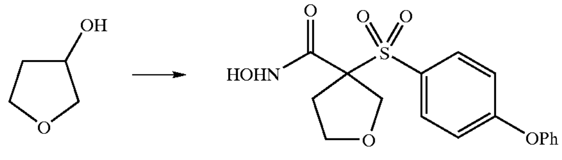
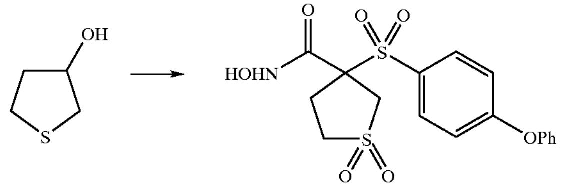

-continued
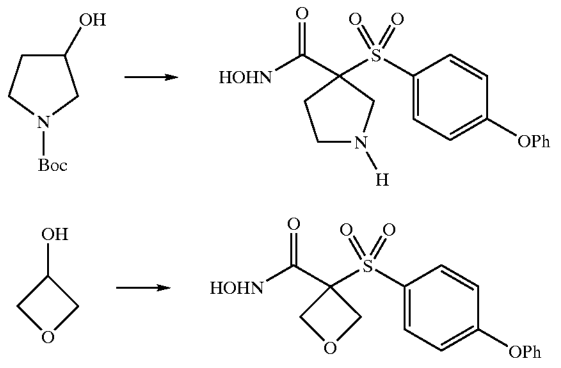
Scheme 14
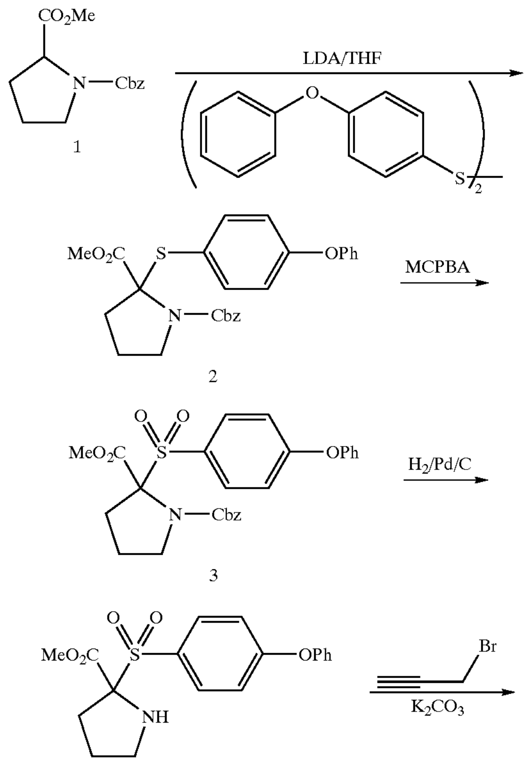
1 2 3 4
-continued
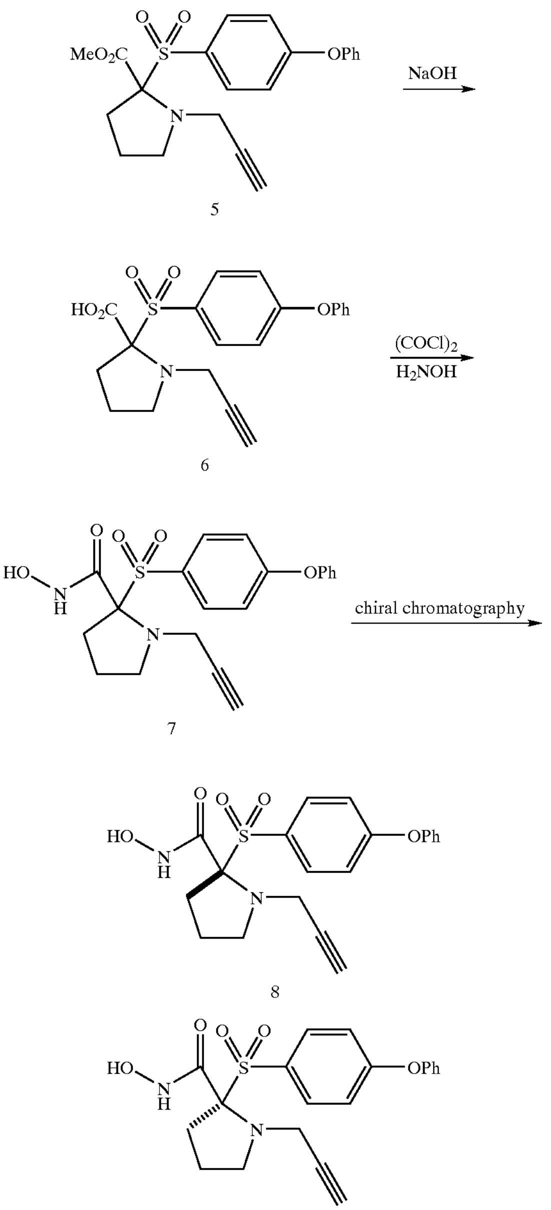
5 6 7 8 9
Scheme 15
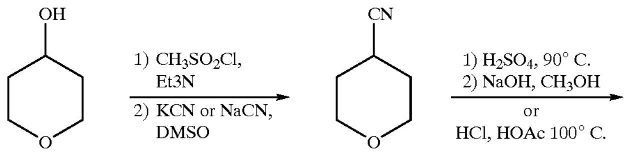
1 2

-continued
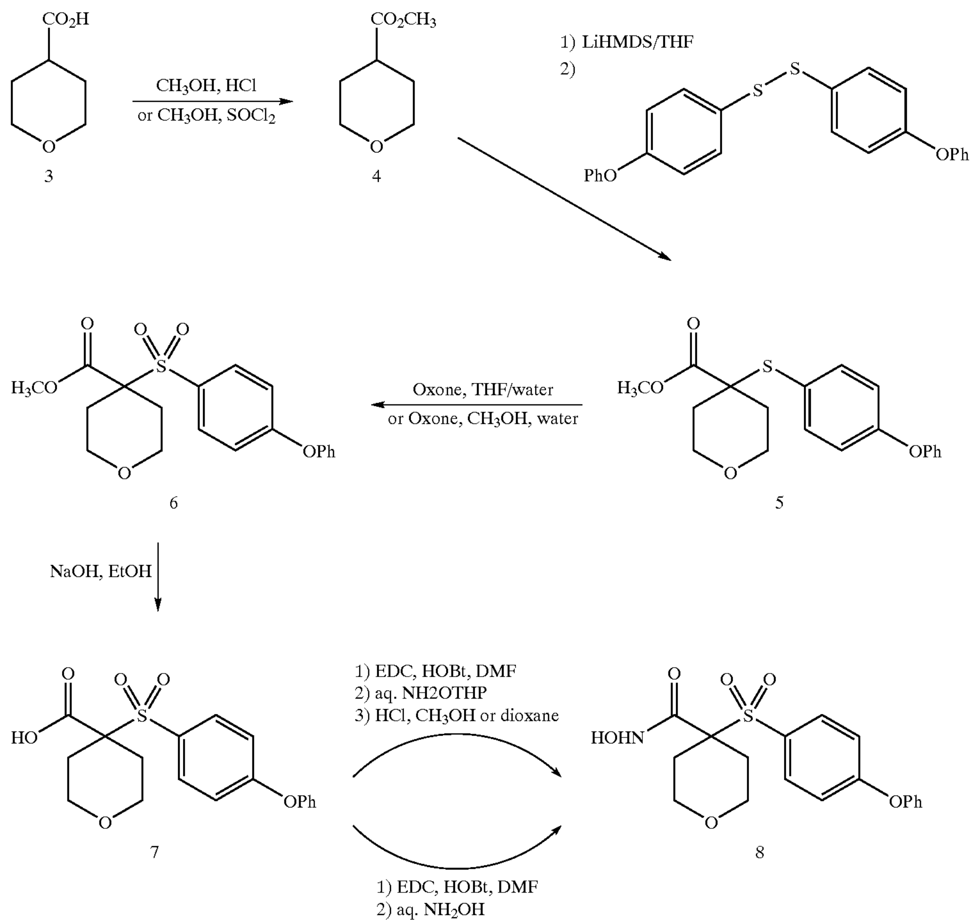
3 4 5 6 7 8
Scheme 16
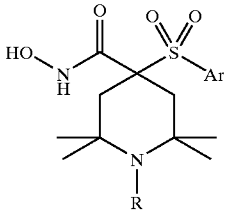
5
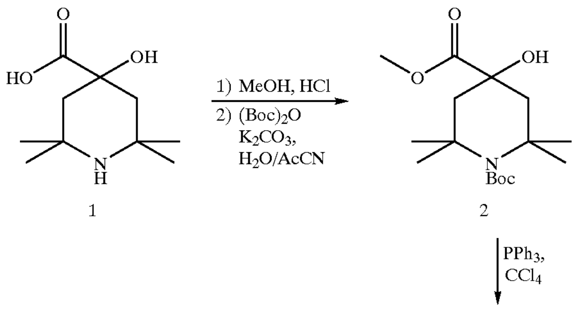
1 2

-continued
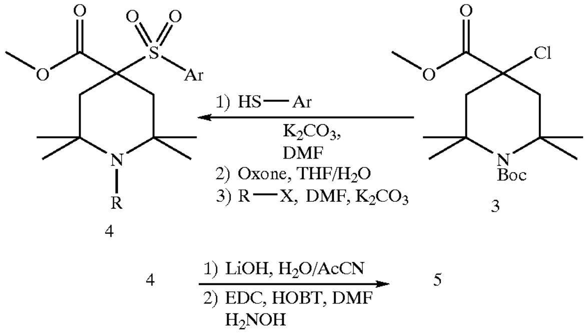
4 3
4 5
Scheme 17
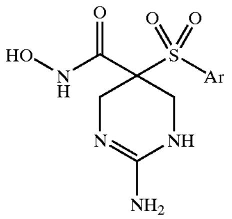
3
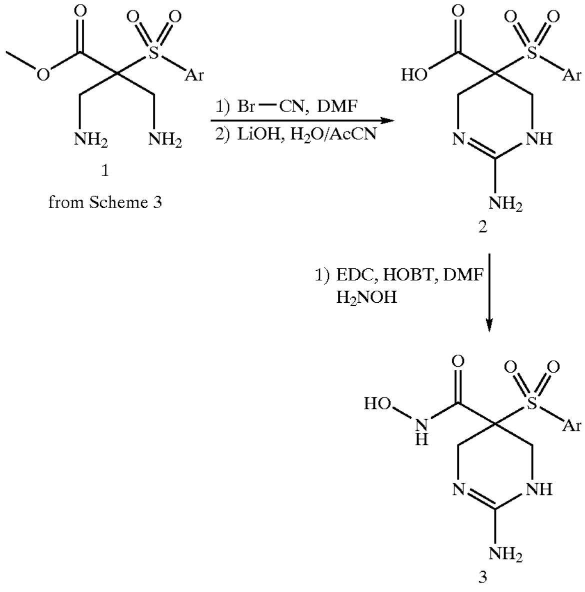
1
from Scheme 3
2
3
Scheme 18
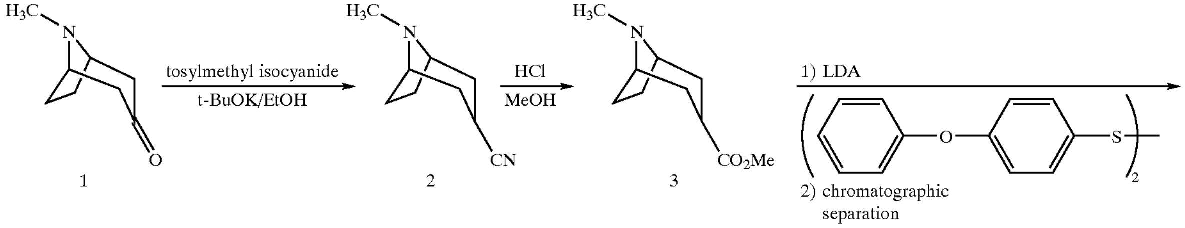
1 2 3

-continued
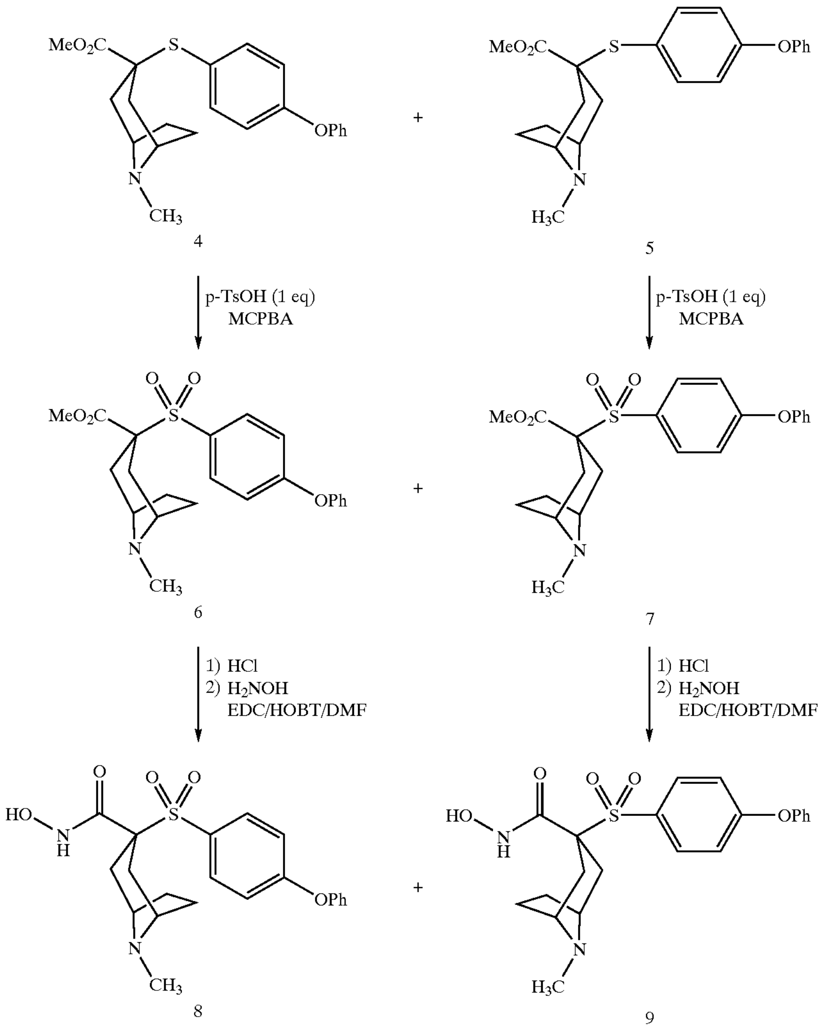
Scheme 19
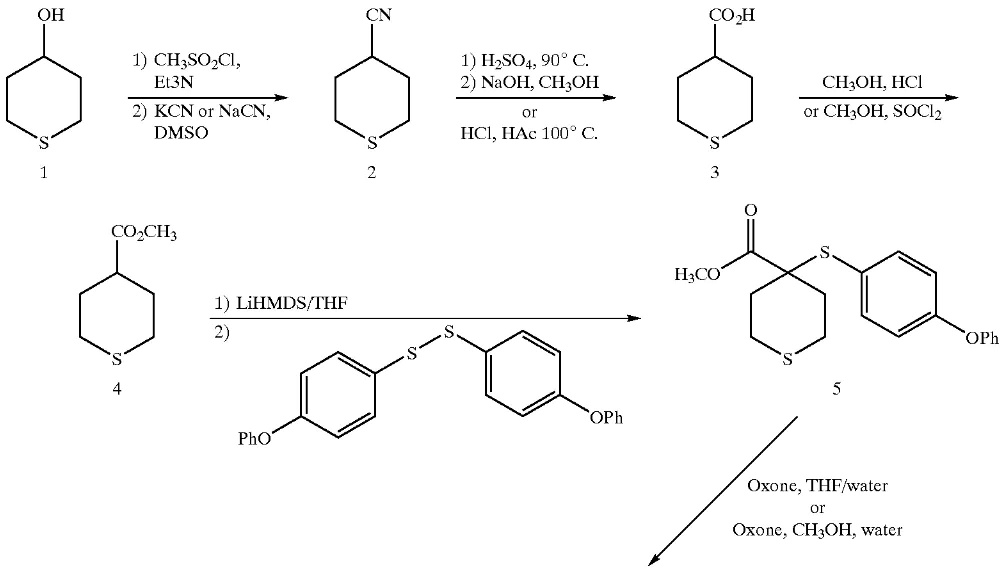

-continued

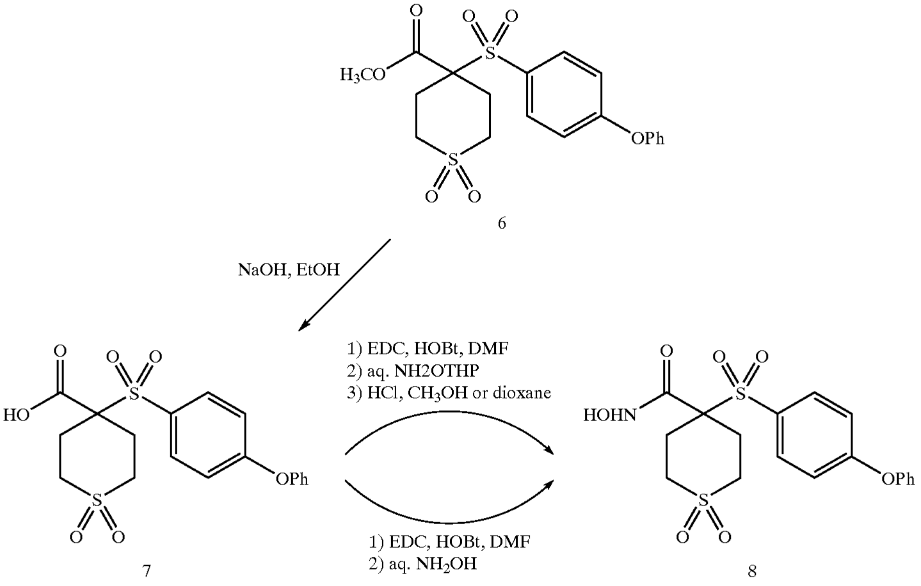

Table 1 through Table 165, below, show several contemplated aromatic sulfone hydroxamic acid inhibitor compounds or structural formulas that illustrate substituent groups. Each group of compounds is illustrated by a generic formula, or formulae, followed by a series of preferred moieties or groups that constitute various substituents that can be attached at the position clearly shown in the generic structure. The substituent symbols, e.g., R1 and R2 and R3, are as shown in each Table, and are typically not those used before. One or two bonds (wavy lines) are shown with those substituents to indicate the respective positions of attachment in the illustrated compound. This system is well known in the chemical communication arts and is widely used in scientific papers and presentations. For example in Table 2, R1 and R2 together with the atoms to which they are bonded is the variable group with the structural entities that can substitute for R1 and R2 together shown in the balance of that table.

TABLE 1

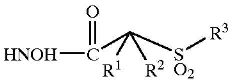

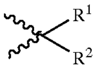

| | |
|---|---|
| 1 | 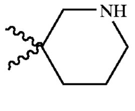 |
| 2 | 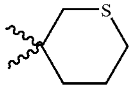 |
| 3 | 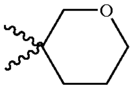 |

TABLE 1-continued

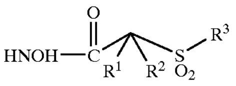

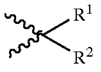

| | |
|---|---|
| 4 | 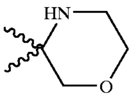 |
| 5 | 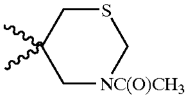 |
| 6 | 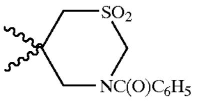 |
| 7 | 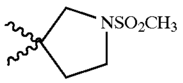 |
| 8 | 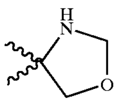 |
| 9 | 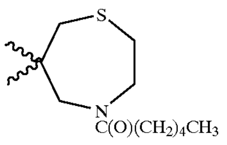 |

TABLE 1-continued
| 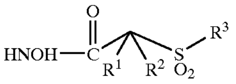 | 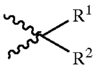 |
|---|---|
| 10 | 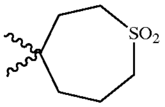 |
| 11 | 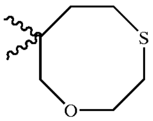 |
| 12 | 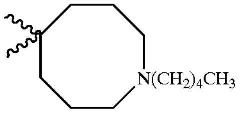 |
TABLE 2
II
| 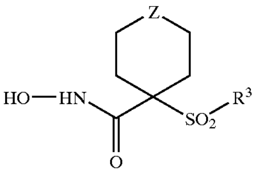 | |
|---|---|
| 1 | 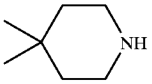 |
| 2 | 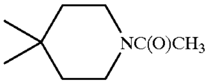 |
| 3 | 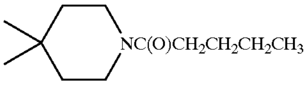 |
| 4 | 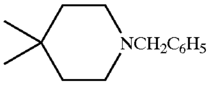 |
| 5 | 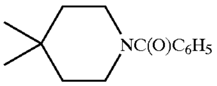 |
| 6 | 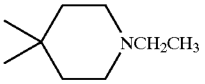 |
| 7 | 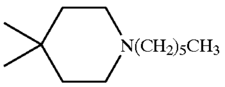 |
TABLE 2-continued
II
| 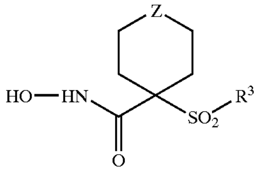 | |
|---|---|
| 8 | 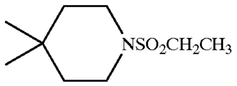 |
| 9 | 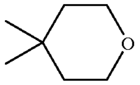 |
| 10 | 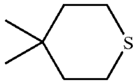 |
| 11 | 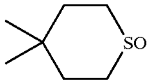 |
| 12 | 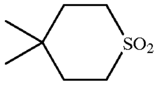 |
TABLE 3
| 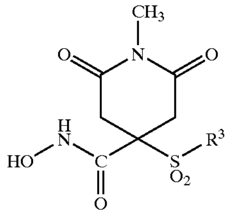 | 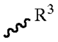 |
|---|---|
| 1 | 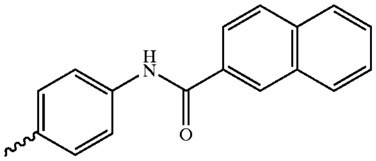 |
| 2 | 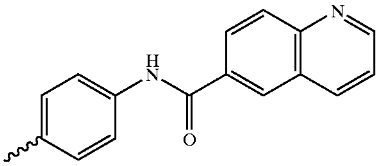 |
| 3 | 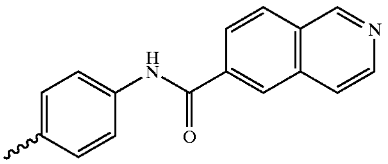 |

TABLE 3-continued
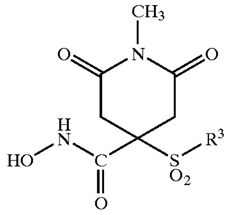
| | 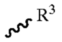 |
|---|---|
| 4 | 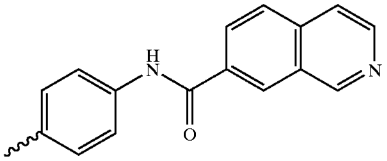 |
| 5 | 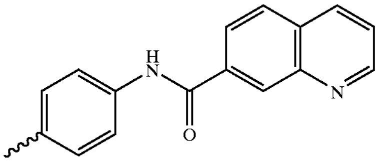 |
| 6 | 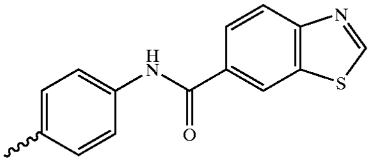 |
| 7 | 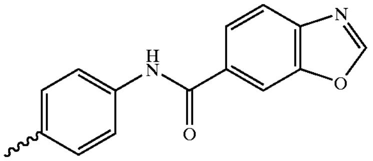 |
| 8 | 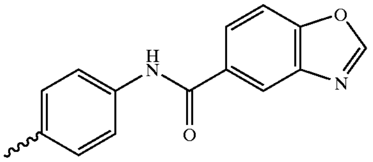 |
| 9 | 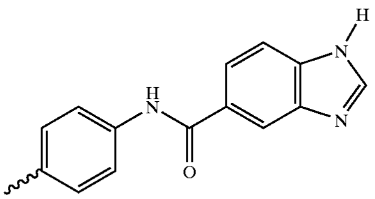 |
| 10 | 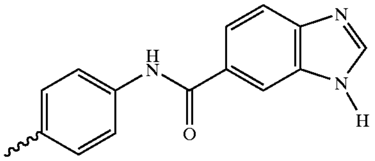 |
TABLE 3-continued
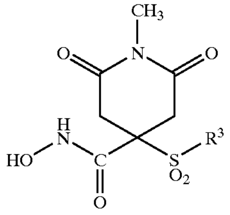
| | 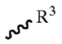 |
|---|---|
| 11 | 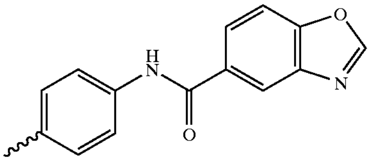 |
| 12 | 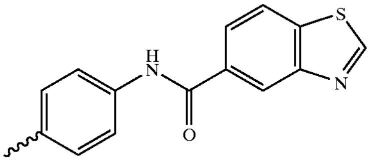 |
| 13 | 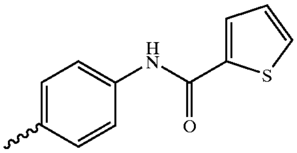 |
| 14 | 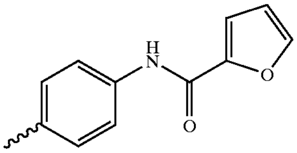 |
| 15 | 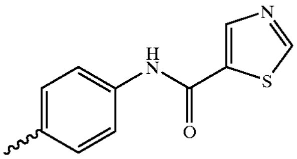 |
| 16 | 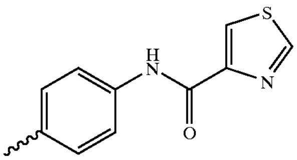 |
| 17 | 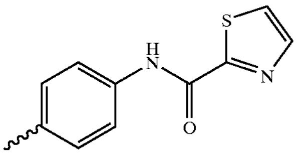 |

TABLE 3-continued
| | |
|---|---|
| 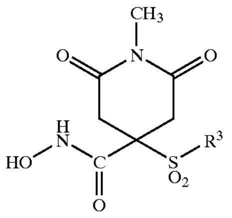 | |
| | 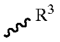 |
| 18 | 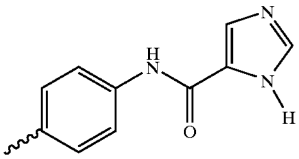 |
TABLE 4
| | |
|---|---|
| 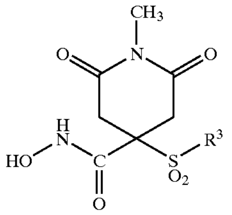 | |
| | 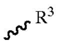 |
| 1 | 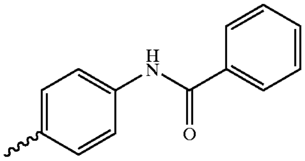 |
| 2 | 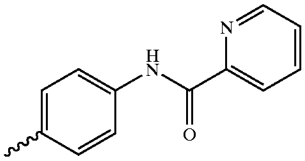 |
| 3 | 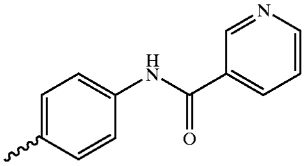 |
| 4 | 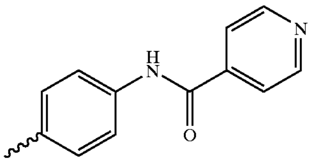 |
TABLE 4-continued
| | |
|---|---|
| 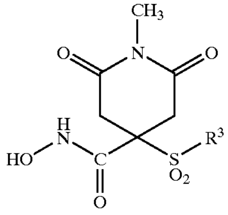 | |
| | 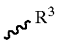 |
| 5 | 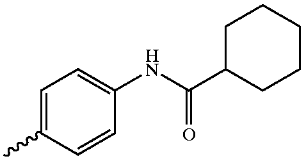 |
| 6 | 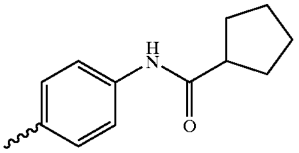 |
| 7 | 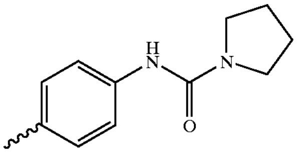 |
| 8 | 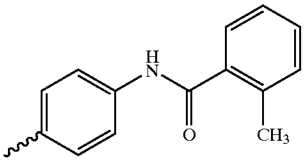 |
| 9 | 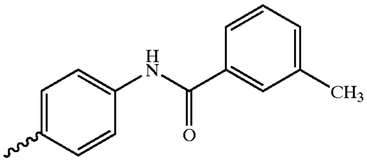 |
| 10 | 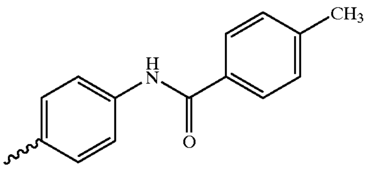 |
| 11 | 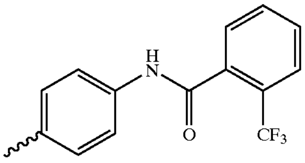 |

TABLE 4-continued
| 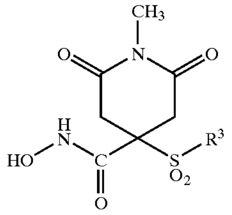 | |
|---|---|
| | 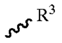 |
| 12 | 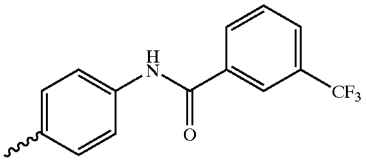 |
| 13 | 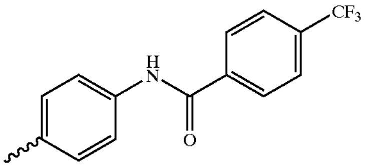 |
| 14 | 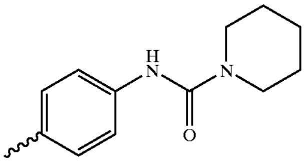 |
| 15 | 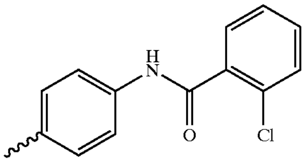 |
| 16 | 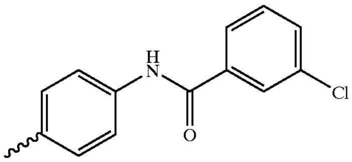 |
| 17 | 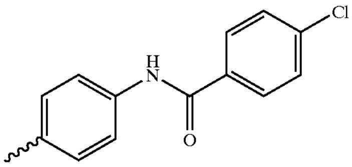 |
| 18 | 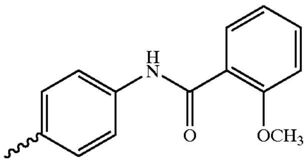 |
TABLE 4-continued
| 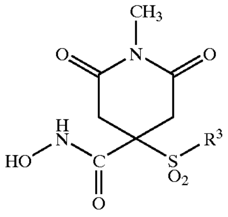 | |
|---|---|
| | 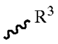 |
| 19 | 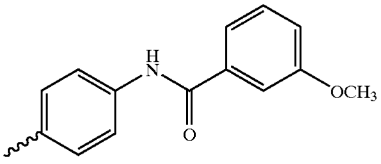 |
| 20 | 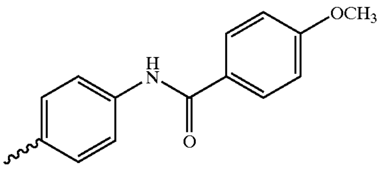 |
| 21 | 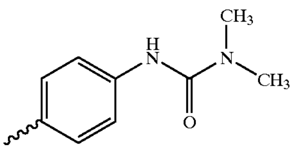 |
TABLE 5
| 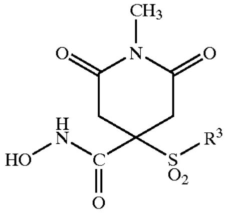 | |
|---|---|
| | 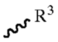 |
| 1 | 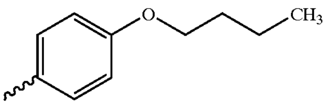 |
| 2 | 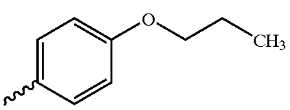 |
| 3 | 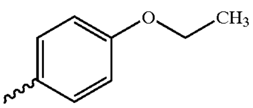 |

TABLE 5-continued
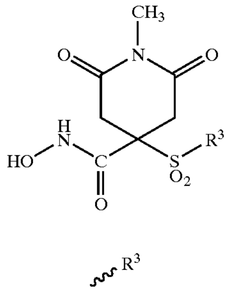
| | |
|---|---|
| 4 | 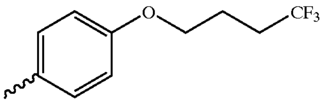 |
| 5 | 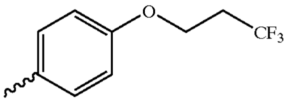 |
| 6 | 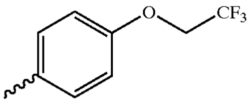 |
| 7 | 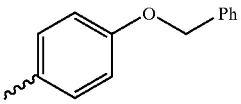 |
| 8 | 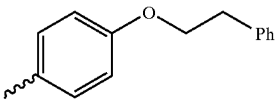 |
| 9 | 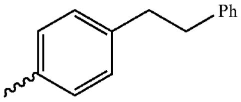 |
| 10 | 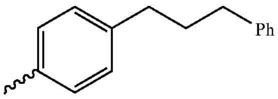 |
| 11 | 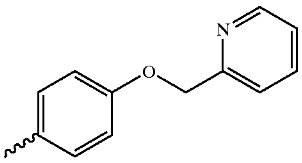 |
| 12 | 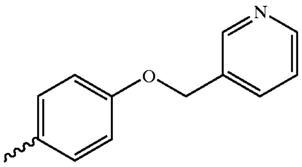 |
TABLE 5-continued
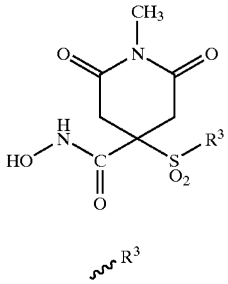
| | |
|---|---|
| 13 | 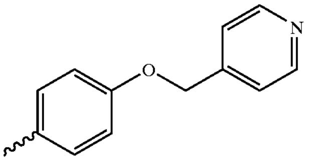 |
| 14 | 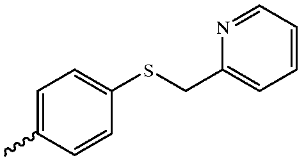 |
| 15 | 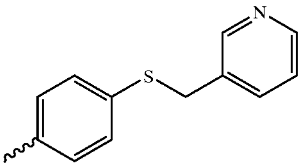 |
| 16 | 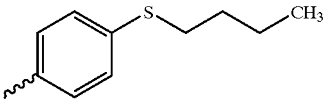 |
| 17 | 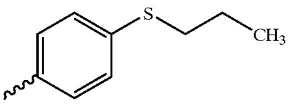 |
| 18 | 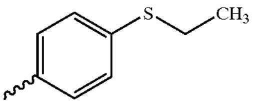 |
| 19 | 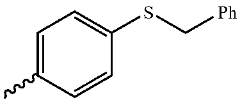 |
| 20 | 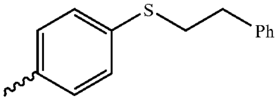 |
| 21 | 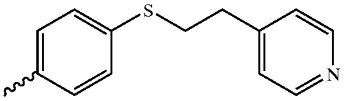 |

TABLE 5-continued
| | 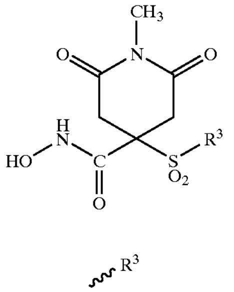 |
|---|---|
| 22 | 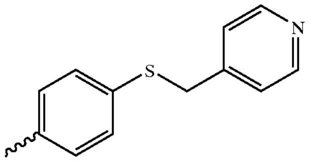 |
TABLE 6
| | 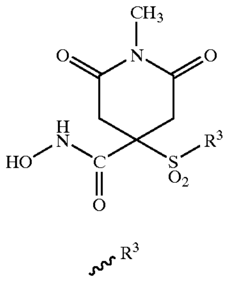 |
|---|---|
| 1 | 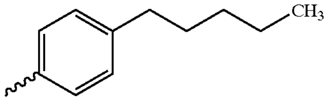 |
| 2 | 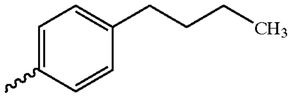 |
| 3 | 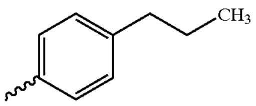 |
| 4 | 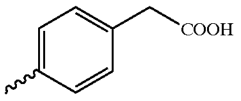 |
| 5 | 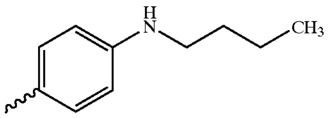 |
| 6 | 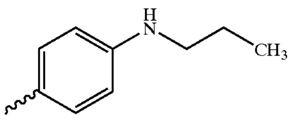 |
TABLE 6-continued
| | 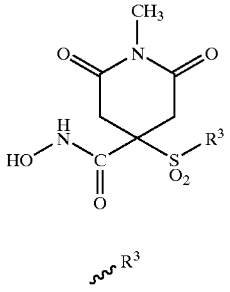 |
|---|---|
| 7 | 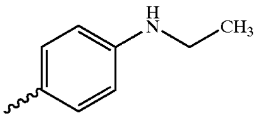 |
| 8 | 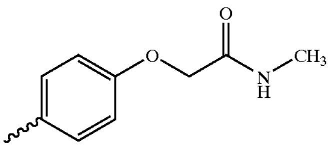 |
| 9 | 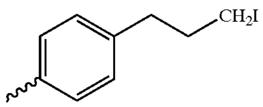 |
| 10 | 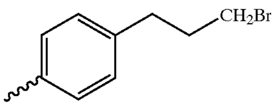 |
| 11 | 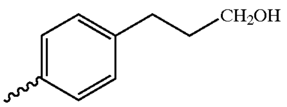 |
| 12 | 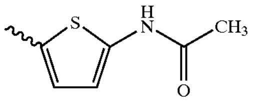 |
| 13 | 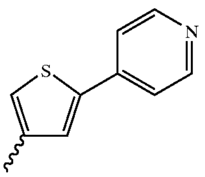 |
| 14 | 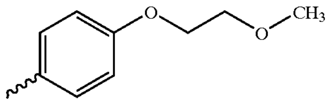 |
| 15 | 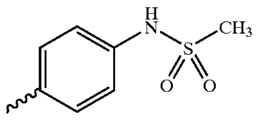 |

TABLE 6-continued
| | 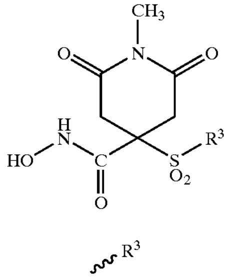 |
| --- | --- |
| 16 | 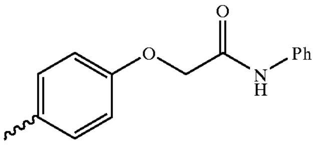 |
| 17 | 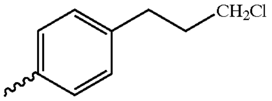 |
| 18 | 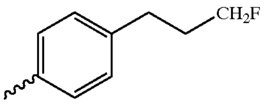 |
| 19 | 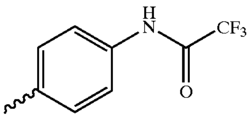 |
| 20 | 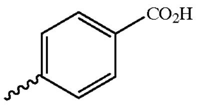 |
| 21 | 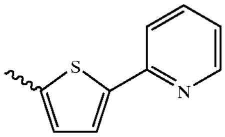 |
| 22 | 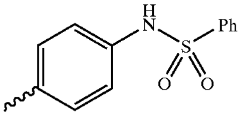 |
| 23 | 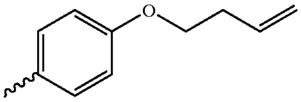 |
| 24 | 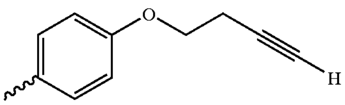 |
| 25 | 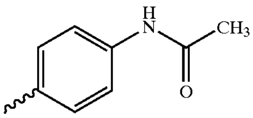 |
TABLE 6-continued
| | 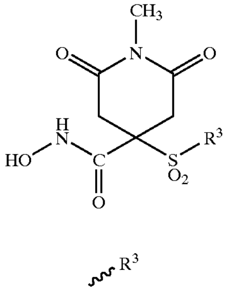 |
| --- | --- |
| 26 | 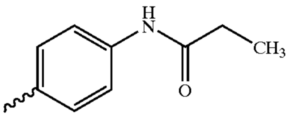 |
| 27 | 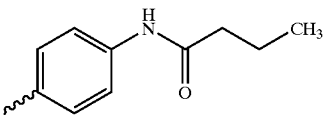 |
| 28 | 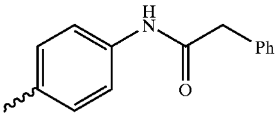 |
| 29 | 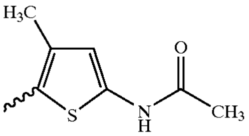 |
| 30 | 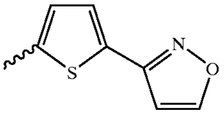 |
TABLE 7
| | 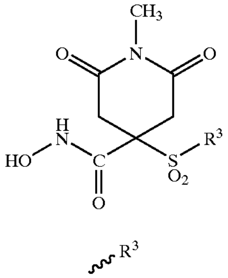 |
| --- | --- |
| 1 | 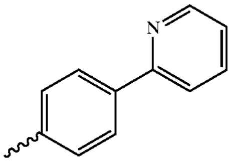 |

TABLE 7-continued
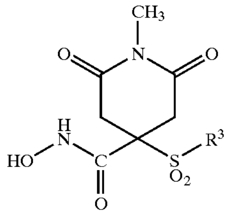
| | 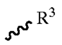 |
|---|---|
| 2 | 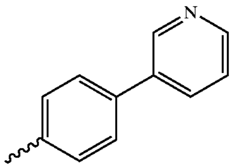 |
| 3 | 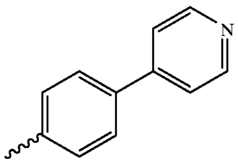 |
| 4 | 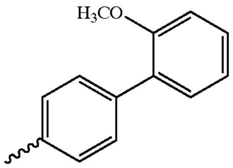 |
| 5 | 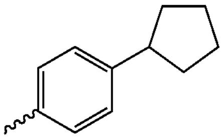 |
| 6 | 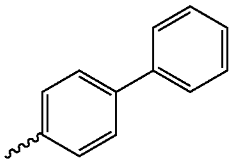 |
| 7 | 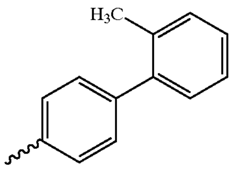 |
| 8 | 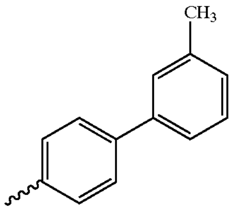 |
TABLE 7-continued
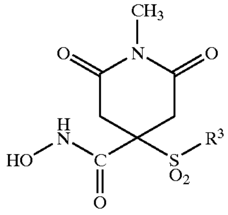
| | 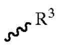 |
|---|---|
| 9 | 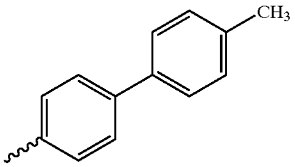 |
| 10 | 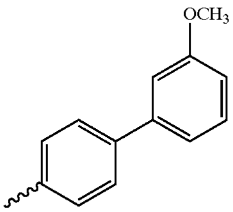 |
| 11 | 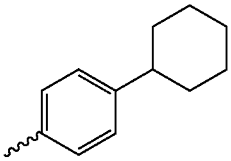 |
| 12 | 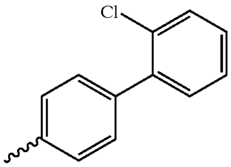 |
| 13 | 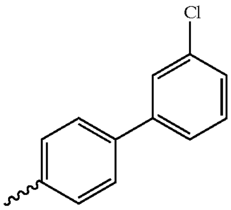 |
| 14 | 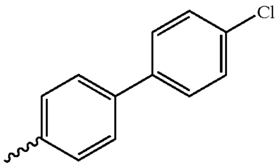 |
| 15 | 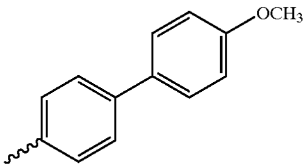 |

TABLE 7-continued
| 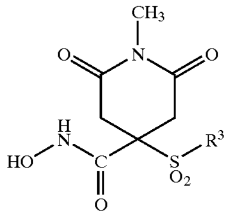 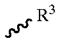 | |
|---|---|
| 16 | 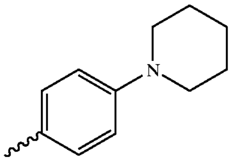 |
| 17 | 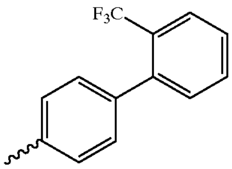 |
| 18 | 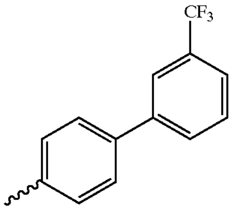 |
| 19 | 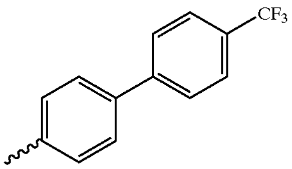 |
| 20 | 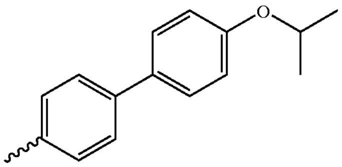 |
| 21 | 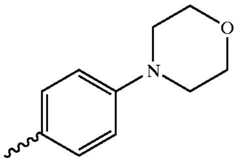 |
TABLE 8
| 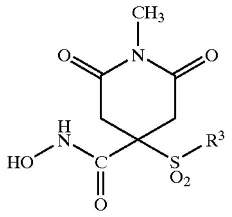 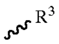 | |
|---|---|
| 1 | 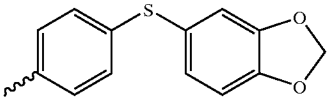 |
| 2 | 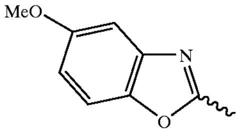 |
| 3 | 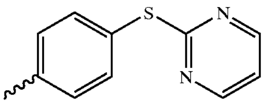 |
| 4 | 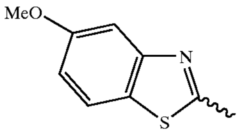 |
| 5 | 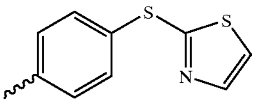 |
| 6 | 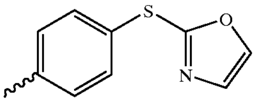 |
| 7 | 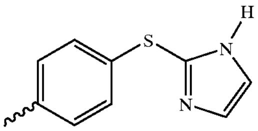 |
| 8 | 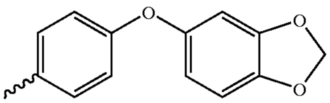 |
| 9 | 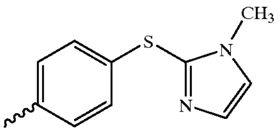 |
| 10 | 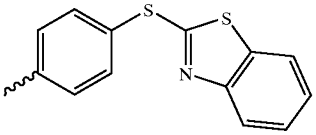 |

TABLE 8-continued
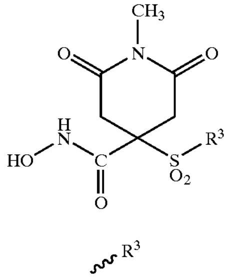
| | |
|---|---|
| 11 | 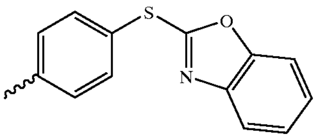 |
TABLE 9
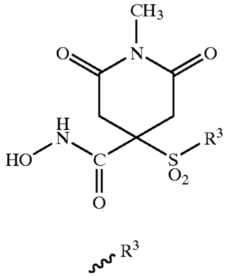
| | |
|---|---|
| 1 | 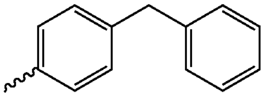 |
| 2 | 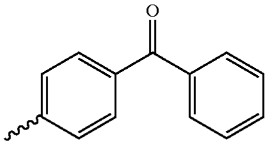 |
| 3 | 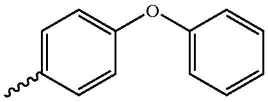 |
| 4 | 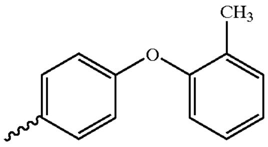 |
| 5 | 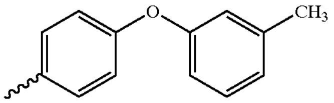 |
| 6 | 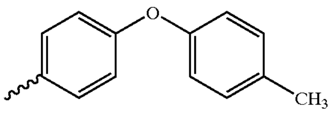 |
TABLE 9-continued
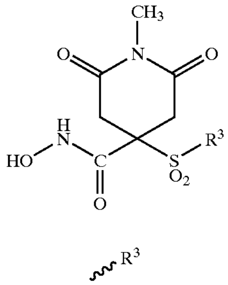
| | |
|---|---|
| 7 | 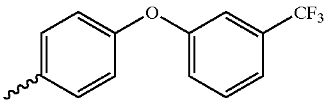 |
| 8 | 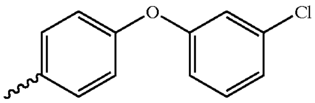 |
| 9 | 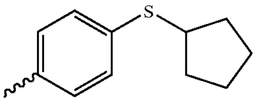 |
| 10 | 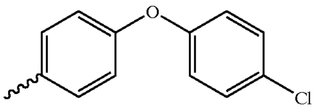 |
| 11 | 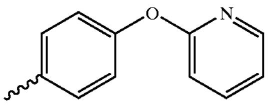 |
| 12 | 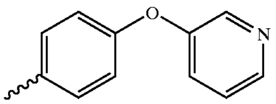 |
| 13 | 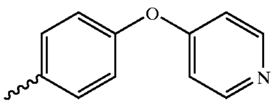 |
| 14 | 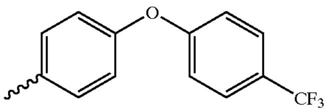 |
| 15 | 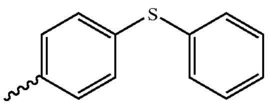 |
| 16 | 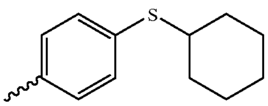 |

TABLE 9-continued
| | |
|---|---|
| 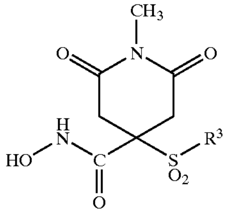 | |
| 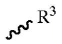 | |
| 17 | 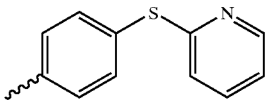 |
| 18 | 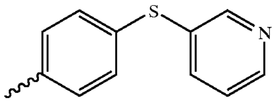 |
| 19 | 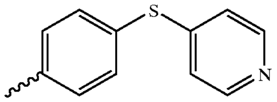 |
| 20 | 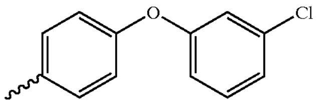 |
| 21 | 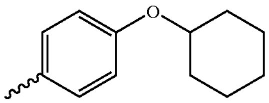 |
TABLE 10
| | |
|---|---|
| 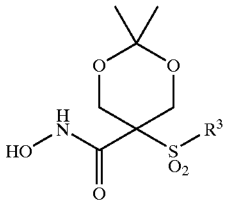 | |
| 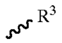 | |
| 1 | 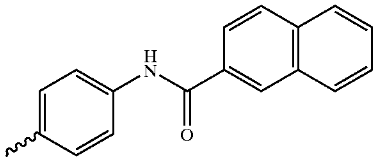 |
| 2 | 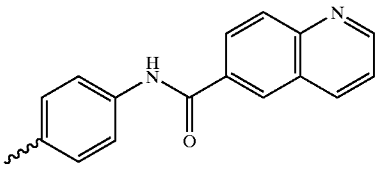 |
TABLE 10-continued
| | |
|---|---|
| 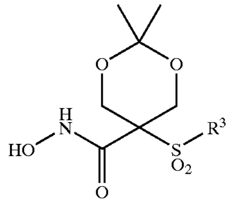 | |
| 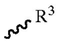 | |
| 3 | 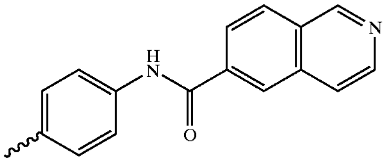 |
| 4 | 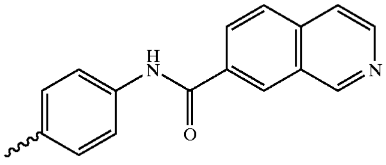 |
| 5 | 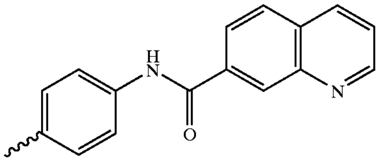 |
| 6 | 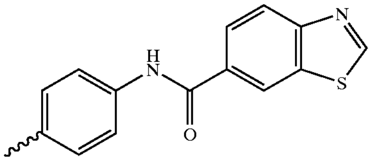 |
| 7 | 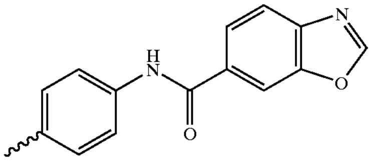 |
| 8 | 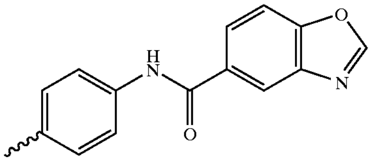 |
| 9 | 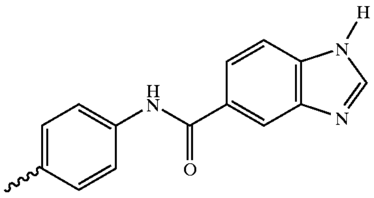 |

TABLE 10-continued
| 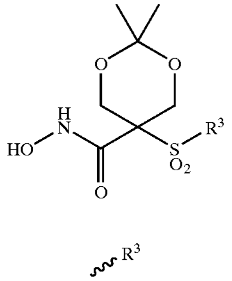 |  |
| --- | --- |
| 10 | 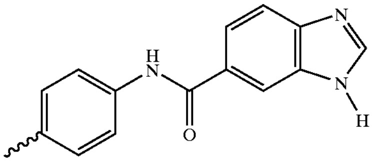 |
| 11 | 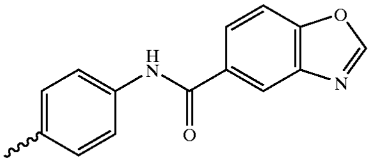 |
| 12 | 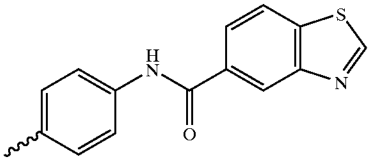 |
| 13 | 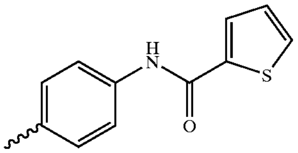 |
| 14 | 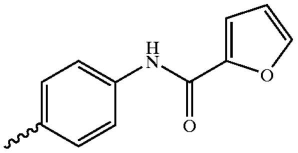 |
| 15 | 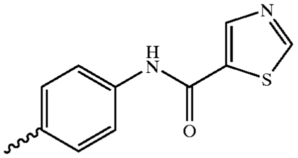 |
| 16 | 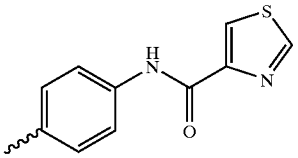 |
TABLE 10-continued
| 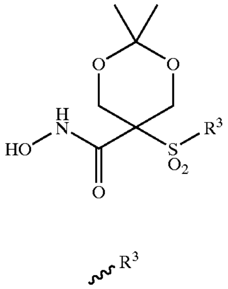 |  |
| --- | --- |
| 17 | 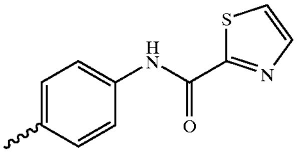 |
| 18 | 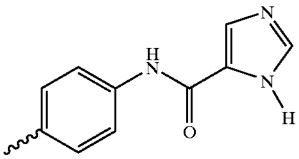 |
TABLE 11
| 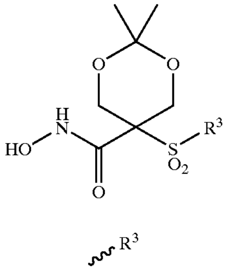 |  |
| --- | --- |
| 1 | 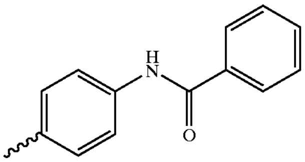 |
| 2 | 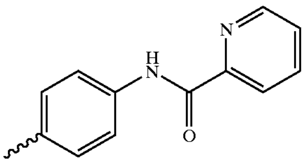 |
| 3 | 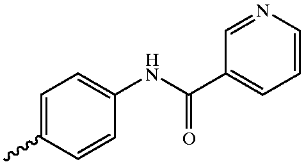 |

TABLE 11-continued
| | |
|---|---|
| | 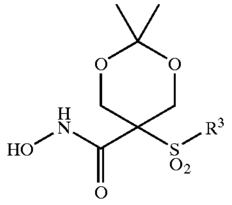 |
| | 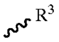 |
| 4 | 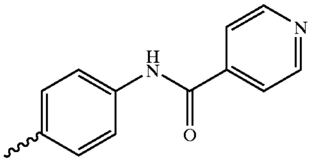 |
| 5 | 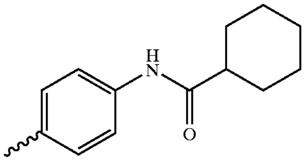 |
| 6 | 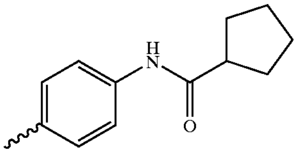 |
| 7 | 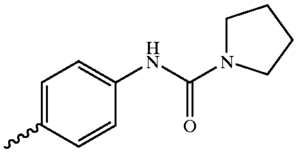 |
| 8 | 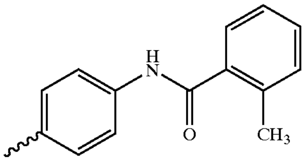 |
| 9 | 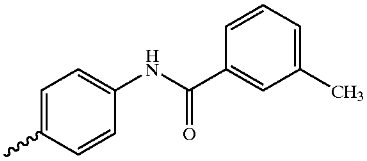 |
| 10 | 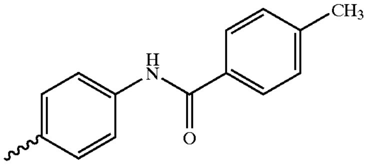 |
TABLE 11-continued
| | |
|---|---|
| | 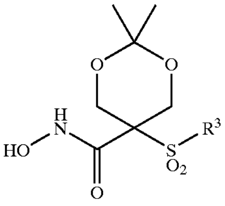 |
| | 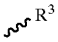 |
| 11 | 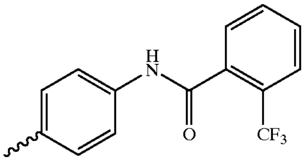 |
| 12 | 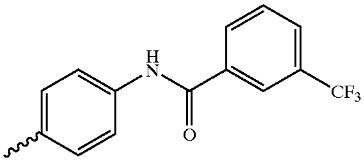 |
| 13 | 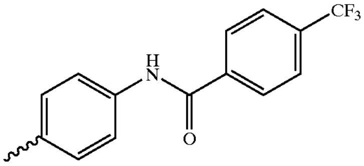 |
| 14 | 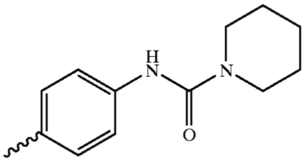 |
| 15 | 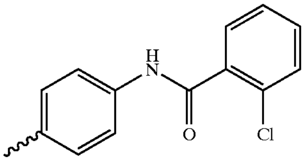 |
| 16 | 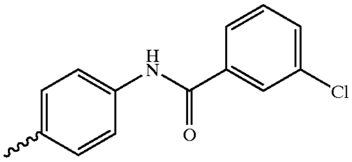 |
| 17 | 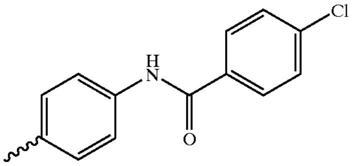 |

TABLE 11-continued
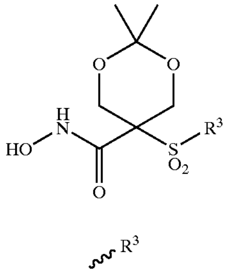
| | |
|---|---|
| 18 | 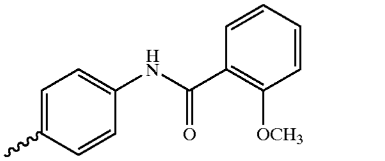 |
| 19 | 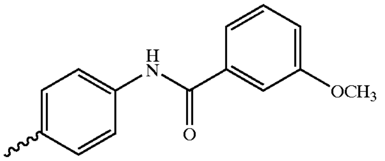 |
| 20 | 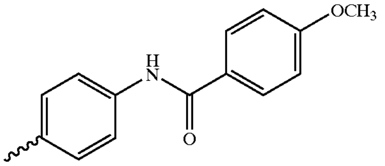 |
| 21 | 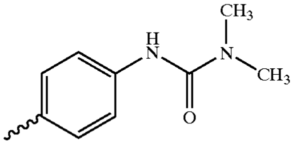 |
TABLE 12
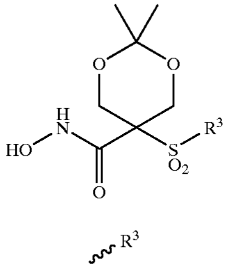
| | |
|---|---|
| 1 | 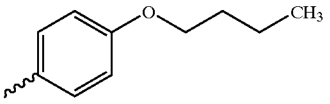 |
| 2 | 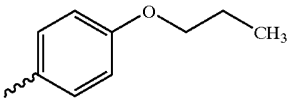 |
TABLE 12-continued
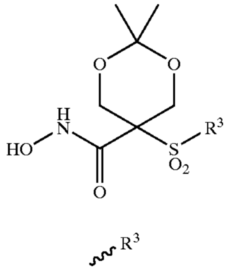
| | |
|---|---|
| 3 | 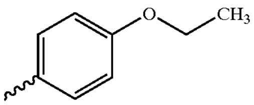 |
| 4 | 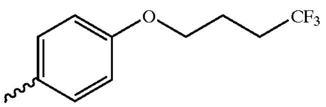 |
| 5 | 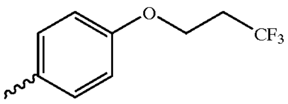 |
| 6 | 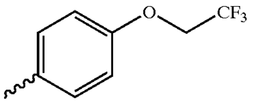 |
| 7 | 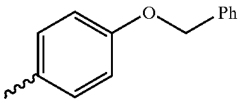 |
| 8 | 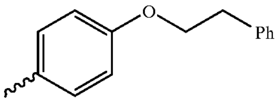 |
| 9 | 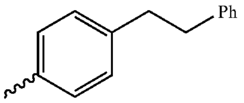 |
| 10 | 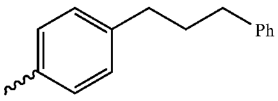 |
| 11 | 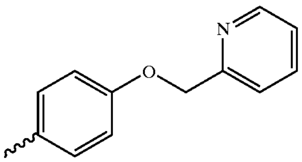 |
| 12 | 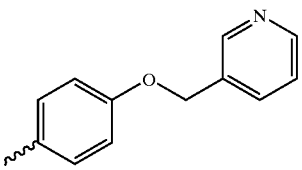 |

TABLE 12-continued
| | |
|---|---|
| 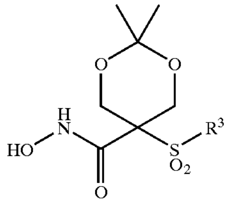 | |
| 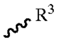 | |
| 13 | 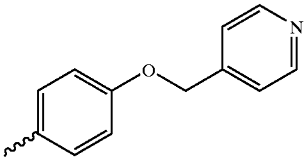 |
| 14 | 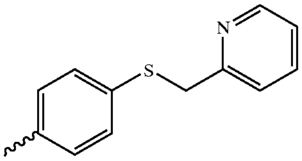 |
| 15 | 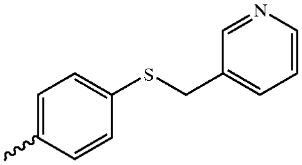 |
| 16 | 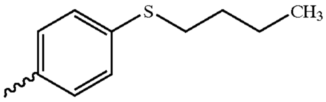 |
| 17 | 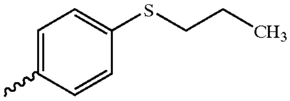 |
| 18 | 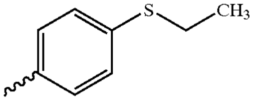 |
| 19 | 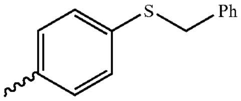 |
| 20 | 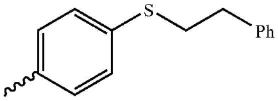 |
| 21 | 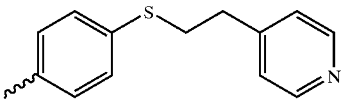 |
TABLE 12-continued
| | |
|---|---|
| 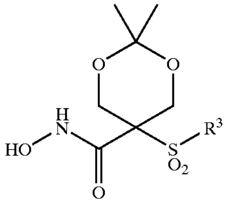 | |
| 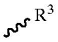 | |
| 22 | 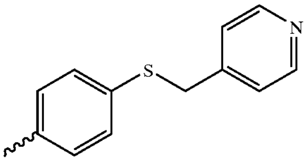 |
TABLE 13
| | |
|---|---|
| 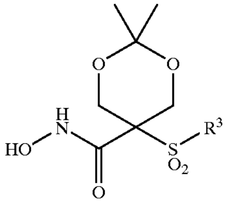 | |
| 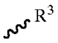 | |
| 1 | 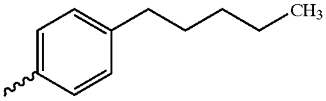 |
| 2 | 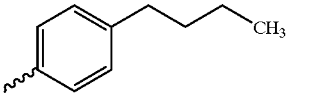 |
| 3 | 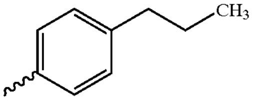 |
| 4 | 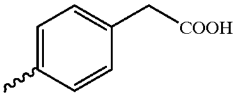 |
| 5 | 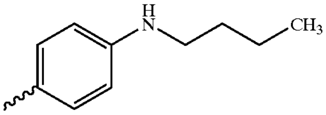 |
| 6 | 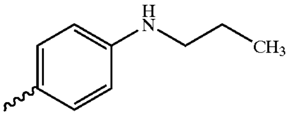 |

TABLE 13-continued
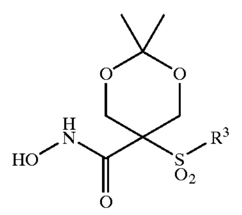
| | 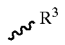 |
|---|---|
| 7 | 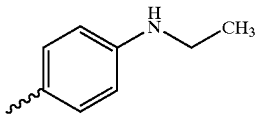 |
| 8 | 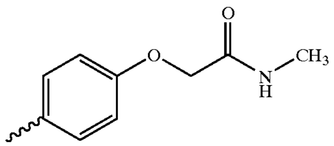 |
| 9 | 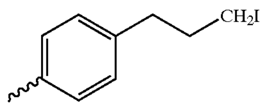 |
| 10 | 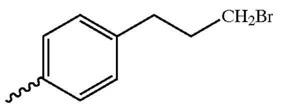 |
| 11 | 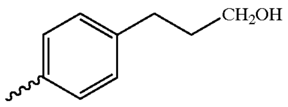 |
| 12 | 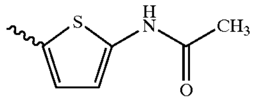 |
| 13 | 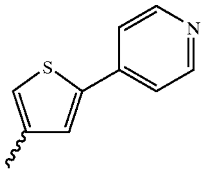 |
| 14 | 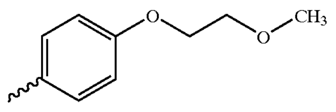 |
| 15 | 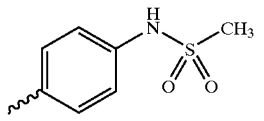 |
TABLE 13-continued
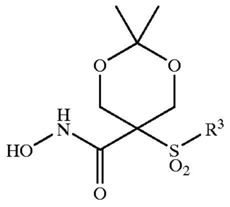
| | 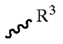 |
|---|---|
| 16 | 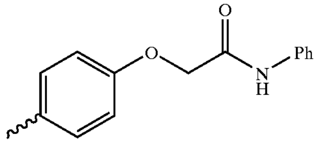 |
| 17 | 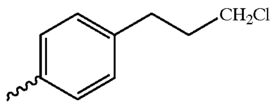 |
| 18 | 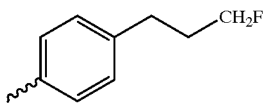 |
| 19 | 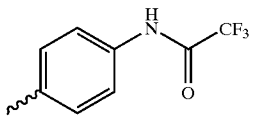 |
| 20 | 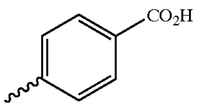 |
| 21 | 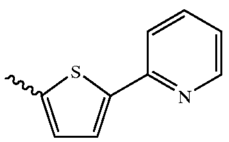 |
| 22 | 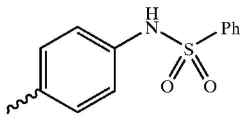 |
| 23 | 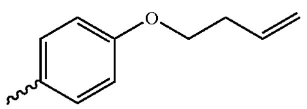 |
| 24 | 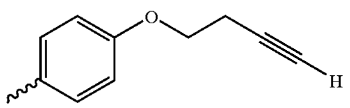 |
| 25 | 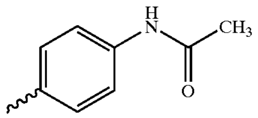 |

TABLE 13-continued
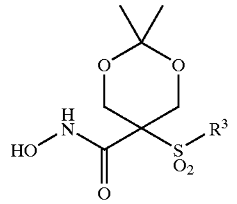
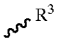
| | |
|---|---|
| 26 | 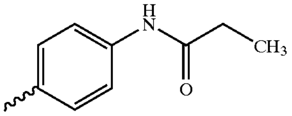 |
| 27 | 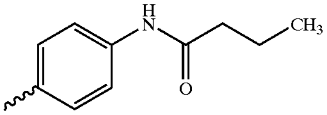 |
| 28 | 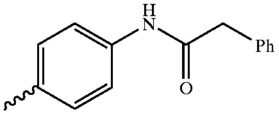 |
| 29 | 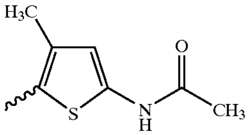 |
| 30 | 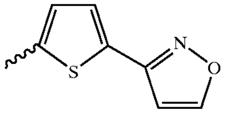 |
TABLE 14
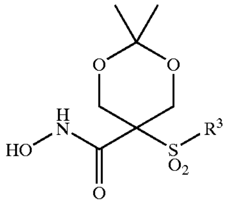
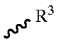
| | |
|---|---|
| 1 | 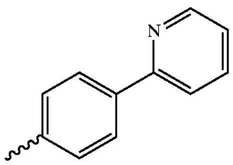 |
TABLE 14-continued
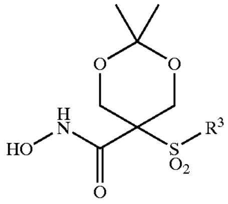
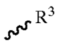
| | |
|---|---|
| 2 | 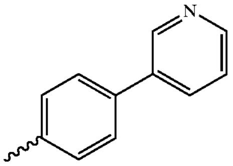 |
| 3 | 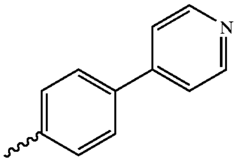 |
| 4 | 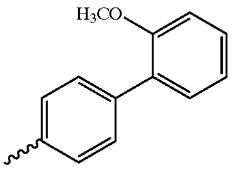 |
| 5 | 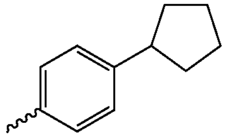 |
| 6 | 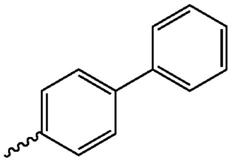 |
| 7 | 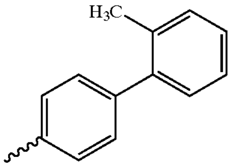 |
| 8 | 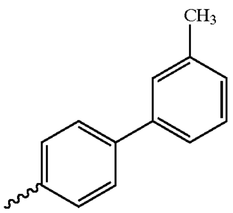 |

TABLE 14-continued
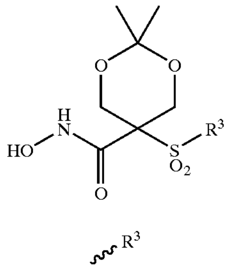
| | |
|---|---|
| 9 | 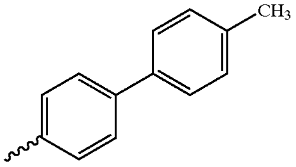 |
| 10 | 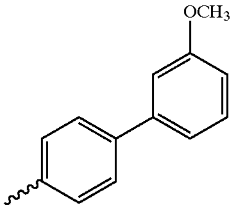 |
| 11 | 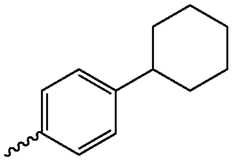 |
| 12 | 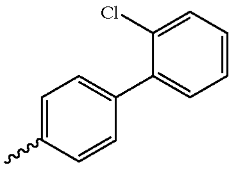 |
| 13 | 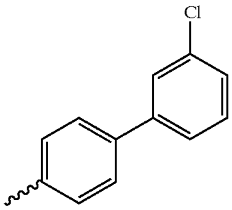 |
| 14 | 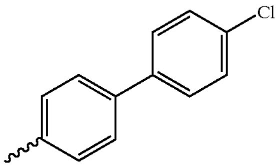 |
| 15 | 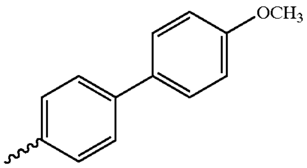 |
TABLE 14-continued
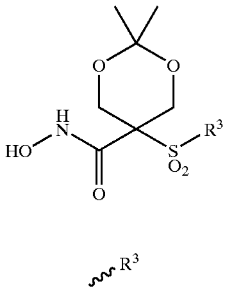
| | |
|---|---|
| 16 | 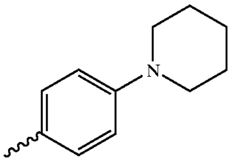 |
| 17 | 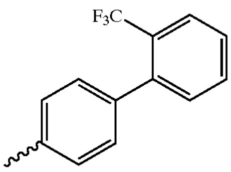 |
| 18 | 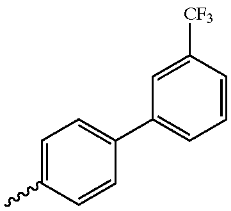 |
| 19 | 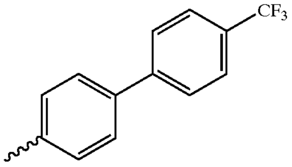 |
| 20 | 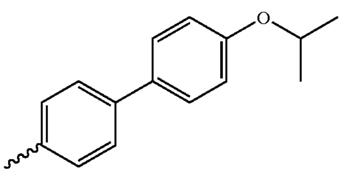 |
| 21 | 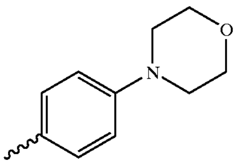 |

TABLE 15
| | |
|---|---|
| | 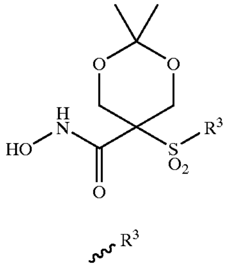 |
| 1 | 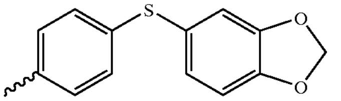 |
| 2 | 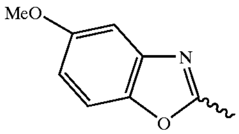 |
| 3 | 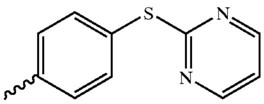 |
| 4 | 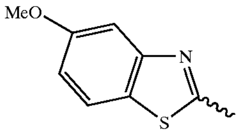 |
| 5 | 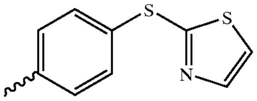 |
| 6 | 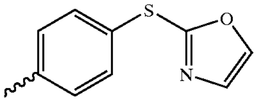 |
| 7 | 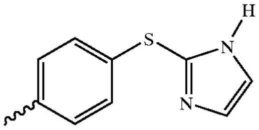 |
| 8 | 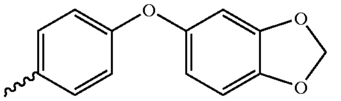 |
| 9 | 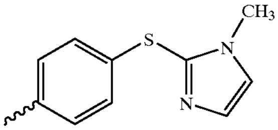 |
| 10 | 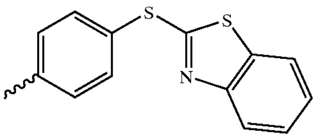 |
TABLE 15-continued
| | |
|---|---|
| | 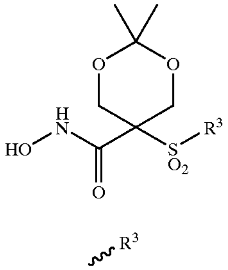 |
| 11 | 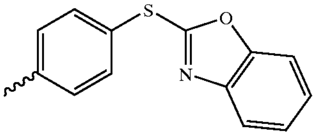 |
TABLE 16
| | |
|---|---|
| | 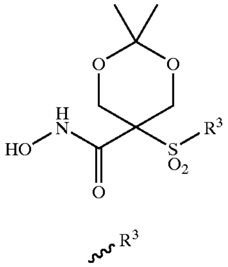 |
| 1 | 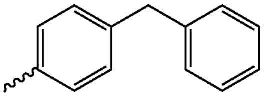 |
| 2 | 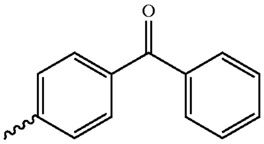 |
| 3 | 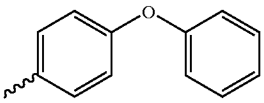 |
| 4 | 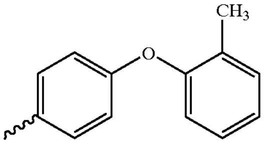 |
| 5 | 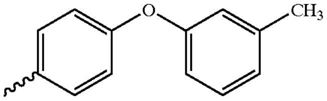 |
| 6 | 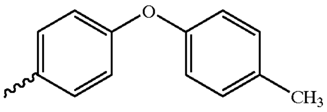 |

TABLE 16-continued
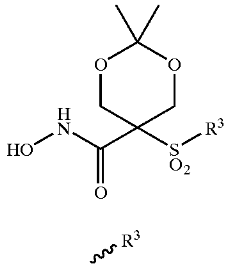
| | |
|---|---|
| 7 | 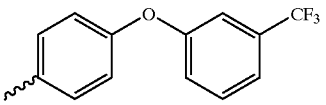 |
| 8 | 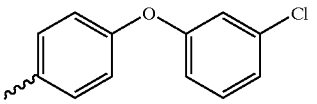 |
| 9 | 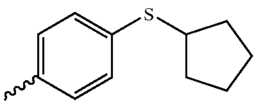 |
| 10 | 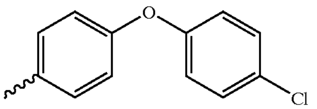 |
| 11 | 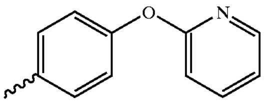 |
| 12 | 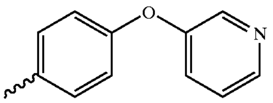 |
| 13 | 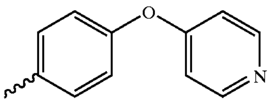 |
| 14 | 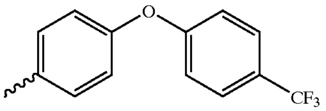 |
| 15 | 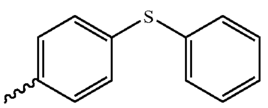 |
| 16 | 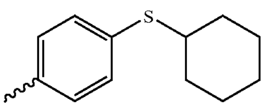 |
| 17 | 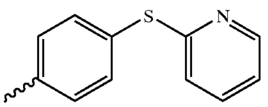 |
TABLE 16-continued
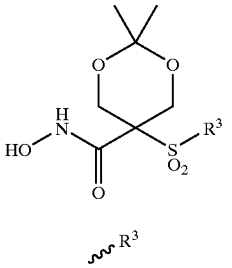
| | |
|---|---|
| 18 | 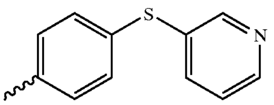 |
| 19 | 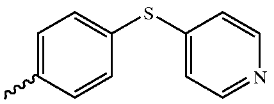 |
| 20 | 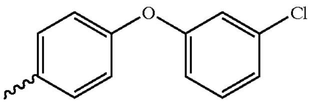 |
| 21 | 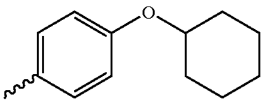 |
TABLE 17
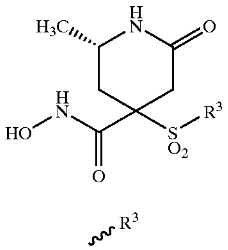
| | |
|---|---|
| 1 | 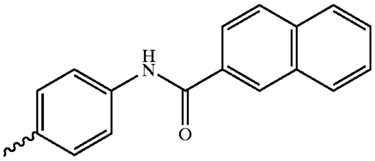 |
| 2 | 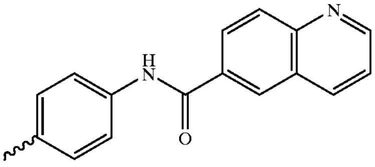 |
| 3 | 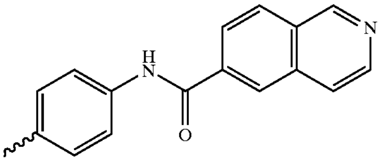 |

TABLE 17-continued
| 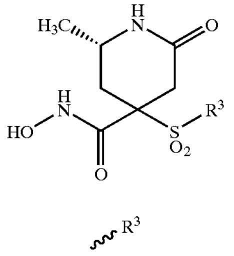 | |
|---|---|
| 4 | 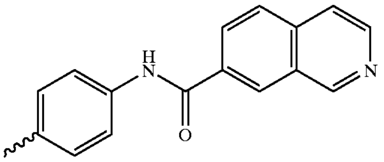 |
| 5 | 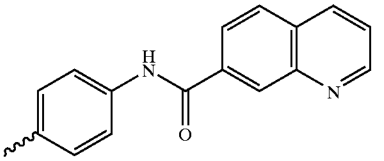 |
| 6 | 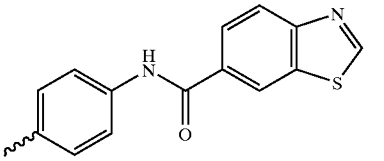 |
| 7 | 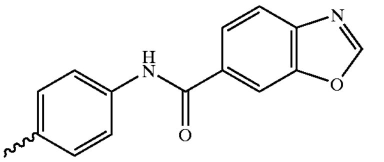 |
| 8 | 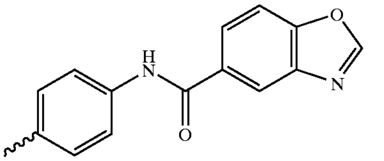 |
| 9 | 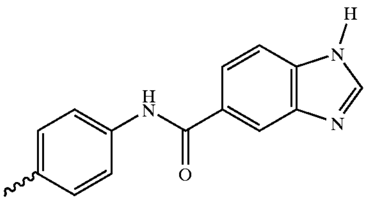 |
| 10 | 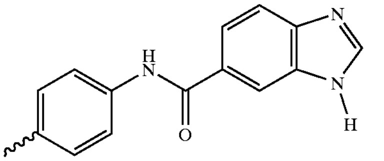 |
TABLE 17-continued
| 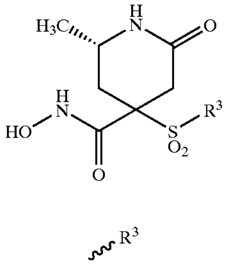 | |
|---|---|
| 11 | 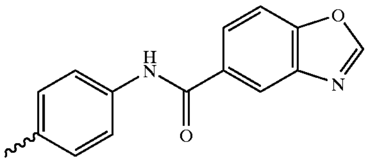 |
| 12 | 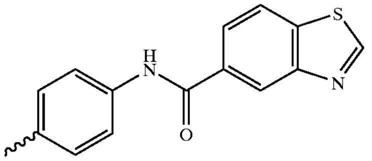 |
| 13 | 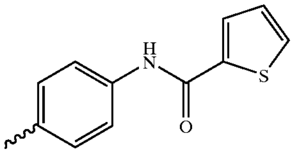 |
| 14 | 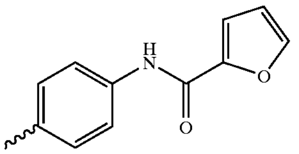 |
| 15 | 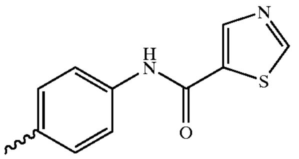 |
| 16 | 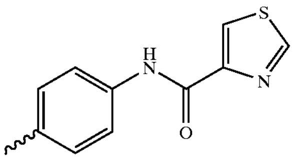 |
| 17 | 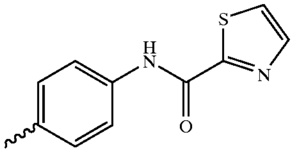 |

TABLE 17-continued
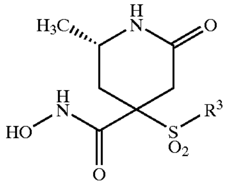
18
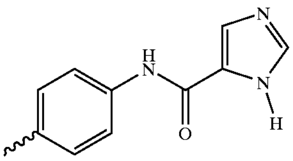
TABLE 18
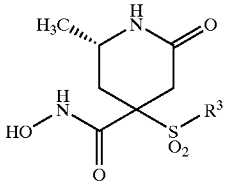
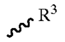
1
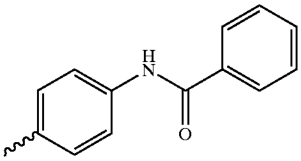
2
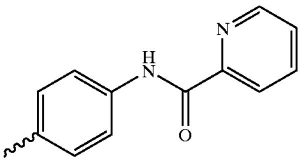
3
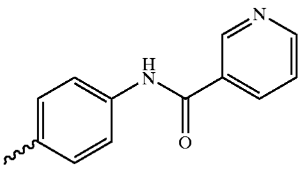
4
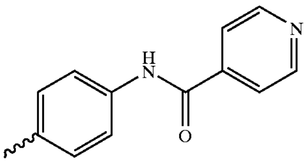
TABLE 18-continued
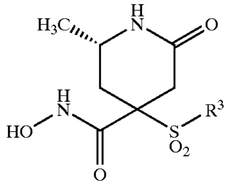
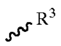
5
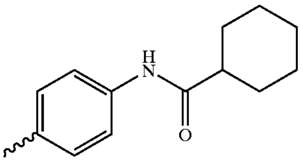
6
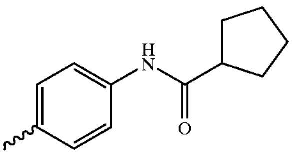
7
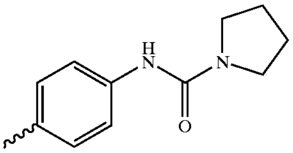
8
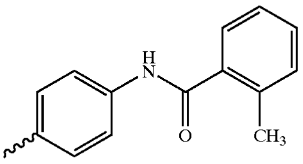
9
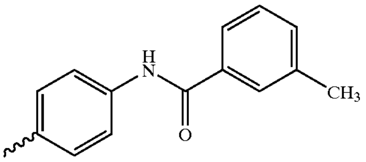
10
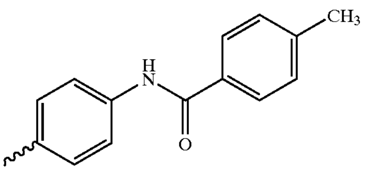
11
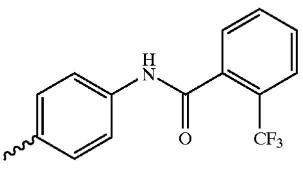

TABLE 18-continued
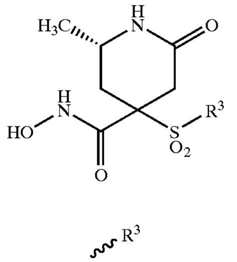
| | |
|---|---|
| 12 | 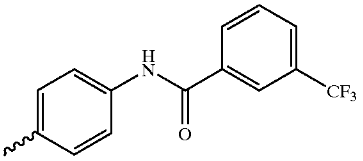 |
| 13 | 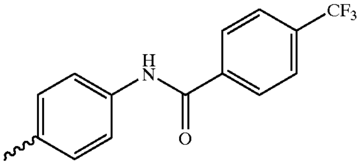 |
| 14 | 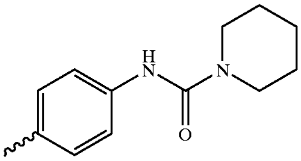 |
| 15 | 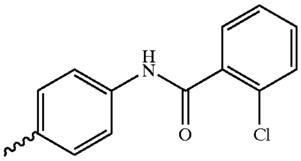 |
| 16 | 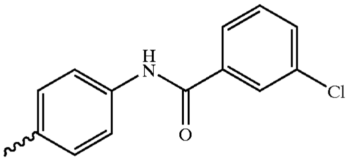 |
| 17 | 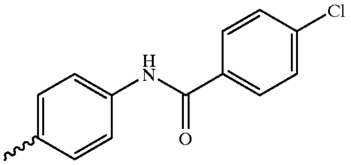 |
| 18 | 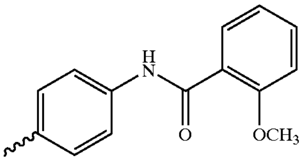 |
TABLE 18-continued
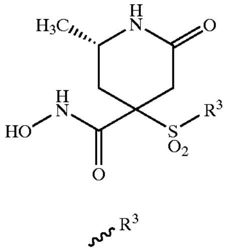
| | |
|---|---|
| 19 | 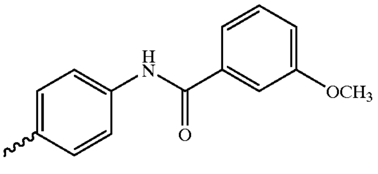 |
| 20 | 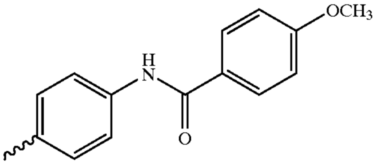 |
| 21 | 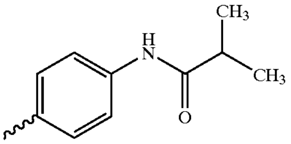 |
TABLE 19
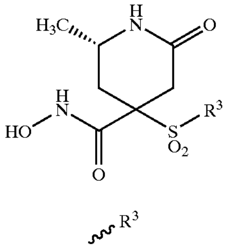
| | |
|---|---|
| 1 | 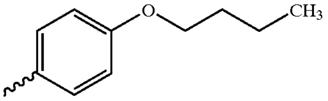 |
| 2 | 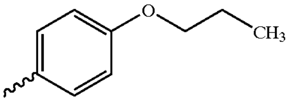 |
| 3 | 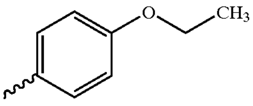 |
| 4 | 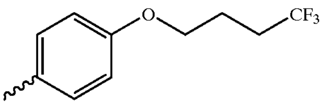 |

TABLE 19-continued
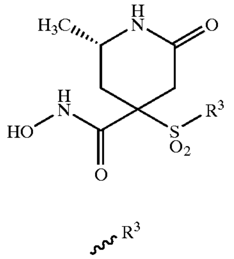
| | |
|---|---|
| 5 | 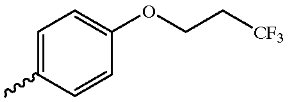 |
| 6 | 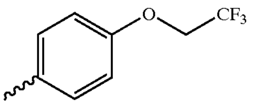 |
| 7 | 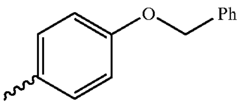 |
| 8 | 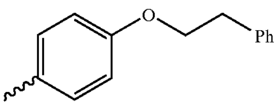 |
| 9 | 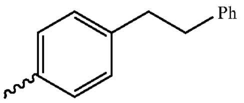 |
| 10 | 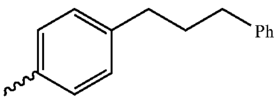 |
| 11 | 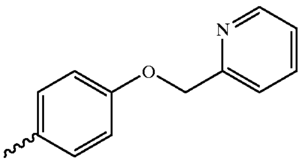 |
| 12 | 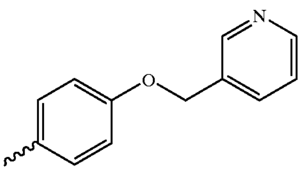 |
| 13 | 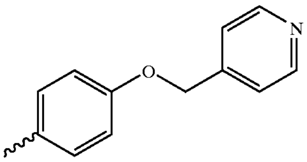 |
TABLE 19-continued
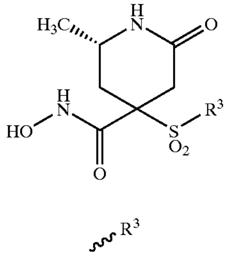
| | |
|---|---|
| 14 | 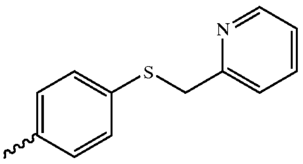 |
| 15 | 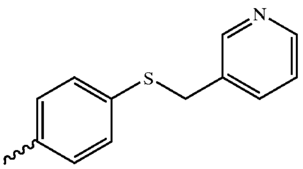 |
| 16 | 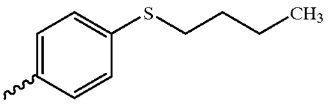 |
| 17 | 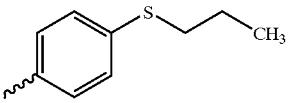 |
| 18 | 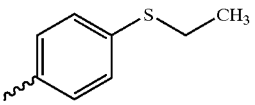 |
| 19 | 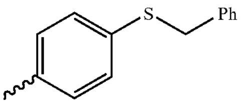 |
| 20 | 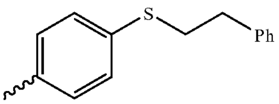 |
| 21 | 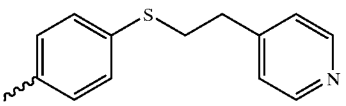 |
| 22 | 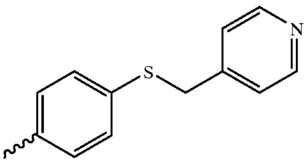 |

TABLE 20
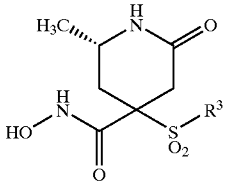
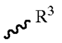
| | |
|---|---|
| 1 | 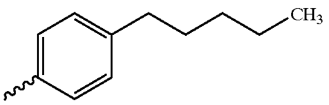 |
| 2 | 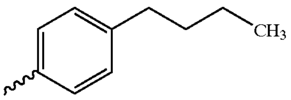 |
| 3 | 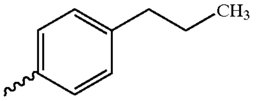 |
| 4 | 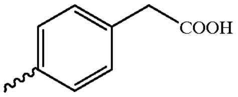 |
| 5 | 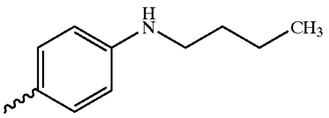 |
| 6 | 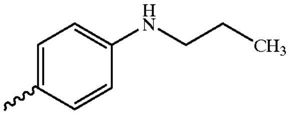 |
| 7 | 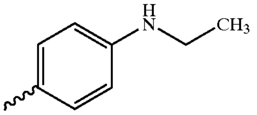 |
| 8 | 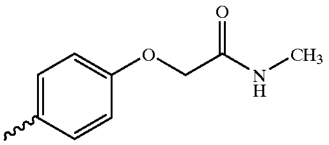 |
| 9 | 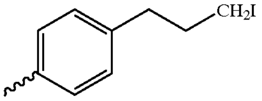 |
| 10 | 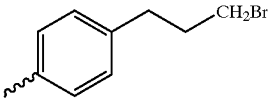 |
TABLE 20-continued
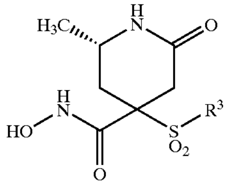
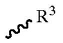
| | |
|---|---|
| 11 | 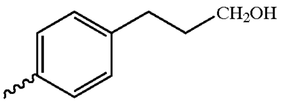 |
| 12 | 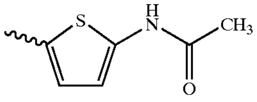 |
| 13 | 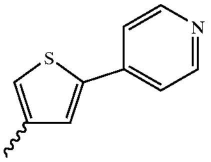 |
| 14 | 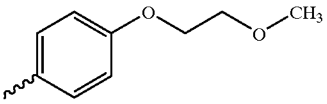 |
| 15 | 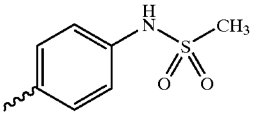 |
| 16 | 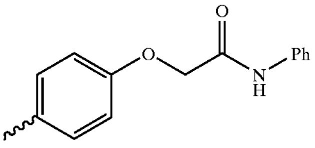 |
| 17 | 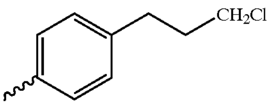 |
| 18 | 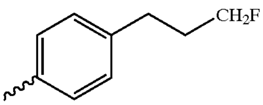 |
| 19 | 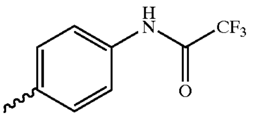 |
| 20 | 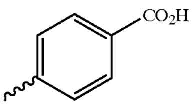 |

TABLE 20-continued
| | |
|---|---|
| | 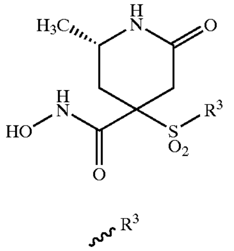 |
| 21 | 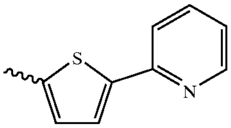 |
| 22 | 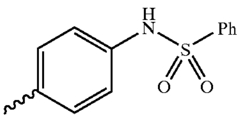 |
| 23 | 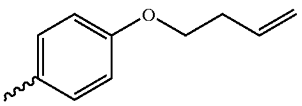 |
| 24 | 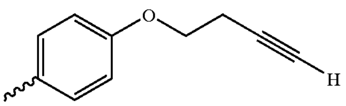 |
| 25 | 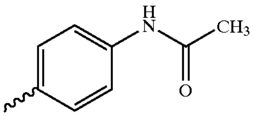 |
| 26 | 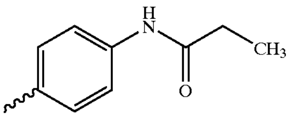 |
| 27 | 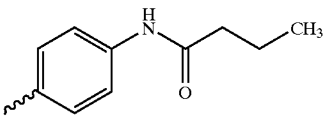 |
| 28 | 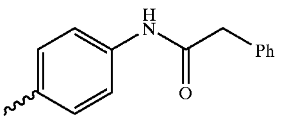 |
| 29 | 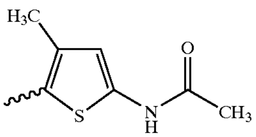 |
| 30 | 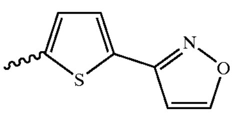 |
TABLE 21
| | |
|---|---|
| | 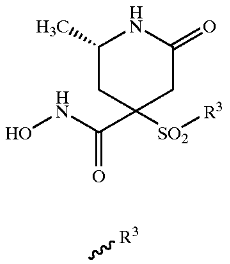 |
| 1 | 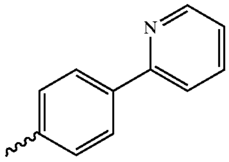 |
| 2 | 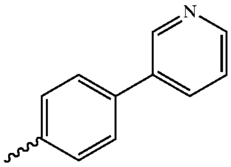 |
| 3 | 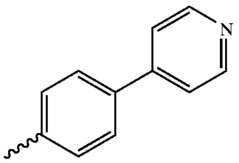 |
| 4 | 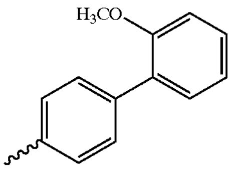 |
| 5 | 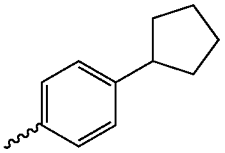 |
| 6 | 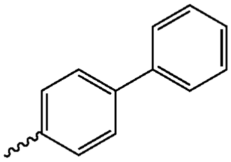 |
| 7 | 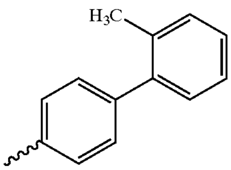

TABLE 21-continued
| | |
|---|---|
| | 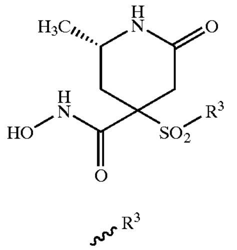 |
| 8 | 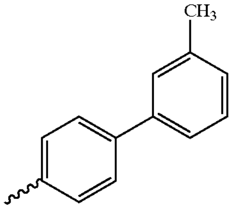 |
| 9 | 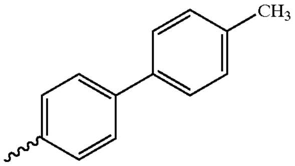 |
| 10 | 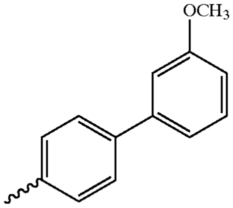 |
| 11 | 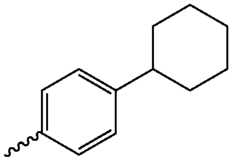 |
| 12 | 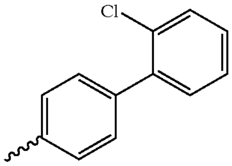 |
| 13 | 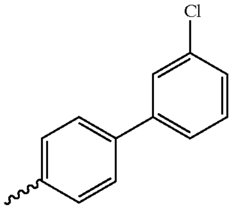 |
| 14 | 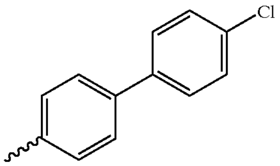 |
TABLE 21-continued
| | |
|---|---|
| | 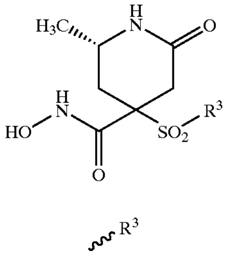 |
| 15 | 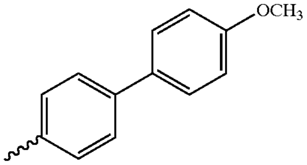 |
| 16 | 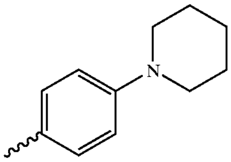 |
| 17 | 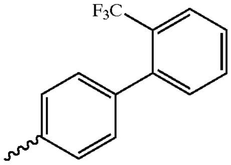 |
| 18 | 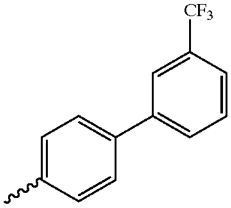 |
| 19 | 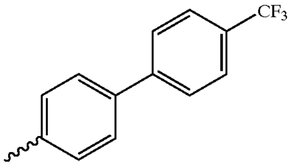 |
| 20 | 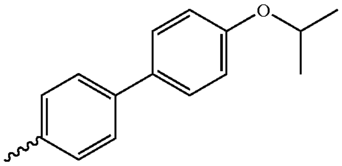 |
| 21 | 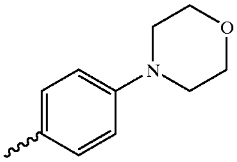 |

TABLE 22
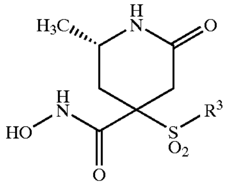
| 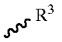 | |
|---|---|
| 1 | 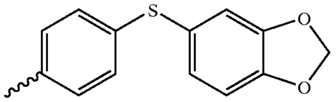 |
| 2 | 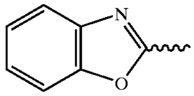 |
| 3 | 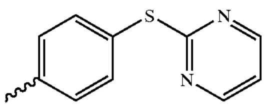 |
| 4 | 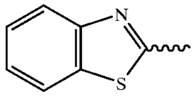 |
| 5 | 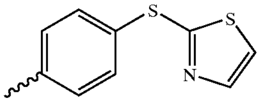 |
| 6 | 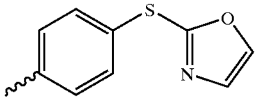 |
| 7 | 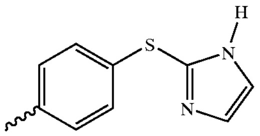 |
| 8 | 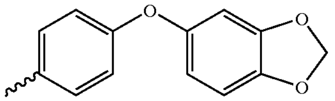 |
| 9 | 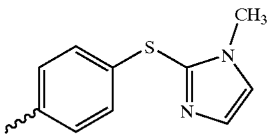 |
| 10 | 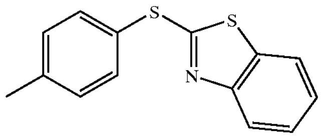 |
TABLE 22-continued
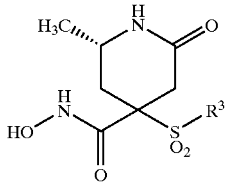
| 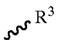 | |
|---|---|
| 11 | 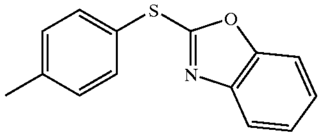 |
TABLE 23
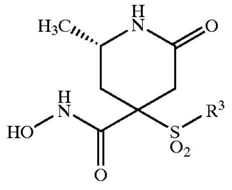
| 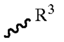 | |
|---|---|
| 1 | 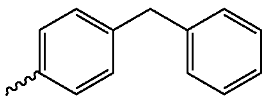 |
| 2 | 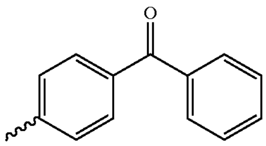 |
| 3 | 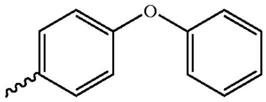 |
| 4 | 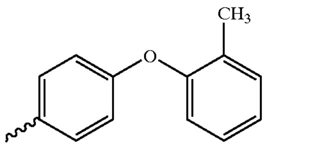 |
| 5 | 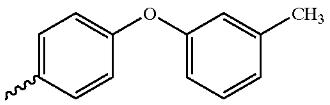 |
| 6 | 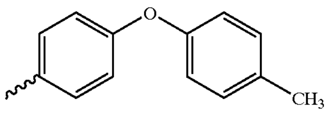 |

TABLE 23-continued
| 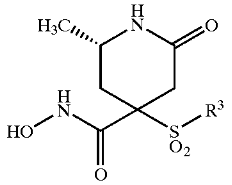 | |
|---|---|
| 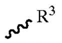 | |
| 7 | 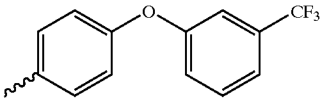 |
| 8 | 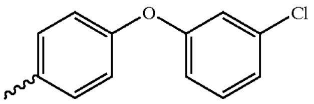 |
| 9 | 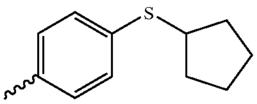 |
| 10 | 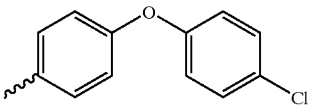 |
| 11 | 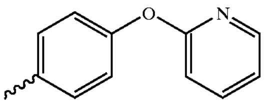 |
| 12 | 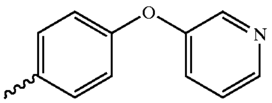 |
| 13 | 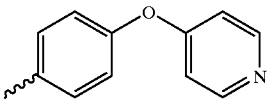 |
| 14 | 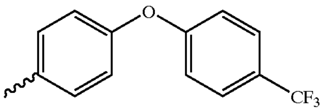 |
| 15 | 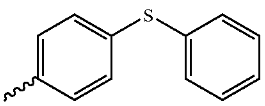 |
| 16 | 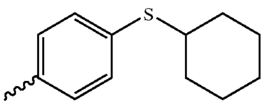 |
| 17 | 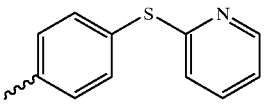 |
TABLE 23-continued
| 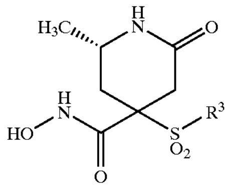 | |
|---|---|
| 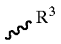 | |
| 18 | 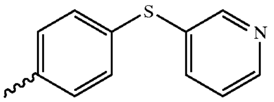 |
| 19 | 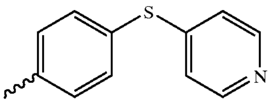 |
| 20 | 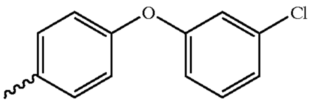 |
| 21 | 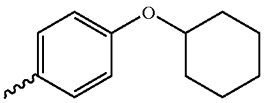 |
TABLE 24
| 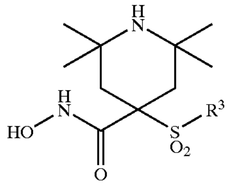 | |
|---|---|
| 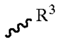 | |
| 1 | 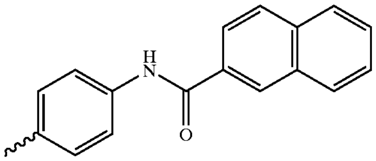 |
| 2 | 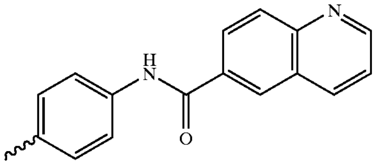 |
| 3 | 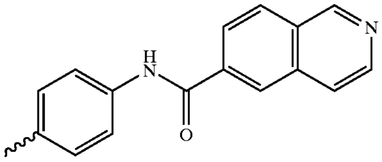 |

TABLE 24-continued
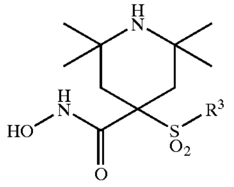
| 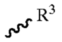 | |
|---|---|
| 4 | 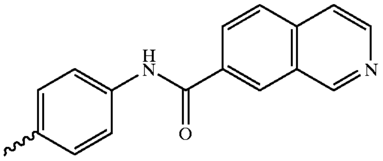 |
| 5 | 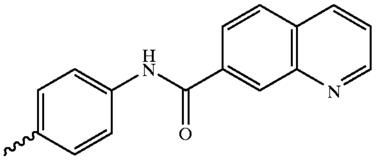 |
| 6 | 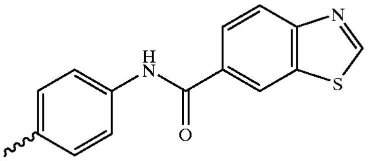 |
| 7 | 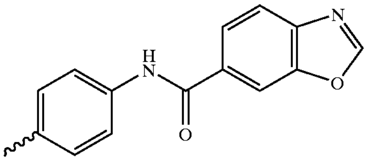 |
| 8 | 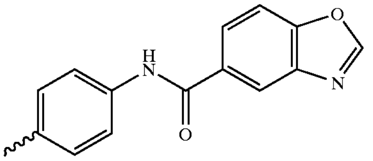 |
| 9 | 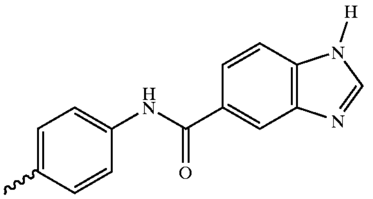 |
| 10 | 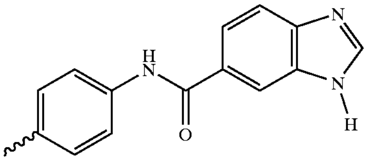 |
TABLE 24-continued
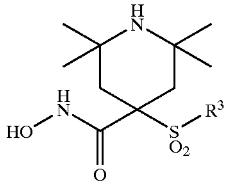
| 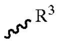 | |
|---|---|
| 11 | 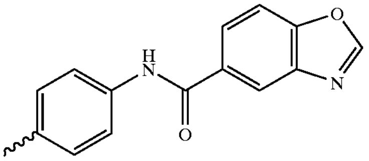 |
| 12 | 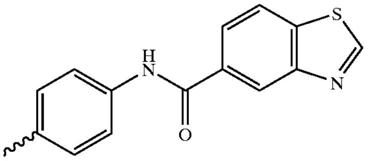 |
| 13 | 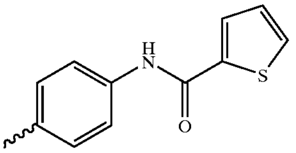 |
| 14 | 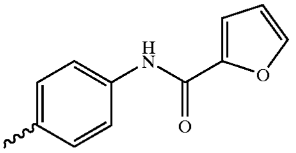 |
| 15 | 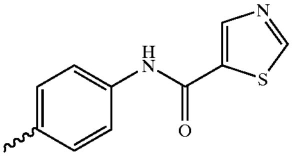 |
| 16 | 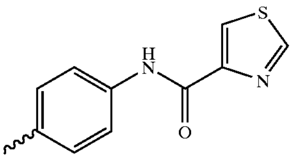 |
| 17 | 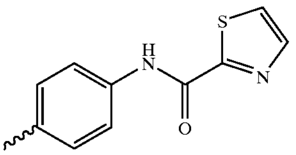 |

TABLE 24-continued
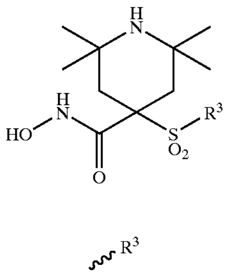
| | |
|---|---|
| 18 | 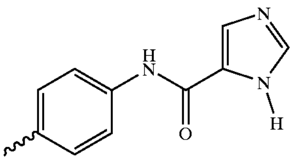 |
TABLE 25
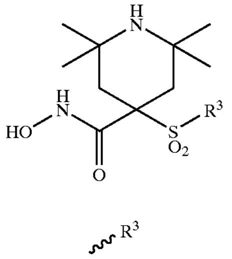
| | |
|---|---|
| 1 | 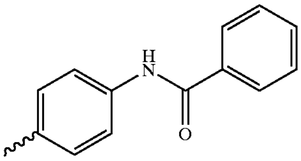 |
| 2 | 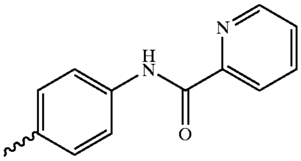 |
| 3 | 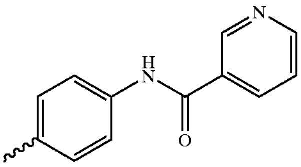 |
| 4 | 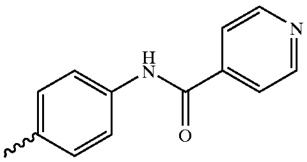 |
TABLE 25-continued
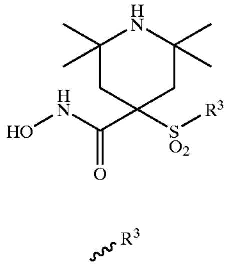
| | |
|---|---|
| 5 | 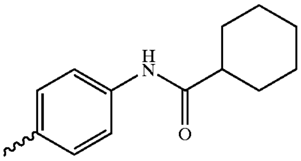 |
| 6 | 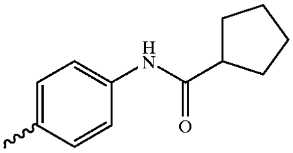 |
| 7 | 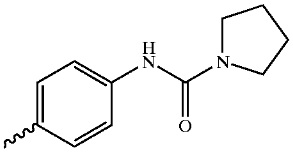 |
| 8 | 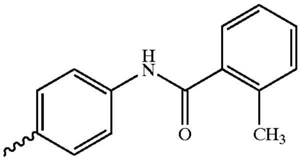 |
| 9 | 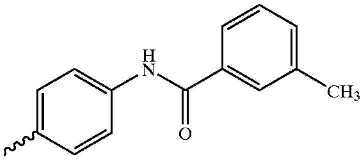 |
| 10 | 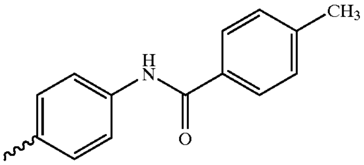 |
| 11 | 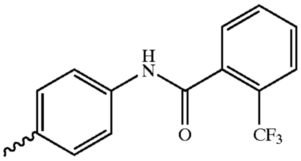 |

TABLE 25-continued
| | 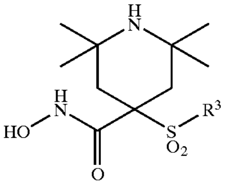 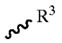 |
|---|---|
| 12 | 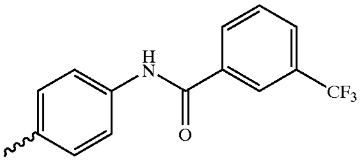 |
| 13 | 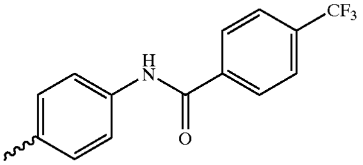 |
| 14 | 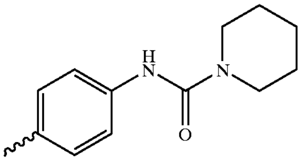 |
| 15 | 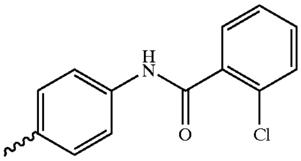 |
| 16 | 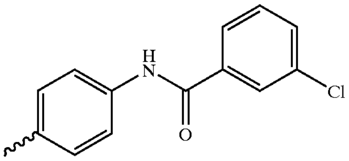 |
| 17 | 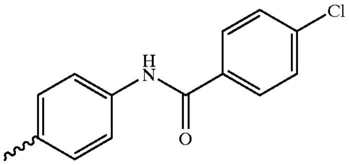 |
| 18 | 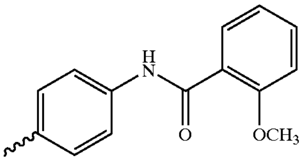 |
TABLE 25-continued
| | 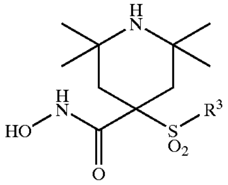 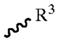 |
|---|---|
| 19 | 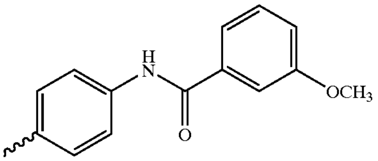 |
| 20 | 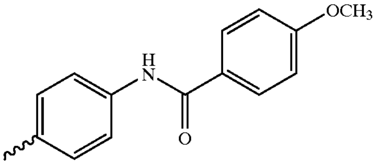 |
| 21 | 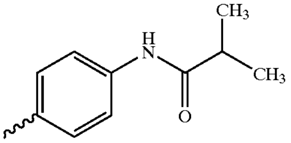 |
TABLE 26
| | 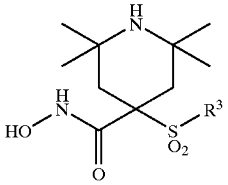 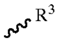 |
|---|---|
| 1 | 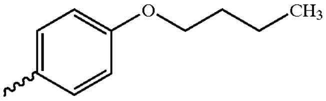 |
| 2 | 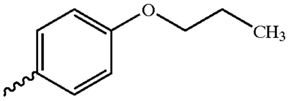 |
| 3 | 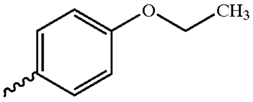 |
| 4 | 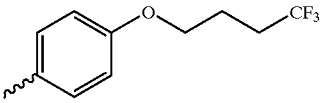 |

TABLE 26-continued
| | 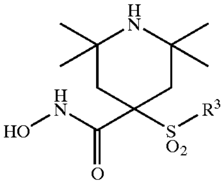 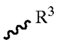 |
|---|---|
| 5 | 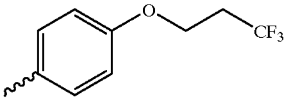 |
| 6 | 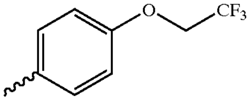 |
| 7 | 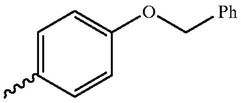 |
| 8 | 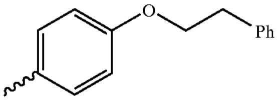 |
| 9 | 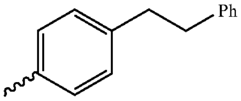 |
| 10 | 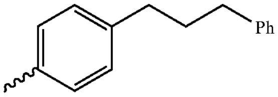 |
| 11 | 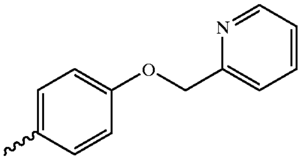 |
| 12 | 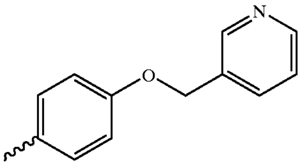 |
| 13 | 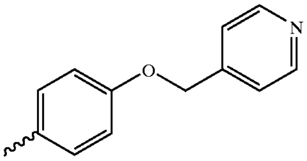 |
TABLE 26-continued
| | 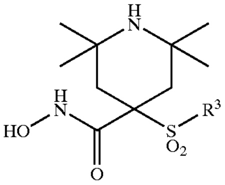 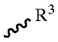 |
|---|---|
| 14 | 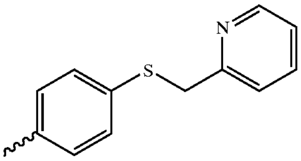 |
| 15 | 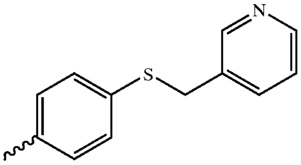 |
| 16 | 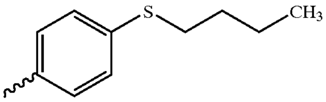 |
| 17 | 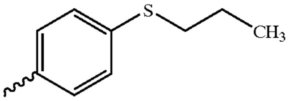 |
| 18 | 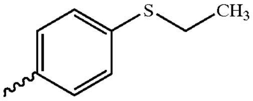 |
| 19 | 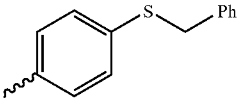 |
| 20 | 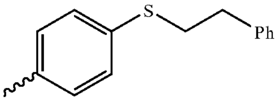 |
| 21 | 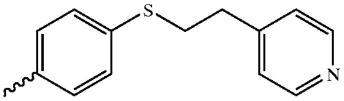 |
| 22 | 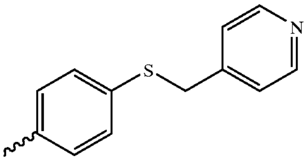 |

TABLE 27
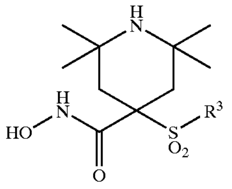
| | 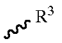 |
|---|---|
| 1 | 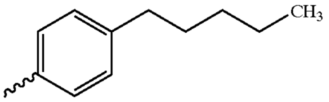 |
| 2 | 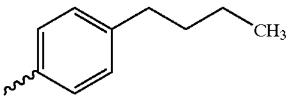 |
| 3 | 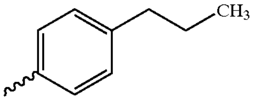 |
| 4 | 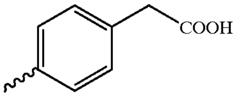 |
| 5 | 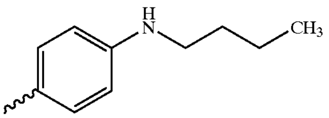 |
| 6 | 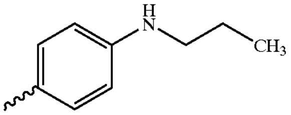 |
| 7 | 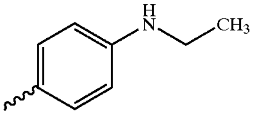 |
| 8 | 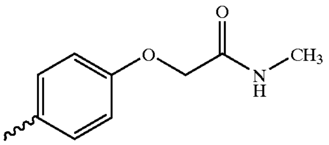 |
| 9 | 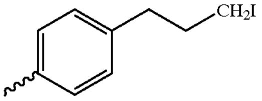 |
| 10 | 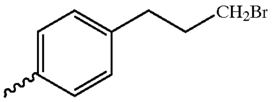 |
TABLE 27-continued
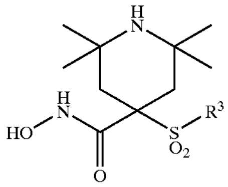
| | 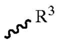 |
|---|---|
| 11 | 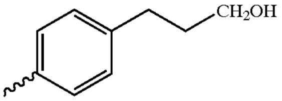 |
| 12 | 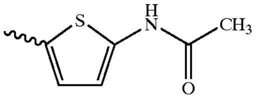 |
| 13 | 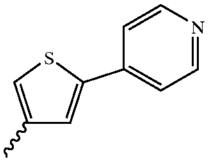 |
| 14 | 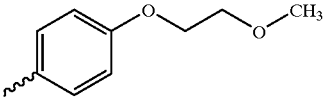 |
| 15 | 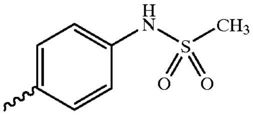 |
| 16 | 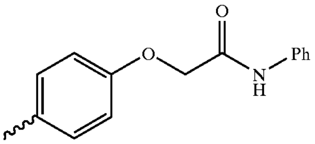 |
| 17 | 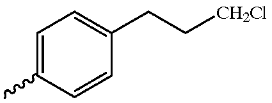 |
| 18 | 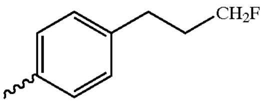 |
| 19 | 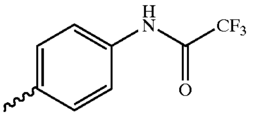 |
| 20 | 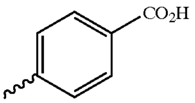 |

TABLE 27-continued
| | 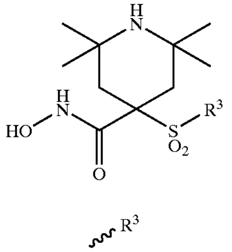 |
|---|---|
| 21 | 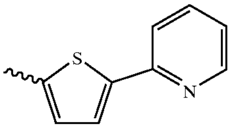 |
| 22 | 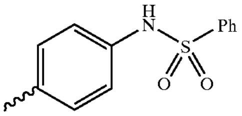 |
| 23 | 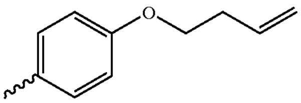 |
| 24 | 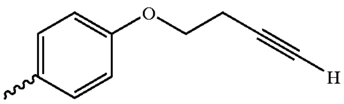 |
| 25 | 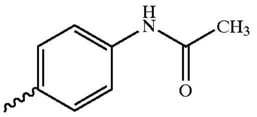 |
| 26 | 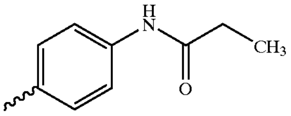 |
| 27 | 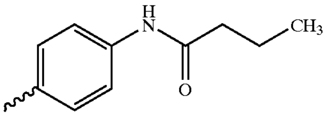 |
| 28 | 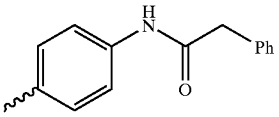 |
| 29 | 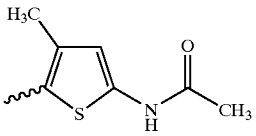 |
| 30 | 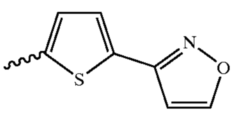 |
TABLE 28
| | 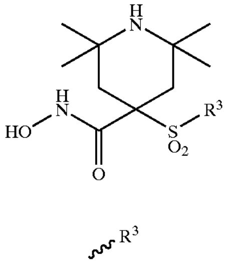 |
|---|---|
| 1 | 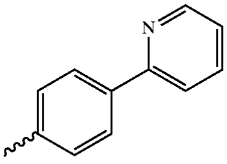 |
| 2 | 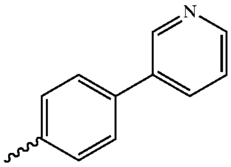 |
| 3 | 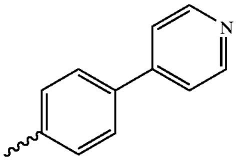 |
| 4 | 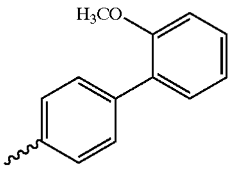 |
| 5 | 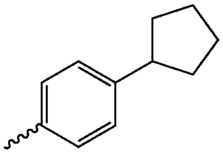 |
| 6 | 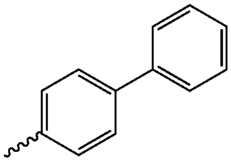 |
| 7 | 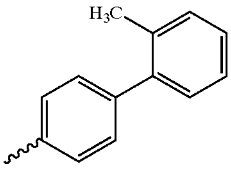 |

TABLE 28-continued
| | 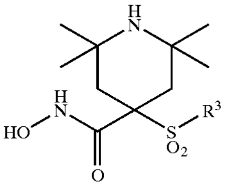 |
|---|---|
| | 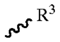 |
| 8 | 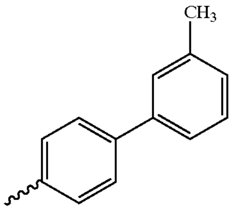 |
| 9 | 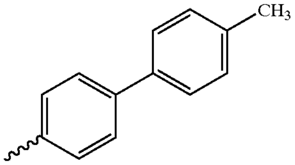 |
| 10 | 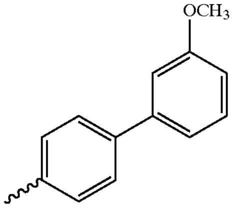 |
| 11 | 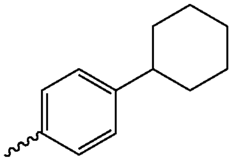 |
| 12 | 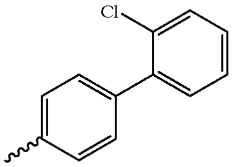 |
| 13 | 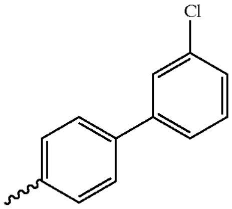 |
| 14 | 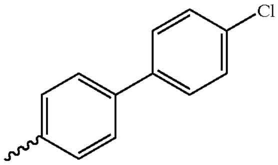 |
TABLE 28-continued
| | 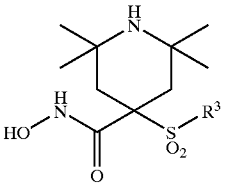 |
|---|---|
| | 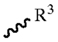 |
| 15 | 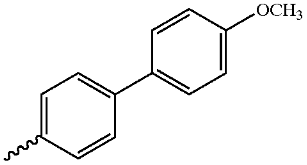 |
| 16 | 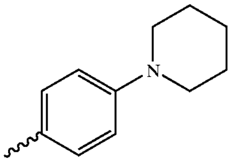 |
| 17 | 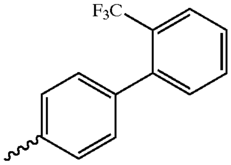 |
| 18 | 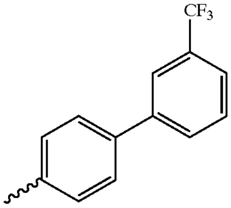 |
| 19 | 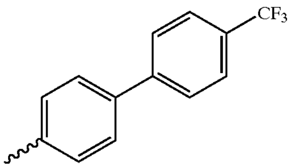 |
| 20 | 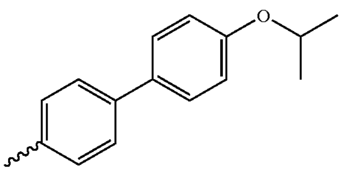 |
| 21 | 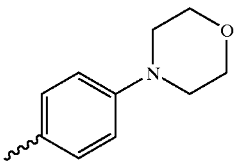 |

TABLE 29
| | |
|---|---|
| | 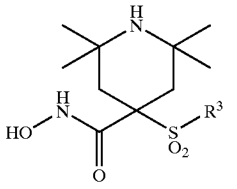 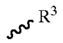 |
| 1 | 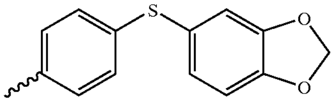 |
| 2 | 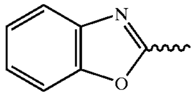 |
| 3 | 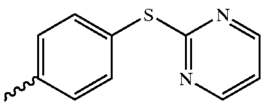 |
| 4 | 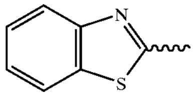 |
| 5 | 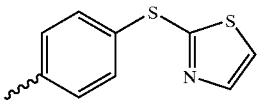 |
| 6 | 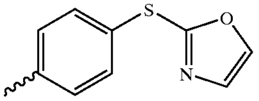 |
| 7 | 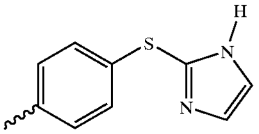 |
| 8 | 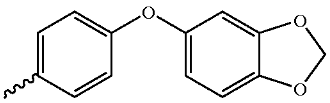 |
| 9 | 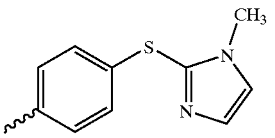 |
| 10 | 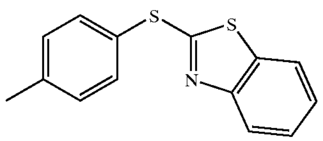 |
TABLE 29-continued
| | |
|---|---|
| | 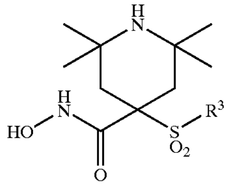 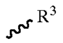 |
| 11 | 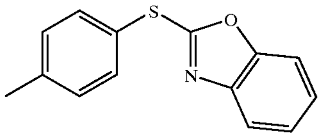 |
TABLE 30
| | |
|---|---|
| | 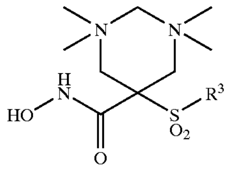 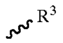 |
| 1 | 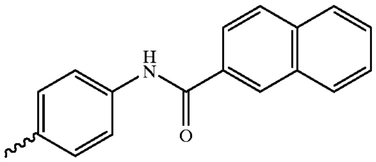 |
| 2 | 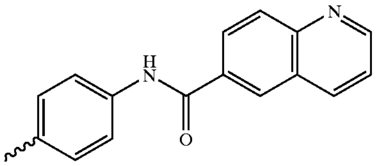 |
| 3 | 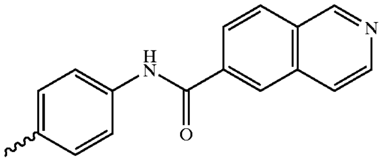 |
| 4 | 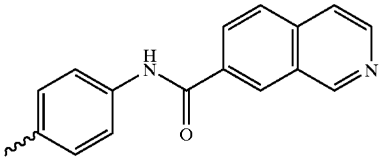 |
| 5 | 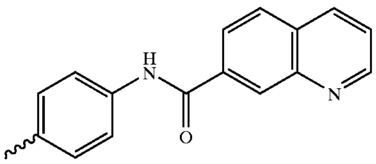 |

TABLE 30-continued
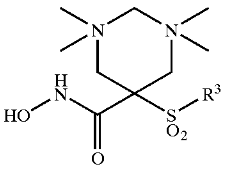
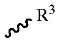
6
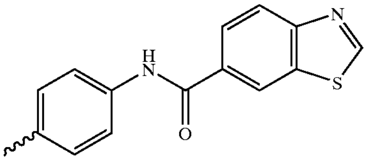
7
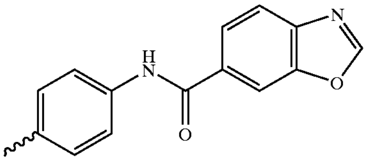
8
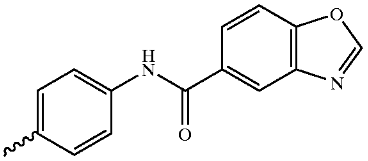
9
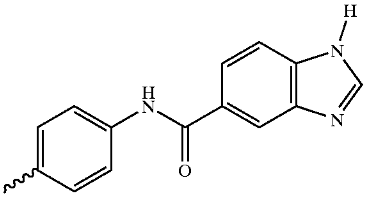
10
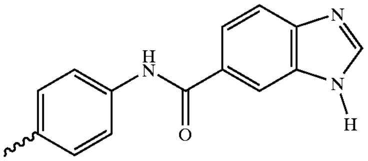
11
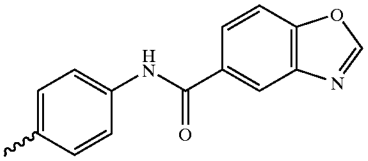
12
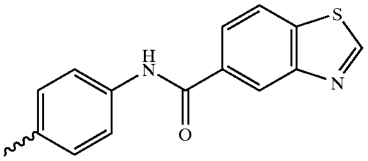
TABLE 30-continued
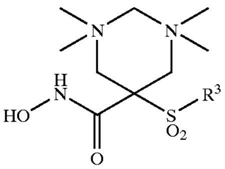
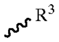
13
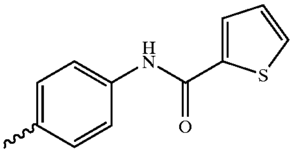
14
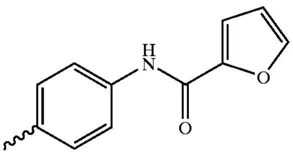
15
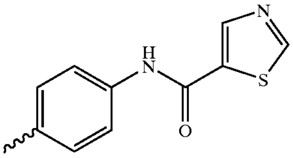
16
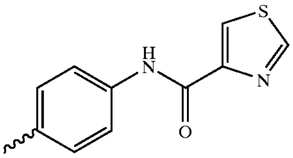
17
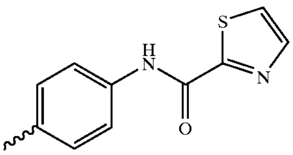
18
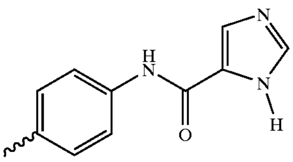

TABLE 31
| | |
|---|---|
| | 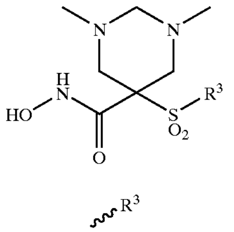 |
| 1 | 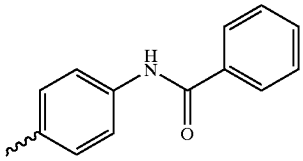 |
| 2 | 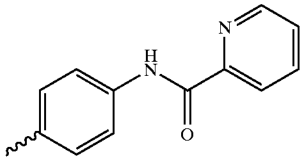 |
| 3 | 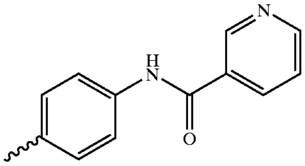 |
| 4 | 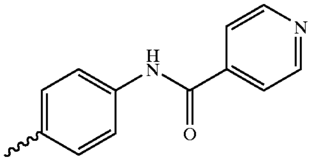 |
| 5 | 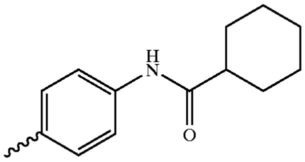 |
| 6 | 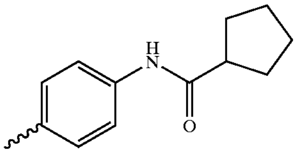 |
| 7 | 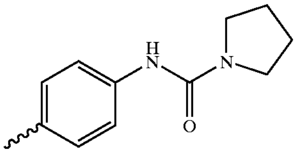 |
| 8 | 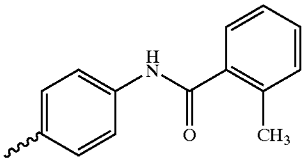 |
TABLE 31-continued
| | |
|---|---|
| | 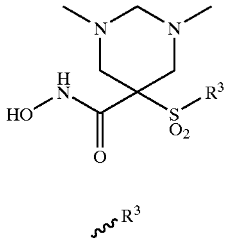 |
| 9 | 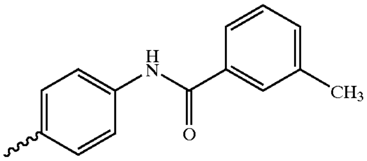 |
| 10 | 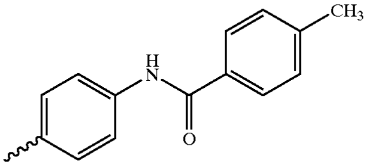 |
| 11 | 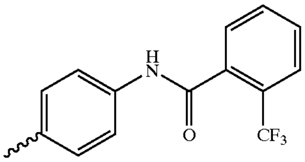 |
| 12 | 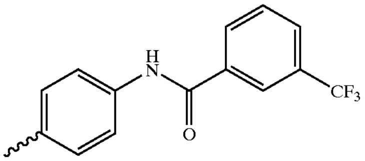 |
| 13 | 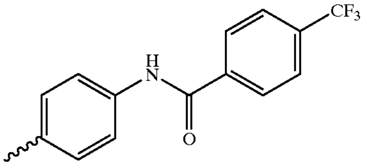 |
| 14 | 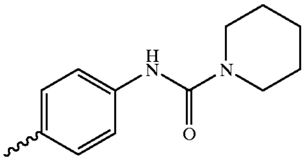 |
| 15 | 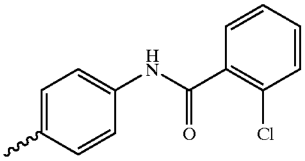 |

TABLE 31-continued
| | |
|---|---|
| 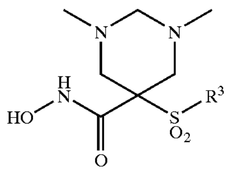 | |
| 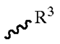 | |
| 16 | 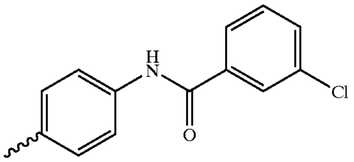 |
| 17 | 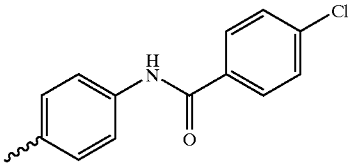 |
| 18 | 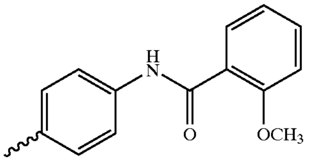 |
| 19 | 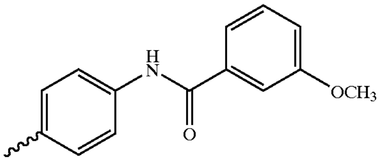 |
| 20 | 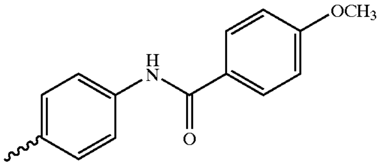 |
| 21 | 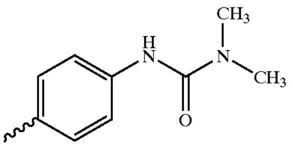 |
TABLE 32
| | |
|---|---|
| 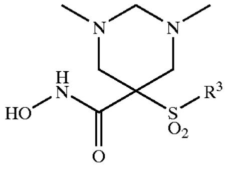 | |
| 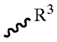 | |
| 1 | 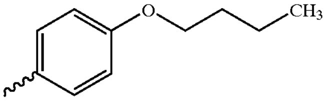 |
| 2 | 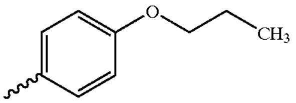 |
| 3 | 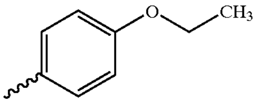 |
| 4 | 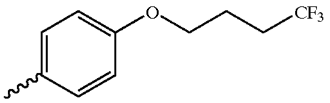 |
| 5 | 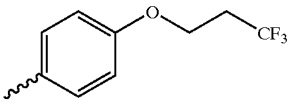 |
| 6 | 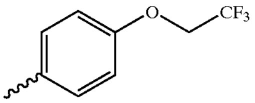 |
| 7 | 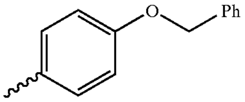 |
| 8 | 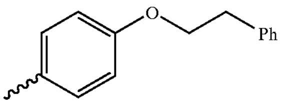 |
| 9 | 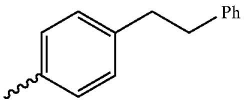 |
| 10 | 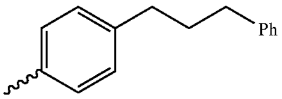 |
| 11 | 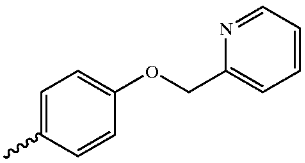 |

TABLE 32-continued
| | |
|---|---|
| | 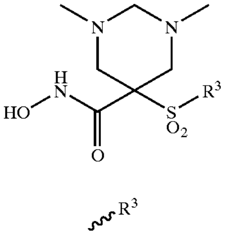 |
| 12 | 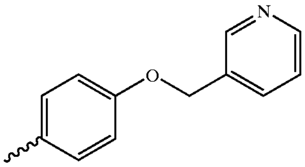 |
| 13 | 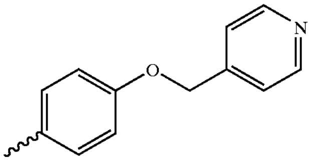 |
| 14 | 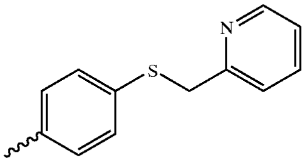 |
| 15 | 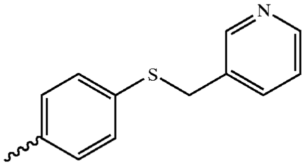 |
| 16 | 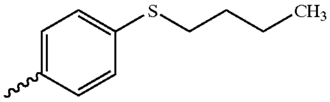 |
| 17 | 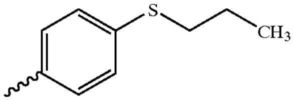 |
| 18 | 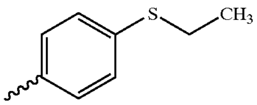 |
| 19 | 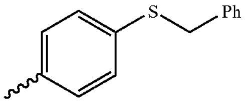 |
| 20 | 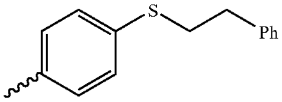 |
TABLE 32-continued
| | |
|---|---|
| | 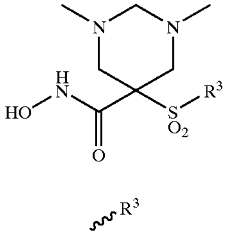 |
| 21 | 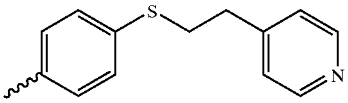 |
| 22 | 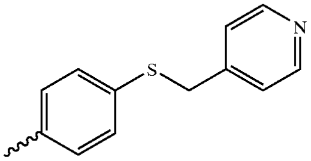 |
TABLE 33
| | |
|---|---|
| | 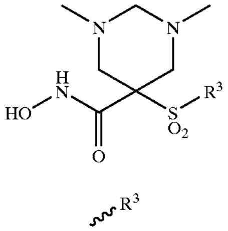 |
| 1 | 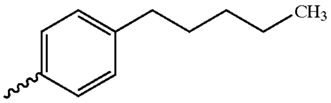 |
| 2 | 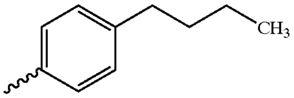 |
| 3 | 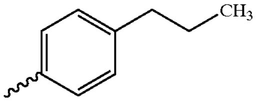 |
| 4 | 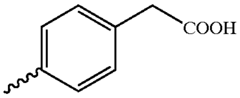 |
| 5 | 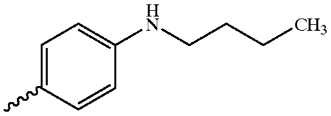 |
| 6 | 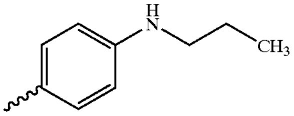 |

TABLE 33-continued
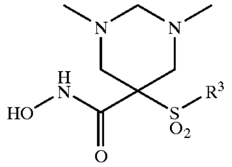
| | 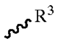 |
|---|---|
| 7 | 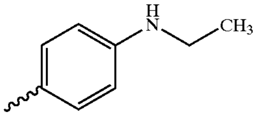 |
| 8 | 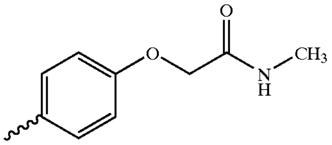 |
| 9 | 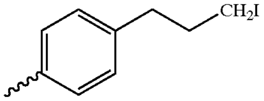 |
| 10 | 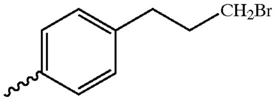 |
| 11 | 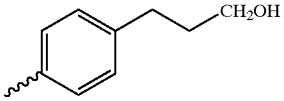 |
| 12 | 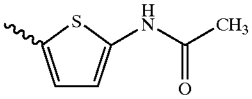 |
| 13 | 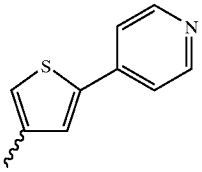 |
| 14 | 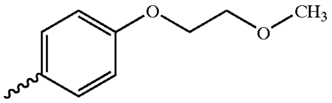 |
| 15 | 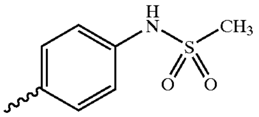 |
| 16 | 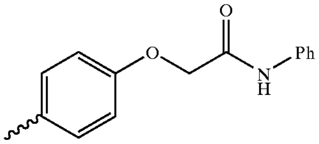 |
TABLE 33-continued
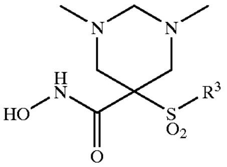
| | 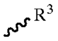 |
|---|---|
| 17 | 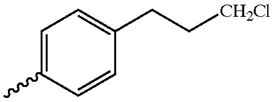 |
| 18 | 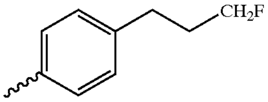 |
| 19 | 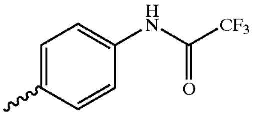 |
| 20 | 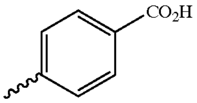 |
| 21 | 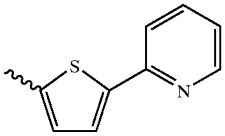 |
| 22 | 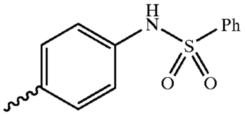 |
| 23 | 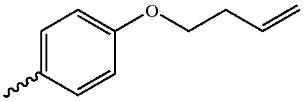 |
| 24 | 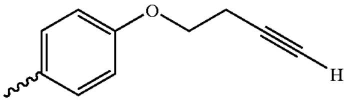 |
| 25 | 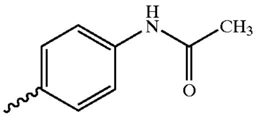 |
| 26 | 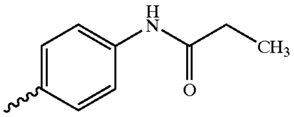 |

TABLE 33-continued
| 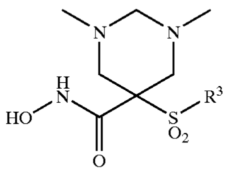 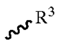 | |
|---|---|
| 27 | 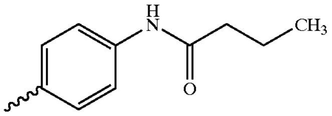 |
| 28 | 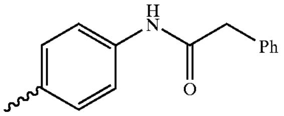 |
| 29 | 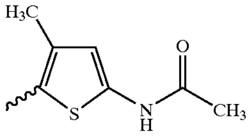 |
| 30 | 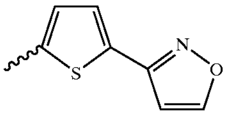 |
TABLE 34
| 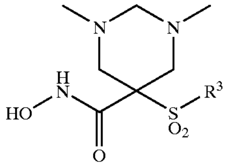 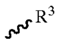 | |
|---|---|
| 1 | 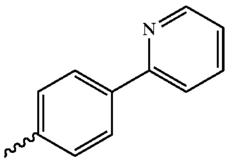 |
| 2 | 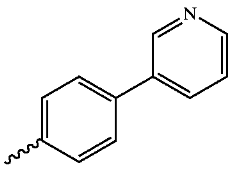 |
TABLE 34-continued
| 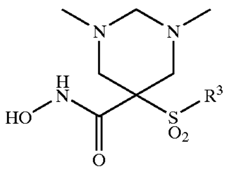 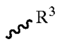 | |
|---|---|
| 3 | 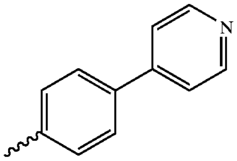 |
| 4 | 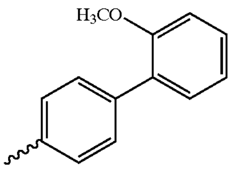 |
| 5 | 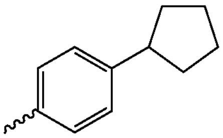 |
| 6 | 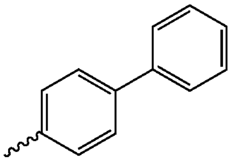 |
| 7 | 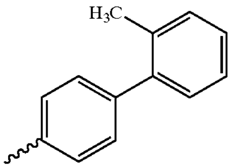 |
| 8 | 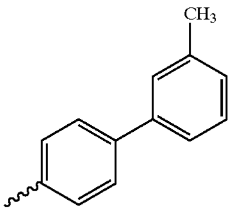 |
| 9 | 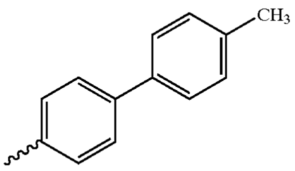 |

TABLE 34-continued
| 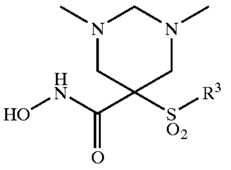 |
|---|
| 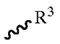 |
| | |
|---|---|
| 10 | 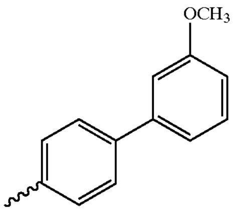 |
| 11 | 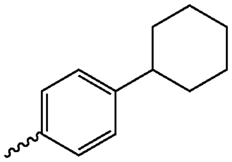 |
| 12 | 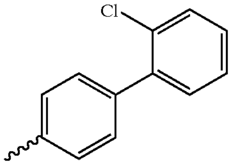 |
| 13 | 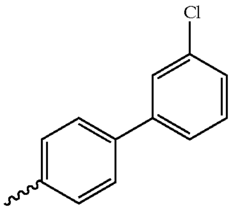 |
| 14 | 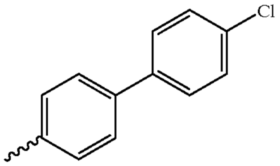 |
| 15 | 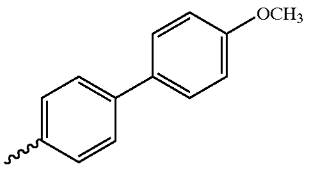 |
| 16 | 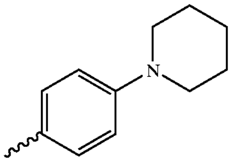 |
TABLE 34-continued
| 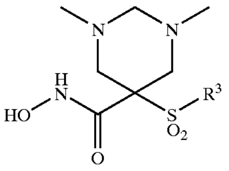 |
|---|
| 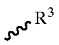 |
| | |
|---|---|
| 17 | 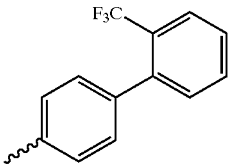 |
| 18 | 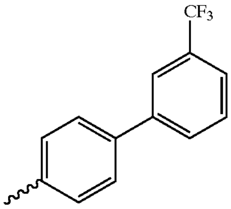 |
| 19 | 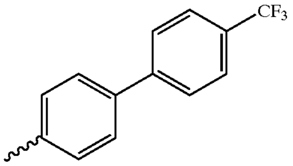 |
| 20 | 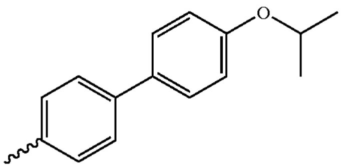 |
| 21 | 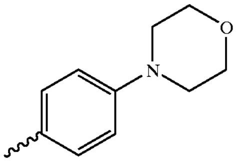 |
TABLE 35
| 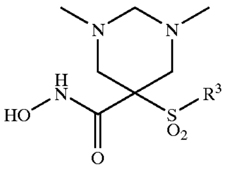 |
|---|
| 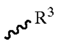 |
| | |
|---|---|
| 1 | 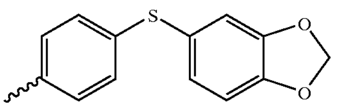 |

TABLE 35-continued
| 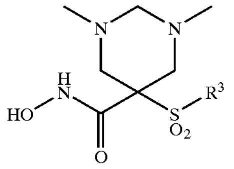 | |
|---|---|
| | 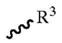 |
| 2 | 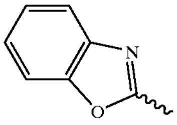 |
| 3 | 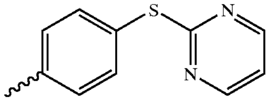 |
| 4 | 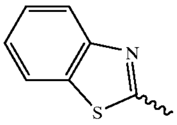 |
| 5 | 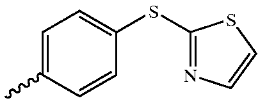 |
| 6 | 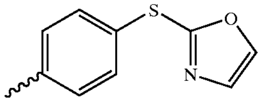 |
| 7 | 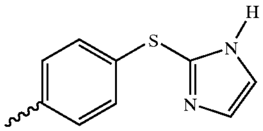 |
| 8 | 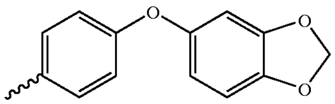 |
| 9 | 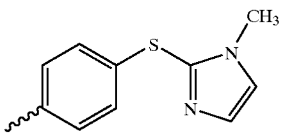 |
| 10 | 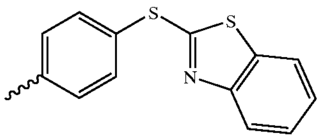 |
TABLE 35-continued
| 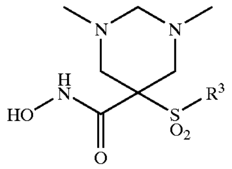 | |
|---|---|
| | 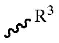 |
| 11 | 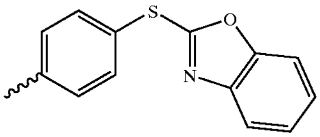 |
TABLE 36
| 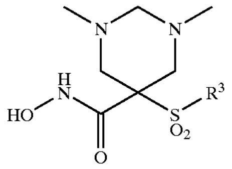 | |
|---|---|
| | 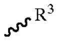 |
| 1 | 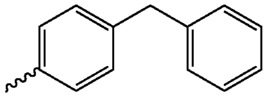 |
| 2 | 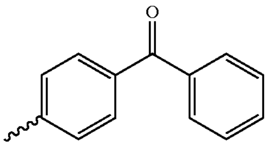 |
| 3 | 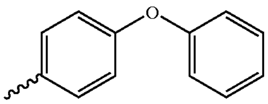 |
| 4 | 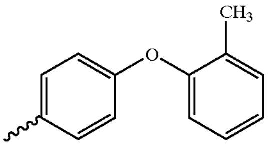 |
| 5 | 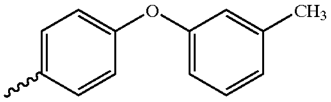 |
| 6 | 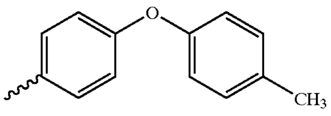 |

TABLE 36-continued
| 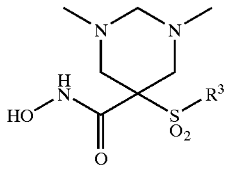 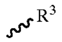 | |
|---|---|
| 7 | 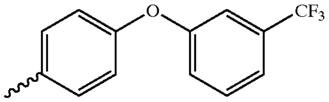 |
| 8 | 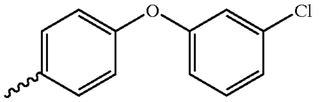 |
| 9 | 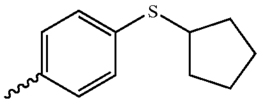 |
| 10 | 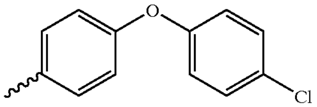 |
| 11 | 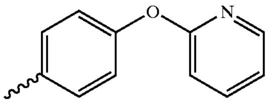 |
| 12 | 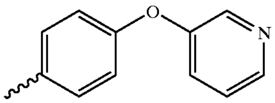 |
| 13 | 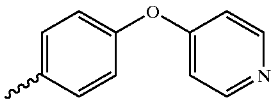 |
| 14 | 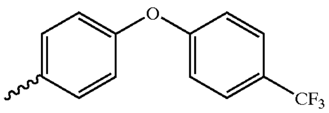 |
| 15 | 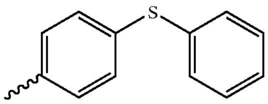 |
| 16 | 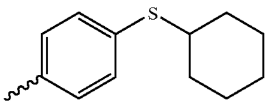 |
| 17 | 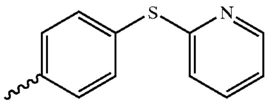 |
TABLE 36-continued
| 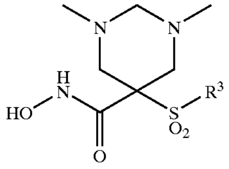 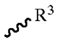 | |
|---|---|
| 18 | 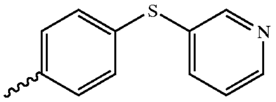 |
| 19 | 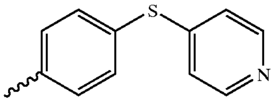 |
| 20 | 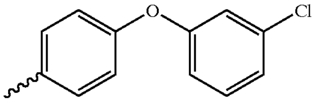 |
| 21 | 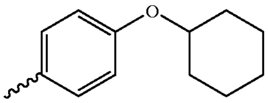 |
TABLE 37
| 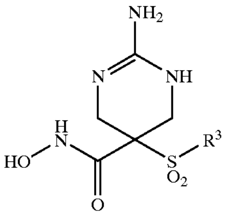 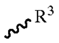 | |
|---|---|
| 1 | 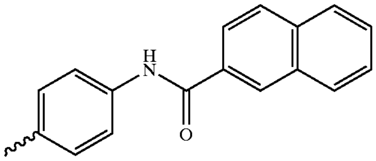 |
| 2 | 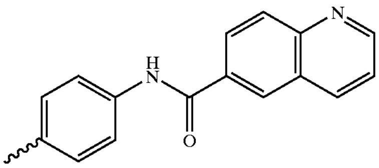 |
| 3 | 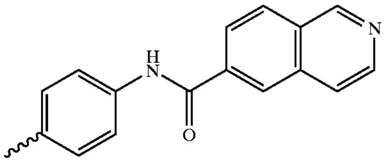 |

TABLE 37-continued
| 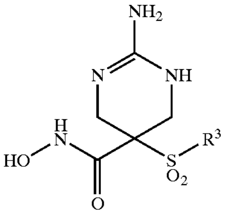 |  |
|---|---|
| 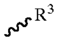 |  |
| 4 | 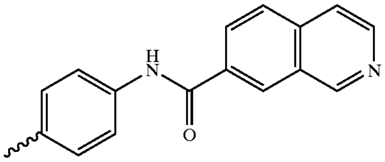 |
| 5 | 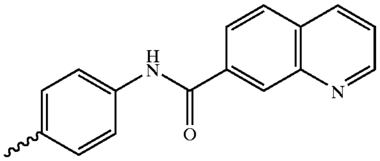 |
| 6 | 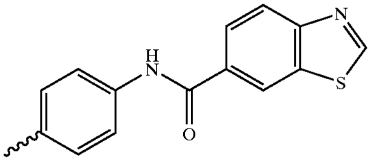 |
| 7 | 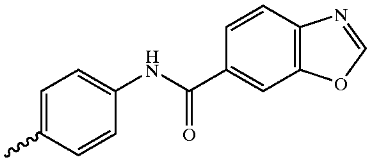 |
| 8 | 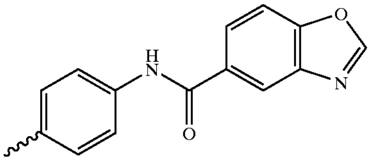 |
| 9 | 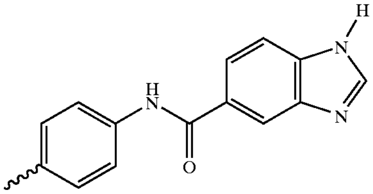 |
| 10 | 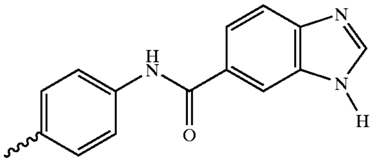 |
TABLE 37-continued
| 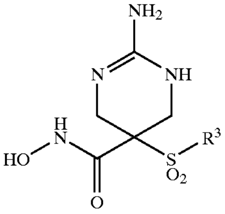 |  |
|---|---|
| 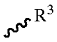 |  |
| 11 | 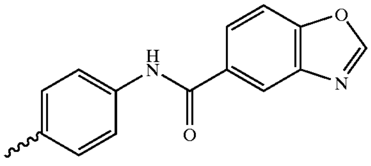 |
| 12 | 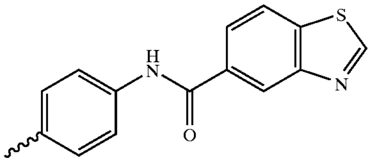 |
| 13 | 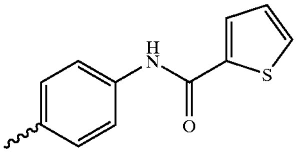 |
| 14 | 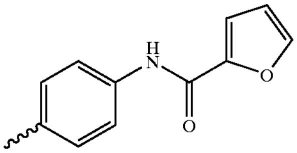 |
| 15 | 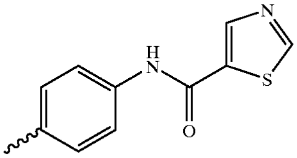 |
| 16 | 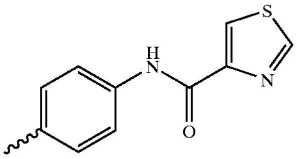 |
| 17 | 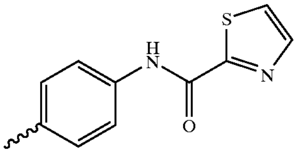 |

TABLE 37-continued
| 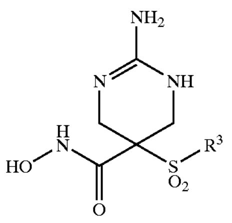 |
| --- |
| 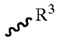 |
| | |
| --- | --- |
| 18 | 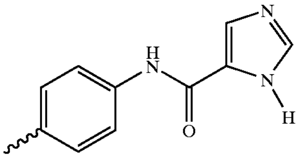 |
TABLE 38
| 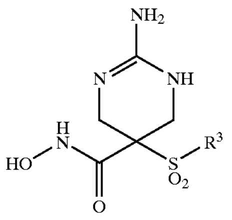 | |
| --- | --- |
| | 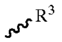 |
| 1 | 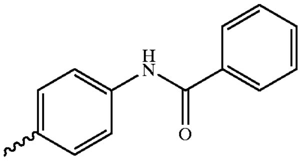 |
| 2 | 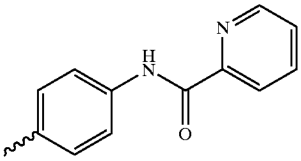 |
| 3 | 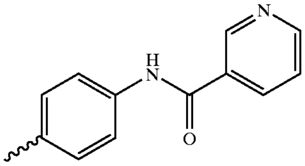 |
| 4 | 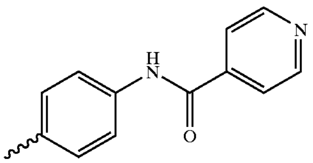 |
TABLE 38-continued
| 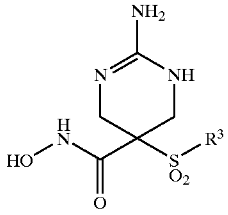 | |
| --- | --- |
| | 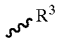 |
| 5 | 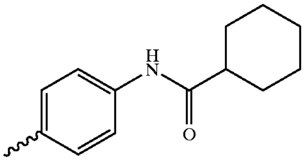 |
| 6 | 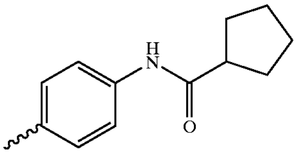 |
| 7 | 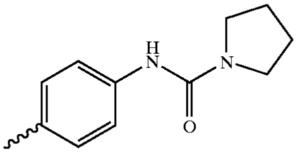 |
| 8 | 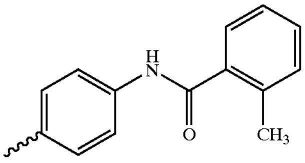 |
| 9 | 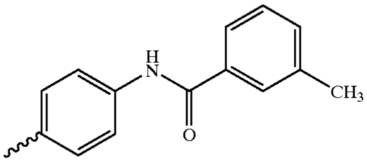 |
| 10 | 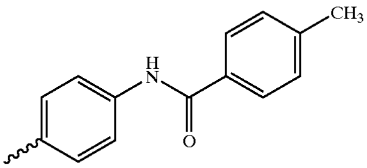 |
| 11 | 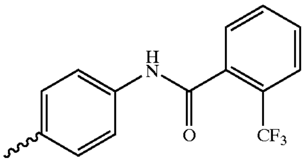 |

TABLE 38-continued
| 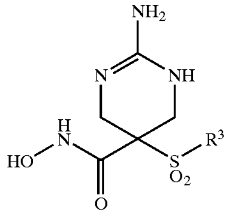 |
| --- |
| 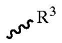 |
| 12 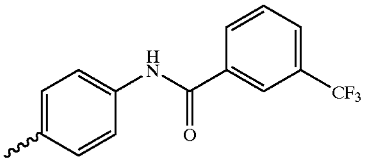 |
| 13 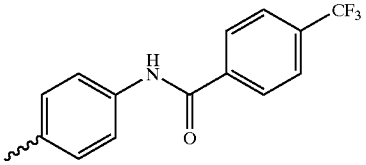 |
| 14 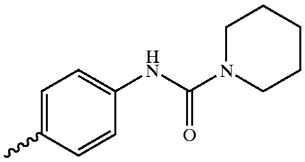 |
| 15 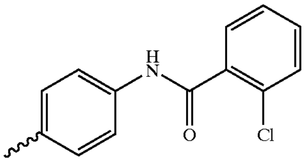 |
| 16 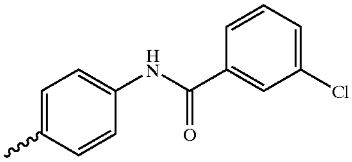 |
| 17 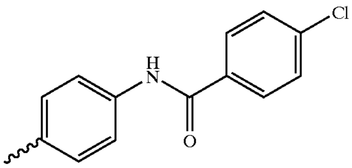 |
| 18 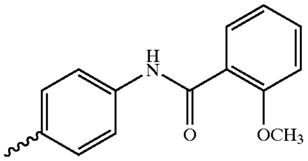 |
TABLE 38-continued
| 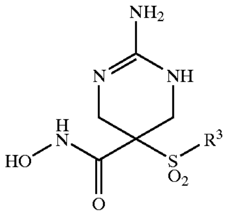 |
| --- |
| 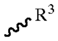 |
| 19 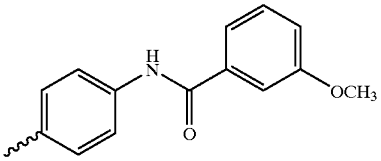 |
| 20 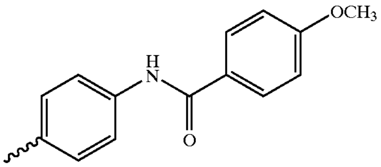 |
| 21 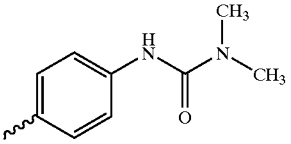 |
TABLE 39
| 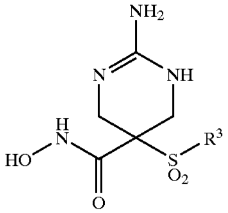 |
| --- |
| 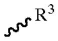 |
| 1 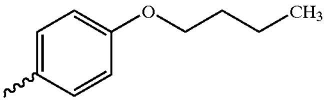 |
| 2 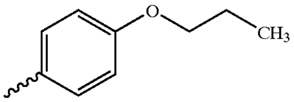 |
| 3 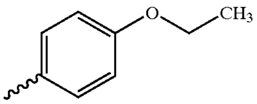 |

TABLE 39-continued
| | |
|---|---|
| | 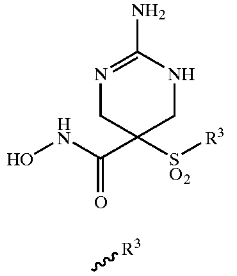 |
| 4 | 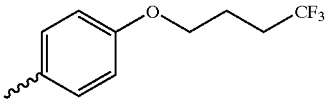 |
| 5 | 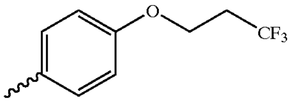 |
| 6 | 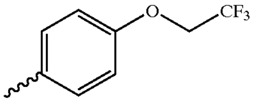 |
| 7 | 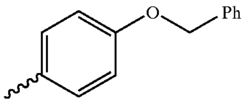 |
| 8 | 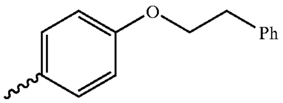 |
| 9 | 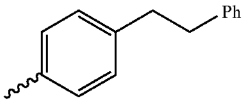 |
| 10 | 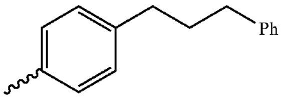 |
| 11 | 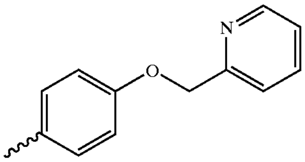 |
| 12 | 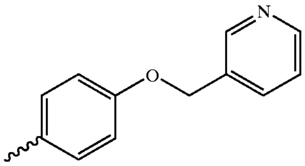 |
| 13 | 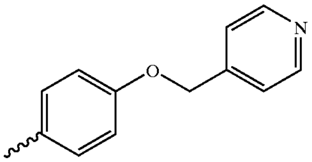 |
TABLE 39-continued
| | |
|---|---|
| | 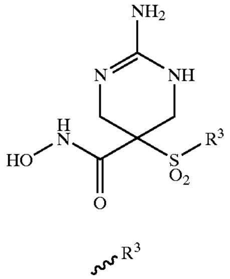 |
| 14 | 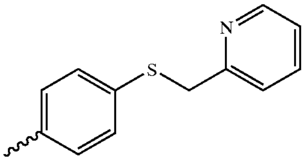 |
| 15 | 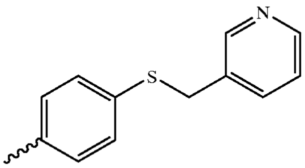 |
| 16 | 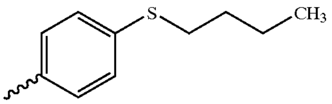 |
| 17 | 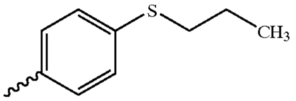 |
| 18 | 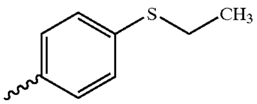 |
| 19 | 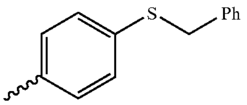 |
| 20 | 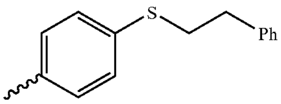 |
| 21 | 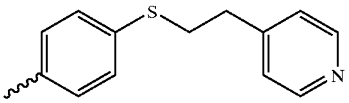 |
| 22 | 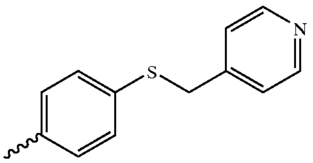 |

TABLE 40
| | |
|---|---|
| | 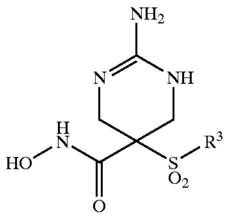 |
| | 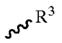 |
| 1 | 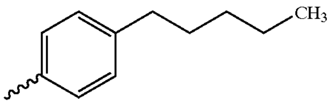 |
| 2 | 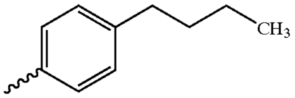 |
| 3 | 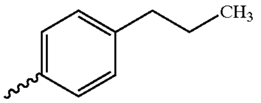 |
| 4 | 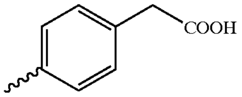 |
| 5 | 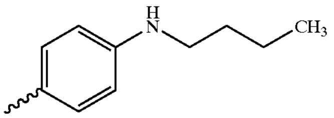 |
| 6 | 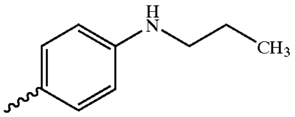 |
| 7 | 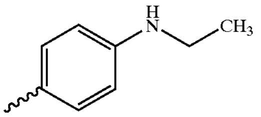 |
| 8 | 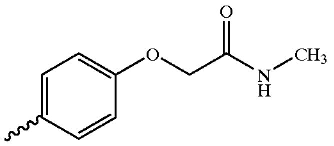 |
| 9 | 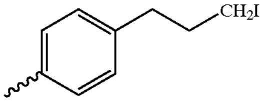 |
| 10 | 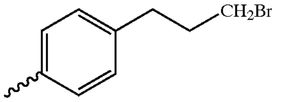 |
TABLE 40-continued
| | |
|---|---|
| | 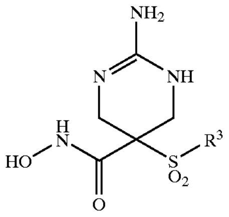 |
| | 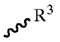 |
| 11 | 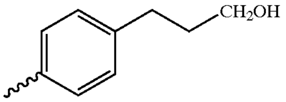 |
| 12 | 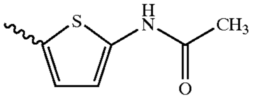 |
| 13 | 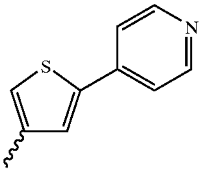 |
| 14 | 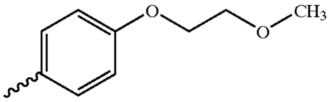 |
| 15 | 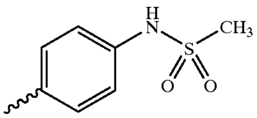 |
| 16 | 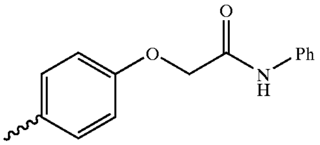 |
| 17 | 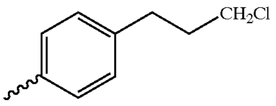 |
| 18 | 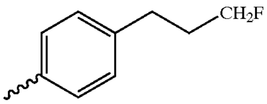 |
| 19 | 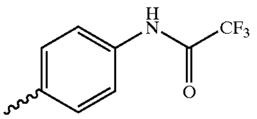 |
| 20 | 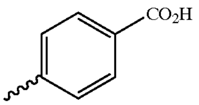 |

TABLE 40-continued
| | |
|---|---|
| | 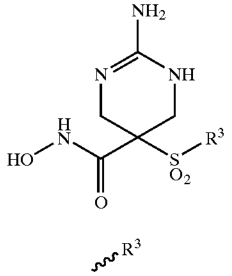 |
| 21 | 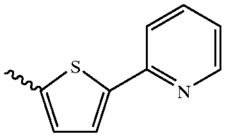 |
| 22 | 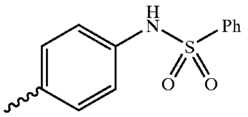 |
| 23 | 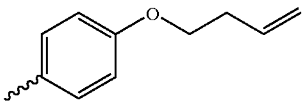 |
| 24 | 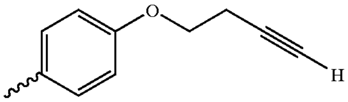 |
| 25 | 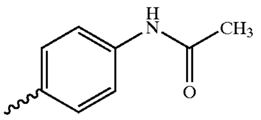 |
| 26 | 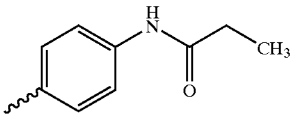 |
| 27 | 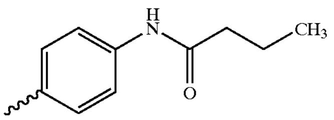 |
| 28 | 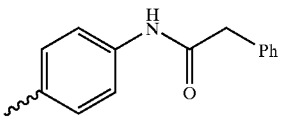 |
| 29 | 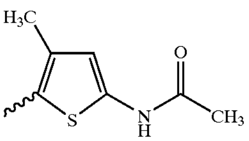 |
| 30 | 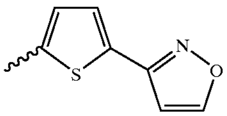 |
TABLE 41
| | |
|---|---|
| | 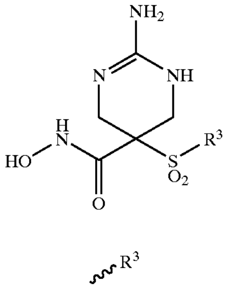 |
| 1 | 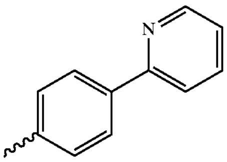 |
| 2 | 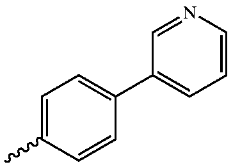 |
| 3 | 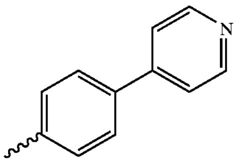 |
| 4 | 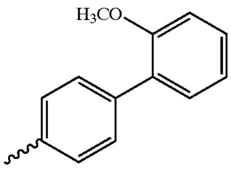 |
| 5 | 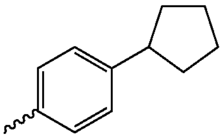 |
| 6 | 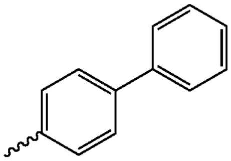 |
| 7 | 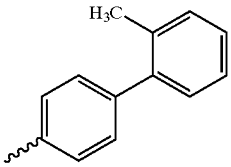 |

TABLE 41-continued
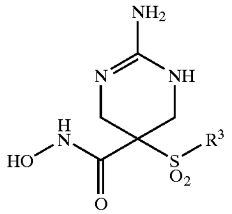
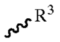
| | |
|---|---|
| 8 | 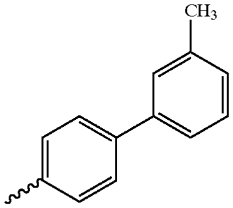 |
| 9 | 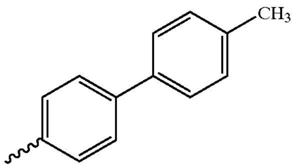 |
| 10 | 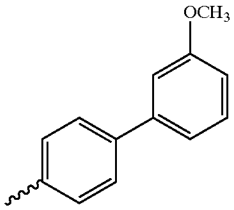 |
| 11 | 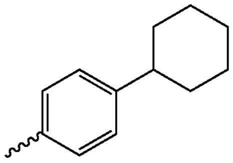 |
| 12 | 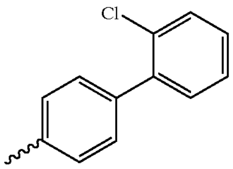 |
| 13 | 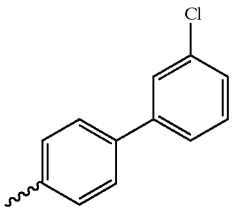 |
TABLE 41-continued
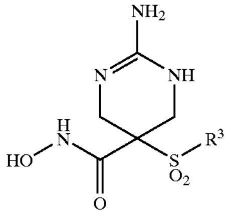
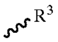
| | |
|---|---|
| 14 | 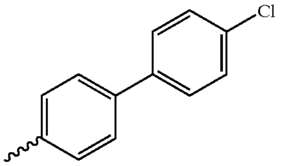 |
| 15 | 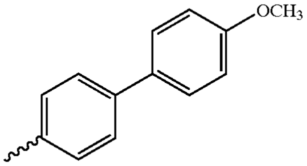 |
| 16 | 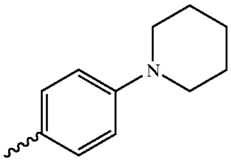 |
| 17 | 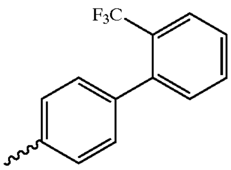 |
| 18 | 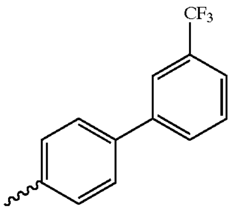 |
| 19 | 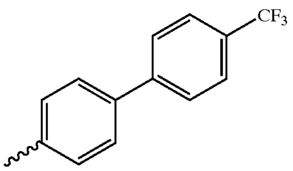 |
| 20 | 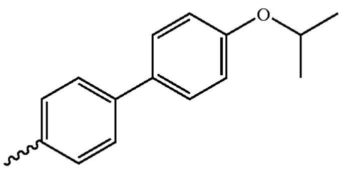 |

TABLE 41-continued
| 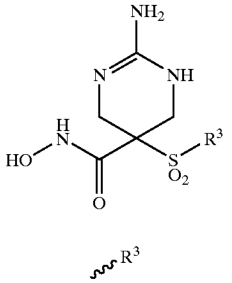 |  |
| --- | --- |
| 21 | 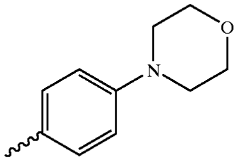 |
TABLE 42
| 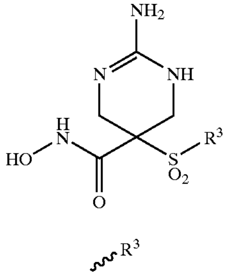 |  |
| --- | --- |
| 1 | 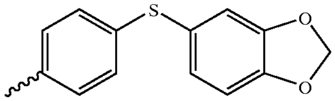 |
| 2 | 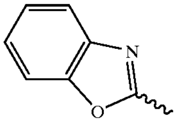 |
| 3 | 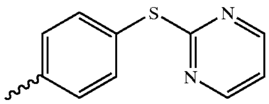 |
| 4 | 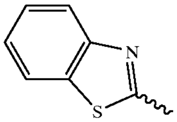 |
| 5 | 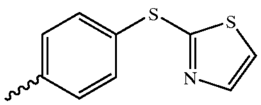 |
| 6 | 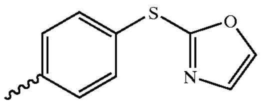 |
TABLE 42-continued
| 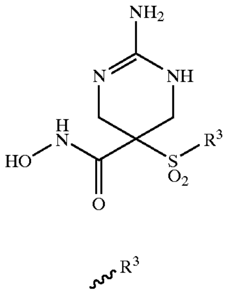 |  |
| --- | --- |
| 7 | 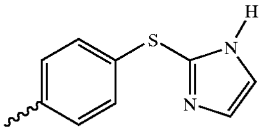 |
| 8 | 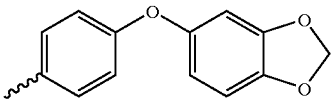 |
| 9 | 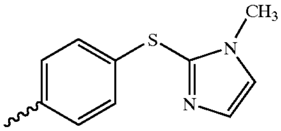 |
| 10 | 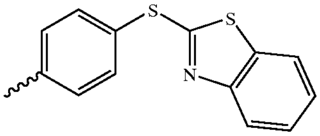 |
| 11 | 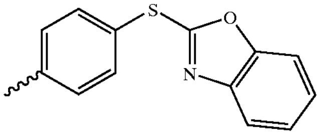 |
TABLE 43
| 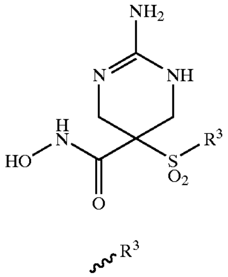 |  |
| --- | --- |
| 1 | 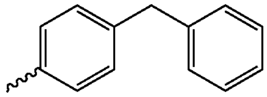 |

TABLE 43-continued
| 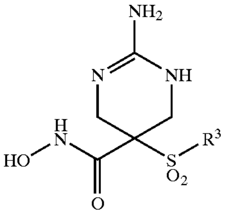 | 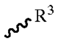 |
| --- | --- |
| 2 | 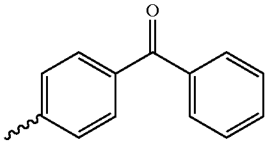 |
| 3 | 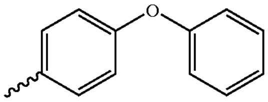 |
| 4 | 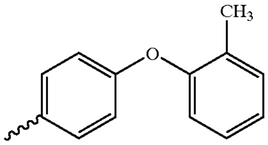 |
| 5 | 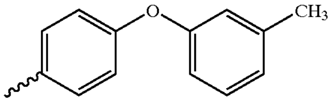 |
| 6 | 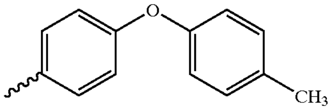 |
| 7 | 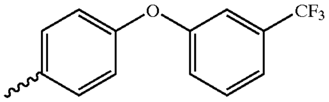 |
| 8 | 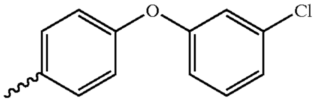 |
| 9 | 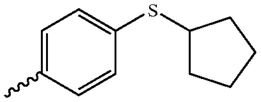 |
| 10 | 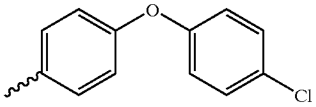 |
| 11 | 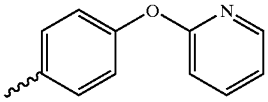 |
TABLE 43-continued
| 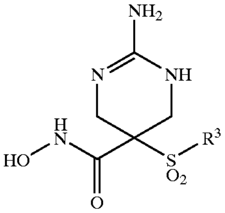 | 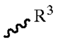 |
| --- | --- |
| 12 | 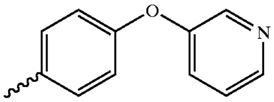 |
| 13 | 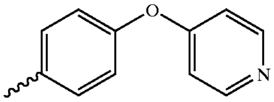 |
| 14 | 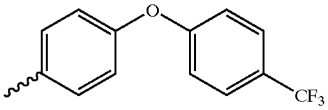 |
| 15 | 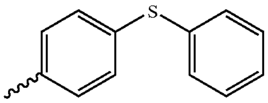 |
| 16 | 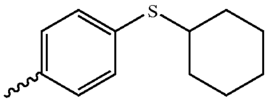 |
| 17 | 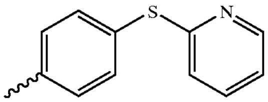 |
| 18 | 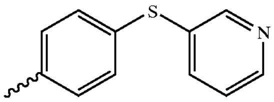 |
| 19 | 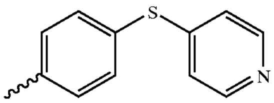 |
| 20 | 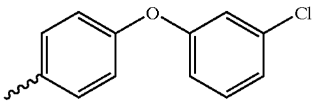 |
| 21 | 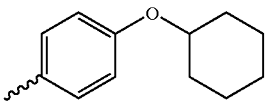 |

TABLE 44
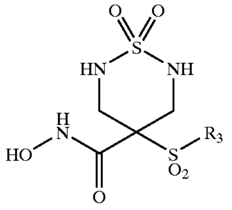
| | |
|---|---|
| 1 | 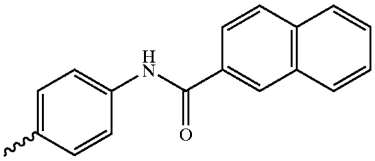 |
| 2 | 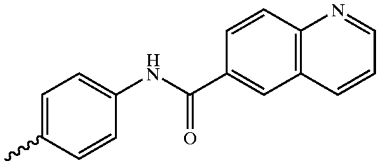 |
| 3 | 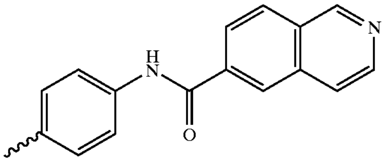 |
| 4 | 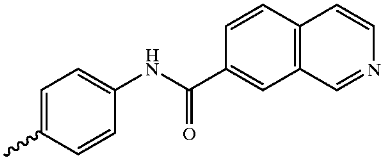 |
| 5 | 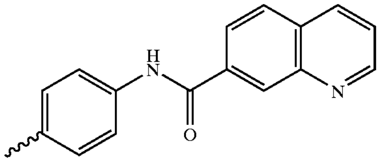 |
| 6 | 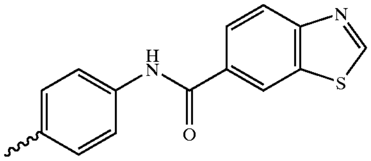 |
| 7 | 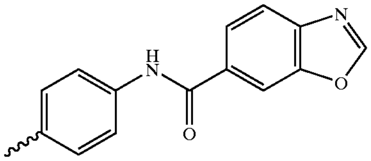 |
TABLE 44-continued
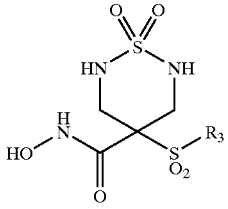
| | |
|---|---|
| 8 | 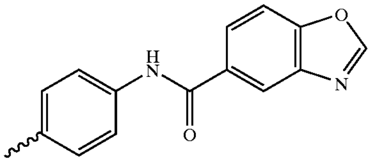 |
| 9 | 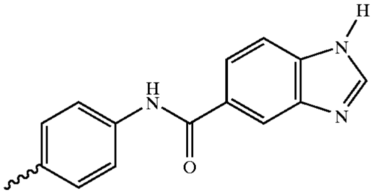 |
| 10 | 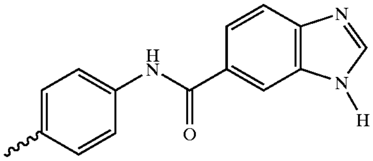 |
| 11 | 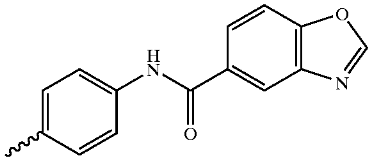 |
| 12 | 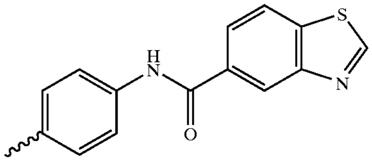 |
| 13 | 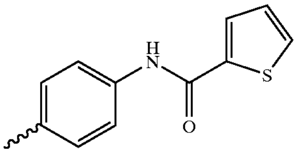 |
| 14 | 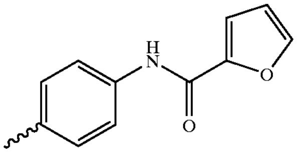 |

TABLE 44-continued
| 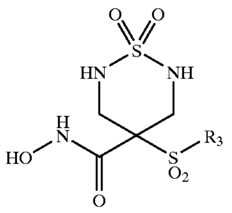 | |
|---|---|
| | 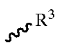 |
| 15 | 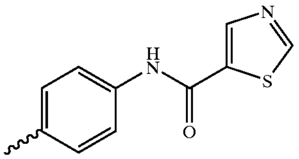 |
| 16 | 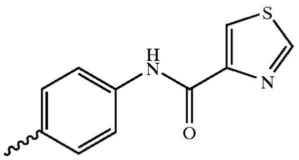 |
| 17 | 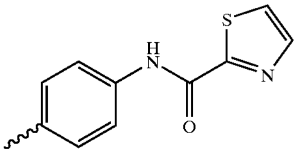 |
| 18 | 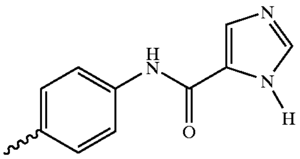 |
TABLE 45
| 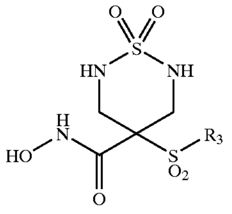 | |
|---|---|
| | 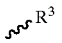 |
| 1 | 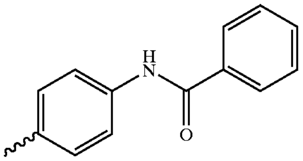 |
TABLE 45-continued
| 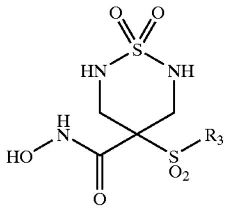 | |
|---|---|
| | 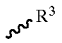 |
| 2 | 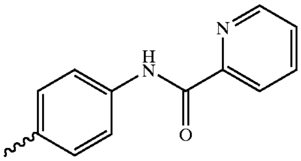 |
| 3 | 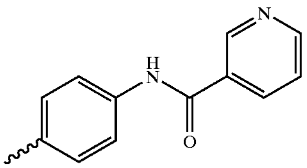 |
| 4 | 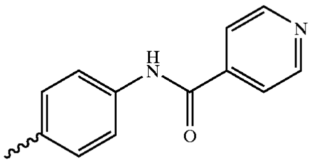 |
| 5 | 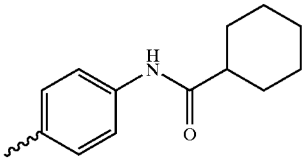 |
| 6 | 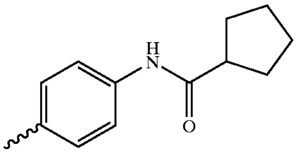 |
| 7 | 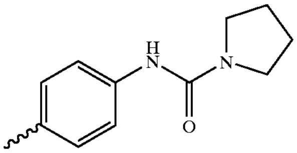 |
| 8 | 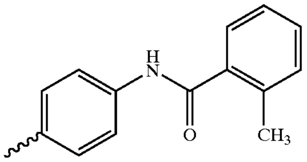 |

TABLE 45-continued
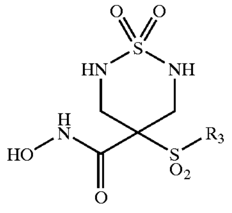
$R^3$
| | |
|---|---|
| 9 | 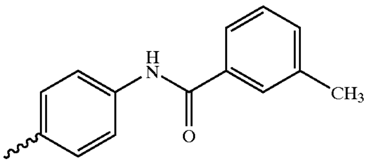 |
| 10 | 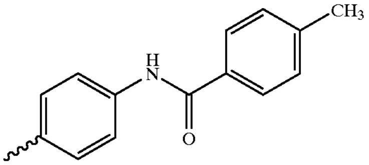 |
| 11 | 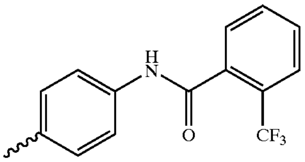 |
| 12 | 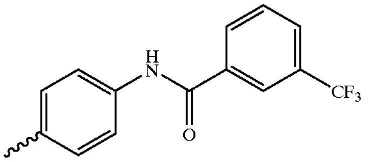 |
| 13 | 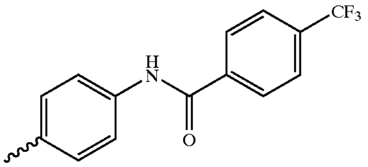 |
| 14 | 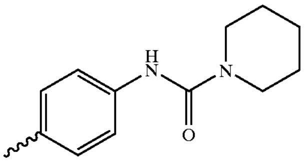 |
| 15 | 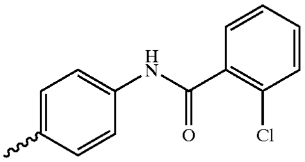 |
TABLE 45-continued
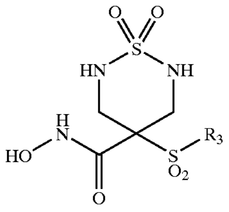
$R^3$
| | |
|---|---|
| 16 | 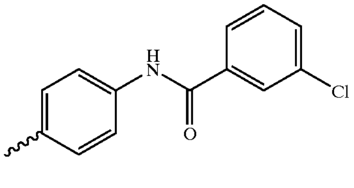 |
| 17 | 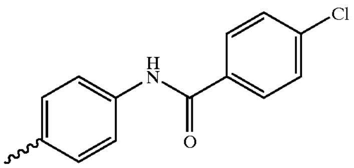 |
| 18 | 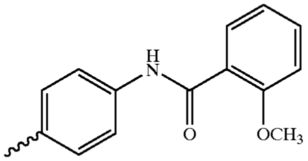 |
| 19 | 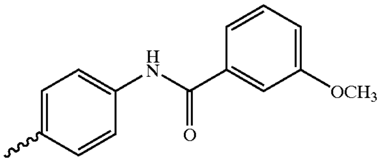 |
| 20 | 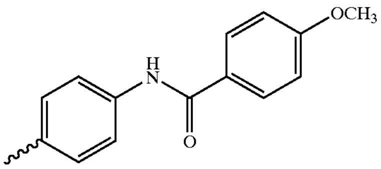 |
| 21 | 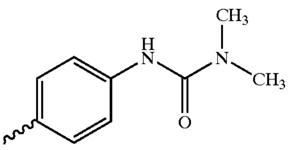 |

TABLE 46
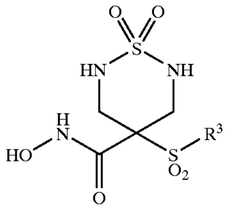
| | 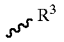 |
|---|---|
| 1 | 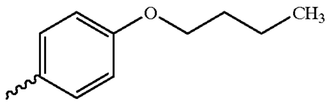 |
| 2 | 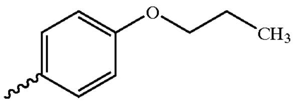 |
| 3 | 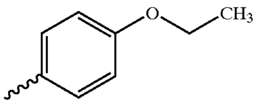 |
| 4 | 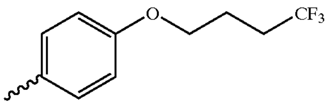 |
| 5 | 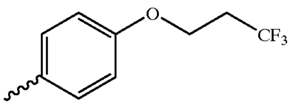 |
| 6 | 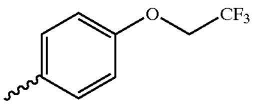 |
| 7 | 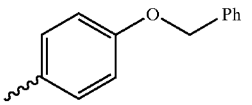 |
| 8 | 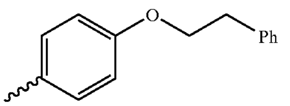 |
| 9 | 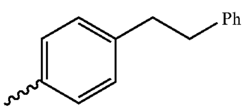 |
| 10 | 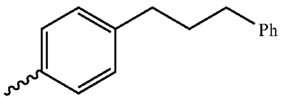 |
TABLE 46-continued
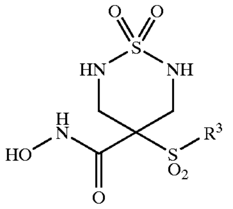
| | 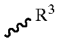 |
|---|---|
| 11 | 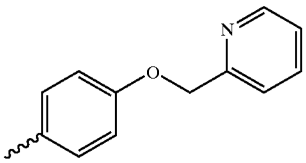 |
| 12 | 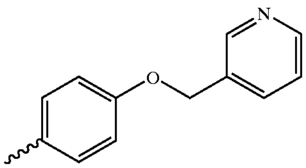 |
| 13 | 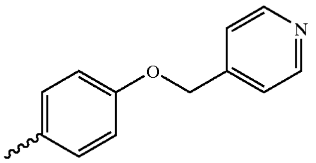 |
| 14 | 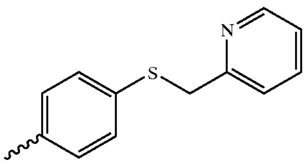 |
| 15 | 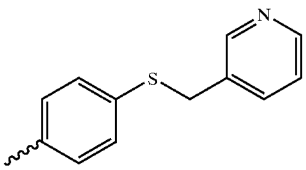 |
| 16 | 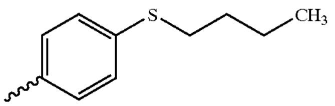 |
| 17 | 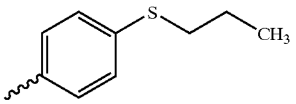 |
| 18 | 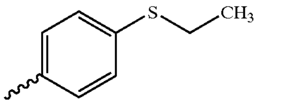 |

TABLE 46-continued
| 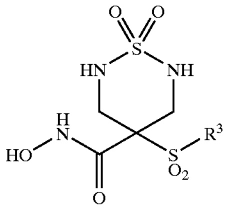 | |
|---|---|
| | 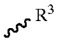 |
| 19 | 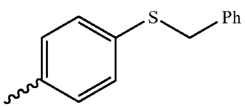 |
| 20 | 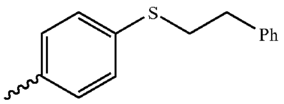 |
| 21 | 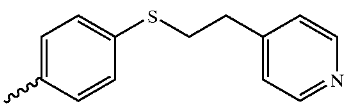 |
| 22 | 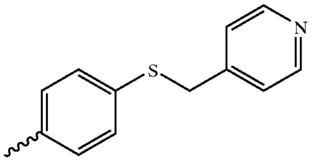 |
TABLE 47
| 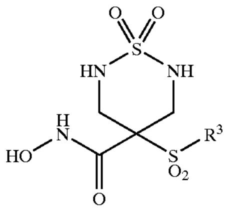 | |
|---|---|
| | 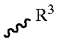 |
| 1 | 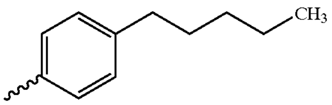 |
| 2 | 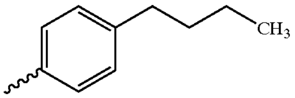 |
| 3 | 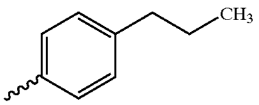 |
TABLE 47-continued
| 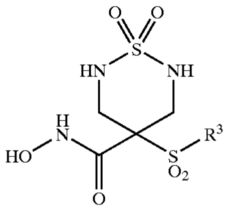 | |
|---|---|
| | 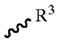 |
| 4 | 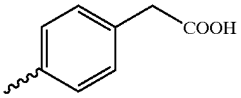 |
| 5 | 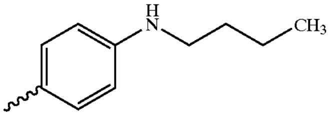 |
| 6 | 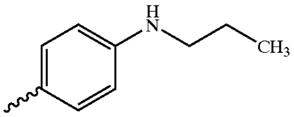 |
| 7 | 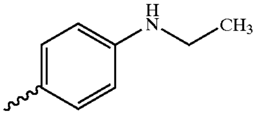 |
| 8 | 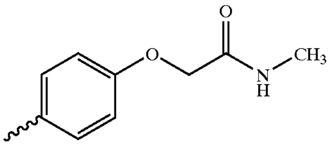 |
| 9 | 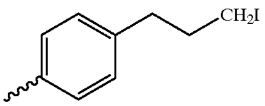 |
| 10 | 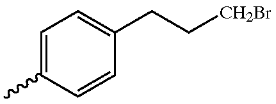 |
| 11 | 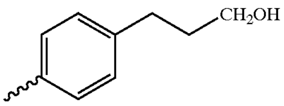 |
| 12 | 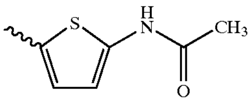 |
| 13 | 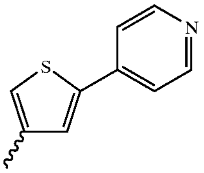 |

TABLE 47-continued
| | 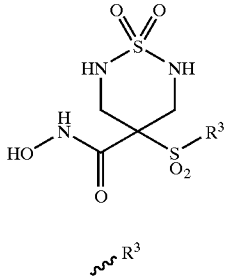 |
|---|---|
| 14 | 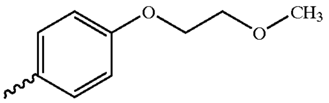 |
| 15 | 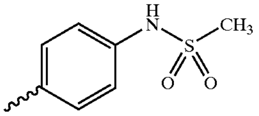 |
| 16 | 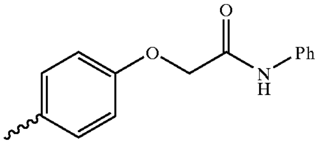 |
| 17 | 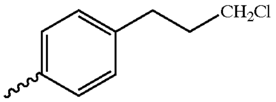 |
| 18 | 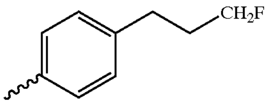 |
| 19 | 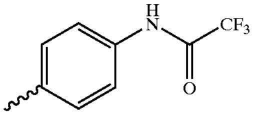 |
| 20 | 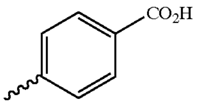 |
| 21 | 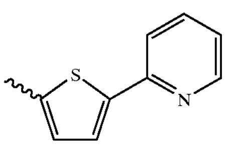 |
TABLE 47-continued
| | 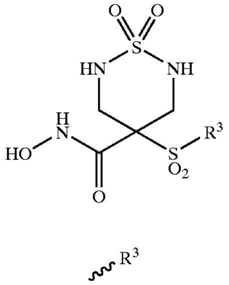 |
|---|---|
| 22 | 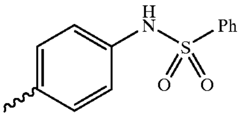 |
| 23 | 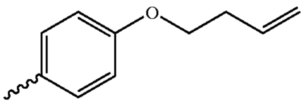 |
| 24 | 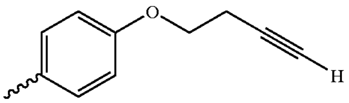 |
| 25 | 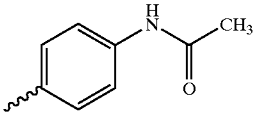 |
| 26 | 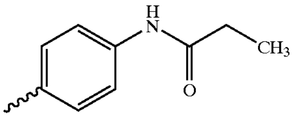 |
| 27 | 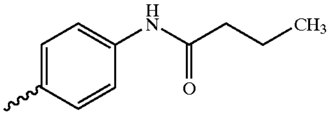 |
| 28 | 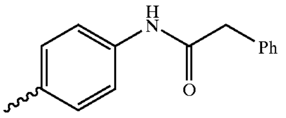 |
| 29 | 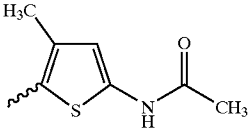 |
| 30 | 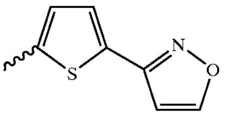 |

TABLE 48
| 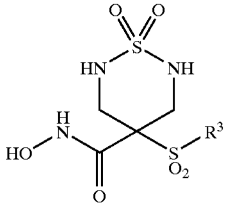 | |
|---|---|
| | 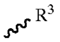 |
| 1 | 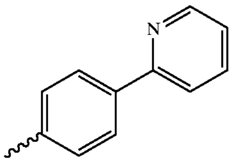 |
| 2 | 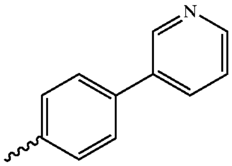 |
| 3 | 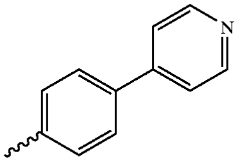 |
| 4 | 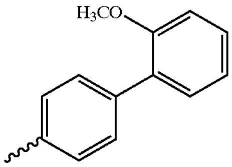 |
| 5 | 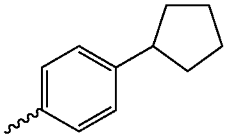 |
| 6 | 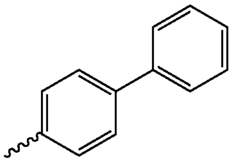 |
| 7 | 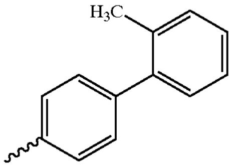 |
TABLE 48-continued
| 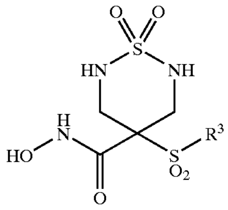 | |
|---|---|
| | 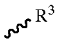 |
| 8 | 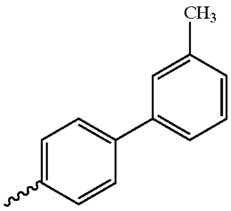 |
| 9 | 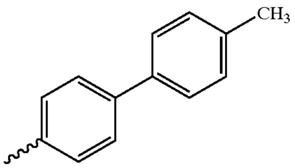 |
| 10 | 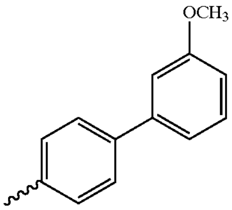 |
| 11 | 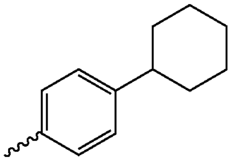 |
| 12 | 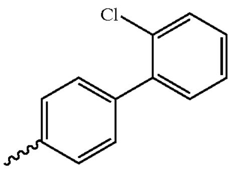 |
| 13 | 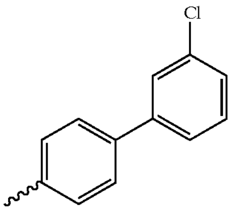 |

TABLE 48-continued
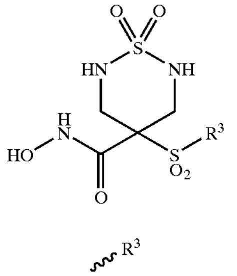
| | |
|---|---|
| 14 | 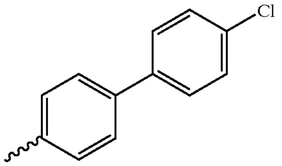 |
| 15 | 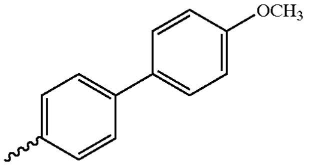 |
| 16 | 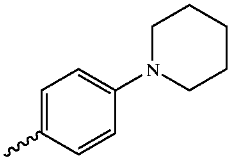 |
| 17 | 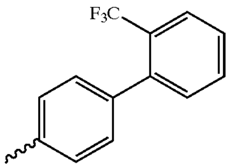 |
| 18 | 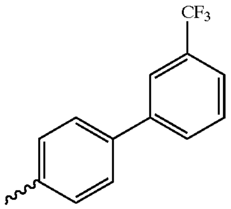 |
| 19 | 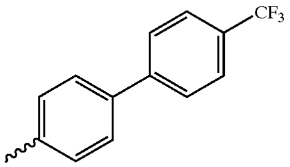 |
| 20 | 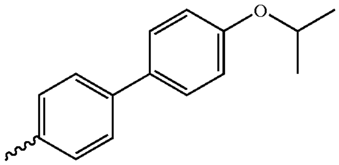 |
TABLE 48-continued
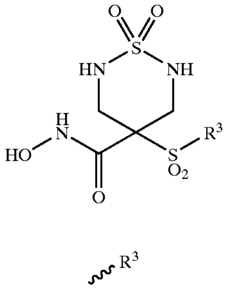
| | |
|---|---|
| 21 | 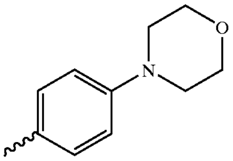 |
TABLE 49
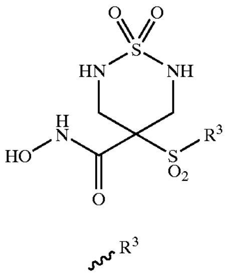
| | |
|---|---|
| 1 | 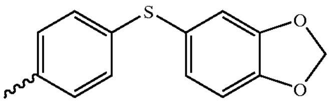 |
| 2 | 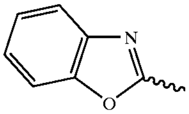 |
| 3 | 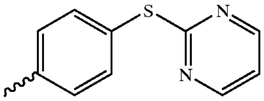 |
| 4 | 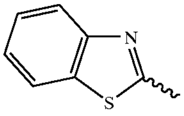 |
| 5 | 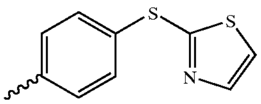 |
| 6 | 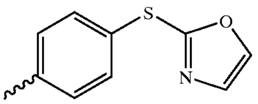 |

TABLE 49-continued
| | |
|---|---|
| | 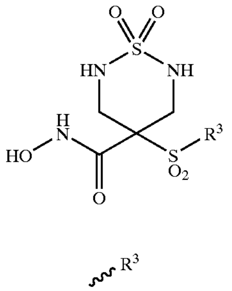 |
| 7 | 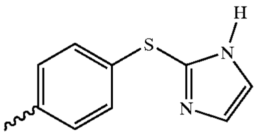 |
| 8 | 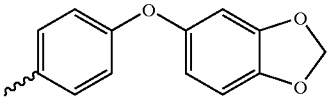 |
| 9 | 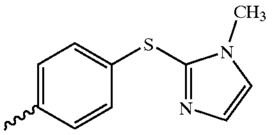 |
| 10 | 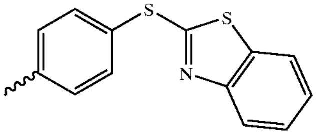 |
| 11 | 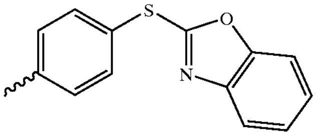 |
TABLE 50
| | |
|---|---|
| | 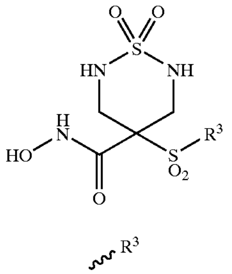 |
| 1 | 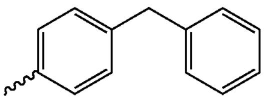 |
TABLE 50-continued
| | |
|---|---|
| | 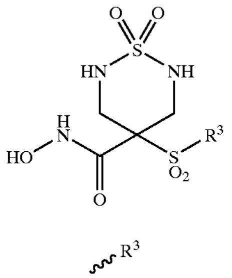 |
| 2 | 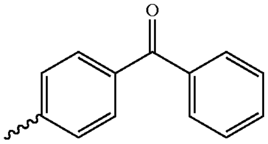 |
| 3 | 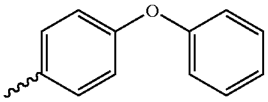 |
| 4 | 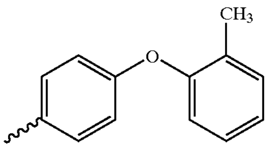 |
| 5 | 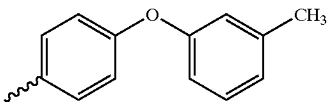 |
| 6 | 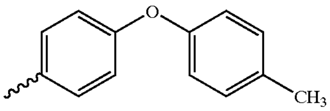 |
| 7 | 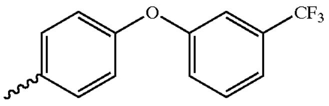 |
| 8 | 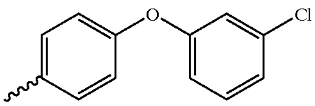 |
| 9 | 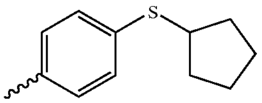 |
| 10 | 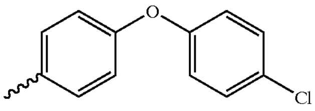 |
| 11 | 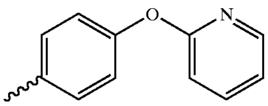 |

TABLE 50-continued
| 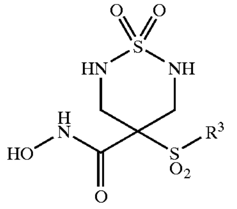 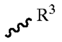 | |
|---|---|
| 12 | 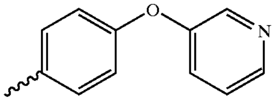 |
| 13 | 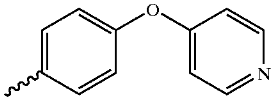 |
| 14 | 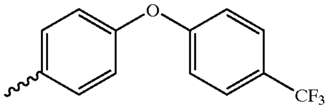 |
| 15 | 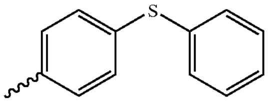 |
| 16 | 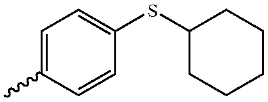 |
| 17 | 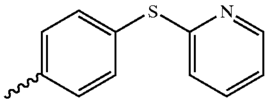 |
| 18 | 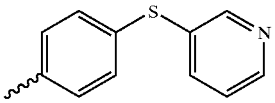 |
| 19 | 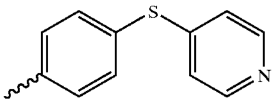 |
| 20 | 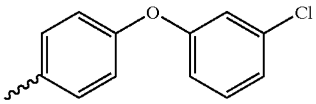 |
| 21 | 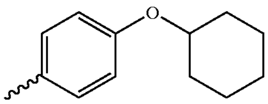 |
TABLE 51
| 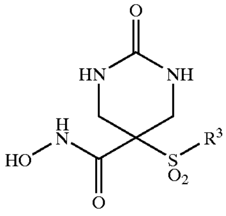 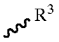 | |
|---|---|
| 1 | 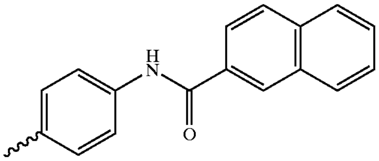 |
| 2 | 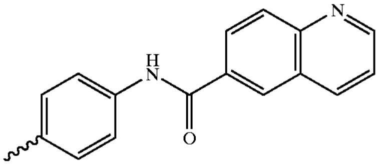 |
| 3 | 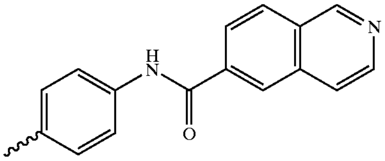 |
| 4 | 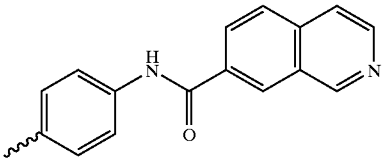 |
| 5 | 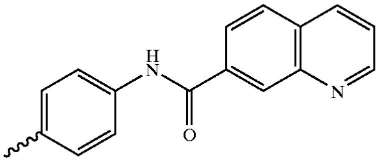 |
| 6 | 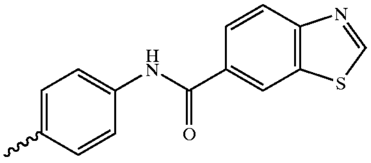 |
| 7 | 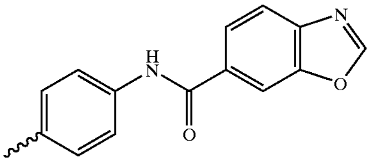 |

TABLE 51-continued
| | 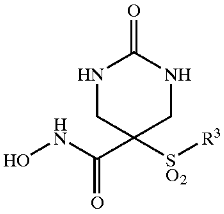 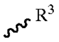 |
|---|---|
| 8 | 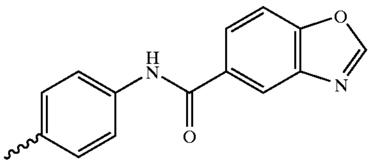 |
| 9 | 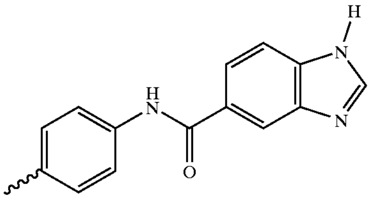 |
| 10 | 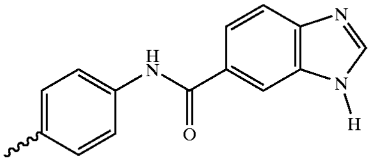 |
| 11 | 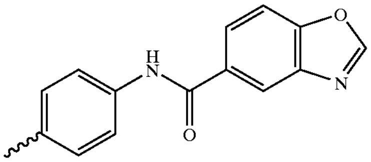 |
| 12 | 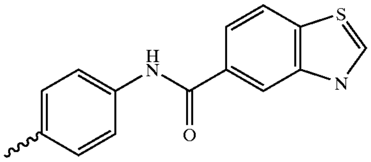 |
| 13 | 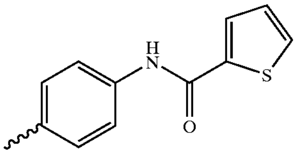 |
| 14 | 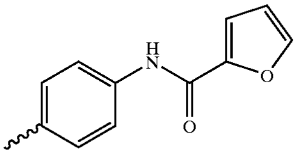 |
TABLE 51-continued
| | 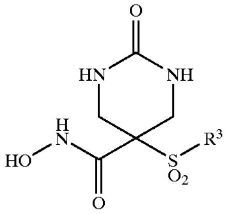 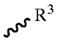 |
|---|---|
| 15 | 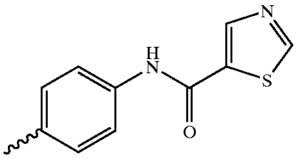 |
| 16 | 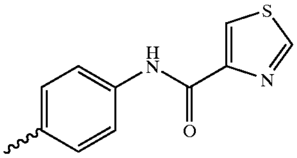 |
| 17 | 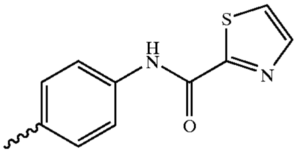 |
| 18 | 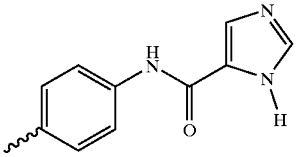 |
TABLE 52
| | 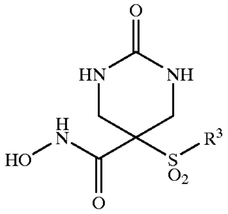 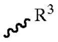 |
|---|---|
| 1 | 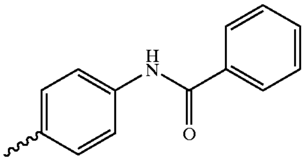 |

TABLE 52-continued
| 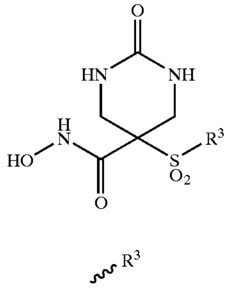 | |
|---|---|
| 2 | 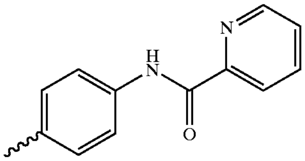 |
| 3 | 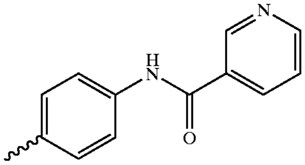 |
| 4 | 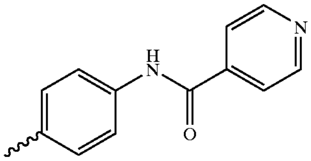 |
| 5 | 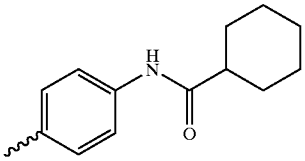 |
| 6 | 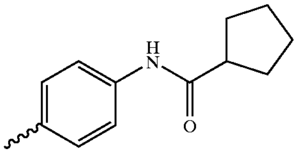 |
| 7 | 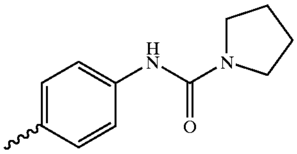 |
| 8 | 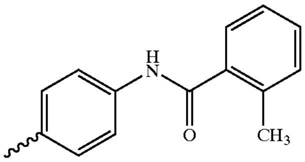 |
TABLE 52-continued
| 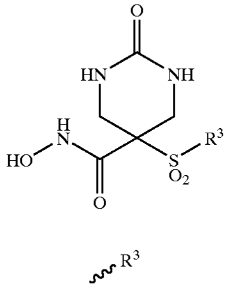 | |
|---|---|
| 9 | 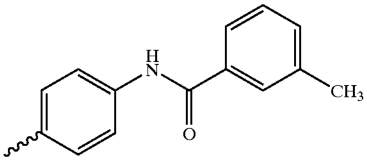 |
| 10 | 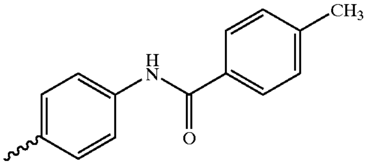 |
| 11 | 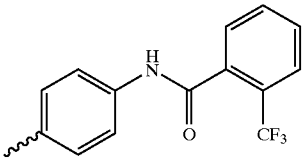 |
| 12 | 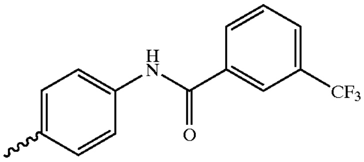 |
| 13 | 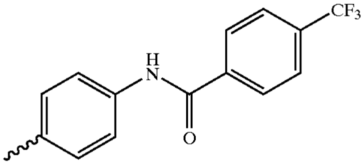 |
| 14 | 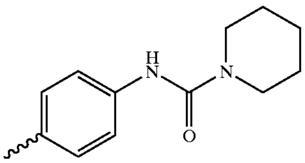 |
| 15 | 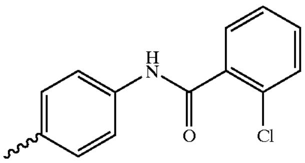 |

TABLE 52-continued
| | |
|---|---|
| | 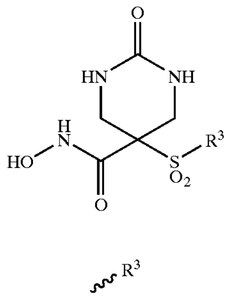 |
| 16 | 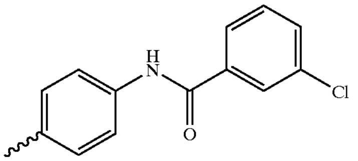 |
| 17 | 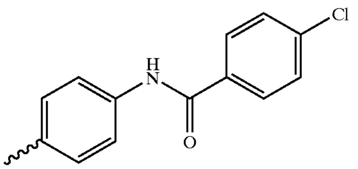 |
| 18 | 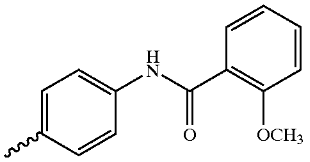 |
| 19 | 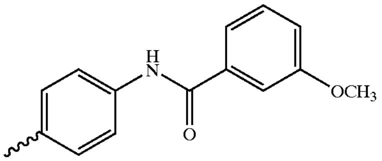 |
| 20 | 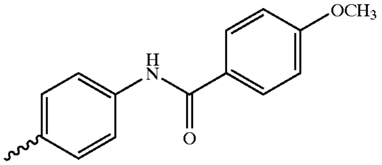 |
| 21 | 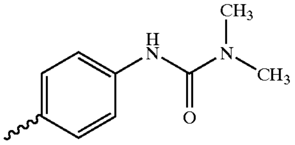 |
TABLE 53
| | |
|---|---|
| | 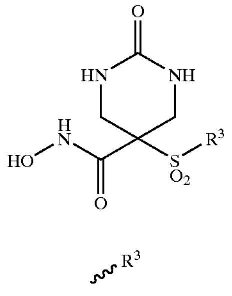 |
| 1 | 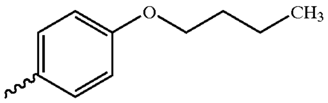 |
| 2 | 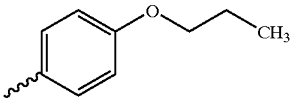 |
| 3 | 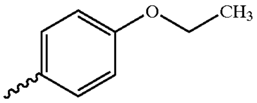 |
| 4 | 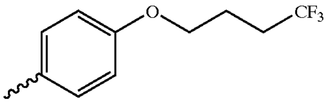 |
| 5 | 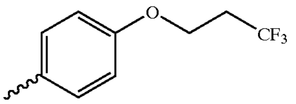 |
| 6 | 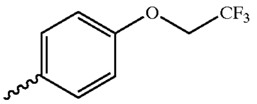 |
| 7 | 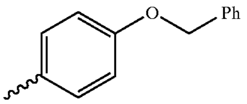 |
| 8 | 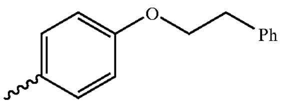 |
| 9 | 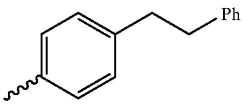 |
| 10 | 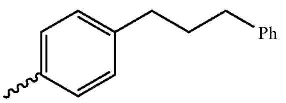 |

TABLE 53-continued
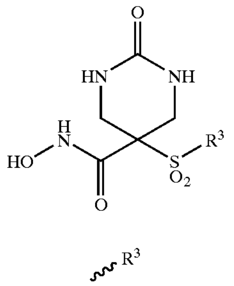
| | |
|---|---|
| 11 | 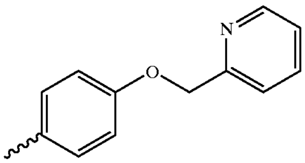 |
| 12 | 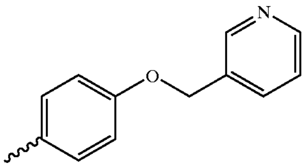 |
| 13 | 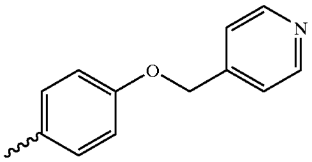 |
| 14 | 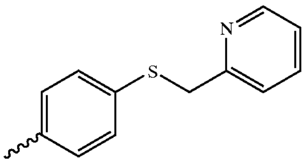 |
| 15 | 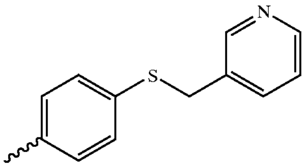 |
| 16 | 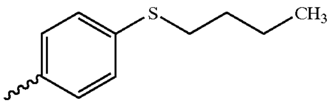 |
| 17 | 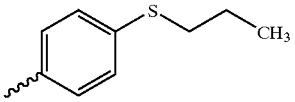 |
| 18 | 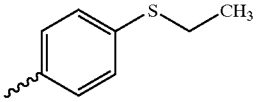 |
TABLE 53-continued
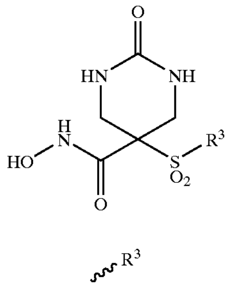
| | |
|---|---|
| 19 | 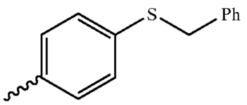 |
| 20 | 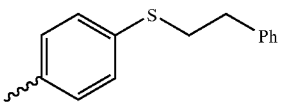 |
| 21 | 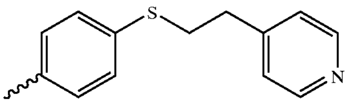 |
| 22 | 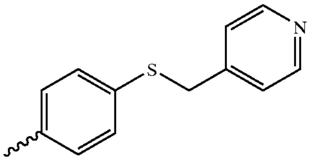 |
TABLE 54
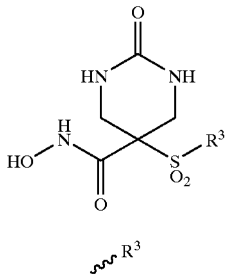
| | |
|---|---|
| 1 | 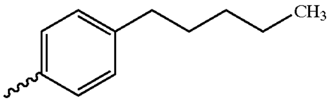 |
| 2 | 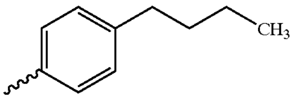 |
| 3 | 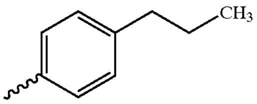 |

TABLE 54-continued
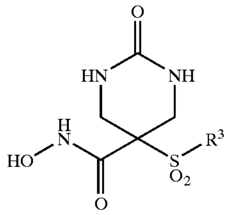
| 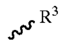 | |
|---|---|
| 4 | 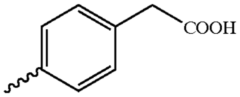 |
| 5 | 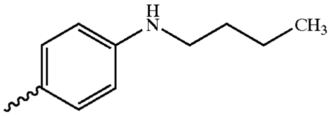 |
| 6 | 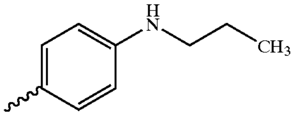 |
| 7 | 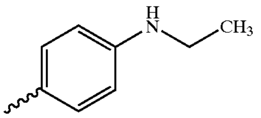 |
| 8 | 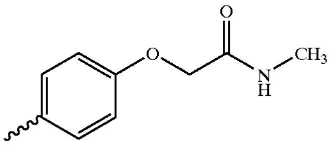 |
| 9 | 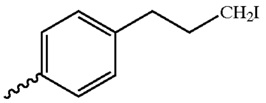 |
| 10 | 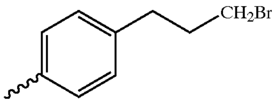 |
| 11 | 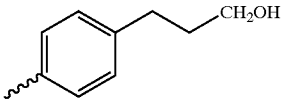 |
| 12 | 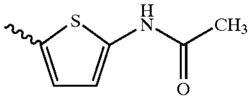 |
| 13 | 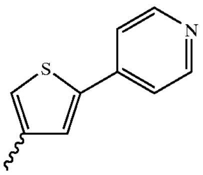 |
TABLE 54-continued
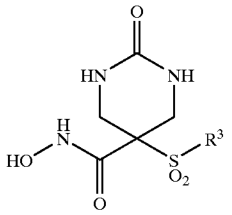
| 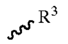 | |
|---|---|
| 14 | 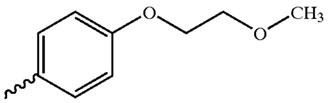 |
| 15 | 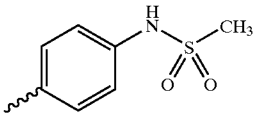 |
| 16 | 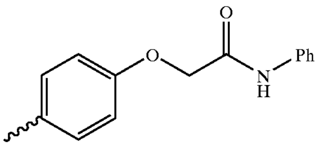 |
| 17 | 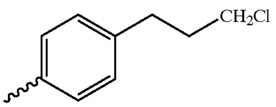 |
| 18 | 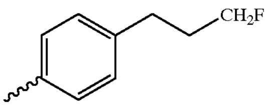 |
| 19 | 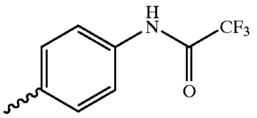 |
| 20 | 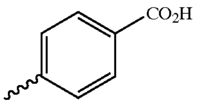 |
| 21 | 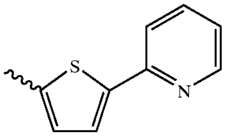 |
| 22 | 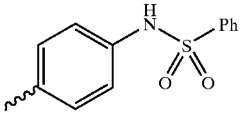 |
| 23 | 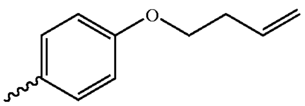 |

TABLE 54-continued
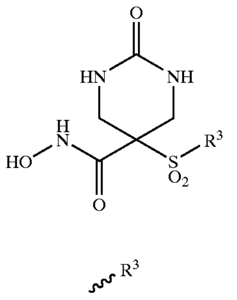
| | |
|---|---|
| 24 | 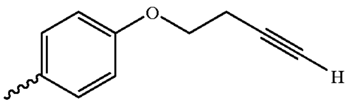 |
| 25 | 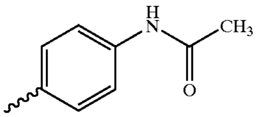 |
| 26 | 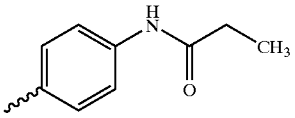 |
| 27 | 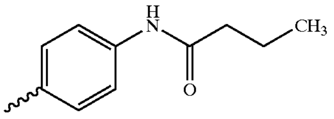 |
| 28 | 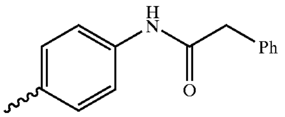 |
| 29 | 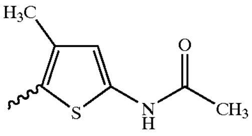 |
| 30 | 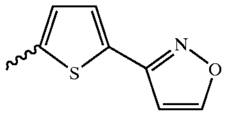 |
TABLE 55
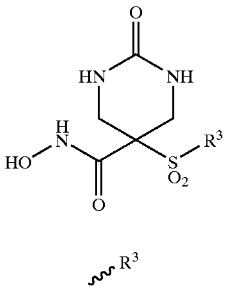
| | |
|---|---|
| 1 | 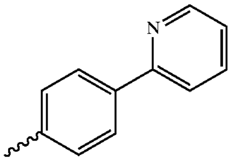 |
| 2 | 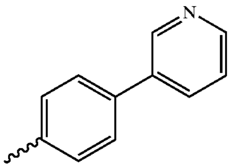 |
| 3 | 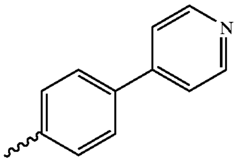 |
| 4 | 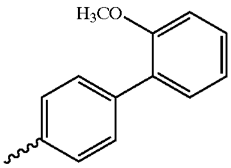 |
| 5 | 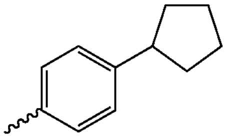 |
| 6 | 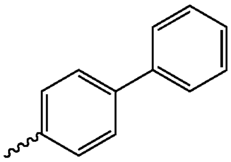 |
| 7 | 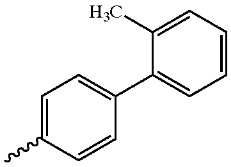 |

TABLE 55-continued
| | |
|---|---|
| 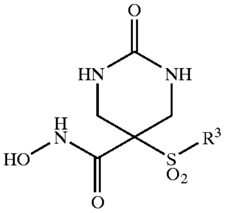 | |
| 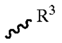 | |
| 8 | 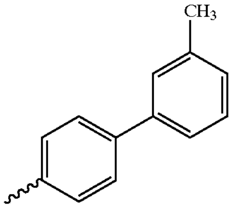 |
| 9 | 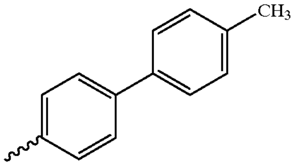 |
| 10 | 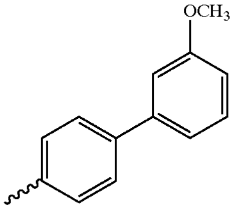 |
| 11 | 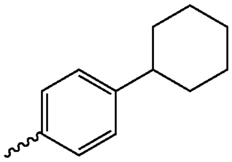 |
| 12 | 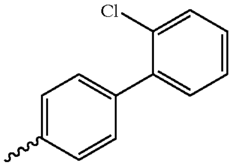 |
| 13 | 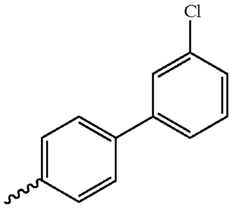 |
TABLE 55-continued
| | |
|---|---|
| 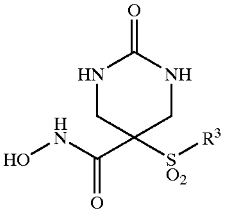 | |
| 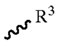 | |
| 14 | 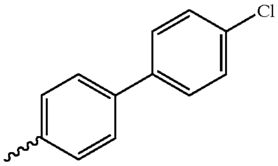 |
| 15 | 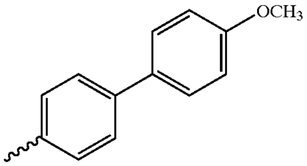 |
| 16 | 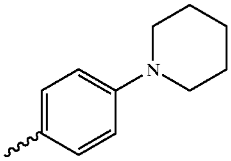 |
| 17 | 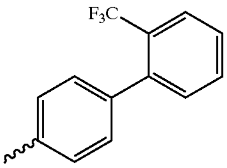 |
| 18 | 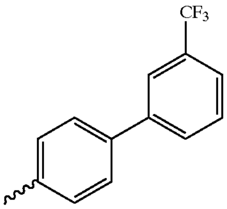 |
| 19 | 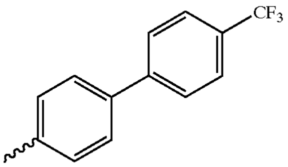 |
| 20 | 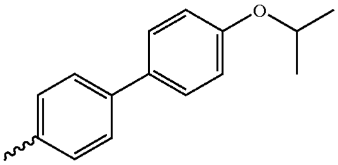 |

TABLE 55-continued
| 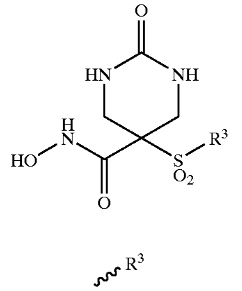 | |
|---|---|
| 21 | 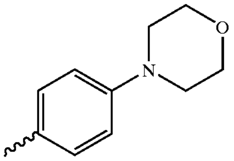 |
TABLE 56
| 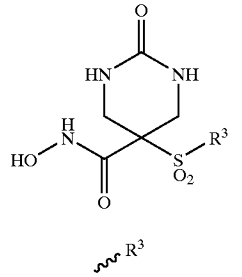 | |
|---|---|
| 1 | 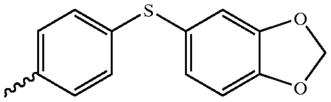 |
| 2 | 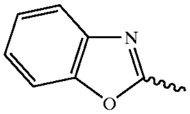 |
| 3 | 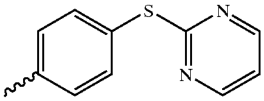 |
| 4 | 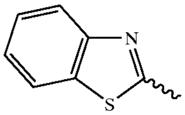 |
| 5 | 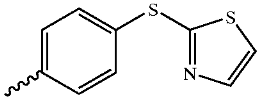 |
| 6 | 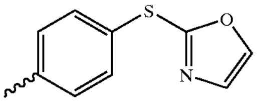 |
TABLE 56-continued
| 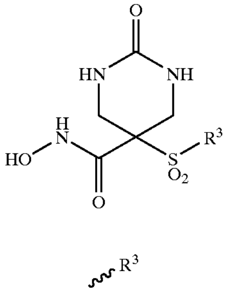 | |
|---|---|
| 7 | 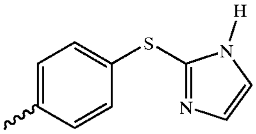 |
| 8 | 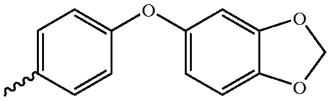 |
| 9 | 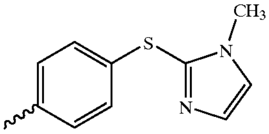 |
| 10 | 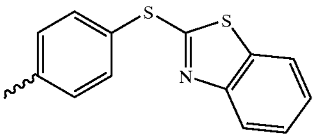 |
| 11 | 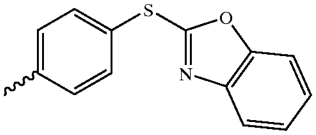 |
TABLE 57
| 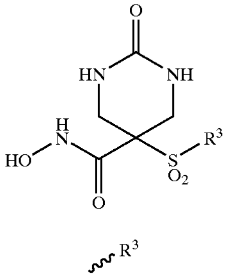 | |
|---|---|
| 1 | 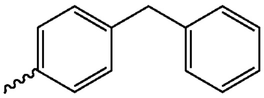 |

TABLE 57-continued
| | |
|---|---|
| | 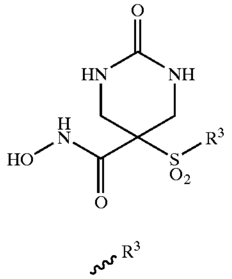 |
| 2 | 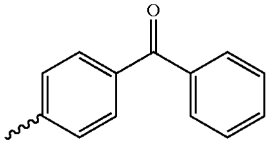 |
| 3 | 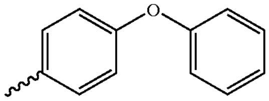 |
| 4 | 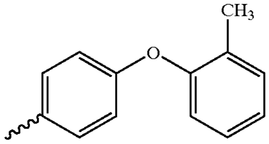 |
| 5 | 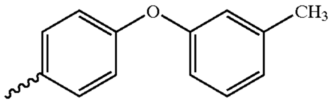 |
| 6 | 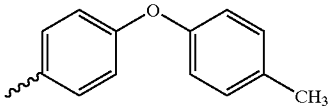 |
| 7 | 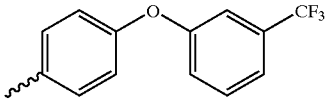 |
| 8 | 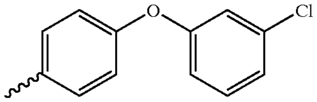 |
| 9 | 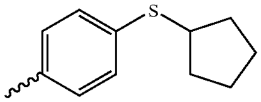 |
| 10 | 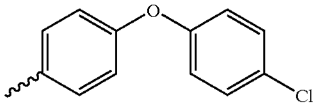 |
| 11 | 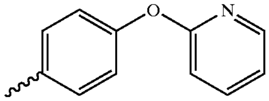 |
TABLE 57-continued
| | |
|---|---|
| | 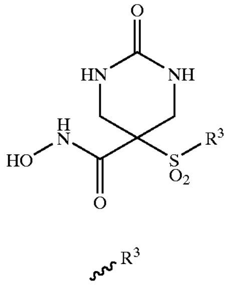 |
| 12 | 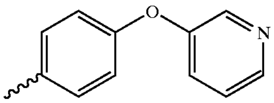 |
| 13 | 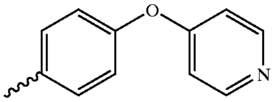 |
| 14 | 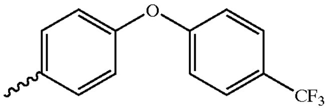 |
| 15 | 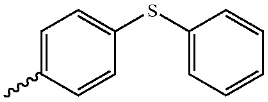 |
| 16 | 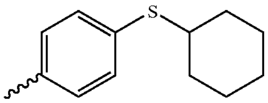 |
| 17 | 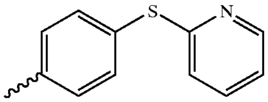 |
| 18 | 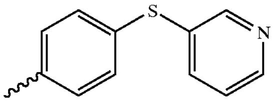 |
| 19 | 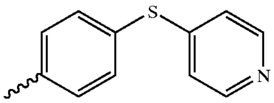 |
| 20 | 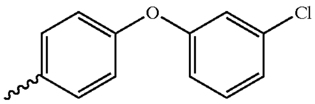 |
| 21 | 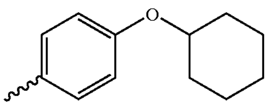 |

TABLE 58
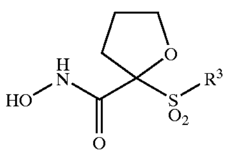
1
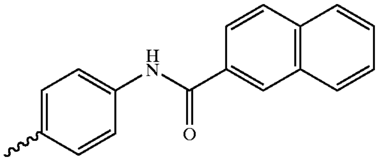
2
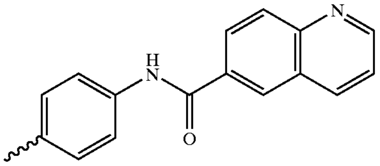
3
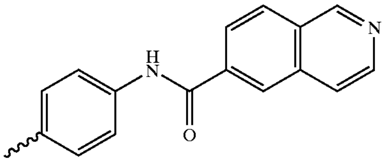
4
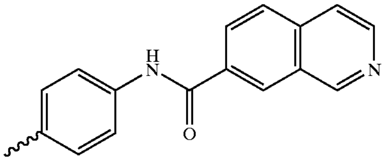
5
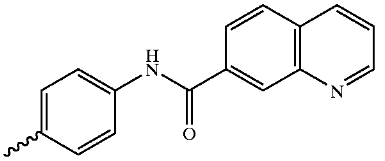
6
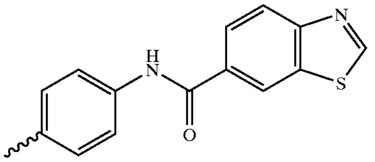
7
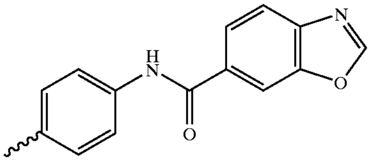
8
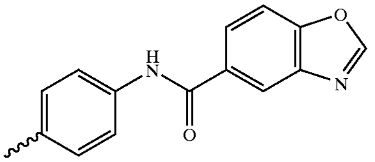
TABLE 58-continued
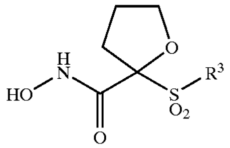
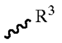
9
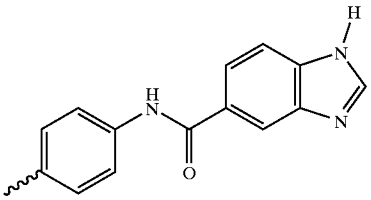
10
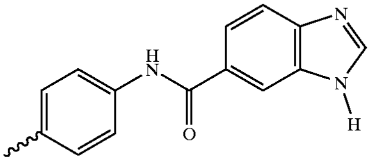
11
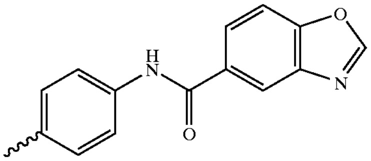
12
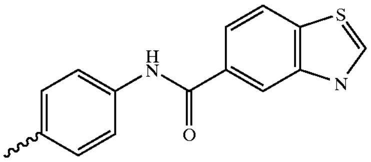
13
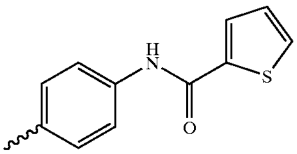
14
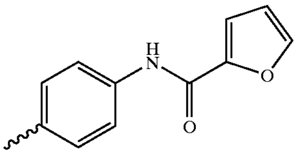
15
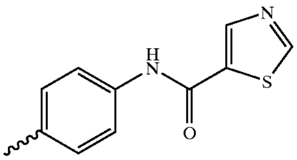

TABLE 58-continued
| 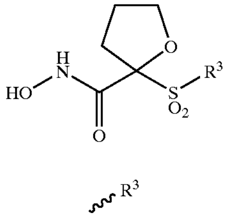 |
|---|
| 16 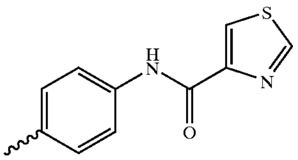 |
| 17 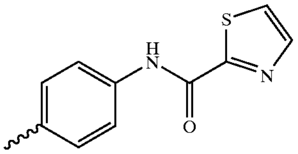 |
| 18 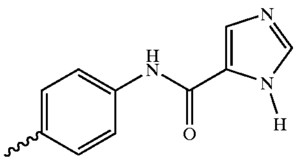 |
TABLE 59
| 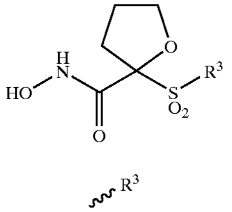 |
|---|
| 1 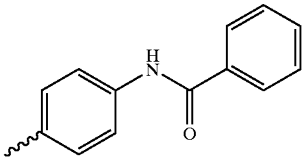 |
| 2 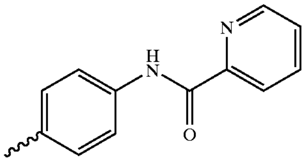 |
| 3 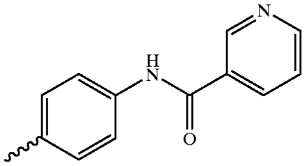 |
TABLE 59-continued
| 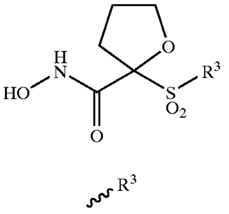 |
|---|
| 4 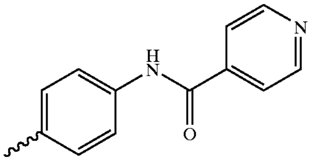 |
| 5 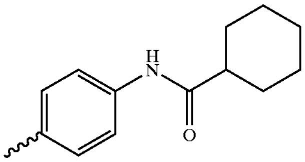 |
| 6 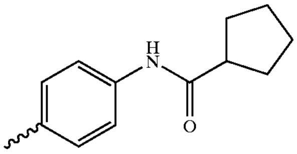 |
| 7 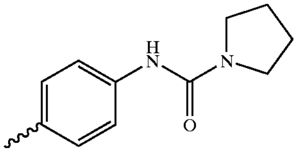 |
| 8 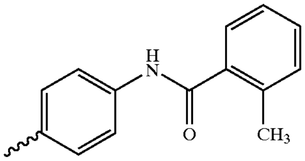 |
| 9 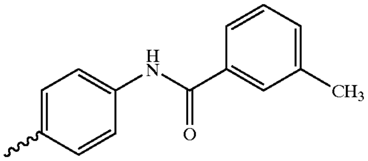 |
| 10 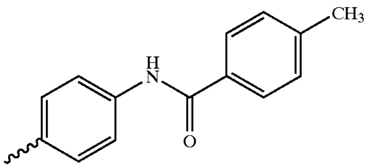 |
| 11 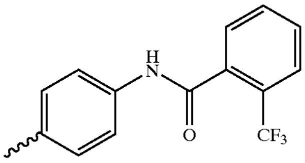 |

TABLE 59-continued
| 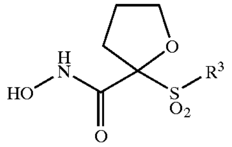 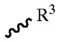 | |
|---|---|
| 12 | 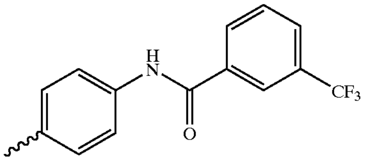 |
| 13 | 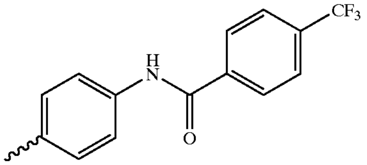 |
| 14 | 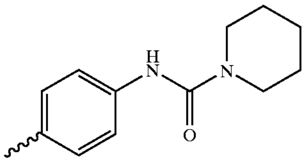 |
| 15 | 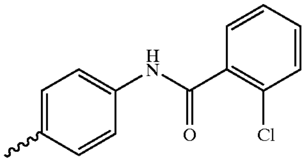 |
| 16 | 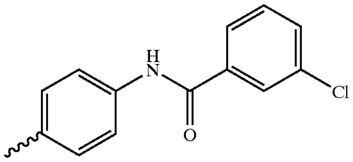 |
| 17 | 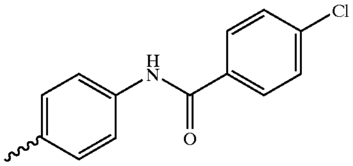 |
| 18 | 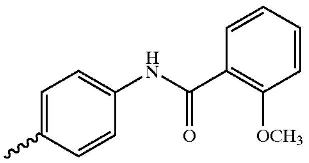 |
TABLE 59-continued
| 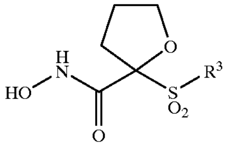 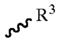 | |
|---|---|
| 19 | 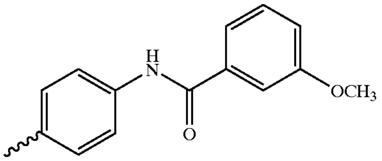 |
| 20 | 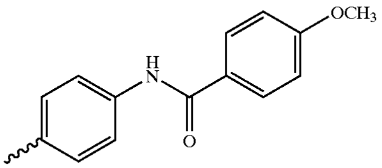 |
| 21 | 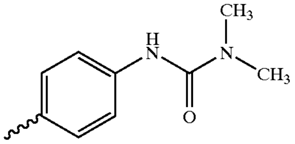 |
TABLE 60
| 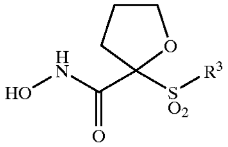 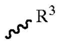 | |
|---|---|
| 1 | 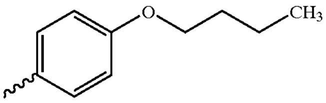 |
| 2 | 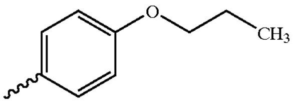 |
| 3 | 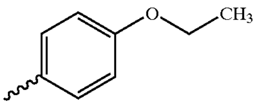 |
| 4 | 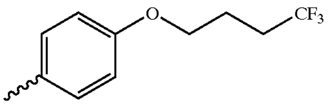 |

TABLE 60-continued
| | |
|---|---|
| | 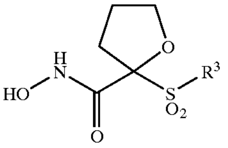 |
| | 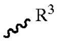 |
| 5 | 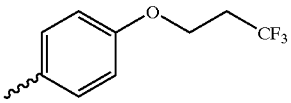 |
| 6 | 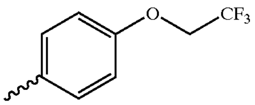 |
| 7 | 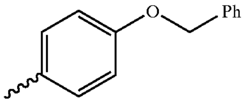 |
| 8 | 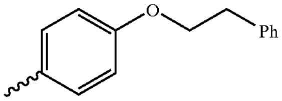 |
| 9 | 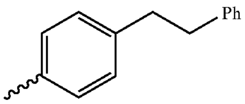 |
| 10 | 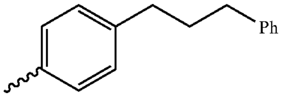 |
| 11 | 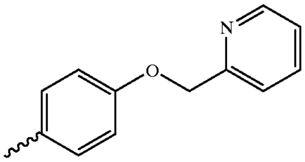 |
| 12 | 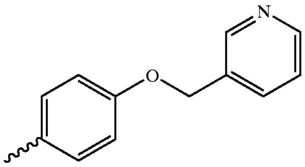 |
| 13 | 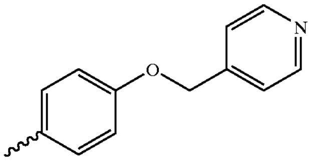 |
TABLE 60-continued
| | |
|---|---|
| | 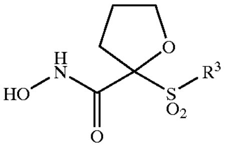 |
| | 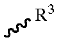 |
| 14 | 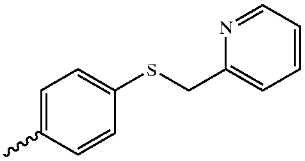 |
| 15 | 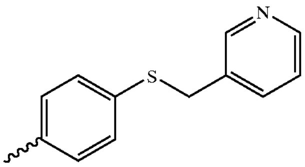 |
| 16 | 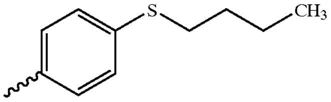 |
| 17 | 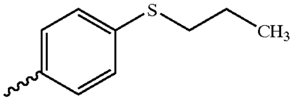 |
| 18 | 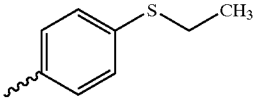 |
| 19 | 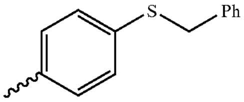 |
| 20 | 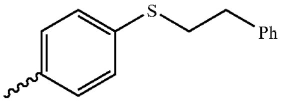 |
| 21 | 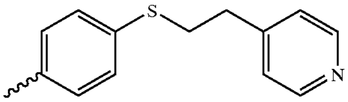 |
| 22 | 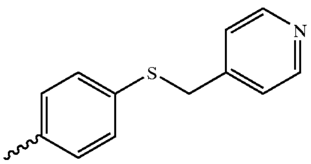 |

TABLE 75
| | |
|---|---|
| 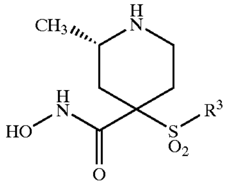 | |
| 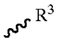 | |
| 1 | 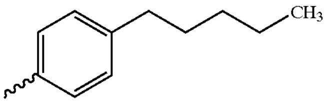 |
| 2 | 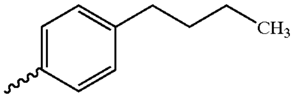 |
| 3 | 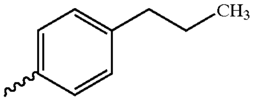 |
| 4 | 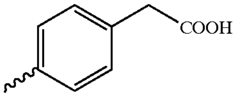 |
| 5 | 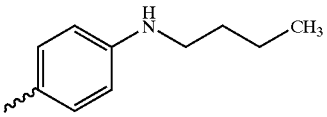 |
| 6 | 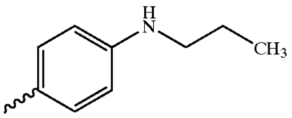 |
| 7 | 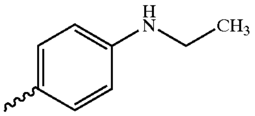 |
| 8 | 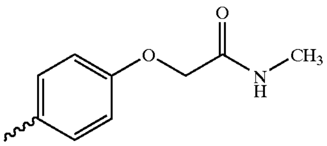 |
| 9 | 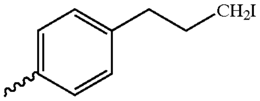 |
| 10 | 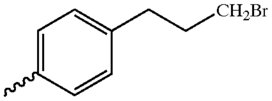 |
| 11 | 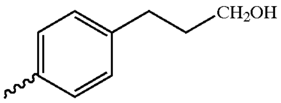 |
TABLE 75-continued
| | |
|---|---|
| 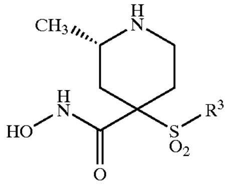 | |
| 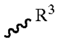 | |
| 12 | 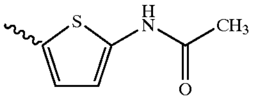 |
| 13 | 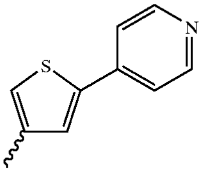 |
| 14 | 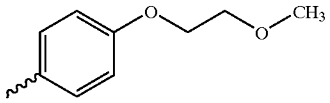 |
| 15 | 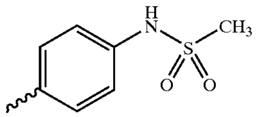 |
| 16 | 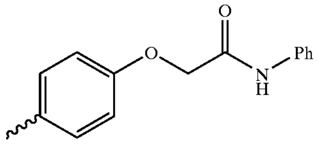 |
| 17 | 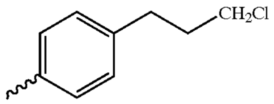 |
| 18 | 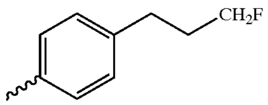 |
| 19 | 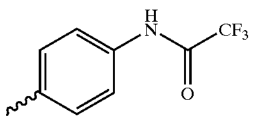 |
| 20 | 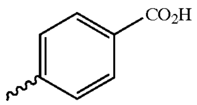 |
| 21 | 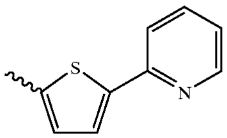 |

TABLE 75-continued
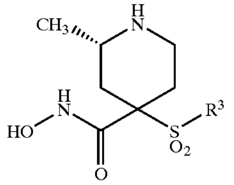
| | 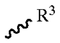 |
|---|---|
| 22 | 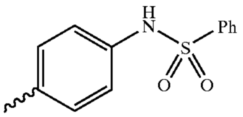 |
| 23 | 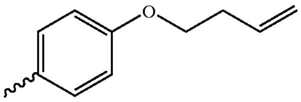 |
| 24 | 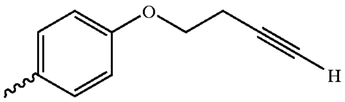 |
| 25 | 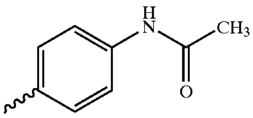 |
| 26 | 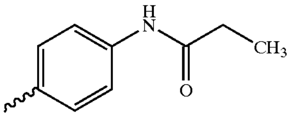 |
| 27 | 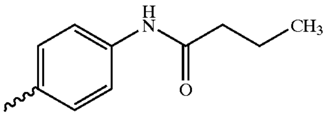 |
| 28 | 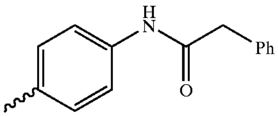 |
| 29 | 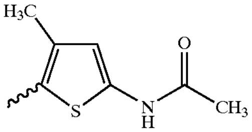 |
| 30 | 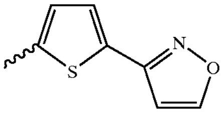 |
TABLE 62
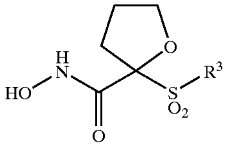
| | 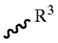 |
|---|---|
| 1 | 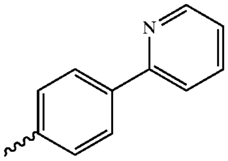 |
| 2 | 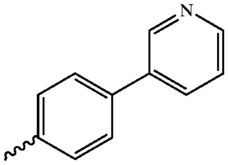 |
| 3 | 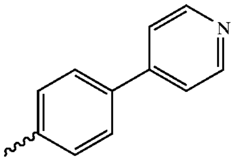 |
| 4 | 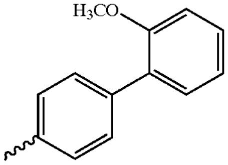 |
| 5 | 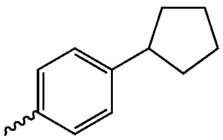 |
| 6 | 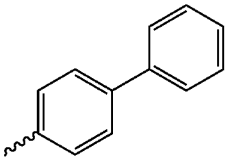 |
| 7 | 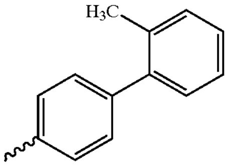 |

TABLE 62-continued
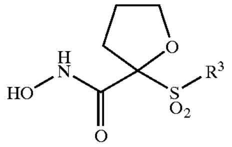
| | 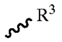 |
|---|---|
| 8 | 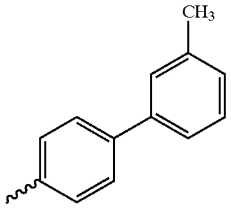 |
| 9 | 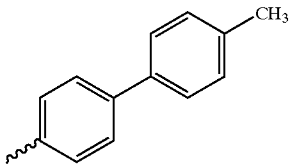 |
| 10 | 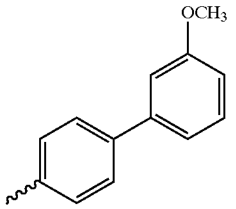 |
| 11 | 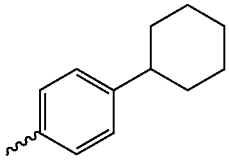 |
| 12 | 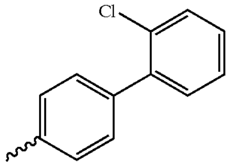 |
| 13 | 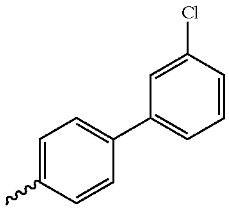 |
| 14 | 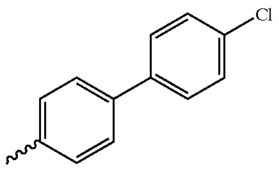 |
TABLE 62-continued
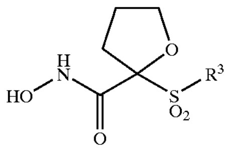
| | 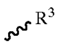 |
|---|---|
| 15 | 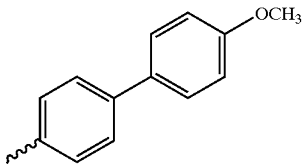 |
| 16 | 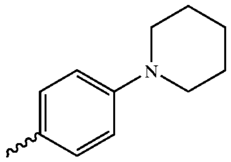 |
| 17 | 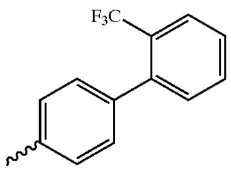 |
| 18 | 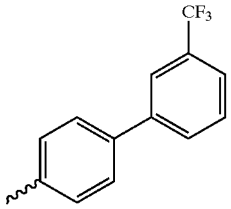 |
| 19 | 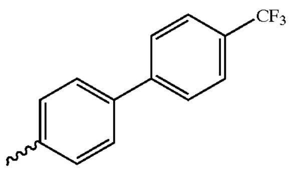 |
| 20 | 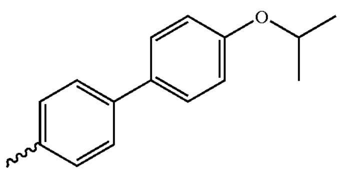 |
| 21 | 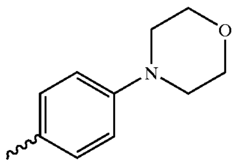 |

TABLE 63
| | |
|---|---|
| | 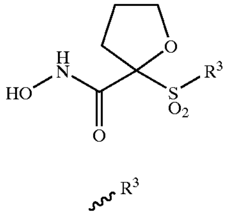 |
| 1 | 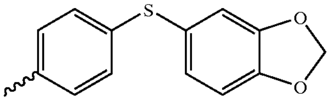 |
| 2 | 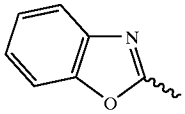 |
| 3 | 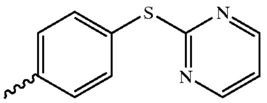 |
| 4 | 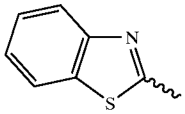 |
| 5 | 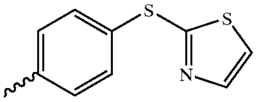 |
| 6 | 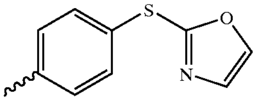 |
| 7 | 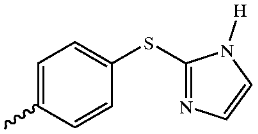 |
| 8 | 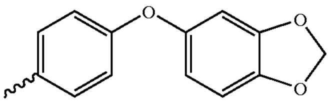 |
| 9 | 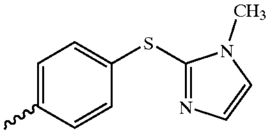 |
| 10 | 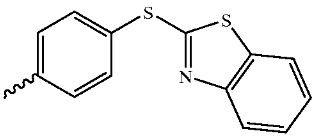 |
TABLE 63-continued
| | |
|---|---|
| | 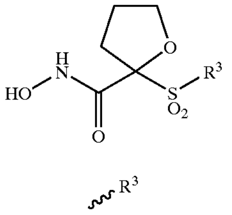 |
| 11 | 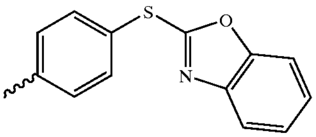 |
TABLE 64
| | |
|---|---|
| | 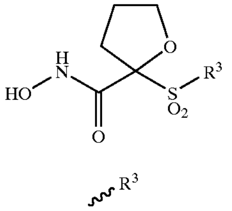 |
| 1 | 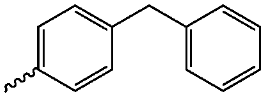 |
| 2 | 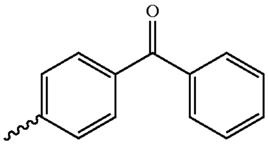 |
| 3 | 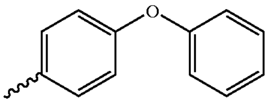 |
| 4 | 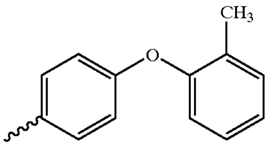 |
| 5 | 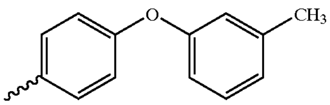 |
| 6 | 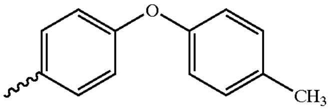 |
| 7 | 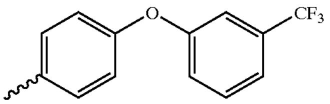 |

TABLE 64-continued
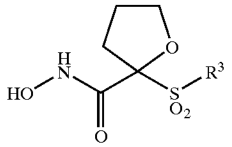
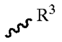
| | |
|---|---|
| 8 | 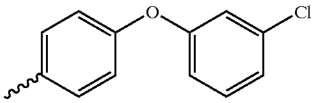 |
| 9 | 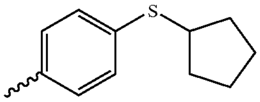 |
| 10 | 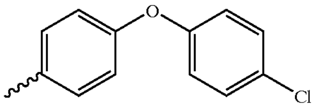 |
| 11 | 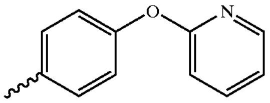 |
| 12 | 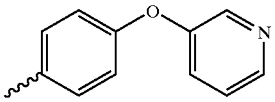 |
| 13 | 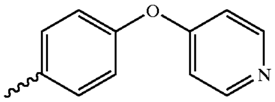 |
| 14 | 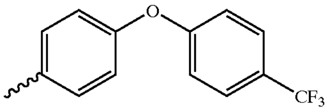 |
| 15 | 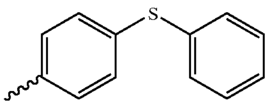 |
| 16 | 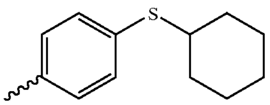 |
| 17 | 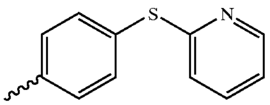 |
| 18 | 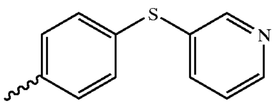 |
TABLE 64-continued
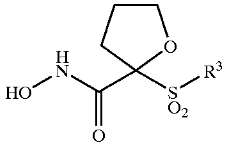
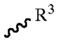
| | |
|---|---|
| 19 | 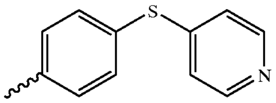 |
| 20 | 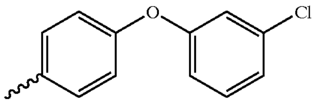 |
| 21 | 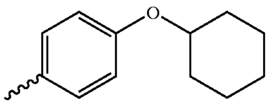 |
TABLE 65
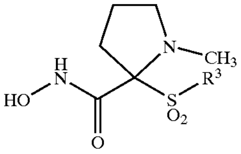
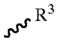
| | |
|---|---|
| 1 | 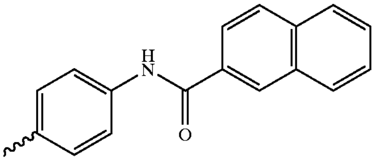 |
| 2 | 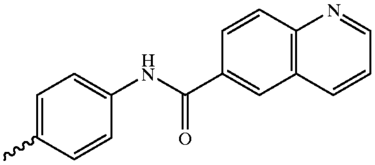 |
| 3 | 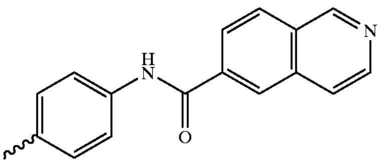 |
| 4 | 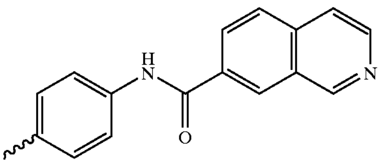 |

TABLE 65-continued
| 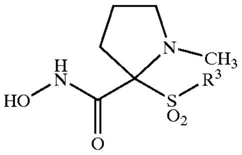 |  |
|---|---|
| 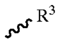 |  |
| 5 | 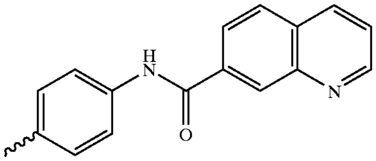 |
| 6 | 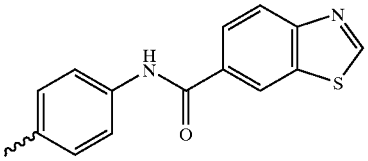 |
| 7 | 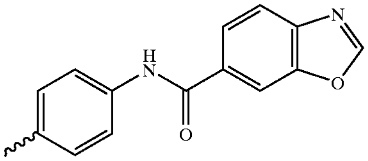 |
| 8 | 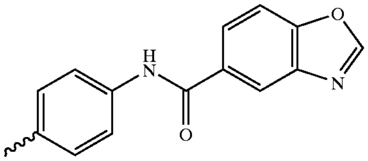 |
| 9 | 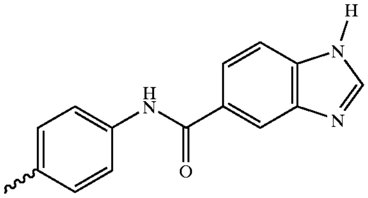 |
| 10 | 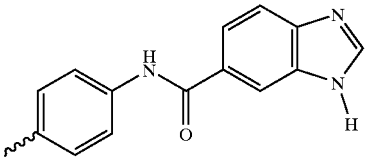 |
| 11 | 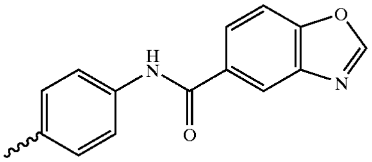 |
TABLE 65-continued
| 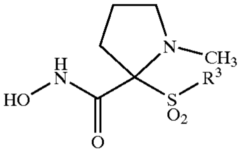 |  |
|---|---|
| 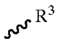 |  |
| 12 | 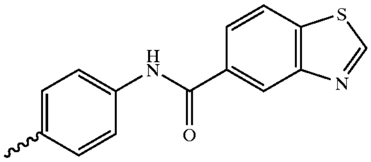 |
| 13 | 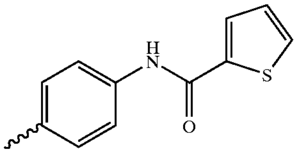 |
| 14 | 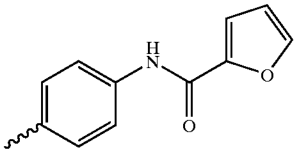 |
| 15 | 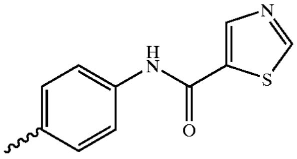 |
| 16 | 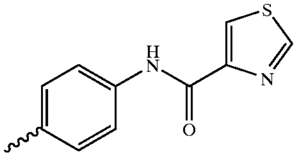 |
| 17 | 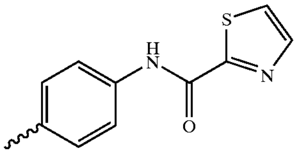 |
| 18 | 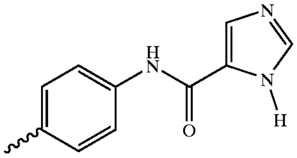 |

TABLE 66
| 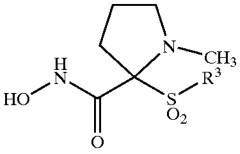<br>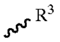 | |
| --- | --- |
| 1 | 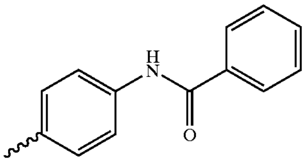 |
| 2 | 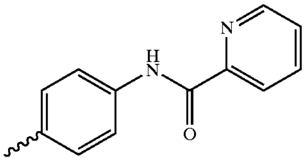 |
| 3 | 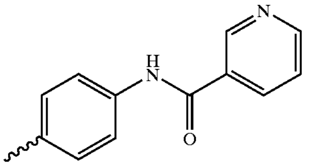 |
| 4 | 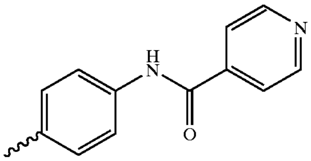 |
| 5 | 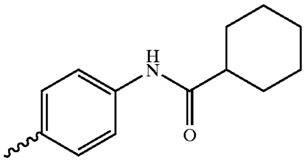 |
| 6 | 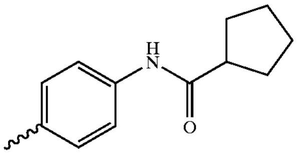 |
| 7 | 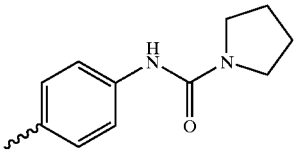 |
| 8 | 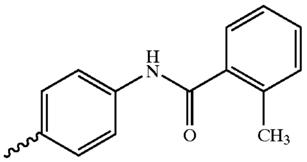 |
TABLE 66-continued
| 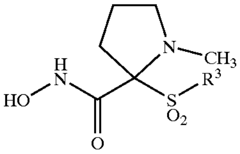<br>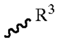 | |
| --- | --- |
| 9 | 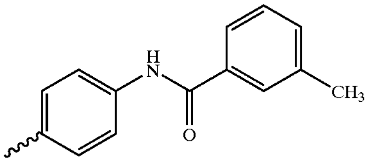 |
| 10 | 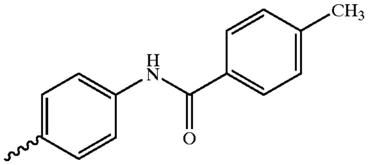 |
| 11 | 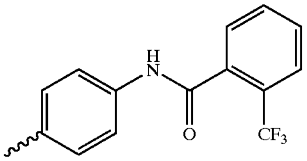 |
| 12 | 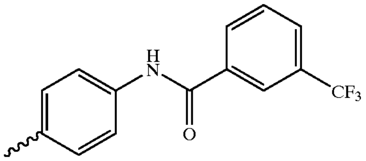 |
| 13 | 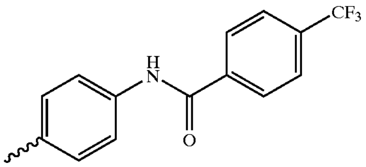 |
| 14 | 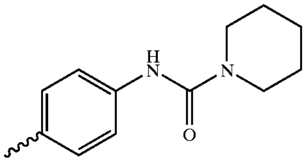 |
| 15 | 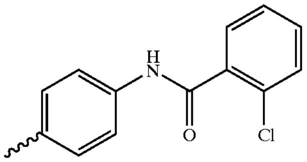 |

TABLE 66-continued
| | |
|---|---|
| | 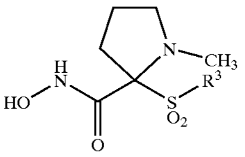 |
| | 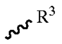 |
| 16 | 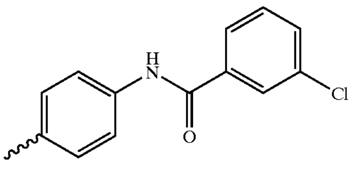 |
| 17 | 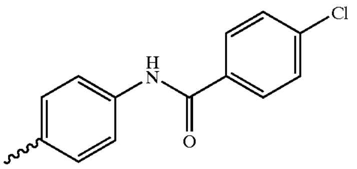 |
| 18 | 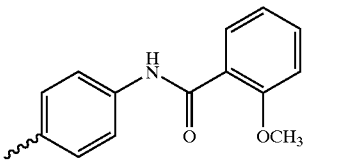 |
| 19 | 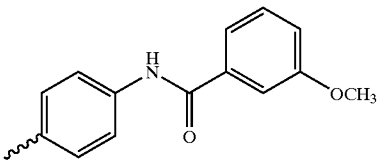 |
| 20 | 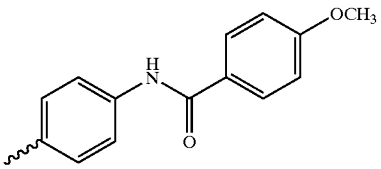 |
| 21 | 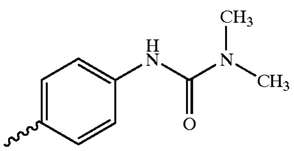 |
TABLE 67
| | |
|---|---|
| | 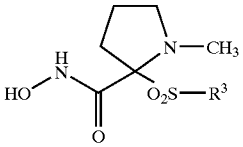 |
| | 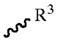 |
| 1 | 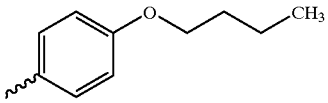 |
| 2 | 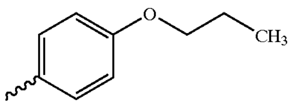 |
| 3 | 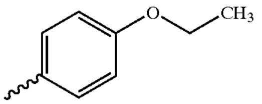 |
| 4 | 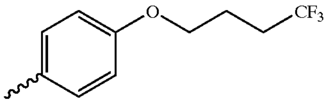 |
| 5 | 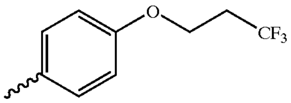 |
| 6 | 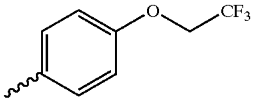 |
| 7 | 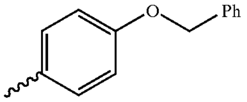 |
| 8 | 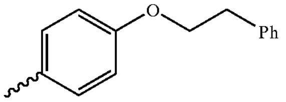 |
| 9 | 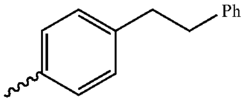 |
| 10 | 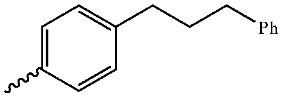 |
| 11 | 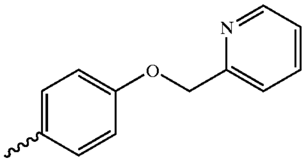 |

TABLE 67-continued
| | |
|---|---|
| 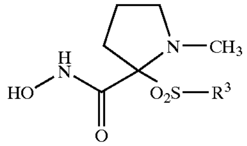 | |
| 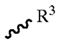 | |
| 12 | 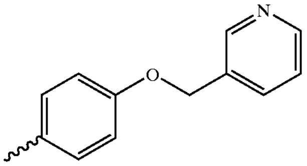 |
| 13 | 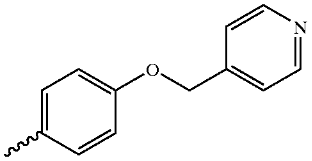 |
| 14 | 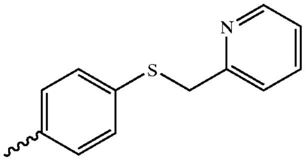 |
| 15 | 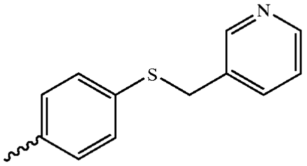 |
| 16 | 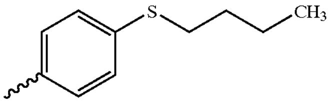 |
| 17 | 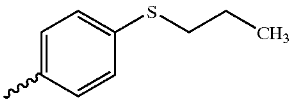 |
| 18 | 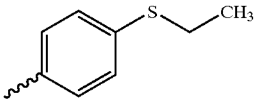 |
| 19 | 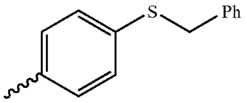 |
| 20 | 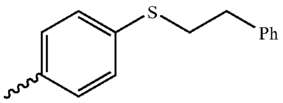 |
TABLE 67-continued
| | |
|---|---|
| 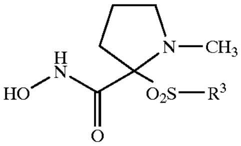 | |
| 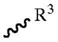 | |
| 21 | 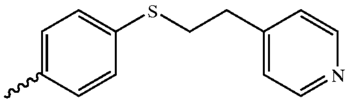 |
| 22 | 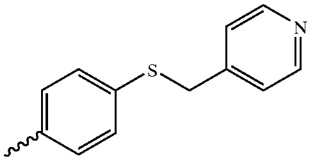 |
TABLE 68
| | |
|---|---|
| 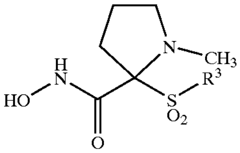 | |
| 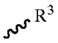 | |
| 1 | 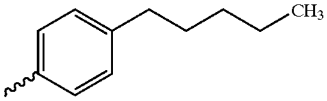 |
| 2 | 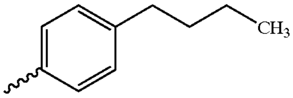 |
| 3 | 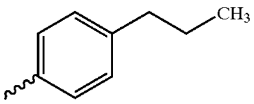 |
| 4 | 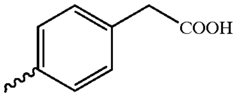 |
| 5 | 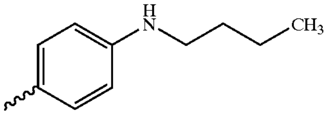 |
| 6 | 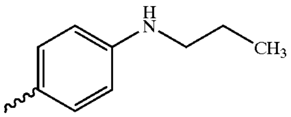 |

TABLE 68-continued
| | 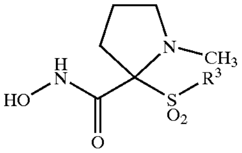<br>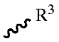 |
|---|---|
| 7 | 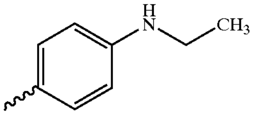 |
| 8 | 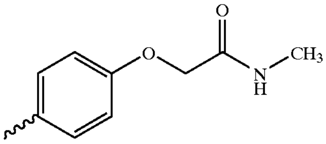 |
| 9 | 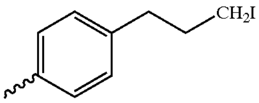 |
| 10 | 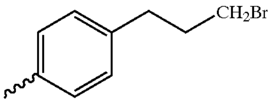 |
| 11 | 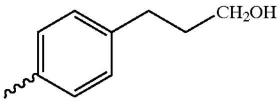 |
| 12 | 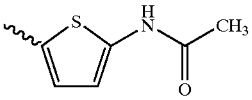 |
| 13 | 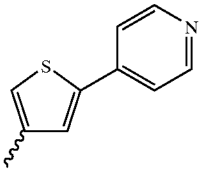 |
| 14 | 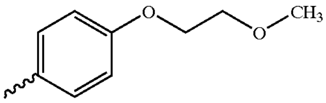 |
| 15 | 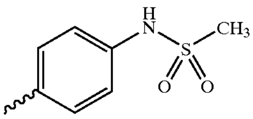 |
| 16 | 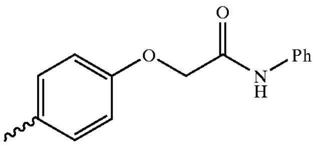 |
TABLE 68-continued
| | 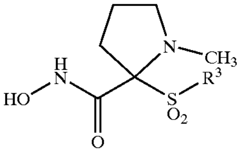<br>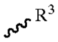 |
|---|---|
| 17 | 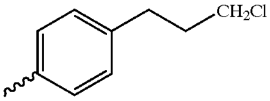 |
| 18 | 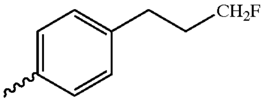 |
| 19 | 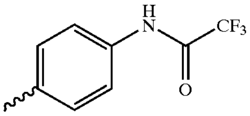 |
| 20 | 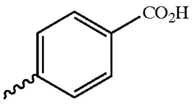 |
| 21 | 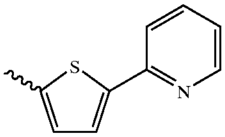 |
| 22 | 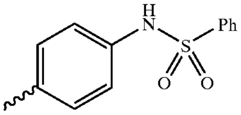 |
| 23 | 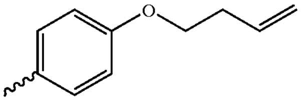 |
| 24 | 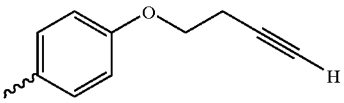 |
| 25 | 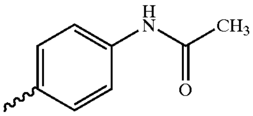 |
| 26 | 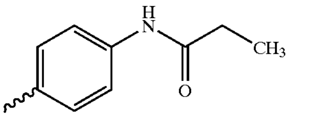 |
| 27 | 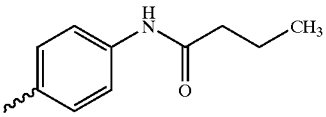 |

TABLE 68-continued
| | |
|---|---|
| | 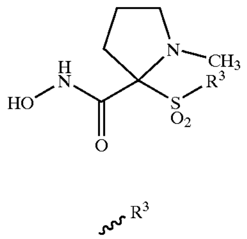 |
| 28 | 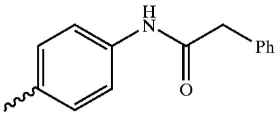 |
| 29 | 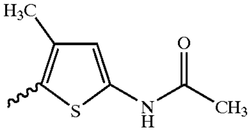 |
| 30 | 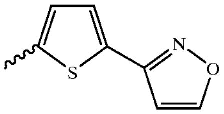 |
TABLE 69
| | |
|---|---|
| | 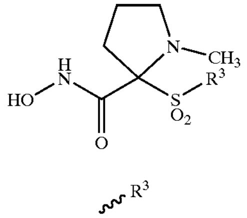 |
| 1 | 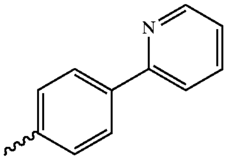 |
| 2 | 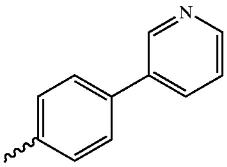 |
| 3 | 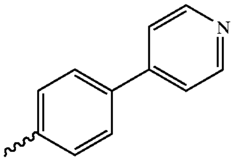 |
TABLE 69-continued
| | |
|---|---|
| | 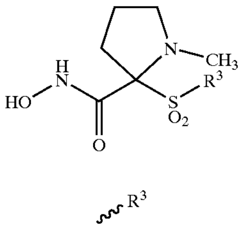 |
| 4 | 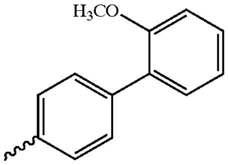 |
| 5 | 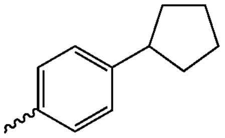 |
| 6 | 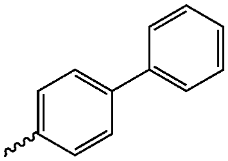 |
| 7 | 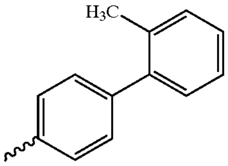 |
| 8 | 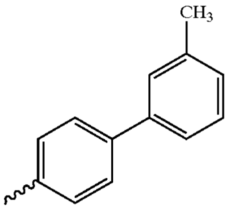 |
| 9 | 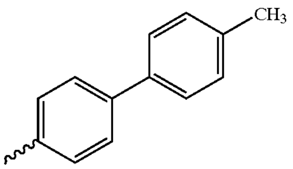 |
| 10 | 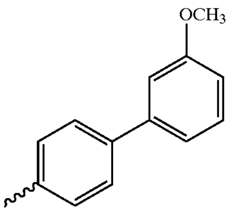 |

TABLE 69-continued
| 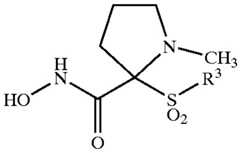 | |
|---|---|
| | 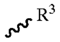 |
| 11 | 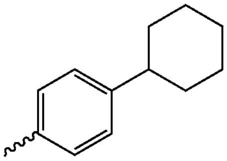 |
| 12 | 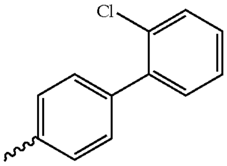 |
| 13 | 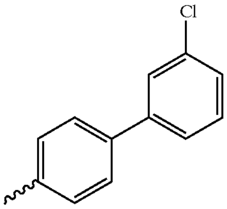 |
| 14 | 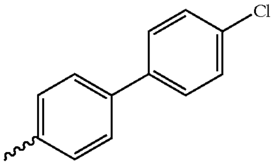 |
| 15 | 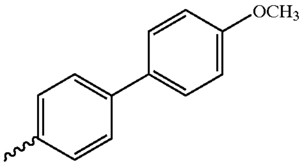 |
| 16 | 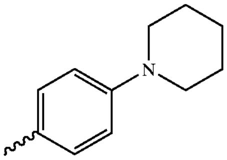 |
| 17 | 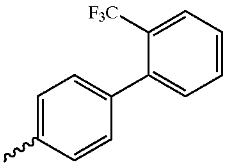 |
TABLE 69-continued
| 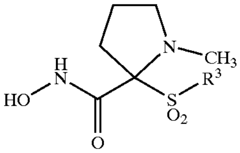 | |
|---|---|
| | 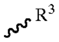 |
| 18 | 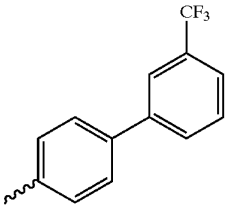 |
| 19 | 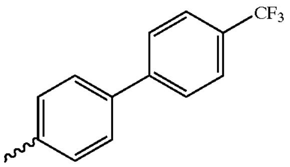 |
| 20 | 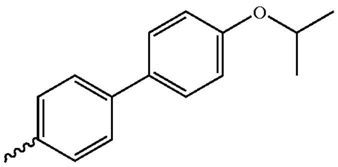 |
| 21 | 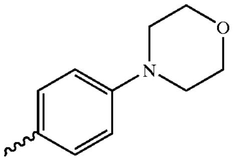 |
TABLE 70
| 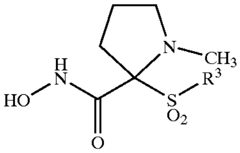 | |
|---|---|
| | 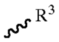 |
| 1 | 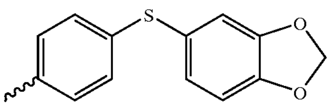 |
| 2 | 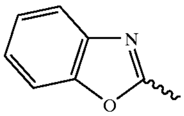 |

TABLE 70-continued
| 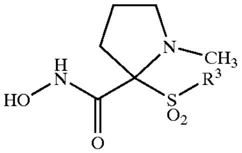 | 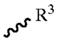 |
| --- | --- |
| 3 | 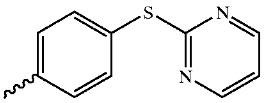 |
| 4 | 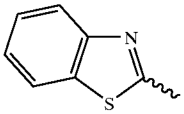 |
| 5 | 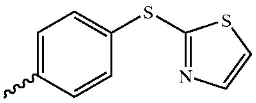 |
| 6 | 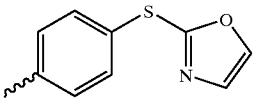 |
| 7 | 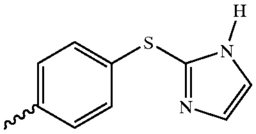 |
| 8 | 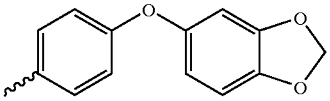 |
| 9 | 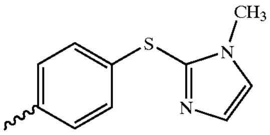 |
| 10 | 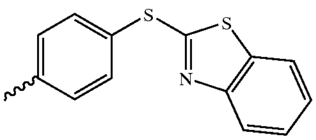 |
| 11 | 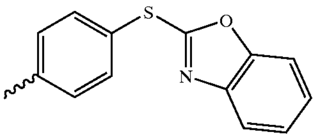 |
TABLE 71
| 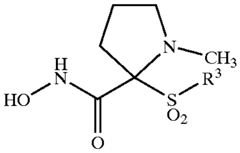 | 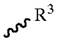 |
| --- | --- |
| 1 | 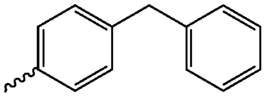 |
| 2 | 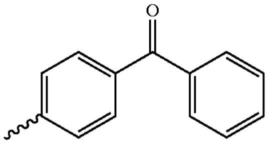 |
| 3 | 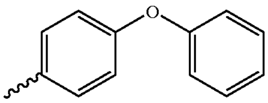 |
| 4 | 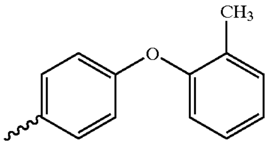 |
| 5 | 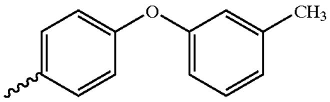 |
| 6 | 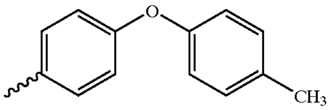 |
| 7 | 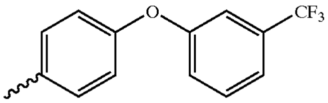 |
| 8 | 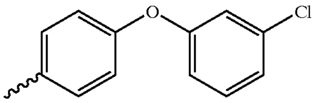 |
| 9 | 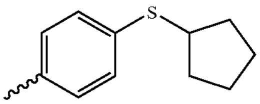 |
| 10 | 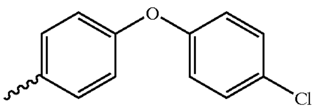 |

TABLE 71-continued
| | |
|---|---|
| | 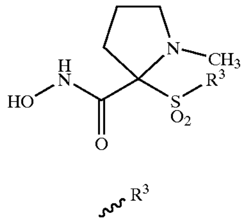 |
| 11 | 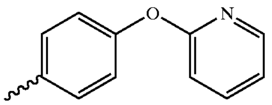 |
| 12 | 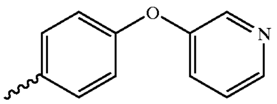 |
| 13 | 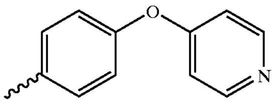 |
| 14 | 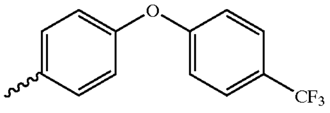 |
| 15 | 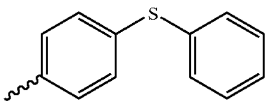 |
| 16 | 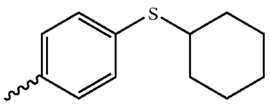 |
| 17 | 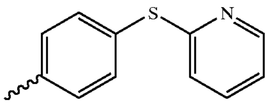 |
| 18 | 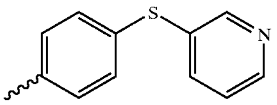 |
| 19 | 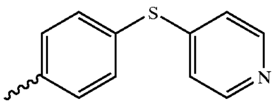 |
| 20 | 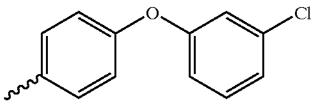 |
| 21 | 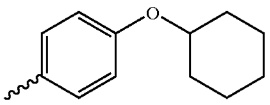 |
TABLE 72
| | |
|---|---|
| | 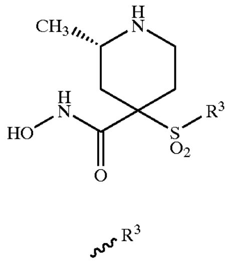 |
| 1 | 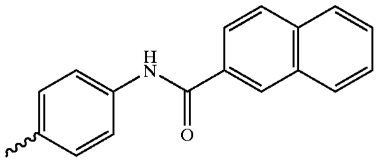 |
| 2 | 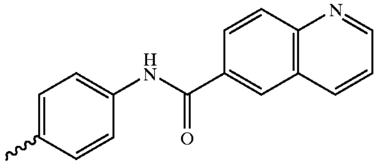 |
| 3 | 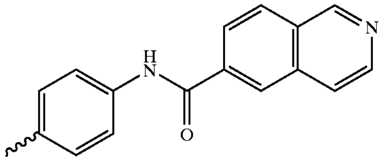 |
| 4 | 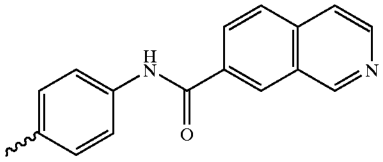 |
| 5 | 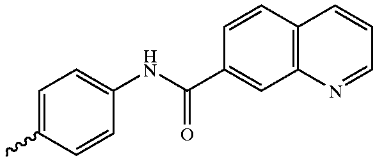 |
| 6 | 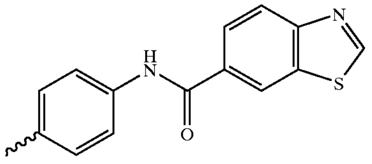 |
| 7 | 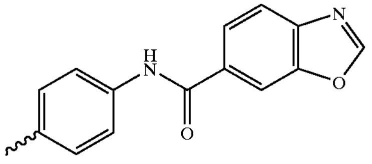 |

TABLE 72-continued
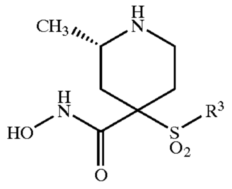
| 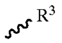 |
|---|
| | |
|---|---|
| 8 | 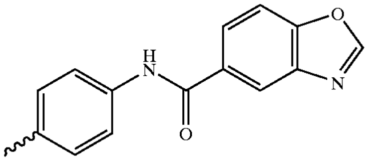 |
| 9 | 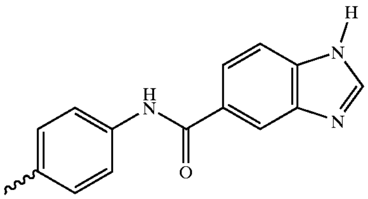 |
| 10 | 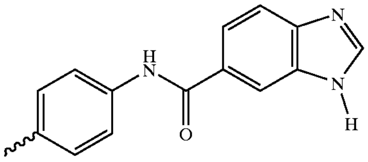 |
| 11 | 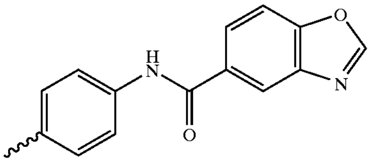 |
| 12 | 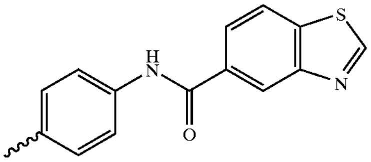 |
| 13 | 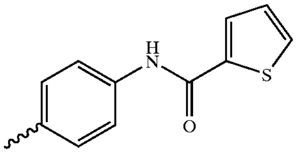 |
| 14 | 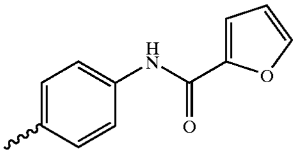 |
TABLE 72-continued
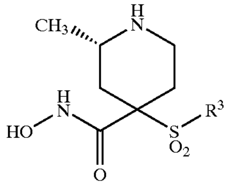
| 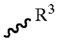 |
|---|
| | |
|---|---|
| 15 | 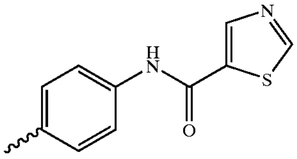 |
| 16 | 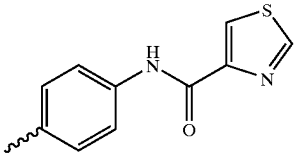 |
| 17 | 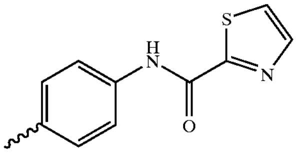 |
| 18 | 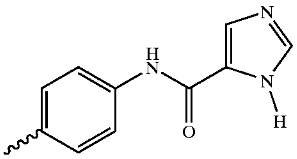 |
TABLE 73
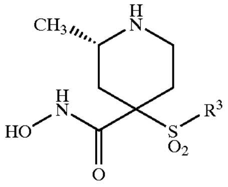
| 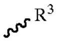 |
|---|
| | |
|---|---|
| 1 | 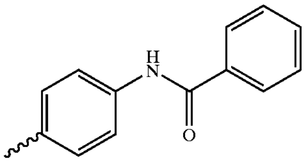 |
| 2 | 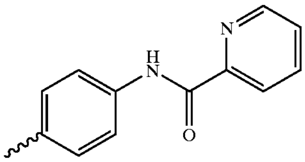 |

TABLE 73-continued
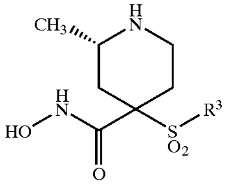
| 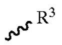 | |
| --- | --- |
| 3 | 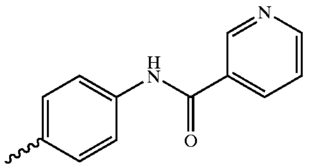 |
| 4 | 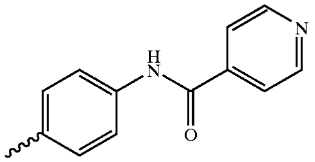 |
| 5 | 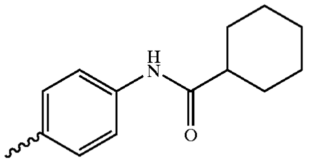 |
| 6 | 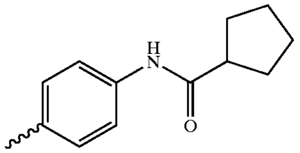 |
| 7 | 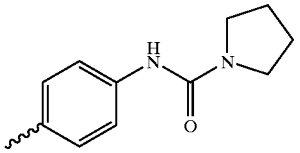 |
| 8 | 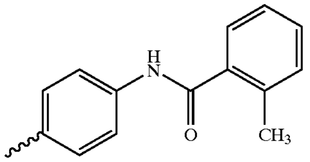 |
| 9 | 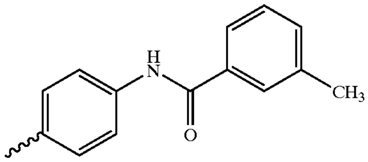 |
TABLE 73-continued
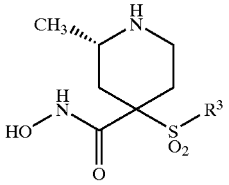
| 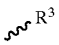 | |
| --- | --- |
| 10 | 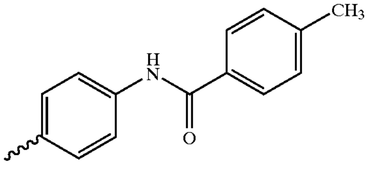 |
| 11 | 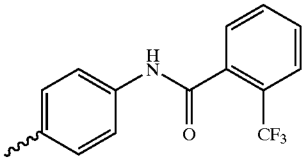 |
| 12 | 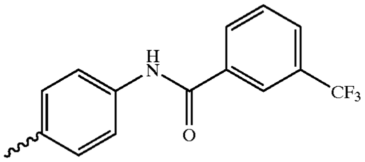 |
| 13 | 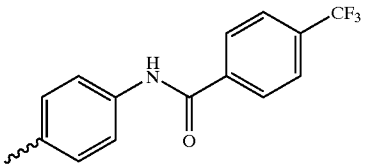 |
| 14 | 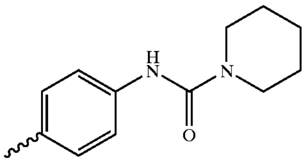 |
| 15 | 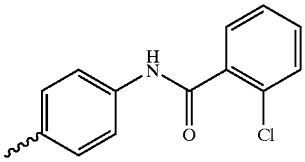 |
| 16 | 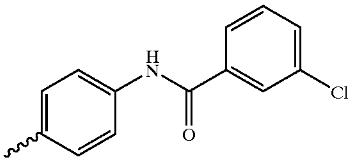 |

TABLE 73-continued
| 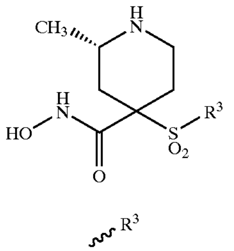 | |
|---|---|
| 17 | 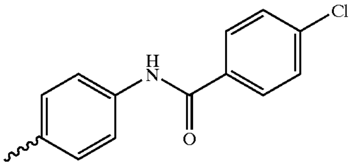 |
| 18 | 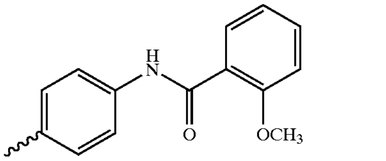 |
| 19 | 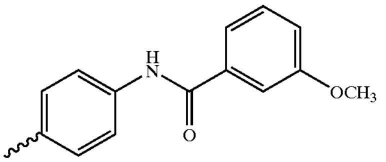 |
| 20 | 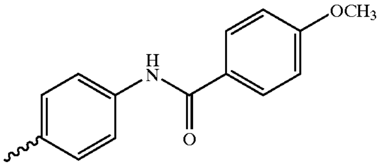 |
| 21 | 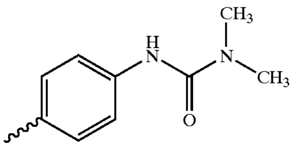 |
TABLE 74
| 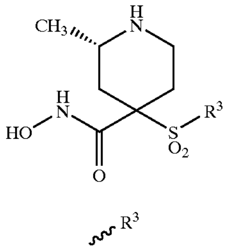 | |
|---|---|
| 1 | 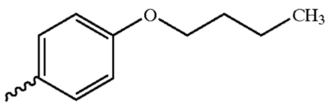 |
TABLE 74-continued
| 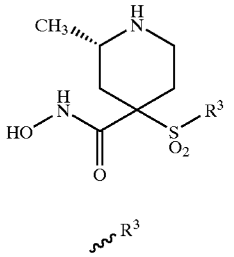 | |
|---|---|
| 2 | 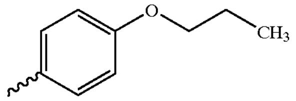 |
| 3 | 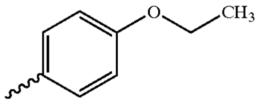 |
| 4 | 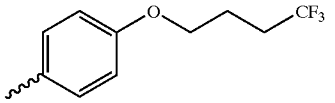 |
| 5 | 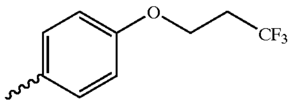 |
| 6 | 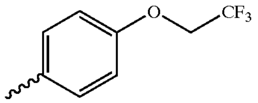 |
| 7 | 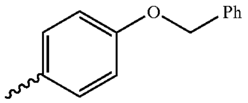 |
| 8 | 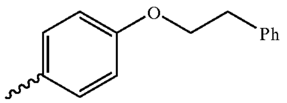 |
| 9 | 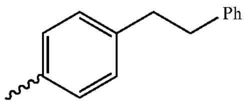 |
| 10 | 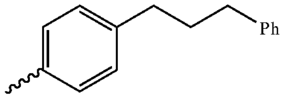 |
| 11 | 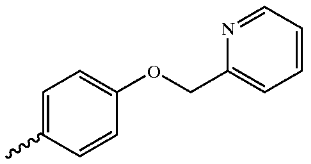 |

TABLE 74-continued
| | 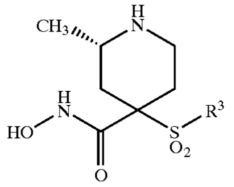 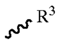 |
|---|---|
| 12 | 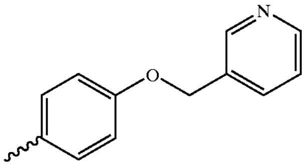 |
| 13 | 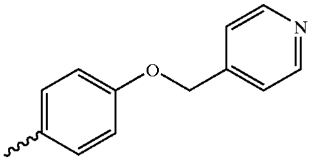 |
| 14 | 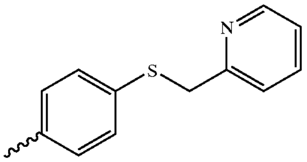 |
| 15 | 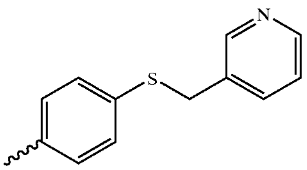 |
| 16 | 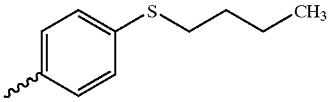 |
| 17 | 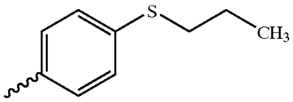 |
| 18 | 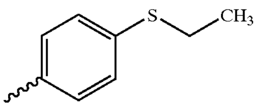 |
| 19 | 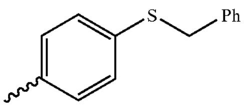 |
| 20 | 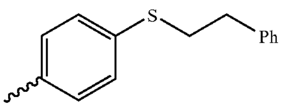 |
TABLE 74-continued
| | 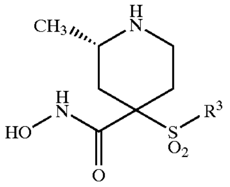 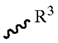 |
|---|---|
| 21 | 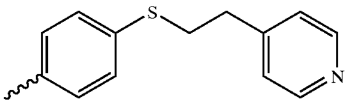 |
| 22 | 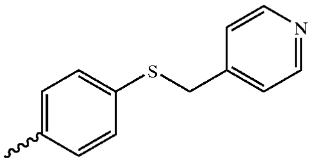 |
TABLE 75
| | 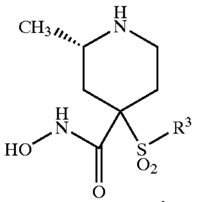 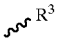 |
|---|---|
| 1 | 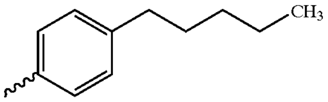 |
| 2 | 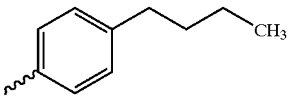 |
| 3 | 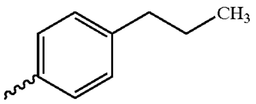 |
| 4 | 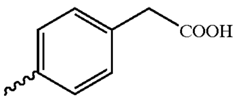 |
| 5 | 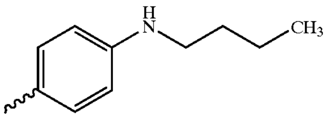 |
| 6 | 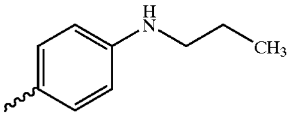 |

TABLE 75-continued
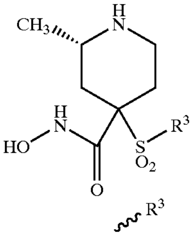
| | |
|---|---|
| 7 | 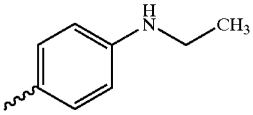 |
| 8 | 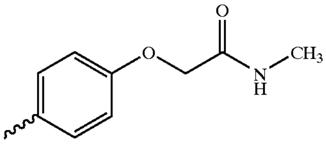 |
| 9 | 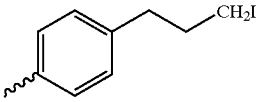 |
| 10 | 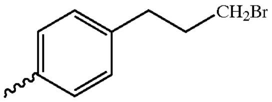 |
| 11 | 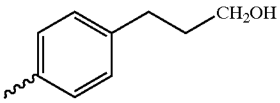 |
| 12 | 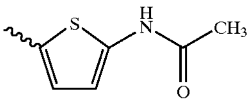 |
| 13 | 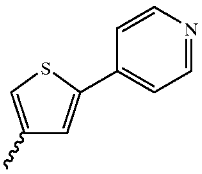 |
| 14 | 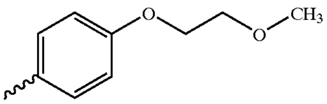 |
| 15 | 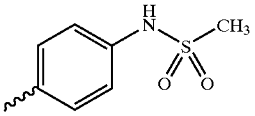 |
TABLE 75-continued
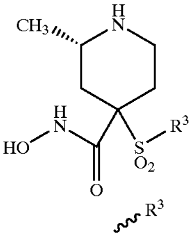
| | |
|---|---|
| 16 | 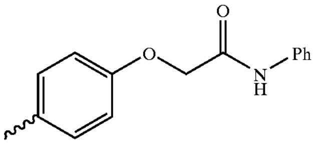 |
| 17 | 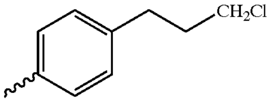 |
| 18 | 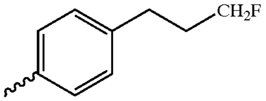 |
| 19 | 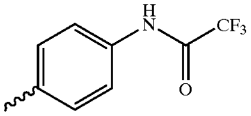 |
| 20 | 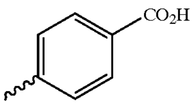 |
| 21 | 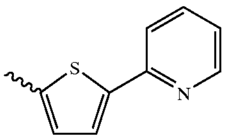 |
| 22 | 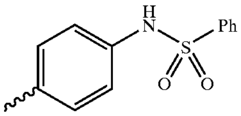 |
| 23 | 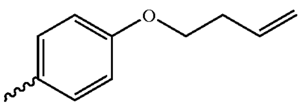 |
| 24 | 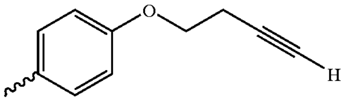 |
| 25 | 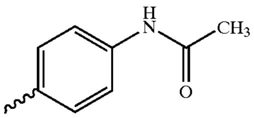 |

TABLE 75-continued
| 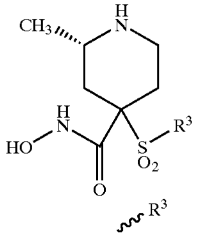 | |
|---|---|
| 26 | 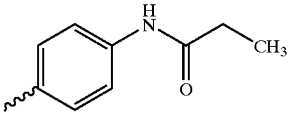 |
| 27 | 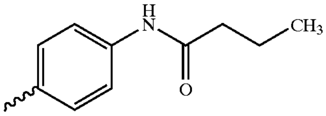 |
| 28 | 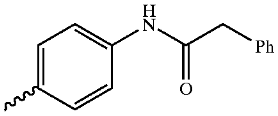 |
| 29 | 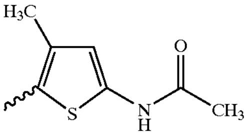 |
| 30 | 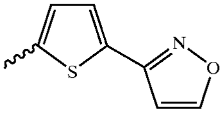 |
TABLE 76
| 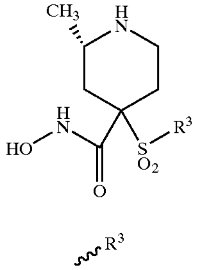 | |
|---|---|
| 1 | 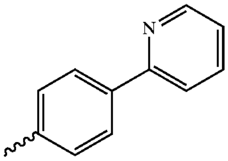 |
TABLE 76-continued
| 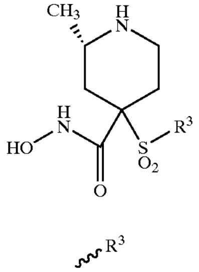 | |
|---|---|
| 2 | 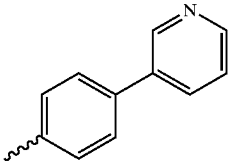 |
| 3 | 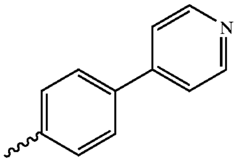 |
| 4 | 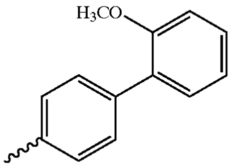 |
| 5 | 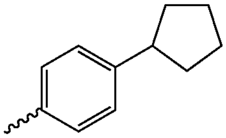 |
| 6 | 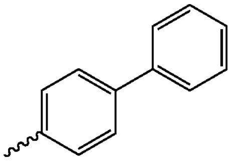 |
| 7 | 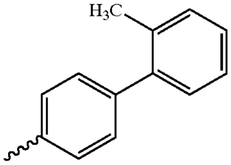 |
| 8 | 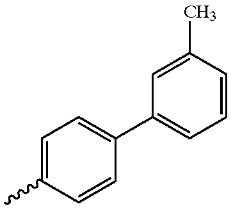 |

TABLE 76-continued
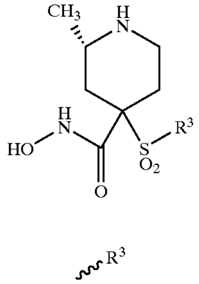
| | |
|---|---|
| 9 | 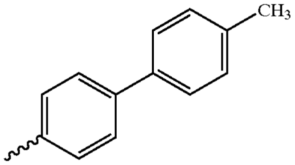 |
| 10 | 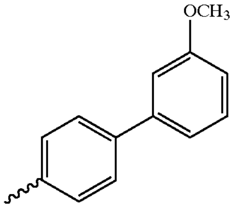 |
| 11 | 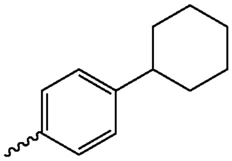 |
| 12 | 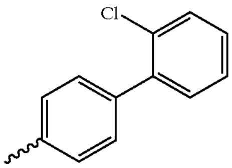 |
| 13 | 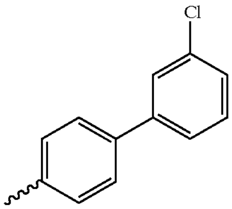 |
| 14 | 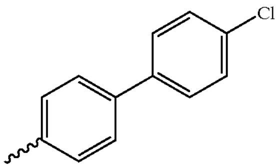 |
TABLE 76-continued
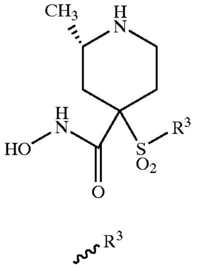
| | |
|---|---|
| 15 | 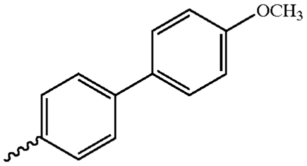 |
| 16 | 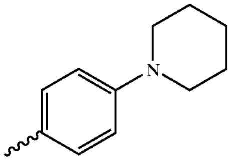 |
| 17 | 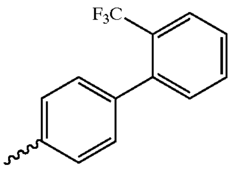 |
| 18 | 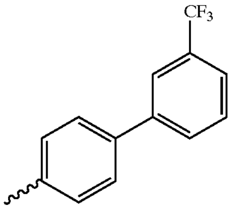 |
| 19 | 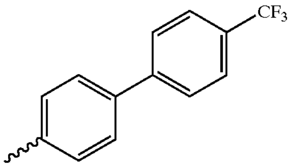 |
| 20 | 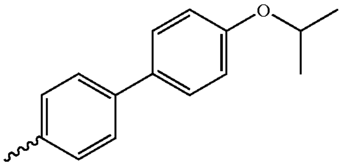 |
| 21 | 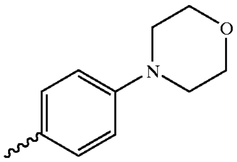 |

TABLE 77
| | |
|---|---|
| | 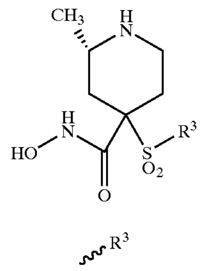 |
| 1 | 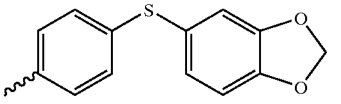 |
| 2 | 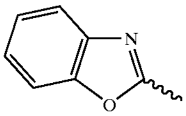 |
| 3 | 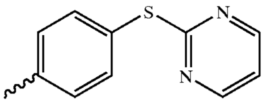 |
| 4 | 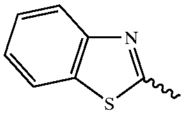 |
| 5 | 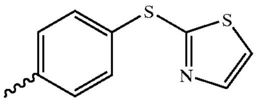 |
| 6 | 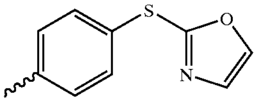 |
| 7 | 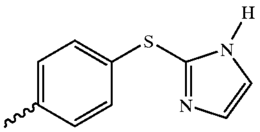 |
| 8 | 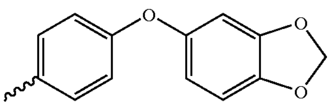 |
| 9 | 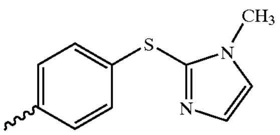 |
| 10 | 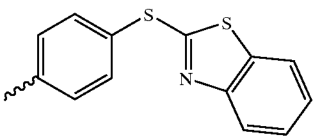 |
TABLE 77-continued
| | |
|---|---|
| | 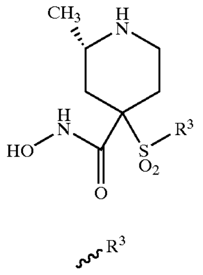 |
| 11 | 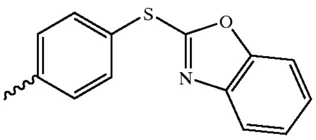 |
TABLE 78
| | |
|---|---|
| | 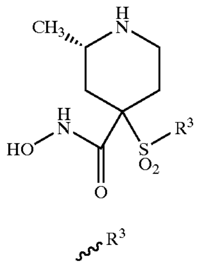 |
| 1 | 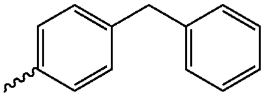 |
| 2 | 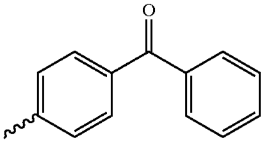 |
| 3 | 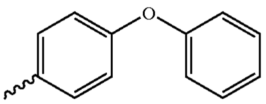 |
| 4 | 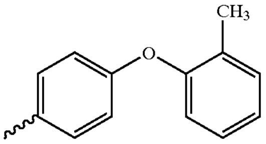 |
| 5 | 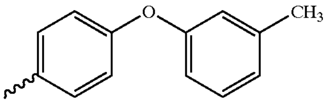 |
| 6 | 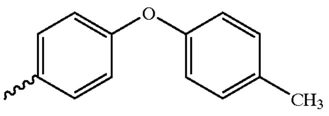 |

TABLE 78-continued
| | |
|---|---|
| | 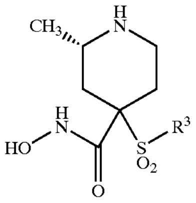 |
| | 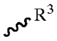 |
| 7 | 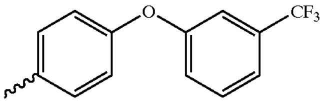 |
| 8 | 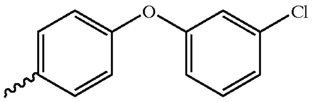 |
| 9 | 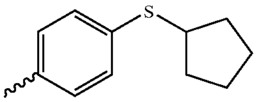 |
| 10 | 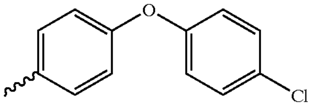 |
| 11 | 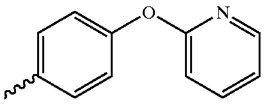 |
| 12 | 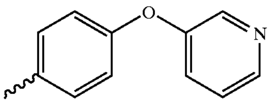 |
| 13 | 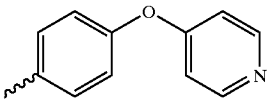 |
| 14 | 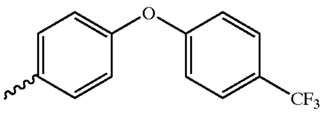 |
| 15 | 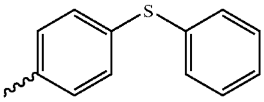 |
| 16 | 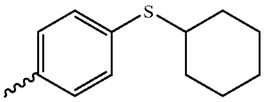 |
| 17 | 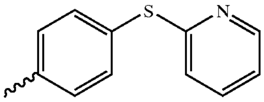 |
TABLE 78-continued
| | |
|---|---|
| | 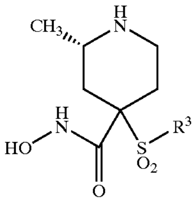 |
| | 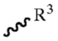 |
| 18 | 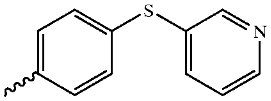 |
| 19 | 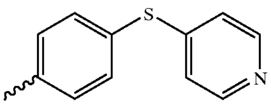 |
| 20 | 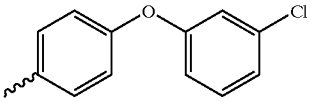 |
| 21 | 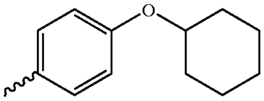 |
TABLE 79
| | |
|---|---|
| | 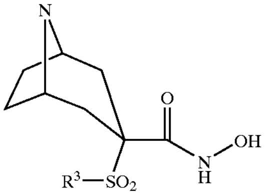 |
| | 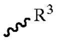 |
| 1 | 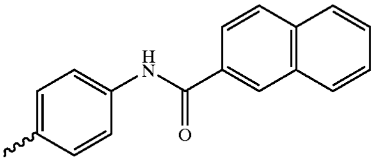 |
| 2 | 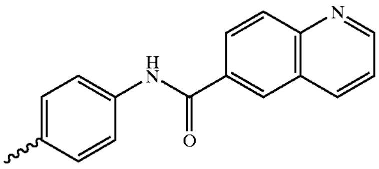 |
| 3 | 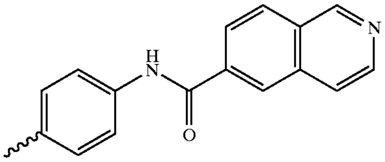 |

TABLE 79-continued
| | 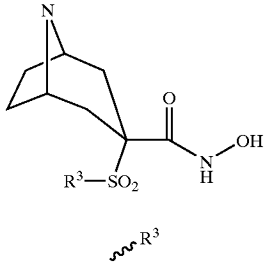 |
| --- | --- |
| 4 | 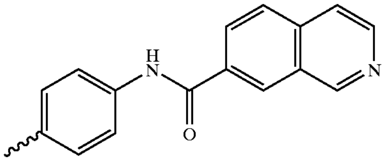 |
| 5 | 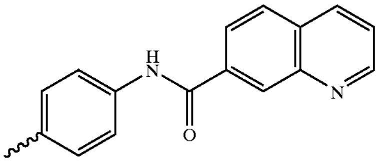 |
| 6 | 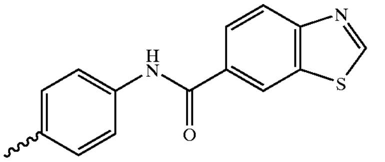 |
| 7 | 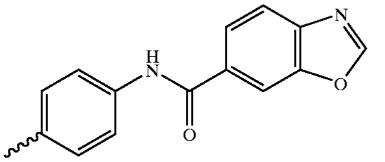 |
| 8 | 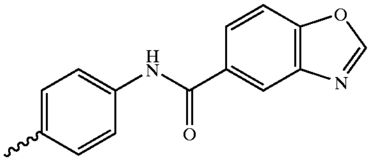 |
| 9 | 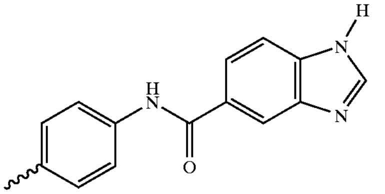 |
| 10 | 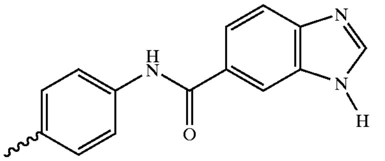 |
TABLE 79-continued
| | 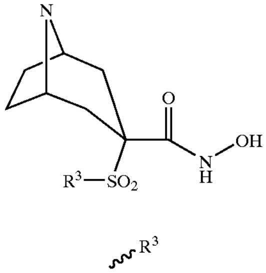 |
| --- | --- |
| 11 | 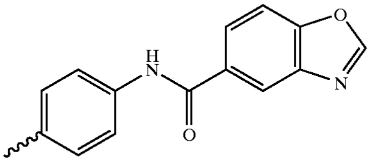 |
| 12 | 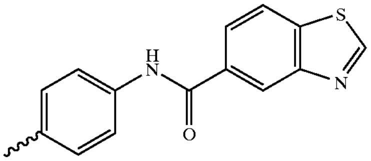 |
| 13 | 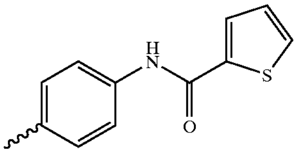 |
| 14 | 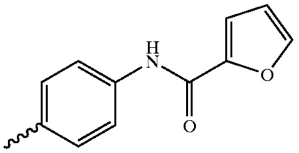 |
| 15 | 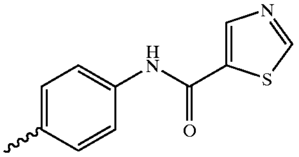 |
| 16 | 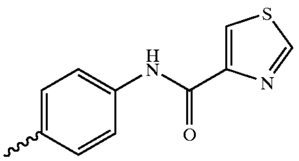 |
| 17 | 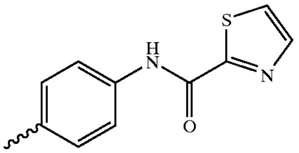 |

TABLE 79-continued
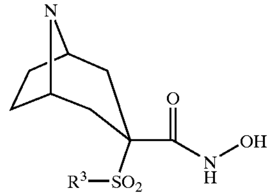
| | 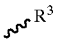 |
|---|---|
| 18 | 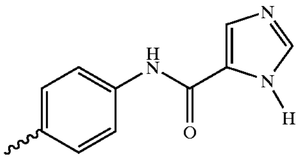 |
TABLE 80
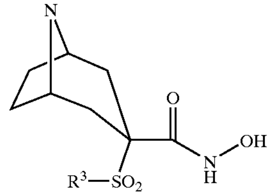
| | 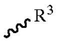 |
|---|---|
| 1 | 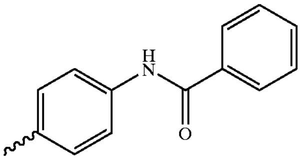 |
| 2 | 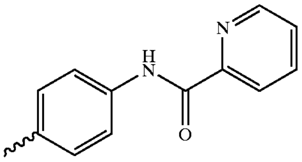 |
| 3 | 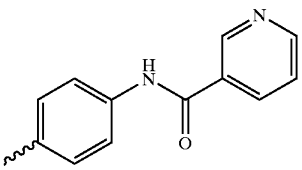 |
| 4 | 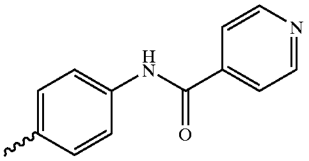 |
TABLE 80-continued
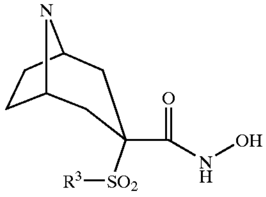
| | 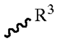 |
|---|---|
| 5 | 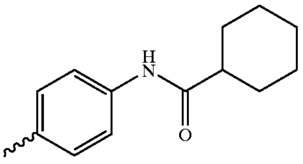 |
| 6 | 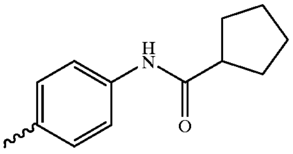 |
| 7 | 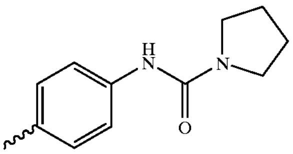 |
| 8 | 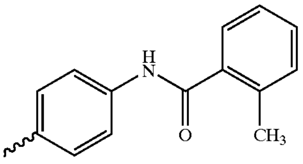 |
| 9 | 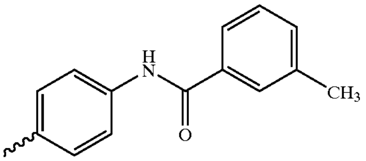 |
| 10 | 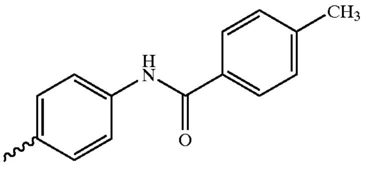 |
| 11 | 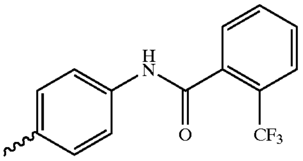 |

TABLE 80-continued
| 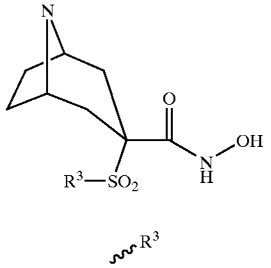 | |
|---|---|
| 12 | 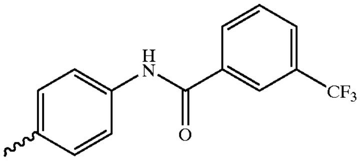 |
| 13 | 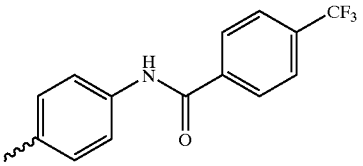 |
| 14 | 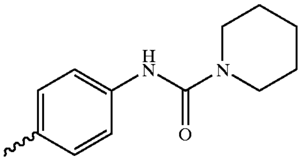 |
| 15 | 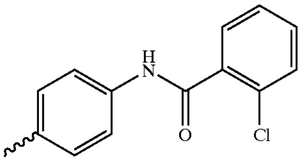 |
| 16 | 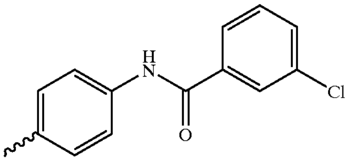 |
| 17 | 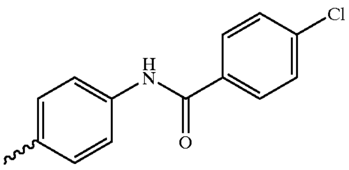 |
| 18 | 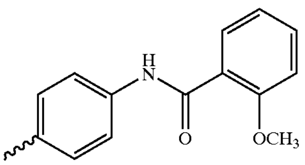 |
TABLE 80-continued
| 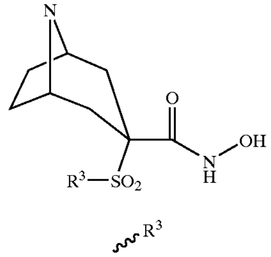 | |
|---|---|
| 19 | 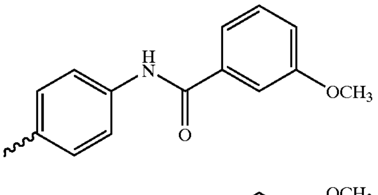 |
| 20 | 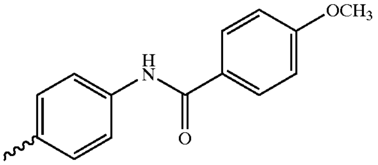 |
| 21 | 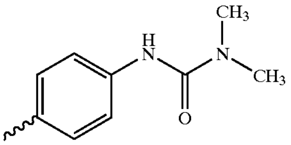 |
TABLE 81
| 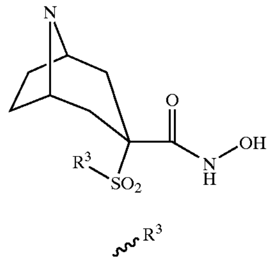 | |
|---|---|
| 1 | 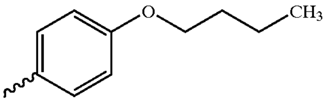 |
| 2 | 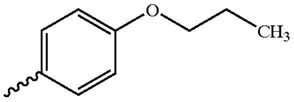 |
| 3 | 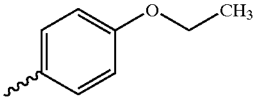 |
| 4 | 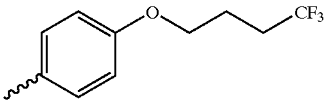 |

TABLE 81-continued
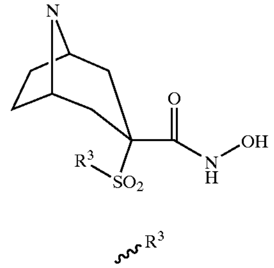
| | |
|---|---|
| 5 | 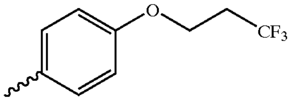 |
| 6 | 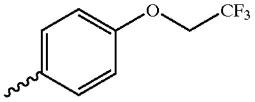 |
| 7 | 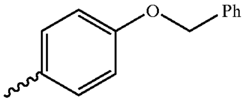 |
| 8 | 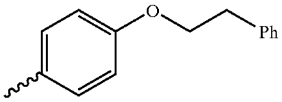 |
| 9 | 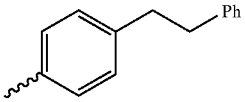 |
| 10 | 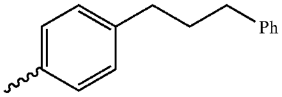 |
| 11 | 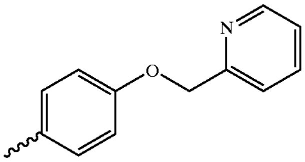 |
| 12 | 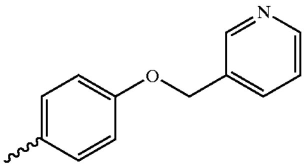 |
| 13 | 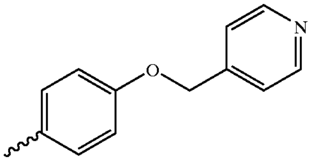 |
TABLE 81-continued
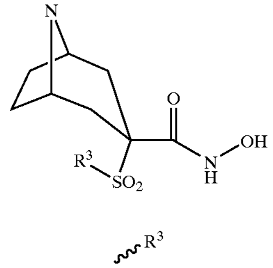
| | |
|---|---|
| 14 | 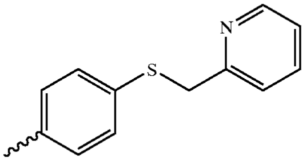 |
| 15 | 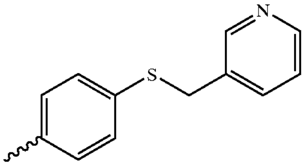 |
| 16 | 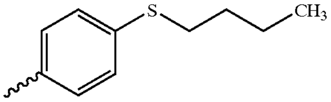 |
| 17 | 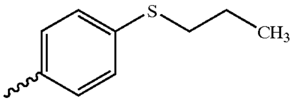 |
| 18 | 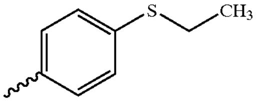 |
| 19 | 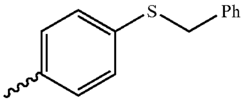 |
| 20 | 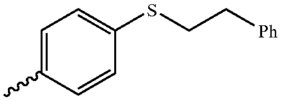 |
| 21 | 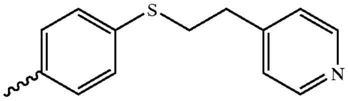 |
| 22 | 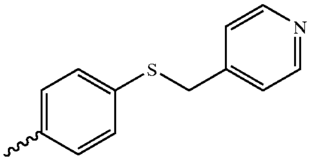 |

TABLE 82
| | |
|---|---|
| | 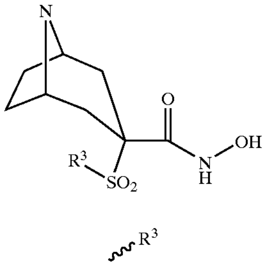 |
| 1 | 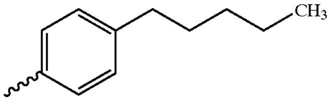 |
| 2 | 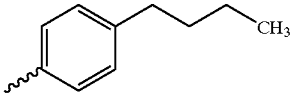 |
| 3 | 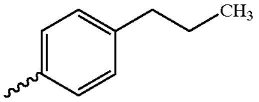 |
| 4 | 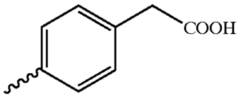 |
| 5 | 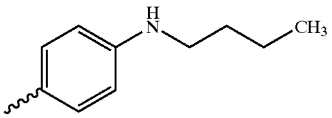 |
| 6 | 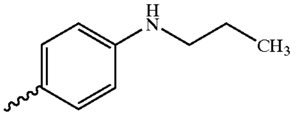 |
| 7 | 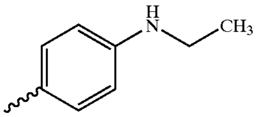 |
| 8 | 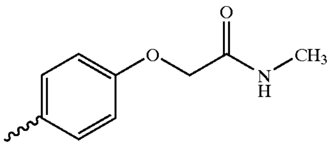 |
| 9 | 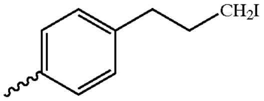 |
| 10 | 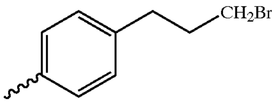 |
TABLE 82-continued
| | |
|---|---|
| | 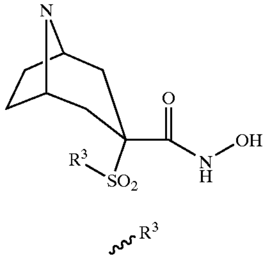 |
| 11 | 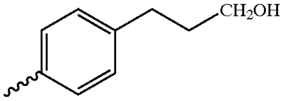 |
| 12 | 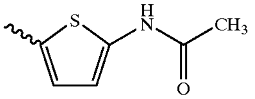 |
| 13 | 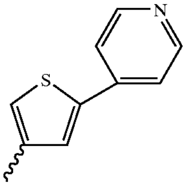 |
| 14 | 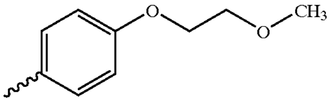 |
| 15 | 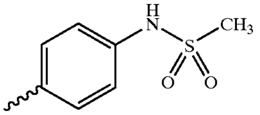 |
| 16 | 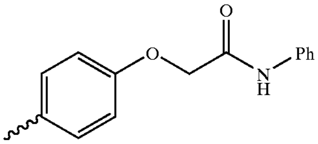 |
| 17 | 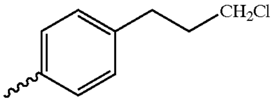 |
| 18 | 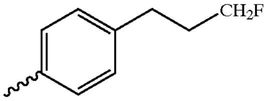 |
| 19 | 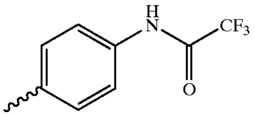 |
| 20 | 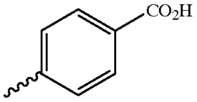 |

TABLE 82-continued
| | |
|---|---|
| 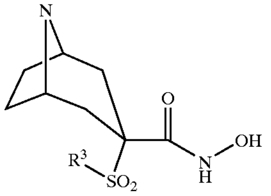 | |
| 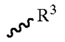 | |
| 21 | 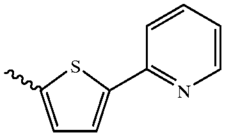 |
| 22 | 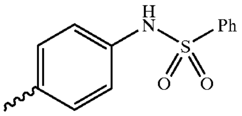 |
| 23 | 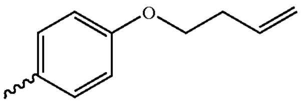 |
| 24 | 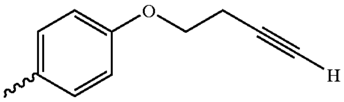 |
| 25 | 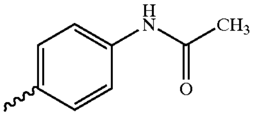 |
| 26 | 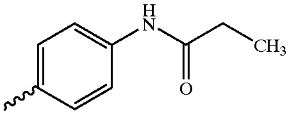 |
| 27 | 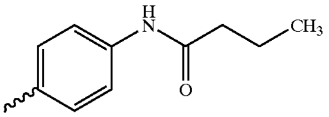 |
| 28 | 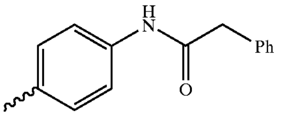 |
| 29 | 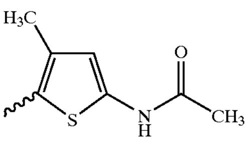 |
| 30 | 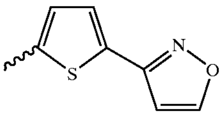 |
TABLE 83
| | |
|---|---|
| 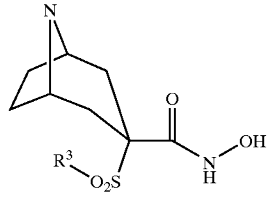 | |
| 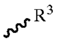 | |
| 1 | 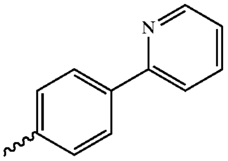 |
| 2 | 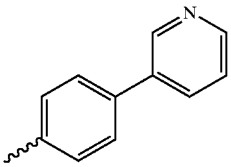 |
| 3 | 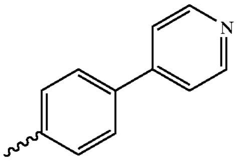 |
| 4 | 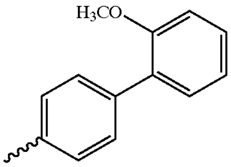 |
| 5 | 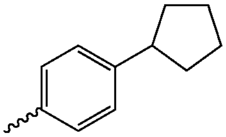 |
| 6 | 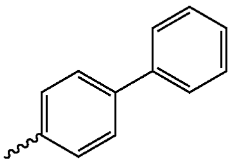 |
| 7 | 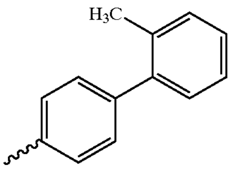 |

TABLE 83-continued
| | |
|---|---|
| 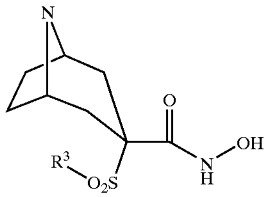 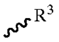 | |
| 8 | 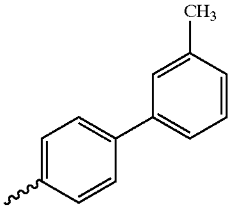 |
| 9 | 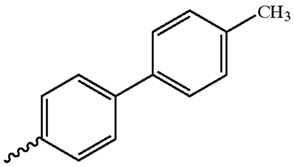 |
| 10 | 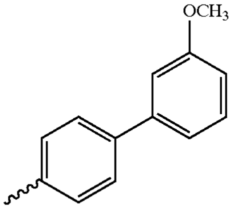 |
| 11 | 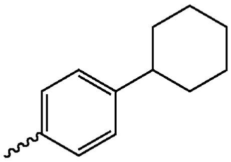 |
| 12 | 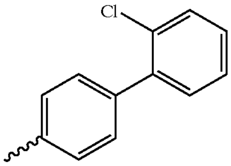 |
| 13 | 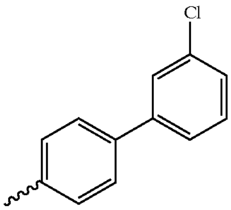 |
TABLE 83-continued
| | |
|---|---|
| 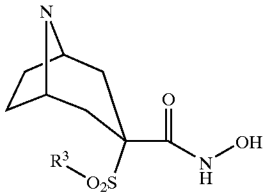 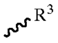 | |
| 14 | 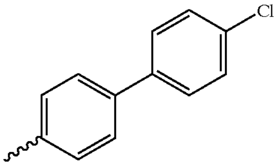 |
| 15 | 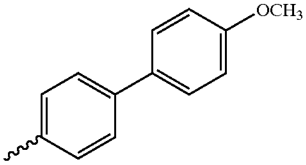 |
| 16 | 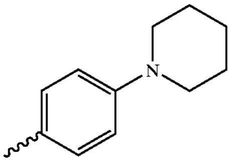 |
| 17 | 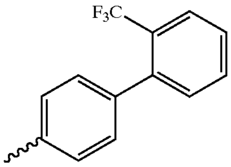 |
| 18 | 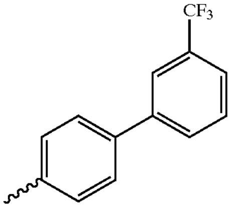 |
| 19 | 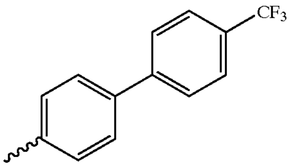 |
| 20 | 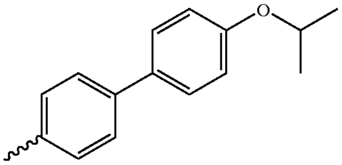 |

TABLE 83-continued
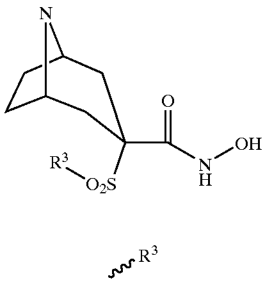
21
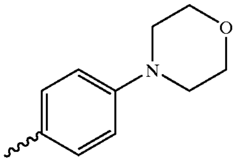
TABLE 84
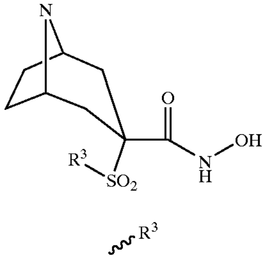
1
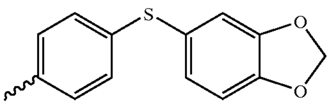
2
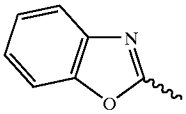
3
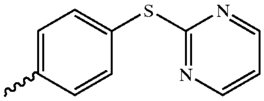
4
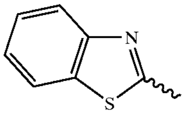
5
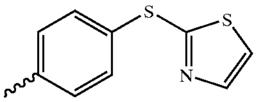
6
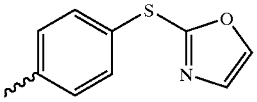
TABLE 84-continued
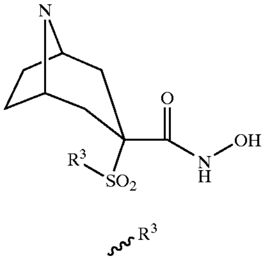
7
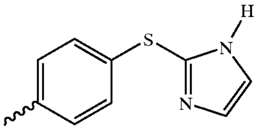
8
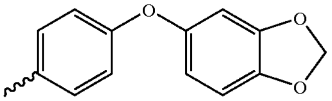
9
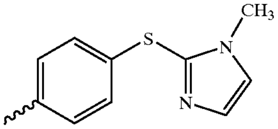
10
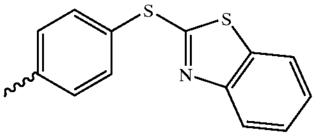
11
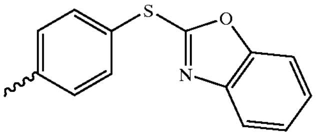
TABLE 85
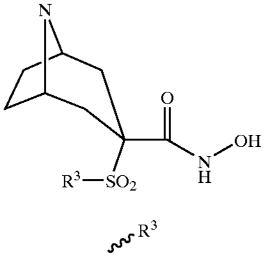
1
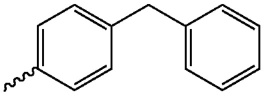
2
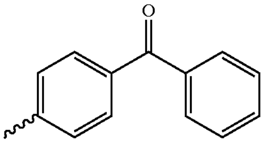

TABLE 85-continued
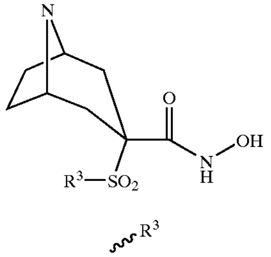
| | |
|---|---|
| 3 | 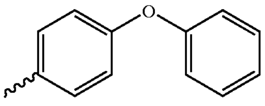 |
| 4 | 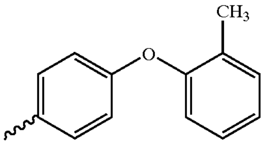 |
| 5 | 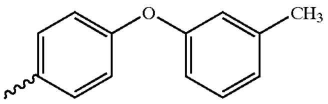 |
| 6 | 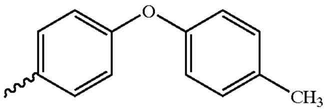 |
| 7 | 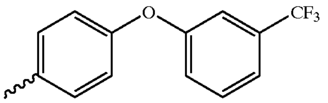 |
| 8 | 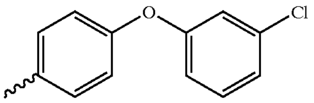 |
| 9 | 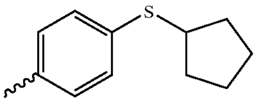 |
| 10 | 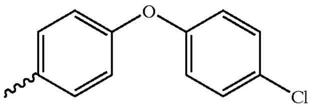 |
| 11 | 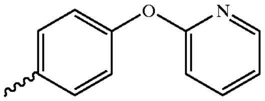 |
| 12 | 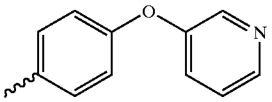 |
TABLE 85-continued
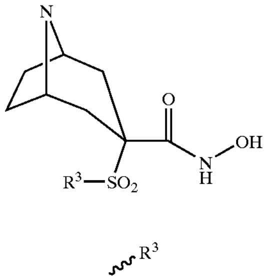
| | |
|---|---|
| 13 | 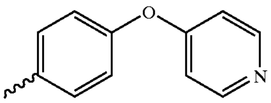 |
| 14 | 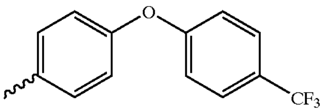 |
| 15 | 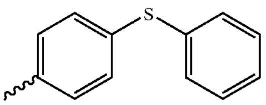 |
| 16 | 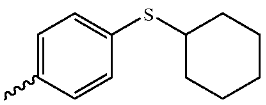 |
| 17 | 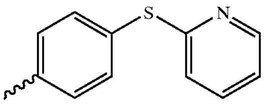 |
| 18 | 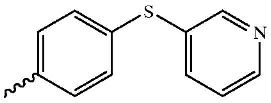 |
| 19 | 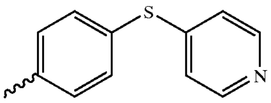 |
| 20 | 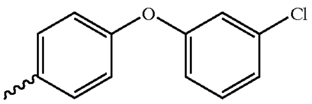 |
| 21 | 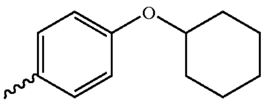 |

TABLE 86
| | |
|---|---|
| 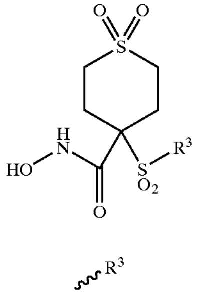 | |
| 1 | 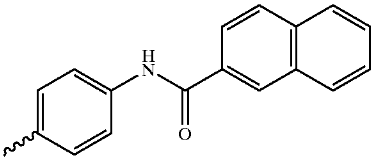 |
| 2 | 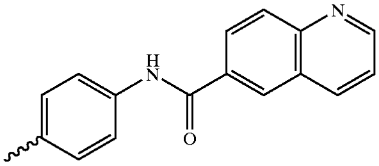 |
| 3 | 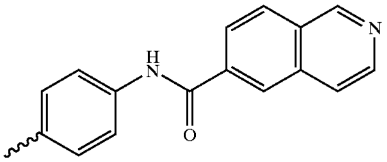 |
| 4 | 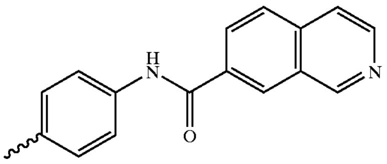 |
| 5 | 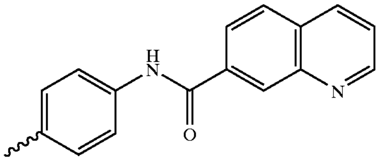 |
| 6 | 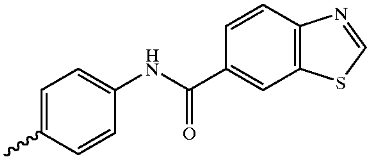 |
| 7 | 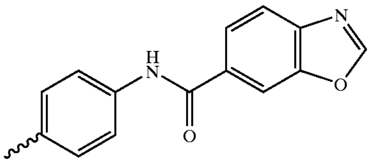 |
TABLE 86-continued
| | |
|---|---|
| 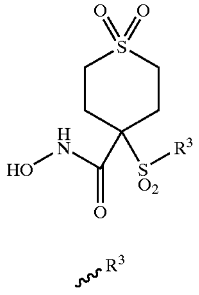 | |
| 8 | 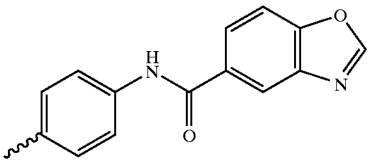 |
| 9 | 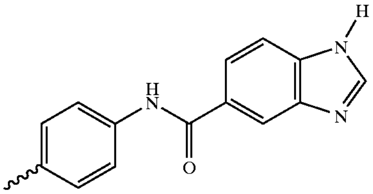 |
| 10 | 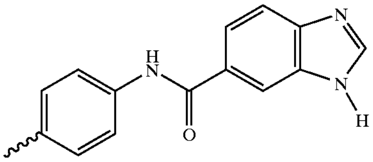 |
| 11 | 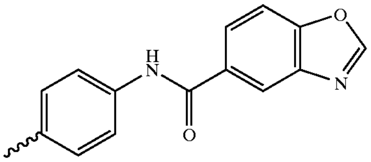 |
| 12 | 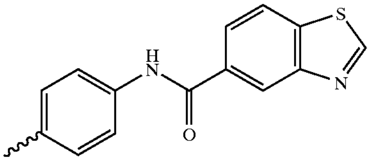 |
| 13 | 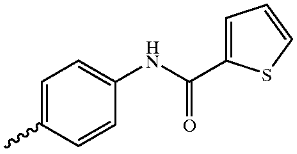 |
| 14 | 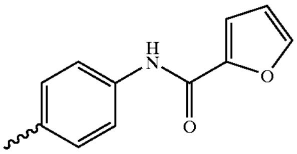 |

TABLE 86-continued
| | |
|---|---|
| | 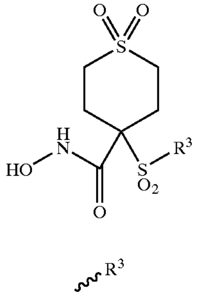 |
| 15 | 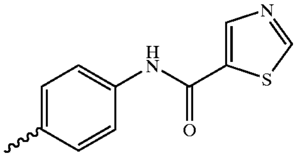 |
| 16 | 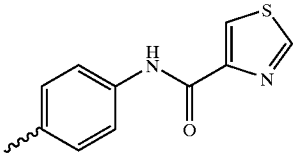 |
| 17 | 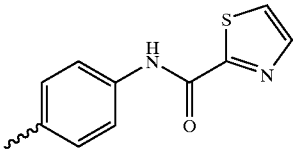 |
| 18 | 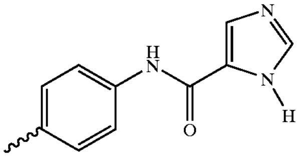 |
TABLE 87
| | |
|---|---|
| | 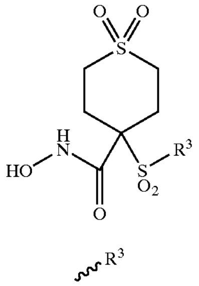 |
| 1 | 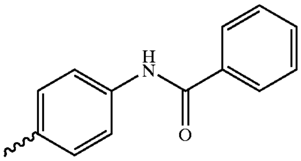 |
TABLE 87-continued
| | |
|---|---|
| | 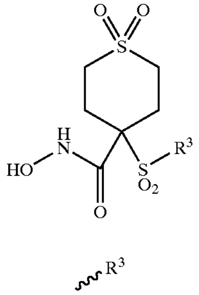 |
| 2 | 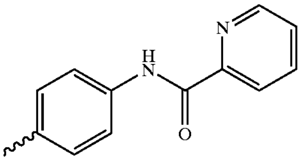 |
| 3 | 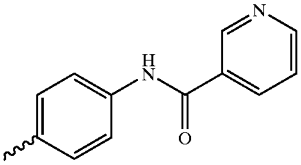 |
| 4 | 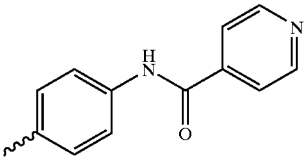 |
| 5 | 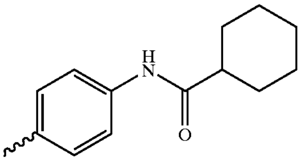 |
| 6 | 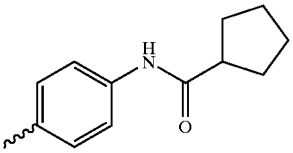 |
| 7 | 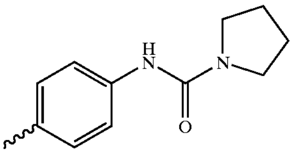 |
| 8 | 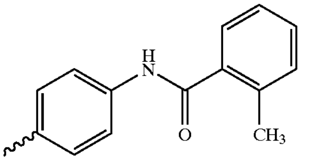 |

TABLE 87-continued
| | |
|---|---|
| 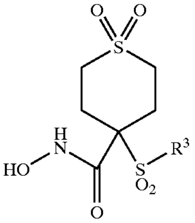 | 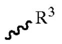 |
| 9 | 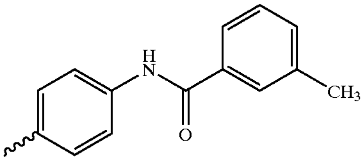 |
| 10 | 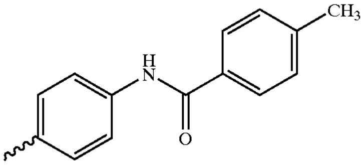 |
| 11 | 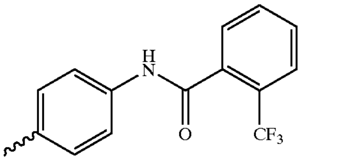 |
| 12 | 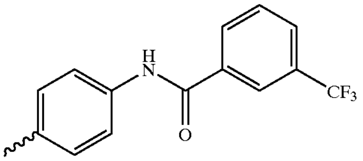 |
| 13 | 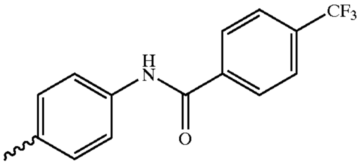 |
| 14 | 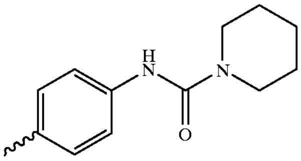 |
| 15 | 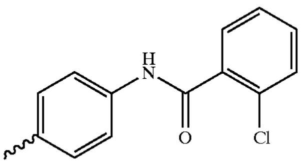 |
TABLE 87-continued
| | |
|---|---|
| 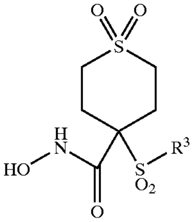 | 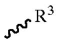 |
| 16 | 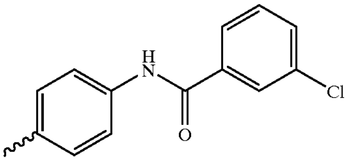 |
| 17 | 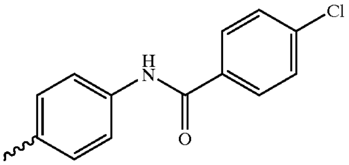 |
| 18 | 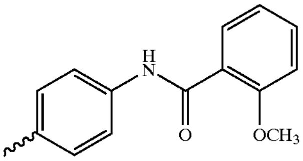 |
| 19 | 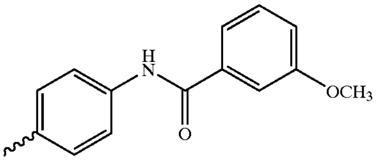 |
| 20 | 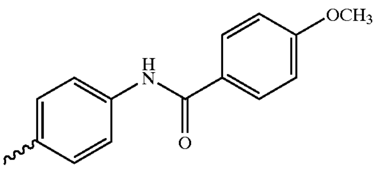 |
| 21 | 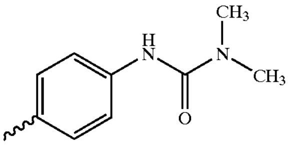 |

TABLE 88
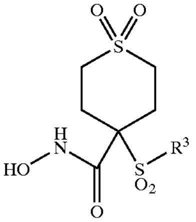
| | 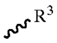 |
|---|---|
| 1 | 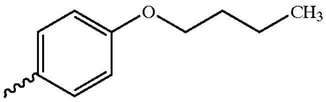 |
| 2 | 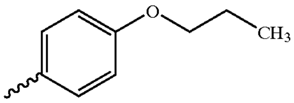 |
| 3 | 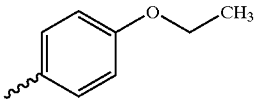 |
| 4 | 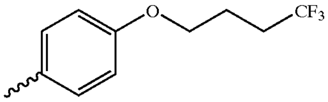 |
| 5 | 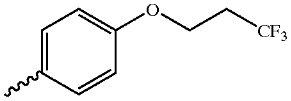 |
| 6 | 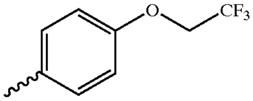 |
| 7 | 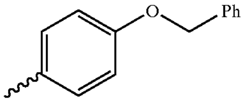 |
| 8 | 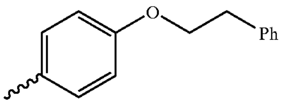 |
| 9 | 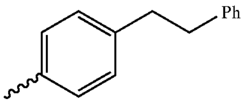 |
| 10 | 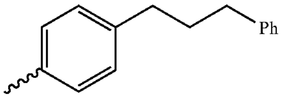 |
TABLE 88-continued
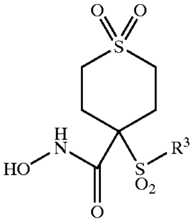
| | 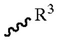 |
|---|---|
| 11 | 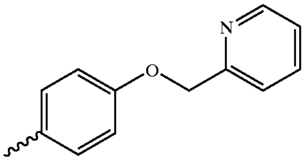 |
| 12 | 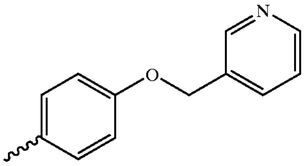 |
| 13 | 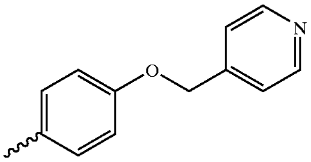 |
| 14 | 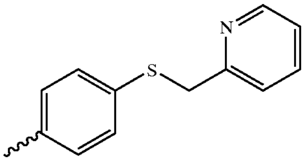 |
| 15 | 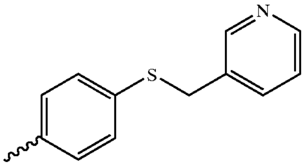 |
| 16 | 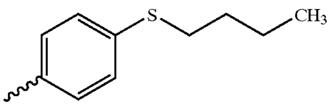 |
| 17 | 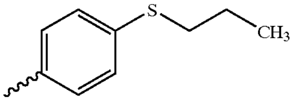 |
| 18 | 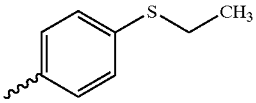 |

TABLE 88-continued
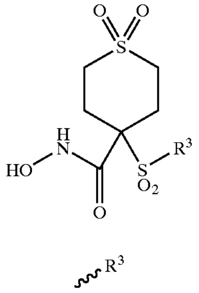
| | |
|---|---|
| 19 | 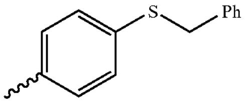 |
| 20 | 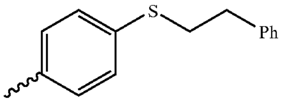 |
| 21 | 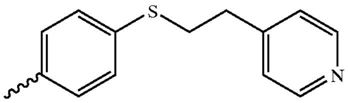 |
| 22 | 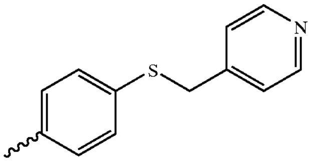 |
TABLE 89
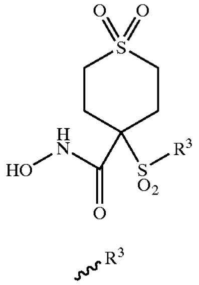
| | |
|---|---|
| 1 | 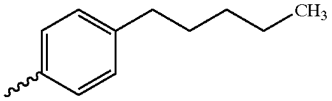 |
| 2 | 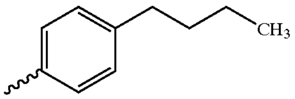 |
| 3 | 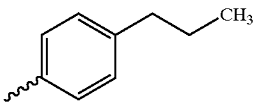 |
TABLE 89-continued
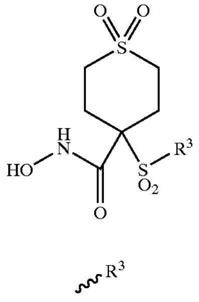
| | |
|---|---|
| 4 | 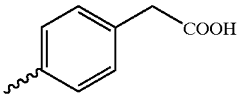 |
| 5 | 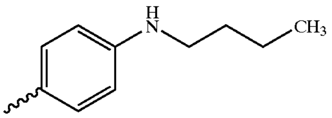 |
| 6 | 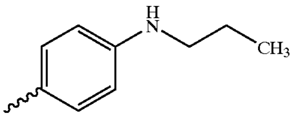 |
| 7 | 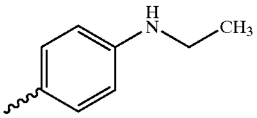 |
| 8 | 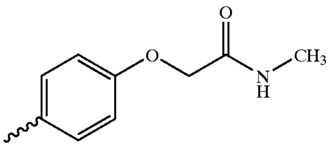 |
| 9 | 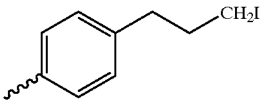 |
| 10 | 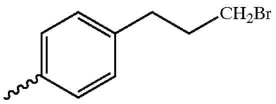 |
| 11 | 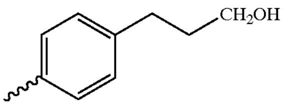 |
| 12 | 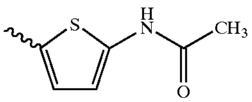 |

TABLE 89-continued
| | |
|---|---|
| | 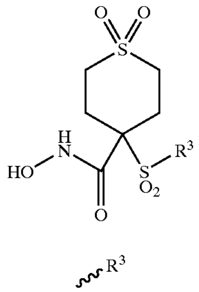 |
| 13 | 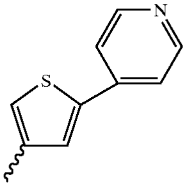 |
| 14 | 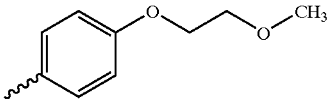 |
| 15 | 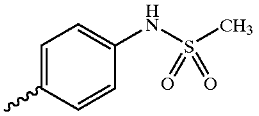 |
| 16 | 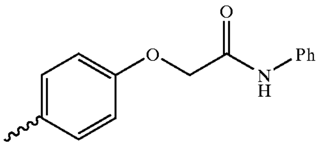 |
| 17 | 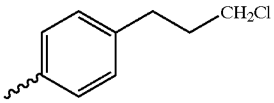 |
| 18 | 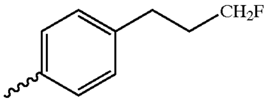 |
| 19 | 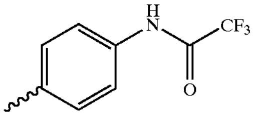 |
| 20 | 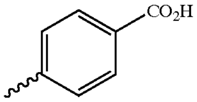 |
| 21 | 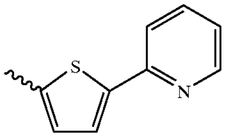 |
TABLE 89-continued
| | |
|---|---|
| | 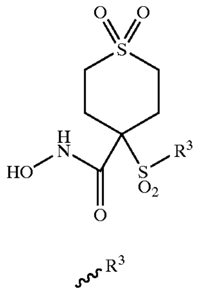 |
| 22 | 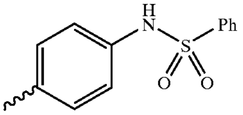 |
| 23 | 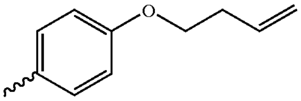 |
| 24 | 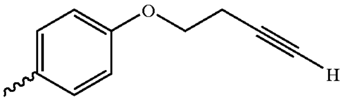 |
| 25 | 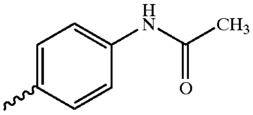 |
| 26 | 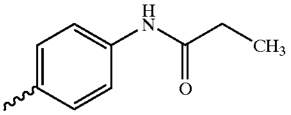 |
| 27 | 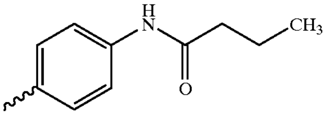 |
| 28 | 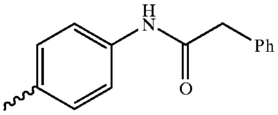 |
| 29 | 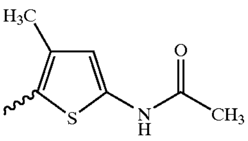 |
| 30 | 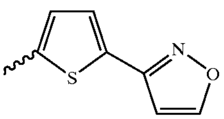 |

TABLE 90
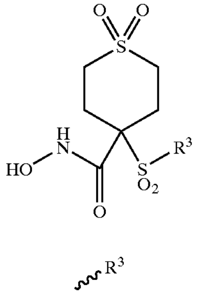
| | |
|---|---|
| 1 | 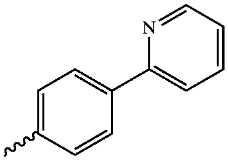 |
| 2 | 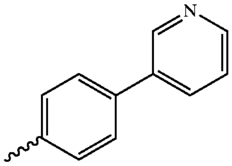 |
| 3 | 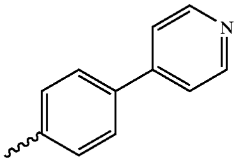 |
| 4 | 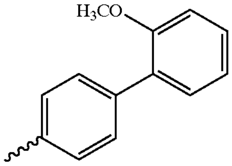 |
| 5 | 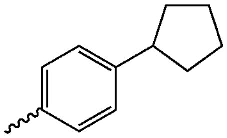 |
| 6 | 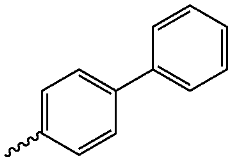 |
| 7 | 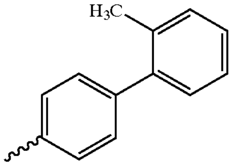 |
TABLE 90-continued
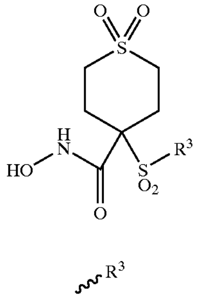
| | |
|---|---|
| 8 | 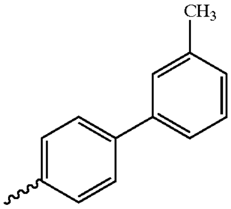 |
| 9 | 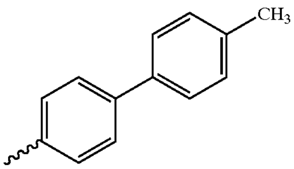 |
| 10 | 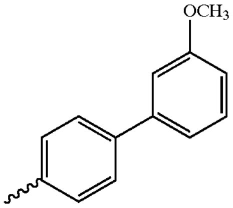 |
| 11 | 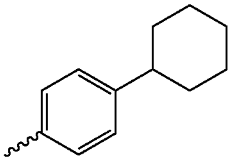 |
| 12 | 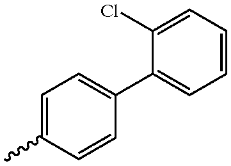 |
| 13 | 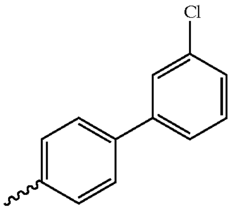 |

TABLE 90-continued
| | 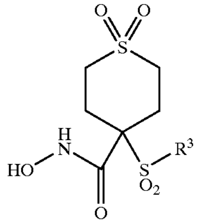 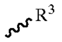 |
|---|---|
| 14 | 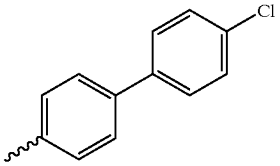 |
| 15 | 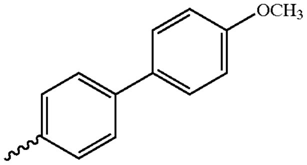 |
| 16 | 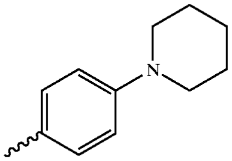 |
| 17 | 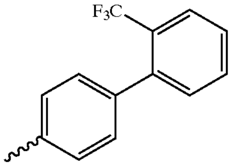 |
| 18 | 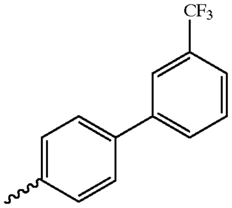 |
| 19 | 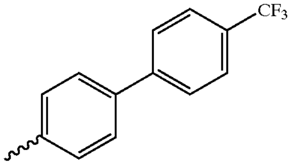 |
| 20 | 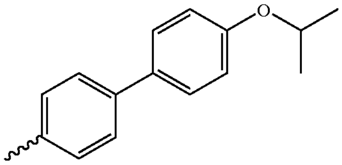 |
TABLE 90-continued
| | 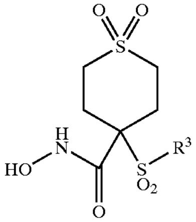 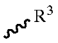 |
|---|---|
| 21 | 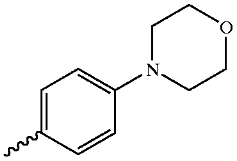 |
TABLE 91
| | 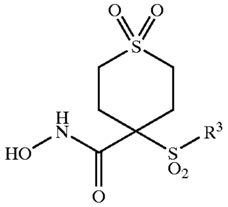 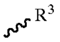 |
|---|---|
| 1 | 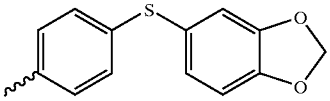 |
| 2 | 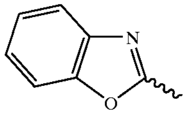 |
| 3 | 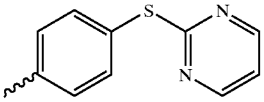 |
| 4 | 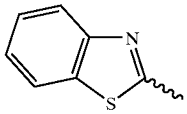 |
| 5 | 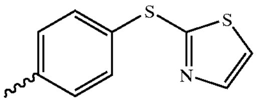 |
| 6 | 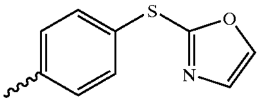 |

TABLE 91-continued
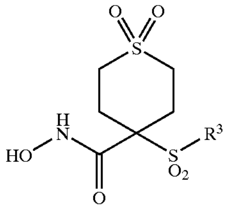
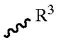
7 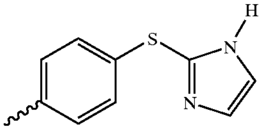
8 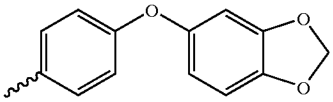
9 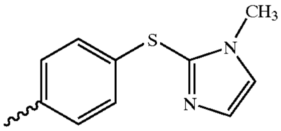
10 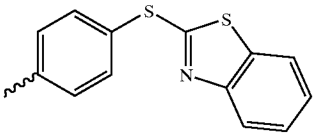
11 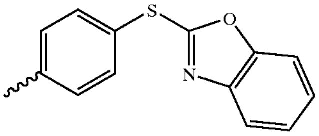
TABLE 92
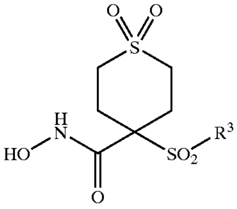
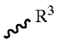
1 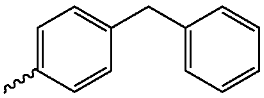
TABLE 92-continued
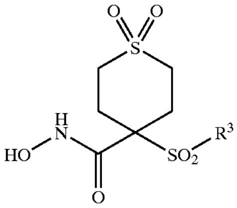
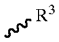
2 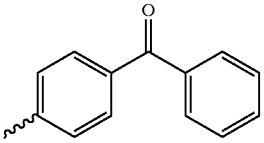
3 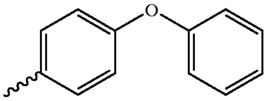
4 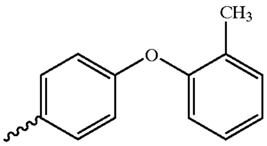
5 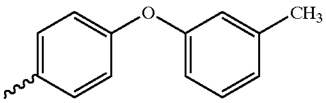
6 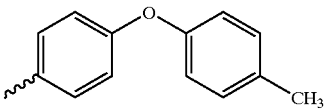
7 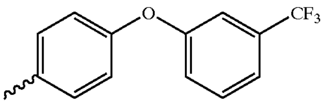
8 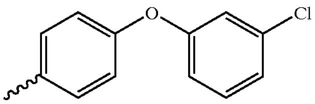
9 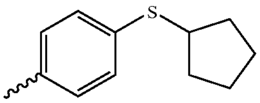
10 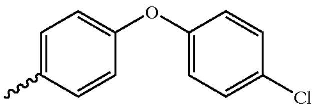
11 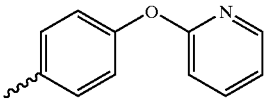

TABLE 92-continued
| 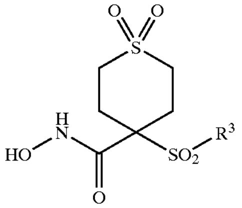 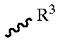 | |
| --- | --- |
| 12 | 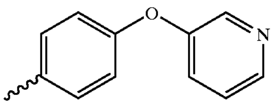 |
| 13 | 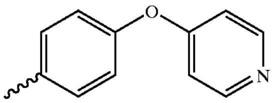 |
| 14 | 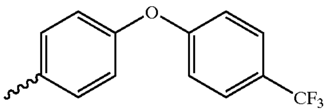 |
| 15 | 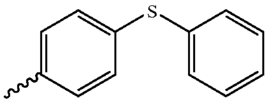 |
| 16 | 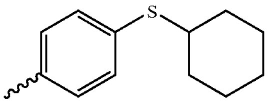 |
| 17 | 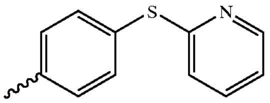 |
| 18 | 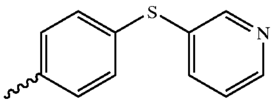 |
| 19 | 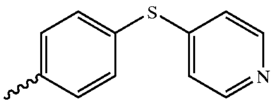 |
| 20 | 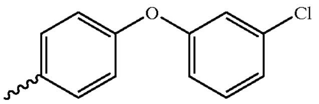 |
| 21 | 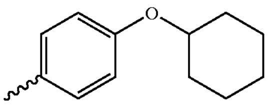 |
TABLE 93
| 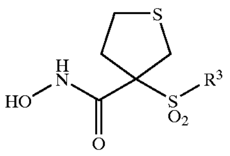 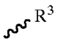 | |
| --- | --- |
| 1 | 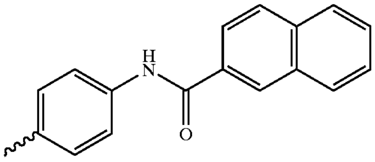 |
| 2 | 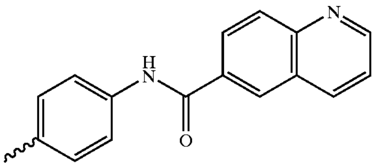 |
| 3 | 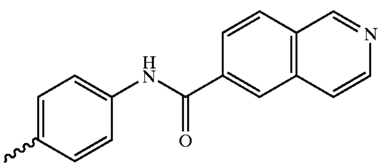 |
| 4 | 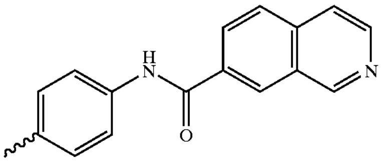 |
| 5 | 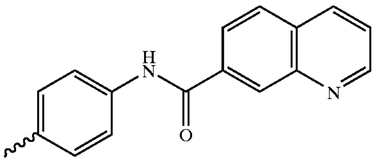 |
| 6 | 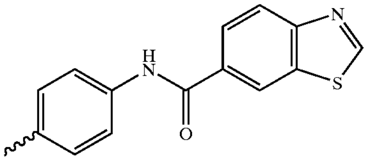 |
| 7 | 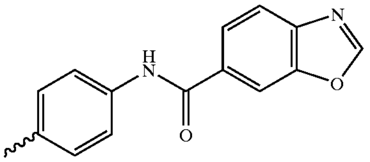 |
| 8 | 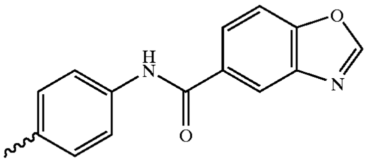 |

TABLE 93-continued
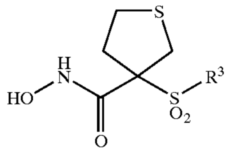
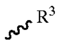
9
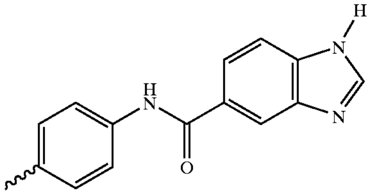
10
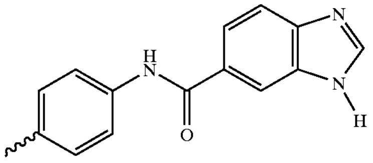
11
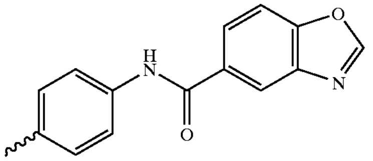
12
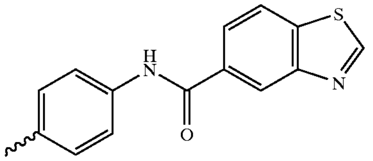
13
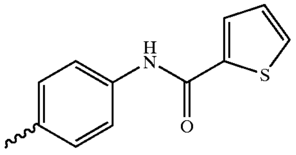
14
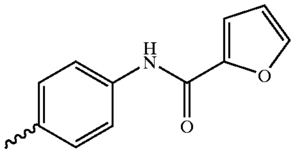
15
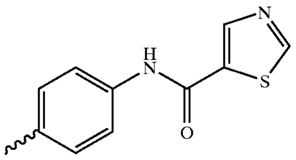
TABLE 93-continued
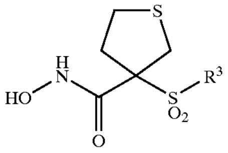
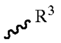
16
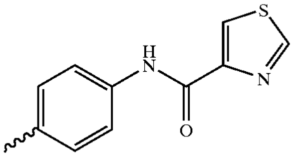
17
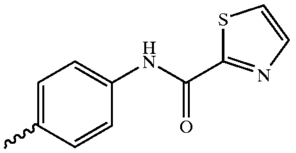
18
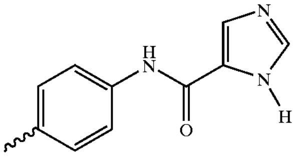
TABLE 94
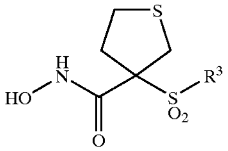
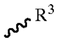
1
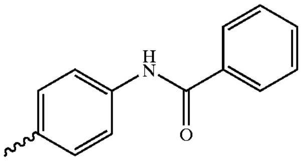
2
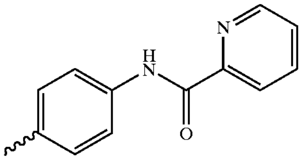
3
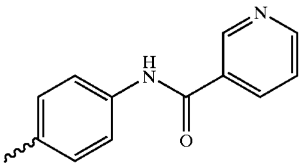

TABLE 94-continued
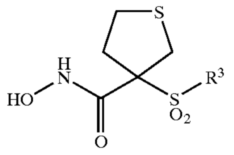
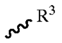
4
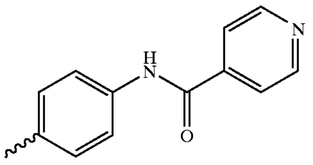
5
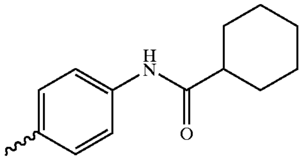
6
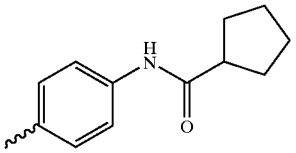
7
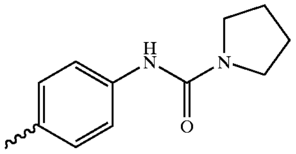
8
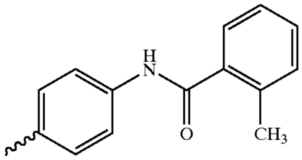
9
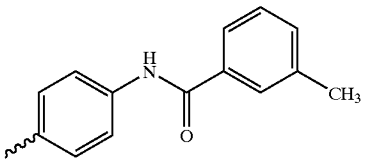
10
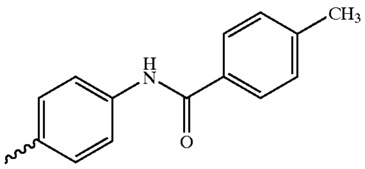
11
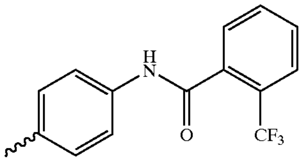
TABLE 94-continued
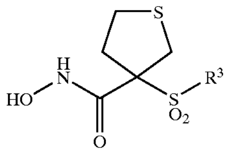
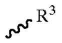
12
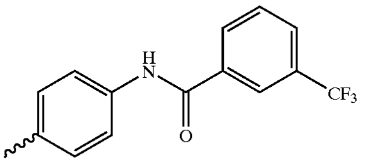
13
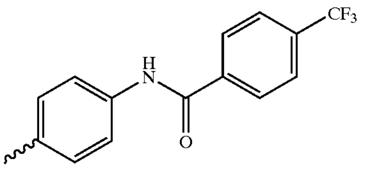
14
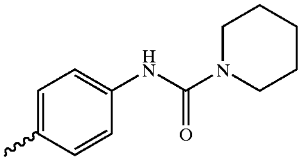
15
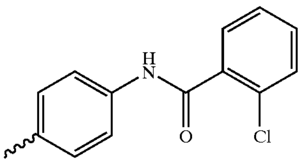
16
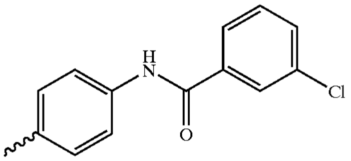
17
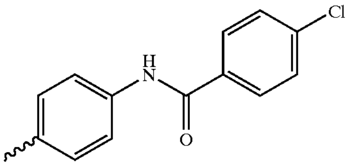
18
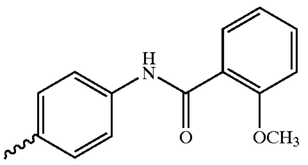
19
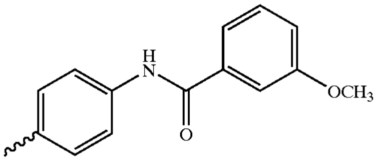

TABLE 94-continued
| 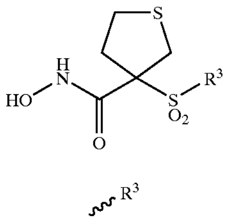 |
|---|
| 20 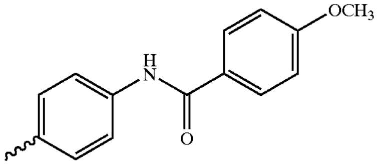 |
| 21 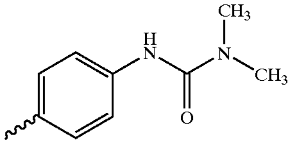 |
TABLE 95
| 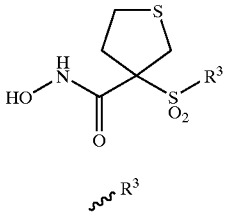 |
|---|
| 1 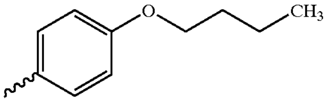 |
| 2 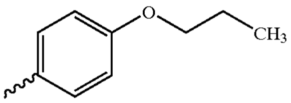 |
| 3 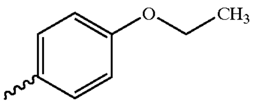 |
| 4 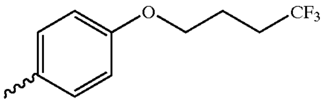 |
| 5 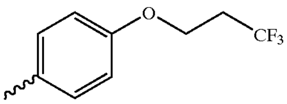 |
| 6 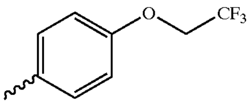 |
TABLE 95-continued
| 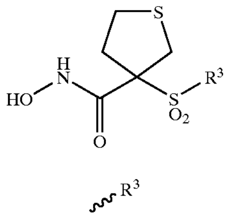 |
|---|
| 7 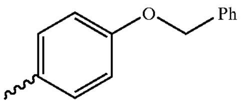 |
| 8 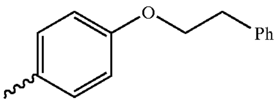 |
| 9 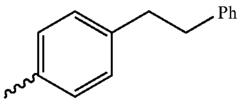 |
| 10 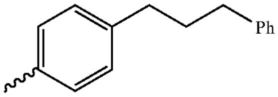 |
| 11 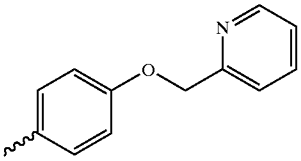 |
| 12 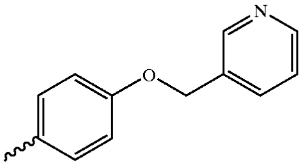 |
| 13 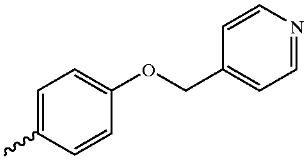 |
| 14 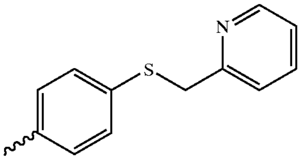 |
| 15 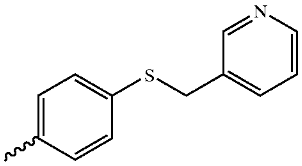 |

TABLE 95-continued
| | |
|---|---|
| | 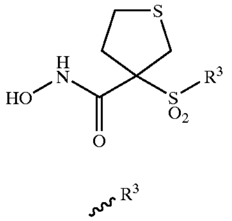 |
| 16 | 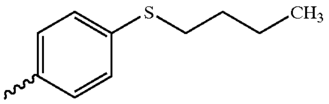 |
| 17 | 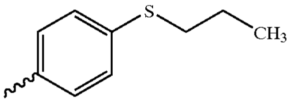 |
| 18 | 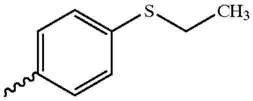 |
| 19 | 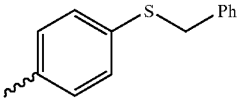 |
| 20 | 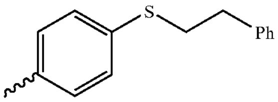 |
| 21 | 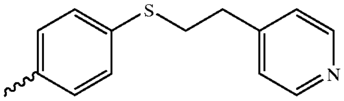 |
| 22 | 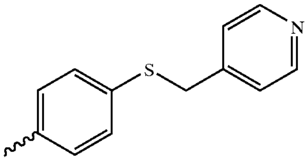 |
TABLE 96
| | |
|---|---|
| | 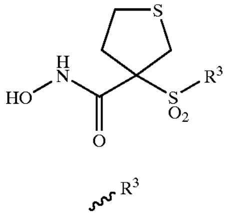 |
| 1 | 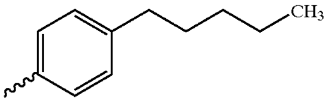 |
TABLE 96-continued
| | |
|---|---|
| | 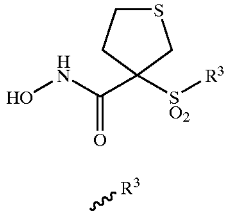 |
| 2 | 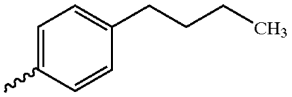 |
| 3 | 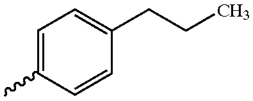 |
| 4 | 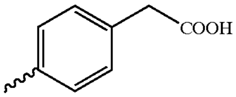 |
| 5 | 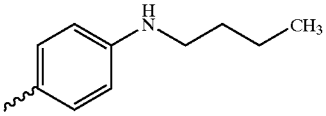 |
| 6 | 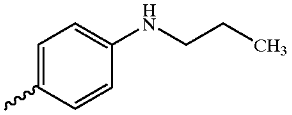 |
| 7 | 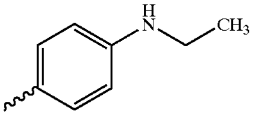 |
| 8 | 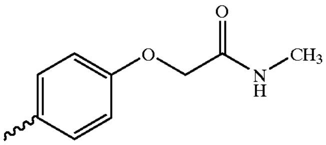 |
| 9 | 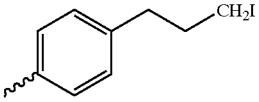 |
| 10 | 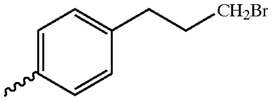 |
| 11 | 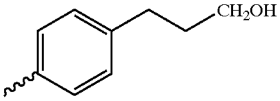 |
| 12 | 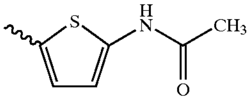 |

TABLE 96-continued
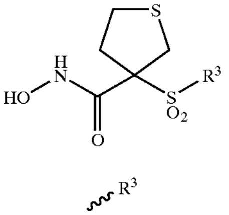
| | |
|---|---|
| 13 | 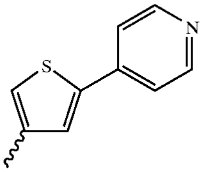 |
| 14 | 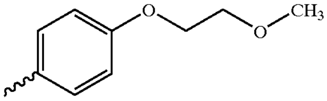 |
| 15 | 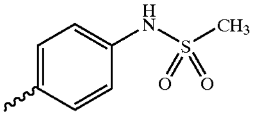 |
| 16 | 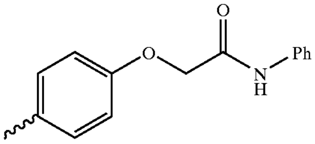 |
| 17 | 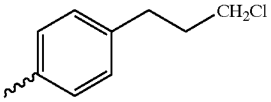 |
| 18 | 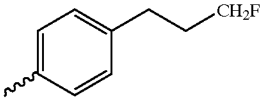 |
| 19 | 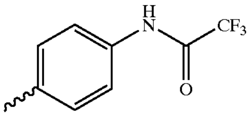 |
| 20 | 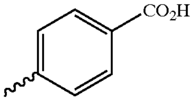 |
| 21 | 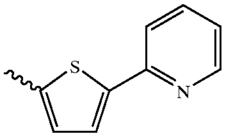 |
TABLE 96-continued
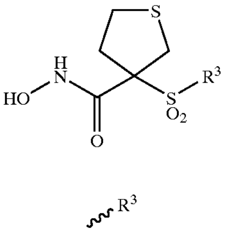
| | |
|---|---|
| 22 | 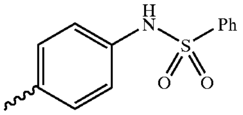 |
| 23 | 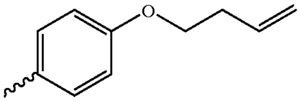 |
| 24 | 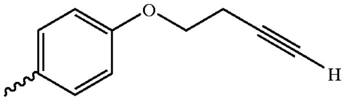 |
| 25 | 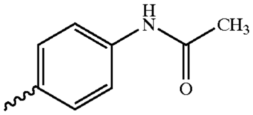 |
| 26 | 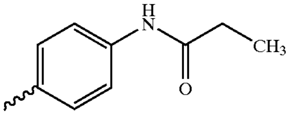 |
| 27 | 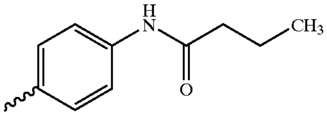 |
| 28 | 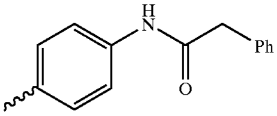 |
| 29 | 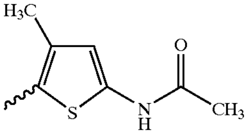 |
| 30 | 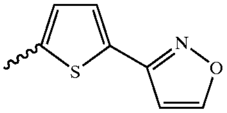 |

TABLE 97
| 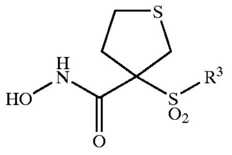 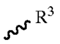 | |
|---|---|
| 1 | 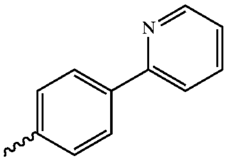 |
| 2 | 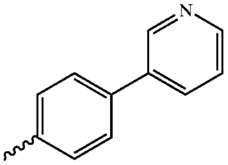 |
| 3 | 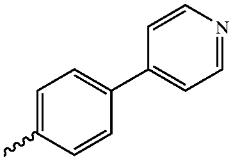 |
| 4 | 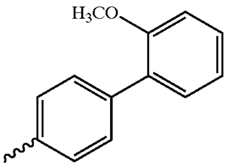 |
| 5 | 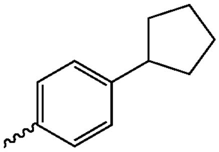 |
| 6 | 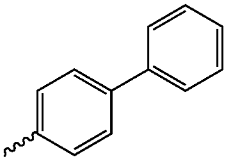 |
| 7 | 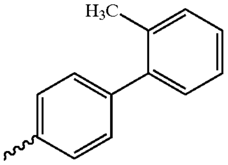 |
TABLE 97-continued
| 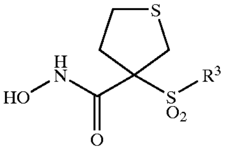 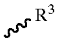 | |
|---|---|
| 8 | 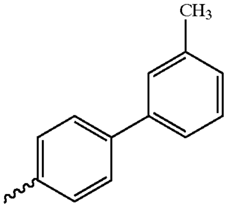 |
| 9 | 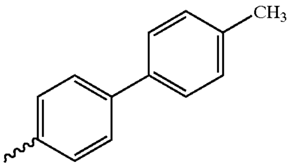 |
| 10 | 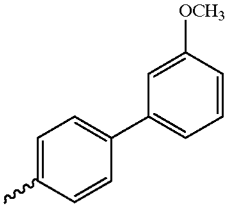 |
| 11 | 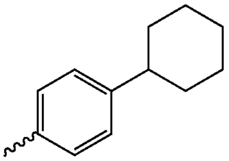 |
| 12 | 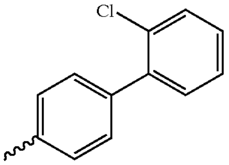 |
| 13 | 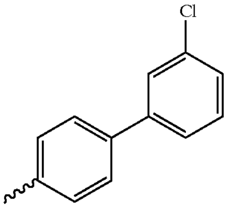 |
| 14 | 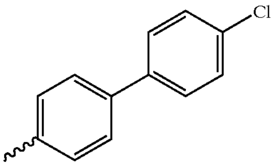 |

TABLE 97-continued
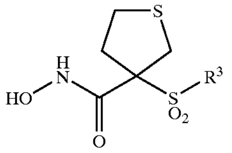
| | 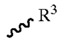 |
|---|---|
| 15 | 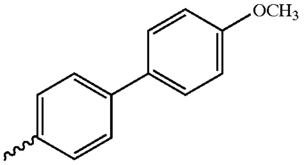 |
| 16 | 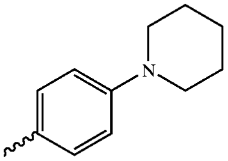 |
| 17 | 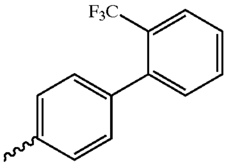 |
| 18 | 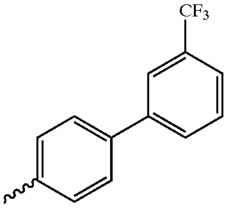 |
| 19 | 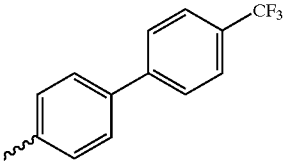 |
| 20 | 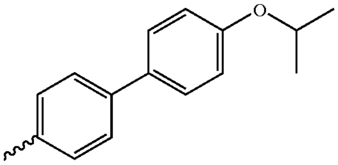 |
| 21 | 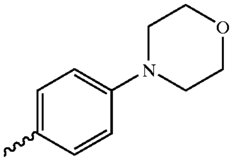 |
TABLE 98
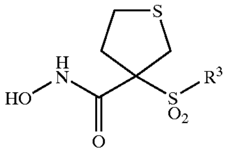
| | 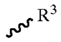 |
|---|---|
| 1 | 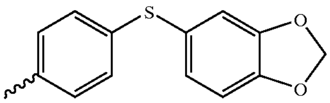 |
| 2 | 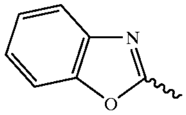 |
| 3 | 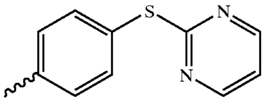 |
| 4 | 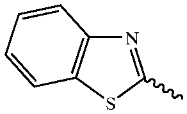 |
| 5 | 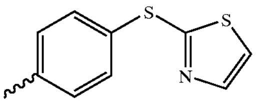 |
| 6 | 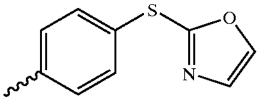 |
| 7 | 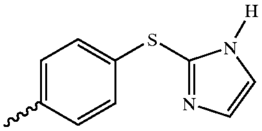 |
| 8 | 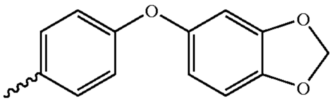 |
| 9 | 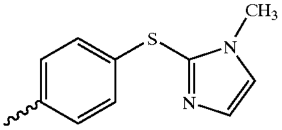 |
| 10 | 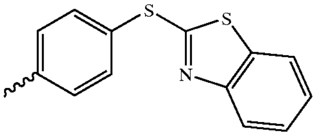 |

TABLE 98-continued
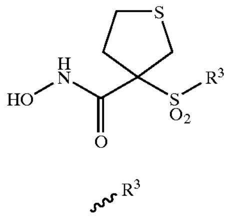
| | |
|---|---|
| 11 | 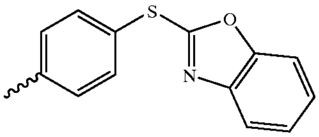 |
TABLE 99
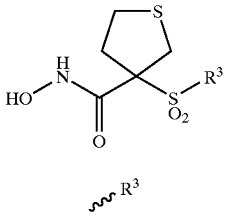
| | |
|---|---|
| 1 | 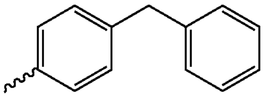 |
| 2 | 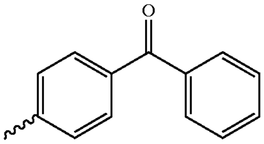 |
| 3 | 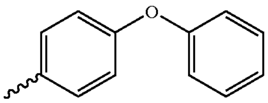 |
| 4 | 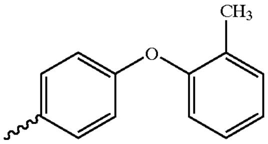 |
| 5 | 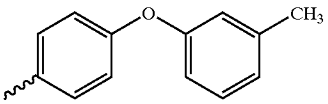 |
| 6 | 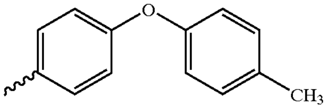 |
| 7 | 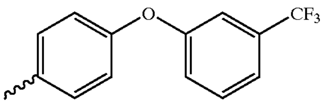 |
TABLE 99-continued
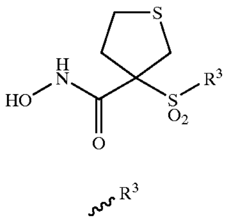
| | |
|---|---|
| 8 | 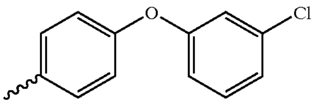 |
| 9 | 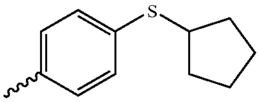 |
| 10 | 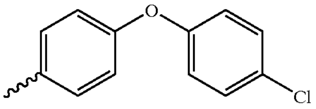 |
| 11 | 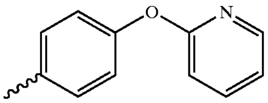 |
| 12 | 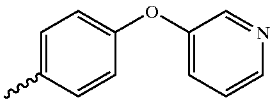 |
| 13 | 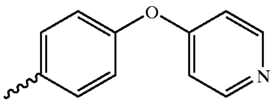 |
| 14 | 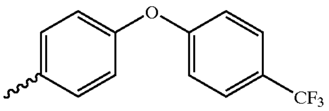 |
| 15 | 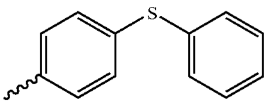 |
| 16 | 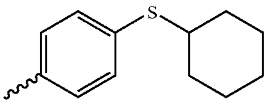 |
| 17 | 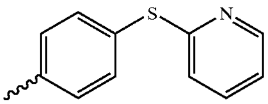 |
| 18 | 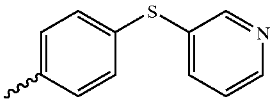 |

TABLE 99-continued
| 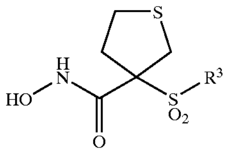 |
|---|
| 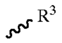 |
| 19 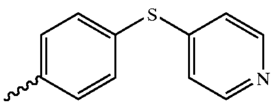 |
| 20 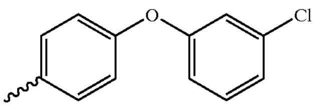 |
| 21 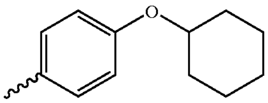 |
TABLE 100
| 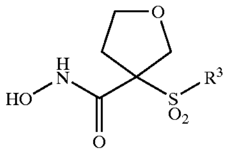 |
|---|
| 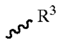 |
| 1 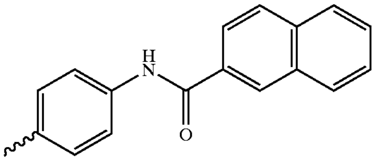 |
| 2 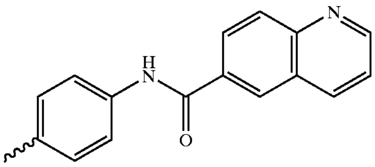 |
| 3 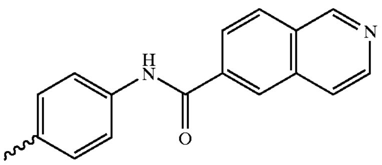 |
| 4 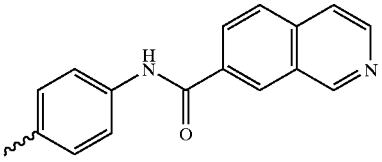 |
TABLE 100-continued
| 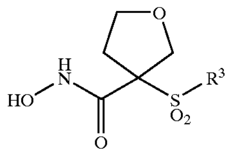 |
|---|
| 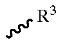 |
| 5 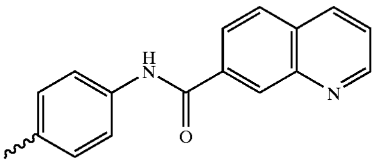 |
| 6 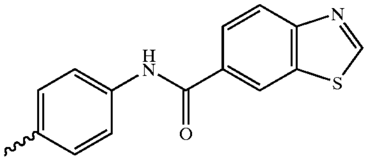 |
| 7 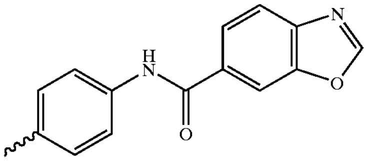 |
| 8 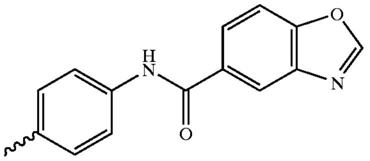 |
| 9 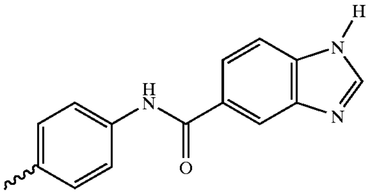 |
| 10 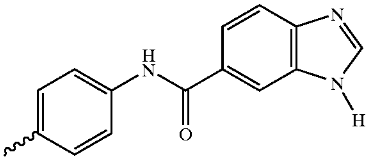 |
| 11 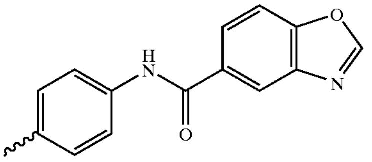 |

TABLE 100-continued
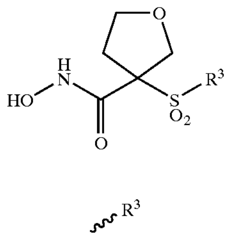
| | |
|---|---|
| 12 | 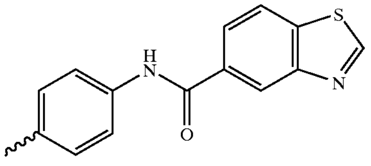 |
| 13 | 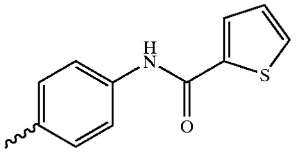 |
| 14 | 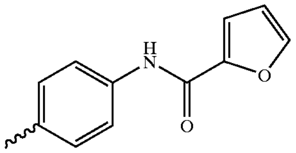 |
| 15 | 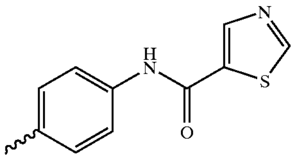 |
| 16 | 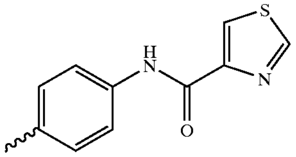 |
| 17 | 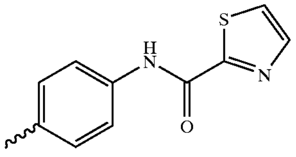 |
| 18 | 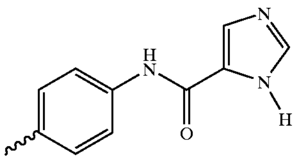 |
TABLE 101
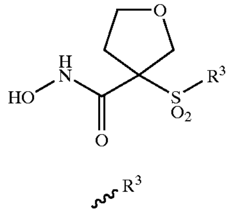
| | |
|---|---|
| 1 | 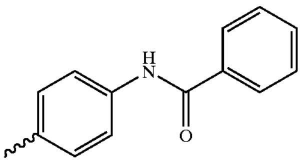 |
| 2 | 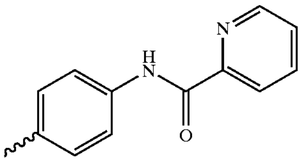 |
| 3 | 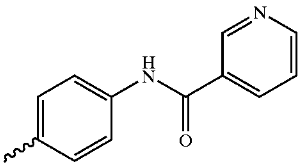 |
| 4 | 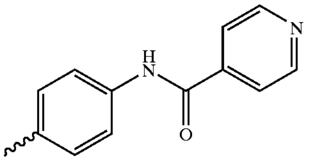 |
| 5 | 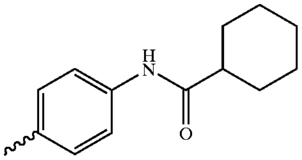 |
| 6 | 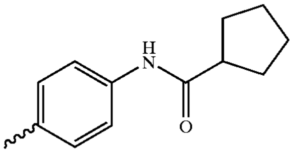 |
| 7 | 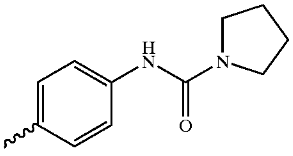 |
| 8 | 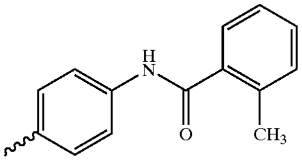 |

TABLE 101-continued
| | |
|---|---|
| | 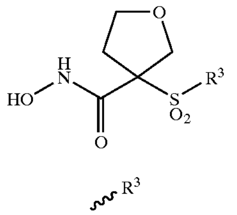 |
| 9 | 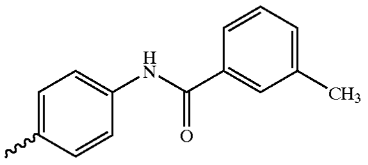 |
| 10 | 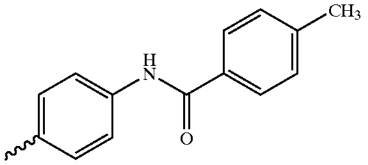 |
| 11 | 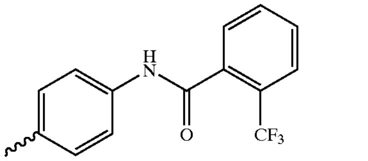 |
| 12 | 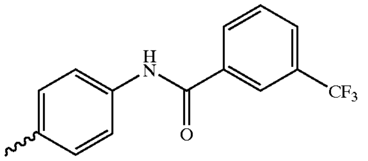 |
| 13 | 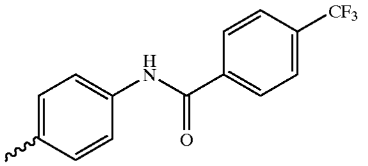 |
| 14 | 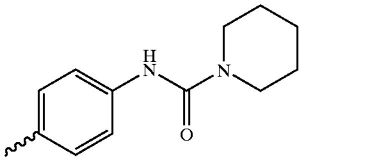 |
| 15 | 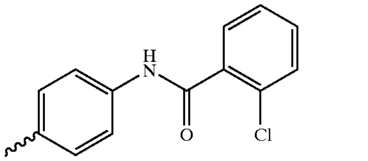 |
| 16 | 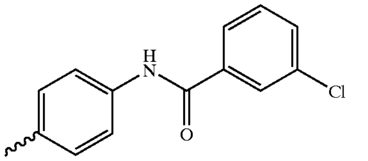 |
TABLE 101-continued
| | |
|---|---|
| | 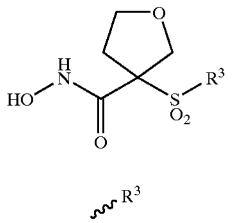 |
| 17 | 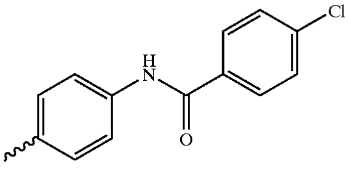 |
| 18 | 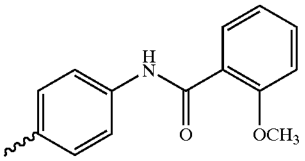 |
| 19 | 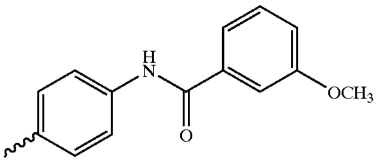 |
| 20 | 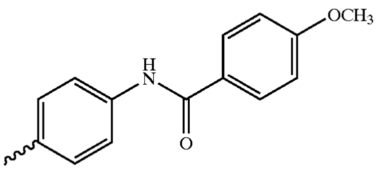 |
| 21 | 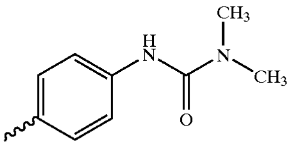 |
TABLE 102
| | |
|---|---|
| | 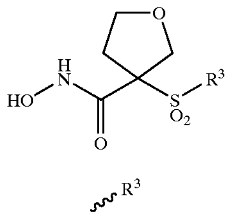 |
| 1 | 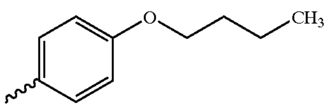 |

TABLE 102-continued
| | |
|---|---|
| | 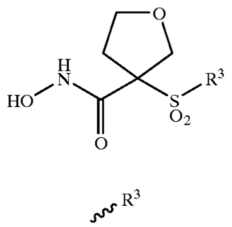 |
| 2 | 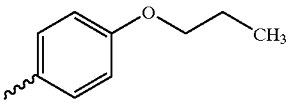 |
| 3 | 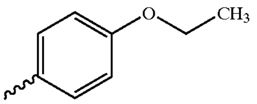 |
| 4 | 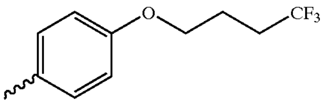 |
| 5 | 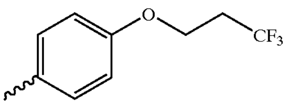 |
| 6 | 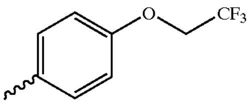 |
| 7 | 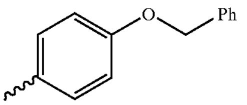 |
| 8 | 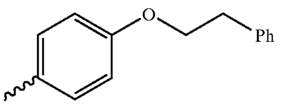 |
| 9 | 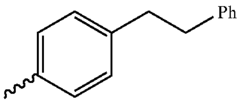 |
| 10 | 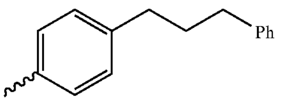 |
| 11 | 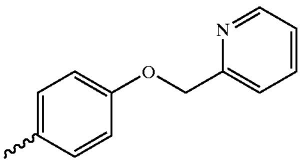 |
TABLE 102-continued
| | |
|---|---|
| | 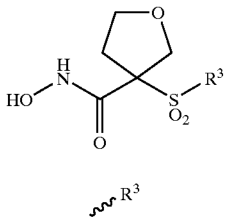 |
| 12 | 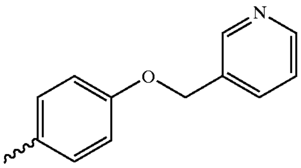 |
| 13 | 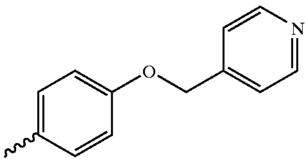 |
| 14 | 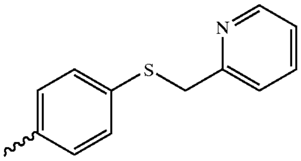 |
| 15 | 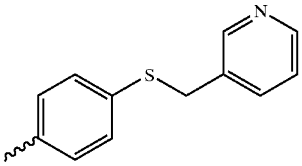 |
| 16 | 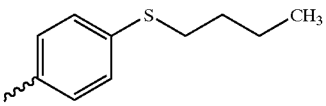 |
| 17 | 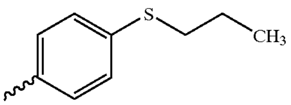 |
| 18 | 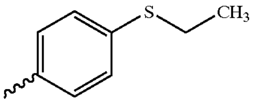 |
| 19 | 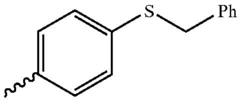 |
| 20 | 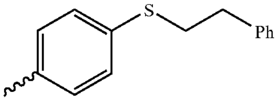 |

TABLE 102-continued
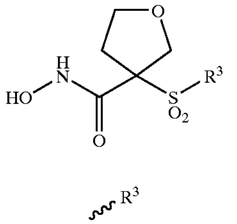
21 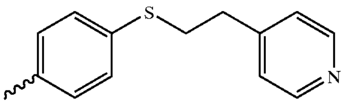
22 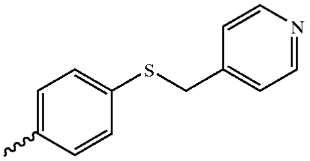
TABLE 103
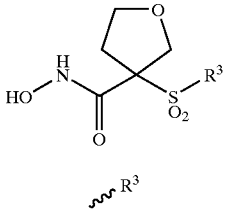
1 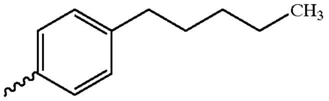
2 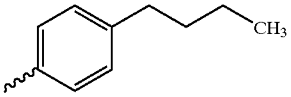
3 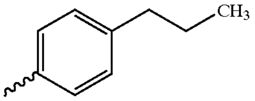
4 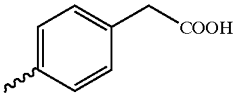
5 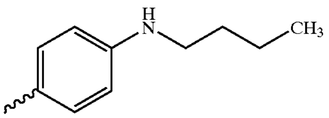
6 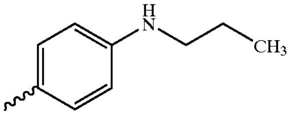
TABLE 103-continued
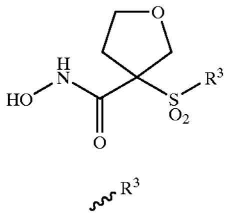
7 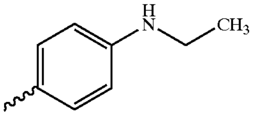
8 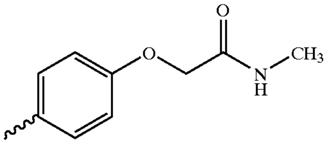
9 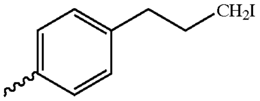
10 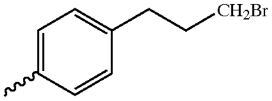
11 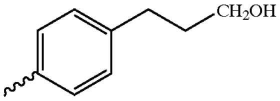
12 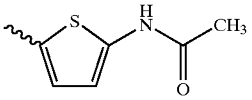
13 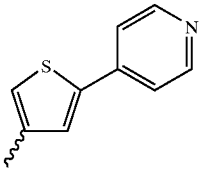
14 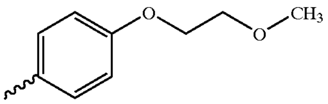
15 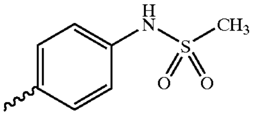
16 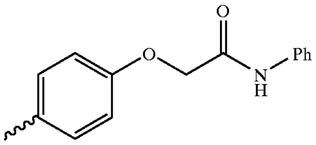

TABLE 103-continued
| | |
|---|---|
| | 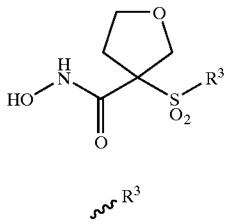 |
| 17 | 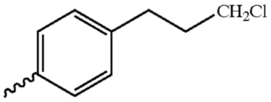 |
| 18 | 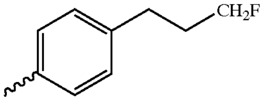 |
| 19 | 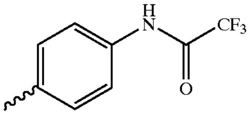 |
| 20 | 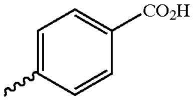 |
| 21 | 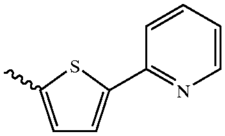 |
| 22 | 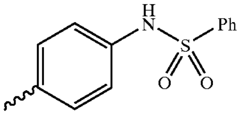 |
| 23 | 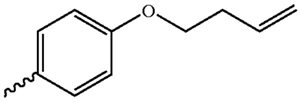 |
| 24 | 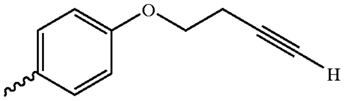 |
| 25 | 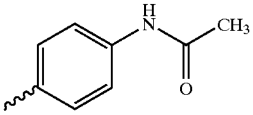 |
| 26 | 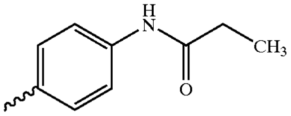 |
TABLE 103-continued
| | |
|---|---|
| | 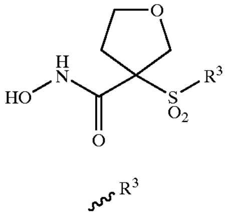 |
| 27 | 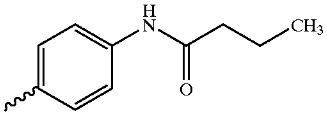 |
| 28 | 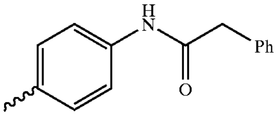 |
| 29 | 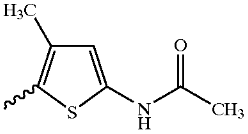 |
| 30 | 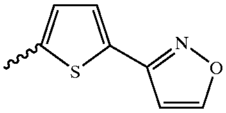 |
TABLE 104
| | |
|---|---|
| | 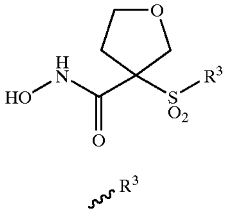 |
| 1 | 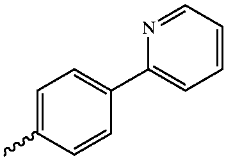 |
| 2 | 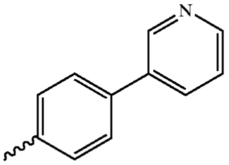 |
| 3 | 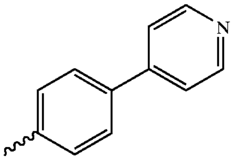 |

TABLE 104-continued
| | |
|---|---|
| | 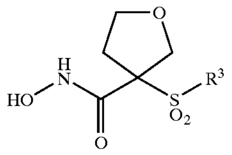 |
| | 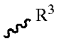 |
| 4 | 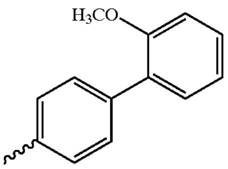 |
| 5 | 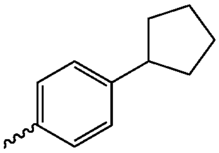 |
| 6 | 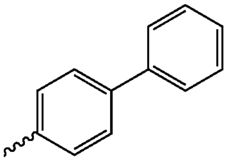 |
| 7 | 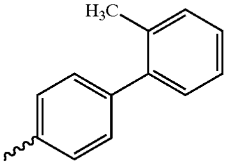 |
| 8 | 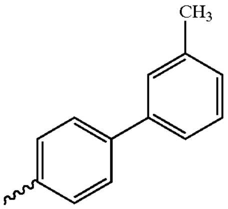 |
| 9 | 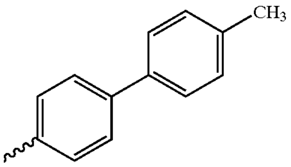 |
| 10 | 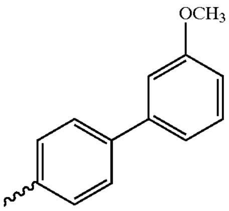 |
TABLE 104-continued
| | |
|---|---|
| | 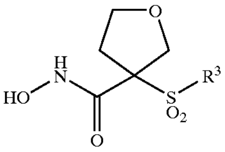 |
| | 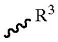 |
| 11 | 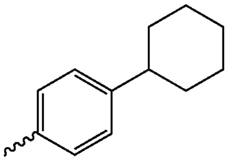 |
| 12 | 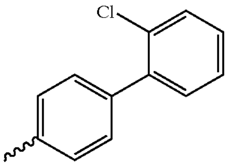 |
| 13 | 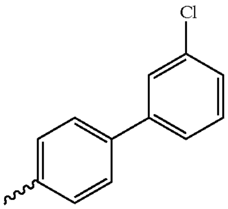 |
| 14 | 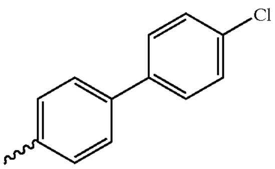 |
| 15 | 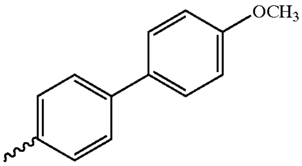 |
| 16 | 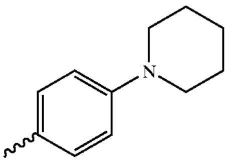 |
| 17 | 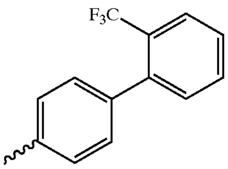 |

TABLE 104-continued
| | |
|---|---|
| | 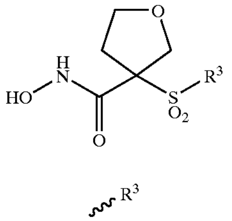 |
| 18 | 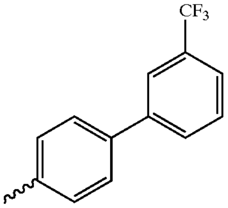 |
| 19 | 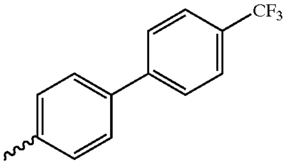 |
| 20 | 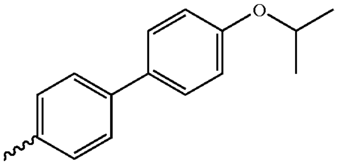 |
| 21 | 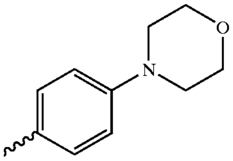 |
TABLE 105
| | |
|---|---|
| | 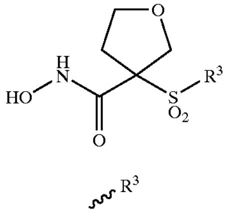 |
| 1 | 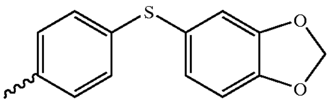 |
| 2 | 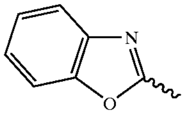 |
TABLE 105-continued
| | |
|---|---|
| | 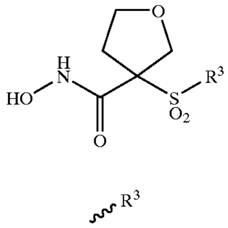 |
| 3 | 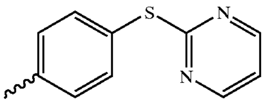 |
| 4 | 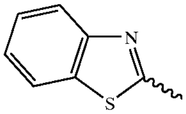 |
| 5 | 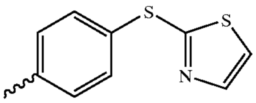 |
| 6 | 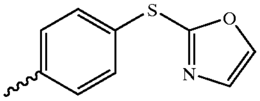 |
| 7 | 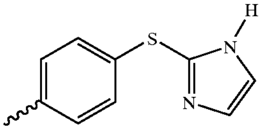 |
| 8 | 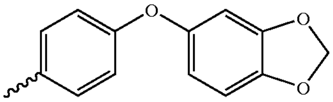 |
| 9 | 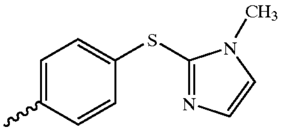 |
| 10 | 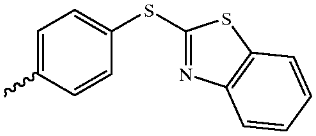 |
| 11 | 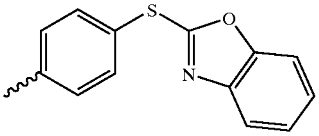 |

TABLE 106
| 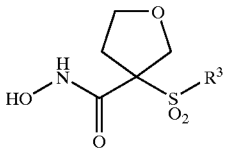 | |
|---|---|
| | 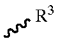 |
| 1 | 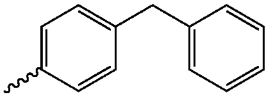 |
| 2 | 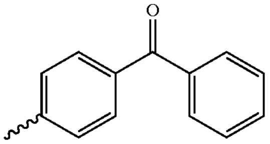 |
| 3 | 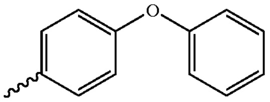 |
| 4 | 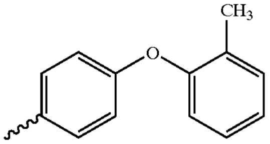 |
| 5 | 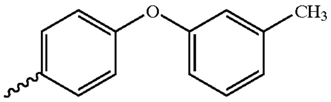 |
| 6 | 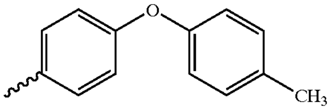 |
| 7 | 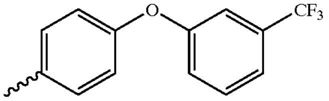 |
| 8 | 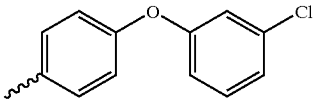 |
| 9 | 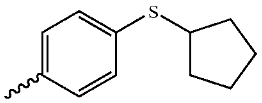 |
| 10 | 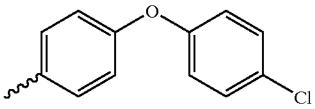 |
| 11 | 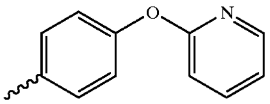 |
TABLE 106-continued
| 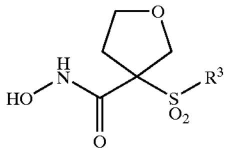 | |
|---|---|
| | 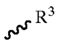 |
| 12 | 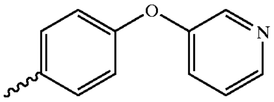 |
| 13 | 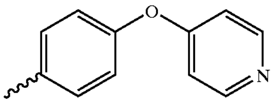 |
| 14 | 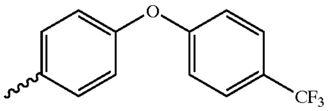 |
| 15 | 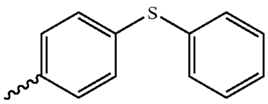 |
| 16 | 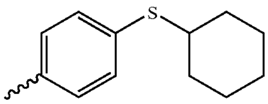 |
| 17 | 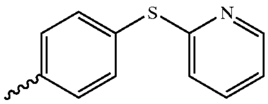 |
| 18 | 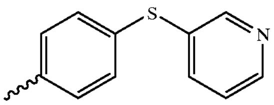 |
| 19 | 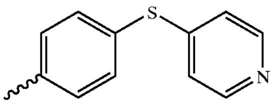 |
| 20 | 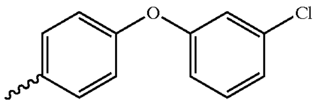 |
| 21 | 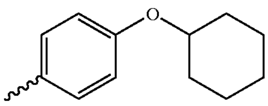 |

TABLE 107
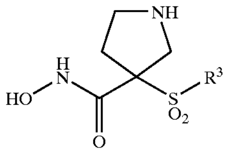
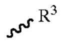
| | |
|---|---|
| 1 | 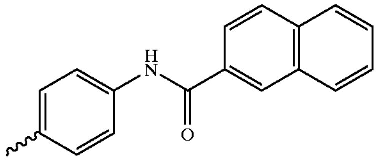 |
| 2 | 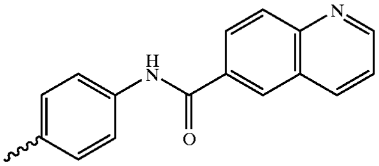 |
| 3 | 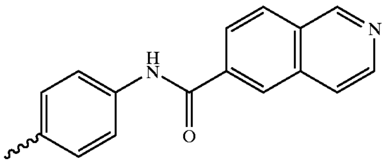 |
| 4 | 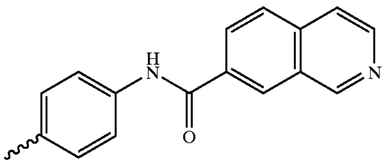 |
| 5 | 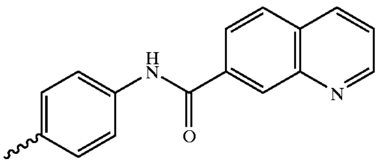 |
| 6 | 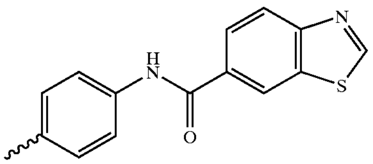 |
| 7 | 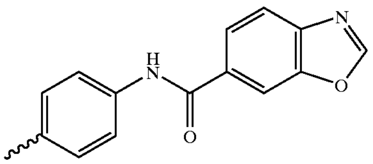 |
| 8 | 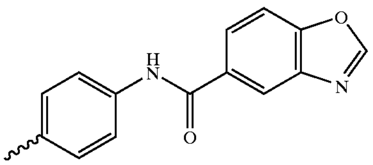 |
TABLE 107-continued
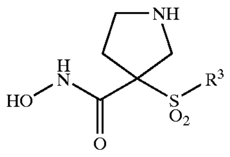
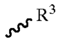
| | |
|---|---|
| 9 | 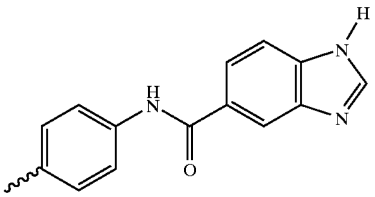 |
| 10 | 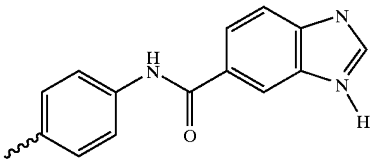 |
| 11 | 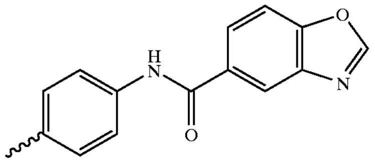 |
| 12 | 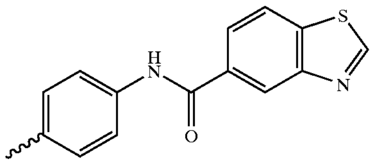 |
| 13 | 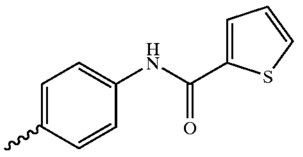 |
| 14 | 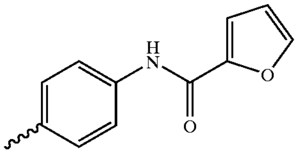 |
| 15 | 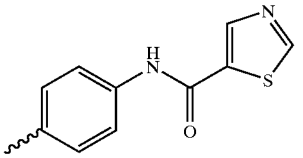 |

TABLE 107-continued
| | |
|---|---|
| | 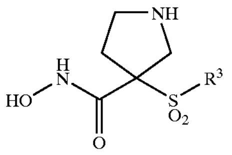 |
| | 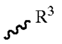 |
| 16 | 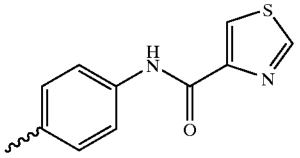 |
| 17 | 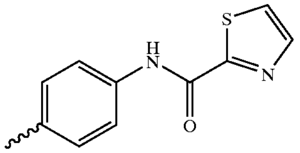 |
| 18 | 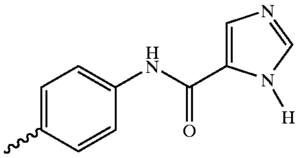 |
TABLE 108
| | |
|---|---|
| | 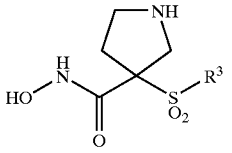 |
| | 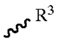 |
| 1 | 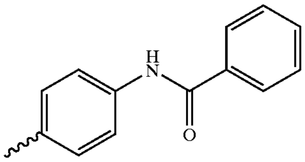 |
| 2 | 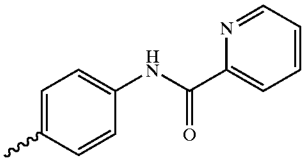 |
| 3 | 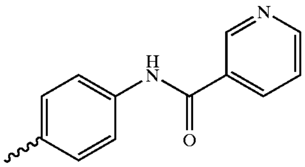 |
TABLE 108-continued
| | |
|---|---|
| | 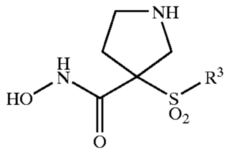 |
| | 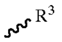 |
| 4 | 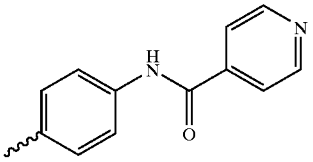 |
| 5 | 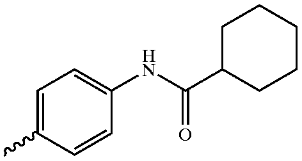 |
| 6 | 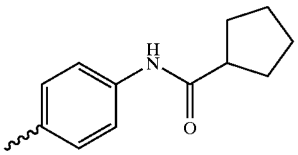 |
| 7 | 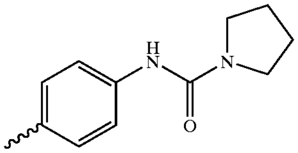 |
| 8 | 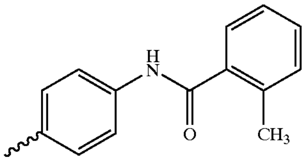 |
| 9 | 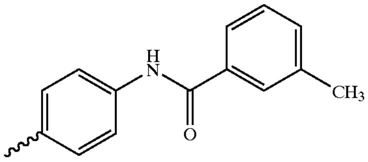 |
| 10 | 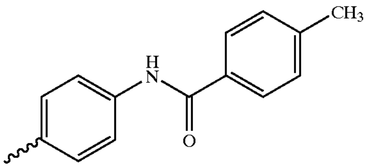 |
| 11 | 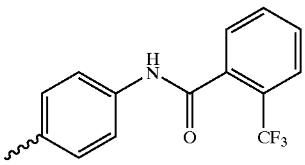 |

TABLE 108-continued
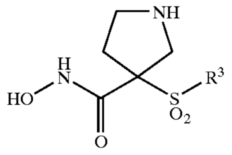
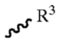
12
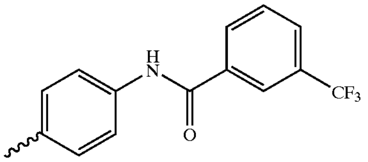
13
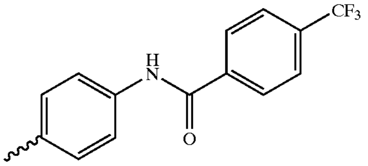
14
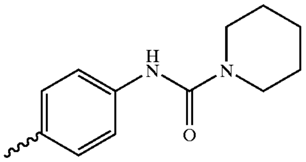
15
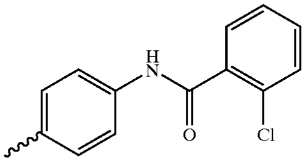
16
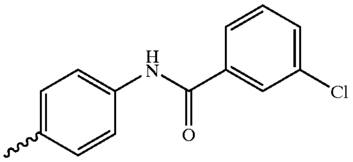
17
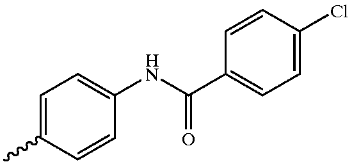
18
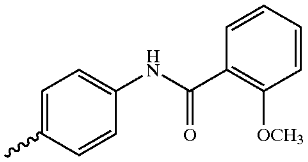
19
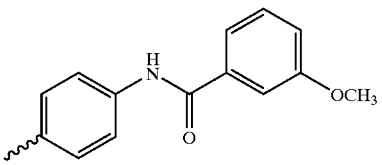
TABLE 108-continued
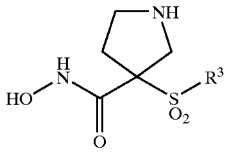
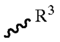
20
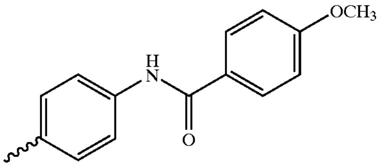
21
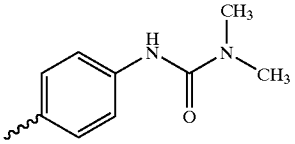
TABLE 109
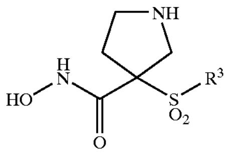
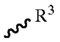
1
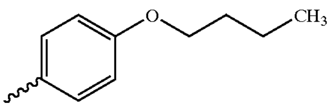
2
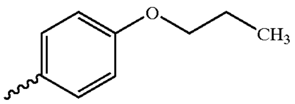
3
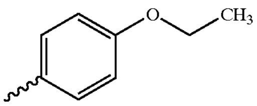
4
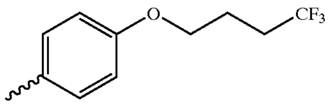
5
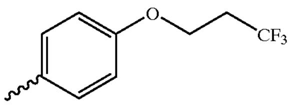
6
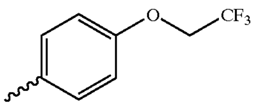

TABLE 109-continued
| | |
|---|---|
| 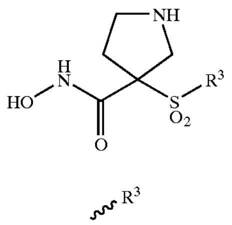 | |
| 7 | 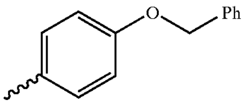 |
| 8 | 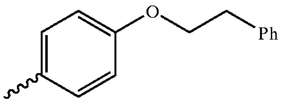 |
| 9 | 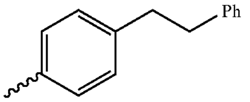 |
| 10 | 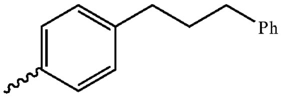 |
| 11 | 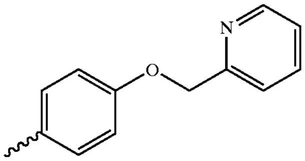 |
| 12 | 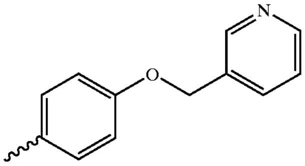 |
| 13 | 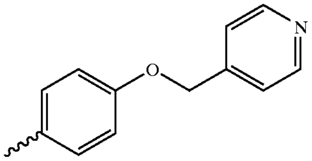 |
| 14 | 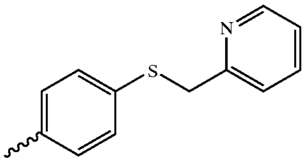 |
| 15 | 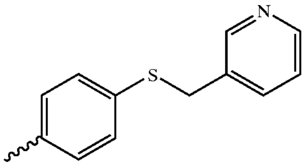 |
TABLE 109-continued
| | |
|---|---|
| 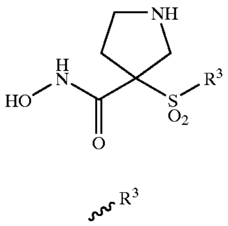 | |
| 16 | 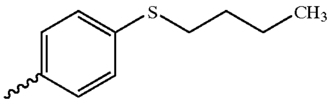 |
| 17 | 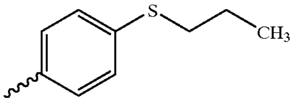 |
| 18 | 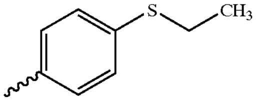 |
| 19 | 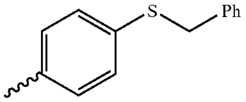 |
| 20 | 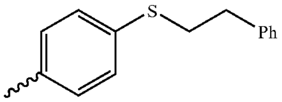 |
| 21 | 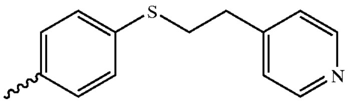 |
| 22 | 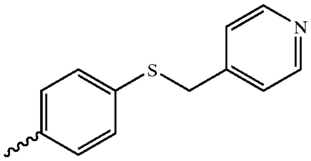 |
TABLE 110
| | |
|---|---|
| 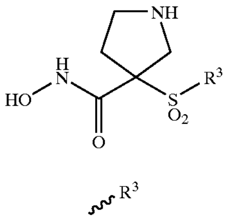 | |
| 1 | 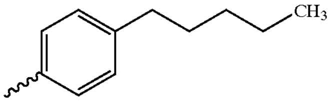 |

TABLE 110-continued
| | |
|---|---|
| | 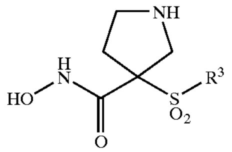 |
| | 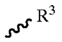 |
| 2 | 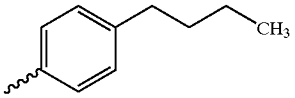 |
| 3 | 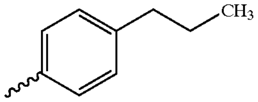 |
| 4 | 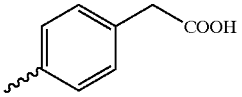 |
| 5 | 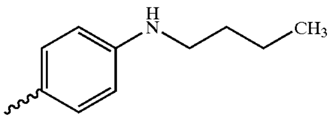 |
| 6 | 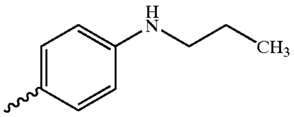 |
| 7 | 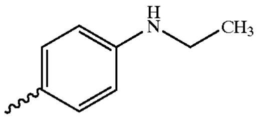 |
| 8 | 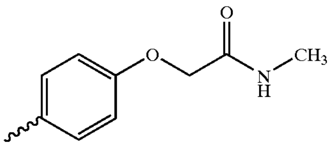 |
| 9 | 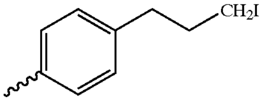 |
| 10 | 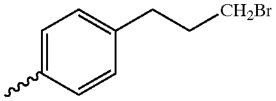 |
| 11 | 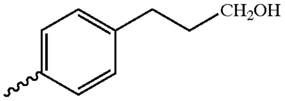 |
| 12 | 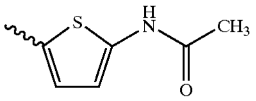 |
TABLE 110-continued
| | |
|---|---|
| | 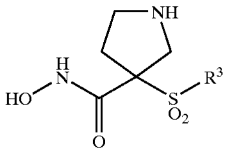 |
| | 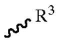 |
| 13 | 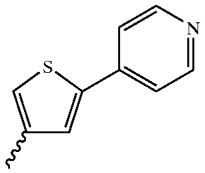 |
| 14 | 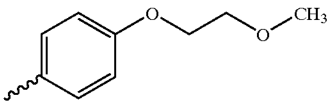 |
| 15 | 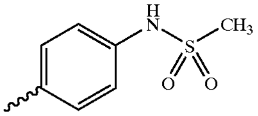 |
| 16 | 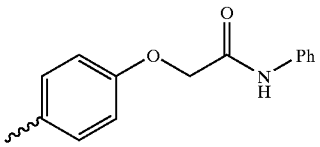 |
| 17 | 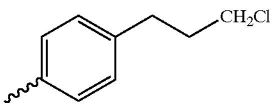 |
| 18 | 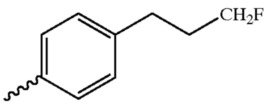 |
| 19 | 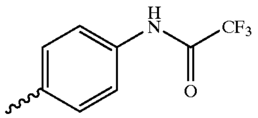 |
| 20 | 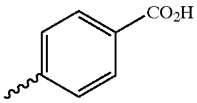 |
| 21 | 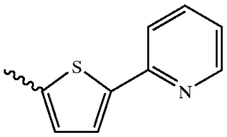 |
| 22 | 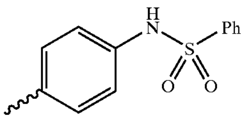 |

TABLE 110-continued
| 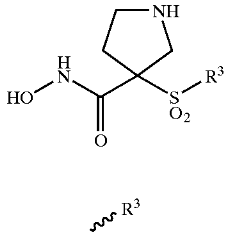 | |
|---|---|
| 23 | 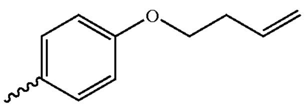 |
| 24 | 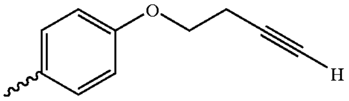 |
| 25 | 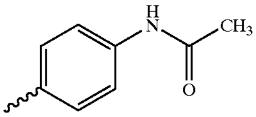 |
| 26 | 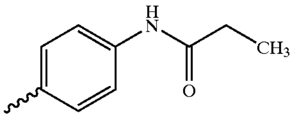 |
| 27 | 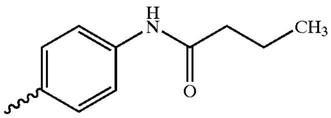 |
| 28 | 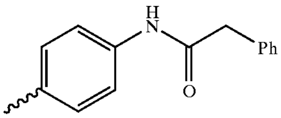 |
| 29 | 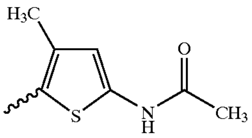 |
| 30 | 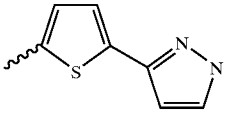 |
TABLE 111
| 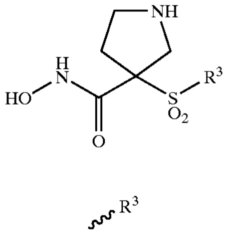 | |
|---|---|
| 1 | 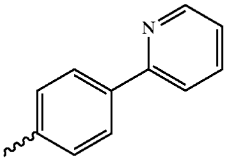 |
| 2 | 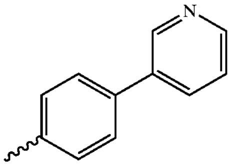 |
| 3 | 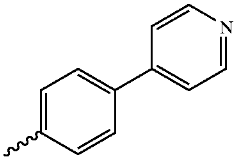 |
| 4 | 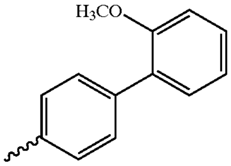 |
| 5 | 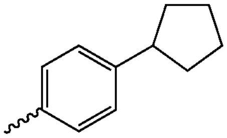 |
| 6 | 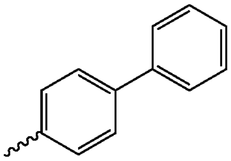 |
| 7 | 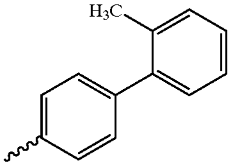 |

TABLE 111-continued
| | |
|---|---|
| | 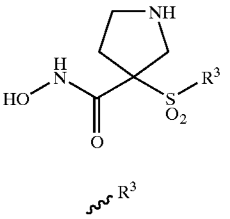 |
| 8 | 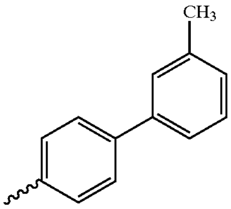 |
| 9 | 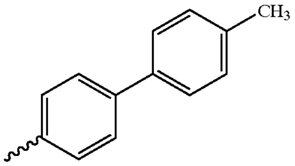 |
| 10 | 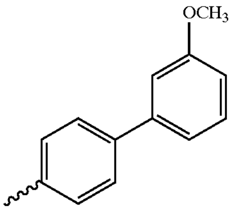 |
| 11 | 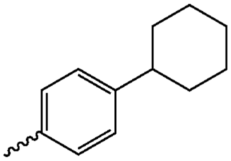 |
| 12 | 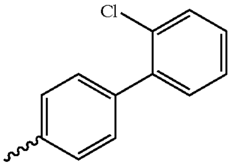 |
| 13 | 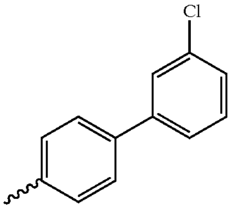 |
| 14 | 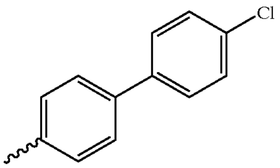 |
TABLE 111-continued
| | |
|---|---|
| | 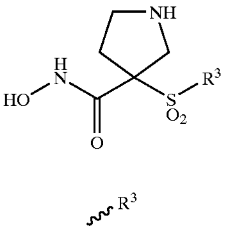 |
| 15 | 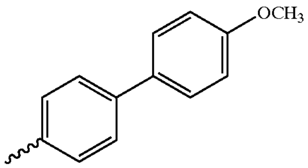 |
| 16 | 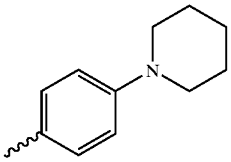 |
| 17 | 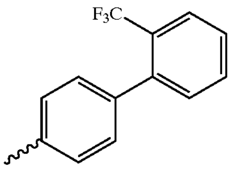 |
| 18 | 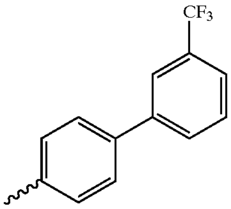 |
| 19 | 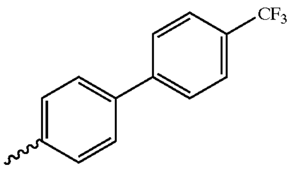 |
| 20 | 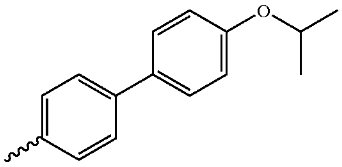 |
| 21 | 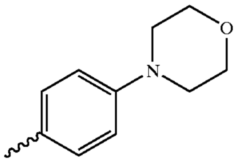 |

TABLE 112
| 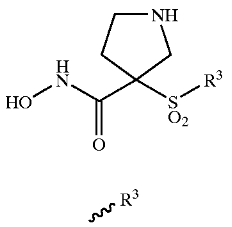 | |
|---|---|
| 1 | 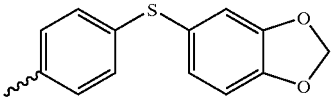 |
| 2 | 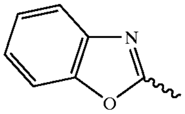 |
| 3 | 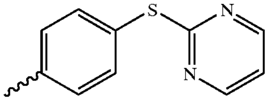 |
| 4 | 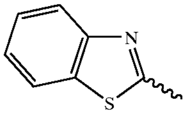 |
| 5 | 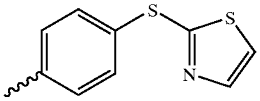 |
| 6 | 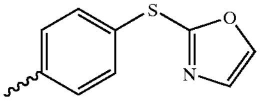 |
| 7 | 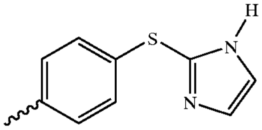 |
| 8 | 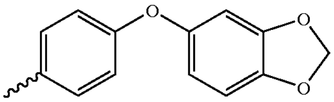 |
| 9 | 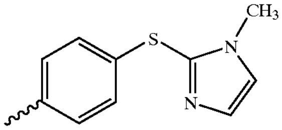 |
| 10 | 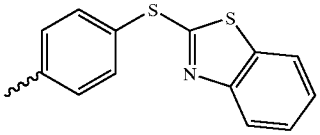 |
TABLE 112-continued
| 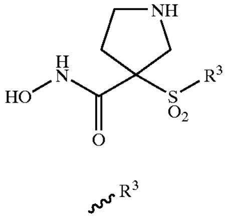 | |
|---|---|
| 11 | 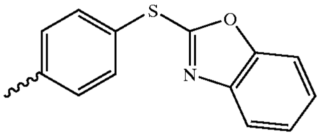 |
TABLE 113
| 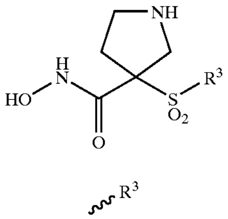 | |
|---|---|
| 1 | 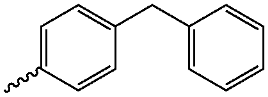 |
| 2 | 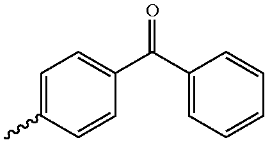 |
| 3 | 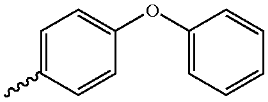 |
| 4 | 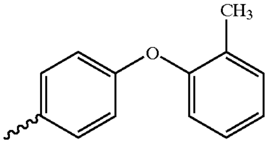 |
| 5 | 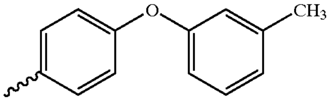 |
| 6 | 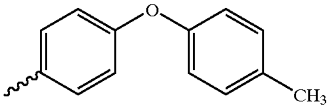 |
| 7 | 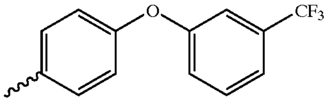 |

TABLE 113-continued
| | |
|---|---|
| 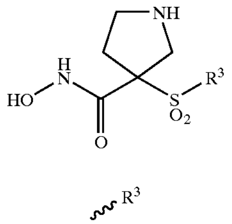 | |
| 8 | 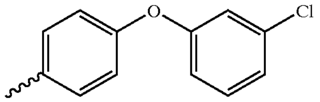 |
| 9 | 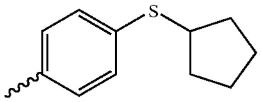 |
| 10 | 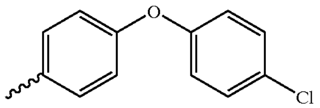 |
| 11 | 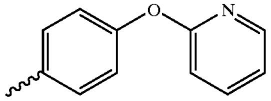 |
| 12 | 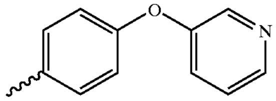 |
| 13 | 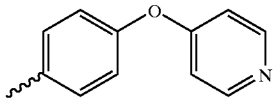 |
| 14 | 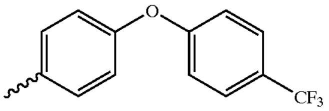 |
| 15 | 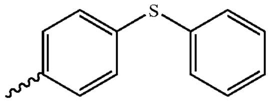 |
| 16 | 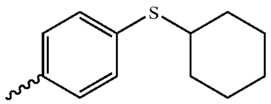 |
| 17 | 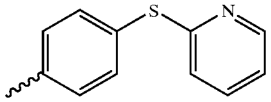 |
| 18 | 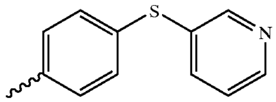 |
TABLE 113-continued
| | |
|---|---|
| 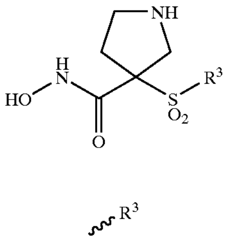 | |
| 19 | 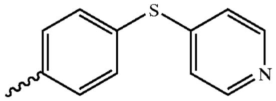 |
| 20 | 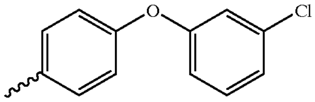 |
| 21 | 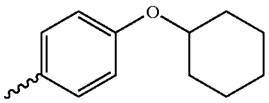 |
TABLE 114
| | |
|---|---|
| 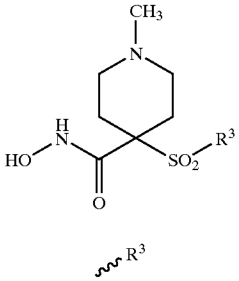 | |
| 1 | 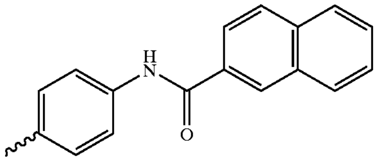 |
| 2 | 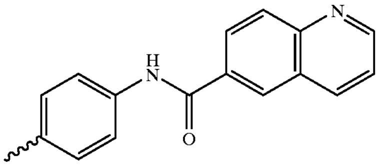 |
| 3 | 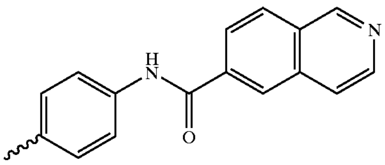 |

TABLE 114-continued
| 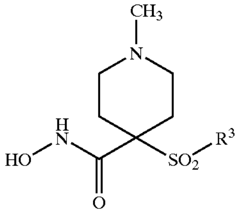 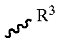 |
| --- |
| 4 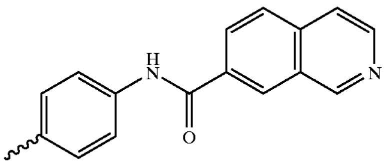 |
| 5 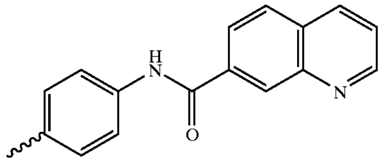 |
| 6 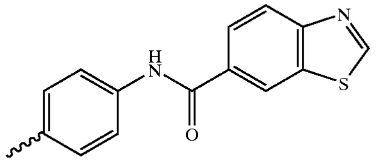 |
| 7 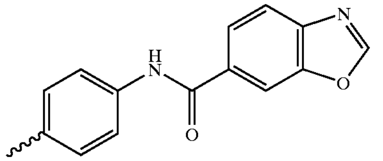 |
| 8 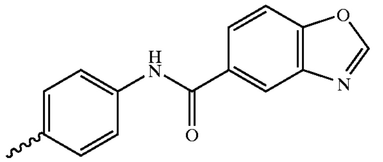 |
| 9 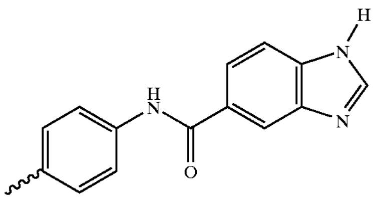 |
| 10 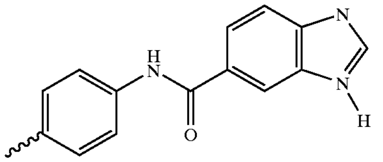 |
TABLE 114-continued
| 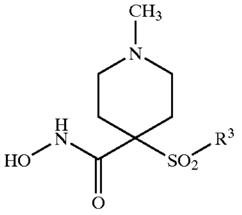 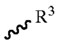 |
| --- |
| 11 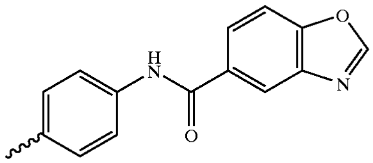 |
| 12 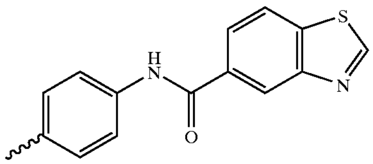 |
| 13 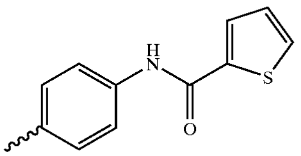 |
| 14 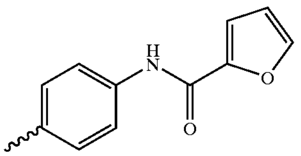 |
| 15 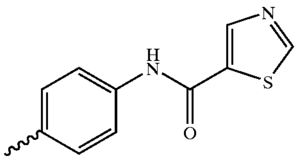 |
| 16 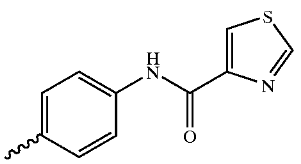 |
| 17 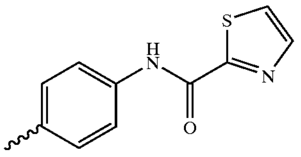 |

TABLE 114-continued
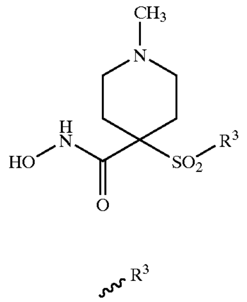
18
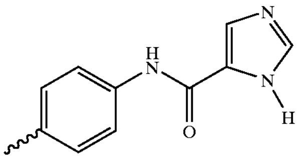
TABLE 115
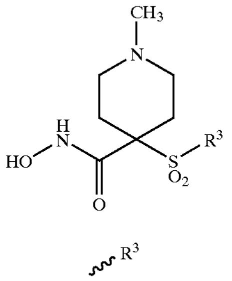
1
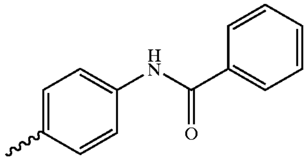
2
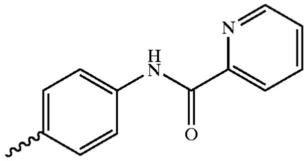
3
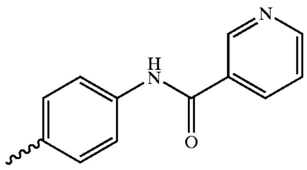
4
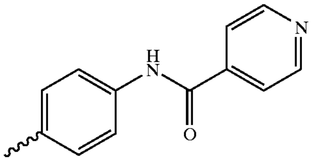
TABLE 115-continued
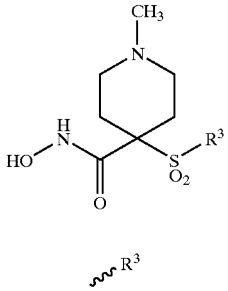
5
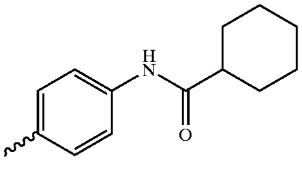
6
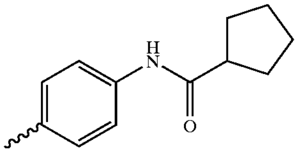
7
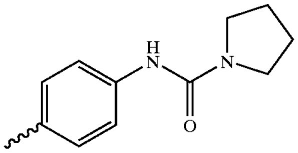
8
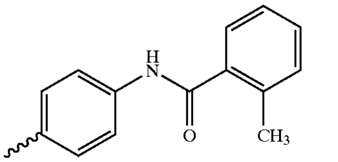
9
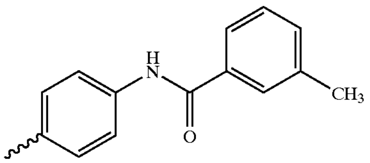
10
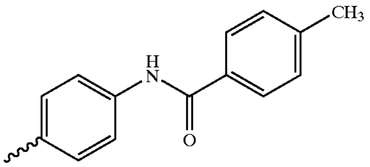
11
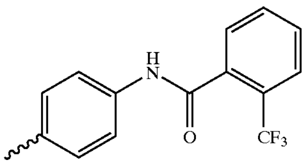

TABLE 115-continued
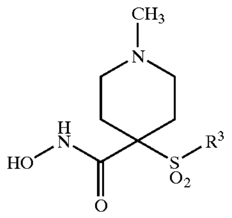
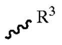
| | |
|---|---|
| 12 | 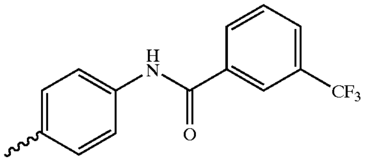 |
| 13 | 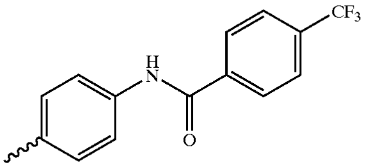 |
| 14 | 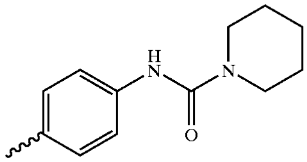 |
| 15 | 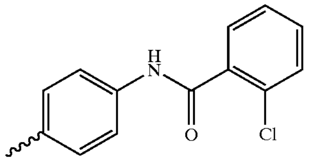 |
| 16 | 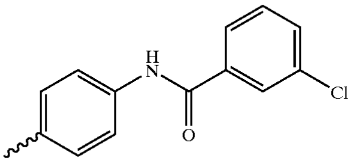 |
| 17 | 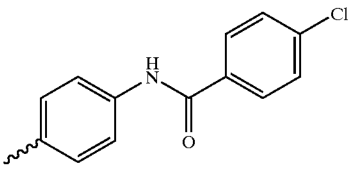 |
| 18 | 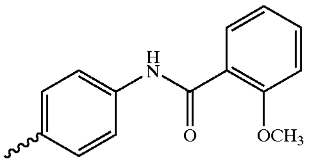 |
TABLE 115-continued
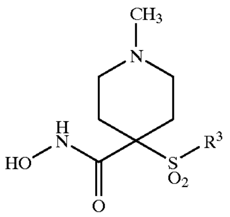
| | |
|---|---|
| 19 | 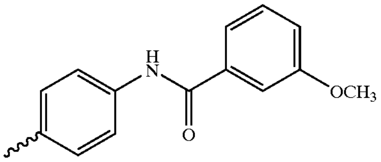 |
| 20 | 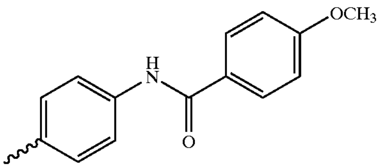 |
| 21 | 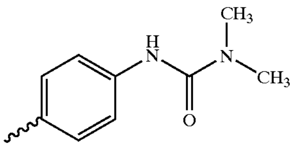 |
TABLE 116
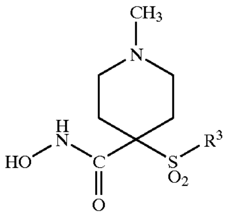
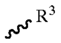
| | |
|---|---|
| 1 | 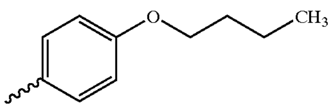 |
| 2 | 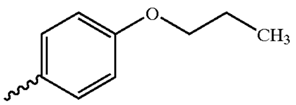 |
| 3 | 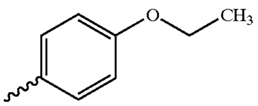 |

TABLE 116-continued
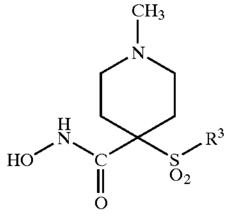
| | 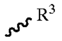 |
| --- | --- |
| 4 | 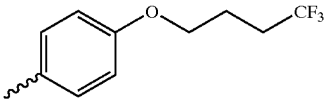 |
| 5 | 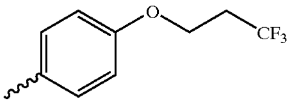 |
| 6 | 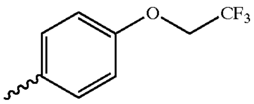 |
| 7 | 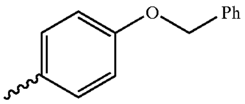 |
| 8 | 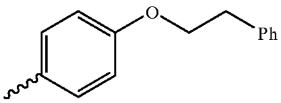 |
| 9 | 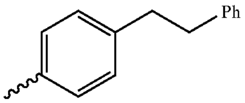 |
| 10 | 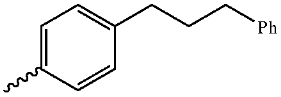 |
| 11 | 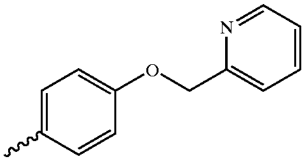 |
| 12 | 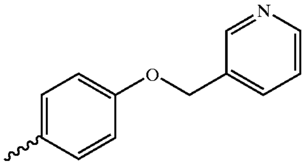 |
| 13 | 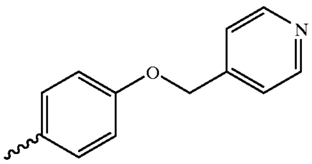 |
TABLE 116-continued
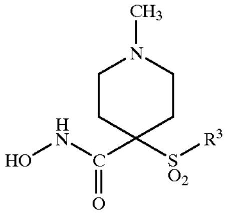
| | 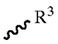 |
| --- | --- |
| 14 | 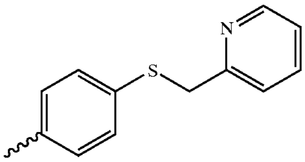 |
| 15 | 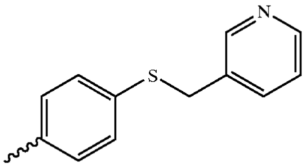 |
| 16 | 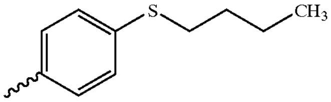 |
| 17 | 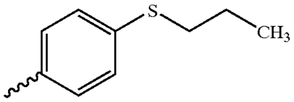 |
| 18 | 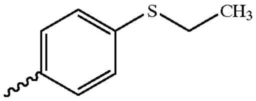 |
| 19 | 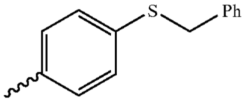 |
| 20 | 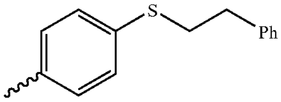 |
| 21 | 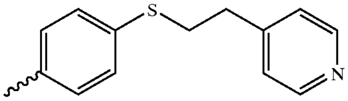 |
| 22 | 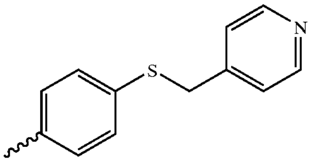 |

TABLE 117
| | |
|---|---|
| | 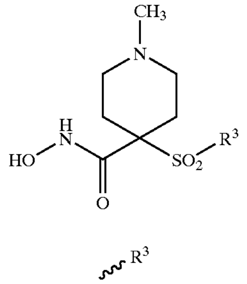 |
| 1 | 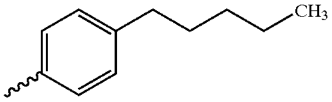 |
| 2 | 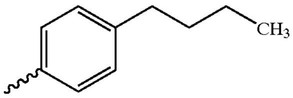 |
| 3 | 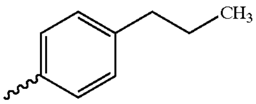 |
| 4 | 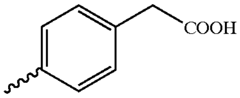 |
| 5 | 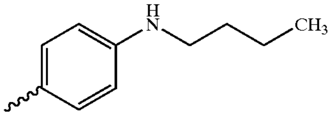 |
| 6 | 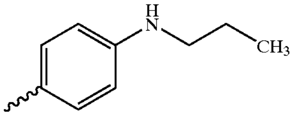 |
| 7 | 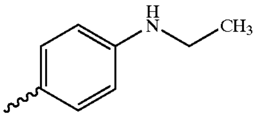 |
| 8 | 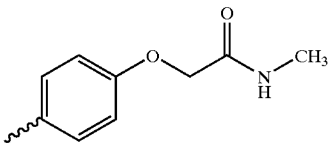 |
| 9 | 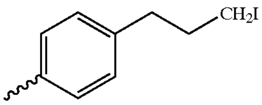 |
| 10 | 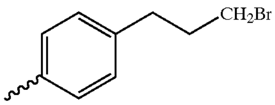 |
TABLE 117-continued
| | |
|---|---|
| | 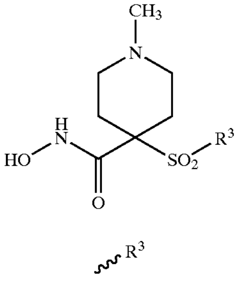 |
| 11 | 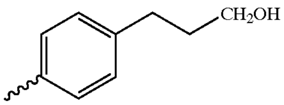 |
| 12 | 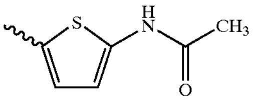 |
| 13 | 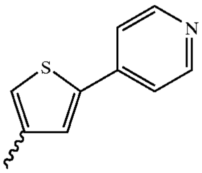 |
| 14 | 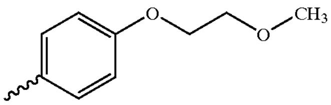 |
| 15 | 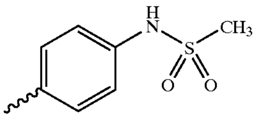 |
| 16 | 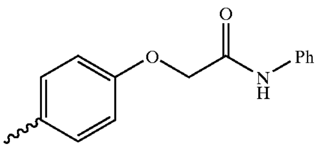 |
| 17 | 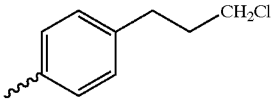 |
| 18 | 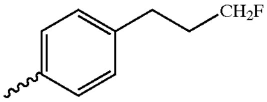 |
| 19 | 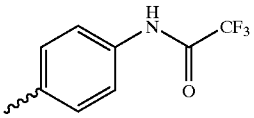 |
| 20 | 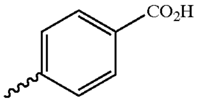 |

TABLE 117-continued
| | |
|---|---|
| 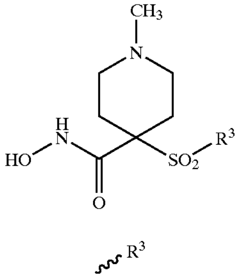 | |
| 21 | 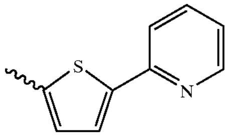 |
| 22 | 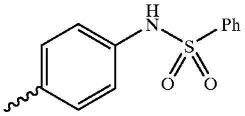 |
| 23 | 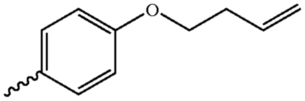 |
| 24 | 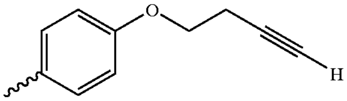 |
| 25 | 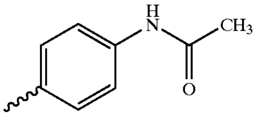 |
| 26 | 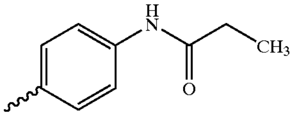 |
| 27 | 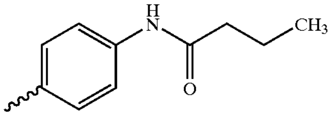 |
| 28 | 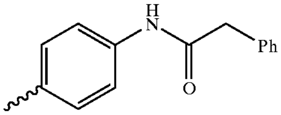 |
| 29 | 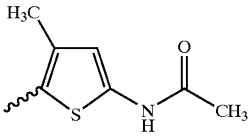 |
| 30 | 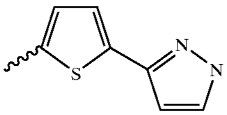 |
TABLE 118
| | |
|---|---|
| 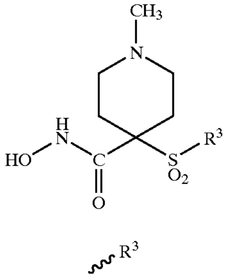 | |
| 1 | 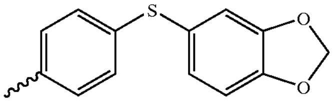 |
| 2 | 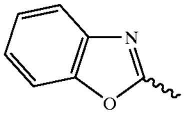 |
| 3 | 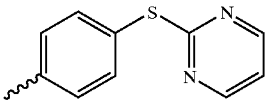 |
| 4 | 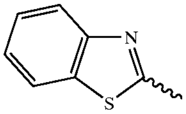 |
| 5 | 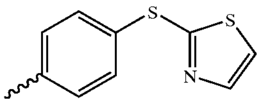 |
| 6 | 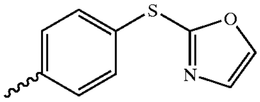 |
| 7 | 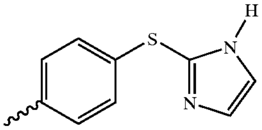 |
| 8 | 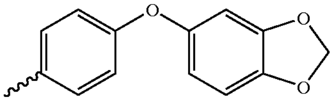 |
| 9 | 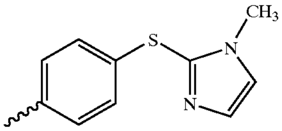 |
| 10 | 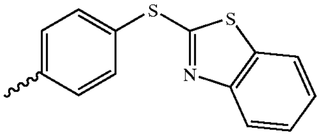 |

TABLE 118-continued
| | |
|---|---|
| | 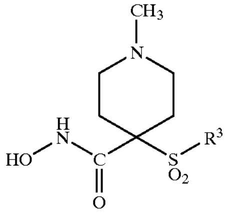 |
| | 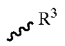 |
| 11 | 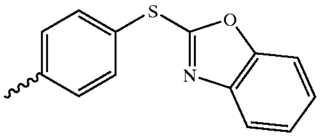 |
TABLE 119
| | |
|---|---|
| | 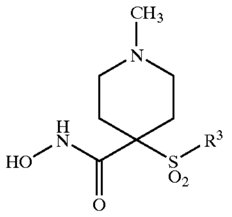 |
| | 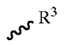 |
| 1 | 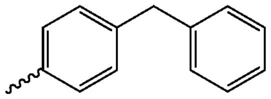 |
| 2 | 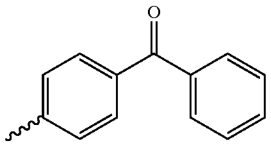 |
| 3 | 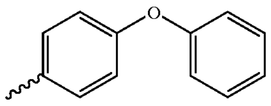 |
| 4 | 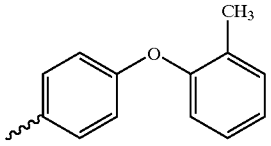 |
| 5 | 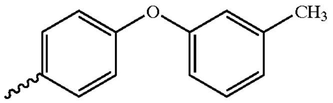 |
| 6 | 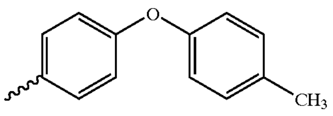 |
TABLE 119-continued
| | |
|---|---|
| | 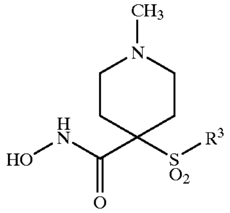 |
| | 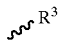 |
| 7 | 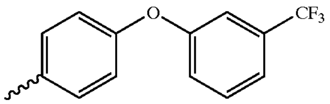 |
| 8 | 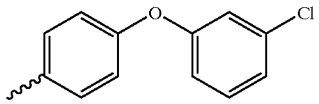 |
| 9 | 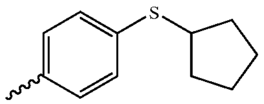 |
| 10 | 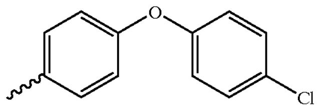 |
| 11 | 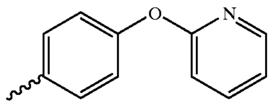 |
| 12 | 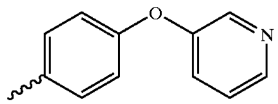 |
| 13 | 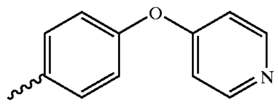 |
| 14 | 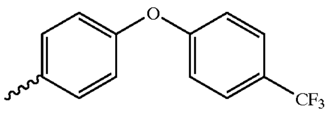 |
| 15 | 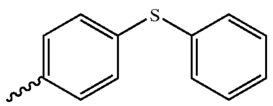 |
| 16 | 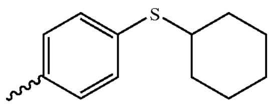 |
| 17 | 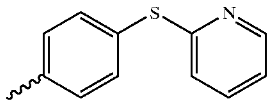 |

TABLE 119-continued
| | |
|---|---|
| | 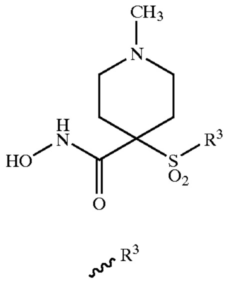 |
| 18 | 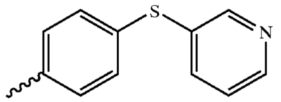 |
| 19 | 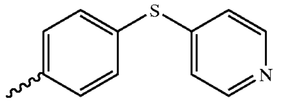 |
| 20 | 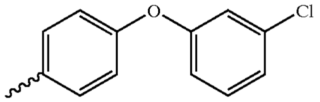 |
| 21 | 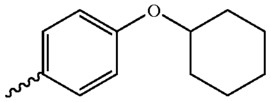 |
TABLE 120
| | |
|---|---|
| | 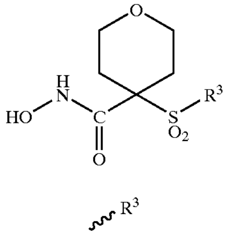 |
| 1 | 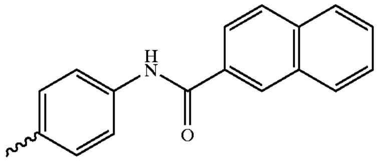 |
| 2 | 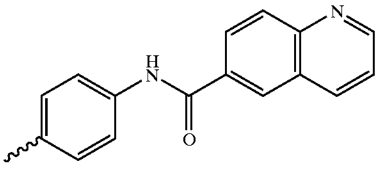 |
| 3 | 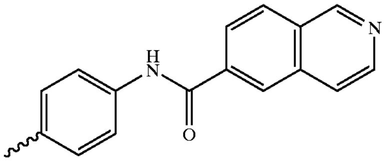 |
TABLE 120-continued
| | |
|---|---|
| | 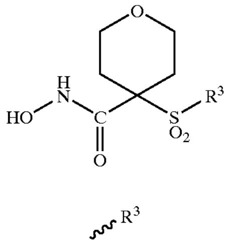 |
| 4 | 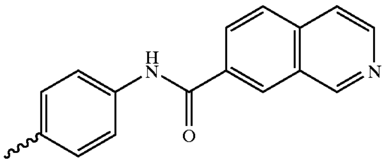 |
| 5 | 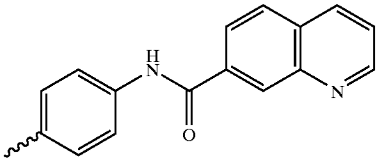 |
| 6 | 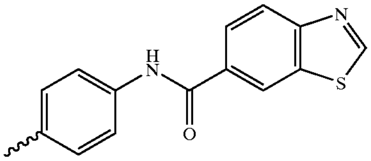 |
| 7 | 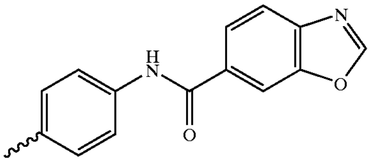 |
| 8 | 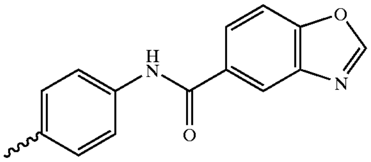 |
| 9 | 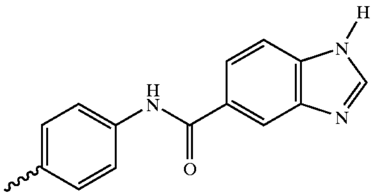 |
| 10 | 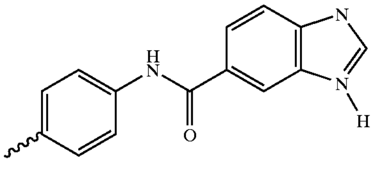 |

TABLE 120-continued
| 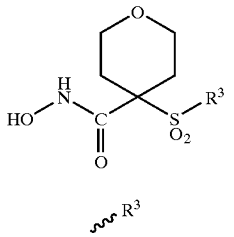 | |
|---|---|
| 11 | 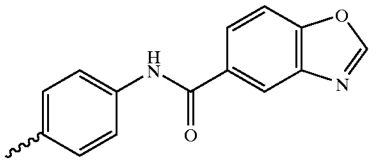 |
| 12 | 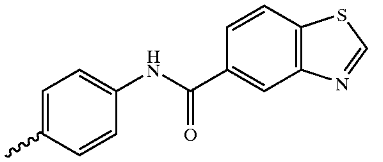 |
| 13 | 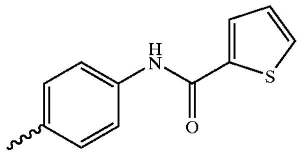 |
| 14 | 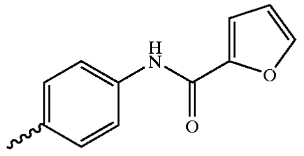 |
| 15 | 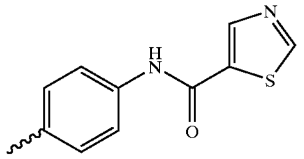 |
| 16 | 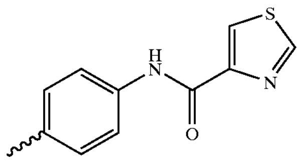 |
| 17 | 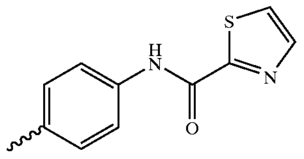 |
| 18 | 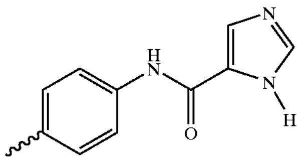 |
TABLE 121
| 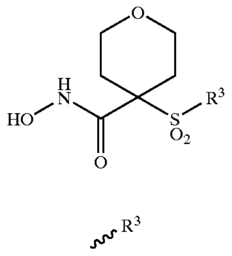 | |
|---|---|
| 1 | 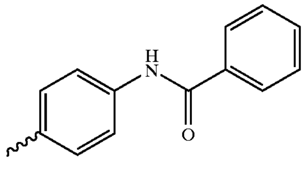 |
| 2 | 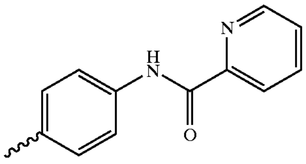 |
| 3 | 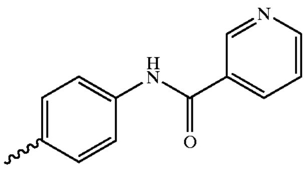 |
| 4 | 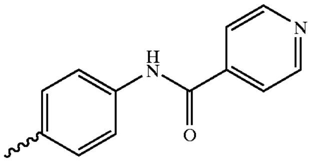 |
| 5 | 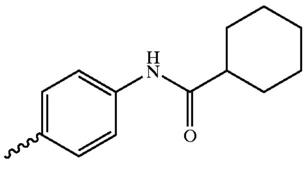 |
| 6 | 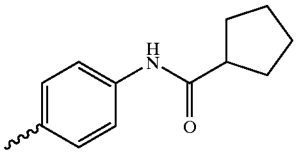 |
| 7 | 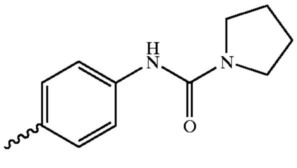 |

TABLE 121-continued
| | 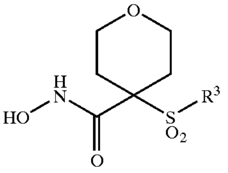<br>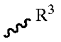 |
|---|---|
| 8 | 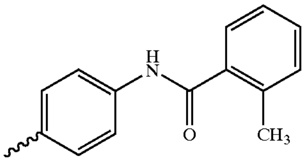 |
| 9 | 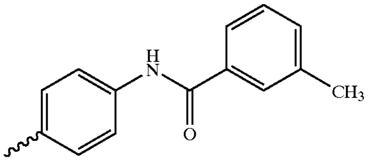 |
| 10 | 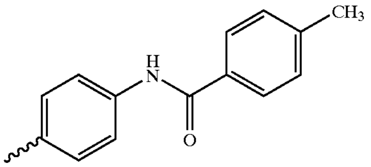 |
| 11 | 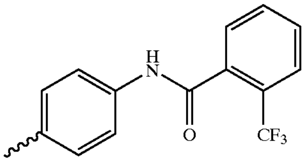 |
| 12 | 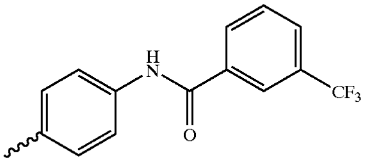 |
| 13 | 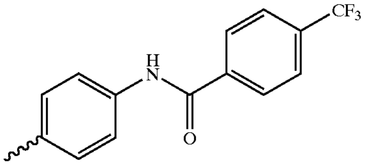 |
| 14 | 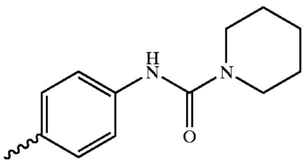 |
TABLE 121-continued
| | 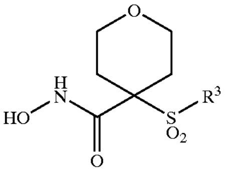<br>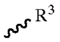 |
|---|---|
| 15 | 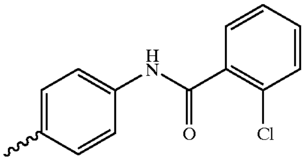 |
| 16 | 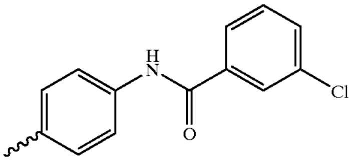 |
| 17 | 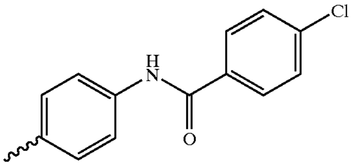 |
| 18 | 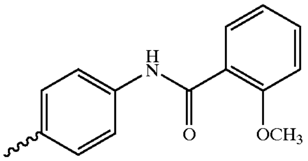 |
| 19 | 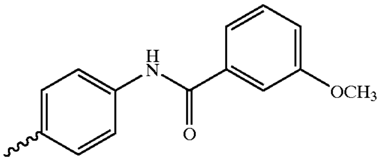 |
| 20 | 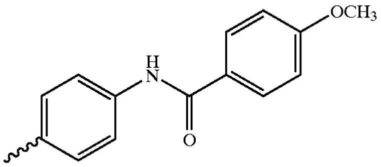 |
| 21 | 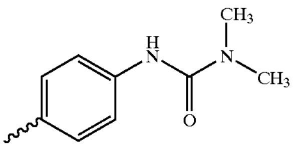 |

TABLE 122
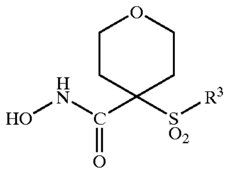
| | 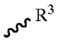 |
|---|---|
| 1 | 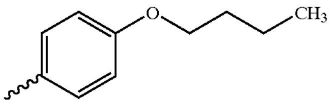 |
| 2 | 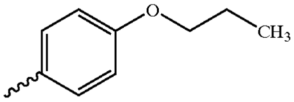 |
| 3 | 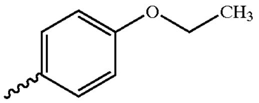 |
| 4 | 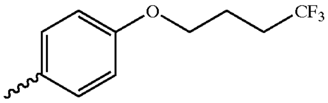 |
| 5 | 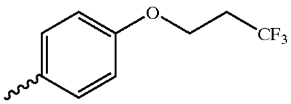 |
| 6 | 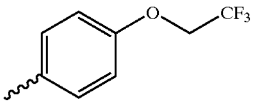 |
| 7 | 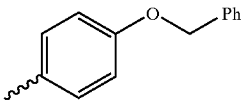 |
| 8 | 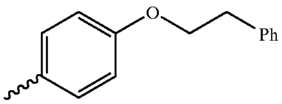 |
| 9 | 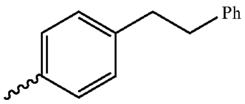 |
| 10 | 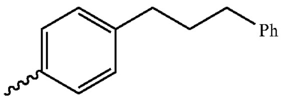 |
| 11 | 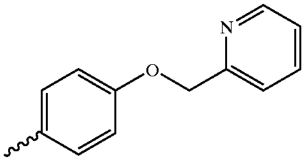 |
TABLE 122-continued
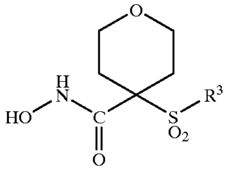
| | 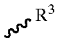 |
|---|---|
| 12 | 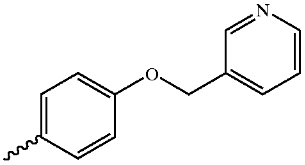 |
| 13 | 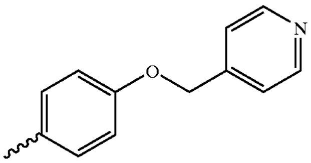 |
| 14 | 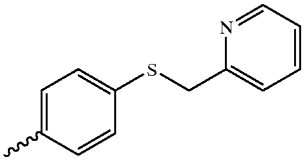 |
| 15 | 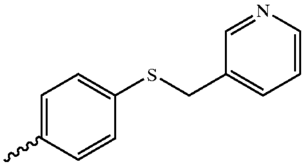 |
| 16 | 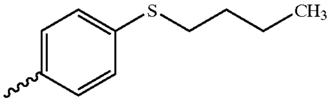 |
| 17 | 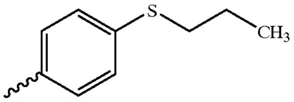 |
| 18 | 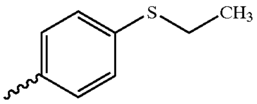 |
| 19 | 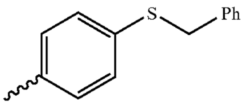 |
| 20 | 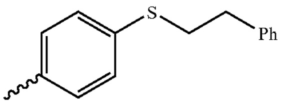 |

TABLE 122-continued
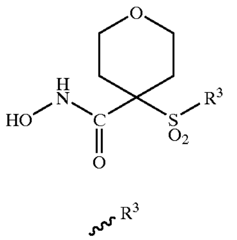
| | |
|---|---|
| 21 | 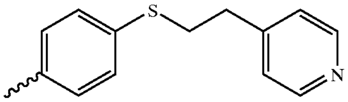 |
| 22 | 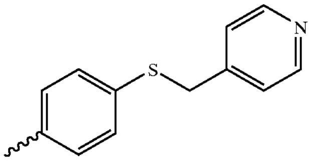 |
TABLE 123
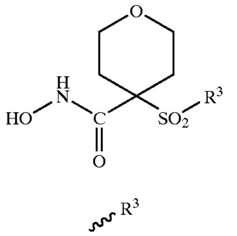
| | |
|---|---|
| 1 | 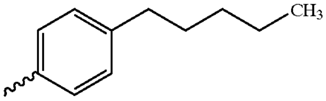 |
| 2 | 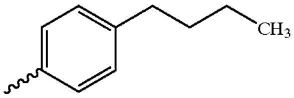 |
| 3 | 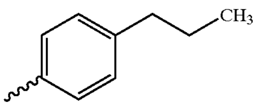 |
| 4 | 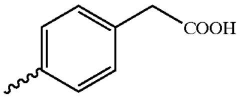 |
| 5 | 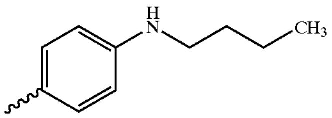 |
| 6 | 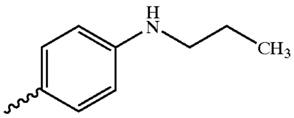 |
TABLE 123-continued
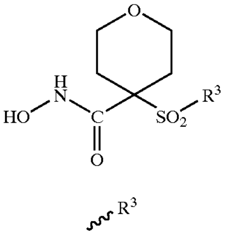
| | |
|---|---|
| 7 | 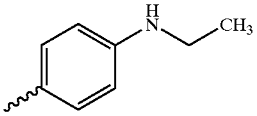 |
| 8 | 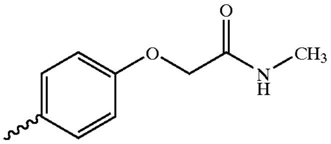 |
| 9 | 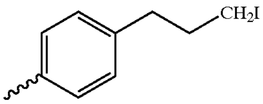 |
| 10 | 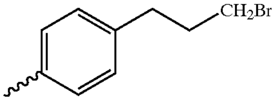 |
| 11 | 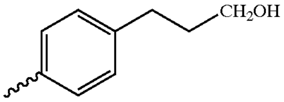 |
| 12 | 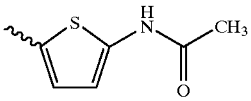 |
| 13 | 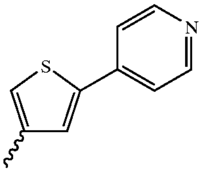 |
| 14 | 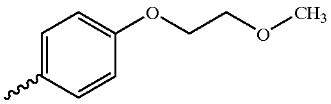 |
| 15 | 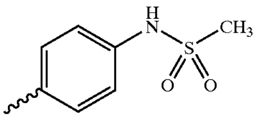 |
| 16 | 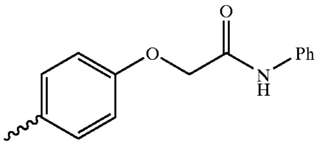 |

TABLE 123-continued
| | 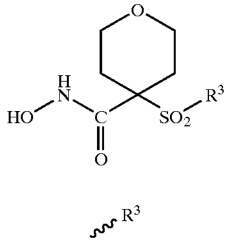 |
|---|---|
| 17 | 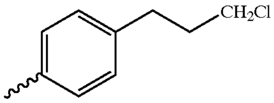 |
| 18 | 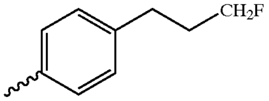 |
| 19 | 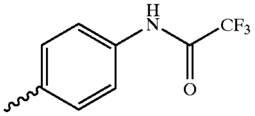 |
| 20 | 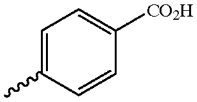 |
| 21 | 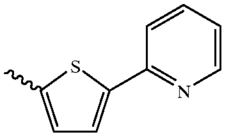 |
| 22 | 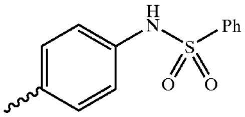 |
| 23 | 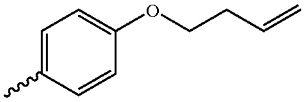 |
| 24 | 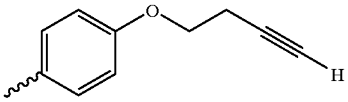 |
| 25 | 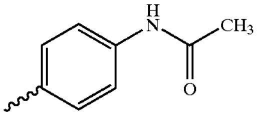 |
| 26 | 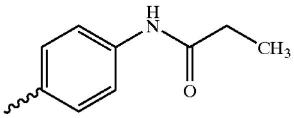 |
TABLE 123-continued
| | 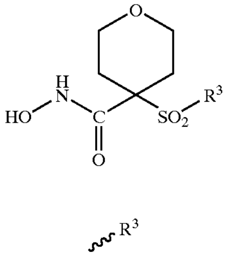 |
|---|---|
| 27 | 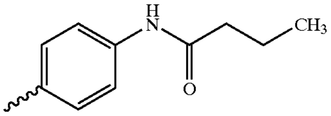 |
| 28 | 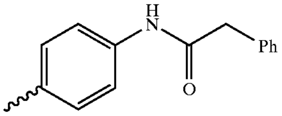 |
| 29 | 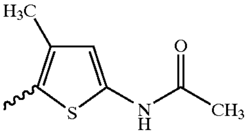 |
| 30 | 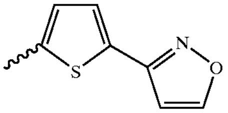 |
TABLE 124
| | 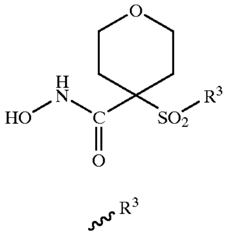 |
|---|---|
| 1 | 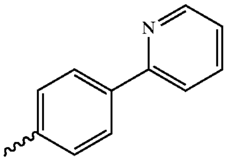 |
| 2 | 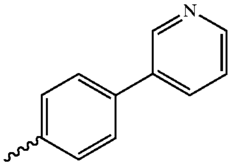 |

TABLE 124-continued
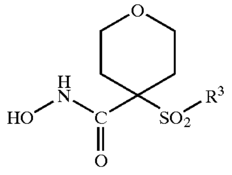
| | 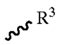 |
|---|---|
| 3 | 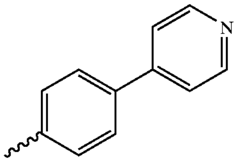 |
| 4 | 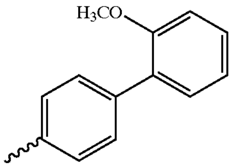 |
| 5 | 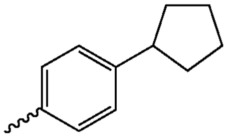 |
| 6 | 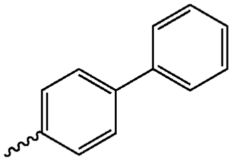 |
| 7 | 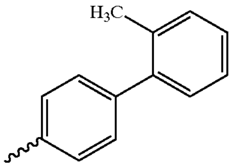 |
| 8 | 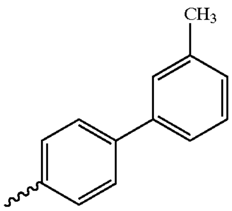 |
| 9 | 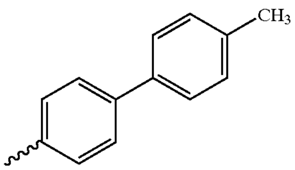 |
TABLE 124-continued
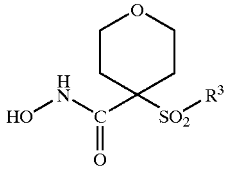
| | 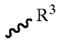 |
|---|---|
| 10 | 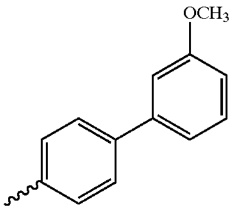 |
| 11 | 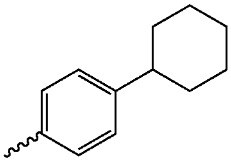 |
| 12 | 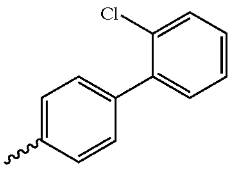 |
| 13 | 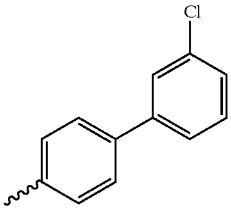 |
| 14 | 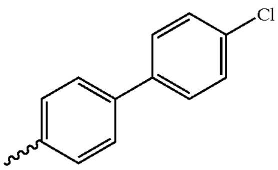 |
| 15 | 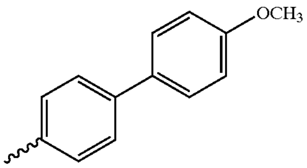 |
| 16 | 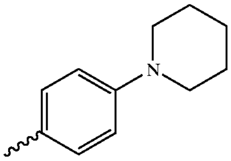 |

TABLE 124-continued
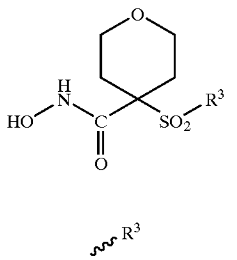
| | |
|---|---|
| 17 | 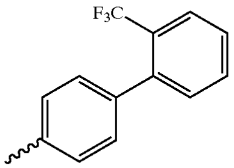 |
| 18 | 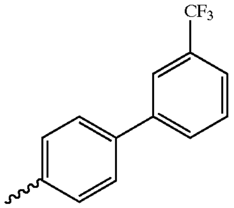 |
| 19 | 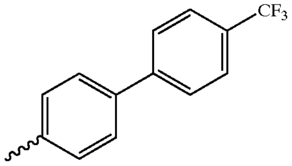 |
| 20 | 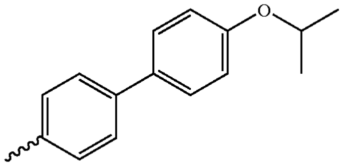 |
| 21 | 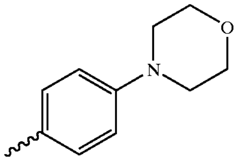 |
TABLE 125
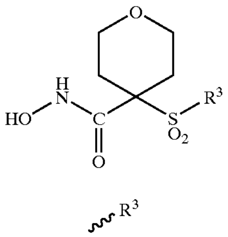
| | |
|---|---|
| 1 | 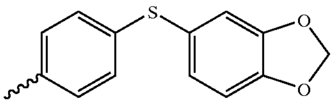 |
| 2 | 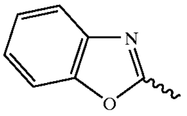 |
| 3 | 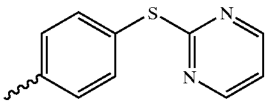 |
| 4 | 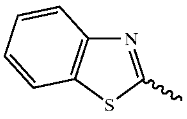 |
| 5 | 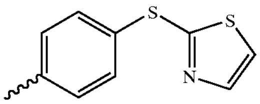 |
| 6 | 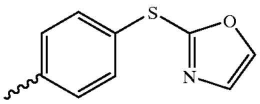 |
| 7 | 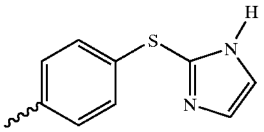 |
| 8 | 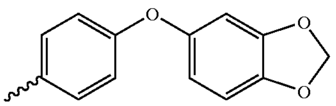 |
| 9 | 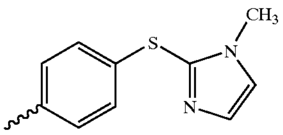 |
| 10 | 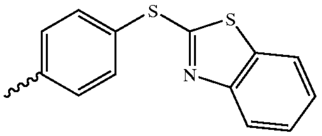 |

TABLE 125-continued
| | 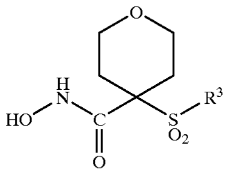 |
|---|---|
| | 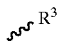 |
| 11 | 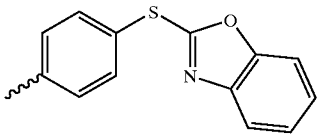 |
TABLE 126
| | 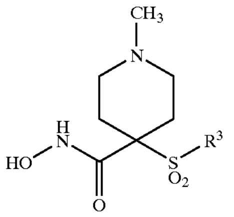 |
|---|---|
| | 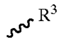 |
| 1 | 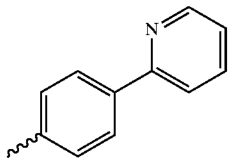 |
| 2 | 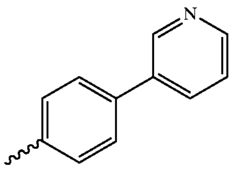 |
| 3 | 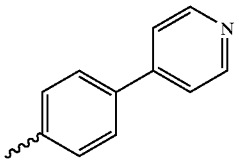 |
| 4 | 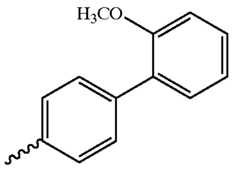 |
TABLE 126-continued
| | 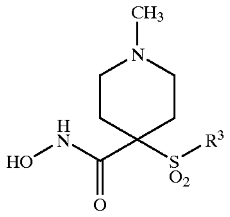 |
|---|---|
| | 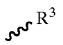 |
| 5 | 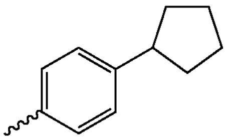 |
| 6 | 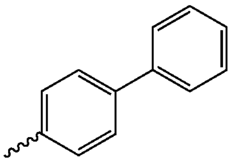 |
| 7 | 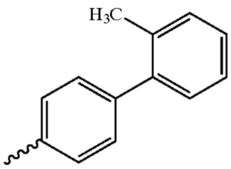 |
| 8 | 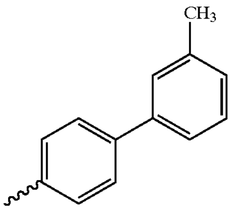 |
| 9 | 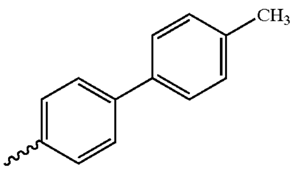 |
| 10 | 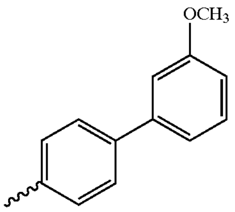 |
| 11 | 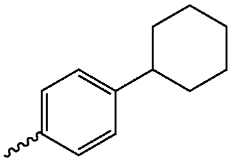 |

TABLE 126-continued
| 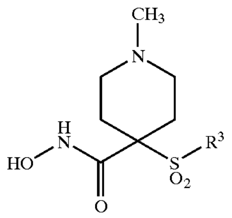 | |
|---|---|
| | 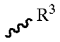 |
| 12 | 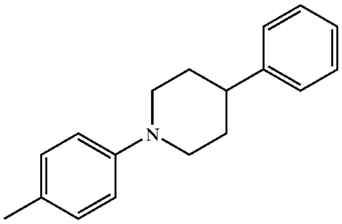 |
| 13 | 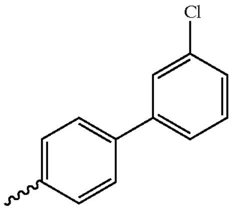 |
| 14 | 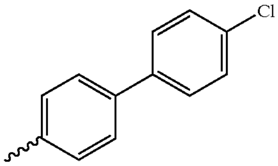 |
| 15 | 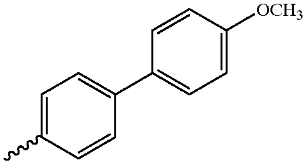 |
| 16 | 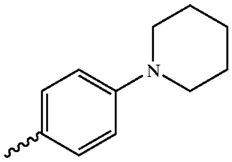 |
| 17 | 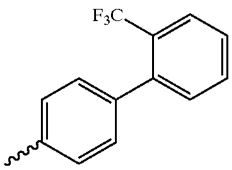 |
TABLE 126-continued
| 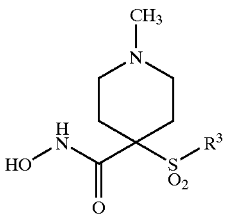 | |
|---|---|
| | 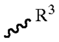 |
| 18 | 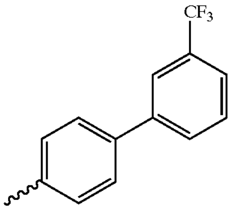 |
| 19 | 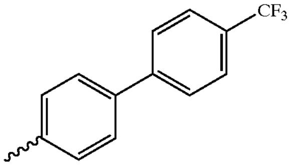 |
| 20 | 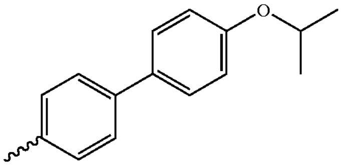 |
| 21 | 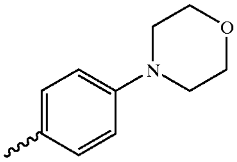 |
TABLE 127
| 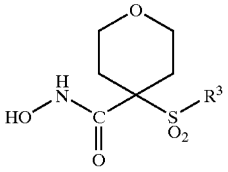 | |
|---|---|
| | 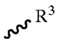 |
| 1 | 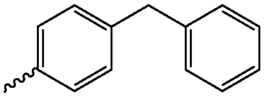 |

TABLE 127-continued
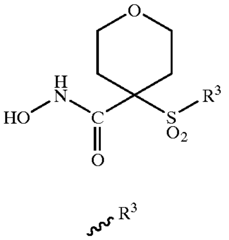
| | |
|---|---|
| 2 | 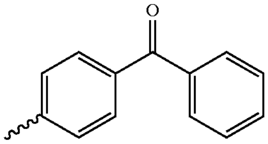 |
| 3 | 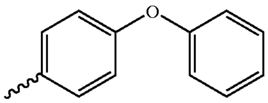 |
| 4 | 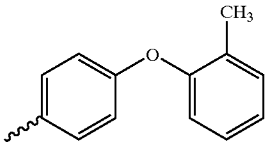 |
| 5 | 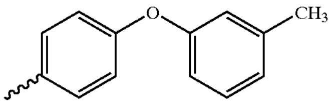 |
| 6 | 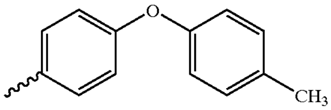 |
| 7 | 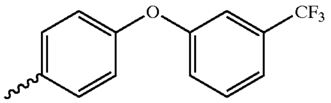 |
| 8 | 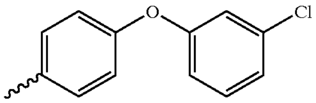 |
| 9 | 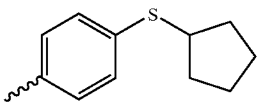 |
| 10 | 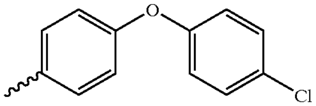 |
| 11 | 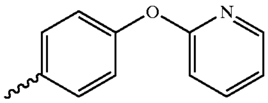 |
TABLE 127-continued
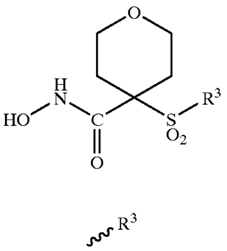
| | |
|---|---|
| 12 | 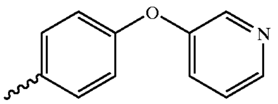 |
| 13 | 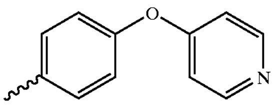 |
| 14 | 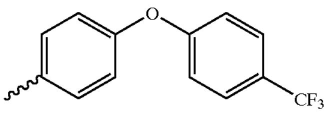 |
| 15 | 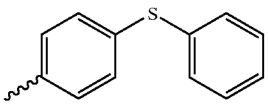 |
| 16 | 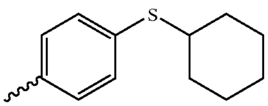 |
| 17 | 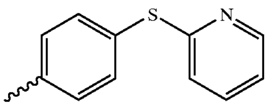 |
| 18 | 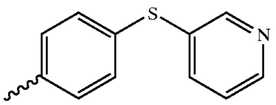 |
| 19 | 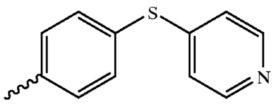 |
| 20 | 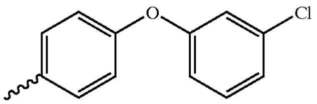 |
| 21 | 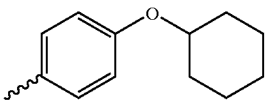 |

TABLE 128
| | 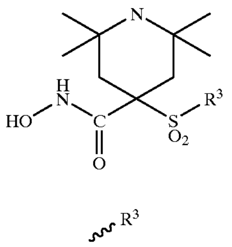 |
|---|---|
| 1 | 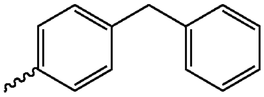 |
| 2 | 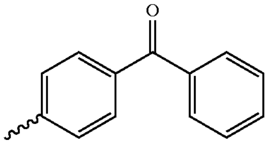 |
| 3 | 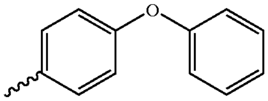 |
| 4 | 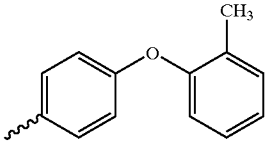 |
| 5 | 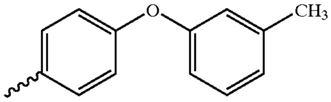 |
| 6 | 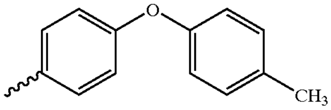 |
| 7 | 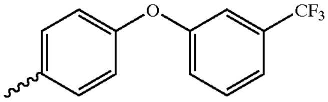 |
| 8 | 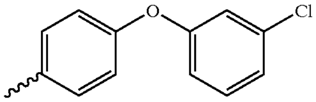 |
| 9 | 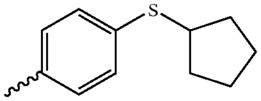 |
| 10 | 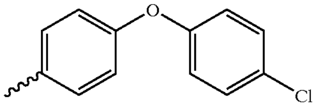 |
TABLE 128-continued
| | 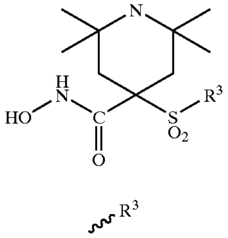 |
|---|---|
| 11 | 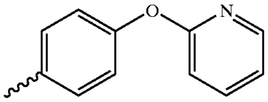 |
| 12 | 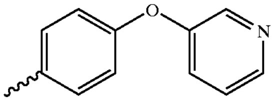 |
| 13 | 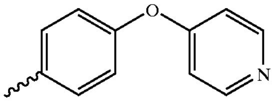 |
| 14 | 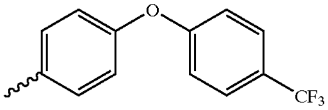 |
| 15 | 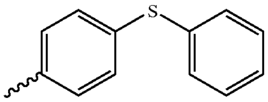 |
| 16 | 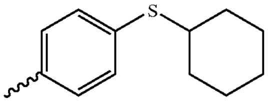 |
| 17 | 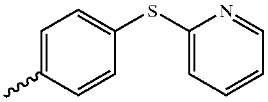 |
| 18 | 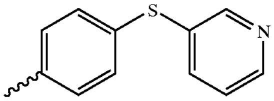 |
| 19 | 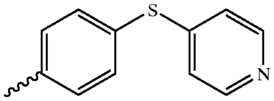 |
| 20 | 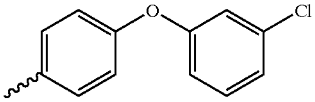 |
| 21 | 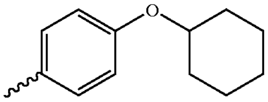 |

TABLE 129
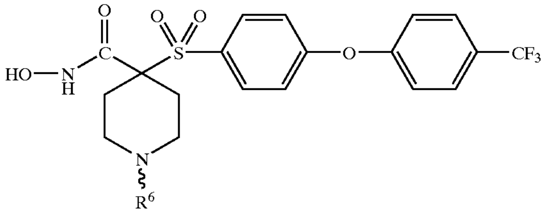
| | $R^6$ |
|---|---|
| 1 | 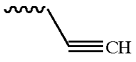 |
| 2 | 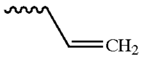 |
| 3 | 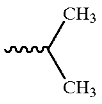 |
| 4 | 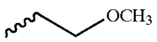 |
| 5 | 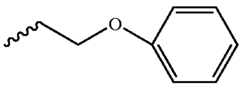 |
| 6 | 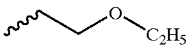 |
| 7 | 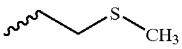 |
| 8 | 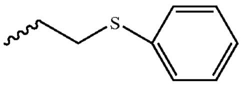 |
| 9 | 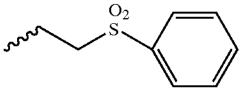 |
| 10 | 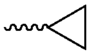 |
| 11 | 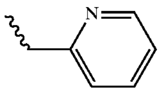 |
| 12 | 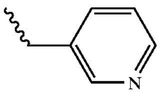 |
| 13 | 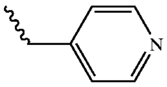 |
| 14 | 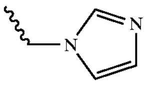 |
TABLE 129-continued
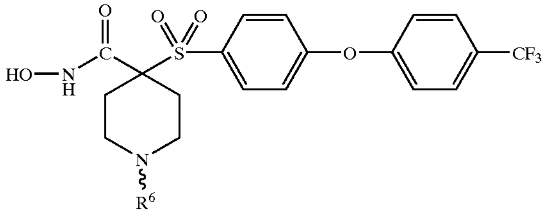
| | $R^6$ |
|---|---|
| 15 | 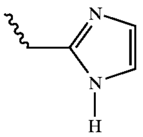 |
| 16 | 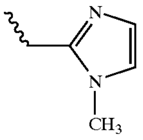 |
| 17 | 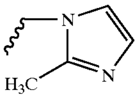 |
| 18 | 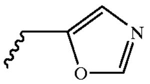 |
| 19 | 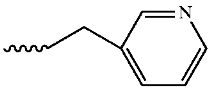 |
| 20 | 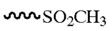 |
| 21 | 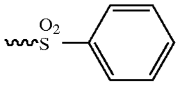 |
| 22 | 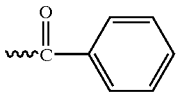 |
| 23 | 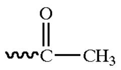 |
| 24 | 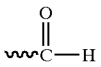 |
| 25 | 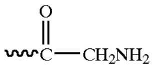 |
| 26 | 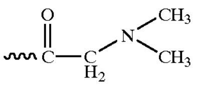 |

TABLE 130
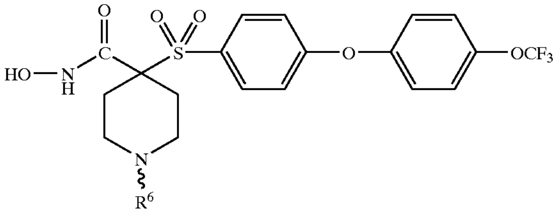
| | $R^6$ |
|---|---|
| 1 | 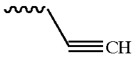 |
| 2 | 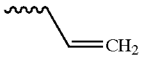 |
| 3 | 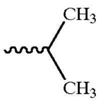 |
| 4 | 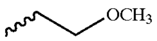 |
| 5 | 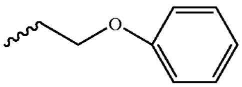 |
| 6 | 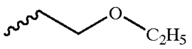 |
| 7 | 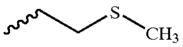 |
| 8 | 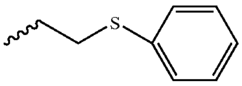 |
| 9 | 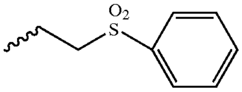 |
| 10 | 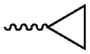 |
| 11 | 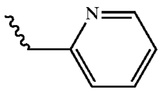 |
| 12 | 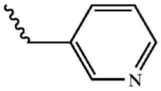 |
| 13 | 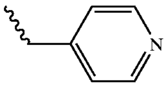 |
| 14 | 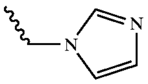 |
TABLE 130-continued
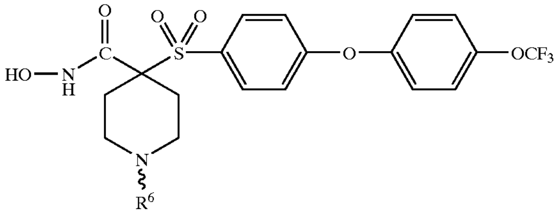
| | $R^6$ |
|---|---|
| 15 | 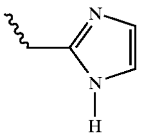 |
| 16 | 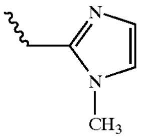 |
| 17 | 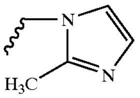 |
| 18 | 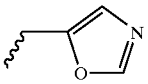 |
| 19 | 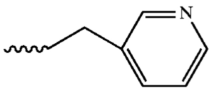 |
| 20 | $SO_2CH_3$ |
| 21 | 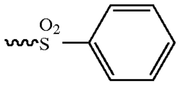 |
| 22 | 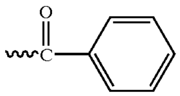 |
| 23 | 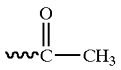 |
| 24 | 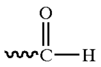 |
| 25 | 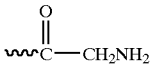 |
| 26 | 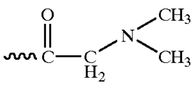 |

TABLE 131
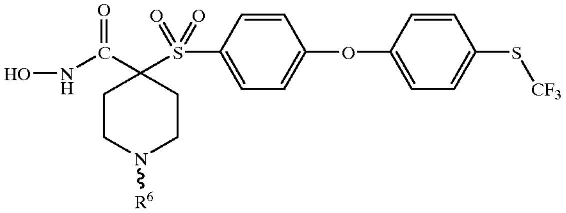
| | $R^6$ |
|---|---|
| 1 | 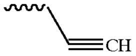 |
| 2 | 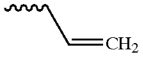 |
| 3 | 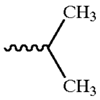 |
| 4 | 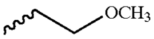 |
| 5 | 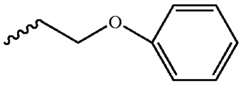 |
| 6 | 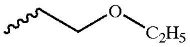 |
| 7 | 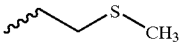 |
| 8 | 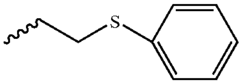 |
| 9 | 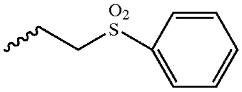 |
| 10 | 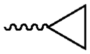 |
| 11 | 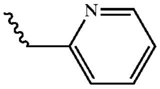 |
| 12 | 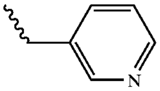 |
| 13 | 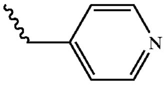 |
| 14 | 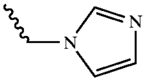 |
TABLE 131-continued
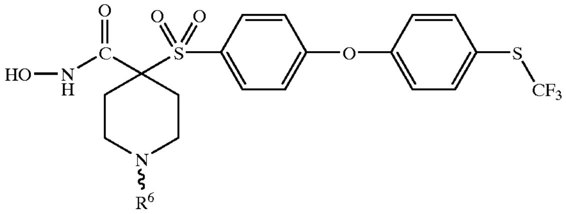
| | $R^6$ |
|---|---|
| 15 | 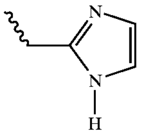 |
| 16 | 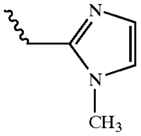 |
| 17 | 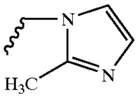 |
| 18 | 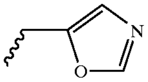 |
| 19 | 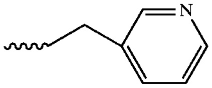 |
| 20 | $SO_2CH_3$ |
| 21 | 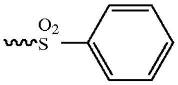 |
| 22 | 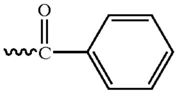 |
| 23 | 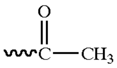 |
| 24 | 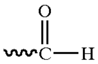 |
| 25 | 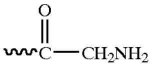 |
| 26 | 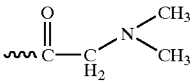 |

TABLE 132
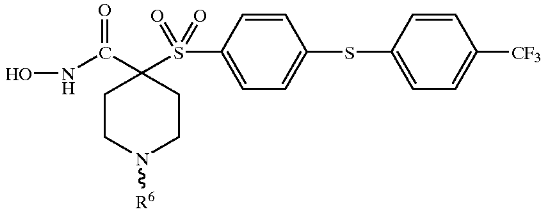
| | $R^6$ |
|---|---|
| 1 | 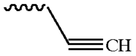 |
| 2 | 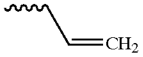 |
| 3 | 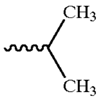 |
| 4 | 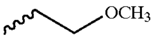 |
| 5 | 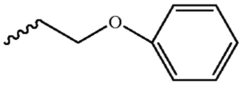 |
| 6 | 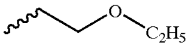 |
| 7 | 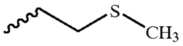 |
| 8 | 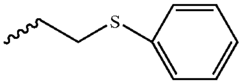 |
| 9 | 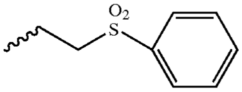 |
| 10 | 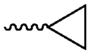 |
| 11 | 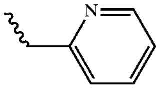 |
| 12 | 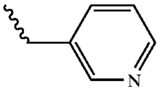 |
| 13 | 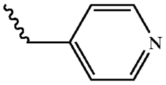 |
| 14 | 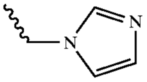 |
TABLE 132-continued
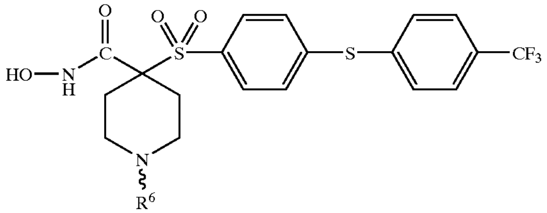
| | $R^6$ |
|---|---|
| 15 | 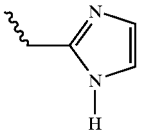 |
| 16 | 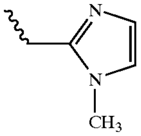 |
| 17 | 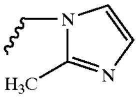 |
| 18 | 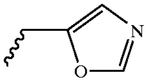 |
| 19 | 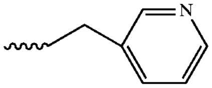 |
| 20 | $SO_2CH_3$ |
| 21 | 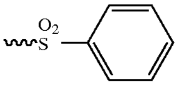 |
| 22 | 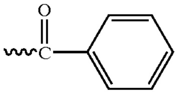 |
| 23 | 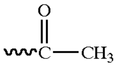 |
| 24 | 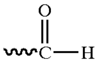 |
| 25 | 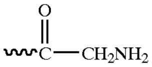 |
| 26 | 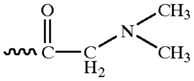 |

TABLE 133
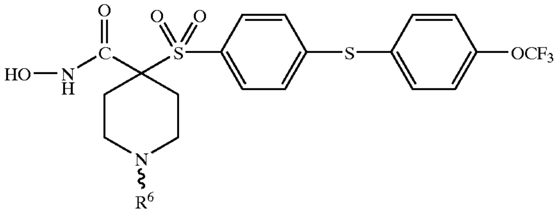
| | |
|---|---|
| 1 | 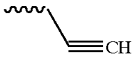 |
| 2 | 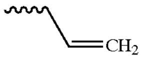 |
| 3 | 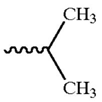 |
| 4 | 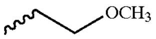 |
| 5 | 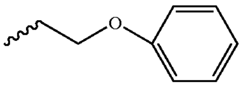 |
| 6 | 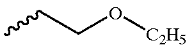 |
| 7 | 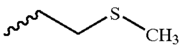 |
| 8 | 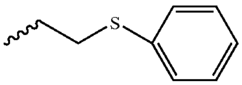 |
| 9 | 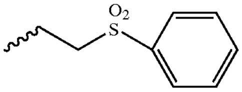 |
| 10 | 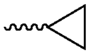 |
| 11 | 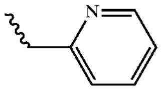 |
| 12 | 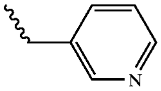 |
| 13 | 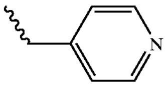 |
| 14 | 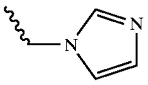 |
TABLE 133-continued
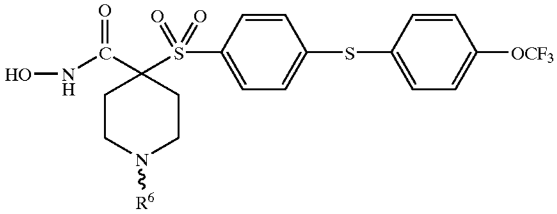
| | |
|---|---|
| 15 | 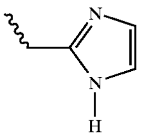 |
| 16 | 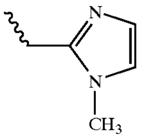 |
| 17 | 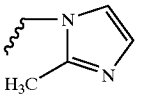 |
| 18 | 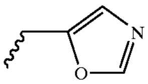 |
| 19 | 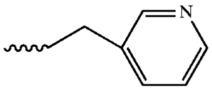 |
| 20 | 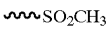 |
| 21 | 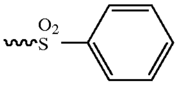 |
| 22 | 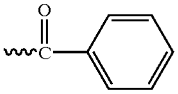 |
| 23 | 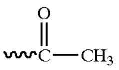 |
| 24 | 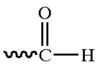 |
| 25 | 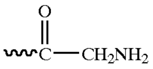 |
| 26 | 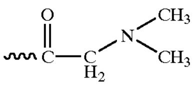 |

TABLE 134
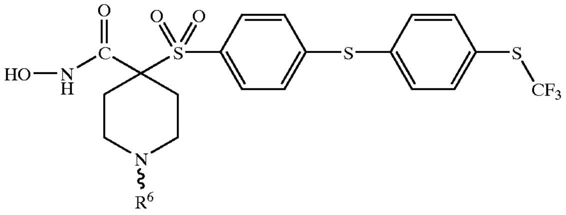
| | |
|---|---|
| | 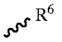 |
| 1 | 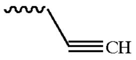 |
| 2 | 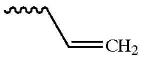 |
| 3 | 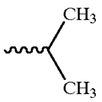 |
| 4 | 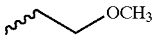 |
| 5 | 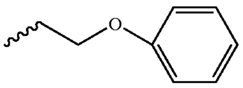 |
| 6 | 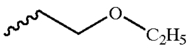 |
| 7 | 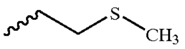 |
| 8 | 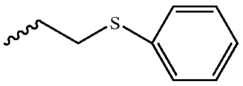 |
| 9 | 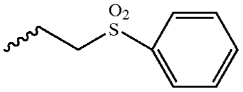 |
| 10 | 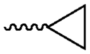 |
| 11 | 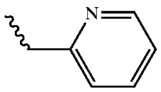 |
| 12 | 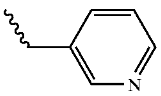 |
| 13 | 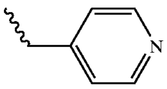 |
| 14 | 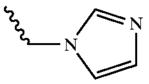 |
TABLE 134-continued
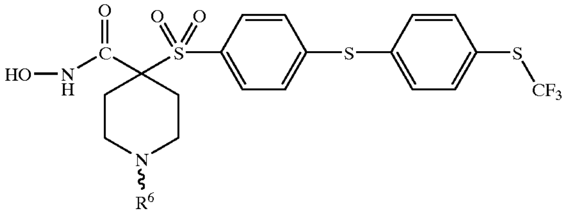
| | |
|---|---|
| | 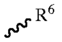 |
| 15 | 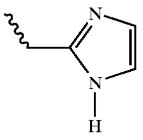 |
| 16 | 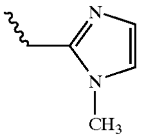 |
| 17 | 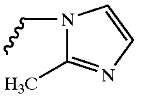 |
| 18 | 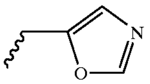 |
| 19 | 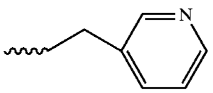 |
| 20 | 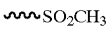 |
| 21 | 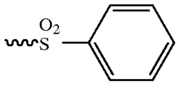 |
| 22 | 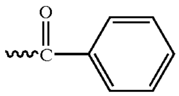 |
| 23 | 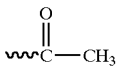 |
| 24 | 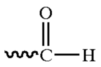 |
| 25 | 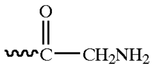 |
| 26 | 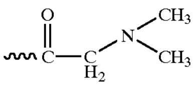 |

TABLE 135
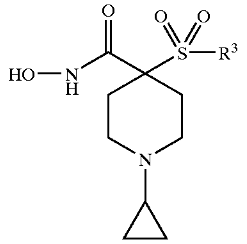
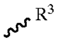
| | |
|---|---|
| 1 | 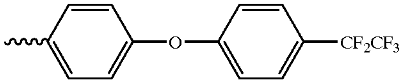 |
| 2 | 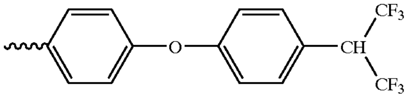 |
| 3 | 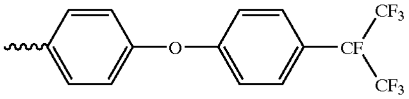 |
| 4 | 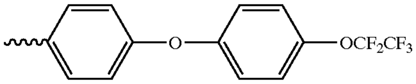 |
| 5 | 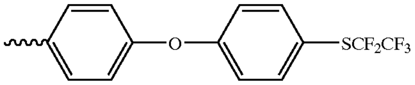 |
| 6 | 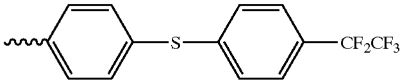 |
| 7 | 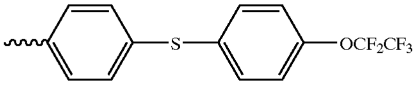 |
| 8 | 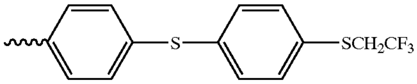 |
| 9 | 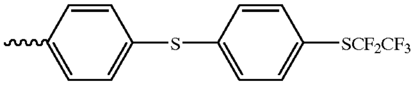 |
| 10 | 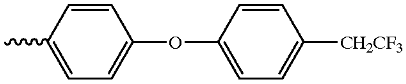 |
| 11 | 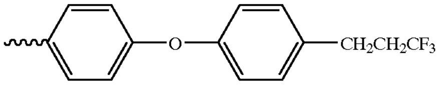 |
| 12 | 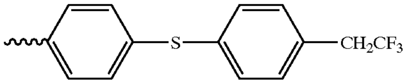 |
TABLE 135-continued
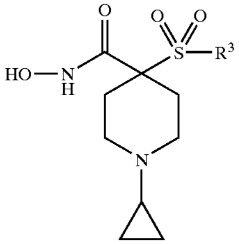
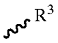
| | |
|---|---|
| 13 | 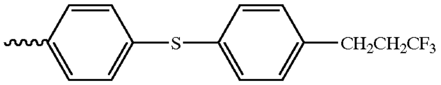 |
| 14 | 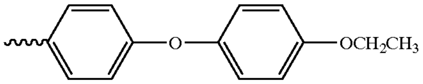 |
| 15 | 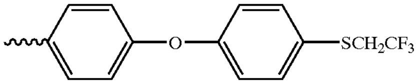 |
| 16 | 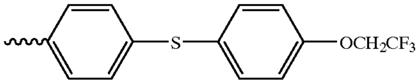 |
TABLE 136
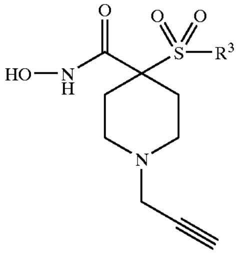
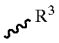
| | |
|---|---|
| 1 | 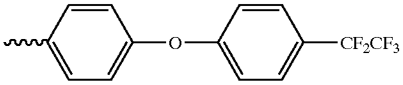 |
| 2 | 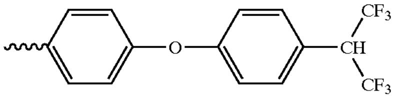 |
| 3 | 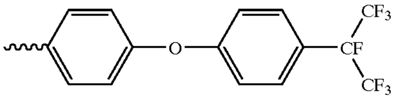 |
| 4 | 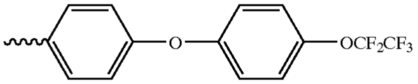 |

TABLE 136-continued
| | |
|---|---|
| 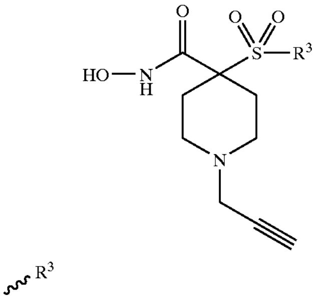 | |
| 5 | 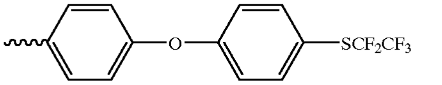 |
| 6 | 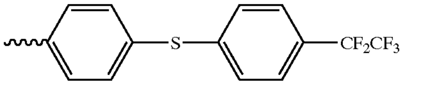 |
| 7 | 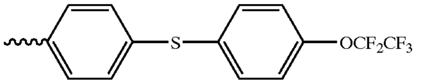 |
| 8 | 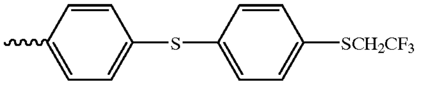 |
| 9 | 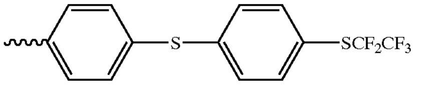 |
| 10 | 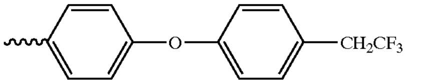 |
| 11 | 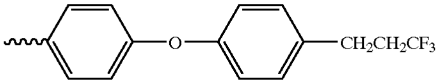 |
| 12 | 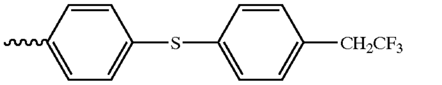 |
| 13 | 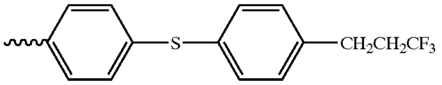 |
| 14 | 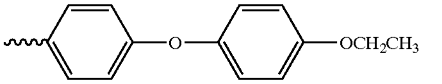 |
| 15 | 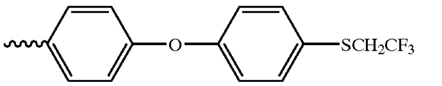 |
| 16 | 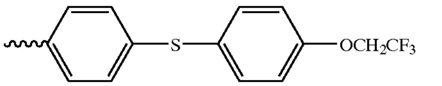 |
TABLE 137
| | |
|---|---|
| 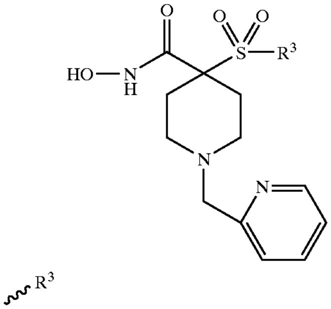 | |
| 1 | 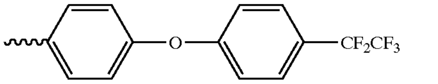 |
| 2 | 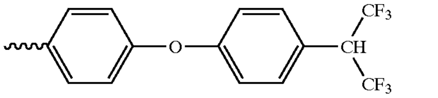 |
| 3 | 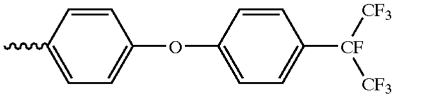 |
| 4 | 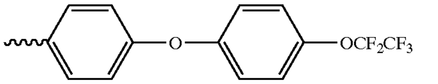 |
| 5 | 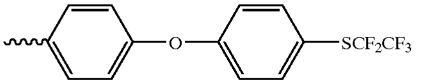 |
| 6 | 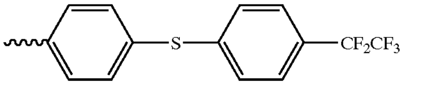 |
| 7 | 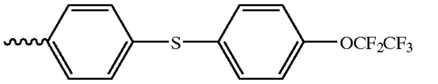 |
| 8 | 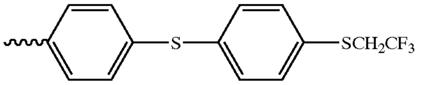 |
| 9 | 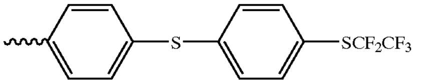 |
| 10 | 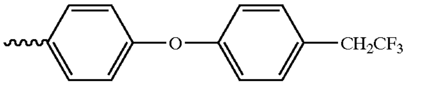 |
| 11 | 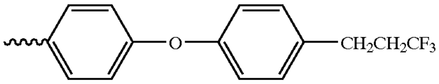 |
| 12 | 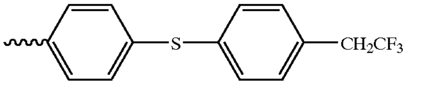 |

TABLE 137-continued
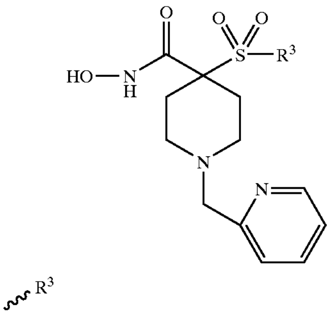
| | |
|---|---|
| 13 | 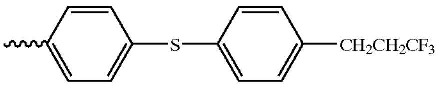 |
| 14 | 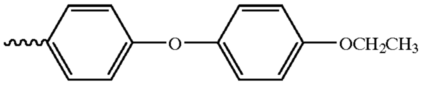 |
| 15 | 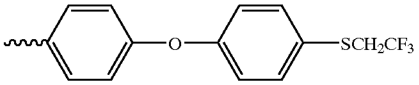 |
| 16 | 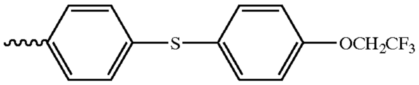 |
TABLE 138
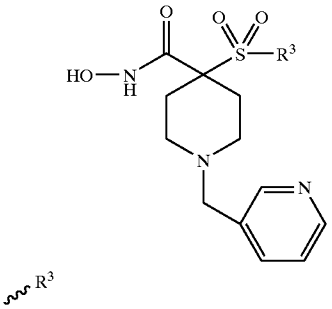
| | |
|---|---|
| 1 | 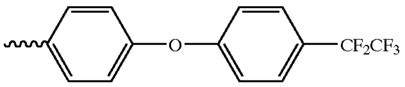 |
| 2 | 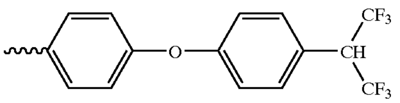 |
| 3 | 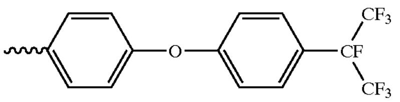 |
| 4 | 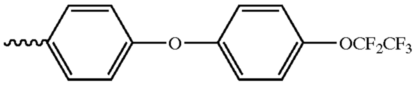 |
TABLE 138-continued
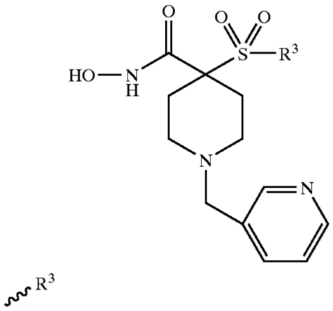
| | |
|---|---|
| 5 | 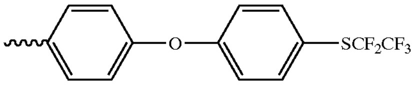 |
| 6 | 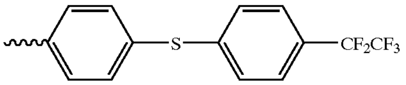 |
| 7 | 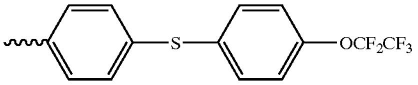 |
| 8 | 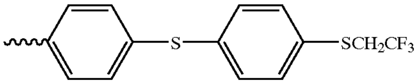 |
| 9 | 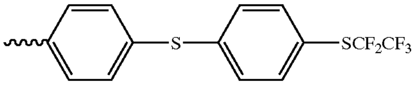 |
| 10 | 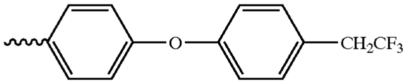 |
| 11 | 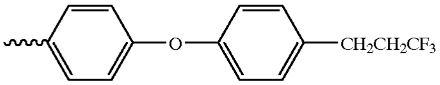 |
| 12 | 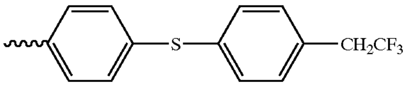 |
| 13 | 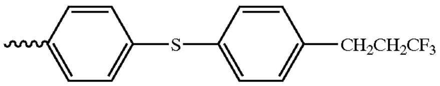 |
| 14 | 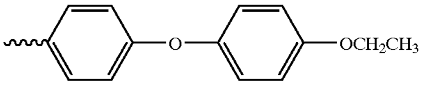 |
| 15 | 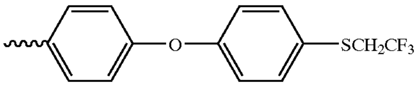 |
| 16 | 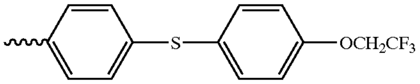 |

TABLE 139
| | 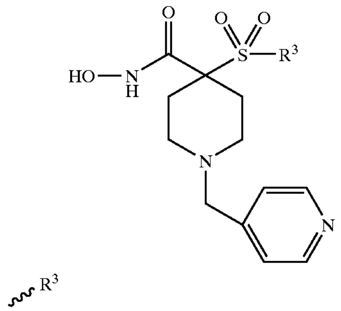 |
|---|---|
| 1 | 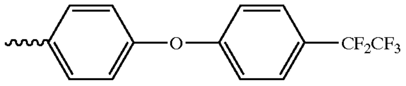 |
| 2 | 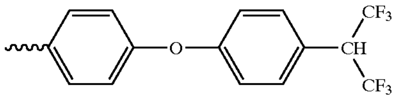 |
| 3 | 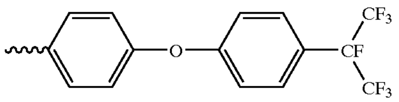 |
| 4 | 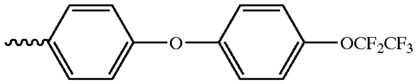 |
| 5 | 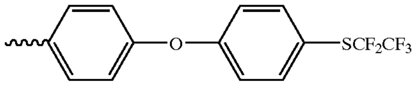 |
| 6 | 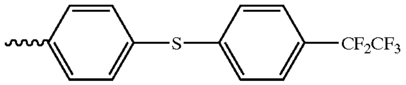 |
| 7 | 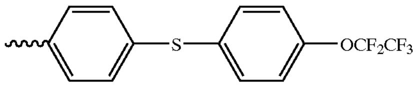 |
| 8 | 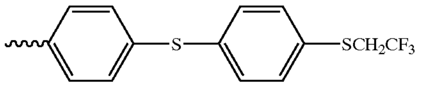 |
| 9 | 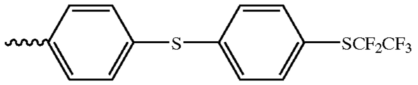 |
| 10 | 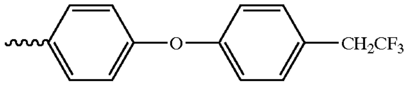 |
| 11 | 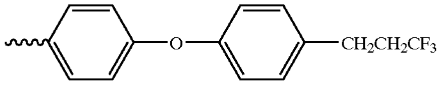 |
| 12 | 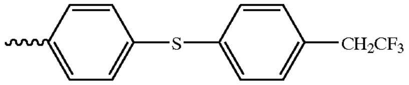 |
TABLE 139-continued
| | 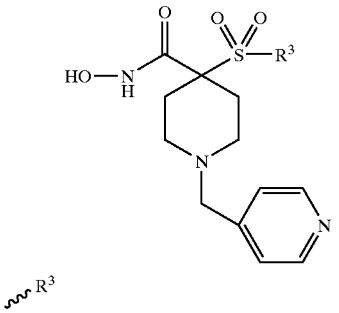 |
|---|---|
| 13 | 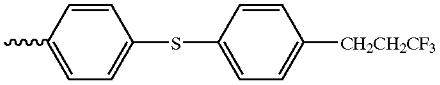 |
| 14 | 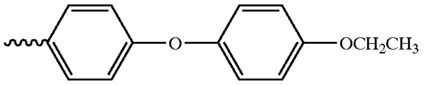 |
| 15 | 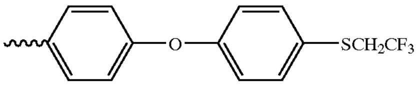 |
| 16 | 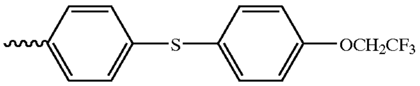 |
TABLE 140
| | 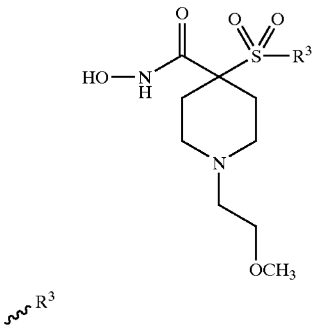 |
|---|---|
| 1 | 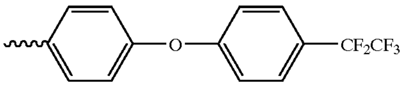 |
| 2 | 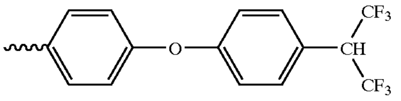 |
| 3 | 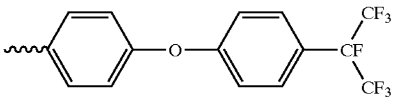 |
| 4 | 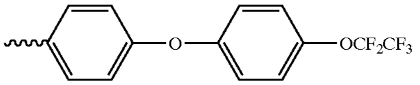 |

TABLE 140-continued
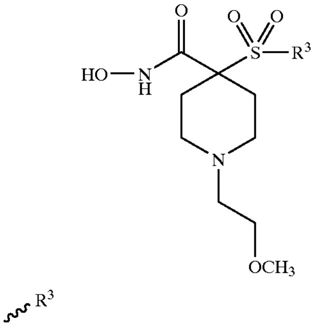
| | |
|---|---|
| 5 | 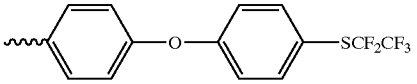 |
| 6 | 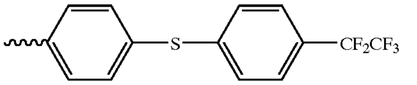 |
| 7 | 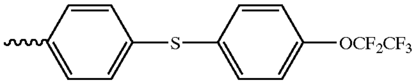 |
| 8 | 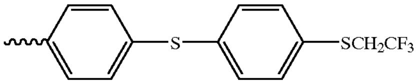 |
| 9 | 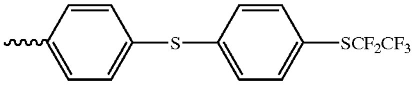 |
| 10 | 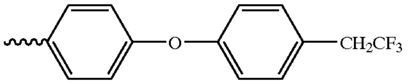 |
| 11 | 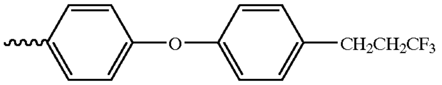 |
| 12 | 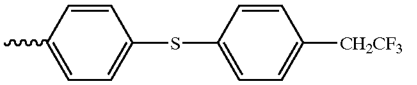 |
| 13 | 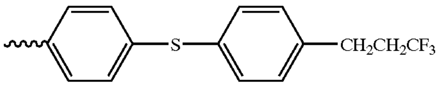 |
| 14 | 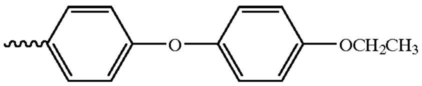 |
| 15 | 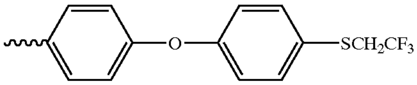 |
| 16 | 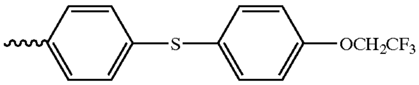 |
TABLE 141
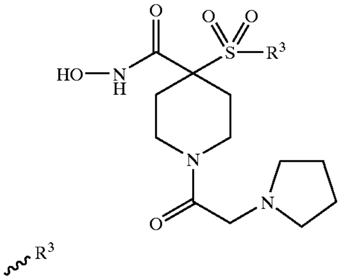
| | |
|---|---|
| 1 | 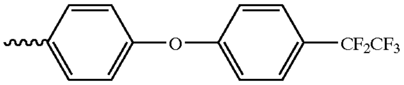 |
| 2 | 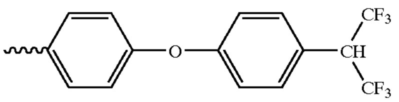 |
| 3 | 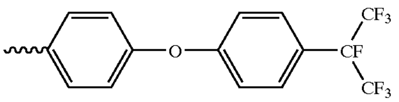 |
| 4 | 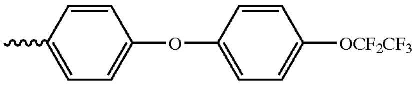 |
| 5 | 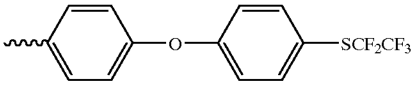 |
| 6 | 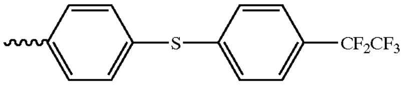 |
| 7 | 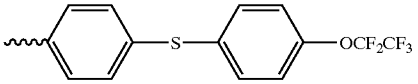 |
| 8 | 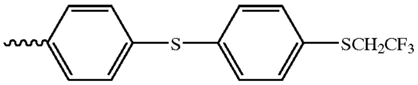 |
| 9 | 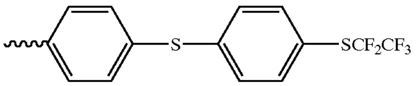 |
| 10 | 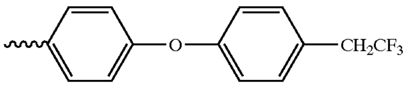 |
| 11 | 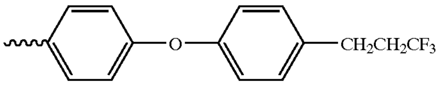 |
| 12 | 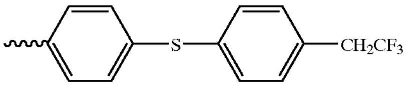 |

TABLE 141-continued
| | |
|---|---|
| | 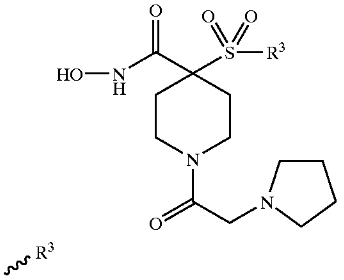 |
| 13 | 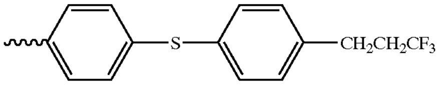 |
| 14 | 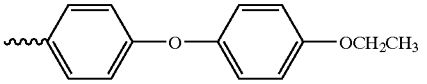 |
| 15 | 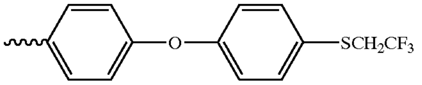 |
| 16 | 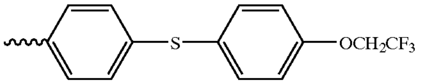 |
TABLE 142
| | |
|---|---|
| | 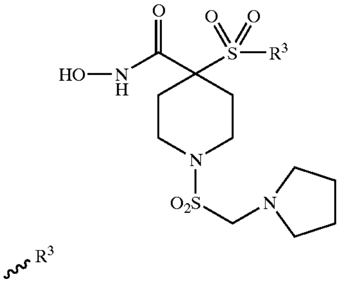 |
| 1 | 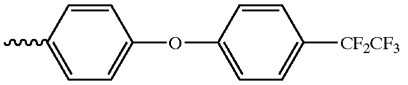 |
| 2 | 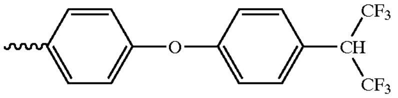 |
| 3 | 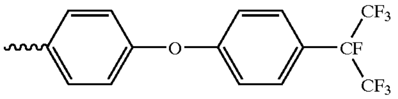 |
| 4 | 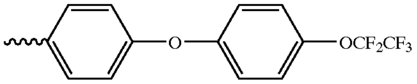 |
| 5 | 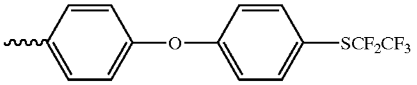 |
TABLE 142-continued
| | |
|---|---|
| | 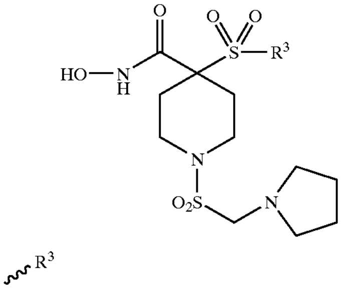 |
| 6 | 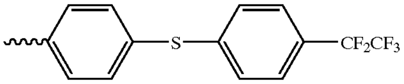 |
| 7 | 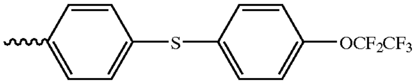 |
| 8 | 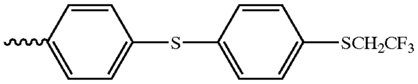 |
| 9 | 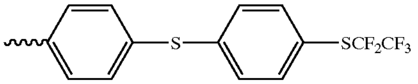 |
| 10 | 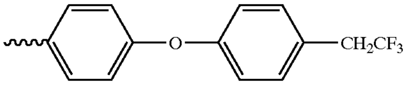 |
| 11 | 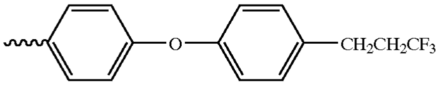 |
| 12 | 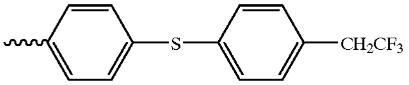 |
| 13 | 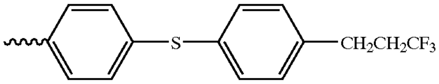 |
| 14 | 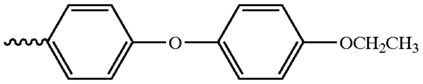 |
| 15 | 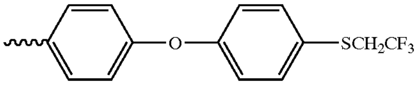 |
| 16 | 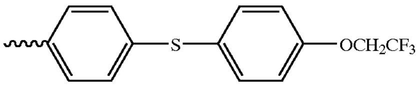 |

TABLE 143
| | |
|---|---|
| | 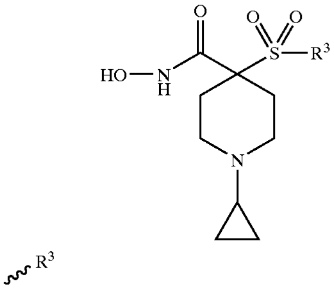 |
| 1 | 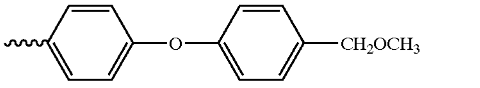 |
| 2 | 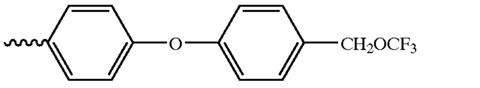 |
| 3 | 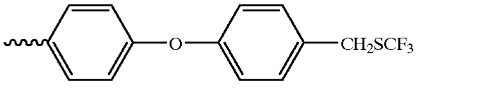 |
| 4 | 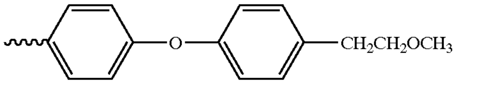 |
| 5 | 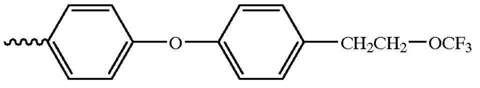 |
| 6 | 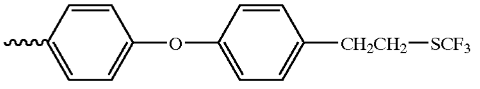 |
| 7 | 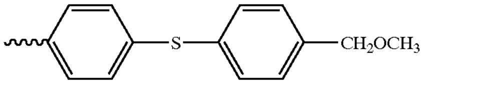 |
| 8 | 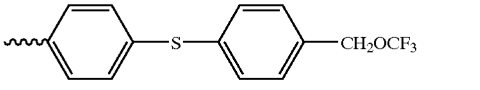 |
| 9 | 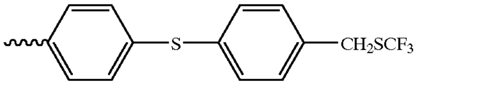 |
| 10 | 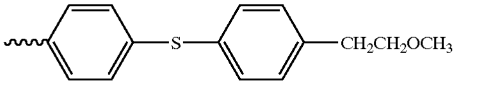 |
| 11 | 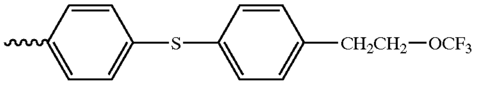 |
| 12 | 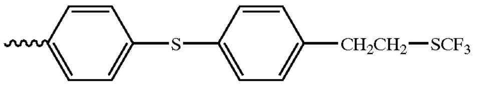 |
TABLE 144
| | |
|---|---|
| | 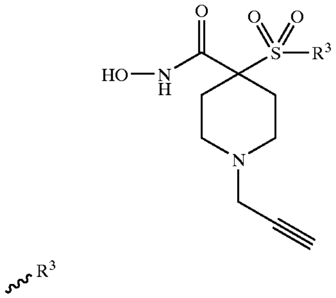 |
| 1 | 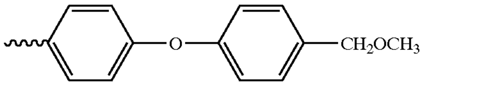 |
| 2 | 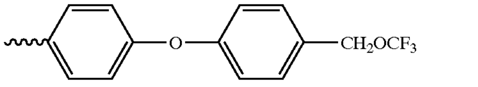 |
| 3 | 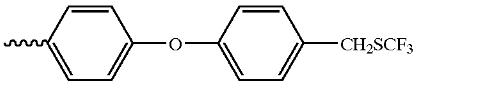 |
| 4 | 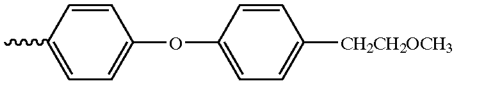 |
| 5 | 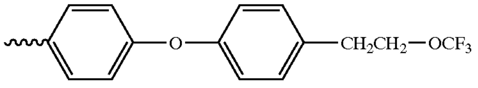 |
| 6 | 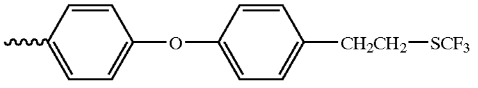 |
| 7 | 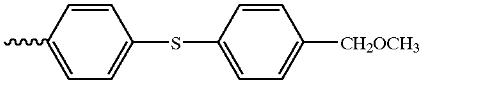 |
| 8 | 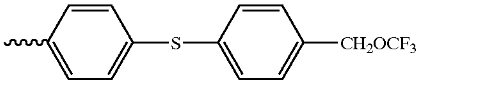 |
| 9 | 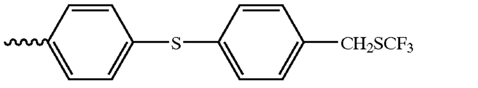 |
| 10 | 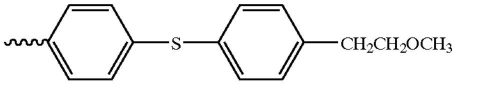 |
| 11 | 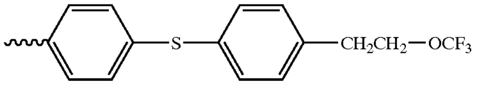 |
| 12 | 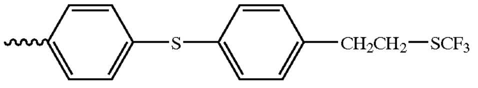 |

TABLE 145
| 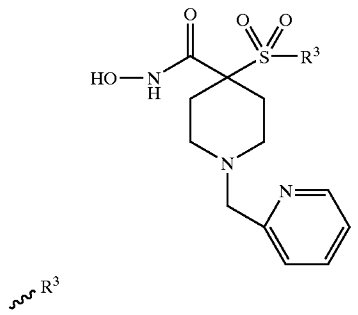 | |
|---|---|
| 1 | 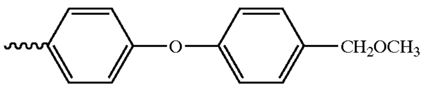 |
| 2 | 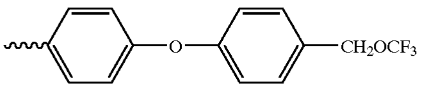 |
| 3 | 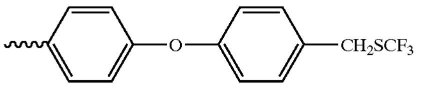 |
| 4 | 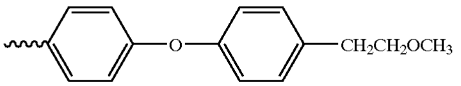 |
| 5 | 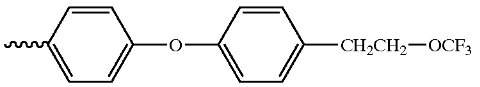 |
| 6 | 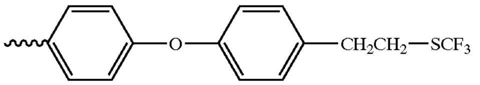 |
| 7 | 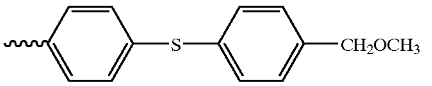 |
| 8 | 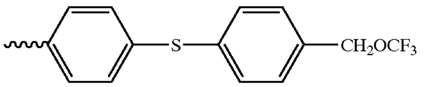 |
| 9 | 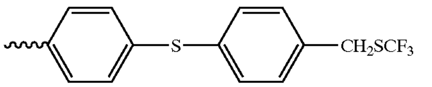 |
| 10 | 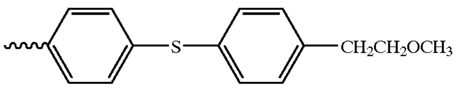 |
| 11 | 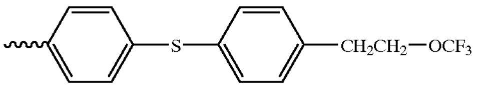 |
| 12 | 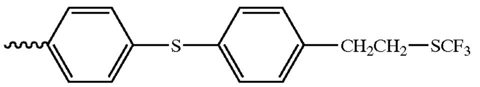 |
TABLE 146
| 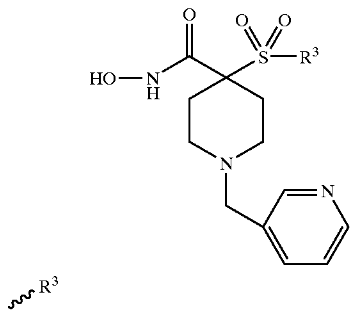 | |
|---|---|
| 1 | 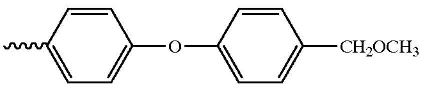 |
| 2 | 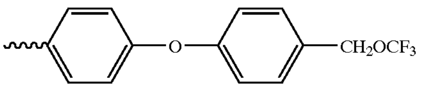 |
| 3 | 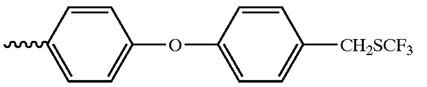 |
| 4 | 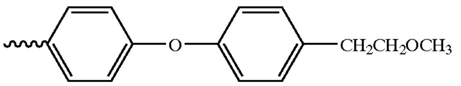 |
| 5 | 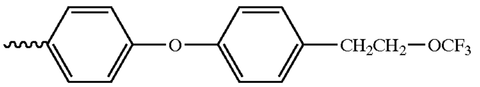 |
| 6 | 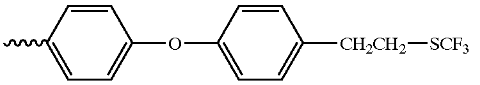 |
| 7 | 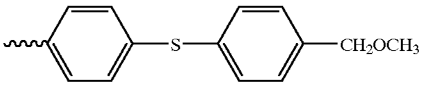 |
| 8 | 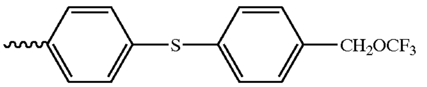 |
| 9 | 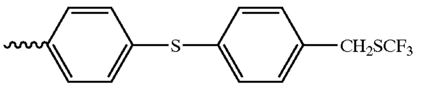 |
| 10 | 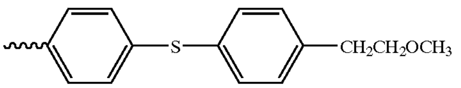 |
| 11 | 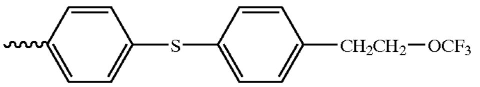 |
| 12 | 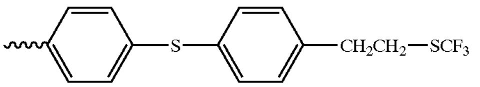 |

TABLE 147
| | |
|---|---|
| 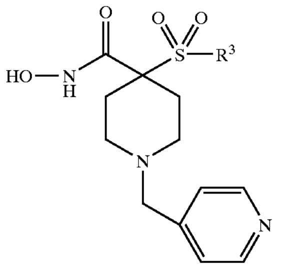 | |
| 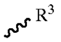 | |
| 1 | 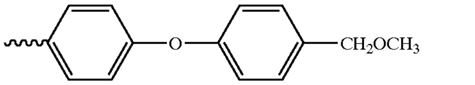 |
| 2 | 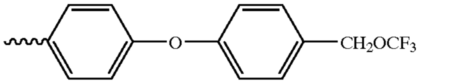 |
| 3 | 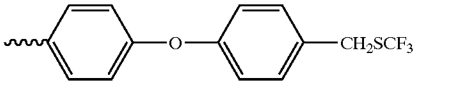 |
| 4 | 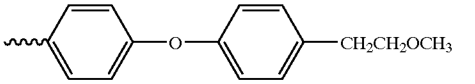 |
| 5 | 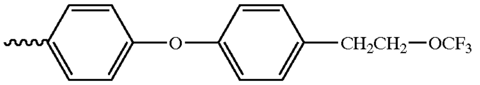 |
| 6 | 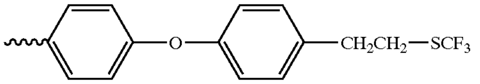 |
| 7 | 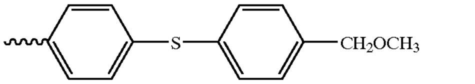 |
| 8 | 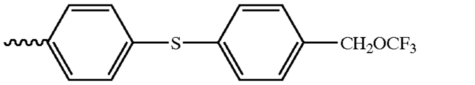 |
| 9 | 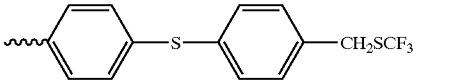 |
| 10 | 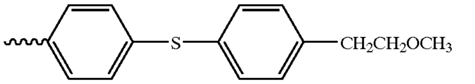 |
| 11 | 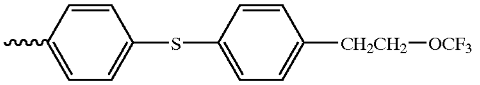 |
| 12 | 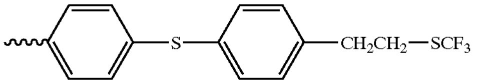 |
TABLE 148
| | |
|---|---|
| 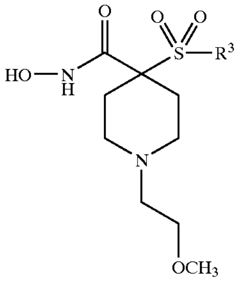 | |
| 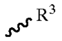 | |
| 1 | 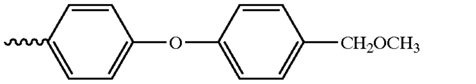 |
| 2 | 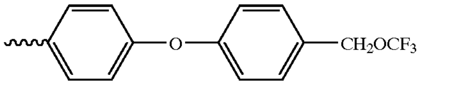 |
| 3 | 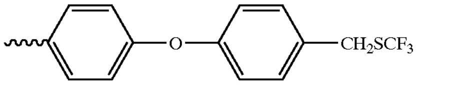 |
| 4 | 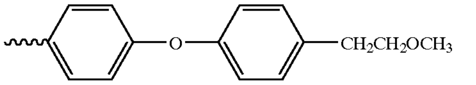 |
| 5 | 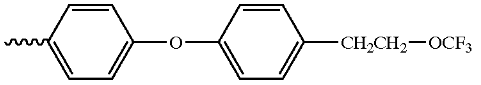 |
| 6 | 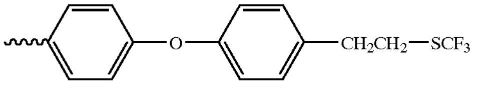 |
| 7 | 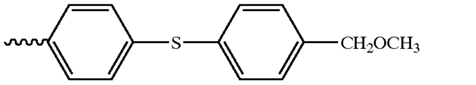 |
| 8 | 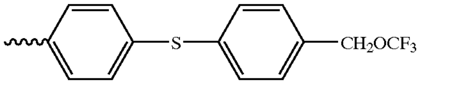 |
| 9 | 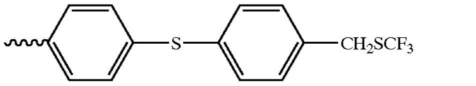 |
| 10 | 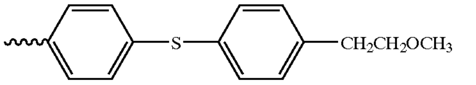 |
| 11 | 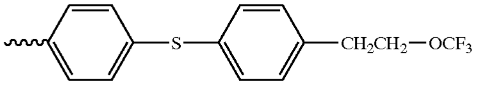 |
| 12 | 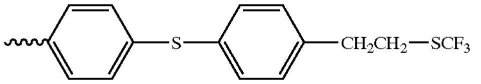 |

TABLE 149
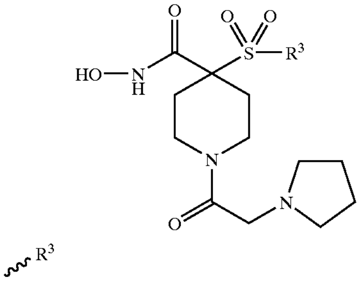
| | |
|---|---|
| 1 | 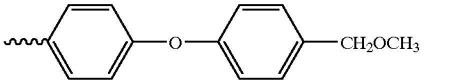 |
| 2 | 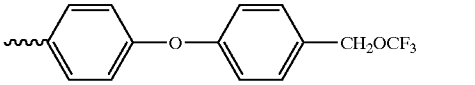 |
| 3 | 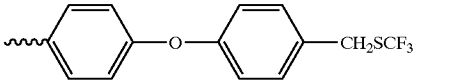 |
| 4 | 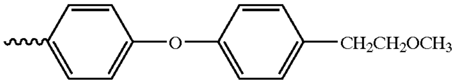 |
| 5 | 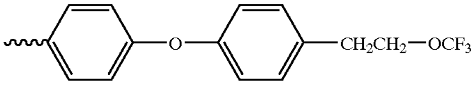 |
| 6 | 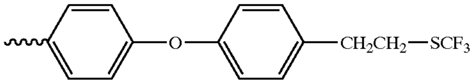 |
| 7 | 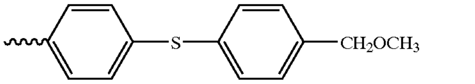 |
| 8 | 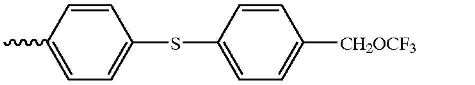 |
| 9 | 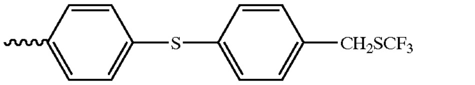 |
| 10 | 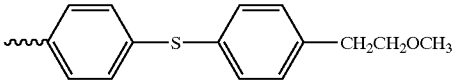 |
| 11 | 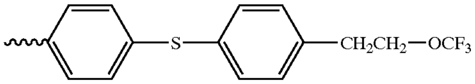 |
| 12 | 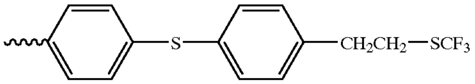 |
TABLE 150
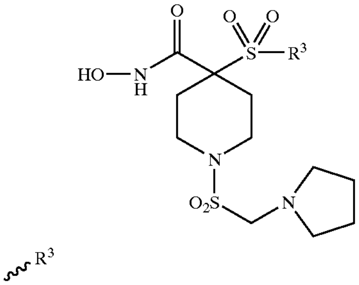
| | |
|---|---|
| 1 | 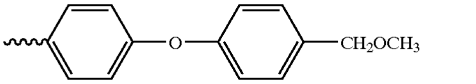 |
| 2 | 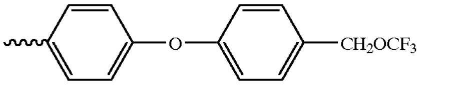 |
| 3 | 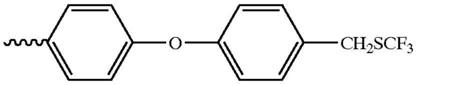 |
| 4 | 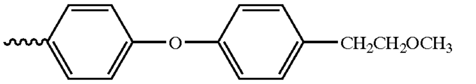 |
| 5 | 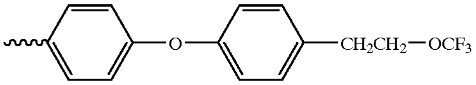 |
| 6 | 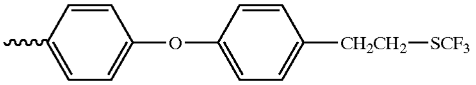 |
| 7 | 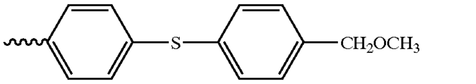 |
| 8 | 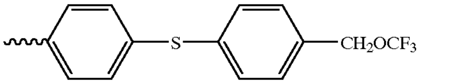 |
| 9 | 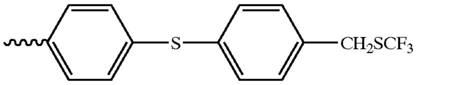 |
| 10 | 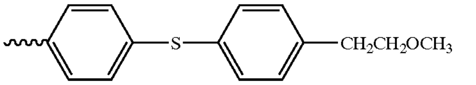 |
| 11 | 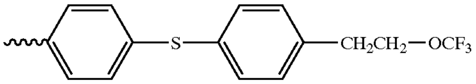 |
| 12 | 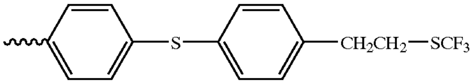 |

TABLE 151
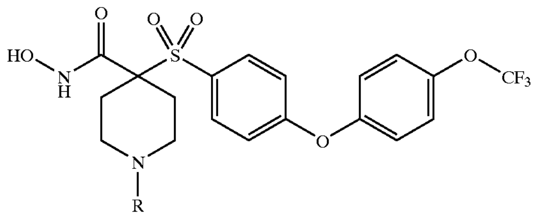
| | 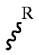 |
| --- | --- |
| 1 | 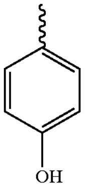 |
| 2 | 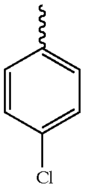 |
| 3 | 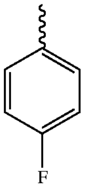 |
| 4 | 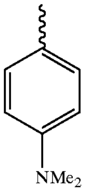 |
| 5 | 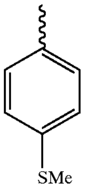 |
| 6 | 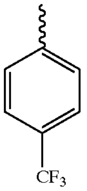 |
TABLE 151-continued
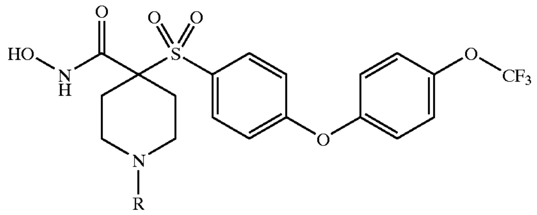
| | 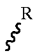 |
| --- | --- |
| 7 | 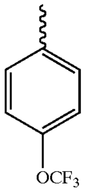 |
| 8 | 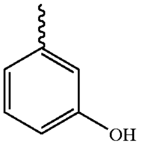 |
| 9 | 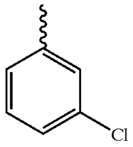 |
| 10 | 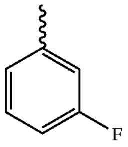 |
| 11 | 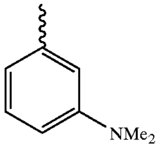 |
| 12 | 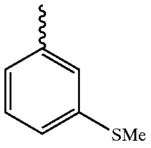 |
| 13 | 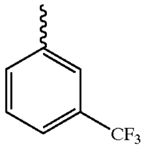 |
| 14 | 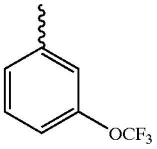 |

TABLE 151-continued
| 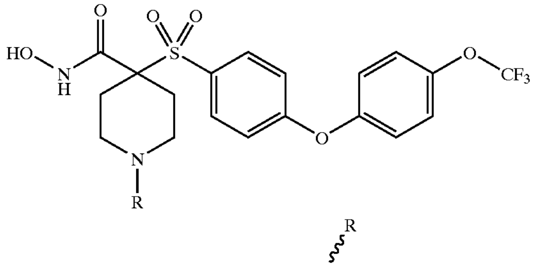 | |
|---|---|
| 15 | 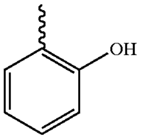 |
| 16 | 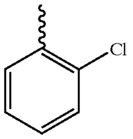 |
| 17 | 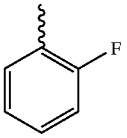 |
| 18 | 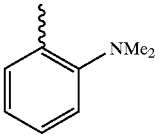 |
| 19 | 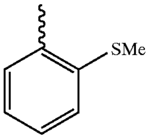 |
| 20 | 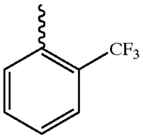 |
| 21 | 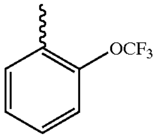 |
| 22 | 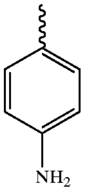 |
TABLE 151-continued
| 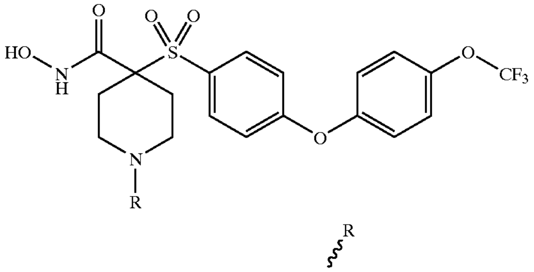 | |
|---|---|
| 23 | 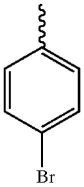 |
| 24 | 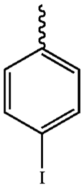 |
| 25 | 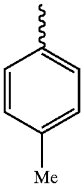 |
| 26 | 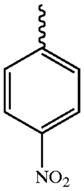 |
| 27 | 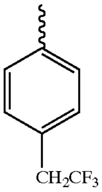 |
| 28 | 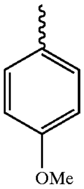 |

TABLE 151-continued
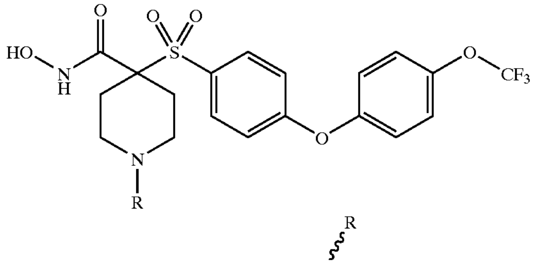
| | |
|---|---|
| 29 | 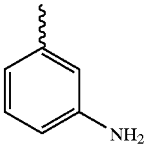 |
| 30 | 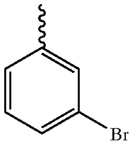 |
| 31 | 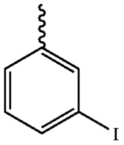 |
| 32 | 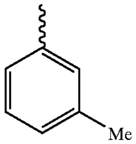 |
| 33 | 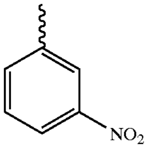 |
| 34 | 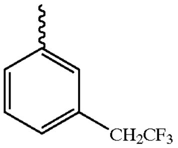 |
| 35 | 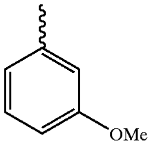 |
TABLE 151-continued
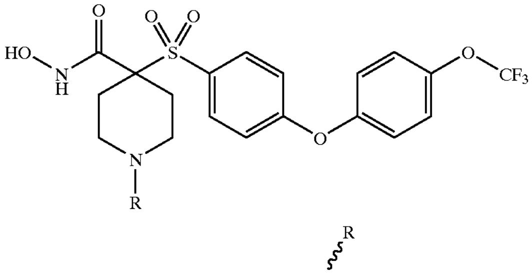
| | |
|---|---|
| 36 | 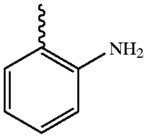 |
| 37 | 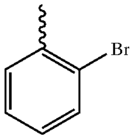 |
| 38 | 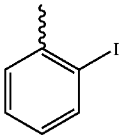 |
| 39 | 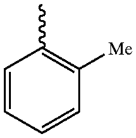 |
| 40 | 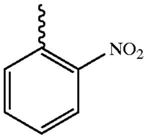 |
| 41 | 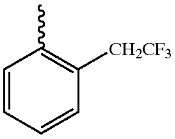 |
| 42 | 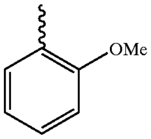 |

TABLE 152
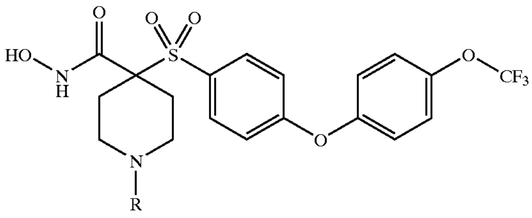
| | 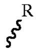 |
|---|---|
| 43 | 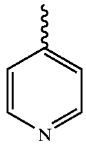 |
| 44 | 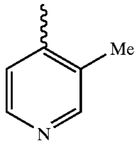 |
| 45 | 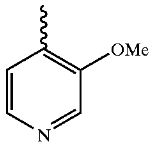 |
| 46 | 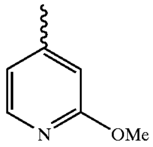 |
| 47 | 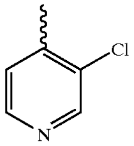 |
| 48 | 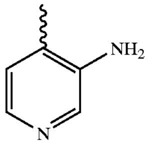 |
| 49 | 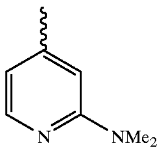 |
| 50 | 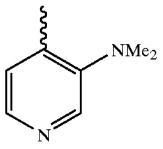 |
TABLE 152-continued
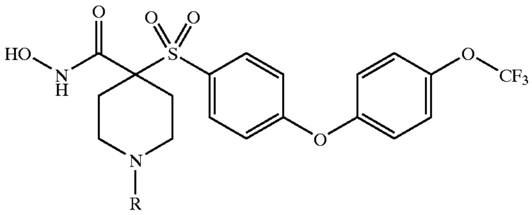
| | 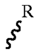 |
|---|---|
| 51 | 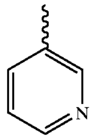 |
| 52 | 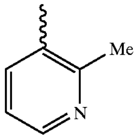 |
| 53 | 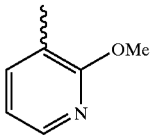 |
| 54 | 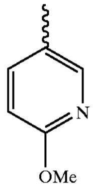 |
| 55 | 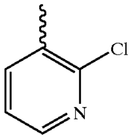 |
| 56 | 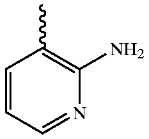 |
| 57 | 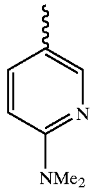 |
| 58 | 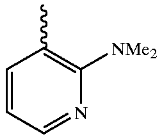 |

TABLE 152-continued
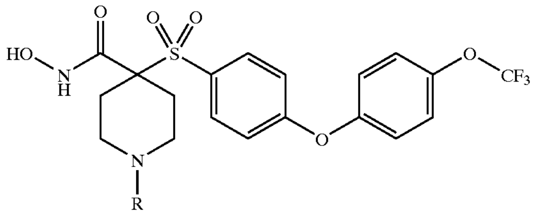
| | 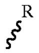 |
|---|---|
| 59 | 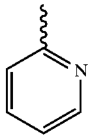 |
| 60 | 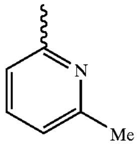 |
| 61 | 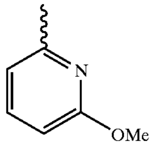 |
| 62 | 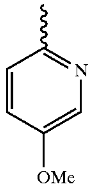 |
| 63 | 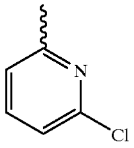 |
| 64 | 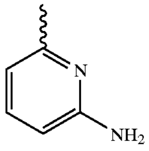 |
| 65 | 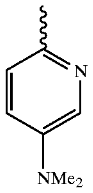 |
| 66 | 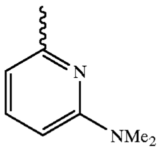 |
TABLE 152-continued
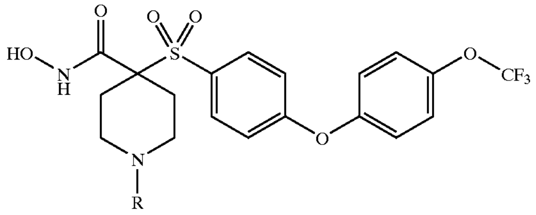
| |  |
|---|---|
| 67 | 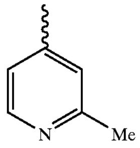 |
| 68 | 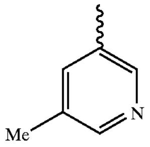 |
| 69 | 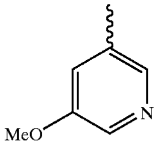 |
| 70 | 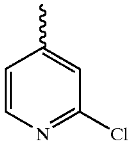 |
| 71 | 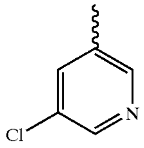 |
| 72 | 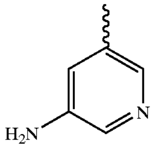 |
| 73 | 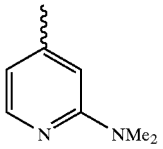 |
| 74 | 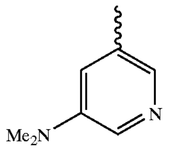 |

TABLE 152-continued
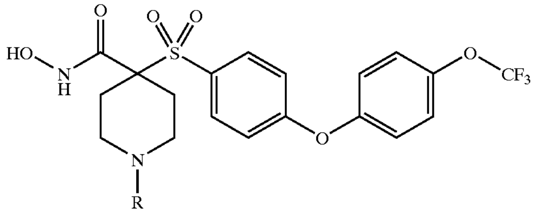
| | 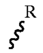 |
|---|---|
| 75 | 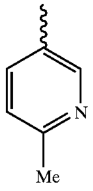 |
| 76 | 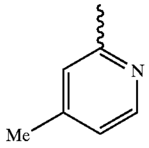 |
| 78 | 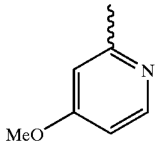 |
| 79 | 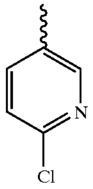 |
| 80 | 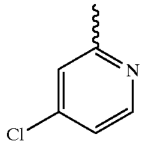 |
| 81 | 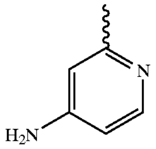 |
| 82 | 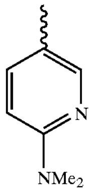 |
TABLE 152-continued
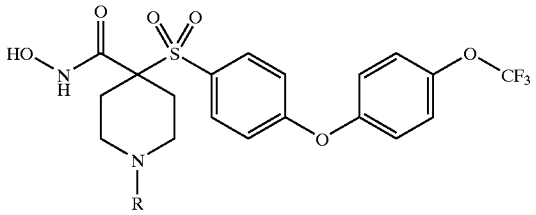
| | 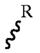 |
|---|---|
| 83 | 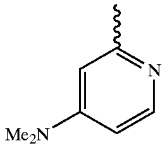 |
| 84 | 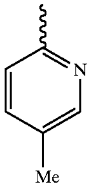 |
| 85 | 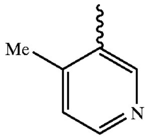 |
| 86 | 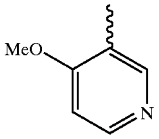 |
| 87 | 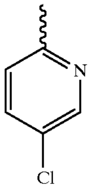 |
| 88 | 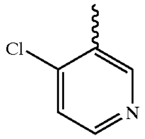 |
| 89 | 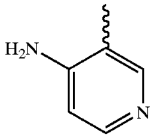 |
| 90 | 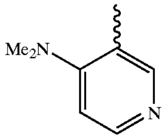 |

TABLE 152-continued
| 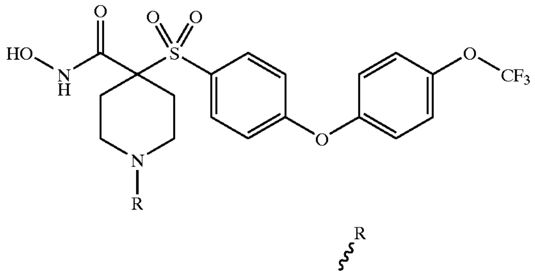 | |
|---|---|
| 91 | 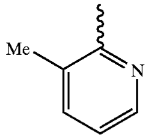 |
| 92 | 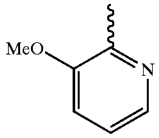 |
| 93 | 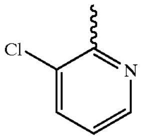 |
| 94 | 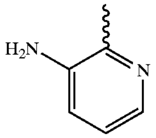 |
| 95 | 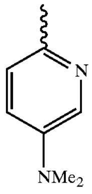 |
| 96 | 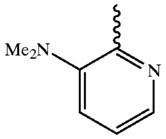 |
TABLE 153
| 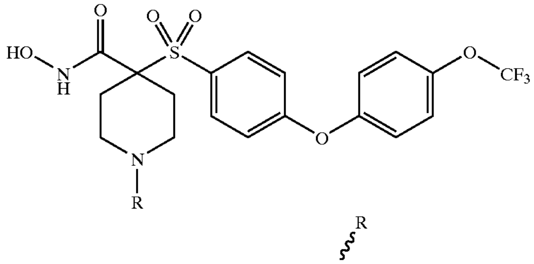 | |
|---|---|
| 97 | 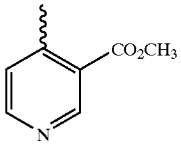 |
| 98 | 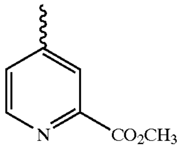 |
| 99 | 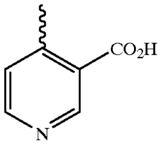 |
| 100 | 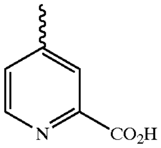 |
| 101 | 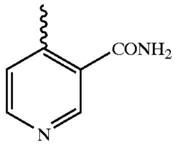 |
| 102 | 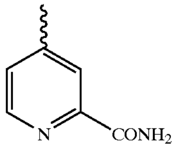 |
| 103 | 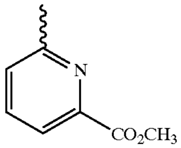 |
| 104 | 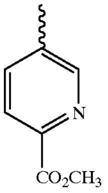 |

TABLE 153-continued
| 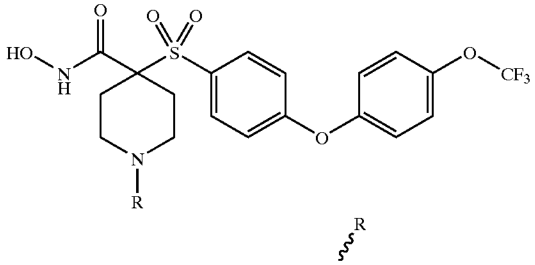 | |
|---|---|
| 105 | 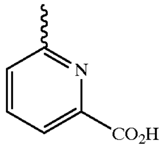 |
| 106 | 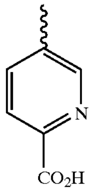 |
| 107 | 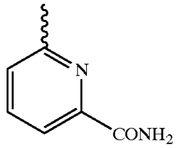 |
| 108 | 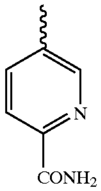 |
| 109 | 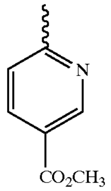 |
| 110 | 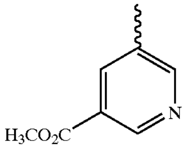 |
| 111 | 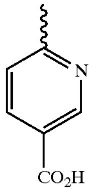 |
TABLE 153-continued
| 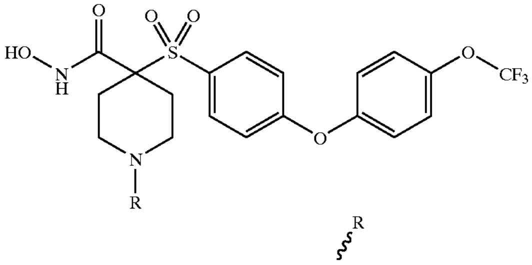 | |
|---|---|
| 112 | 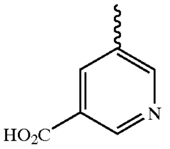 |
| 113 | 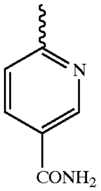 |
| 114 | 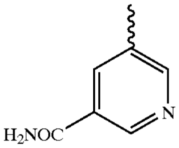 |
| 115 | 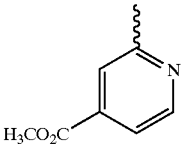 |
| 116 | 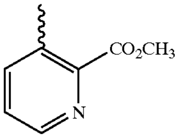 |
| 117 | 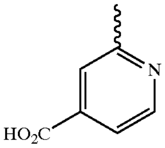 |
| 118 | 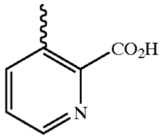 |
| 119 | 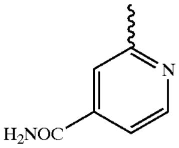 |

TABLE 153-continued
| 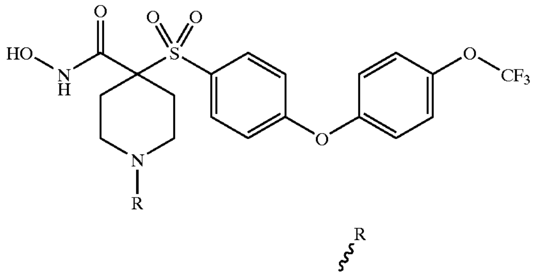 | |
|---|---|
| 120 | 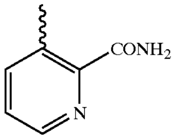 |
| 121 | 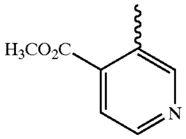 |
| 122 | 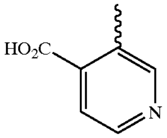 |
| 123 | 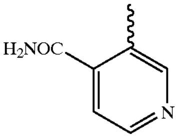 |
| 124 | 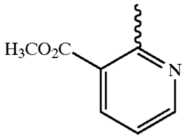 |
| 125 | 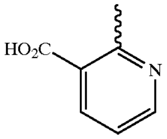 |
| 126 | 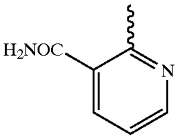 |
TABLE 154
| 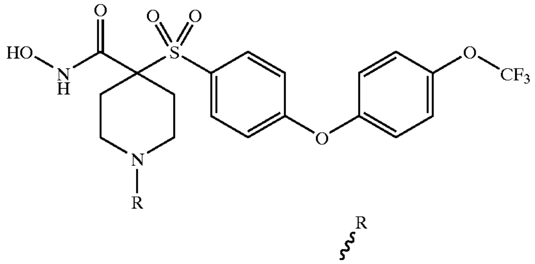 | |
|---|---|
| 127 | 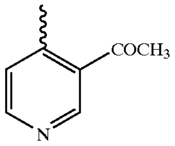 |
| 128 | 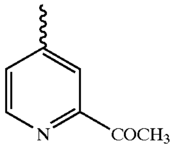 |
| 129 | 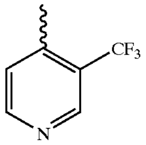 |
| 130 | 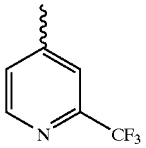 |
| 131 | 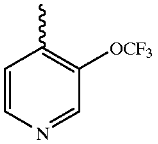 |
| 132 | 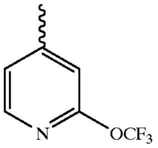 |
| 133 | 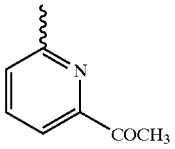 |
| 134 | 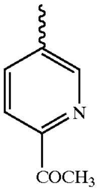 |

135
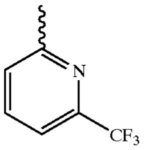
136
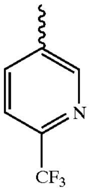
137
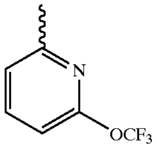
138
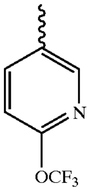
139
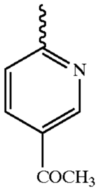
140
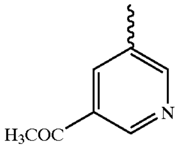
141
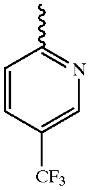
142
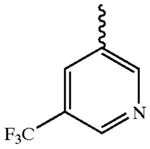
143
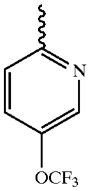
144
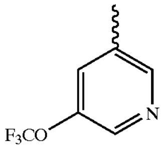
145
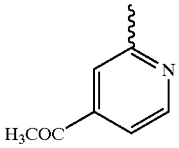
146
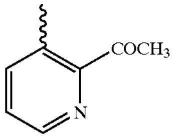
147
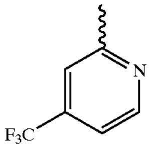
148
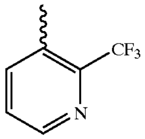
149
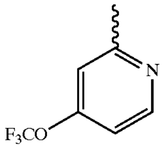
150
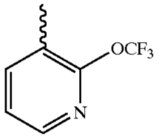
151
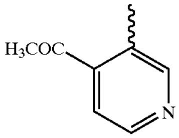
152
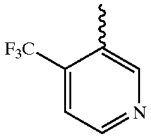
153
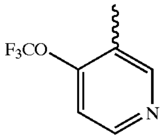

| | |
|---|---|
| 154 | 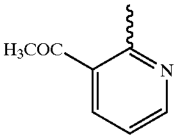 |
| 155 | 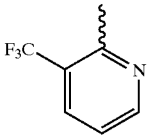 |
| 156 | 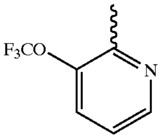 |
TABLE 155
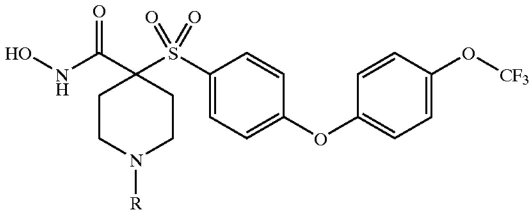
| 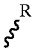 | |
|---|---|
| 157 | 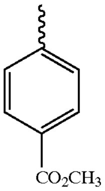 |
| 158 | 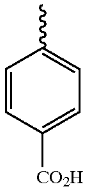 |
| 159 | 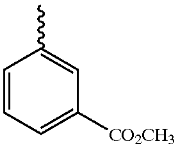 |
| 160 | 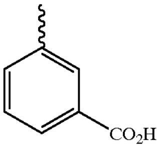 |
TABLE 155-continued
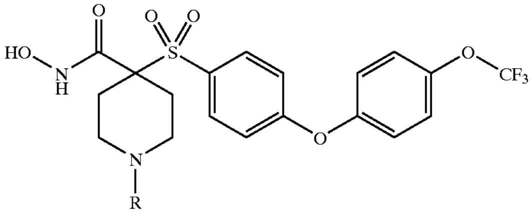
| 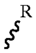 | |
|---|---|
| 161 | 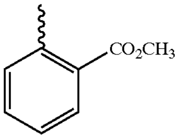 |
| 162 | 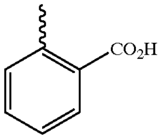 |
| 163 | 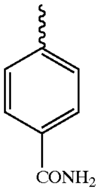 |
| 164 | 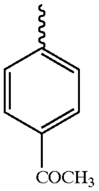 |
| 165 | 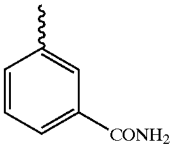 |
| 166 | 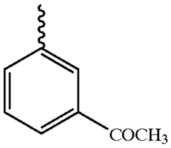 |
| 167 | 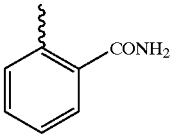 |
| 168 | 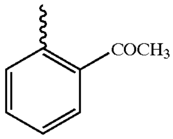 |

TABLE 155-continued
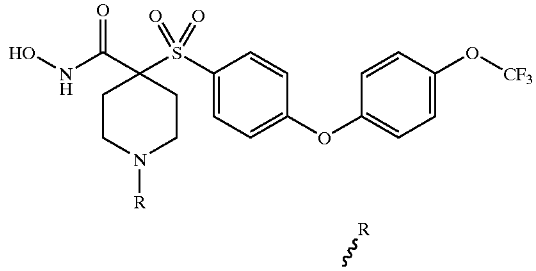
| | |
|---|---|
| 169 | 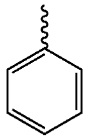 |
| 170 | 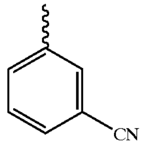 |
| 171 | 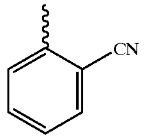 |
| 172 | 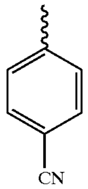 |
TABLE 156
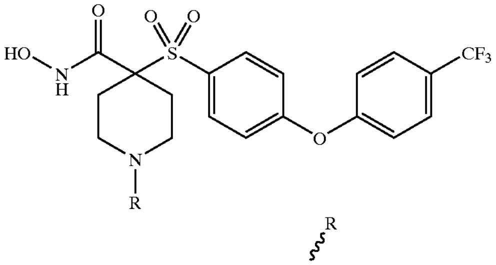
| | |
|---|---|
| 1 | 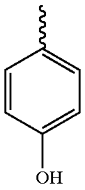 |
TABLE 156-continued
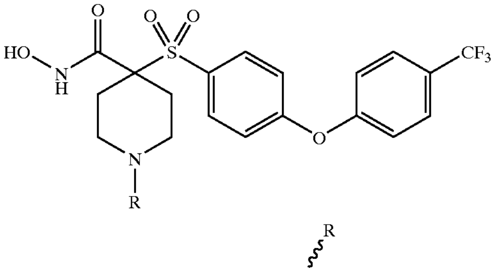
| | |
|---|---|
| 2 | 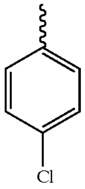 |
| 3 | 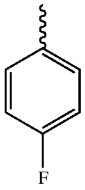 |
| 4 | 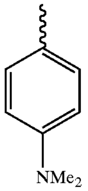 |
| 5 | 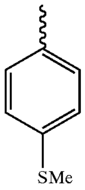 |
| 6 | 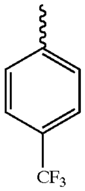 |
| 7 | 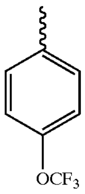 |

TABLE 156-continued
| 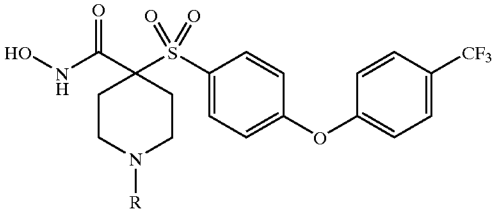 | 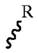 |
| --- | --- |
| 8 | 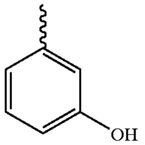 |
| 9 | 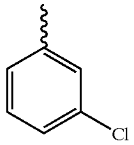 |
| 10 | 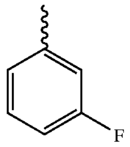 |
| 11 | 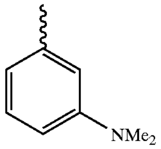 |
| 12 | 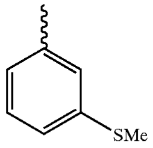 |
| 13 | 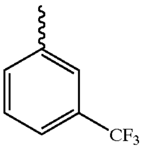 |
| 14 | 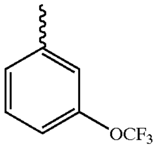 |
| 15 | 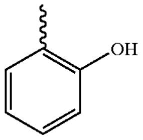 |
TABLE 156-continued
| 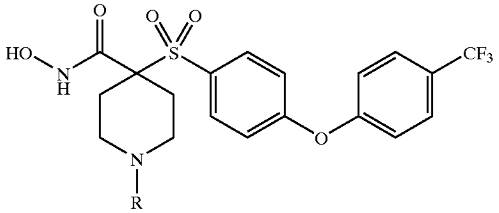 | 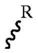 |
| --- | --- |
| 16 | 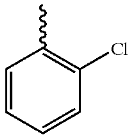 |
| 17 | 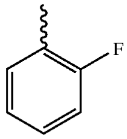 |
| 18 | 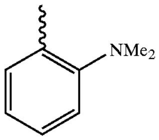 |
| 19 | 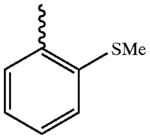 |
| 20 | 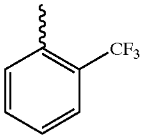 |
| 21 | 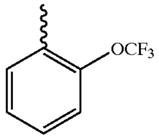 |
| 22 | 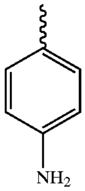 |
| 23 | 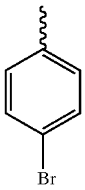 |

TABLE 156-continued
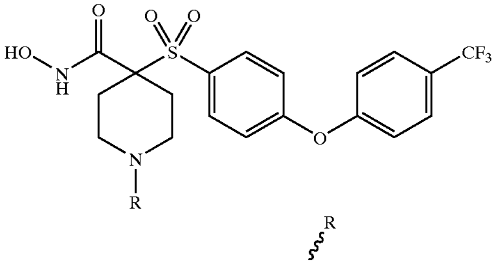
| | |
|---|---|
| 24 | 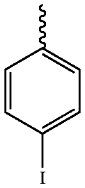 |
| 25 | 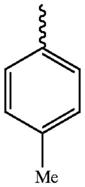 |
| 26 | 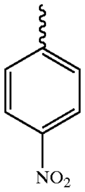 |
| 27 | 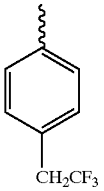 |
| 28 | 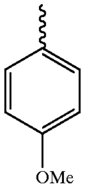 |
| 29 | 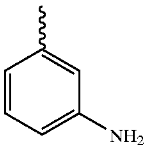 |
| 30 | 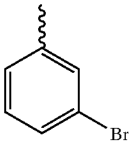 |
TABLE 156-continued
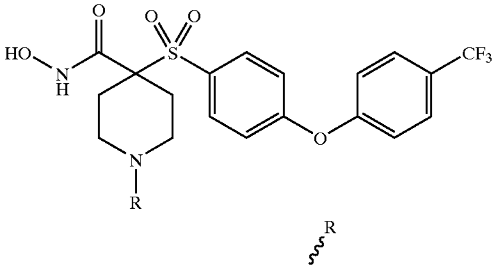
| | |
|---|---|
| 31 | 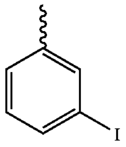 |
| 32 | 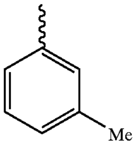 |
| 33 | 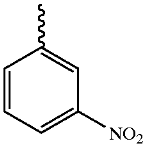 |
| 34 | 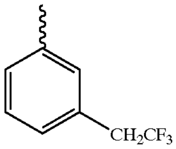 |
| 35 | 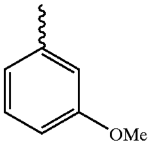 |
| 36 | 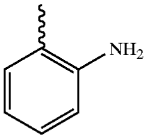 |
| 37 | 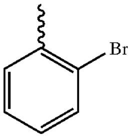 |
| 38 | 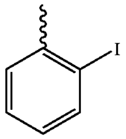 |

TABLE 156-continued
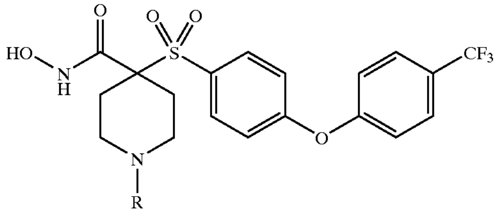
| | 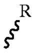 |
|---|---|
| 39 | 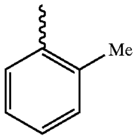 |
| 40 | 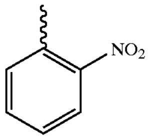 |
| 41 | 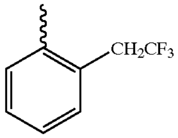 |
| 42 | 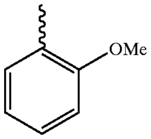 |
TABLE 157
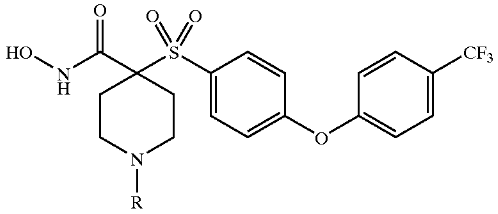
| | 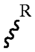 |
|---|---|
| 43 | 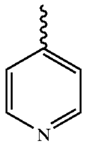 |
| 44 | 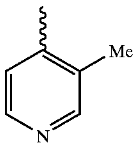 |
TABLE 157-continued
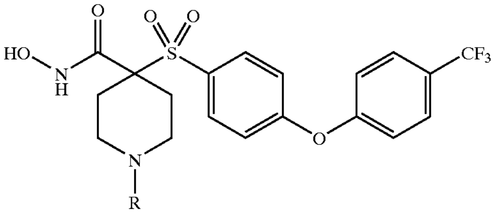
| | 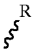 |
|---|---|
| 45 | 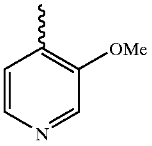 |
| 46 | 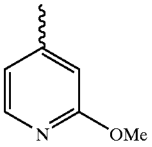 |
| 47 | 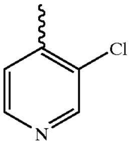 |
| 48 | 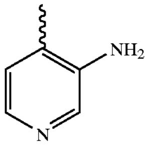 |
| 49 | 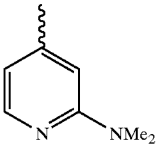 |
| 50 | 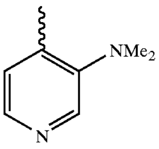 |
| 51 | 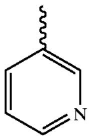 |
| 52 | 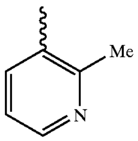 |

TABLE 157-continued
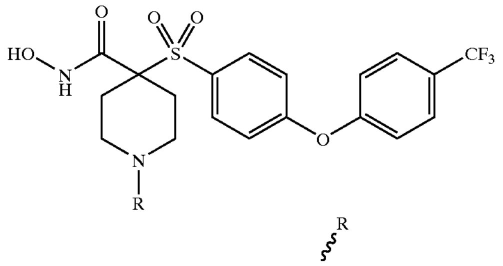
| | |
|---|---|
| 53 | 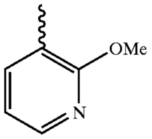 |
| 54 | 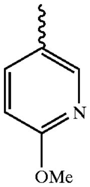 |
| 55 | 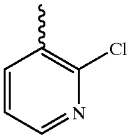 |
| 56 | 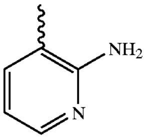 |
| 57 | 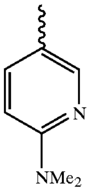 |
| 58 | 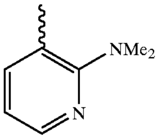 |
| 59 | 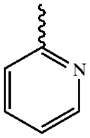 |
| 60 | 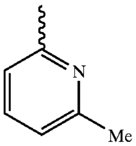 |
TABLE 157-continued
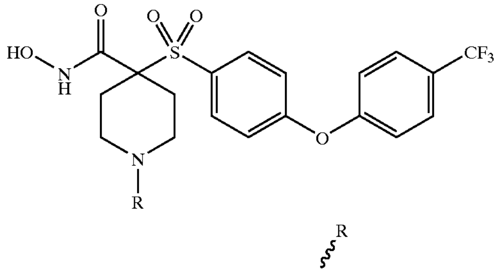
| | |
|---|---|
| 61 | 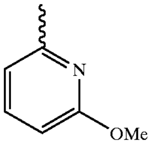 |
| 62 | 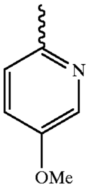 |
| 63 | 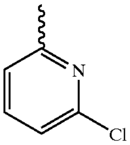 |
| 64 | 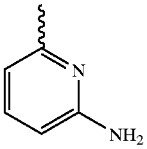 |
| 65 | 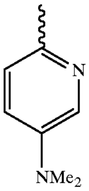 |
| 66 | 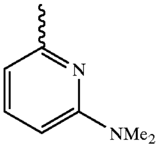 |
| 67 | 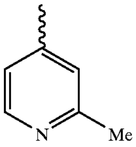 |

TABLE 157-continued
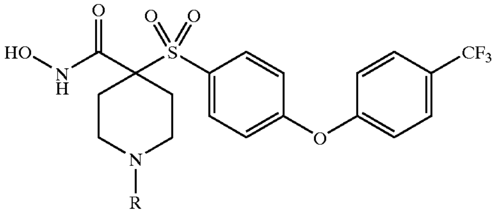
| | 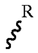 |
|---|---|
| 68 | 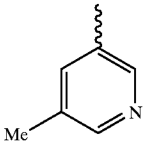 |
| 69 | 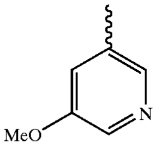 |
| 70 | 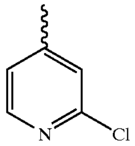 |
| 71 | 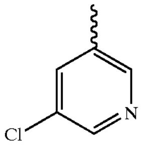 |
| 72 | 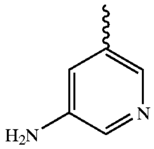 |
| 73 | 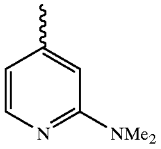 |
| 74 | 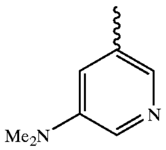 |
| 75 | 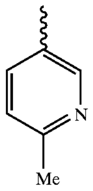 |
TABLE 157-continued
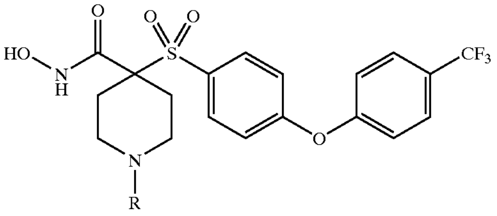
| | 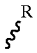 |
|---|---|
| 76 | 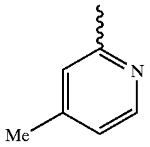 |
| 78 | 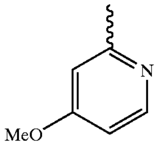 |
| 79 | 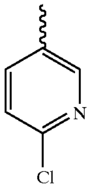 |
| 80 | 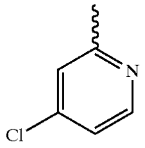 |
| 81 | 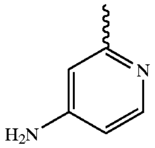 |
| 82 | 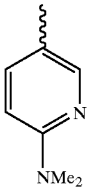 |
| 83 | 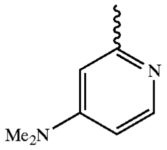 |

TABLE 157-continued
| 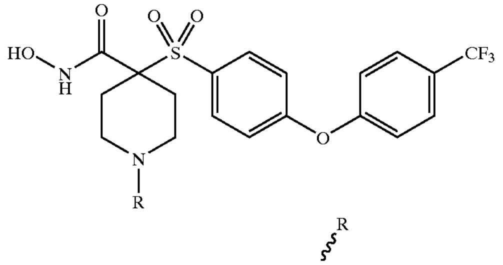 | |
|---|---|
| 84 | 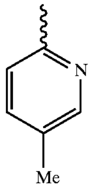 |
| 85 | 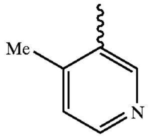 |
| 86 | 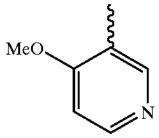 |
| 87 | 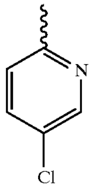 |
| 88 | 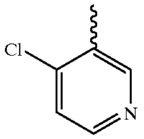 |
| 89 | 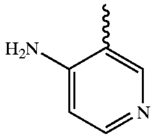 |
| 90 | 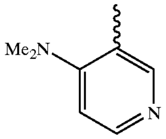 |
| 91 | 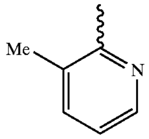 |
TABLE 157-continued
| 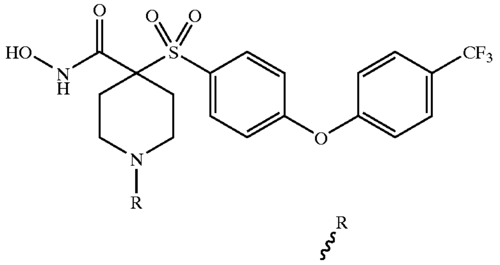 | |
|---|---|
| 92 | 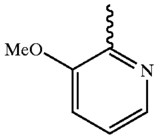 |
| 93 | 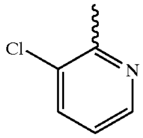 |
| 94 | 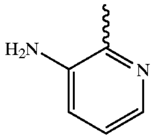 |
| 95 | 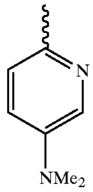 |
| 96 | 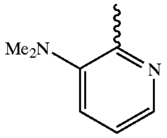 |
TABLE 158
| 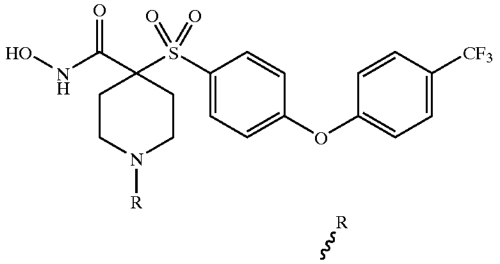 | |
|---|---|
| 97 | 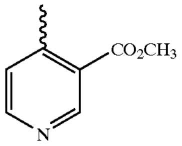 |

TABLE 158-continued
| | 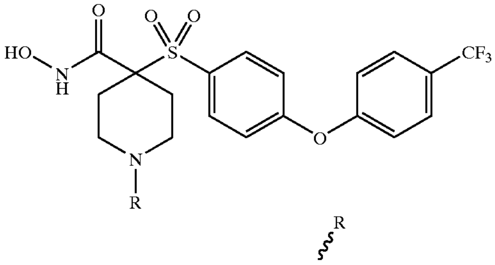 |
|---|---|
| 98 | 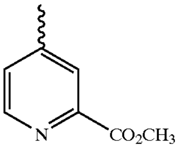 |
| 99 | 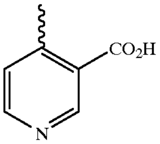 |
| 100 | 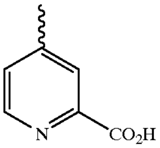 |
| 101 | 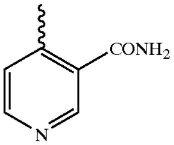 |
| 102 | 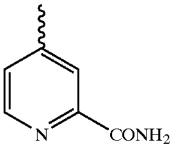 |
| 103 | 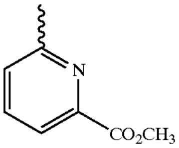 |
| 104 | 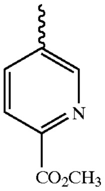 |
| 105 | 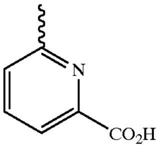 |
TABLE 158-continued
| | 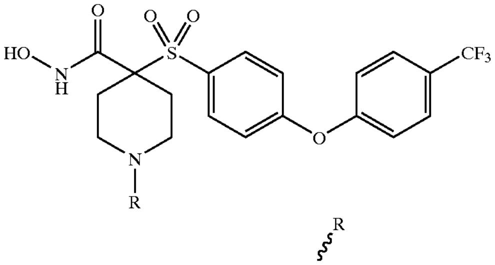 |
|---|---|
| 106 | 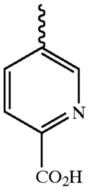 |
| 107 | 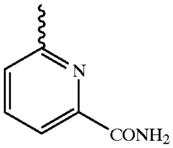 |
| 108 | 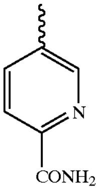 |
| 109 | 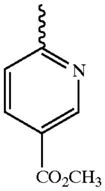 |
| 110 | 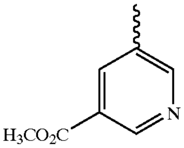 |
| 111 | 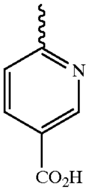 |
| 112 | 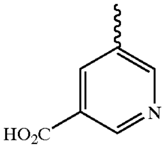 |

TABLE 158-continued
| | |
|---|---|
| | 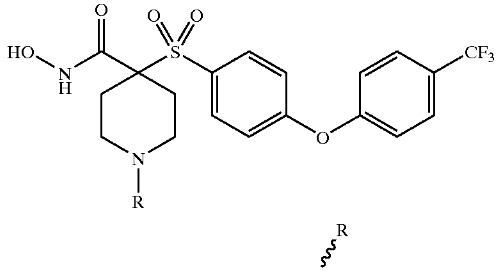 |
| 113 | 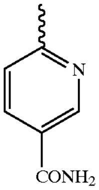 |
| 114 | 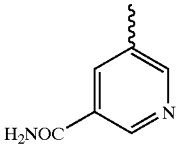 |
| 115 | 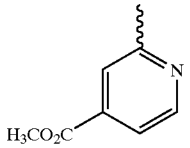 |
| 116 | 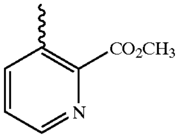 |
| 117 | 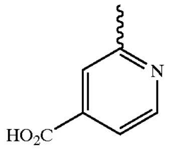 |
| 118 | 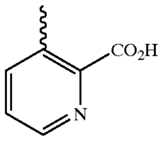 |
| 119 | 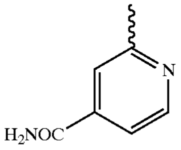 |
TABLE 158-continued
| | |
|---|---|
| | 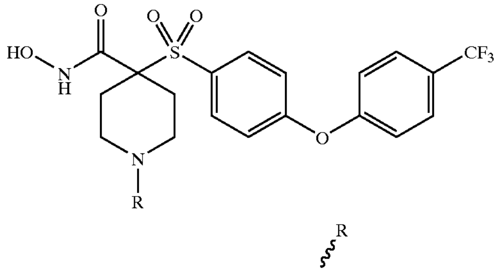 |
| 120 | 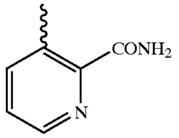 |
| 121 | 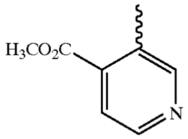 |
| 122 | 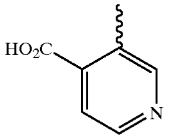 |
| 123 | 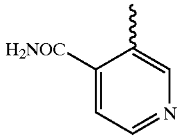 |
| 124 | 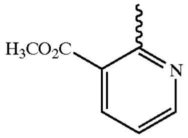 |
| 125 | 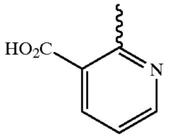 |
| 126 | 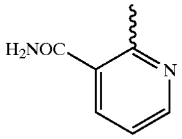 |

TABLE 159
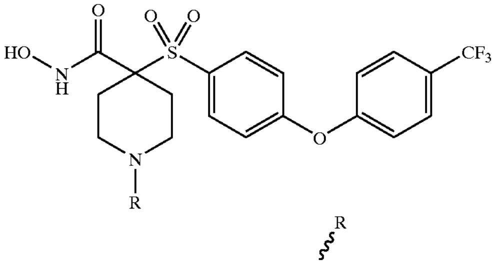
| | R |
|---|---|
| 127 | 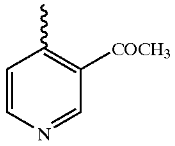 |
| 128 | 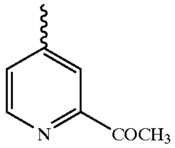 |
| 129 | 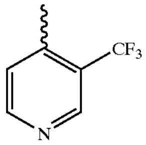 |
| 130 | 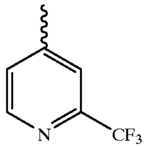 |
| 131 | 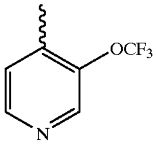 |
| 132 | 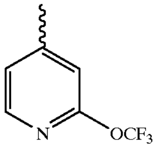 |
| 133 | 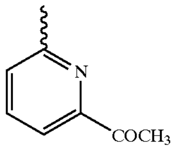 |
| 134 | 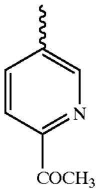 |
TABLE 159-continued
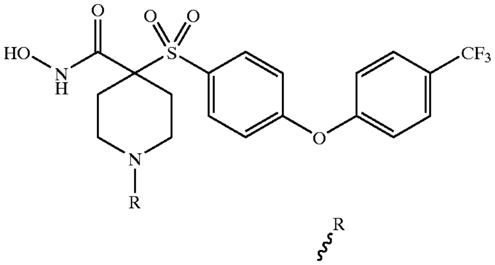
| | R |
|---|---|
| 135 | 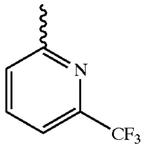 |
| 136 | 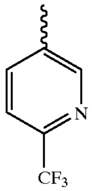 |
| 137 | 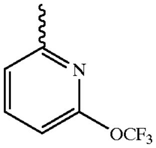 |
| 138 | 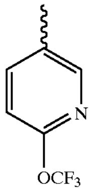 |
| 139 | 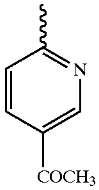 |
| 140 | 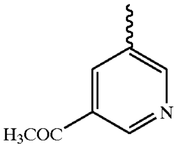 |
| 141 | 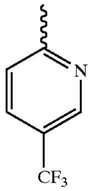 |

TABLE 159-continued
| 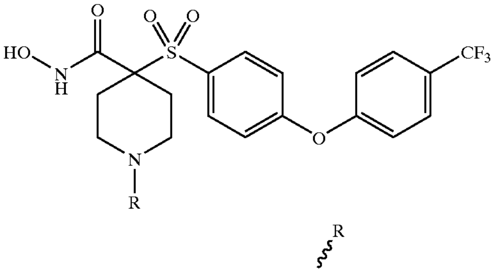 | |
|---|---|
| 142 | 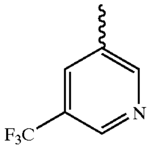 |
| 143 | 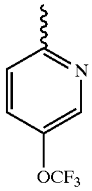 |
| 144 | 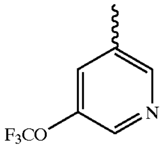 |
| 145 | 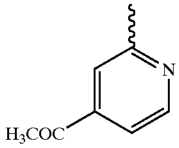 |
| 146 | 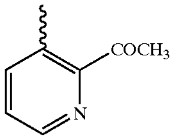 |
| 147 | 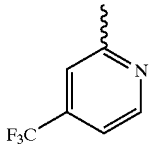 |
| 148 | 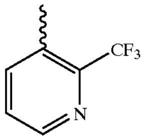 |
TABLE 159-continued
| 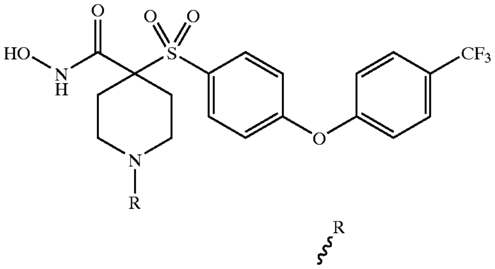 | |
|---|---|
| 149 | 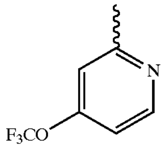 |
| 150 | 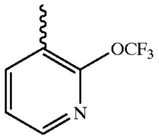 |
| 151 | 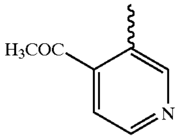 |
| 152 | 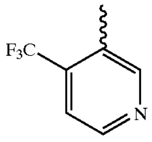 |
| 153 | 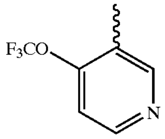 |
| 154 | 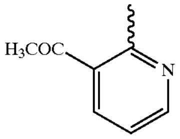 |
| 155 | 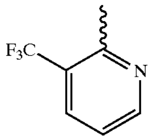 |
| 156 | 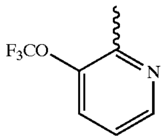 |

TABLE 160
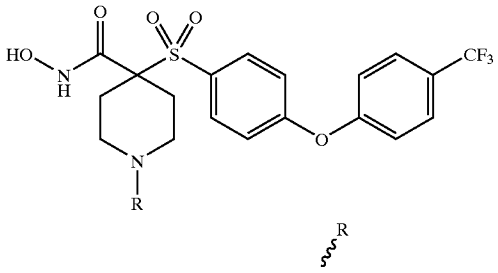
| | |
|---|---|
| 157 | 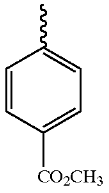 |
| 158 | 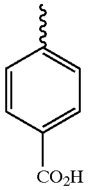 |
| 159 | 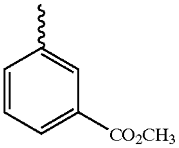 |
| 160 | 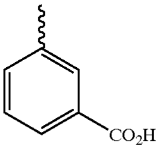 |
| 161 | 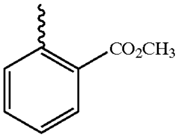 |
| 162 | 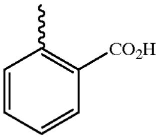 |
| 163 | 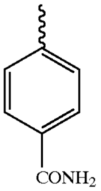 |
TABLE 160-continued
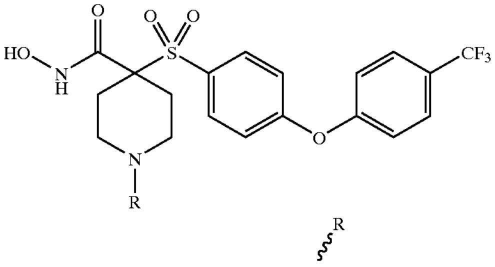
| | |
|---|---|
| 164 | 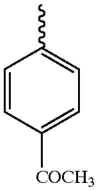 |
| 165 | 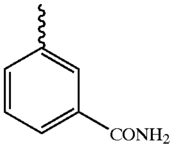 |
| 166 | 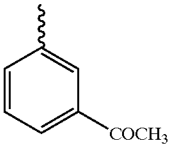 |
| 167 | 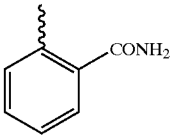 |
| 168 | 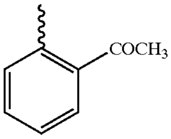 |
| 169 | 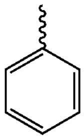 |
| 170 | 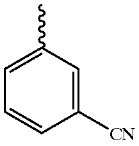 |
| 171 | 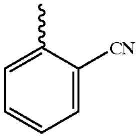 |

TABLE 160-continued
| 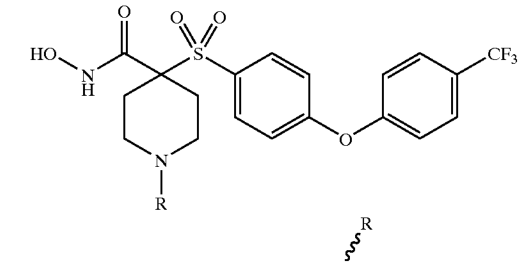 | |
|---|---|
| 172 | 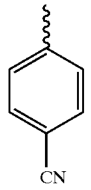 |
TABLE 161
| 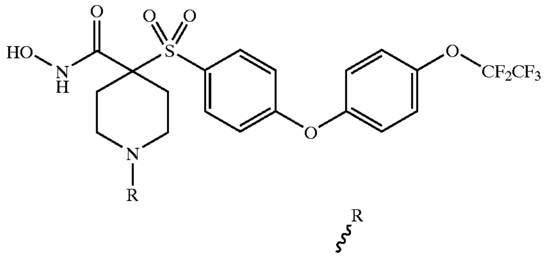 | |
|---|---|
| 1 | 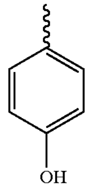 |
| 2 | 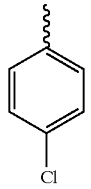 |
| 3 | 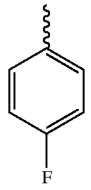 |
| 4 | 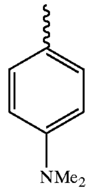 |
TABLE 161-continued
| 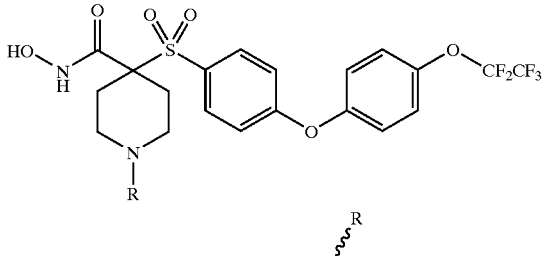 | |
|---|---|
| 5 | 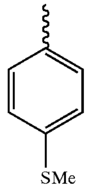 |
| 6 | 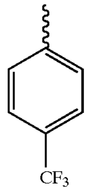 |
| 7 | 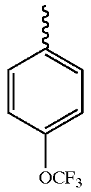 |
| 8 | 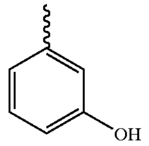 |
| 9 | 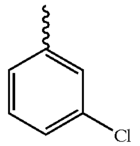 |
| 10 | 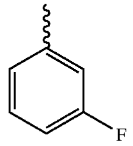 |
| 11 | 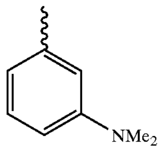 |

TABLE 161-continued
| 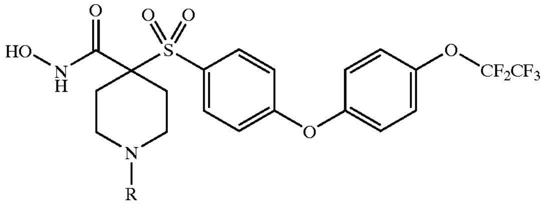 | 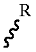 |
|---|---|
| 12 | 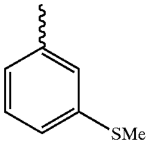 |
| 13 | 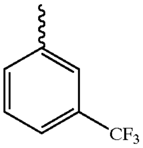 |
| 14 | 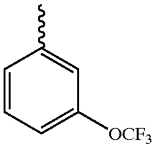 |
| 15 | 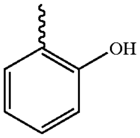 |
| 16 | 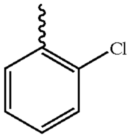 |
| 17 | 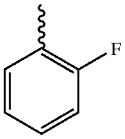 |
| 18 | 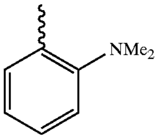 |
| 19 | 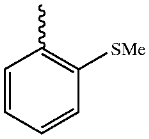 |
TABLE 161-continued
| 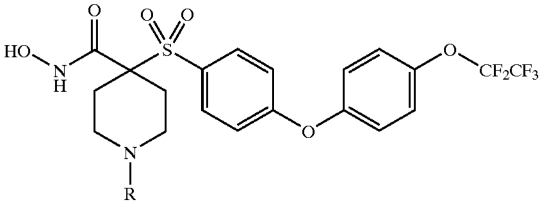 | 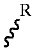 |
|---|---|
| 20 | 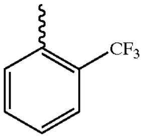 |
| 21 | 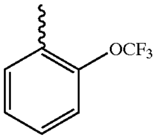 |
| 22 | 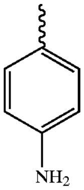 |
| 23 | 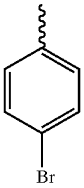 |
| 24 | 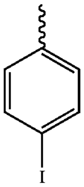 |
| 25 | 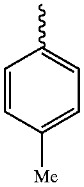 |
| 26 | 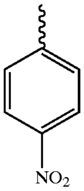 |

TABLE 161-continued
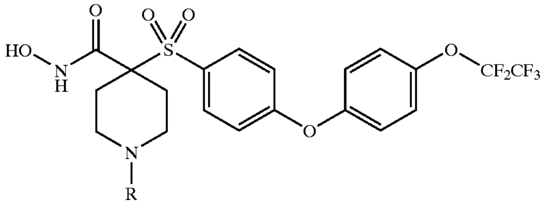
| | |
|---|---|
| |  |
| 27 | 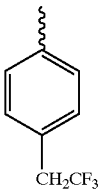 |
| 28 | 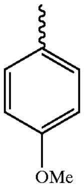 |
| 29 | 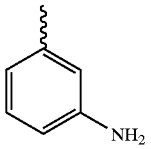 |
| 30 | 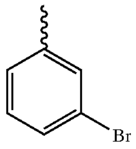 |
| 31 | 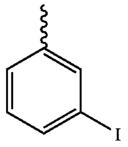 |
| 32 | 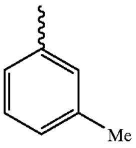 |
| 33 | 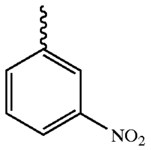 |
TABLE 161-continued
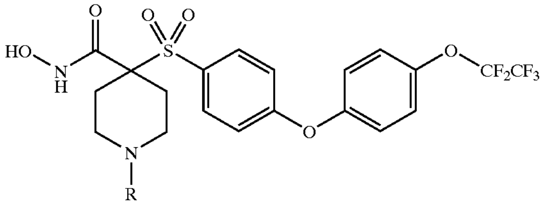
| | |
|---|---|
| | 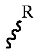 |
| 34 | 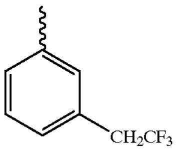 |
| 35 | 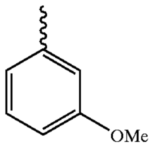 |
| 36 | 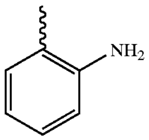 |
| 37 | 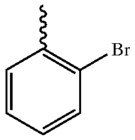 |
| 38 | 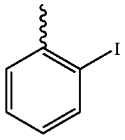 |
| 39 | 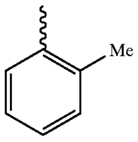 |
| 40 | 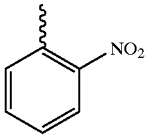 |
| 41 | 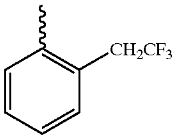 |

TABLE 161-continued
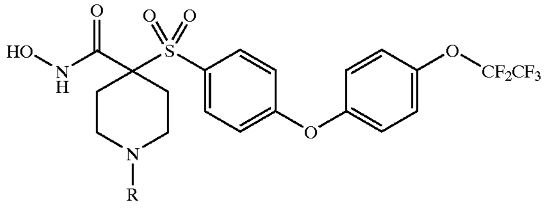
| | 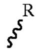 |
|---|---|
| 42 | 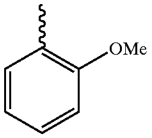 |
TABLE 162
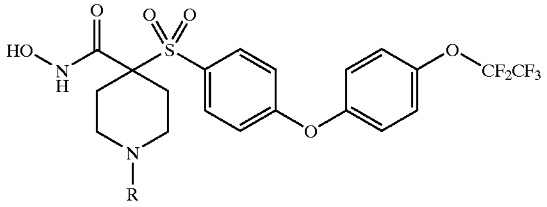
| | 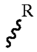 |
|---|---|
| 43 | 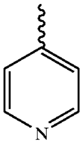 |
| 44 | 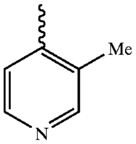 |
| 45 | 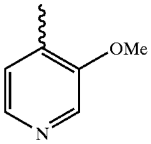 |
| 46 | 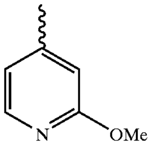 |
| 47 | 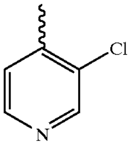 |
TABLE 162-continued
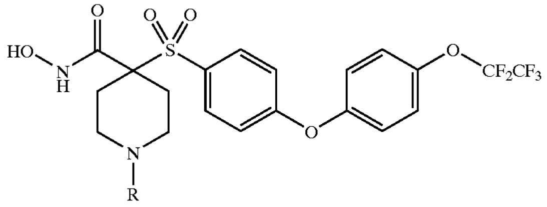
| | 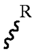 |
|---|---|
| 48 | 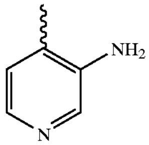 |
| 49 | 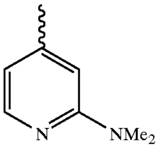 |
| 50 | 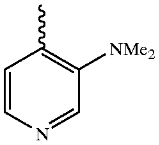 |
| 51 | 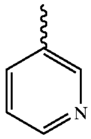 |
| 52 | 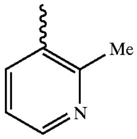 |
| 53 | 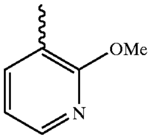 |
| 54 | 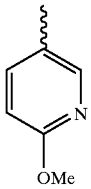 |
| 55 | 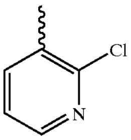 |

TABLE 162-continued
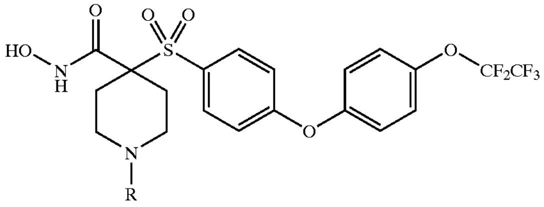
| | 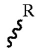 |
|---|---|
| 56 | 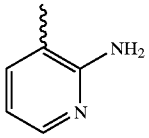 |
| 57 | 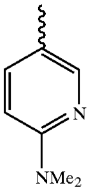 |
| 58 | 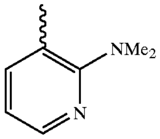 |
| 59 | 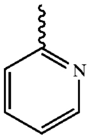 |
| 60 | 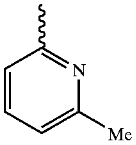 |
| 61 | 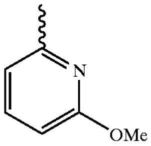 |
| 62 | 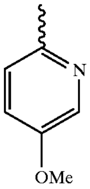 |
| 63 | 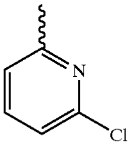 |
TABLE 162-continued
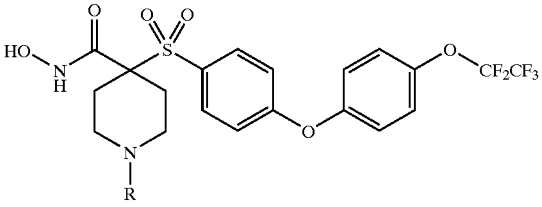
| | 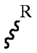 |
|---|---|
| 64 | 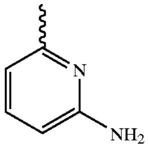 |
| 65 | 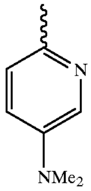 |
| 66 | 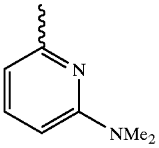 |
| 67 | 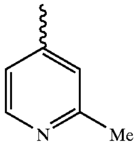 |
| 68 | 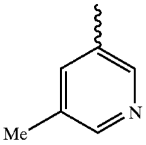 |
| 69 | 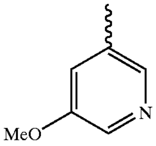 |
| 70 | 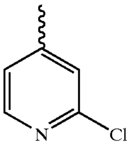 |
| 71 | 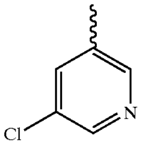 |

TABLE 162-continued
| | |
|---|---|
| | 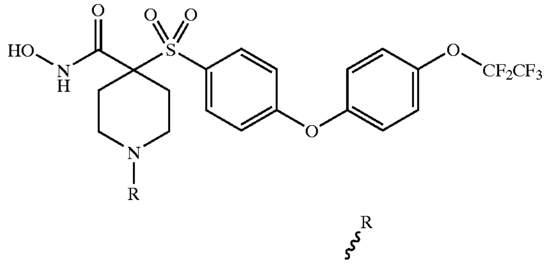 |
| 72 | 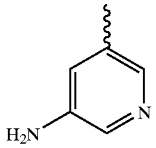 |
| 73 | 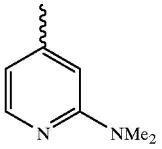 |
| 74 | 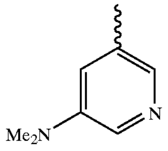 |
| 75 | 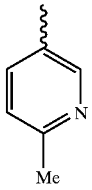 |
| 76 | 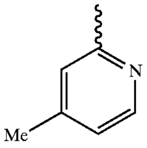 |
| 78 | 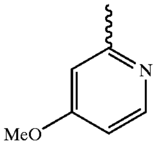 |
| 79 | 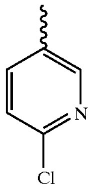 |
TABLE 162-continued
| | |
|---|---|
| | 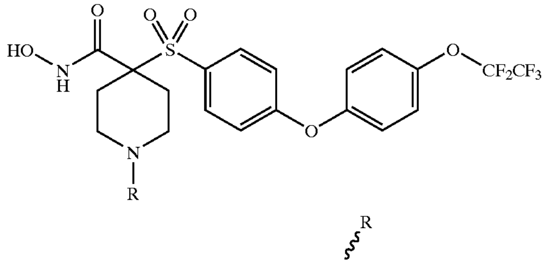 |
| 80 | 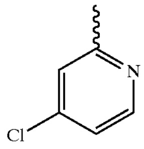 |
| 81 | 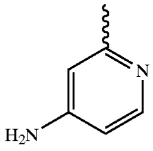 |
| 82 | 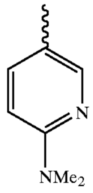 |
| 83 | 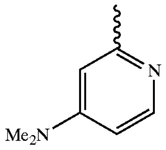 |
| 84 | 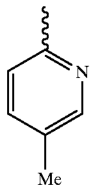 |
| 85 | 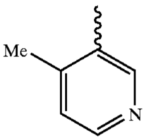 |
| 86 | 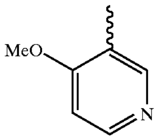 |

TABLE 162-continued
| 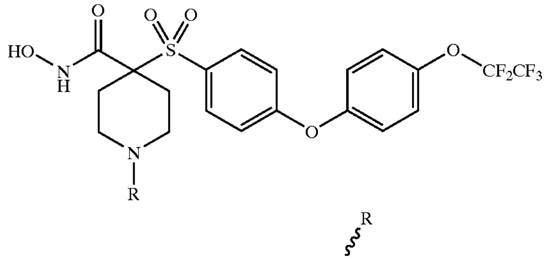 | |
|---|---|
| 87 | 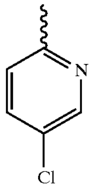 |
| 88 | 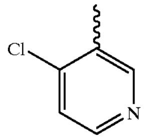 |
| 89 | 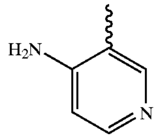 |
| 90 | 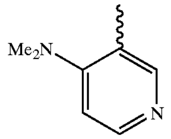 |
| 91 | 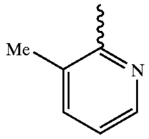 |
| 92 | 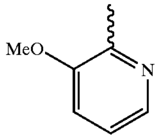 |
| 93 | 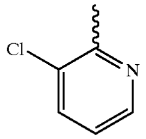 |
| 94 | 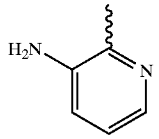 |
TABLE 162-continued
| 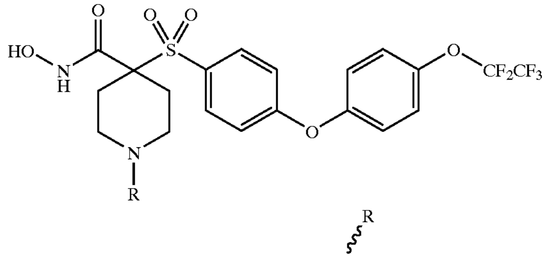 | |
|---|---|
| 95 | 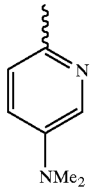 |
| 96 | 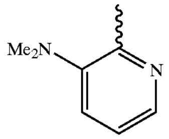 |
TABLE 163
| 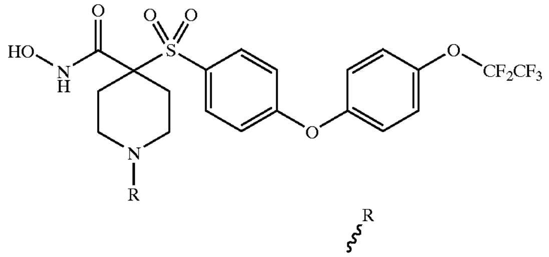 | |
|---|---|
| 97 | 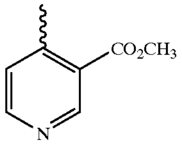 |
| 98 | 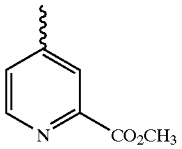 |
| 99 | 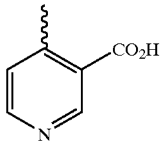 |
| 100 | 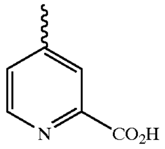 |

TABLE 163-continued
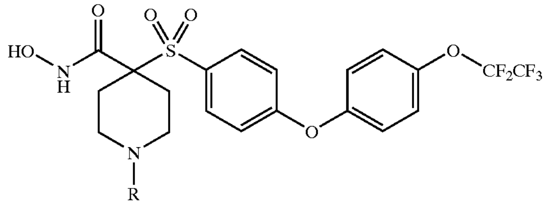
| | 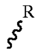 |
|---|---|
| 101 | 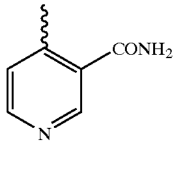 |
| 102 | 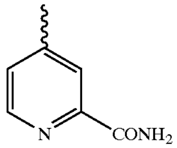 |
| 103 | 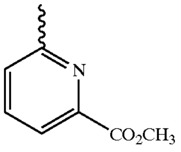 |
| 104 | 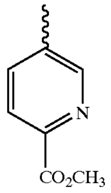 |
| 105 | 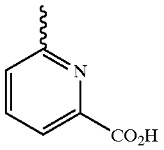 |
| 106 | 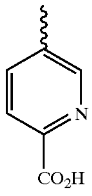 |
| 107 | 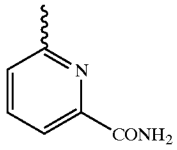 |
TABLE 163-continued
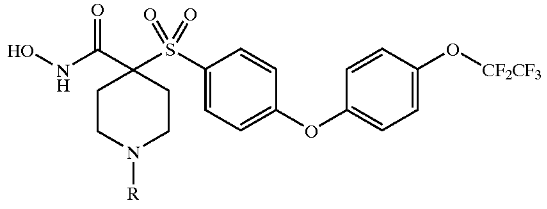
| | 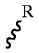 |
|---|---|
| 108 | 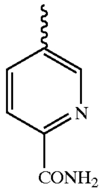 |
| 109 | 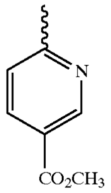 |
| 110 | 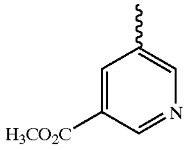 |
| 111 | 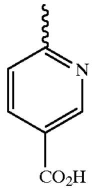 |
| 112 | 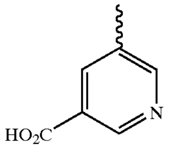 |
| 113 | 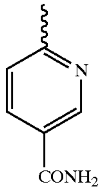 |
| 114 | 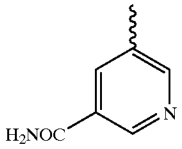 |

TABLE 163-continued
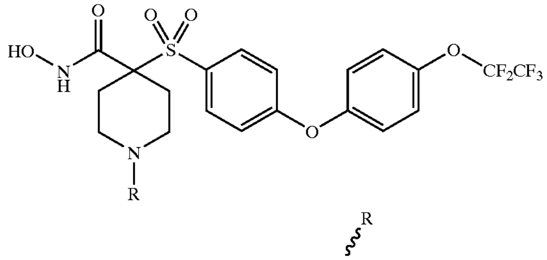
| | |
|---|---|
| 115 | 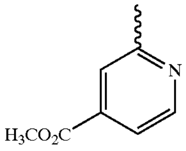 |
| 116 | 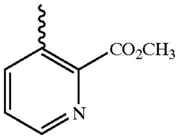 |
| 117 | 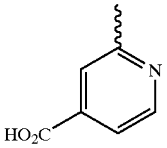 |
| 118 | 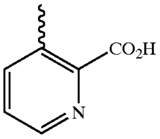 |
| 119 | 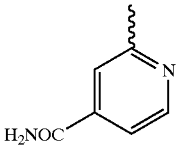 |
| 120 | 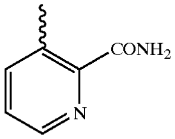 |
| 121 | 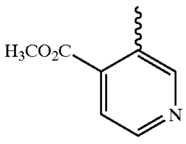 |
| 122 | 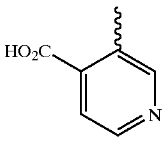 |
TABLE 163-continued
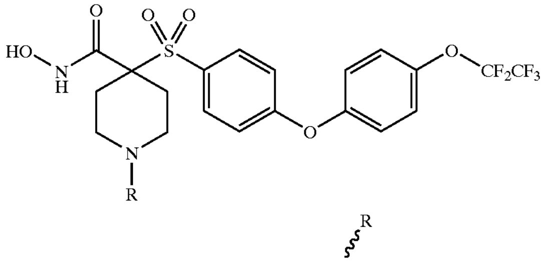
| | |
|---|---|
| 123 | 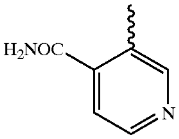 |
| 124 | 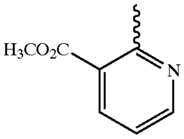 |
| 125 | 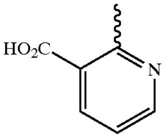 |
| 126 | 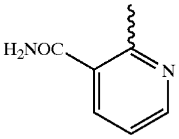 |
TABLE 164
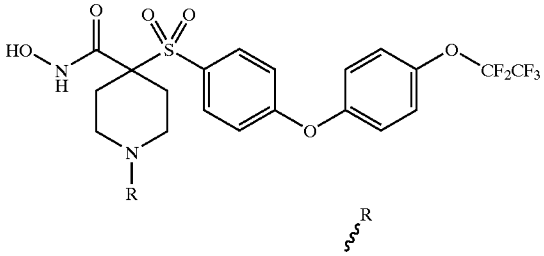
| | |
|---|---|
| 127 | 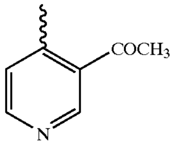 |
| 128 | 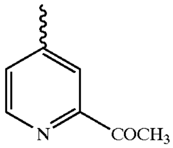 |

TABLE 164-continued
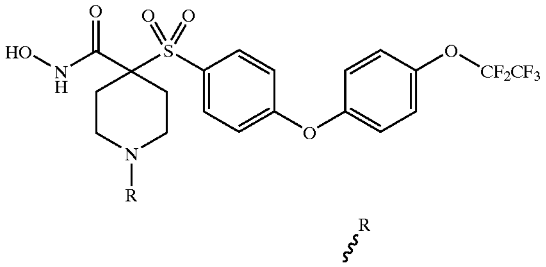
| | |
|---|---|
| 129 | 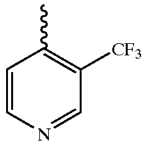 |
| 130 | 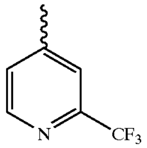 |
| 131 | 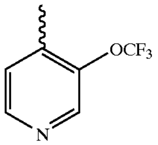 |
| 132 | 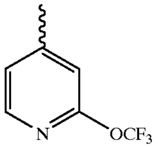 |
| 133 | 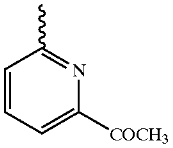 |
| 134 | 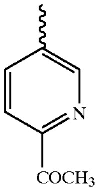 |
| 135 | 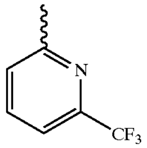 |
TABLE 164-continued
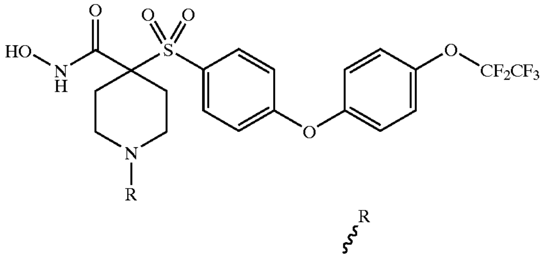
| | |
|---|---|
| 136 | 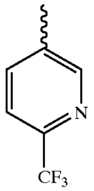 |
| 137 | 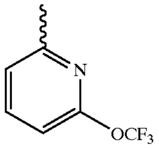 |
| 138 | 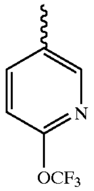 |
| 139 | 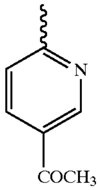 |
| 140 | 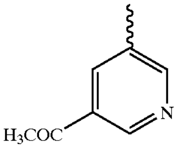 |
| 141 | 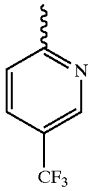 |
| 142 | 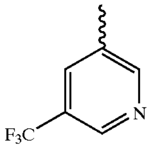 |

TABLE 164-continued
| 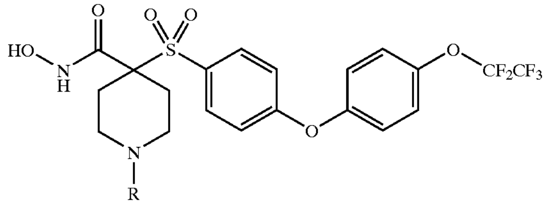 |  |
|---|---|
| 143 | 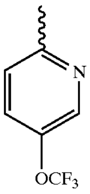 |
| 144 | 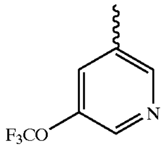 |
| 145 | 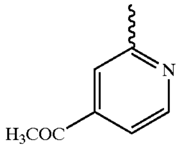 |
| 146 | 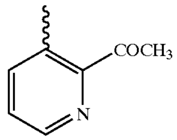 |
| 147 | 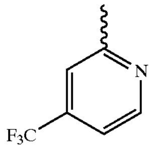 |
| 148 | 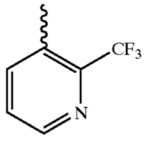 |
| 149 | 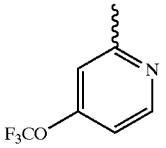 |
TABLE 164-continued
| 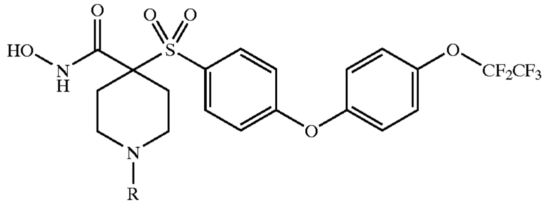 | 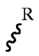 |
|---|---|
| 150 | 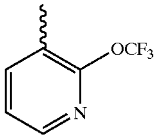 |
| 151 | 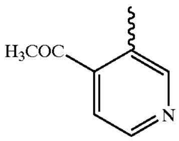 |
| 152 | 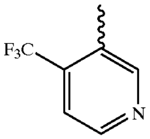 |
| 153 | 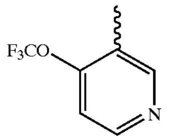 |
| 154 | 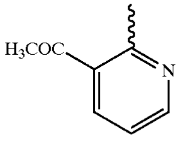 |
| 155 | 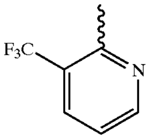 |
| 156 | 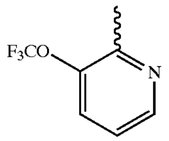 |

TABLE 165
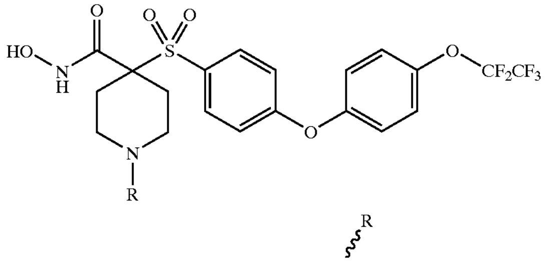
| | |
|---|---|
| 157 | 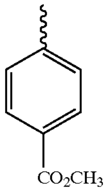 |
| 158 | 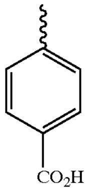 |
| 159 | 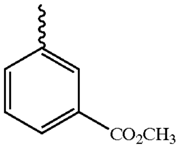 |
| 160 | 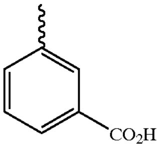 |
| 161 | 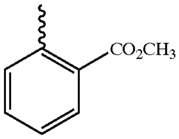 |
| 162 | 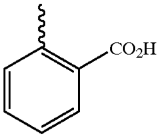 |
| 163 | 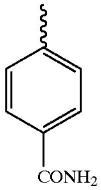 |
TABLE 165-continued
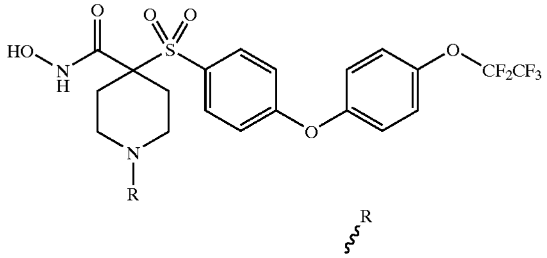
| | |
|---|---|
| 164 | 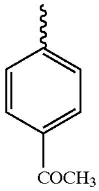 |
| 165 | 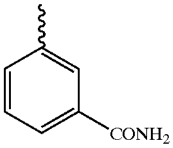 |
| 166 | 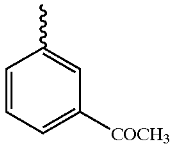 |
| 167 | 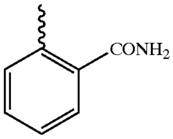 |
| 168 | 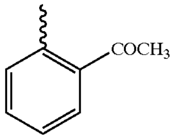 |
| 169 | 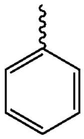 |
| 170 | 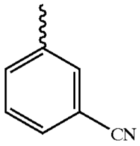 |
| 171 | 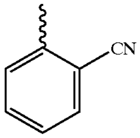 |

TABLE 165-continued

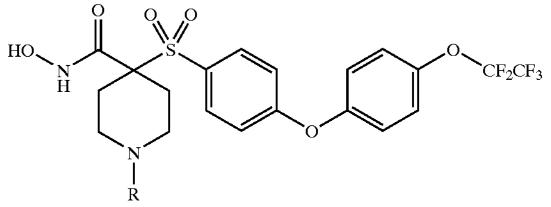

| | 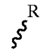 |
|---|---|
| 172 | 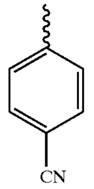 |

Treatment Method

A contemplated inhibitor compound is used for treating a host mammal such as a mouse, rat, rabbit, dog, horse, primate such as a monkey, chimpanzee or human that has a condition associated with pathological matrix metalloprotease activity.

Also contemplated is use of a contemplated metalloprotease inhibitor compound in the treatment of a disease state that can be affected by the activity of metalloproteases TNF-α convertase. Exemplary of such disease states are the acute phase responses of shock and sepsis, coagulation responses, hemorrhage and cardiovascular effects, fever and inflammation, anorexia and cachexia.

In treating a disease condition associated with pathological matrix metalloproteinase activity, a contemplated MMP inhibitor compound can be used in the form of an amine salt derived from an inorganic or organic acid. Exemplary salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

Also, a basic nitrogen-containing group can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others to provide enhanced water-solubility. Water or oil-soluble or dispersible products are thereby obtained as desired. The salts are formed by combining the basic compounds with the desired acid.

Other compounds useful in this invention that are acids can also form salts. Examples include salts with alkali metals or alkaline earth metals, such as sodium, potassium, calcium or magnesium or with organic bases or basic quaternary ammonium salts.

In some cases, the salts can also be used as an aid in the isolation, purification or resolution of the compounds of this invention.

Total daily dose administered to a host mammal in single or divided doses can be in amounts, for example, for 0.001 to 30 mg/kg body weight daily and more usually 0.01 to 10 mg. Dosage unit compositions can contain such amounts or submultiples thereof to make up the daily dose. A suitable dose can be administered, in multiple sub-doses per day. Multiple doses per day can also increase the total daily dose, should this be desired by the person prescribing the drug.

The dosage regimen for treating a disease condition with a compound and/or composition of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed can vary widely and therefore can deviate from the preferred dosage regimen set forth above.

A compound of the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and nonionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, a contemplated aromatic sulfone hydroximate inhibitor compound can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A contemplated aromatic sulfone hydroximate inhibitor compound can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

Best Mode For Carrying Out The Invention

Without further elaboration, it is believed that one skilled in the art can, using the preceding description, utilize the present invention to its fullest extent. The following preferred specific embodiments are, therefore, to be construed as merely illustrative, and not limiting of the remainder of the disclosure in any way whatsoever.

Abbreviations are often used for reagents and solvents in the specific examples that follow. Those abbreviations and their meanings are as follows:

BOC=t-butoxycarbonyl

DEAD=diethyl azodicarboxylate

DMF=dimethylformamide

DMPU=1,3-dimethyl-3,4,5,6-tetrahydro-2(1H)-pyrimidinone

EtOAc=ethyl acetate

EDC=1-ethyl-3-[3-(dimethylamino)propyl]carbodiimide hydrochloride $Et_2O$=diethyl ether HOBT=1-hydroxybenzotriazole MeOH=methanol $MeCl_2$=methylene chloride MsCl=methanesulfonyl chloride NMM=N-methyl morpholine THF=tetrahydrofuran TsCl=toluenesulfonyl chloride THP-O-hydroxylamine=O-tetrahydropyran-hydroxylamine and O-tetrahydro-2H-pyran-2-yl-hydroxylamine The preparation of compounds useful in the synthesis of compounds of the invention are provided herein below in Preparative Examples I through XI.

PREPARATIVE EXAMPLE I

Preparation of 1,1-Dimethylethyl Ester 4-[(Hydroxyamino)carbonyl]-4-[(phenoxyphenyl)-sulfonyl]-1-piperidinecarboxylic Acid

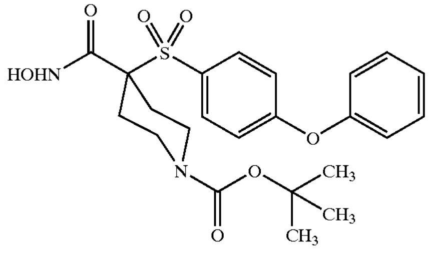

Part A: A solution of 4-(phenoxy)benzenethiol (2.03 g, 10.0 mmol) in DMSO (DMSO; 20 mL) was heated to sixty-five degrees Celsius for 5 hours. The solution remained at ambient temperature for 18 hours. The solution was extracted with ethyl acetate and the combined organic layers were washed with $H_2O$ and saturated NaCl and dried over magnesium sulfate. Concentration in vacuo provided the disulfide as a yellow oil (2.3 g, quantitative yield).

Part B: To a solution of ethyl isonipecotate (15.7 g, 0.1 mol) in THF (100 mL) was added a solution of di-tert-butyl dicarbonate (21.8 g, 0.1 mol) in THF (5 mL) drop-wise over 20 minutes. The solution was stirred overnight (about eighteen hours) at ambient temperature and concentrated in vacuo to yield a light oil. The oil was filtered through silica gel (7:3 ethyl acetate/hexanes) and concentrated in vacuo to give the BOC-piperidine compound (26.2 g, quantitative yield) as a clear, colorless oil.

Part C: To a solution of diisopropylamine (2.8 mL, 20 mmoL) in THF (30 mL), cooled to minus seventy-eight degrees Celsius, was added n-butyl lithium (12.5 mL, 20 mmol) drop-wise. After 15 minutes, the BOC-piperidine compound of part B (2.6 g, 10 mmol) in THF (10 mL) was added drop-wise. After 1.5 hours the solution was cooled to minus sixty degrees Celsius and the disulfide of part A (2.0 g, 10 mmol) in THF (7 mL). The solution was stirred at ambient temperature for 2 hours. The solution was diluted with $H_2O$ and extracted with ethyl acetate. The organic layer was washed with $H_2O$ and saturated NaCl and dried over magnesium sulfate. Chromatography (on silica, ethyl acetate/hexane) provided the sulfide as an oil (1.8 g, 40%).

Part D: To a solution of the sulfide of part C (1.8 g, 3.95 mmol) in dichloromethane (75 mL) cooled to zero degrees Celsius, was added m-chloroperbenzoic acid (1.7 g, 7.9 mmol). The solution was stirred for 1.5 hours followed by dilution with $H_2O$ and extraction with dichloromethane. The organic layer was washed with 10 percent $Na_2SO_4$, $H_2O$, and saturated NaCl and dried over magnesium sulfate.

Chromatography (on silica, ethyl acetate/hexane) provided the sulfone as a solid (1.15 g, 59%).

Part E: To a solution of the sulfone of part D (800 mg, 1.63 mmol) in THF (9 mL) and ethanol (9 mL) was added NaOH (654 mg, 16.3 mmol) in $H_2O$ (3 mL). The solution was heated at sixty-five degrees Celsius for 18 hours. The solution was concentrated in vacuo and the residue was dissolved in $H_2O$. Following acidification with 2N HCl to pH 4, the solution was extracted with ethyl acetate and the organic layer was washed with saturated NaCl and dried over magnesium sulfate. Concentration in vacuo provided the acid as a white foam (790 mg, quantitative yield). Analytical calculated for $C_{23}H_{27}NO_7S$: C, 59.86; H, 5.90; N, 3.04; S, 6.95. Found: C, 59.49; H, 6.37; N, 2.81; S, 6.59.

Part F: To a solution of the acid of part G (730 mg, 1.58 mmol) in DMF (9 mL) was added HOBT (256 mg, 1.90 mmol) followed by EDC (424 mg, 2.21 mmol), 4-methylmorpholine (0.521 mL, 4.7 mmol) and 50 percent aqueous hydroxylamine (1.04 mL, 15.8 mmol). The solution was stirred for 20 hours and additional N-hydroxybenzotriazole.$H_2O$ (256 mg), EDC (424 mg) and 50 percent aqueous hydroxylamine (1.04 mL) were added. After an additional 24 hours of stirring the solution was diluted with $H_2O$ and extracted with ethyl acetate and the organic layer was washed with saturated NaCl and dried over magnesium sulfate. Reverse phase chromatography (on silica, acetonitrile/$H_2O$) provided the title compound as a white solid (460 mg, 61%). HPLC purity: >99%. Analytical calculated for $C_{23}H_{28}N_2O_7S$: C, 57.97; H, 5.92; N, 5.88; S, 6.73. Found: C, 57.95; H, 6.02; N, 5.81; S, 6.85.

PREPARATIVE EXAMPLE II

Preparation of N-Hydroxy-4-[[4-(phenylthio) phenyl]sulfonyl]-1-(2-propynyl)-4-piperidinecarboxamide, Monohydrochloride

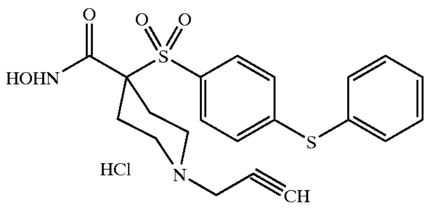

Part A: To a solution of ethyl isonipecotate (15.7 g, 0.1 mol) in THF (100 mL) was added a solution of di-tert-butyl dicarbonate (21.8 g, 0.1 mol) in THF (5 mL) drop-wise over 20 minutes. The solution was stirred overnight (about eighteen hours) at ambient temperature and concentrated in vacuo to yield a light oil. The oil was filtered through silica gel (ethyl acetate/hexanes) and concentrated in vacuo to give the BOC-piperidine compound as a clear, colorless oil (26.2 g, quantitative yield).

Part B: A solution of 4-fluorothiophenol (50.29 g, 390 mmol) in DMSO (500 mL) was heated to 65 degrees Celsius for 6 hours. The reaction was quenched into wet ice and the resulting solid was collected by vacuum filtration to provide the disulfide as a white solid (34.4 g, 68.9%).

Part C: To a solution of the BOC-piperidine compound of part A (16 g, 62 mmol) in THF (300 mL) cooled to minus 50 degrees Celsius was added lithium diisopropylamide (41.33 mL, 74 mmol) and the solution was stirred for 1.5 hours at zero degrees Celsius. To this solution was added the disulfide of part B (15.77 g, 62 mmol), and the resulting solution was stirred at ambient temperature for 20 hours. The reaction was quenched with the addition of $H_2O$ and the solution was concentrated in vacuo. The aqueous residue was extracted with ethyl acetate and the organic layer was washed with 0.5N KOH, $H_2O$, and saturated NaCl. Chromatography (on silica, hexane/ethyl acetate) provided the sulfide as an oil (18.0 g, 75%).

Part D: To a solution of the sulfide of part C (16.5 g, 43 mmol) in dichloromethane (500 mL) cooled to zero degrees Celsius was added 3-chloroperbenzoic acid (18.0 g, 86 mmol) and the solution was stirred for 20 hours. The solution was diluted with $H_2O$ and extracted with dichloromethane. The organic layer was washed with 10 percent $Na_2SO_3$, $H_2O$, and saturated NaCl and dried over magnesium sulfate. Chromatography (on silica, ethyl acetate/hexane) provided the sulfone as a solid (10.7 g, 60%).

Part E: Into a solution of the sulfone of part D (10 g, 24.0 mmol) in ethyl acetate (250 mL) was bubbled HCl gas for 10 minutes followed by stirring at ambient temperature for 4 hours. Concentration in vacuo provided the amine hydrochloride salt as a white solid (7.27 g, 86%).

Part F: To a solution of the amine hydrochloride salt of part E (5.98 g, 17.0 mmol) in DMF (120 mL) was added potassium carbonate (4.7 g, 34.0 mmol) followed by propargyl bromide (2.02 g, 17.0 mmol) and the solution was stirred for 4 hours at ambient temperature. The solution was partitioned between ethyl acetate and $H_2O$, and the organic layer was washed with $H_2O$ and saturated NaCl and dried over magnesium sulfate. Chromatography (on silica, ethyl acetate/hexane) provided the propargyl amine as a yellow oil (5.2 g, 86%).

Part G: To a solution of the propargyl amine of part F in DMF (15 mL) was added thiophenol (0.80 mL, 7.78 mmol) and $CsCO_3$ (2.79 g, 8.56 mmol) and the solution was heated to 70 degrees Celsius for 6 hours. The solution was partitioned between ethyl ether and $H_2O$. The organic layer was washed with $H_2O$ and saturated NaCl, and dried over magnesium sulfate. Chromatography (on silica, ethyl acetate/hexane) provided the S-phenoxyphenyl compound as an oil (1.95 g, 56%).

Part H: To a solution of the S-phenoxyphenyl of part G (1.81 g, 4.06 mmol) in ethanol (21 mL) and $H_2O$ (3.5 mL) was added KOH (1.37 g, 24.5 mmol) and the solution was heated to 105 degrees Celsius for 4.5 hours. The solution was acidified to a pH value of 1 with concentrated HCl solution and then concentrated to provide the acid as a yellow residue that was used without additional purification (1.82 g).

Part I: To a solution of the acid of part H (1.82 g, 4.06 mmol) in acetonitrile (20 mL) was added O-tetrahydro-2H-pyran-2-yl-hydroxylamine (723 mg, 6.17 mmol) and triethylamine (0.67 mL, 4.86 mmol). To this stirring solution was added EDC (1.18 g, 6.17 mmol) and the solution was stirred for 18 hours. The solution was partitioned between $H_2O$ and ethyl acetate. The organic layer was washed with $H_2O$, saturated $NaHCO_3$ and saturated NaCl and dried over magnesium sulfate. Chromatography (on silica, ethyl acetate/hexane) provided the protected hydroxamate as a white solid (1.32 g, 63%).

Part J: To a solution of the protected hydroxamate of part I (9.65 g, 18.7 mmol) in methanol (148 mL) cooled to zero degrees Celsius was added acetyl chloride (4.0 mL, 56.2 mmol), and the solution was stirred for 45 minutes at ambient temperature. Concentration in vacuo followed by trituration with ethyl ether provided the title compound as a white solid (8.10 g, 94%). MS(CI) $MH^+$ calculated for $C_{21}H_{22}N_2O_4S_2$: 431, found 431.

PREPARATIVE EXAMPLE III

Preparation of N-Hydroxy-4-[(4-phenoxyphenyl) sulfonyl]-1-(2-propynyl)-4-piperidinecarboxamide, Monohydrochloride

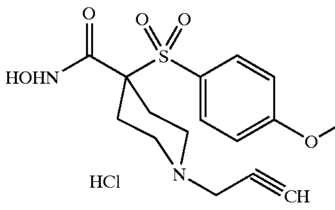

Part A: A solution of 4-(phenoxy)benzenethiol (2.03 g, 10.0 mmol) in DMSO (20 mL) was heated to 65 degrees Celsius for 5 hours. The solution remained at ambient temperature for 18 hours. The solution was extracted with ethyl acetate and the combined organic layers were washed with $H_2O$ and saturated NaCl, and dried over magnesium sulfate. Concentration in vacuo provided the disulfide as a yellow oil (2.3 g, quantitative yield).

Part B: To a solution of ethyl isonipecotate (15.7 g, 0.1 mol) in THF (100 mL) was added a solution of di-tert-butyl dicarbonate (21.8 g, 0.1 mol) in THF (5 mL) dropwise over 20 minutes. The solution was stirred overnight at ambient temperature and concentrated in vacuo to yield a light oil. The oil was filtered through silica gel (ethyl acetate/hexane) and concentrated in vacuo to give the BOC-piperidine compound as a clear, colorless oil (26.2 g, quantitative yield).

Part C: To a solution of diisopropylamine (2.8 mL, 20 mmoL) in THF (30 mL), cooled to minus seventy-eight degrees Celsius, was added n-butyl lithium (12.5 mL, 20 mmol) dropwise. After 15 minutes, the BOC-piperidine compound of Part B (2.6 g, 10 mmol) in THF (10 mL) was added dropwise. After 1.5 hours, the solution was cooled to minus sixty degrees Celsius and the disulfide of Part A (2.0 g, 10 mmol) in THF (7 mL) was added. The solution was stirred at ambient temperature for 2 hours. The solution was diluted with $H_2O$ and extracted with ethyl acetate. The organic layer was washed with $H_2O$ and saturated NaCl and dried over magnesium sulfate. Chromatography (on silica, ethyl acetate/hexane) provided the sulfide as an oil (1.8 g, 40%).

Part D: To a solution of the sulfide of Part C (1.8 g, 3.95 mmol) in dichloromethane (75 mL) cooled to zero degrees Celsius, was added m-chloroperbenzoic acid (1.7 g, 7.9 mmol). The solution was stirred for 1.5 hours followed by dilution with $H_2O$ and extraction with dichloromethane. The organic layer was washed with 10 percent $Na_2SO_4$, $H_2O$, and saturated NaCl and dried over magnesium sulfate. Chromatography (on silica, ethyl acetate/hexane) provided the sulfone as a solid (1.15 g, 59%).

Part E: Into a solution of the sulfone of Part D (3.56 g, 7.0 mmol) in ethyl acetate (100 mL) cooled to zero degrees Celsius was bubbled HCl gas for 5 minutes. Concentration in vacuo followed by trituration with ethyl ether provided the amine hydrochloride salt as a white solid (3.5 g, quantitative yield). MS(CI) $MH^+$ calculated for $C_{20}H_{23}NO_5S$: 390, found 390.

Part F: To a solution of the amine hydrochloride salt of part E (2.6 g, 6 mmol) and $K_2CO_3$ (1.66 g, 12 mmol) in DMF (50 mL) was added propargyl bromide (892 mg, 6 mmol) and the solution was stirred at ambient temperature for 4 hours. The solution was diluted with $H_2O$ and extracted with ethyl acetate. The combined organic layers were washed with saturated NaCl and dried over magnesium sulfate. Chromatography (on silica, ethyl acetate/hexane) provided the propargyl amine as a white solid (2.15 g, 82%).

Part G: To a solution of the propargyl amine of part F (2.15 g, 5 mmol) in THF (30 mL) and ethanol (30 mL) was added NaOH (2.0 g, 50 mmol) and the solution was heated at 65 degrees Celsius for 48 hours. The solution was concentrated in vacuo and the aqueous residue was acidified to a pH value of 5. Vacuum filtration of the resulting precipitate provided the acid as a white solid (2.04 g, quantitative yield).

Part H: To a solution of the acid of part G (559 mg, 1.4 mmol) in dichloromethane (5 mL) was added triethylamine (0.585 mL, 4.2 mmol) and 50 percent aqueous hydroxylamine (0.925 mL, 14.0 mmol) followed by bromotris (pyrrolidino)phosphonium hexafluourphosphate (PyBroP; 718 mg, 1.54 mmol). The solution was stirred at ambient temperature for 4 hours. The solution was diluted with $H_2O$ and extracted with dichloromethane. The organic layer was washed with saturated NaCl and dried over magnesium sulfate. Reverse phase chromatography (on silica, acetonitrile/$H_2O$) provided the hydroxamate as a white solid (140 mg, 25%). Analytical calculation for $C_{21}H_{22}N_2O_5S$: C, 60.85; H, 5.37; N, 6.76; S, 7.74. Found: C, 60.47; H, 5.35; N, 6.61; S, 7.46.

Part I: To a solution of the hydroxamate of part H (121 mg, 0.292 mmol) in methanol (2 mL) cooled to zero degrees Celsius was added acetyl chloride (0.228 mL, 0.321 mmol) in methanol (1 mL). After stirring at ambient temperature for 30 minutes the solution was concentrated under a stream of $N_2$. Trituration with ethyl ether provided the title compound as a white solid (107 mg, 81%). Analytical calculation for $C_{21}H_{22}N_2O_5S.HCl.0.3H_2O$: C, 55.27; H, 5.21; N, 6.14. Found: C, 54.90; H, 5.37; N, 6.07.

PREPARATIVE EXAMPLE IV

Preparation of 4-[(4-Fluorophenyl)sulfonyl] tetrahydro-N-[(tetrahydro-2H-pyran-2-yl)oxy]-2H-pyran-4-carboxamide

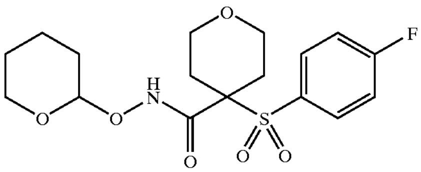

Part A: In dry equipment under nitrogen, sodium metal (8.97 g, 0.39 mol) was added to methanol (1000 mL) at two degrees Celsius. The reaction was stirred at ambient temperature for forty five minutes at which time the sodium had dissolved. The solution was chilled to five degrees Celsius and p-fluorothiophenol (41.55 mL, 0.39 mmol) was added, followed by methyl 2-chloroacetate (34.2 mL, 0.39 mol). The reaction was stirred at ambient temperature for four hours, filtered, and concentrated in vacuo to give the sulfide as a clear colorless oil (75.85 g, 97%).

Part B: To a solution of the sulfide from part A (75.85 g, 0.38 mol) in methanol (1000 mL) were added water (100 mL) and Oxone (720 g, 1.17 mol) at 20 degrees Celsius. An exotherm to 67 degrees Celsius was noted. After two hours, the reaction was filtered and the cake was washed well with methanol. The filtrate was concentrated in vacuo. The residue was taken up in ethyl acetate and washed with brine, dried over $MgSO_4$, filtered, and concentrated in vacuo to give the sulfone as a crystalline solid (82.74 g, 94%).

Part C: To a solution of the sulfone from part B (28.5 g, 0.123 mol) in N,N-dimethylacetamide (200 mL) were added potassium carbonate (37.3 g, 0.27 mol), bis-(2-bromoethyl) ether (19.3 mL, 0.147 mol), 4-dimethylaminopyridine (0.75 g, 6 mmol), and tetrabutylammonium bromide (1.98 g, 6 mmol). The reaction was stirred overnight (about 18 hours) at ambient temperature. The reaction was slowly poured into 1N HCl (300 mL), the resultant solid filtered and the cake washed well with hexanes. The solid was recrystallized from ethyl acetate/hexanes to give the pyran compound as a beige solid (28.74 g, 77%). MS (ES+) MH+ calculated for $C_{13}H_{15}O_5S_1F_1$: 303, found 303.

Part D: In dry equipment under nitrogen, the pyran compound from part C (8.0 g, 26.5 mmol) was dissolved in dry tetrahydrofuran (250 mL) and a solution of potassium trimethylsilonate (10.2 g, 79.5 mmol) in dry tetrahydrofuran (15 mL) was added at ambient temperature. After ninety minutes, water (100 mL) was added and the solution concentrated in vacuo. The residue was taken up in water and extracted with ethyl acetate to remove unreacted starting material. The aqueous solution was treated with 6N HCl until pH=1. The slurry was extracted with ethyl acetate and the combined extracts washed with water, dried over $Na_2SO_4$, filtered, and concentrated in vacuo. The residue was heated in diethyl ether, the solid filtered and dried to give the carboxylic acid as a crystalline solid (5.78 g, 76%). HRMS (ES−) M−H calculated for $C_{12}H_{13}O_5S_1F_1$: 287.04, found 287.04.

Part E: In dry equipment under nitrogen, the carboxylic acid from part D (9.1 g, 31.6 mmol) was dissolved in dry N,N-dimethylformamide (70 mL) and the remaining reagents were added to the solution in the following order: N-hydroxybenzotriazole hydrate (5.1 g, 37.9 mmol), N-methylmorpholine (10.4 mL, 94.8 mmol), O-tetrahydro-2H-pyran-2-yl-hydroxylamine (11.5 g, 98 mmol), and 1-(3-dimethylaminopropyl)-3-ethylcarbodiimide hydrochloride (8.48 g, 44.2 mmol). After three hours at ambient temperature, the reaction was concentrated in vacuo. The residue was taken up in ethyl acetate, washed with water, 5% $KHSO_4$, saturated $NaHCO_3$, brine, dried over $Na_2SO_4$, filtered, and concentrated in vacuo. Chromatography (on silica, ethyl acetate/hexanes) provided the title compound as a crystalline solid (9.7 g, 80%). HRMS (ES+) MH+ calculated for $C_{17}H_{22}NO_6S_1F_1$: 388.12, found 388.12.

PREPARATIVE EXAMPLE V

Preparation of Tetrahydro-N-hydroxy-4-[[4-[4-trifluoromethoxy)phenoxy)phenyl]sulfonyl]-2H-pyran-4-carboxamide

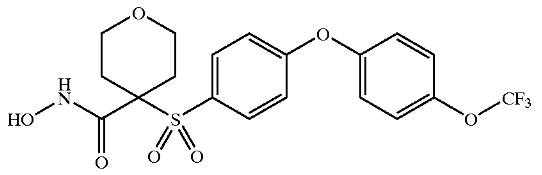

Part A: To a solution of the title compound of Preparative Example IV (3.1 g, 8 mmol) in N,N-dimethylacetamide (20 mL) were added cesium carbonate (8.8 g, 27 mmol) and p-(trifluoromethoxy)phenol (2.1 mL, 16 mmol). The slurry was stirred at 95 degrees Celsius for nineteen hours. The reaction was concentrated in vacuo. The residue was taken up in ethyl acetate, washed with brine, dried over $Na_2SO_4$, filtered, and concentrated in vacuo. Chromatography (on silica, ethyl acetate/hexanes) provided the substituted THP-protected hydroxamate as a white foam (4.2 g, 96%). HRMS (ES+) MH+ calculated for $C_{24}H_{26}N_1O_8S_1F_3$: 546.14, found 546.14.

Part B: To a slurry of the THP-protected hydroxamate from part A (4.0 g, 7.3 mmol) in dioxane (20 mL) were added a 4N HCl dioxane solution (20 mL) and methanol (20 mL). After fifteen minutes at ambient temperature, the reaction was diluted with ethyl acetate and washed with water, dried over $Na_2SO_4$, filtered, and concentrated in vacuo. The product was recrystallized (acetone/hexanes) to give the title compound as a white solid (2.2 g, 65%). HRMS (ES+) M+ $NH_4^+$ calculated for $C_{19}H_{18}N_1O_7S_1F_3$: 479.11, found 479.11.

PREPARATIVE EXAMPLE VI

Preparation of 1-Cyclopropyl-N-hydroxy-4-[[4-(2-phenoxyethoxy)phenyl]sulfonyl]-4-piperidine Carboxamide, Monohydrochloride

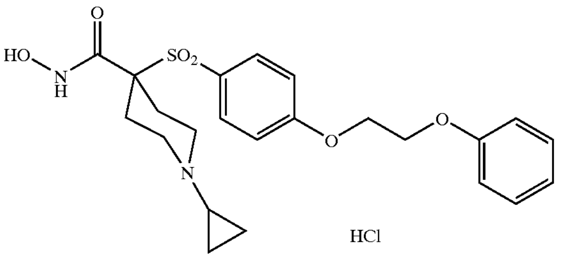

Part A: To a solution of the product of Preparative Example II, part E, (14.36 g, 40 mmol) in methanol (50 mL) was added acetic acid (24.5 g, 400 mmol), a portion (about 2 g) of 4-Ångstrom molecular sieves, (1-ethoxycyclopropyl)-oxytrimethyl silane (25.8 mL, 148 mmol) and sodium cyanoborohydride (7.05 g, 112 mmol). The solution was heated at reflux for 8 hours. The precipitated solids were removed by filtration and the filtrate was concentrated in vacuo. The residue was diluted with $H_2O$ (400 mL) and extracted with ethyl acetate. The organic layer was washed with saturated NaCl and dried over $MgSO_4$, filtered and concentrated in vacuo. The solid was filtered, washed with $H_2O$/diethyl ether to give the desired cyclopropyl amine {ethyl 4-[(4-fluorophenyl-sulfonyl)]-1-cyclopropyl-4-piperidinecarboxylate} as a white solid (11.83 g, 81.5%). MS $MH^+$ calculated for $C_{17}H_{22}NO_4SF$: 356, found: 356.

Part B: A solution of the cyclopropyl amine of Part A (2.0 g, 5.6 mmol), ethylene glycol phenyl ether (2.8 mL, 23 mmol), and cesium carbonate (7.3 g, 23 mmol) in DMAC (10 mL) was heat at 125–135 degrees Celsius for 18 hours under an atmosphere of nitrogen. The mixture was concentrated in vacuo, diluted with water, and extracted with ethyl acetate. The combined ethyl acetate layers were washed with water and brine, dried over magnesium sulfate, concentrated in vacuo, dissolved in diethyl ether, precipitated as the hydrochloride salt, and dried at 40 degrees Celsius in a vacuum oven. The solid was dissolved into a mixture of water, acetonitrile, and ethanol and then the pH was adjusted to 12 with 1N NaOH solution. The mixture was concentrated in vacuo to remove ethanol and acetonitrile. The solid was isolated by filtration, washed with water, and dried at 50 degrees Celsius in a vacuum oven to afford the ether as a white solid (1.8 g, 68%): MS+ calcd. for $C_{25}H_{31}NO_6S$ 474, found 474. Anal. calcd. for $C_{25}H_{31}NO_6S$: C, 63.40; H, 6.60; N, 2.96; S, 6.77. Found: C, 63.35; H, 6.59; N, 2.99; S, 6.61.

Part C: A mixture of the ether of part B (1.8 g, 3.7 mmol) and a 50% NaOH aqueous solution (3.0 g, 37 mmol) in THF (32 mL), EtOH (32 mL), and $H_2O$ (16 mL) was heated at 60 degrees Celsius under a nitrogen atmosphere for 24 hours. The material was concentrated in vacuo and triturated with diethyl ether to give a solid. The tan solid was dissolved into a mixture of water, ethanol, and THF, precipitated by adjusting the pH to 3 with concentrated hydrochloric acid, concentrated in vacuo, triturated with water, and dried at 50 degrees Celsius in a vacuum oven to give a crude white solid acid (2.3 g).

A mixture of the crude white solid acid (2.3 g), N-hydroxybenzotriazole (1.9 g, 14 mmol), 4-methylmorpholine (1.6 mL, 14 mmol), O-tetrahydro-2H-pyran-2-yl-hydroxylamine (1.1 g, 9.4 mmol), and 1-(3-dimethylaminopropyl)-3-ethylcarbodiimide hydrochloride (2.7 g, 14 mmol) in DMF (90 mL) was stirred at ambient temperature under a nitrogen atmosphere for 2 days. The mixture was concentrated in vacuo, diluted with water, and extracted with ethyl acetate. The organic layer was washed with 1N NaOH solution, water, and brine, dried over magnesium sulfate, concentrated in vacuo, and purification by flash chromatography (20:80 to 40:60 ethyl acetate/toluene) to afford the protected hydroxamate as a white solid: (0.43 g, 21%): MS MH+ calcd. for $C_{28}H_{36}N_2O_7S$ 545, found 545. Anal. calcd. for $C_{28}H_{36}N_2O_7S$: C, 61.74; H, 6.66; N, 5.14; S, 5.89. Found: C, 61.72; H, 6.75; N, 5.06; S, 5.91.

Additional compound was isolated by acidifying the aqueous layer to pH of 3, collecting the solid by filtration, and drying to give a white solid (0.80 g).

Part D: To an ambient temperature solution of acetyl chloride (0.31 mL, 4.4 mmol) in methanol (11 mL) under a nitrogen atmosphere was added the protected hydroxamate of part C (0.80 g, 1.5 mmol). After stirring for 2.5 hours, the precipitate was collected by filtration, washed with diethyl ether, and dried at 45 degrees Celsius in a vacuum oven to afford the title compound as a white solid (0.58 g, 79%): MS MH+ calcd. for $C_{23}H_{28}N_2O_6S$ 461, found 461. Anal. calcd. for $C_{23}H_{28}N_2O_6S.1.5HCl$: C, 53.62; H, 5.77; N, 5.44; S, 6.22. Found: C, 53.47; H, 5.79; N, 5.41; S, 6.16.

PREPARATIVE EXAMPLE VII

Preparation of N-Hydroxy-1-(2-methoxyethyl)-4-[[4-[4-(trifluoromethoxy)phenoxy]phenyl]sulfonyl}-4-piperidinecarboxamide, Monohydrochloride

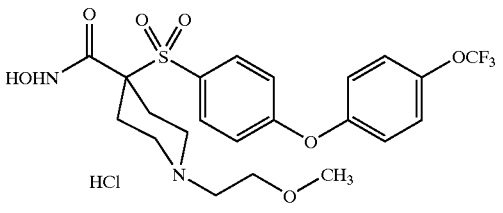

Part A: To a solution of the product of Preparative Example II, Part D (30 g, 161 mmol) in dichloromethane (50 mL) cooled to zero degrees Celsius was added trifluroacetic acid (25 mL) and the solution was stirred at ambient temperature for 1 hour. Concentration in vacuo provided the amine trifluoroacetate salt as a light yellow gel. To the solution of the trifluoroacetate salt and $K_2CO_3$ (3.6 g, 26 mmol) in N,N-dimethylformamide (50 mL) cooled to zero degrees Celsius was added 2-bromoethyl methyl ether (19 mL, 201 mmol), and solution was stirred at ambient temperature for 36 hours. Then, N,N-dimethylformamide was evaporated under high vacuum and the residue was diluted with ethyl acetate. The organic layer was washed with water and dried over $MgSO_4$. Concentration in vacuo provided the methoxyethyl amine as a light yellow gel (26.03 g, 86.8%).

Part B: To a solution of methoxyethyl amine (6.0 g, 16.0 mmol) of Part A and powdered $K_2CO_3$ (4.44 g, 32 mmol) in N,N-dimethylformamide (30 mL) was added 4-(trifluoromethoxy)phenol (5.72 g, 32 mmol) at ambient temperature and the solution was heated to ninety degrees Celsius for 25 hours. The solution was concentrated under high vacuum and the residue was dissolved in ethyl acetate. The organic layer was washed with 1N NaOH, $H_2O$ and dried over $MgSO_4$. Chromatography on silica eluting with ethyl acetate/hexane provided trifluoromethoxy phenoxyphenyl sulfone as a light yellow gel (7.81 g, 91.5%).

Part C: To a solution of trifluoromethoxy phenoxyphenyl sulfone of Part B (7.81 g, 14.7 mmol) in ethanol (14 mL) and tetrahydrofuran (14 mL) was added NaOH (5.88 g, 147 mmol) in $H_2O$ (28 mL) from an addition funnel at ambient temperature. The solution was then heated to sixty degrees Celsius for 18 hours. The solution was concentrated in vacuo and diluted with water. The aqueous layer was extracted with ether and acidified to pH=2. Vacuum filtration of white precipitation provided the acid as a white solid (5.64 g, 73.3%).

Part D: To a solution of the acid of Part C (5.64 g, 10.8 mmol), N-methyl morpholine (4.8 mL, 43.1 mmol), 1-hydroxybenzotriazole (4.38 g, 32.4 mmol) and O-tetrahydropyranyl hydroxyl amine (2.5 g, 21.6 mmol) in N,N-dimethylformamide (50 mL) was added 1-[3-(dimethylamino)propyl]-3-ethylcarbodiimide hydrochloride (6.2 g, 32.4 mmol), and the solution was stirred at ambient temperature for 24 hours. The solution was concentrated under high vacuum and the residue was dissolved in ethyl acetate. The organic layer was washed with saturated aqueous $NaHCO_3$, $H_2O$ and dried over $MgSO_4$. Concentration in vacuo and chromatography on silica eluting with ethyl acetate/hexane provided the tetrahydropyranyl-protected hydroxamate as a white foam (6.65 g, quantitative yield).

Part E: To a solution of 4N HCl in dioxane (28 mL, 110 mmol) was added a solution of the tetrahydropyranyl-protected hydroxamate of Part D (6.65 g, 11.03 mmol) in methanol (3 mL) and dioxane (9 mL) and was stirred at ambient temperature for 3 hours. Concentration in vacuo and trituration with diethyl ether provided the title compound as a white solid (4.79 g, 78.2%). Analytical calculation for $C_{22}H_{25}N_2O_7SF_3.HCl.0.5H_2O$: C, 46.85; H, 4.83; N, 4.97; S, 5.69. Found: C, 46.73; H, 4.57; N, 4.82; S, 5.77.

PREPARATIVE EXAMPLE VIII

Preparation of N-Hydroxy-1-[2-(4-morpholinyl)-ethyl]-4-[[4-[4-(trifluoromethyl)phenoxy]-phenyl] sulfonyl]-4-piperidinecarboxamide, Dihydrochloride

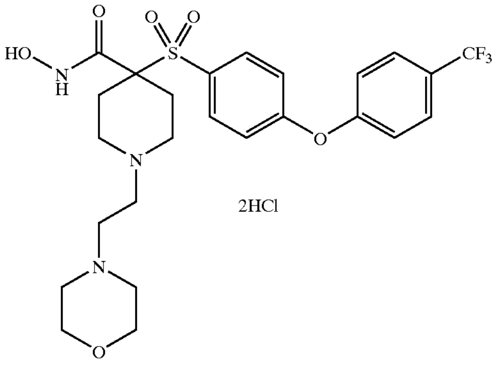

2HCl

Part A: To a suspension of 4-bromopiperidine hydrobromide (107.0 g, 0.436 mol) in tetrahydrofuran (1 L) was slowly added triethylamine (122 mL, 0.872 mol) followed by di-tert-butyl dicarbonate (100 g, 0.458 mol), which was added in several portions. The resulting mixture was stirred at ambient temperature for 22 hours then filtered and concentrated in vacuo. The solids were washed with hexanes and then collected by filtration to give the Boc-piperidine compound as an amber oil (124 g, >100%).

Part B: To a solution of 4-fluorophenol (50.0 g, 0.390 mol) in acetone (400 mL), degassed with $N_2$, was added $Cs_2CO_3$ (159 g, 0.488 mol). After degassing the resulting mixture with $N_2$ for 5 minutes, the Boc-piperidine compound of Part A (85.9 g, 0.325 mol) was added. The resulting mixture was stirred at ambient temperature for 18 hours and then filtered through a pad of Celite®, washing with acetone. The filtrate was concentrated in vacuo to provide the sulfide as a tan residue (98.5 g, 97%).

Part C: To a solution of the sulfide of Part B (8.00 g, 25.7 mmol) in dichloromethane (90 mL) and methanol (15 mL) was added monoperoxyphthalic acid magnesium salt hexahydrate (19.1 g, 38.6 mmol) in two portions. The resulting mixture was stirred at ambient temperature for 1.5 hours and then filtered. The filtrate was washed with saturated $NaHCO_3$ and then with saturated NaCl. The combined aqueous layers were extracted with dichloromethane (100 mL). The combined organic layers were dried over $Na_2SO_4$ and then concentrated in vacuo. The resulting solids were washed with hexanes then dissolved in dichloromethane and filtered through a pad of Celite®, washing with dichloromethane. The filtrate was concentrated in vacuo and recrystallization from ethyl acetate provided the sulfone as a white crystalline solid (4.45 g, 50%).

Part D: To a solution of sulfone of Part C (7.00 g, 20.4 mmol) in N,N-dimethylformamide (40 mL) was added $Cs_2CO_3$ (19.9 g, 61.2 mmol) and α,α,α-trifluoro-p-cresol (3.97 g, 24.5 mmol). The resulting mixture was heated at eighty degrees Celsius for 16 hours. After cooling to ambient temperature the reaction mixture was concentrated in vacuo. The resulting residue was treated with $H_2O$ and the solids were collected by filtration. The solids were then washed with hexanes then methanol to provide the biaryl ether as a tan solid (8.60 g, 87%).

Part E: To a solution of the biaryl ether of Part D (8.59 g, 17.7 mmol) in tetrahydrofuran (100 mL), cooled to zero degrees Celsius, was slowly added lithium bis (trimethylsilyl)amide (22.0 mL, 1.0M in tetrahydrofuran, 22.0 mmol), at such a rate that the temperature of the reaction never exceeded one degree Celsius. The resulting mixture was stirred at zero degrees Celsius for 1 hour then a solution of methyl chloroformate (2.05 mL, 26.6 mmol) in tetrahydrofuran (5.0 mL) was slowly added, at such a rate that the temperature of the reaction mixture never exceeded four degrees Celsius. After the addition was complete, the mixture was slowly permitted to warm to ambient temperature. Saturated $NH_4Cl$ (50 mL) was added and the tetrahydrofuran was removed in vacuo. Water (50 mL) was added to the residue which was then extracted with ethyl acetate. The combined organic layers were washed with saturated NaCl and dried over $Na_2SO_4$. Recrystallization from methanol provided the methyl ester as a pale yellow crystalline solid (7.66 g, 80%).

Part F: To a solution of the methyl ester of Part E (7.66 g, 14.1 mmol) in dioxane (30 mL) and methanol (10 mL) was added a solution of 4N HCl in dioxane (10 mL, 40 mmol). After stirring at ambient temperature for 2 hours additional 4N HCl in dioxane (10 mL, 40 mmol) was added. After stirring at ambient temperature for 2.5 hours, the reaction mixture was concentrated in vacuo to provide the amine as an off-white solid (6.80 g, >100%).

Part G: To a suspension of the amine of Part F (3.00 g, 6.25 mmol) in acetonitrile (20 mL) was added $K_2CO_3$ (3.46 g, 25.0 mmol), 4-(2-chloroethyl)morpholine hydrochloride (1.22 g, 6.56 mmol) and a catalytic amount of NaI. The resulting mixture was heated at reflux for 22 hours. After cooling to ambient temperature, the reaction mixture was filtered through a pad of Celite®, washing with ethyl acetate. The filtrate was concentrated in vacuo to provide the morpholinyl ethyl amine as a tan solid (3.45 g, >100%).

Part H: To a solution of the morpholinyl ethyl amine of Part G (3.45 g, 6.25 mmol) in tetrahydrofuran (60 mL) was added potassium trimethylsilanolate (1.60 g, 12.50 mmol). After stirring at ambient temperature for 25 hours, $H_2O$ was added. The reaction mixture was then neutralized (pH 7) with 1N HCl. The tetrahydrofuran was removed in vacuo and the resulting precipitate was collected by filtration and washed with diethyl ether to provide the amino acid as an off-white solid (2.87 g, 85%).

Part I: To a suspension of the amino acid of Part H (2.87 g, 5.29 mmol) in dichloromethane (25 mL) was added N-methylmorpholine (1.74 mL, 15.9 mmol), O-(tetrahydropuranyl) hydroxylamine (0.682 g, 5.82 mmol) and PyBroP® (2.96 g, 6.35 mmol). After stirring at ambient temperature for 19 hours additional N-methylmorpholine (0.872 mL, 7.94 mmol), O-(tetrahydropuranyl) hydroxylamine (0.310 g, 2.65 mmol) and PyBroP® (1.48 g, 3.17 mmol) were added. The resulting mixture was stirred at ambient temperature for 3 hours and then concentrated in vacuo. The residue was partitioned between ethyl acetate and $H_2O$. The organic layers were washed with saturated NaCl and dried over $Na_2SO_4$. Chromatography (on silica, methanol/chloroform) provided the protected hydroxamate as an off-white solid (2.62 g, 77%).

Part J: To a solution of the protected hydroxamate of Part I (2.62 g, 4.08 mmol) in dioxane (9 mL) and methanol (3 mL) was added a solution of 4N HCl in dioxane (10 mL, 40.0 mmol). The resulting mixture was stirred at ambient temperature for 2 hours and then diethyl ether (20 mL) was added. The resulting solids were collected by filtration to give the title compound as an off-white solid (2.31 g, 90%). MS $MH^+$ calculated for $C_{25}H_{31}O_6N_3SF_3$: 558, found 558.

PREPARATIVE EXAMPLE IX

Preparation of 1-Cyclopropyl-N-hydroxy-4-[[4-[4-(trifluoromethoxy)phenoxy]-phenyl]sulfonyl]-4-piperidinecarboxamide, Monohydrochloride

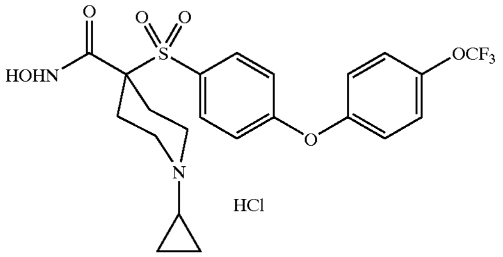

Part A: To a solution of the product of Preparative Example VI, Part A, (6.97 g, 19.6 mmol) in DMF (500 mL) was added $K_2CO_3$ (3.42 g, 18.0 mmol) and 4-(triflouromethoxy)phenol (3.7 g, 24.8 mmol). The solution was stirred at ninety degrees Celsius for 40 hours. The solution was diluted with $H_2O$ (600 mL) and extracted with ethyl acetate. The organic layer was washed with water, saturated NaCl and dried over $MgSO_4$, filtered and concentrated in vacuo to afford the desired diaryl ether as an oil (8.5 g, quantitative). HRMS $MH^+$ calculated for $C_{24}H_{26}NSO_6F_3$: 514.1511. Found 514.1524.

Part B: To a solution of diaryl ether from Part A (8.4 g, 16.4 mmol) in ethanol (50 mL) and tetrahydrofuran (50 mL) was added a solution of NaOH (6.54 g, 164 mmol) in water (20 mL) and the solution was heated at sixty degrees Celsius for 18 hours. The solution was concentrated in vacuo to remove most of organic solvents and the aqueous residue was acidified to pH=4.0. The resulting precipitate was filtered to give the desired filtered to give the hydrochloride salt as a white solid (5.01 g, 63%). HRMS $MH^+$ calculated for $C_{22}H_{22}NSO_6F_3$: 486.1198, found 486.1200.

Part C: To a solution of the hydrochloride salt of Part B (5.0 g, 10.3 mmol) in DMF (80 mL) were added 1-hydroxybenzotriazole (1.65 g, 12.3 mmol), N-methyl morpholine (3.4 mL, 30.9 mmol) and O-tetrahydropyranyl hydroxylamine hydrochloride (1.8 g, 15.4 mmol) followed by 1-3-(dimethylamino)propyl]-3-ethylcarbodiimide hydrochloride (1.60 g, 12.3 mmol). The solution was stirred at ambient temperature for 42 hours. The solution was diluted with $H_2O$ (400 mL) and extracted with ethyl acetate. The organic layer was washed with saturated NaCl and dried over $MgSO_4$, filtered and concentrated in vacuo. Chromatography on silica gel, eluting with 30% ethyl acetate/hexane provided the desired tetrahydropyranyl-protected hydroxamate as a white solid (5.41 g, 89%).

Part D: To a solution of tetrahydropyranyl-protected hydroxamate of Part C (5.4 g, 9.2 mmol) in dioxane (80 mL) and methanol (20 mL) was added 4 N HCl/dioxane (50 mL). The reaction was stirred at ambient temperature for 2.5 hours, the solution was concentrated in vacuo. Trituration with diethyl ether afforded the title compound as a white solid (4.02 g, 81%). HRMS $MH^+$ calculated for $C_{22}H_{23}N_2SO_6F_3$: 501.1307, found 501.1324.

PREPARATIVE EXAMPLE X

Preparation of 1-Cyclopropyl-N-hydroxy-4-[[4-[4-(trifluoromethyl)phenoxy]phenyl]sulfonyl]-4-piperidinecarboxamide, Monohydrochloride

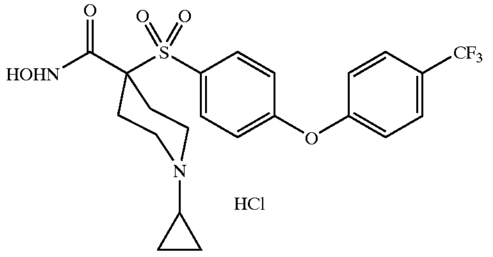

Part A: To a solution of the product of Preparative Example VI, Part A, (5.96 g, 15.0 mmol) in DMF (100 mL) was added $K_2CO_3$ (12.34 g, 38.0 mmol) and α,α,α-trifluoromethyl phenol (3.65 g, 22.5 mmol). The solution was stirred ninety degrees Celsius for 28 hours. The solution was diluted with $H_2O$ (400 mL) and extracted with ethyl acetate. The organic layer was washed with water, saturated NaCl and dried over $MgSO_4$, filtered and concentrated in vacuo to afford desired aryl ether as an oil (7.54 g, quantitative)

Part B: To a solution of aryl ether from Part A (7.54 g, 15.0 mmol) in ethanol (40 mL) and tetrahydrofuran (40 mL) was added a solution of NaOH (6.06 g, 151.0 mmol) in water (20 mL) and the solution was heated at sixty degrees Celsius for 18 hours. The solution was concentrated in vacuo and the aqueous residue was acidified to pH=2.0. The resulting precipitate was filtered to give the desired hydrochloride salt as a white solid (7.98 g, quantitative). MS $MH^+$ calculated for $C_{22}H_{22}NSO_5F_3$: 470, found 470.

Part C: To a solution of the hydrochloride salt of Part B (7.60 g, 15.0 mmol) in DMF (100 mL) were added 1-hydroxybenzotriazole (2.44 g, 18.0 mmol), N-methyl morpholine (3.4 mL, 30.9 mmol ) and O-tetrahydropyranyl hydroxyl amine hydrochloride (2.63 g, 22.5 mmol) followed by 1-3-(dimethylamino)propyl]-3-ethylcarbodiimide hydrochloride (4.02 g, 21.0 mmol). The solution was stirred at ambient temperature for 96 hours. The solution was diluted with $H_2O$ (400 mL) and extracted with ethyl acetate. The organic layer was washed with saturated NaCl and dried over $MgSO_4$, filtered and concentrated in vacuo. Chromatography on silica eluting with 30% ethyl acetate/hexane provided the desired tetrahydropyranyl-protected hydroxamate as a white solid (5.93 g, 69%).

Part D: To a solution of tetrahydropyranyl-protected hydroxamate of Part C (3.8 g, 6.7 mmol) in dioxane (100 mL) was added 4 N HCl/dioxane (30 mL). The reaction was stirred at ambient temperature for 2 hours, then the solution was concentrated in vacuo. Trituration with diethyl ether afforded the title compound as a white solid (3.33 g, 96%). MS $MH^+$ calculated for $C_{22}H_{23}N_2SO_5F_3$: 485, found 485.

PREPARATIVE EXAMPLE XI

Preparation of Resin II

Step 1: Attachment of Compound of Preparative Example IV to Resin I

A 500 mL round-bottomed flask was charged with of resin I [Floyd et al., *Tetrahedron Lett.* 1996, 37, 8045–8048] (8.08 g, 9.7 mmol) and 1-methyl-2-pyrrolidinone (50 mL). A magnetic stirring bar was added, and the resin slurry slowly stirred. A separate solution of the compound of Part D, Preparative Example IV (5.58 g, 19.4 mmol) in 1-methyl-2-pyrrolidinone (35 mL) was added to the slurry followed by addition of benzotriazole-1-yl-oxy-tris-pyrrolidino-phosphonium hexafluorophosphate (10.1 g, 19.4 mmol) in one portion. Once the hexafluorophosphate salt had dissolved, 4-methylmorpholine (4.26 mL, 39 mmol) was added dropwise. The reaction slurry was stirred at room temperature for 24 hours, then the resin was collected in a sintered-disc funnel and washed with N,N-dimethylformamide, methanol, methylene chloride and diethyl ether (3x30 mL each solvent). The resin was dried in vacuo to yield 10.99 g polymer-bound hydroxymate as a tan polymeric solid. Theoretical loading on polymer was 0.91 mmol/g. FTIR microscopy showed bands at 1693 and 3326 $cm_{-1}$ indicative of the hydroxamate carbonyl and nitrogen-hydrogen stretches, respectively.

Step 2: Preparation of Resin III: Reaction of Resin II With Nucleophiles

Resin II (50 mg, 0.046 mmol) was weighed into an 8 mL glass vial, and a 0.5 M solution of a nucleophile in 1-methyl-2-pyrrolidinone (1 mL) was added to the vessel. In the case of phenol and thiophenol nucleophiles, cesium carbonate (148 mg, 0.46 mmol) was added, and in the case of substituted piperazine nucleophiles, potassium carbonate (64 mg, 0.46 mmol) was added. The vial was capped and heated to 70 to 155 degrees Celsius for 24–48 hours, then cooled to room temperature. The resin was drained and washed with 1-methyl-2-pyrrolidinone, 1-methyl-2-pyrrolidinone/water (1:1), water, 10% acetic acid/water, methanol, and methylene chloride (3x3 mL each solvent).

Large Scale Preparation of Resin IIIa:

Resin II (5 g, 0.91 mmol) was weighed into an oven-dried three-necked round bottom flask fitted with a temperature probe, an overhead stirring paddle, and a nitrogen inlet. Anhydrous 1-methyl-2-pyrrolidinone (35 mL) was added to the flask followed by ethyl isonipecotate (7.0 mL, 45.5 mmol). The resin slurry was stirred slowly with the overhead stirrer, and the mixture was heated to 80 degrees Celsius with a heating mantle for 65 hours. The flask was thereafter cooled to room temperature.

The resin was collected in a sintered-disk glass funnel and washed with N,N-dimethylformamide, methanol and methylene chloride (3x30 mL each solvent). The resin was dried in vacuo to provide 5.86 g of resin IIIa as off-white resin beads. The theoretical loading of the polymer was 0.81 mmol/g. TFA cleavage performed on 50 mg of resin IIIa as described in step 3 yielded 10.4 mg of off-white solid spectroscopically indistinguishable from a known sample.

Step 3: Cleavage of Hydroxamic Acids From The Polymer-support

Resin III was treated with a trifluoroacetic acid/ water mixture (19:1, 1 mL) for 1 hour at room temperature. During that time, the resin became a deep red color. The resin was then drained and washed with trifluoroacetic acid/water (19:1) and methylene chloride (2x1 mL each solvent), collecting the combined filtrates in a tared vial. The volatiles were removed in vacuo, then a toluene/methylene chloride mixture (2 mL each) was added to the residue. The mixture was again concentrated in vacuo. The product was characterized by electrospray mass spectroscopy.

Step 4: Hydrolysis of Polymer-bound Ester: Preparation of Resin IVa

Resin IIIa (5.8 g, 4.5 mmol) was weighed into a three-necked round bottomed flask fitted with an overhead stirring paddle. 1,4-Dioxane was added to the flask, and the resin slurry was stirred for 15 minutes. Then, a 4 M solution of KOH (5 mL, 20 mmol) was added, and the mixture was stirred for 44 hours. The resin was thereafter collected in a sintered-disk glass funnel and washed with dioxane/water (9:1), water, 10% acetic acid/water, methanol and methylene chloride (3x30 mL each solvent). The resin was dried in vacuo to yield 5.64 g of resin IVa as off-white polymer beads. FTIR microscopy showed bands at 1732 and 1704 $cm_{-1}$ and a broad band from 2500–3500 $cm_{-1}$. The theoretical loading of the polymer-bound acid was 0.84 mmol/g.

EXAMPLE 1

Preparation of 1-(2-Methoxyethyl)-4-[[4-[4-(trifluoromethoxy)phenoxy]phenyl]sulfonyl]-4-piperidinecarboxamide

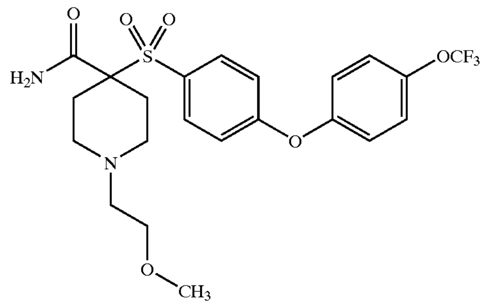

Part A: To a solution of the product of Preparative Example II, part D, (30 g, 161 mmol) in dichloromethane (50 mL) cooled to zero degrees Celsius was added trifluroacetic acid (25 mL) and the solution was stirred at ambient temperature for 1 hour. Concentration in vacuo provided the amine trifluoroacetate salt as a light yellow gel. To the solution of the trifluoroacetate salt and $K_2CO_3$ (3.6 g, 26 mmol) in N,N-dimethylformamide (50 mL) cooled to zero degrees Celsius was added 2-bromoethyl methyl ether (19 mL, 201 mmol) and solution was stirred at ambient temperature for 36 hours. Then N,N-dimethylformamide was evaporated under high vacuum and the residue was diluted with ethyl acetate. The organic layer was washed with water and dried over $MgSO_4$. Concentration in vacuo provided the methoxyethyl amine as a light yellow gel (26.03 g, 86.8%).

Part B: To a solution of the methoxyethyl amine (6.0 g, 16.0 mmol) of part A and powdered $K_2CO_3$ (4.44 g, 32 mmol) in N,N-dimethylformamide (30 mL) was added 4-(trifluoromethoxy)phenol (5.72 g, 32 mmol) at ambient temperature and the solution was heated to ninety degrees Celsius for 25 hours. The solution was concentrated under high vacuum and the residue was dissolved in ethyl acetate. The organic layer was washed with 1N NaOH, $H_2O$ and dried over $MgSO_4$. Chromatography on silica eluting with ethyl acetate/hexane provided trifluoromethoxy phenoxyphenyl sulfone as a light yellow gel (7.81 g, 91.5%).

Part C: To a solution of trifluoromethoxy phenoxyphenyl sulfone of part B (7.81 g, 14.7 mmol) in ethanol (14 mL) and tetrahydrofuran (14 mL) was added NaOH (5.88 g, 147 mmol) in $H_2O$ (28 mL) from an addition funnel at ambient temperature. The solution was then heated to sixty degrees Celsius for 18 hours. The solution was concentrated in vacuo and diluted with water. The aqueous layer was extracted with ether and acidified to pH=2. Vacuum filtration of the white precipitation provided the carboxylic acid as a white solid (5.64 g, 73.3%).

Part D: To a suspension of the carboxylic acid of part C (200 mg, 0.397 mmol) in methylene chloride (4 mL) was added oxalyl chloride (101 mg, 0.80 mmol). After 15 minutes at ambient temperature the volatiles were removed under vacuum. The solid residue was resuspended in methylene chloride (4 mL) and gaseous ammonia was bubbled through the suspension. Triethylamine (81 mg, 0.80 mmol) was added and the stream of ammonia gas through the reaction was continued for 1 minute. Concentration afforded a solid which was chromatographed (reverse phase $C_{18}$ silica eluting with a gradient of 30% acetonitrile/water to 100% acetonitrile) to afford the desired primary amide as a colorless powder (6 mg, 3 mg). MS $MH^+$ calculated for $C_{22}H_{25}N_2F_3O_6S$: 503, found 503. HRMS M+ calculated for $C_{22}H_{25}N_2F_3O_6S$: 503.1464, found 503.1472.

EXAMPLE 2

Preparation of 4-[(4-Phenylthiophenyl)sulfonyl]-1-(2-propynyl)-4-piperidinecarboxamide

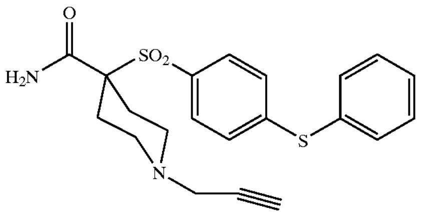

A mixture of the acid from Preparative Example II, part H, (1.29 g, 2.85 mMol), N-hydroxybenzotriazole (1.15 g, 8.54 mMol), 4-methylmorpholine (0.94 mL, 14 mMol), concentrated $NH_4OH$ (3 mL), and 1-(3-dimethylaminopropyl)-3-ethylcarbodiimide hydrochloride (1.64 g, 8.54 mMol) in DMF (25 mL) was stirred at ambient temperature for 20 hours. The mixture was concentrated in vacuo, diluted with water, and extracted with ethyl acetate. The organic layer was washed with saturated $NaHCO_3$, water, and brine, dried over magnesium sulfate, and concentrated in vacuo. Chromatography (on silica, MeOH/$CHCl_3$) afford the title amide as a white solid (0.143 g, 12%). Analytical calculation for $C_{21}H_{22}N_2O_3S_2$: C, 60.84; H, 5.35; N, 6.76; S, 15.47. Found: C, 60.74; H, 5.31; N, 6.74; S, 15.43.

EXAMPLES 3–58

The following compounds were prepared by parallel synthesis (resin based synthesis, automated synthesis) using parallel synthesis from Resin IVa as described previously in Preparative Example XI the following compounds were prepared:

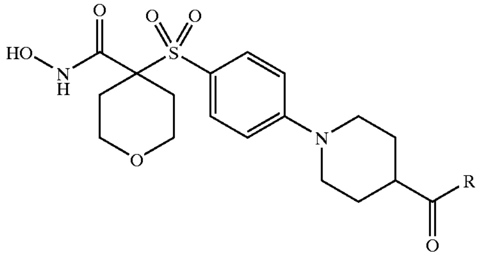

| Example | Amine | R | MS (M + H) |
|---|---|---|---|
| 3 | 3,5-Dimethylpiperidine | 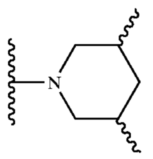 | 508 |
| 4 | N-Methylpropargylamine | 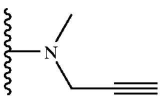 | 464 |
| 5 | N-Methylallylamine | 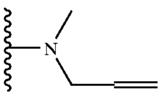 | 466 |

-continued
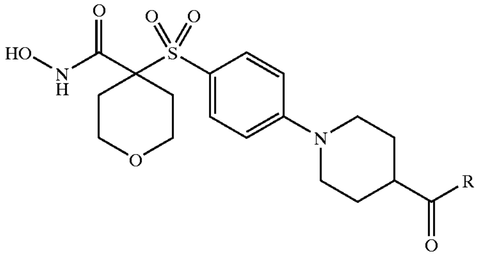
| Example | Amine | R | MS (M + H) |
| --- | --- | --- | --- |
| 6 | 1-(1-phenylethyl)-piperazine | 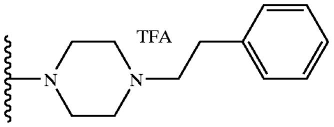 | 585 |
| 7 | 1-(2-phenylethyl)-piperazine | 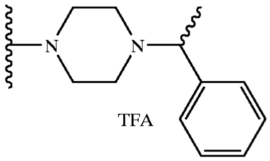 | 585 |
| 8 | 1-(2-chlorophenyl)-piperazine | 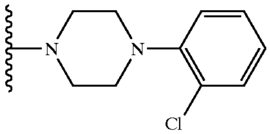 | 591 |
| 9 | 1-(4-methoxyphenyl)-2-methylpiperazine | 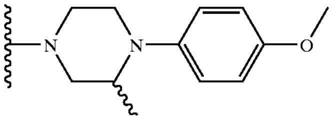 | 585 |
| 10 | 1-(5-Chloro-2-methylphenyl)piperazine | 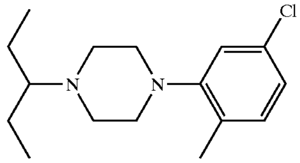 | 605 |
| 11 | 1-(2-methoxyphenyl)-piperazine | 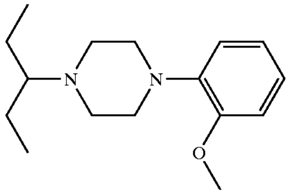 | 587 |
| 12 | 1-Acetylpiperazine | 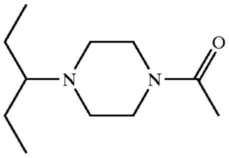 | 523 |

-continued
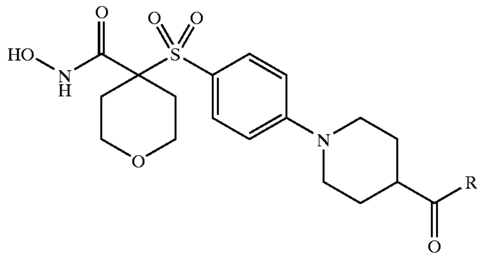
| Example | Amine | R | MS (M + H) |
|---|---|---|---|
| 13 | 1-(2,4-Dimethylphenyl)-piperazine | 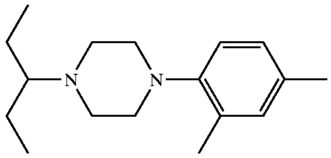 | 585 |
| 14 | N-(2-hydroxyethyl)-piperazine | 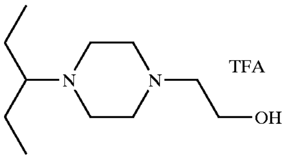 | 525 |
| 15 | 1-(Ethoxy-carbonylmethyl)-piperazine | 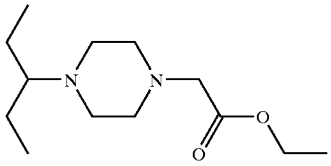 | 567 |
| 16 | 1-(2-Fluorophenyl)-piperazine | 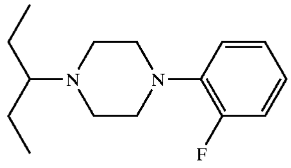 | 575 |
| 17 | 1-(2-Furoyl)-piperazine | 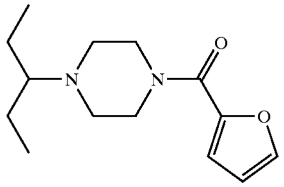 | 575 |
| 18 | 1-(Cyclopentyl)-piperazine | 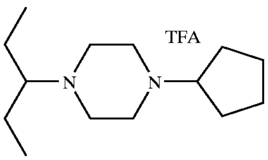 | 549 |
| 19 | 1-(2-Propyl)-piperazine | 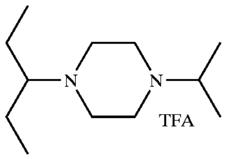 | 523 |

-continued
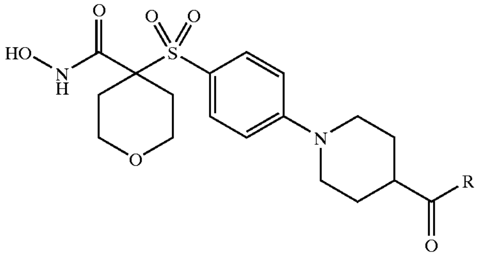
| Example | Amine | R | MS (M + H) |
|---|---|---|---|
| 20 | N-(2-(1-Piperazino)-acetyl)pyrrolidine | 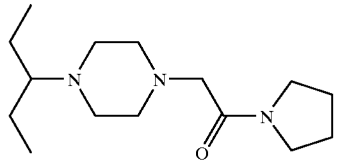 | 592 |
| 21 | 1-(3-Dimethyl-aminopropyl)-piperazine | 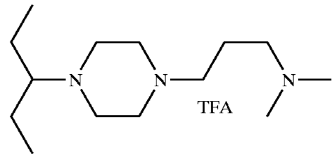 | 566 |
| 22 | 1-(2-Methoxyethyl)-piperazine | 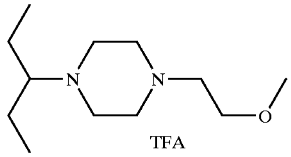 | 539 |
| 23 | 1-(2-Dimethyl-aminoethyl)-piperazine | 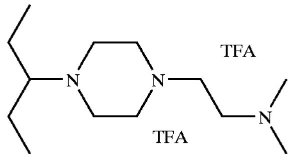 | 552 |
| 24 | 1-(2-Ethoxyphenyl)-piperazine | 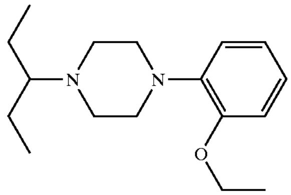 | 601 |
| 25 | 1-(4-Fluorophenyl)-piperazine | 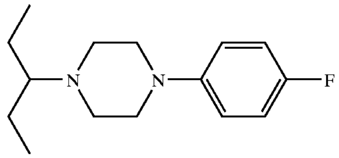 | 575 |
| 26 | 1-(2-Pyridyl)-piperazine | 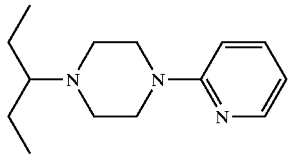 | 558 |

-continued
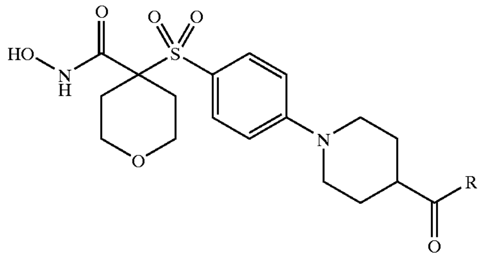
| Example | Amine | R | MS (M + H) |
|---|---|---|---|
| 27 | 2-(1-piperazinyl)-pyrimidine | 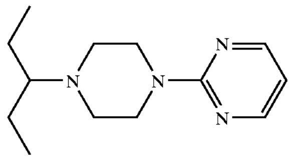 | 559 |
| 28 | 4-Piperazino-acetophenone | 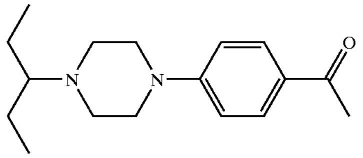 | 599 |
| 29 | 1-(4-Nitrophenyl)-piperazine | 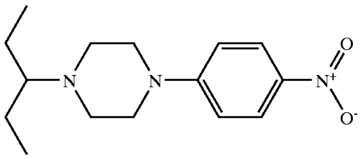 | 602 |
| 30 | 1-(3,5-Dichloropyrid-4-yl)piperazine | 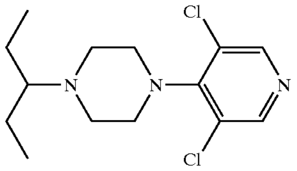 | 626 |
| 31 | 4-(2-Methoxyphenyl)-piperidine | 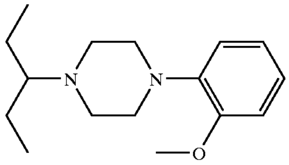 | 586 |
| 32 | N-[2-Nitro-4-(trifluoromethyl)-phenyl]piperazine | 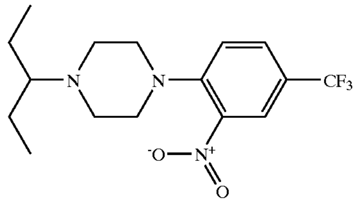 | 670 |
| 33 | 1-[3-(Trifluoromethyl)-pyrid-2-yl]-piperazine | 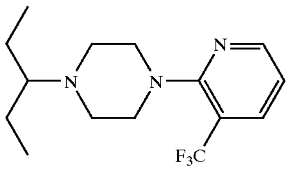 | 626 |

-continued
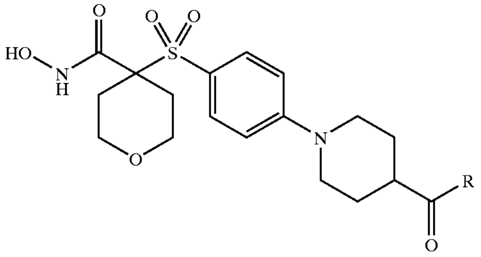
| Example | Amine | R | MS (M + H) |
|---|---|---|---|
| 34 | cis-3,5-Dimethyl-morpholine | 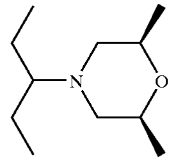 | 510 |
| 35 | N-Propylcyclopropane-methylamine | 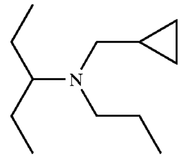 | 508 |
| 36 | 1-(2,4-Difluorphenyl)-piperazine | 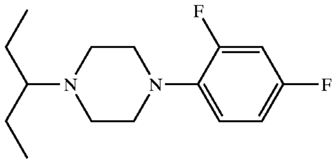 | 593 |
| 37 | 1-(4-Pyridyl)-piperazine | 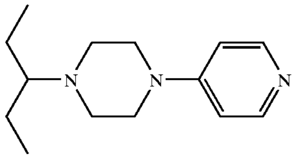 | 558 |
| 38 | 1-(4-Trifluoromethyl-phenyl)-piperazine | 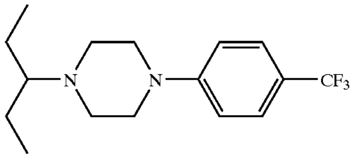 | 625 |
| 39 | 1-Allylpiperazine | 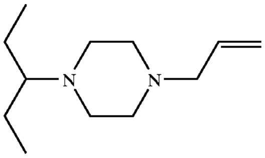 | 521 |
| 40 | 1-(2-Pyrazinyl)-piperazine | 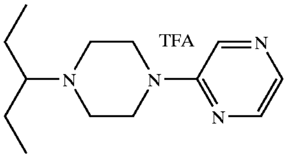 | 559 |

-continued
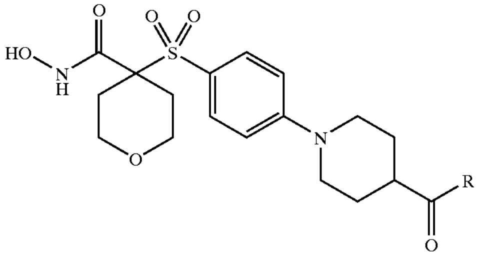
| Example | Amine | R | MS (M + H) |
|---|---|---|---|
| 41 | 1-[3-Chloro-5-(trifluoromethyl)pyrid-2-yl)]piperazine | 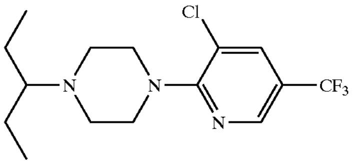 | 660 |
| 42 | 1-(2-(4-Morpholino)-ethyl)piperazine | 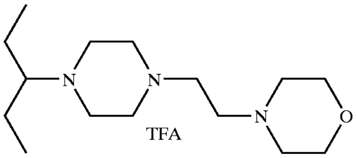 TFA | 594 |
| 43 | 3-Chlorophenyl-piperazine | 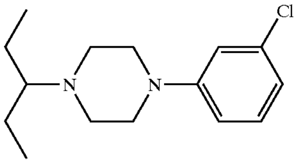 | 591 |
| 44 | 4-(Hydroxymethyl)-piperidine | 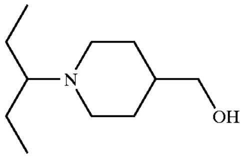 | 510 |
| 45 | Diisobutylamine | 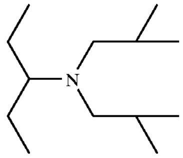 | 524 |
| 46 | cis-2,6-Dimethyl-piperazine | 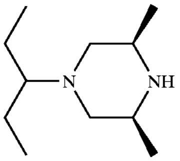 TFA | 509 |
| 47 | 3-Methylpiperidine | 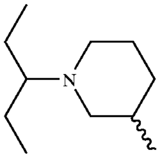 | 494 |

-continued
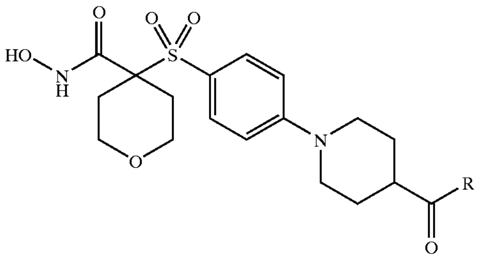
| Example | Amine | R | MS (M + H) |
|---|---|---|---|
| 48 | N,N-Diallylamine | 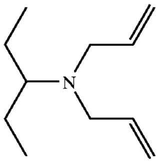 | 492 |
| 49 | 1-[4-(Trifluormethyl)-2-pyrimidyl]-piperazine | 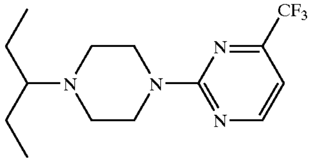 | 627 |
| 50 | 1-[4-(Trifluoromethyl)-2-pyridyl]-piperazine | 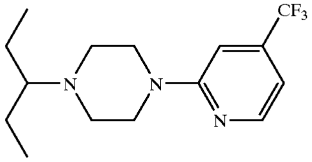 | 626 |
| 51 | N,N,N'-Trimethyl-ethylenediamine | 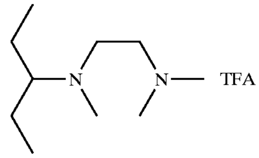 | 497 |
| 52 | (4-Ethylaminomethyl)-pyridine | 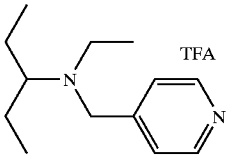 | 531 |
| 53 | Methyl-cyclopropylamine | 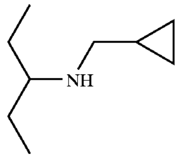 | 466 |
| 54 | 3,5-Dimethyl-piperidine | 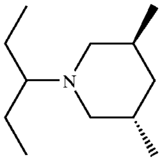 | 508 |

-continued

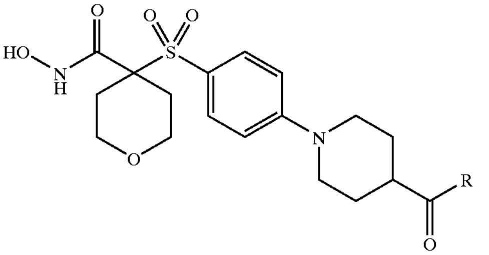

| Example | Amine | R | MS (M + H) |
|---|---|---|---|
| 55 | 3,5-Dimethyl-piperidine | 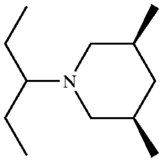 | 508 |
| 56 | Isobutylamine | 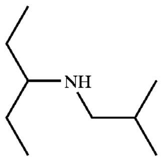 | 468 |
| 57 | Propylamine | 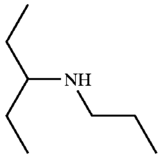 | 454 |
| 58 | N-Methyl-isobutylamine | 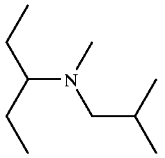 | 482 |

EXAMPLES 59–78

Step 5: Preparation of Resin V

Into a fritted reaction vessel was weighed resin IVa (100 mg, 0.083 mmol), and the vessel was capped under nitrogen and cooled to zero degrees Celsius. A 1.0 M solution of 2-chloro-4,6-dimethoxy-1,3,5-triazine in methylene chloride (0.4 mL, 0.4 mmol) was added followed by a 1.0 M solution of N-methylmorpholine in methylene chloride (0.6 mL, 0.6 mmol). The solutions were stirred for 4 hours at zero degrees Celsius and warmed to ambient temperature. A 0.7 M solution of the appropriate amine to be reacted in methylene chloride (0.4 mL, 0.28 mmol) was added and the reaction mixture stirred for 24 hours. The reaction mixture was stirred for 24 hours, then the resin was drained and washed with 1-methyl-2-pyrrolidinone and methylene chloride (4x3 mL each solvent). The reaction was repeated using the same amounts of reagents described above. The reaction was stirred for 4 hours at zero degrees Celsius after the activating step and ambient temperature for 24 hours following amine solution addition. After 24 hours, the resin was drained and washed with 1-methyl-2-pyrrolidinone, 1:1 1-methyl-2-pyrrolidinone/water, water, 1:9 acetic acid/water, methanol and methylene chloride (3x3 mL each solvent).

The following hydroxamic acids were synthesized using the indicated polymer-bound acid and the indicated amine in Step 5 followed by release from the polymer using Step 3, before:

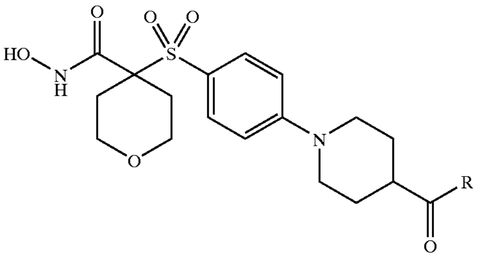
| Example | Amine | R | MS (M + H) |
|---|---|---|---|
| 59 | Aniline | 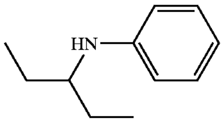 | 488 |
| 60 | N-Methylaniline | 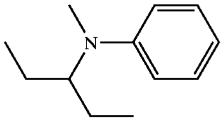 | 502 |
| 61 | 4-(Trifluoromethyl)-aniline | 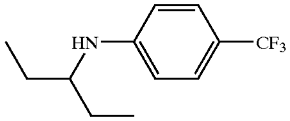 | 556 |
| 62 | 4-Aminopyridine | 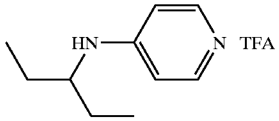 | 489 |
| 63 | 2-(Trifluoromethoxy)-aniline | 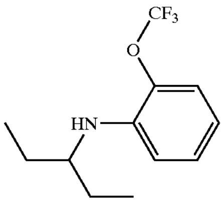 | 572 |
| 64 | 2-Chloroaniline | 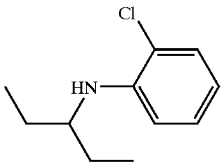 | 522 |
| 65 | 2-Fluoroaniline | 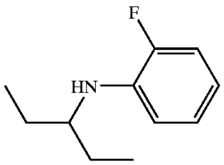 | 506 |
| 66 | o-Anisole | 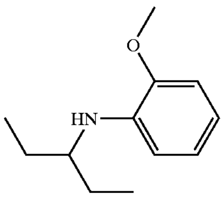 | 518 |

-continued
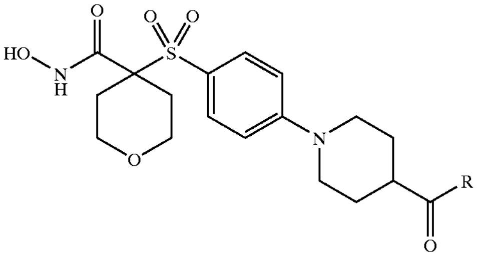
| Example | Amine | R | MS (M + H) |
|---|---|---|---|
| 67 | 2-(Methylamino)-pyridine | 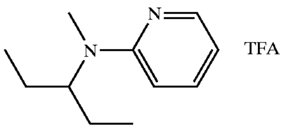 | 503 |
| 68 | 3-(Trifluoromethoxy)-aniline | 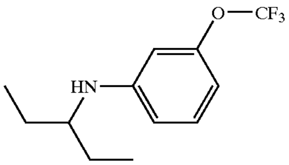 | 572 |
| 69 | 3-(Trifluoromethyl)-aniline | 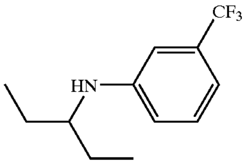 | 556 |
| 70 | 3-Chloroaniline | 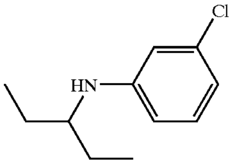 | 522 |
| 71 | 3-Fluoroaniline | 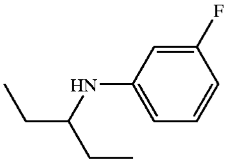 | 506 |
| 72 | m-Anisole | 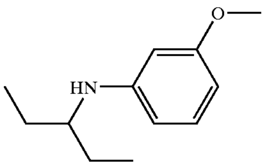 | 518 |
| 73 | 4-(Trifluoromethoxy)-aniline | 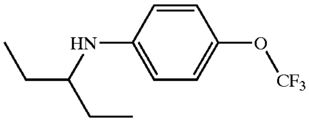 | 572 |

-continued

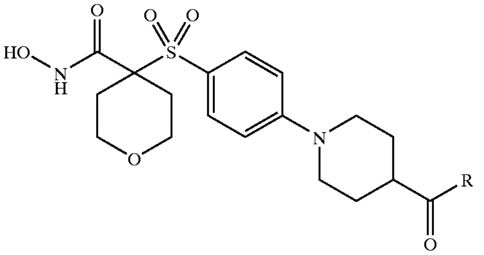

| Example | Amine | R | MS (M + H) |
|---|---|---|---|
| 74 | 4-Aminopyrmidine | 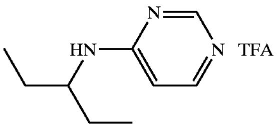 | 490 |
| 75 | 4-Fluoroaniline | 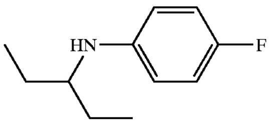 | 506 |
| 76 | p-Anisole | 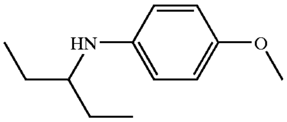 | 518 |
| 77 | N,N-Dimethyl-1,3-phenylenediamine | 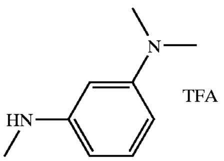 | 531 |
| 78 | N,N-Dimethyl-p-phenylenediamine | 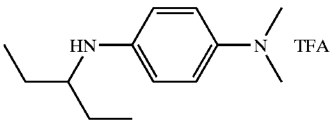 | 531 |

EXAMPLES 79–88

Step 12: Further Synthesis of Resin III.

Into a 8 mL glass vial was placed resin II (200 mg, 0.18 mmol) and cesium carbonate (0.98 g mg, 3 mmol) (no cesium carbonate used with piperidine and pyrrolidine nucleophiles). One mL of a 1.8 M solution of the amine nucleophile to be reacted in 1-methyl-2-pyrrolidinone (1.8 mmol) was added and the vial was capped and heated to 100 degrees Celsius for 30 hours. Then the vessel was cooled to room temperature, and the resin was drained and washed with 1-methyl-2-pyrrolidinone, 1:1 1-methyl-2-pyrrolidinone/water, water, 1:9 acetic acid/water, methanol and methylene chloride (3x3 mL each solvent).

The following hydroxamic acids were synthesized from Resin III using Step 11 with the indicated amines, followed by release from the polymer using the reaction conditions in Step 3.

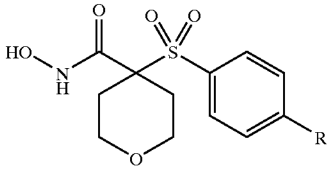
| Example | Amine | R | MS (M + H) |
|---|---|---|---|
| 79 | 1-(2-Methoxyphenyl)-piperidine | 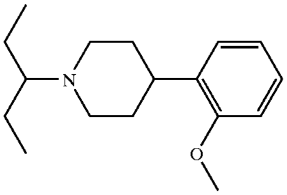 | 475 |
| 80 | 4-(4-Methoxybenzoyl)-piperidine | 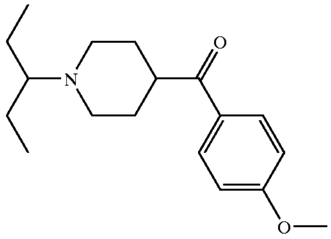 | 503 |
| 81 | Pyrrolidine | 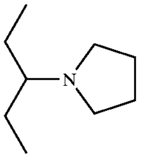 | 355 |
| 82 | 1-(4-Methoxyphenyl)-2-piperazine | TFA 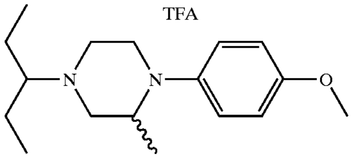 | 490 |
| 83 | 1-(2-Fluorophenyl)-piperazine | 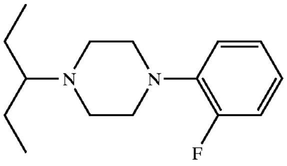 | 464 |
| 84 | 1-(2,4-Dimethylphenyl)-piperazine | TFA 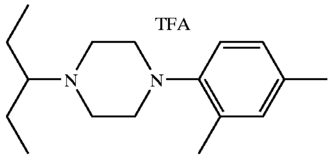 | 474 |
| 85 | 1-(2-Methoxyphenyl-piperazine | TFA 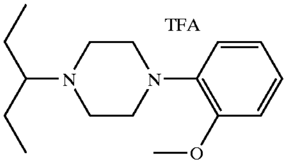 | 476 |

-continued

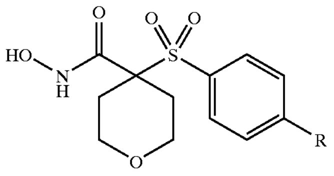

| Example | Amine | R | MS (M + H) |
|---|---|---|---|
| 86 | 1-(4-Trifluoromethyl-phenyl)piperazine | 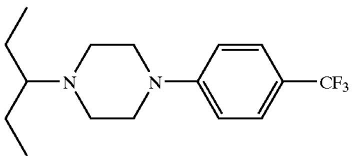 | 514 |
| 87 | 1-(2,4-Difluorophenyl)-piperazine | 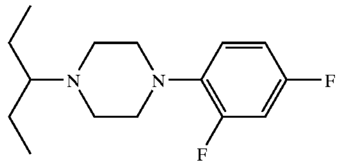 | 482 |
| 88 | 1-(2-Chlorphenyl)-piperazine | 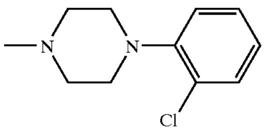 | 480 |

EXAMPLE 89

Preparation of N-Hydroxy-4[[4-(4-trifluoromethoxyphenoxy)phenyl]sulfonyl]-1-(9-fluorenylmethoxycarbonyl)-4-piperidinecarboxamide

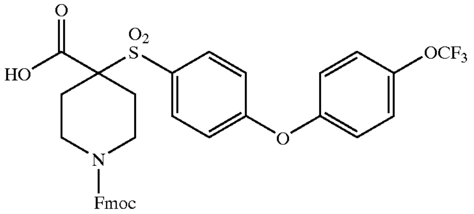

To a solution of 4-[[4-(4-trifluoromethoxyphenoxy) phenyl]sulfonyl]-1-[(1,1diemthylethoxy)carbonyl] piperidinecarboxylic acid (6.25 g, 11.5 mmol) prepared using techniques discussed elsewhere herein was added 50% trifluoroacetic acid solution in dichloromethane (100 mL) and stirred 1 hour at room temperature. The solvent was evaporated to afford 9.91 g of an oil. The oil was dissolved in acetonitrile (50 mL) and water (50 mL). To the solution was added sodium carbonate to a pH~9–10 followed by a solution of N-(9-fluorenylmethoxycarbonyloxy)succinimide (3.88 g, 11.5 mmol) in acetone (25 mL). The pH value of the solution was adjusted to 9–10 with sodium carbonate. The reaction mixture was stirred 16 hours. To the reaction mixture was added 2M aqueous hydrochloric acid to a pH value of about 3. The solution was extracted with dichloromethane (3×100 mL). The combined organics were dried over magnesium sulfate, filtered and the solvent evaporated to afford N-hydroxy-4[[4-(4-trifluoromethoxyphenoxy) phenyl]sulfonyl]-1-(9-fluorenylmethoxycarbonyl)-4-piperidinecarboxamide (8.15 g) as a yellow oil. MS (ES) m/z 668 $(M+H)^+$.

EXAMPLE 90

Preparation of N-Hydroxy-4[[4-(4-trifluoromethylphenoxy)phenyl]sulfonyl]-1-(9-fluorenylmethoxycarbonyl)-4-piperidinecarboxamide

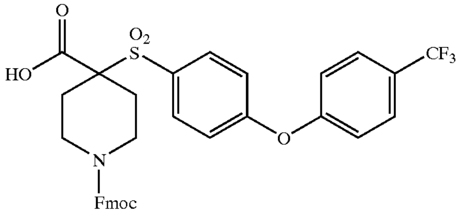

Using the method of Example 89, N-hydroxy-4-[[4-(4-trifluoromethyl-phenoxy)phenyl]sulfonyl]-1-(9-fluorenyl-methoxycarbonyl)-4-piperidinecarboxamide was prepared from 4-[[4-(4-trifluoromethylphenoxy)phenyl]-sulfonyl]-1-[(1,1-dimethylethoxy)carbonyl]-piperidinecarboxylic acid, which itself was prepared using techniques discussed elsewhere herein. MS (ES) m/z 652 $(M+H)^+$.

EXAMPLE 91

Preparation of N-Hydroxy-4-[[4-(4-trifluoromethoxyphenoxy)phenyl]sulfonyl]-1-(phenylcarbonyl)-4-piperidinecarboxamide

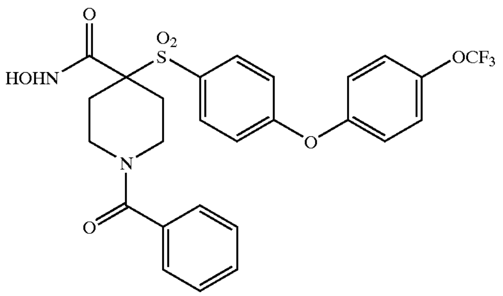

Step 1: Preparation of Resin MT-I. To a solution of N-hydroxy-4-[[4-(4-trifluoromethoxyphenoxy)phenyl]sulfonyl]-1-(9-fluorenylmethoxycarbonyl)-4-piperidinecarboxamide of Example 89 (11.5 mmol) in dimethylformamide (75 mL) were added resin I (Floyd et al., *Tetrahedron Lett.* 1996, 37, 8045–8048) (7.0 g, 7.67 mmol), pyBOP (8.0 g) and N-methylmorpholine (5.05 mL), and the mixture was stirred with an overhead stirrer 4 days. The resin was filtered and washed with dimethylformamide (3×50 mL), methanol (3×50 mL), dichloromethane (3×50 mL) and ether (3×50 mL). The resin was dried in vacuo to provide resin MT-I.

Step 2: Fmoc deprotection of Resin MT-I. Resin MT-I was swelled with dimethylformamide (2×100 mL) and drained. To swollen resin MT-1, was added a 20% solution of piperidine in dimethylformamide (100 mL). After 1 hour, the resin was drained and retreated with 20% piperidine in dimethylformamide (100 mL). After 15 minutes the resin was filtered and washed with dimethylformamide (3×100 mL), methanol (3×100 mL), dichloromethane (3×100 mL) and ether (3×100 mL). The resin was dried in vacuo to afford resin MT-II (7.23 g).

Step 3: Preparation of N-hydroxy-4-[[4-(4-trifluoromethoxyphenoxy)phenyl]sulfonyl]-1-(phenylcarbonyl)-4-piperidinecarboxamide from Resin MT-II. To a suspension of resin MT-II (250 mg) in dichloromethane (2 mL) was added diisopropylethylamine (165 μL) and benzoyl chloride (110 μL) and agitated 3 hours. The resin was filtered and washed with dichloromethane (2×10 mL) and methanol (2×10 mL). To the resin was added a solution of 95% trifluoroacetic acid in water and agitated for 1 hour. The resin was drained and washed with methanol (1×2 mL) and dichloromethane (1×2 mL). The filtrate was evaporated. The residue was purified by RPHPLC to afford N-hydroxy-4-[[4-(4-trifluoromethoxyphenoxy)phenyl]sulfonyl]-1-(phenylcarbonyl)-4-piperidinecarboxamide (9.8 mg) as a solid. MS (ES) m/z 565 $(M+H)^+$.

EXAMPLE 92

Preparation of N-Hydroxy-4-[[4-(4-trifluoromethylphenoxy)phenyl]sulfonyl]-1-(phenylcarbonyl)-4-piperidinecarboxamide

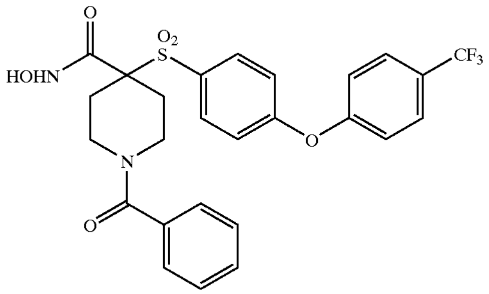

N-hydroxy-4-[[4-(4-trifluoromethylphenoxy)phenyl]sulfonyl]-1-(phenylcarbonyl)-4-piperidinecarboxamide was prepared by the method of Example 91 from N-hydroxy-4-[[4-(4-trifluoromethylphenoxy)phenyl]sulfonyl]-1-(9-fluorenylmethoxycarbonyl)-4-piperidinecarboxamide (the product of Example 90). MS (ES) m/z 549 $(M+H)^+$.

EXAMPLE 93

Preparation of N-(2-Tetrahydropyranoxy)-4-[[4-(4-trifluoromethoxyphenoxy)phenyl]sulfonyl]-4-piperidinecarboxamide

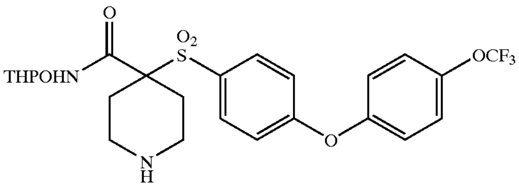

Step 1: Boc deprotection of ethyl 4-[[4-(4-trifluoromethoxyphenoxy)phenyl]sulfonyl]-1-[(1,1-dimethylethoxy)carbonyl]piperidinecarboxylate. To a solution of ethyl 4-[[4-(4-trifluoromethoxyphenoxy)phenyl]sulfonyl]-1-[(1,1-dimethylethoxy)carbonyl]piperidinecarboxylate (12.58 g, 19.1 mmol; see Example 89) in dichloromethane (50 mL) was added trifluoroacetic acid (50 mL) and the mixture was stirred at room temperature for 1 hour. The reaction mixture was evaporated to afford a pale yellow oil.

Step 2: Cbz protection of step 1. The material from step 1 was dissolved in dichloromethane (200 mL). To this solution was added diisopropylethylamine (33.3 mL) and benzyl chloroformate (5.5 mL) and the mixture was stirred at room temperature for 1 hour. To the reaction mixture was added 2M aqueous hydrochloric acid to a pH value of about 1 and extracted with dichloromethane (2×100 mL). The combined organics were washed with 2M aqueous HCl (1×100 mL) and brine (1×100 mL), dried over magnesium sulfate, filtered and the solvent evaporated to afford a pale yellow oil.

Step 3: Hydrolysis of the product of step 2. The material prepared in step 2 was dissolved in tetrahydrofuran (100 mL) and ethanol (50 mL). To this solution was added 1M aqueous sodium hydroxide (50 mL) and 50% aqueous sodium hydroxide (10 mL) and stirred 16 hours. To the solution was added 50% aqueous sodium hydroxide (2 mL) and stirred and additional 24 hours. The tetrahydrofuran and ethanol were evaporated. The pH value of the solution was adjusted to pH about 1 with concentrated hydrochloric acid. The reaction mixture was extracted with ethyl acetate (2×100 mL), washed with brine (1×100 mL), dried over magnesium sulfate, filtered and the solvent evaporated to afford a pale yellow oil.

Step 4: Cbz deprotection of step 3. The material prepared in step 3 was dissolved in ethanol (100 mL). This solution was added to 10% palladium on carbon (1.0 g). The solution was placed under 45 psi hydrogen. Additional catalyst was added at 6 hours (1.75 g) and 20 hours (1.0 g 4% Pd/C). After 48 hours the reaction mixture was filtered through a plug of Celite. The filtrate was evaporated and triturated with ether to afford N-(2-tetrahydropyranoxy)-4[[4-(4-trifluoromethoxyphenoxy)phenyl]sulfonyl]-4-piperidinecarboxamide (4.47 g) as a white solid. MS (ES) m/z 545 $(M+H)^+$.

EXAMPLE 94

Preparation of N-(2-Tetrahydropyranoxy)-4[[4-(4-trifluoromethylphenoxy)phenyl]sulfonyl]-4-piperidinecarboxamide

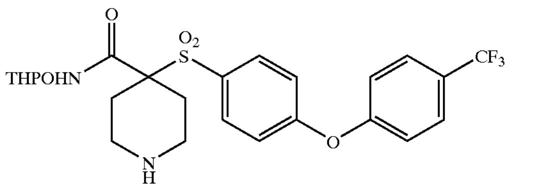

N-(2-tetrahydropyranoxy)-4[[4-(4-trifluoromethylphenoxy)phenyl]sulfonyl]-4-piperidinecarboxamide was prepared by the method of Example 93 starting from ethyl 4-[[4-(4-trifluoromethylphenoxy)phenyl]sulfonyl]-1-[(1,1-dimethylethoxy)carbonyl]piperidinecarboxylate (see Example 90). MS (ES) m/z 529 $(M+H)^+$.

EXAMPLE 95

Preparation of N-Hydroxy-4-[[4-(4-trifluoromethylphenoxy)phenyl]sulfonyl]-1-(2-fluorophenylcarbonyl)-4-piperidinecarboxamide

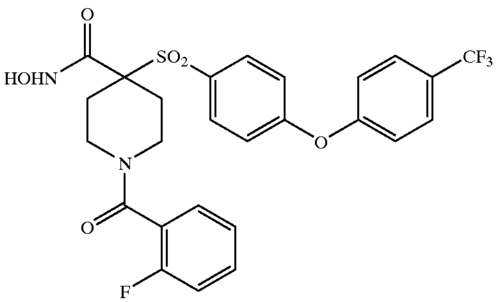

To a solution of N-(2-tetrahydropyranoxy)-4[[4-(4-trifluoromethylphenoxy)phenyl]sulfonyl]-4-piperidinecarboxamide, the product of Example 94, (50 mg) dissolved in dichloromethane (2.5 mL) was added PS-NMM (135 mg, Argonaut) and 2-fluorobenzoyl chloride (12.1 [L] and stirred for 2 hours. To the reaction mixture was added PS-trisamine (50 mg, Argonaut) and the mixture was stirred 1 hour. The reaction mixture was filtered and washed with dichloromethane (2×2 mL) and methanol (1×2 mL). The combined organics were evaporated to afford N-hydroxy-4[[4-(4-trifluoromethylphenoxy)phenyl]-sulfonyl]-1-(2-fluorophenylcarbonyl)-4-piperidinecarboxamide (53.5 mg) as a white solid. MS (ES) m/z 583 $(M+H)^+$.

EXAMPLES 96–124

The following hydroxamic acids were prepared by the method of Example 95 using the appropriate acylating agent.

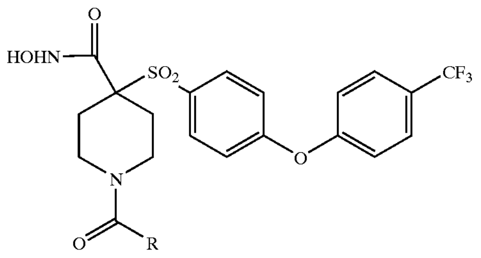

| Example | R | Acylating Agent | MS (ES) m/z |
|---|---|---|---|
| 96 | 3-fluorophenyl | 3-fluorobenzoyl chloride | 583 $(M + H)^+$ |
| 97 | 4-fluorophenyl | 4-fluorobenzoyl chloride | 583 $(M + H)^+$ |
| 98 | 2-trifluoro-methylphenyl | 2-trifluoromethyl-benzoyl chloride | 633 $(M + H)^+$ |
| 99 | 3-trifluoro-methylphenyl | 3-trifluoro-methylbenzoyl chloride | 633 $(M + H)^+$ |
| 100 | phenylmethyl | phenylacetyl chloride | 579 $(M + H)^+$ |
| 101 | 2-tolyl | 2-toluoyl chloride | 579 $(M + H)^+$ |
| 102 | 4-tolyl | 4-toluoyl chloride | 579 $(M + H)^+$ |
| 103 | 4-methoxy-carbonylphenyl | methyl 4-chlorocarbonyl benzoate | 623 $(M + H)^+$ |
| 104 | 4-methoxyphenyl | 4-anisoyl chloride | 595 $(M + H)^+$ |
| 105 | 2-thienyl | 2-thiophenecarbonyl chloride | 571 $(M + H)^+$ |
| 106 | 2-furyl | 2-furoyl chloride | 555 $(M + H)^+$ |
| 107 | 3-pyridyl | nicotinoyl chloride | 566 $(M + H)^+$ |
| 108 | 4-pyridyl | isonicotinoyl chloride | 566 $(M + H)^+$ |
| 109 | c-propyl | cyclopropanecarbonyl chloride | 529 $(M + H)^+$ |
| 110 | trichloromethyl | trichloroacetic anhydride | 622 $(M + H)^+$ |
| 111 | trifluoromethyl | trifluoroacetic anhydride | 574 $(M + H)^+$ |
| 112 | pentafluorophenyl | pentafluorobenzoyl chloride | 655 $(M + H)^+$ |
| 113 | 4-nitrophenyl | 4-nitrobenzoyl chloride | 610 $(M + H)^+$ |
| 114 | 4-trifluoro-methylphenyl | 4-trifluoromethyl-benzoyl chloride | 633 $(M + H)^+$ |
| 115 | 4-trifluoro-methoxyphenyl | 4-trifluoromethoxy-benzoyl chloride | 649 $(M + H)^+$ |
| 116 | 4-methoxy-phenylmethyl | 4-methoxyphenyl-acetyl chloride | 609 $(M + H)^+$ |
| 117 | 3-methoxyphenyl | 3-anisoyl chloride | 595 $(M + H)^+$ |
| 118 | 2-methoxyphenyl | 2-anisoyl chloride | 595 $(M + H)^+$ |
| 119 | 3,5-dimethoxyphenyl | 3,5-dimethoxybenzoyl chloride | 625 $(M + H)^+$ |
| 120 | 3,4-dimethoxyphenyl | 3,4-dimethoxybenzoyl chloride | 625 $(M + H)^+$ |
| 121 | 2,5-difluorophenyl | 2,5-difluorobenzoyl chloride | 601 $(M + H)^+$ |
| 122 | methoxy-carbonylmethyl | methyl malonyl chloride | 561 $(M + H)^+$ |
| 123 | 4-dimethyl-aminophenyl | 4-dimethylamino-benzoyl chloride | 608 $(M + H)^+$ |
| 124 | 1,1-dimethylethyl | pivaloyl chloride | 545 $(M + H)^+$ |

EXAMPLES 125–138

The following hydroxamic acids were prepared by the method of Example of 95 using the appropriate isocyanate as the acylating agent.

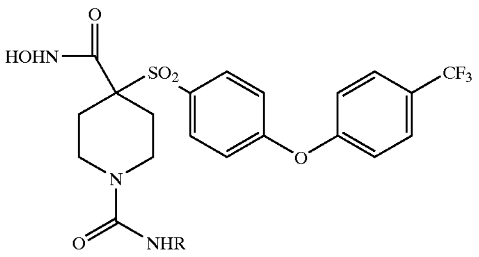

| Example | RNCO | Isocyanate | MS (ES) m/z |
|---|---|---|---|
| 125 | 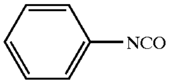 | Phenyl isocyanate | 580 (M + H) |
| 126 | 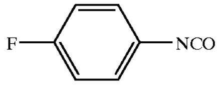 | 4-Fluorophenyl isocyanate | 598 (M + H) |
| 127 | 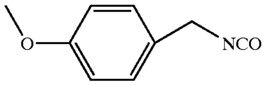 | 4-Methoxybenzyl isocyanate | 624 (M + H) |
| 128 | 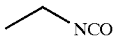 | Ethyl isocyanate | 532 (M + H) |
| 129 | 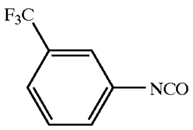 | 3-Trifluoromethyl phenyl isocyanate | 648 (M + H) |
| 130 | 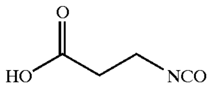 | 3-Isocyanate propionic acid | 576 (M + H) |
| 131 | 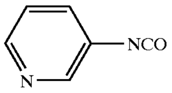 | 3-Pyridyl isocyanate | 581 (M + H) |
| 132 | 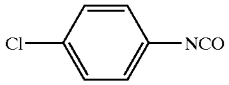 | 4-Chlorophenyl isocyanate | 614 (M + H) |
| 133 | 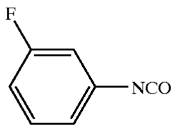 | 3-Fluorophenyl isocyanate | 598 (M + H) |
| 134 | 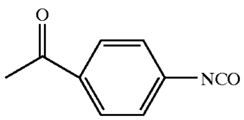 | 4-Acetylphenyl isocyanate | 622 (M + H) |

-continued

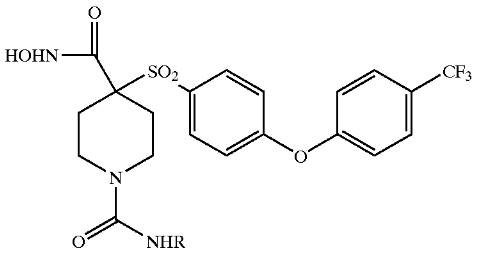

| Example | RNCO | Isocyanate | MS (ES) m/z |
|---|---|---|---|
| 135 | 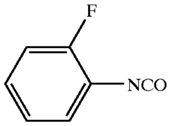 | 2-Fluorophenyl isocyanate | 598 (M + H) |
| 136 | 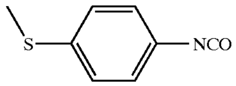 | 4-(Methylthio) phenyl isocyanate | 626 (M + H) |
| 137 | 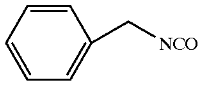 | Benzyl isocyanate | 594 (M + H) |
| 138 | 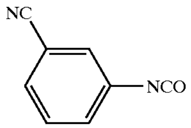 | 3-Cyanophenyl isocyanate | 605 (M + H) |

EXAMPLES 140–143

The following hydroxamic acids were prepared by the method of Example 95 using the appropriate acylating agent (electophile) and starting from N-(2-tetrahydropyranoxy)-4 [[4-(4-trifluoromethylphenoxy)phenyl]sulfonyl]-4-piperidinecarboxamide, the product of Example 94.

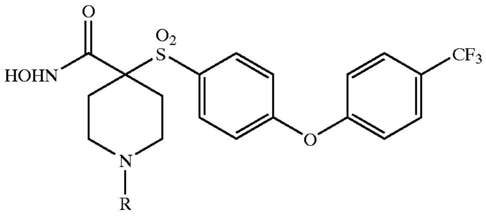

| Example | R | Electrophile | MS (ES) m/z |
|---|---|---|---|
| 140 | 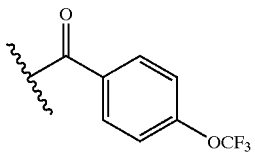 | 4-trifluoro-methoxybenzoyl chloride | 633 $(M + H)^+$ |
| 141 | 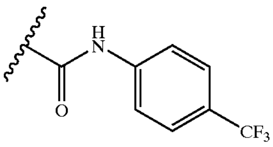 | 4-trifluoromethyl-phenyl isocyantate | 632 $(M + H)^+$ |

-continued

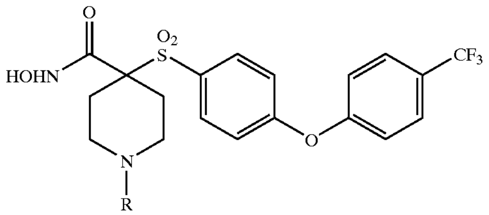

| Example | R | Electrophile | MS (ES) m/z |
|---|---|---|---|
| 142 | 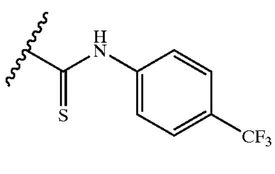 | 4-trifluoro-methylphenyl thioisocyanate | 648 $(M + H)^+$ |
| 143 | 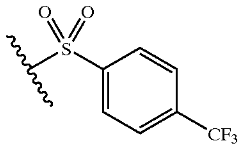 | 4-trifluoromethyl-benzenesulfonyl chloride | 653 $(M + H)^+$ |

EXAMPLE 144

Preparation of N-Hydroxy-4[[4-(4-trifluoromethylphenoxy)phenyl]sulfonyl]-1-(4-aminophenylcarbonyl)-4-piperidinecarboxamide

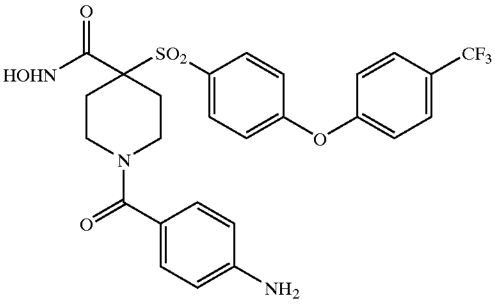

A solution of N-hydroxy-4[[4-(4-trifluoromethylphenoxy)phenyl]sulfonyl]-1-(4-nitrophenylcarbonyl)-4-piperidinecarboxamide, the product of Example 113, (56.0 mg) dissolved in acetic acid (2.5 mL) was added to 4% palladium on carbon (20 mg) and placed under 43 psi hydrogen gas for 2.5 h. The reaction mixture was filtered through a pad of celite. The solvent was evaporated to afford N-hydroxy-4-[[4-(4-trifluoromethylphenoxy)phenyl]sulfonyl]-1-(4-aminophenylcarbonyl)-4-piperidinecarboxamide (50.2 mg) as a pale yellow solid. MS (ES) m/z 580 $(M+H)^+$.

EXAMPLE 145

Preparation of N-Hydroxy-4[[4-(4-trifluoromethylphenoxy)phenyl]-sulfonyl]-1-(4-carboxyphenylcarbonyl)-4-piperidinecarboxamide

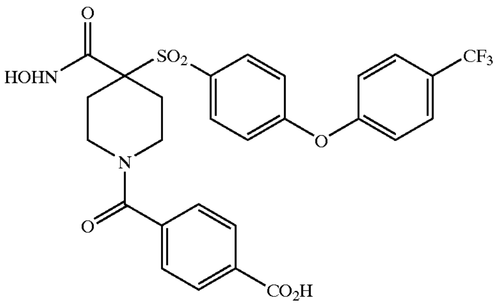

To a solution of the product of Example 103 (57 mg) dissolved in tetrahydrofuran (1 mL) and ethanol (1 mL) was added 1M aqueous sodium hydroxide solution (1 mL) plus 50% aqueous sodium hydroxide (50 μL) and the reaction mixture was stirred 2 hours. The pH value of the reaction mixture was adjusted to 1 with 6M hydrochloric acid. The solution was extracted with ethyl acetate. The organics were dried over sodium sulfate, filtered and the solvent evaporated. The residue was purified by RPHPLC to afford the acid N-hydroxy-4[[4-(4-trifluoromethylphenoxy)phenyl]sulfonyl]-1-(4-carboxyphenylcarbonyl)-4-piperidinecarboxamide (12.8 mg). MS (ES) m/z 631 $(M+NH_4)^+$.

EXAMPLE 146

Preparation of N-Hydroxy-4-[[4-(4-methoxyphenoxy)phenyl]sulfonyl]-4-thianecarboxamide

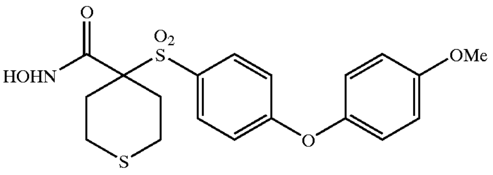

Step 1: Hydrolysis of methyl 4-[[4-(4-methoxyphenoxy) phenyl]sulfonyl]-4-thianecarboxylate. To a solution of methyl 4-[[4-(4-methoxyphenoxy)phenyl]sulfonyl]-4-thianecarboxylate (10.0 g, 31 mmol) dissolved in tetrahydrofuran (150 mL) was added potassium trimethylsilanolate (12.1 g) and stirred 2 hours. Water was added to the reaction mixture and extracted with ethyl acetate (2×100 mL). The pH value of the aqueous layer was adjusted to 2 with 2M hydrochloric acid and extracted with ethyl acetate (2×100 mL). The latter organics were washed with brine, dried over magnesium sulfate, filtered and the solvent evaporated to afford a pale yellow solid (8.20 g).

Step 2: Loading on resin. The compound obtained in step 1 (4.0 g, 13.1 mmol) was dissolved in 1-methyl-2-pyrrolidinone (15 mL) and added to a suspension of resin I (6.0 g, 6.6 mmol; Preparative Example XI) in 1-methyl-2-pyrrolidinone (40 mL). To this solution were added pyBOP (6.85 g) and N-methylmorpholine (2.9 mL), and the mixture was stirred with overhead stirring 16 hours. The resin was filtered and washed with dimethylformamide (3×50 mL), methanol (3×50 mL), dichloromethane (3×50 mL) and ether (3×50 mL). The resin was dried in vacuo to provide resin MT-III (6.79 g).

Step 3: Aryl fluoride displacement of resin MT-III. A suspension of resin MT-III (200 mg, 0.17 mmol), 1-methyl-2-pyrrolidinone (2 mL), cesium carbonate (560 mg) and 4-methoxyphenyl (306 mg) were stirred at 105° C. for 16 hours. The reaction mixture was cooled and the resin filtered. The resin was washed with dimethylformamide (3×5 mL), methanol (3×5 mL), 10% aqueous acetic acid (3×5 mL), methanol (3×5 mL) and dichloromethane (3×5 mL). To the resin was added 95% aqueous trifluoroacetic acid and the reaction mixture was agitated for 1 hour. The resin was drained and washed with dichloromethane (2×1 mL). The solvent was evaporated. The residue was purified by RPHPLC to provide N-hydroxy-4-[[4-(4-methoxyphenoxy) phenyl]sulfonyl]-4-thianecarboxamide (17.9 mg) as a pale yellow oil.

EXAMPLES 147–151

The following hydroxamic acids were prepared by the method of Example 146 using the appropriate alcohol.

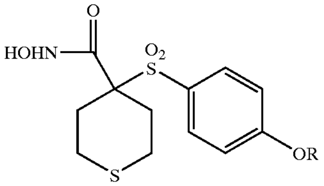

| Example | R | Alcohol | MS (ES) m/z |
|---|---|---|---|
| 147 | 4-trifluoro-methoxyphenyl | 4-trifluoro-methoxyphenol | 495 $(M + NH_4)^+$ |
| 148 | 4-isopropyl-phenyl | 4-isopropylphenol | 453 $(M + NH_4)^+$ |
| 149 | 3-pyridyl | 3-hydroxypyridine | 395 $(M + H)^+$ |
| 150 | 3,4-dimethoxy-phenyl | 3,4-dimethoxyphenyl | 471 $(M + NH_4)^+$ |
| 151 | 4-pyridyl | 4-hydroxypyridine | 395 $(M + H)^+$ |

EXAMPLES 152–155

The following hydroxamic acids were prepared by the method of Example 146 using the appropriate amine.

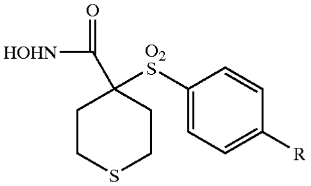

| Example | R | Amine | MS (ES) m/z |
|---|---|---|---|
| 152 | 4-(4-fluoro-benzoyl) piperidyl | 4-(4-fluorobenzoyl)-piperidine | 507 $(M + H)^+$ |
| 153 | 4-(2-methoxy-phenyl) piperidyl | 4-(2-methoxyphenyl)-piperidine | 491 $(M + H)^+$ |

-continued

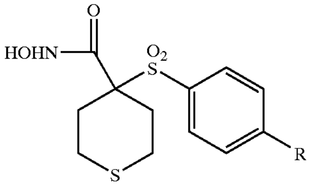

| Example | R | Amine | MS (ES) m/z |
|---|---|---|---|
| 154 | 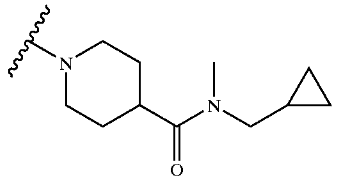 | N-cyclopropyl-methyl-N-methyl-4-piperidine carboxamide | 496 $(M + H)^+$ |
| 155 | pyrrolidinyl | pyrrolidine | 371 $(M + H)^+$ |

EXAMPLE 156

Preparation of N-Hydroxy-4-[[4-(4-methoxyphenoxy)phenyl]sulfonyl]-4-thianecarboxamide-1,1-dioxide

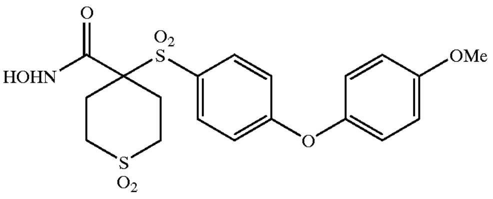

Step 1: Oxidation of Resin MT-III. A suspension of resin MT-III (2.0 g, 1.72 mmol), m-chloroperbenzoic acid (4.37 g) and dichloromethane (25 mL) was stirred at room temperature for 20 hours. The resin was filtered and washed with dichloromethane (3×25 mL), dimethylformamide (3×25 mL), methanol (3×25 mL), 1M aqueous sodium bicarbonate (2×25 mL), methanol (3×25 mL), dichloromethane (3×25 mL) and ether (3×25 mL). The resin was dried in vacuo to afford resin MT-IV 2.16 g).

Step 2: Aryl fluoride displacement of resin MT-IV. N-hydroxy-4-[[4-(4-methoxyphenoxy)phenyl]sulfonyl]-4-thianecarboxamide 1,1-dioxide was prepared by the method of Example 146 using resin MT-IV in the place of resin MT-III. ES (MS) m/z 473 $(M+NH_4)^+$.

EXAMPLES 156–160

The following hydroxamic acids were prepared by the method of Example 156 using the appropriate alcohol.

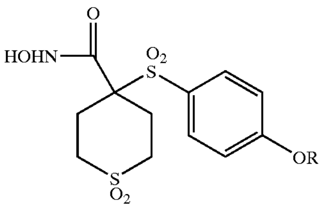

| Example | R | Alcohol | MS (ES) m/z |
|---|---|---|---|
| 157 | 4-trifluoro-methoxyphenyl | 4-trifluoro-methoxyphenol | 527 $(M + NH_4)^+$ |
| 158 | 4-isopropylphenyl | 4-isopropylphenol | 485 $(M + NH_4)^+$ |
| 159 | 3-pyridyl | 3-hydroxypyridine | 427 $(M + H)^+$ |
| 160 | 4-pyridyl | 4-hydroxypyridine | 427 $(M + H)^+$ |

EXAMPLE 161

The following hydroxamic acids were prepared by the method of Example 156 using the appropriate amine.

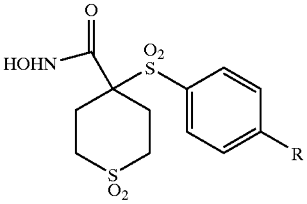

| Example | R | Amine | MS (ES) m/z |
|---|---|---|---|
| 161 | 4-(4-fluorobenzoyl) piperidyl | 4-(4-fluoro-benzoyl)-piperidine | 539 $(M + H)^+$ |

EXAMPLE 162

Preparation of N-Hydroxy-4-[[4-[4-[(3,5-dimethylpiperidyl)carbonyl]-piperidyl]phenyl]sulfonyl]-4-thianecarboxamide

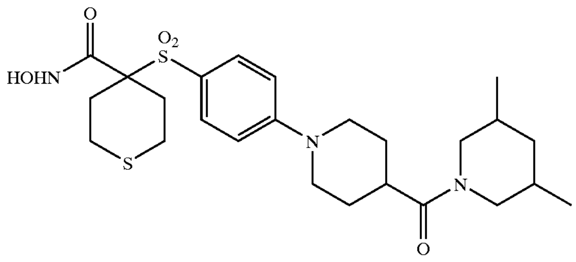

Step 1: Aryl fluoride displacement of Resin MT-III. To a suspension of resin MT-III (4.06 g, 3.4 mmol) in 1-methyl-2-pyrrolidinone (40 mL) was added ethyl isonipecotate (5.25 mL), and the mixture was heated to 100° C. for 16 hours. The cooled reaction mixture was filtered and the resin was washed with methanol (3x25 mL), dichloromethane (1x10 mL) and ether (3x25 mL). The resin was dried in vacuo to afford resin MT-V (4.21 g).

Step 2: Hydrolysis of resin MT-V. To a suspension of resin MT-V (4.13 g) in tetrahydrofuran (20 mL) was added 4M aqueous potassium hydroxide (10 mL) and stirred at room temperature for 5 days. The resin was filtered and washed with methanol (3x25 mL), dichloromethane (3x25 mL) and ether (3x25 mL). The resin was dried in vacuo to afford resin MT-VI.

Step 3: Conversion to amide. To a suspension of resin MT-VI (268 mg) in 1-methyl-2-pyrrolidinone (2 mL) were added 3,5-dimethylpiperidine (299 μL), pyBOP (587 mg) and diisopropylethyl amine (393 μL), and mixture was stirred 40 hours. The resin was filtered and washed with dimethylformamide (3x2 mL), methanol (3x2 mL), 10% aqueous acetic acid (3x2 mL), methanol (3x2 mL), dichloromethane (3x2 mL) and glacial acetic acid (1x2 mL). The resin was treated with 95% aqueous trifluoroacetic acid (2 mL) and agitated 1 hour. The resin was washed with dichloromethane (2 mL) and methanol (2 mL). The filtrate was evaporated. The residue was purified by RPHPLC to afford N-hydroxy-4-[[4-[4-[(3,5-dimethylpiperidyl)carbonyl]piperidyl]phenyl]sulfonyl]-4-thianecarboxamide (7.5 mg) MS (ES) m/z 524 $(M+H)^+$.

EXAMPLE 163

Preparation of N-Hydroxy-4-[[4-[4-[(3,5-dimethylpiperidyl)carbonyl]-piperidyl]phenyl]sulfonyl]-4-thianecarboxamide N-hydroxy-4-[[4-[4-[(3,5-dimethylpiperidyl)carbonyl]piperidyl]phenyl]sulfonyl]-4-thianecarboxamide was prepared by the method of using cis-2,6-dimethylmorpholine as the amine. MS (ES) m/z 526 $(M+H)^+$.

EXAMPLE 164

N-Hydroxy-4[[[4-[4-(4-fluorophenyl)methoxy]piperidyl]phenyl]sulfonyl]-1-tetrahydropyrancarboxamide

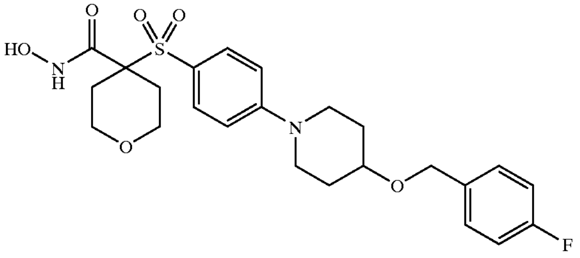

Step 1: Preparation of amine 4-(4-fluorophenyl)methoxy piperidine. Ninety-five percent dry sodium hydride is weighted in a 25 mL vial. Boc-(4-hydroxy)-piperidine (1 g, 4.97 mmol) in 10 mL of dimethyl formamide is added and the reaction mixture is stirred at room temperature for 15 minutes 4-fluoro benzyl bromide (1.4 g, 7.5 mmol) is added and the reaction mixture is stirred at room temperature for 16 hours, then quenched with water and diluted with ethyl acetate. The organic layer was washed with brine, then dried over $MgSO_4$, and concentrated in vacuo. The crude product was purified by flash column chromatography on silica gel eluting with ethyl acetate:hexane 1:10. The Boc-protected amine is dissolved in 3 mL of dichloromethane and 3 mL of trifluoroacetic acid and the reaction mixture is stirred at room temperature for 16 hours and the solvent is evaporated to give 1.8 g of 4-(4-fluorophenyl)-methoxy piperidine. MS: M+H=210.1319.

Step 2: Preparation of N-hydroxy-4[[[4-[4-(4-fluorophenyl)methoxy]piperidyl]phenyl]sulfonyl]-1-tetrahydropyrancarboxamide. To a solution of N-tetrahydropyranoxy-4-fluorophenylsulfonyl-1-tetrahydropyrancarboxamide (100 mg, 0.26 mmol) in 1.5 mL of DMA are added the amine from step 1 (0.52 mmol, 2 eq.) and cesium carbonate (420 mg, 1.29 mmol). The reaction mixture is stirred at 100° C. for 48 hours. The reaction is treated with water and filtered through Celite eluting with dichloromethane. The solvent was evaporated and the residue is dissolved in 2 mL of 4M HCl in dioxane. The mixture is stirred at room temperature for 1 hour and 1 mL of methanol is added. After stirring 15 minutes at room temperature, the solvent is evaporated and the residue was purified by RPHPLC eluting with 10% to 90% acetonitrile/water to give N-hydroxy-4-[[[4-[4-(4-fluorophenyl)methoxy]piperidyl]phenyl]sulfonyl]-1-tetrahydropyrancarboxamide. MS: M+H=493.1792.

EXAMPLES 165–181
The following hydroxamic acids were synthesized by the procedure of Example 164:
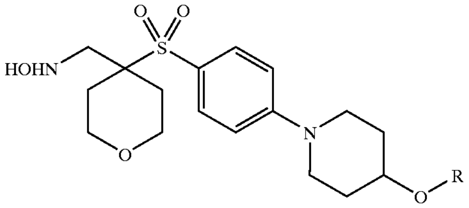
| Example | Halide starting material | R | HI RES MS M + H |
|---|---|---|---|
| 165 | benzyl bromide | 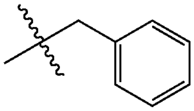 | 475.1913 |
| 166 | ethyl iodide | 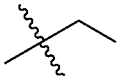 | 413.1764 |
| 167 | 4-fluoro benzyl bromide | 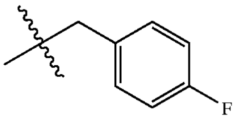 | 493.1792 |
| 168 | iodopropane | 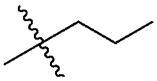 | 427.1918 |
| 169 | 3,5-dimethyl benzyl bromide | 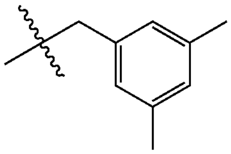 | 144.1391 |
| 170 | 4-chloro benzyl bromide | 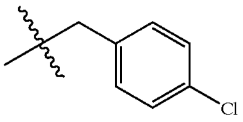 | 509.1515 |
| 171 | 3-methyl benzyl bromide | 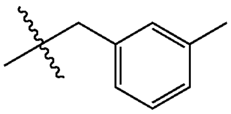 | 489.2059 |
| 172 | 4-methyl benzyl bromide | 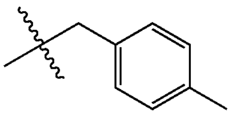 | 489.2074 |
| 173 | 3-trifluoro-methoxy benzyl bromide | 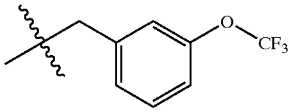 | 559.1738 |

-continued
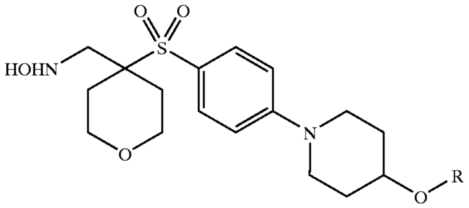
| Example | Halide starting material | R | HI RES MS M + H |
|---|---|---|---|
| 174 | 2-trifluoro-methyl benzyl bromide | 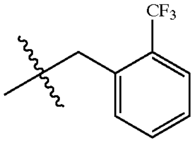 | 543.1780 |
| 175 | 4-trifluoro-methoxy benzyl bromide | 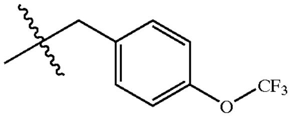 | 559.1730 |
| 176 | 3,4-dichloro-benzyl bromide | 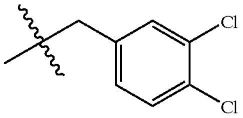 | 543.1155 |
| 177 | 3-trifluoro-methyl benzyl bromide | 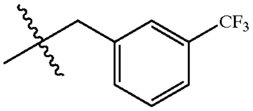 | 543.1779 |
| 178 | 3,5-dimethoxy-benzyl bromide | 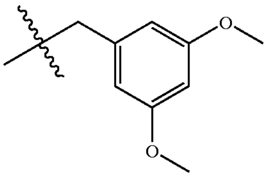 | 535.2120 |
| 179 | 3,4-difluoro-benzyl bromide | 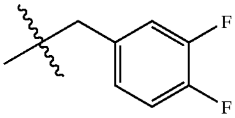 | 511.1705 |
| 180 | 4-cyano-benzyl bromide | 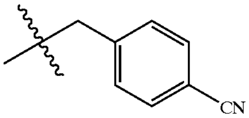 | 500.1835 |
| 181 | 2-phenyl benzyl bromide | 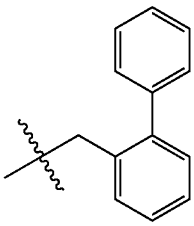 | 551.2196 |

EXAMPLE 182

N-Hydroxy-4-[[[4-[3-(4-fluorophenyl)methoxy]piperidyl]phenyl]sulfonyl]-1-tetrahydropyrancarboxamide

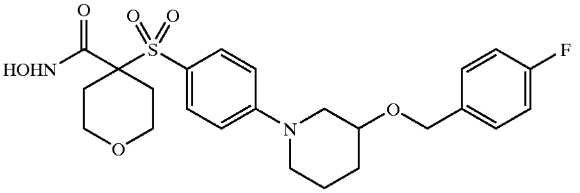

N-hydroxy-4[[[4-[3-(4-fluorophenyl)methoxy]piperidyl]phenyl]sulfonyl]-1-tetrahydropyrancarboxamide is prepared by the method of Example 164 starting from Boc-(3-hydroxy)-piperidine in step 1.

EXAMPLES 183–184

The following hydroxamic acids were synthesized using a procedure similar to that of Example 182:

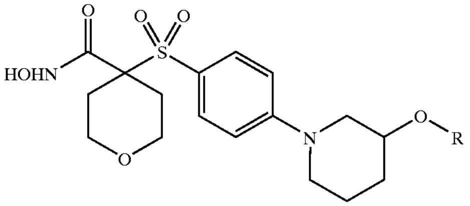

| Example | Halide starting material | R | HI RES MS |
|---|---|---|---|
| 183 | 4-fluroro benzyl bromide | 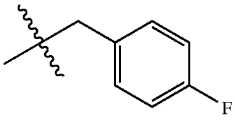 | M + H = 475.1913 |
| 184 | benzyl bromide | 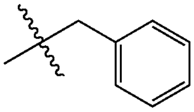 | M + H = 551.2196 |

EXAMPLE 185

N-Hydroxy-4[[[4-(4-phenoxy)piperidyl]phenyl]sulfonyl]-1-tetrahydropyrancarboxamide

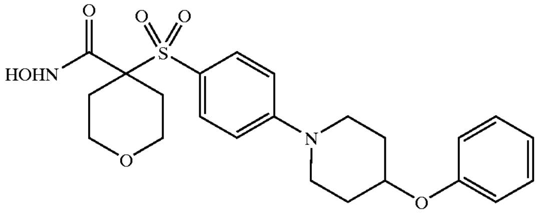

N-hydroxy-4[[[4-(4-phenoxy)piperidyl]phenyl]sulfonyl]-1-tetrahydropyrancarboxamide is prepared by the method of Example 164 starting from 4-phenoxypiperidine in step 2.

EXAMPLES 186–187

The following hydroxamic acids were synthesized using a procedure similar to that of Example 185:

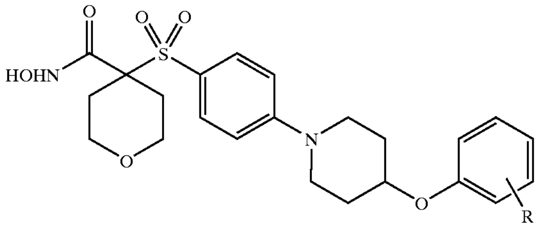

| Example | Amine starting material | R | HI RES MS |
|---|---|---|---|
| 186 | | H | M + H = 461.1749 |
| 187 | 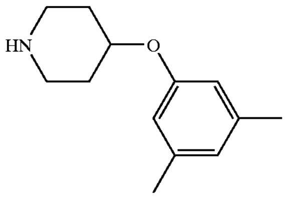 | 3,5-dimethyl | M + H = 489.2065 |

EXAMPLE 188

Preparation of N-Hydroxy-4[[[4-[(3-trifluoromethyl) phenylcarbamoxy]piperidyl]phenyl]sulfonyl]-1-tetrahydropyrancarboxamide

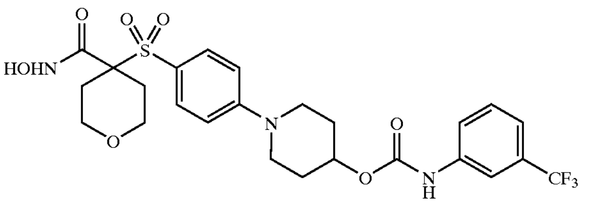

Step 1: A solution of N-tetrahydropyranoxy-4-fluorophenylsulfonyl-1-tetrahydropyrancarboxamide (1 g, 2.58 mmol), 4-hydroxypiperidine (392 mg, 3.87 mmol) and cesium carbonate (2.52 g, 7.74 mmol) in 20 mL of NMP is stirred at 100° C. for 48 hours. The reaction mixture is treated with water and neutralized to pH 4 with 5% aqueous HCl. The aqueous layer is extracted twice with ethyl acetate and the combined organic layer is dried using magnesium sulfate and concentrated in vacuo. The crude product was purified by flash column chromatography on silica gel eluting with ethyl acetate:hexane 1:10 to give N-tetrahydropyranoxy-4-[[(4-hydroxypiperidyl)phenyl] sulfonyl]-1-tetrahydropyrancarboxamide. MS: M+Na=491.2.

Step 2: To a solution of alcohol N-tetrahydropyranoxy-4 [[(4-hydroxypiperidyl)phenyl]sulfonyl]-1-tetrahydropyrancarboxamide (50 mg, 0.107 mmol) in 2 mL of dichloromethane is added alpha, alpha, alpha-trifluoro-M-tolyl isocyanate (21 mg, 0.112 mmol). The reaction mixture is stirred for 16 hours at room temperature and 21 mg of alpha, alpha, alpha-trifluoro-m-tolyl isocyanate is added. The mixture is stirred 48 hours at room temperature and treated with water. The solvent is evaporated and the residue is dissolved in 2 mL of 4M HCl in dioxane. The mixture is stirred at room temperature for 1 hour and 1 mL of methanol is added. After stirring 15 minutes at room temperature the solvent is evaporated and the residue was purified by RPHPLC eluting with 10% to 90% acetonitrile/water to give N-hydroxy-4-[[[4-[(3-trifluoromethyl) phenylcarbamoxy]piperidyl]phenyl]sulfonyl]-1-tetrahydropyrancarboxamide. MS: M+Na=594.1.

EXAMPLES 189–191

The following hydroxamic acids were synthesized using a procedure similar to that of Example 188:

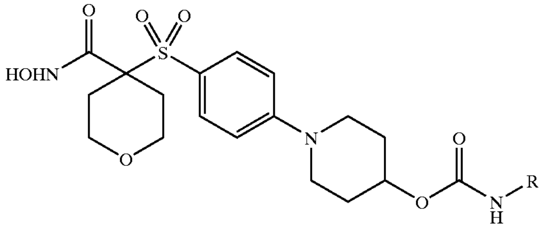

| Example | Isocyanate starting material | R | MS |
|---|---|---|---|
| 189 | alpha,alpha,alpha-trifluoro-M-tolyl isocyanate | 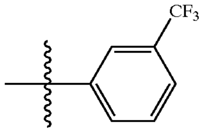 | M + Na = 594.1 |
| 190 | 4-ethoxyphenyl isocyanate | 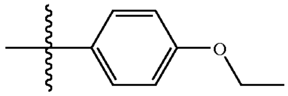 | M + Na = 570.2 |
| 191 | 4-fluorophenyl isocyanate | 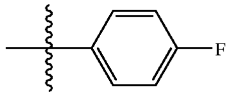 | M + H = 522.1742 |

EXAMPLE 192

Preparation of N-Hydroxy-4[[4-(4-trifluoromethoxyphenoxy)-phenyl]-sulfonyl]-1-[[(2-trifluoromethoxy)phenyl]-sulfonyl-4-piperidinecarboxamide

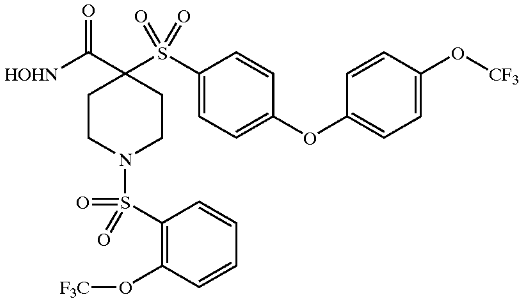

N-hydroxy-4[[4-(4-trifluoromethoxyphenoxy)-phenyl] sulfonyl]-1-[[(2-trifluoromethoxy)phenyl]-sulfonyl-4-piperidinecarboxamide can be prepared using the method of Example 93 starting from 2-trifluoromethoxybenzene sulfonyl chloride.

EXAMPLES 193–197

The following hydroxamic acids were synthesized using a procedure similar to that of Example 192:

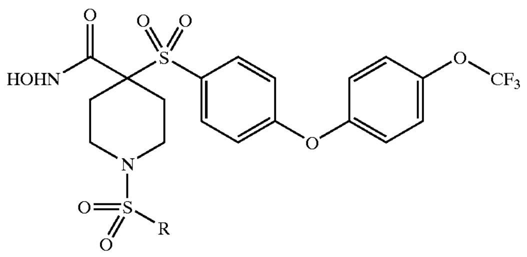

| Example | Sulfonyl chloride starting material | R | MS |
|---|---|---|---|
| 193 | 2-trifluoro-methoxybenzene sulfonyl chloride | 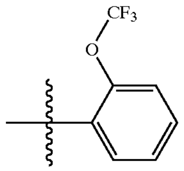 | M + NH4 = 702.1003 |
| 194 | benzene sulfonyl chloride | 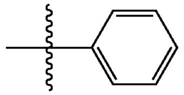 | M + NH4 = 618.1216 |
| 195 | alpha-toluenesulfonyl chloride | 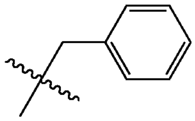 | M + NH4 = 632.1337 |
| 196 | 3-trifluoro-methylbenzene sulfonyl chloride | 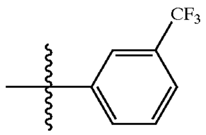 | M + NH4 = 686.1027 |
| 197 | 3-trifluoromethane sulfonyl chloride | 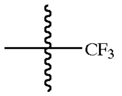 | M − H = 591.1 |

EXAMPLE: 198

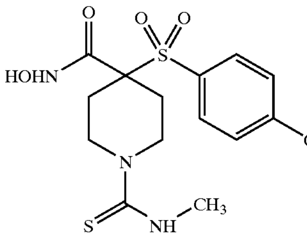

N-hydroxy-4[[4-(4-trifluoromethoxyphenoxy)-]sulfonyl]-1-(N-methylthiourea)-4-piperidinecarboxamide was prepared by the method of Example 192 starting with methyl isothiocyanate. M+H=534.0977.

EXAMPLES 199–202

The following hydroxamic acids were synthesized using the procedure of Example 198:

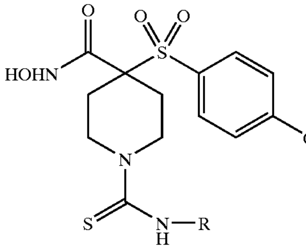

| Example | Sulfonyl chloride starting material | R | MS M + H |
| --- | --- | --- | --- |
| 199 | 2-morpholinoethyl isothiocyanate | 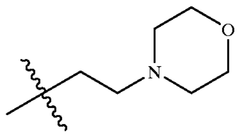 | 633.1643 |
| 200 | 2-piperidinoethyl isothiocyanate | 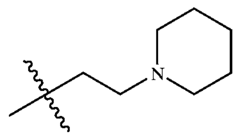 | 653.1694 |
| 201 | pyridine-3-isothiocyanate | 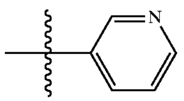 | 597.1094 |
| 202 | 4-dimethyl-aminophenyl isothiocyanate | 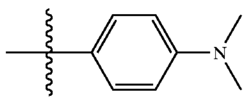 | 639.1526 |

EXAMPLE 203

Preparation of 1,1-Dimethylethyl-3,6-dihydro-4-[2-(trifluoromethyl)phenyl]-1(2H)-pyridinecarboxylate

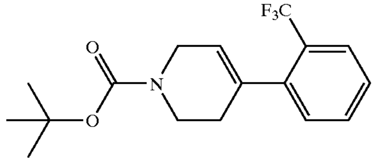

Part A: An oven-dried 1.0 liter flask fitted with a thermometer and nitrogen inlet was charged with 55 mL of a 2 M solution of lithium diisopropoylamide in tetrahydrofuran and 50 mL of tetrahydrofuran. The flask was immersed in a dry ice/acetone bath. When the temperature of the solution was less than −70 degrees, a solution of N-t-butoxycarbonylpiperidinone (20.0 g, 0.1 mole) in 100 mL tetrahydrofuran was added dropwise, maintaining the temperature less than −6,5 degrees. After complete addition, the flask was stirred with cooling for 20 minutes. Then a solution of N-trifluoromethanesulfonimide (38.2 g, 0.107 mole) was added drop-wise maintaining the temperature less than −65 degrees. After complete addition, the dry ice/acetone bath was swapped with an ice/water bath. The reaction was stirred overnight (about eighteen hours), slowly warming to room temperature. After 16 hours, the solvent was removed in vacuo, and the residue was purified by column chromatography on neutral alumina, yielding 26.53 g of product as a yellow oil. Electrospray mass spectroscopy showed m/z 332 (M+H).

Part B: A three-necked 15 mL round-bottom flask was charged with the product from Part A (6 g, 18.1 mmol), o-trifluorobenzeneboronic acid (4.94 g, 26 mmol), lithium chloride (2.34 g, 55 mmol), 2 M sodium carbonate (26 mL, 52 mmol) and ethylene glycol dimethyl ether (60 mL). Nitrogen was bubbled through the solution for 10 minutes, then palladium tetrakistriphenylphosphine (1.06 g, 0.92 mmol) was added. The mixture was heated to reflux for 1.5 hours, then cooled to room temperature. The solvent was removed in vacuo, then the residue was partitioned between 100 mL of methylene chloride and 100 mL of 2 M sodium carbonate with 3 mL concentrated ammonium hydroxide. The aqueous layer was extracted with an additional 100 mL methylene chloride, then the combined organic layers were dried over magnesium sulfate and concentrated to give 8.42 g of crude product as a dark brown oil. Purification via flash column chromatography (10% ethyl acetate3/hexanes) yielded 2.76 g of pure product as a yellow oil. Electrospray mass spectroscopy showed m/z 328 (M+H).

EXAMPLE 204

Preparation of 1,2,3,6-Tetrahydro-4-[2-trifluoromethyl)phenyl]pyridine

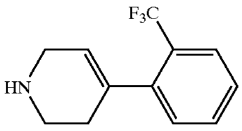

The title compound of Example 203 (300 mg, 0.92 mmol) was dissolved in methylene chloride (5 mL) in a 15 mL round-bottom flask, and 5 mL of trifluoroacetic acid was added dropwise. After 15 minutes, the solvent was removed in vacuo, and the residue partitioned between 20 mL of ethyl acetate and 20 mL of 2 M sodium carbonate. The organic layer was washed with additional 2 M sodium carbonate, dried over magnesium carbonate and concentrated in vacuo to yield 195 mg of pure product as a colorless oil. Electrospray mass spectroscopy showed m/z 228 (M+H).

EXAMPLE 205

Preparation of 4-[2-(Trifluoromethyl)phenyl] piperidine

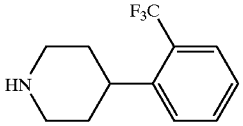

Part A: A solution of the title compound of Example 203 (2.3 g, 7 mmol) in 20 mL ethanol was added to a hydrogenation flask containing 1 g of 4% palladium on carbon (0.38 mmol). The mixture was placed under 100 PSI hydrogen and heated to 50 degrees Celsius for 5 hours. Then the mixture was cooled to room temperature and filtered through Celite. The filtrate was concentrated in vacuo to give 2.27 g of pure product as a colorless oil. Electrospray mass spectroscopy showed m/z 330 (M+H).

Part B: The product from Part A above (2.24 g, 6.8 mmol) was dissolved in 100 mL methylene chloride, and 100 mL of trifluoroacetic acid was added dropwise. After 15 minutes, the solvent was removed in vacuo, and the residue partitioned between 100 mL of ethyl acetate and 100 mL of 2 M sodium carbonate. The organic layer was washed with additional 2 M sodium carbonate, dried over magnesium carbonate and concentrated in vacuo to yield 1.12 g of pure product as a colorless oil. Electrospray mass spectroscopy showed m/z 230 (M+H).

EXAMPLE 206

General Description for Preparation of Hydroxamic Acids via Aryl Fluoride Displacement With Amines Part A: A 2 dram vial was charged with aryl fluoro compound of Preparative Example IV (170 mg, 0.44 mmol), 1 ml of 2-methylpyrrolidinone, cesium carbonate (360 mg, 1.1 mmol) and 0.66 mmol of an amine. A small magnetic stirring bar was added, then the vial was capped and placed in a Pierce Reacti-therm™ at 115 degrees Celsius. The reaction progress was followed by analytical HPLC. When the reaction was greater than 90% complete, the vial was cooled to room temperature. The reaction mixture was diluted with 5 mL of water, then 1.2 mL of 5% hydrogen chloride/water was added dropwise. Then, the entire mixture was poured onto a column of Celite. The column was washed exhaustively with ethyl acetate (30–40 mL) and the filtrate was collected and concentrated to give the crude products.

Part B: The product from above was dissolved in 2 mL 1,4-dioxane and 2 mL of methanol in a 4 dram vial with a small magnetic stirring bar. A solution of 4 N hydrogen chloride in 1,4-dioxane was carefully added to the reaction, and the mixture was stirred for 2 hours. Then the solvent was removed in vacuo and the residue purified by preparative reversed-phase HPLC.

EXAMPLES 207–214

The following hydroxamic acids were prepared using the method described above in Example 106 with the indicated amine as the starting material.

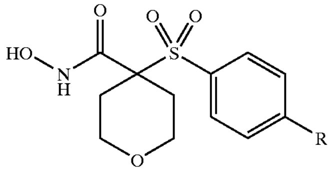

| Example | amine | R | m/z from electrospray mass spectroscopy |
|---|---|---|---|
| 207 | Product of Example 205 | 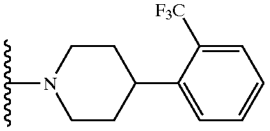 | 513.3 (M + H) |
| 208 | Product of Example 204 | 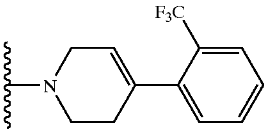 | 511.2 (M + H) |
| 209 | piperidine | 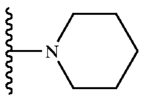 | 369.2 (M + H) |
| 210 | tetrahydro-piperidine | 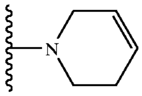 | 367.2 (M + H) |
| 211 | 4-(2-keto-benzimid-azolinyl)-piperidine | 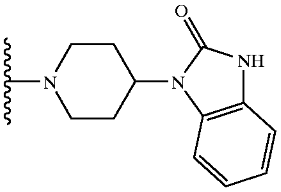 | 501 (M + H) |
| 212 | hexamethyl-eneimine | 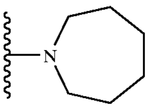 | 383.2 (M + H) |
| 213 | 1-methylhomo-piperazine | 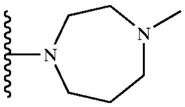 | 398.2 (M + H) |
| 214 | 1,3,3-trimethyl-6-azabicyclo-[3.2.1]octane | 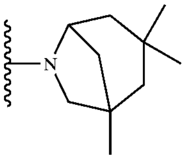 | 437.3 (M + H) |

EXAMPLES 215–223

Using the procedures outlined in Examples 203, 204, 206 and other methods outlined above, the following analogs are made from the indicated boronic acid:

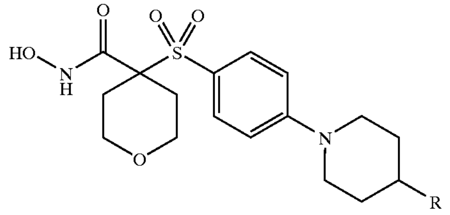

| Example | Boronic acid | R |
|---|---|---|
| 215 | 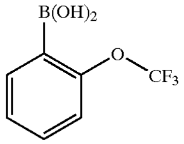 | 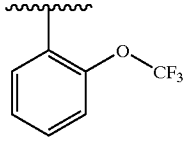 |
| 216 | 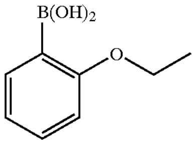 | 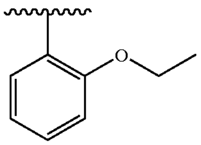 |
| 217 | 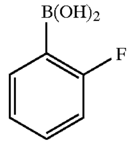 | 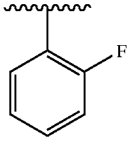 |
| 218 | 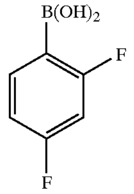 | 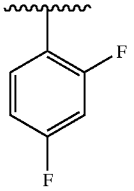 |
| 219 | 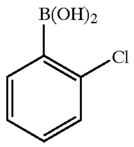 | 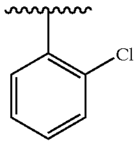 |
| 220 | 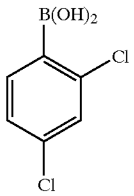 | 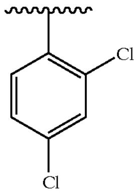 |
| 221 | 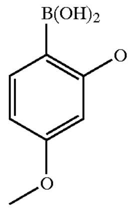 | 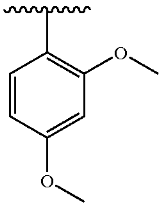 |

-continued

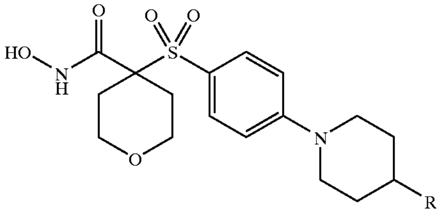

| Example | Boronic acid | R |
|---|---|---|
| 222 | 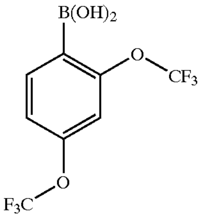 | 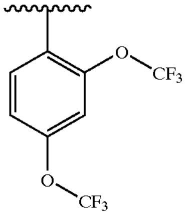 |
| 223 | 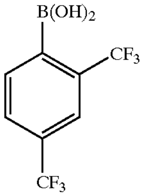 | 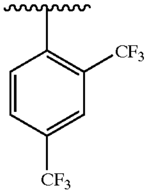 |

EXAMPLE 224

Preparation of Tetrahydro-N-hydroxy-4-[[4-(pentaflourooxy)phenyl]sulfonyl]-2H-thiopyran-4-carboxamide

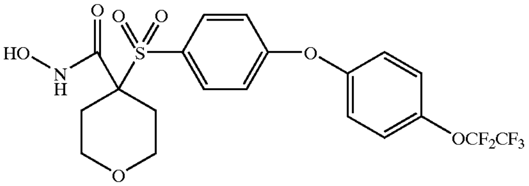

Part A: To a solution of the product of Preparative Example IV (2.5 g, 6 mmol ) in dimethylformamide (50 mL) was added 4-pentafluroethyloxy phenol (2.0 g, 6 mmol) followed by cesium carbonate (5 g, 12 mmol). The reaction was heated at eighty degrees Celsius for twelve hours. Stripping the dimethylformamide in vacuo afforded a brown solid (5.5 g). The product was dissolvent in ethylacetate (150 ml) and extracted with water, brine and dried over sodium sulfate. The $^{1}H$ NMR, MS, and HPLC was consistent with desired compound.

Part B: To the product of part A, crude THP-protected hydroxamate was disolved in acetonitrile/water (40 ml) was slowly added 10% aq HCl (10 ml). After stirring two hours, the acetonitrile was stripped. The resultant precipitate was collected, giving the title compound as a white solid (2.1 g). The $^{1}H$ NMR, MS, and HPLC was consistent with desired compound. This solid was recrystallized from ethylacetate and hexanes (1.8 g). The $^{1}H$ NMR, MS, and HPLC was consistent with desired compound. MS (CI) M+H calculated for $C_{23}H_{27}BrNO_6S$: 511, found 511.

EXAMPLE 225

Preparation of Tetrahydro-4-[[4-(pentaflourooxy) phenyl]sulfonyl]-2H-thiopyran-4-carboxamide

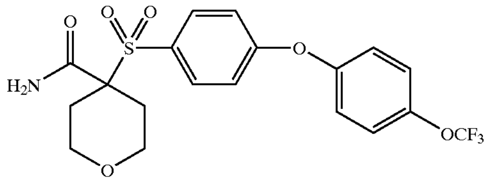

Part A. The product of Preparative Example V (2.5 g) was dissolved in methanol (60 mL). To this solution ammonium formate (3 g) was added, followed by Pd on charcoal 20% catalyst. The mixture was heated to reflux for 24 hour. After complete reaction the mixture was cooled filtered through a plug of Celite and the solvent removed under reduced pressure to give pure amide (1.7 g). The $^1$H NMR, MS, and HPLC was consistent with desired compound. MS (CI) M+H calculated for $C_{23}H_{27}BrNO_6S$: 445, found 445.

EXAMPLE 226

Preparation of 4-(4-Pyridyloxy)thiophenol Hydrochloride

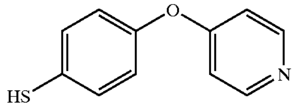

Part A: Phenol (1500 g, 15.9 mol) and 4-chloropyridine hydrochloride (800 g, 7.1 mol) were combined in a melt at 150° C. under a nitrogen atmosphere. After fifteen hours, the reaction was dissolve in 3N sodium hydroxide solution (5400 mL) and extracted with methylene chloride (4×). The organic extracts were combined, washed with 1N sodium hydroxide solution, water and brine, dried over $Na_2SO_4$, filtered, and concentrated in vacuo. The isolated oil was dissolved in hexanes (1000 mL) and cooled to −60° C. The precipitate was collected and dried in vacuo to yield 452 g (38%) of the 4-phenoxypyridine as a white solid.

Part B: A solution of the 4-phenylpyridine from part A (400 g, 2.3 mol) in 1,2-dichloroethane (1250 mL) was cooled in an ice bath under a nitrogen atmosphere and treated with chlorosulfonic acid (400 mL, 6.0 mol). The reaction temperature was held below 12° C. during the addition. The reaction was then heated to 45° C. for 15 hours. The standard work-up procedure afforded 270 grams (40%) of the desired 4-[(pyrid-4-yl)oxy]benzenesulfonic acid.

Part C: A slurry of the sulfonic acid part B (420 g, 1.5 mol) in acetonitrile (2500 mL) and DMF (40 mL) was warmed to 75° C. under a nitrogen atmosphere and treated with thionyl chloride (243 mL, 3.3 mol) added dropwise over 3 hours. After stirring for one-half hour, the standard work-up procedure afforded 483 grams (100%) of the desired 4-[(pyrid-4-yl)oxy]benzenesulfonyl chloride hydrochloride.

Part D: A solution of triphenylphosphine (65.6 g, 250.28 mmol) in dry methylene chloride (240 mL) was cooled to zero degrees C. in an ice-water bath, then treated with dimethylformamide (3.4 mL, 3.2 g, 43.40 mmol). The reaction mixture was then treated with the sulfonyl chloride from part C (25.5 g, 83.43 mmol), added as a solid over one-half hour. After two hours in the ice bath, the reaction was treated with 1 N aqueous hydrochloric acid solution (150 mL) and stirred vigorously for one hour. The layers were separated and the aqueous layer was extracted with methylene chloride (1×). The aqueous layer was concentrated in vacuo to yield 17.9 grams (90%) of the 4-(4-pyridyloxy)thiophenol hydrochloride as a tan solid, m/z=204 (M+H).

EXAMPLE 227

Preparation of

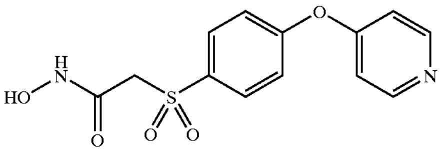

Part A: A solution of 4-(4-pyridyloxy)thiophenol (2.0 g, 8.34 mmol) and tert-butylbromoacetate (1.2 mL, 1.6 g, 8.34 mmol) in dry methanol (30 mL) was cooled to zero degrees C. and treated with triethylamine (2.4 mL, 1.8 g, 17.52 mmol). The addition was done at a rate which held the reaction temperature below 10° C. The ice bath was removed and after two hours at ambient temperature, the reaction was concentrated in vacuo. The residue was partitioned between ethyl acetate and saturated sodium bicarbonate, the layers were separated and the aqueous layer was extracted with ethyl acetate (2×). The organic extracts were combined, washed with water and brine, dried over $Na_2SO_4$, filtered, and concentrated in vacuo to yield 2.3 grams of the tert-butyl ester of the sulfide acid suitable for the next step.

Part B: To a solution of the tert-butyl ester of the sulfide acid from part A (2.3 g, 7.25 mmol) in dry anisole (85 mL, 8.1 g, 74.67 mmol) was added trifluoroacetic acid (25.5 mL, 37.7 g, 330.6 mmol). After one-half hour at ambient temperature, the reaction was concentrated in vacuo to 3.7 g of the TFA salt of the sulfide acid suitable for the next step.

Part C: To a solution of the TFA salt of the acid obtained from part B (2.7 g, 7.19 mmol) in dimethylformamide (10 mL) was added N-hydroxybenzotriazole hydrate (1.5 g, 10.79 mmol), N-methylmorpholine (4.7 mL, 4.4 g, 43.16 mmol), O-(tetrahydro-2H-pyran-2-yl)hydroxylamine (2.5 g, 21.58 mmol), and 1-(3-dimethylaminopropyl)-3-ethylcarbodiimide hydrochloride (1.8 g, 9.35 mmol). After sixteen hours at ambient temperature, the reaction was concentrated in vacuo. The residue was partitioned between ethyl acetate and saturated sodium bicarbonate, the layers were separated and the aqueous layer was extracted with ethyl acetate (3×). The organic extracts were combined, washed with brine, dried over $Na_2SO_4$, filtered, and concentrated in vacuo. Chromatography (on silica, methanol-ethyl acetate/hexanes) afforded 2.1 g (81%) of the THP sulfide hydroxamate as a dry, white foam, m/z=361 (M+H).

Part D: To a solution of the THP sulfide hydroxamate from part C (2.1 g, 5.83 mmol) in methanol/water (13 mL/2 mL) was added tetrabutylammonium Oxone (5.8 g, 61.29 mmol). After 2 days at ambient temperature, the reaction was concentrated in vacuo. The residue was partitioned between ethyl acetate and saturated sodium bicarbonate, the layers were separated and the aqueous layer was extracted with ethyl acetate (6×). The organic extracts were combined, washed with water and brine, dried over $Na_2SO_4$, filtered, and concentrated in vacuo. Chromatography (on silica, methanol-ethyl acetate/hexanes) afforded 0.9 g (40%) of the THP sulfone hydroxamate as a dry, white foam, m/z=393 (M+H).

Part E: To a slurry of the THP sulfone hydroxamate from part D (0.9 g, 2.29 mmol) in methanol (0.6 mL) was added 4N HCl dioxane solution (6 mL). After one hour at ambient temperature, the reaction mixture was slowly poured into diethyl ether (200 mL). Filtration afforded 0.6 grams (78%) of the title compound as a white solid, m/z=309 (M+H).

EXAMPLE 228

Preparation of

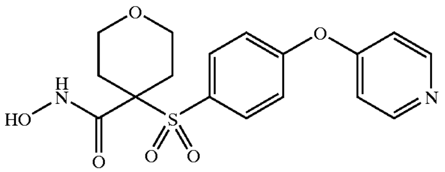

Part A: A solution of 4-(4-pyridyloxy)thiophenol (18.0 g, 75.08 mmol) and tert-butylbromoacetate (10.5 mL, 13.9 g, 71.33 mmol) in dry methanol (250 mL) was cooled to 0° C. and treated with triethylamine (22.0 mL, 16.0 g, 157.68 mmol). The addition was done at a rate which held the reaction temperature below 1° C. The ice bath was removed and after one-half hour at ambient temperature, the reaction was concentrated in vacuo. The residue was partitioned between ethyl acetate and saturated sodium bicarbonate, the layers were separated and the aqueous layer was extracted with ethyl acetate (2×). The organic extracts were combined, washed with water and brine, dried over $Na_2SO_4$, filtered, and concentrated in vacuo to yield 21.7 grams of the tert-butyl ester of the sulfide acid suitable for the next step.

Part B: To a solution of the tert-butyl ester of the sulfide acid from part A (221.7 g, 68.37 mmol) in dry anisole (76.5 mL, 76.1 g, 704.12 mmol) was added trifluoroacetic acid (240 mL, 355 g, 3,117 mmol). After one hour at ambient temperature, the reaction was concentrated in vacuo to yield 34.7 g of the TFA salt of the sulfide acid suitable for the next step.

Part C: To a solution of the TFA salt of the sulfide acid from part B (34.7 g, 68.37 mmol) in dry methanol (100 mL) was added thionyl chloride (7.5 mL, 12.2 g, 102.5 mmol). After twelve hours at ambient temperature, the reaction was concentrated in vacuo. The residue was partitioned between ethyl acetate and saturated sodium bicarbonate, the layers were separated and the aqueous layer was extracted with ethyl acetate (3×). The organic extracts were combined, washed with water and brine, dried over $Na_2SO_4$, filtered, and concentrated in vacuo to yield 18.7 grams of the methyl ester of the sulfide acid suitable for the next step.

Part D: To a solution of the methyl ester of the sulfide acid obtained from part C (18.7 g, 67.92 mmol) in methylene chloride (325 mL) was added tetrabutylammonium Oxone (193 g, 543.4 mmol). After 2 days at ambient temperature, the reaction was concentrated in vacuo. The residue was partitioned between ethyl acetate and saturated sodium bicarbonate, the layers were separated and the aqueous layer was extracted with ethyl acetate (9×). The organic extracts were combined, washed with water and brine, dried over $Na_2SO_4$, filtered, and concentrated in vacuo. Chromatography (on silica, methanol-ethyl acetate/hexanes) afforded 7.3 g (35%) of the methyl ester of the sulfone acid as a dry, white foam, m/z=308 (M+H).

Part E: To a solution of the methyl ester of the sulfone acid obtained from part D (2.7 g, 8.79 mmol) in dry dimethylformamide (20 mL) was added 18-crown-6 ether (0.5 g, 1.90 mmol) and potassium carbonate (4.9 g, 35.14 mmol). The reaction slurry was treated with bis-(2-bromoethyl)ether (1.1 mL, 2.0 g, 8.79 mmol) and then heated to 60° C. After fifteen hours at 60° C., the reaction was concentrated in vacuo. The residue was partitioned between ethyl acetate and water, the layers were separated and the aqueous layer was extracted with ethyl acetate (3×). The organic extracts were combined, washed with brine (3×), dried over $Na_2SO_4$, filtered, and concentrated in vacuo. Chromatography (on silica, $NH_3$-methanol-ethyl acetate/hexanes) afforded 1.6 g (48%) of the THP sulfone methyl ester as a tan solid, m/z=378 (M+H).

Part F: To a solution of the THP sulfone methyl ester from part E (1.6 g, 4.24 mmol) in dry tetrahydrofuran (20 mL) was added potassium trimethylsilanoate (1.6 g, 12.72 mmol). After five hours at ambient temperature, the reaction was concentrated in vacuo to yield the potassium salt of the THP sulfone acid as a tan solid suitable for use in the next step.

Part G: To a slurry of the potassium salt of the THP sulfone acid obtained from part F (1.7 g, 4.24 mmol) in dimethylformamide (20 mL) was added N-hydroxybenzotriazole hydrate (1.1 g, 8.48 mmol) and 1-(3-dimethylaminopropyl)-3-ethylcarbodiimide hydrochloride (1.6 g, 8.48 mmol). After heating the reaction mixture at 40° C. for one-half hour, N-methylmorpholine (1.4 mL, 1.3 g, 12.72 mmol) and O-(tetrahydro-2H-pyran-2-yl)hydroxylamine (1.0 g, 8.48 mmol) were added. After heating at 45° C. for 15 hours, the reaction was concentrated in vacuo. The residue was partitioned between ethyl acetate and 10% potassium carbonate, the layers were separated and the aqueous layer was extracted with ethyl acetate (13×). The organic extracts were combined, washed with water and brine (3×), dried over $Na_2SO_4$, filtered, and concentrated in vacuo. Chromatography (on silica, (2M ammonia in methanol-ethyl acetate)/hexanes) afforded 0.7 g (35%) of the THP-protected THP sulfone hydroxamate as a dry, white foam, m/z=463 (M+H).

Part H: To a slurry of the THP-protected THP sulfone hydroxamate from part G (0.7 g, 1.43 mmol) in methanol (0.4 mL) was added 4N HCl dioxane solution (4 mL). After thirty minutes at ambient temperature, the reaction mixture was slowly poured into diethyl ether (200 mL) and stirred for fifteen minutes. Filtration afforded 0.5 grams (83%) of the title compound as the HCl salt, m/z=379 (M+H).

EXAMPLE 229

Preparation of N-Hydroxy-1-(4-methylphenyl)-4-[[4-[4-(trifluoromethoxy)phenoxy]phenyl]sulfonyl]-4-piperidinecarboxamide Monohydrochloride

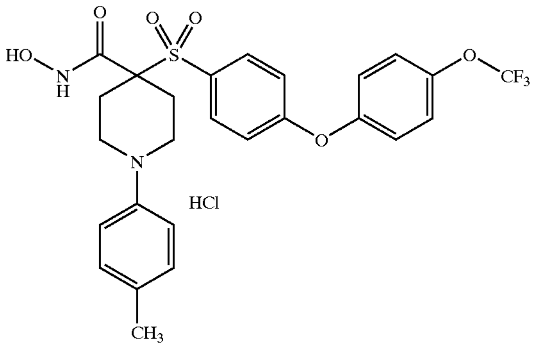

Part A: To a suspension of ethyl 4-(4-fluorophenylsulfonyl]-4-piperidinecarboxylate, hydrochloride Preparative Example II (2.56 g, 7.28 mmol) in $H_2O$ (50 mL) was added 1.25N NaOH (pH=9.0). The aqueous layer was extracted with diethyl ether (2×75 mL). The combined organic layers were washed with saturated NaCl and dried over $Na_2SO_4$. Concentration in vacuo provided the free amine as an off-white solid (1.72 g). To a solution of the free amine (1.70 g, 5.39 mmol) in toluene (25 mL) was added $Cs_2CO_3$ (2.34 g, 7.19 mmol) and a solution of 4-bromotoluene (0.877 g, 5.13 mmol) in toluene (5 mL). This was followed by the addition of tris (dibenzyldeneacetone)dipallidium (0) (0.047 g, 0.0513 mmol) and BINAP (0.096 g, 0.154 mmol). The resulting mixture was then heated to one hundred degress Celsius for 17 hours. After cooling to ambient temperature, the reaction mixture was filtered through a pad of Celite®, washing with ethyl acetate and the filtrate was concentrated in vacuo. Chromatography (on silica, ethyl acetate/hexane) provided the aniline as a yellow oil (1.59 g, 76%).

Part B: To a solution of the aniline of part A (1.56 g, 3.85 mmol) in N,N-dimethylformamide (8.0 mL) was added $K_2CO_3$ (1.06 g, 7.70 mmol) and 4-(trifluoromethoxy)phenol (0.823 g, 4.62 mmol). The resulting mixture was heated to ninety degrees Celsius for 19 hours. The reaction was cooled to ambient temperature and concentrated in vacuo. The residue was partitioned between $H_2O$ and diethyl ether. The organic layer was washed with saturated NaCl and dried over $Na_2SO_4$. Concentration in vacuo provided the biaryl ether as a brown oil (2.42 g, >100%).

Part C: To a solution of the biaryl ether of part B (2.42 g, 3.85 mmol) in tetrahydrofuran (10 mL) and $H_2O$ (10 mL) was added NaOH (1.54 g, 38.50 mmol) in $H_2O$ (5.0 mL). The mixture was heated to sixty degrees Celsius for 6 hours then cooled to ambient temperature. The mixture was then acidified (pH=7) with 1N HCl. The solids were collected by vacuum filtration, then suspended in acetonitrile and concentrated in vacuo to give the acid as a tan solid (1.95 g, 95%).

Part D: To a suspension of the acid of part C (1.95 g, 3.64 mmol) in N,N-dimethylformamide (15 mL) was added 1-hydroxybenzotriazole (0.596 g, 4.37 mmol), N-methylmorpholine (1.19 mL, 10.92 mmol), O-(tetrahydropuranyl) hydroxylamine (1.28 g, 10.92 mmol) and 1-3-[(dimethylamino)propyl]-3-ethylcarbodiimide hydrochloride (0.977 g, 5.10 mmol). The resulting mixture was stirred at ambient temperature for 16 hours then concentrated in vacuo. The residue was partitioned between $H_2O$ and ethyl acetate. The combined organic layers were washed with $H_2O$, saturated $NaHCO_3$, saturated NaCl and dried over $Na_2SO_4$. Chromatography (on silica, methanol/ethyl acetate) provided the protected hydroxamate as a pale-yellow foam (1.90 g, 83%).

Part E: To the protected hydroxamate of part D (1.89 g, 3.00 mmol) was added 4N HCl in dioxane (7.50 mL, 30.0 mmol) and methanol (1.22 mL, 30.0 mmol). The resulting mixture was stirred at ambient temperature for 2 hours, then diethyl ether (5 mL) was added and the precipitate was collected by filtration to provide the title compound as a fine white solid (1.56 g, 89%). MS $MH^+$ calculated for $C_{26}H_{25}O_6N_2S_1F_3$: 551, found 551.

EXAMPLE 230

Preparation of N-Hydroxy-1-(2-hydroxyethyl)-4-[4-(4-trifluoromethoxyphenoxy)phenyl]sulfonyl]-4-piperidinecarboxamide, Hydrochloride

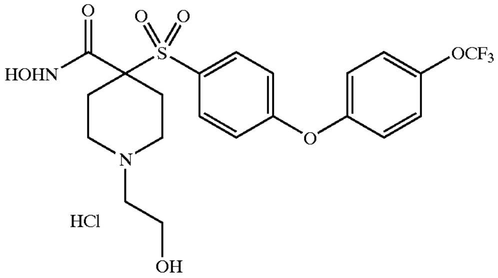

Part A: Ethyl 4-(4-Fluorophenylsulfonyl]-4-piperidinecarboxylate, hydrochloride (3.95 g, 11.3 mmol) Preparative Example II, powdered potassium carbonate (3.45 g, 25 mmol), and N,N-dimethylformamide (11.3 mL) were combined. 2-(2-Bromoethoxy)tetrahydro-2H-pyran (1.85 mL, 12 mmol) was added and the mixture was stirred for 48 hours at ambient temperature. The reaction was diluted with water (100 mL) and extracted with ethyl acetate (100 mL, then 50 mL). The combined organic layers were dried over magnesium sulfate, concentrated, and chromatographed to afford the desired tetrahydropyranyl ether as an oil (4.44 g, 88%)

Part B: The tetrahydropyranyl ether from Part A was stirred at 110 degrees Celsius for 20 hours in the presence of powdered potassium carbonate (2.07 g, 15 mmol), 4-(trifluoromethoxy)phenol (2.67 mL, 15 mmol), and N,N-dimethyformamide (5 mL). The mixture was diluted with saturated sodium bicarbonate (50 mL) and was extracted with ethyl acetate (150, then 50 mL). The combined organic layers were dried over magnesium sulfate, concentrated, and chromatographed to afford the desired aryl ether as an oil (5.72 g, quantitative).

Part C: The aryl ether from Part C (1.28 g, 2.1 mmol) was refluxed in the presence of potassium hydroxide (954 mg, 16.8 mmol), ethanol (9 mL), and water (3 mL). After 2 hours, the reaction vessel was cooled to zero degrees Celsius. Concentrated hydrochloric acid was added drop-wise to adjust the pH to 4.0. The acidified reaction was concentrated, azeotroped with acetonitrile, and dried in vacuo, affording the crude carboxylic acid, which was used directly in Part D.

Part D: The carboxylic acid from Part C was converted to O-tetrahydropyranyl hydroxamate using O-tetrahydropyranyl hydroxylamine (351 mg, 3 mmol), N-methylmorpholine (0.5 mL), N-hydroxybenzotriazole (405 mg, 3 mmol), and 1-(3-dimethylaminopropyl)-3-ethylcarbodiimide hydrochloride (573 mg, 3 mmol) in N,N-dimethylformamide (9 mL). The tetrahydropyranyl hydroxamate (855 mg, 60%) was obtained as an oil.

Part E: The tetrahydropyranyl hydroxamate (855 mg, 1.26 mmol) was dissolved in absolute methanol (10 mL). Acetyl chloride (0.78 mL, 11 mmol) was added over 2–3 minutes. After 4 hours both tetrahydropyranyl groups had been cleaved. The reaction was concentrated, azeotroped with chloroform/acetonitrile, and dried in vacuo affording the title compound as a white foam (676 mg, 98%). MS (EI) $MH^+$ calculated for $C_{21}H_{23}F_3N_2O_7S$: 505, found 505.

EXAMPLE 231

Preparation of N-Hydroxy-4-[[4-[4-[(trifluoromethyl)thio]phenoxy]phenyl]-sulfonyl]-4-piperidinecarboxamide, Monohydrochloride

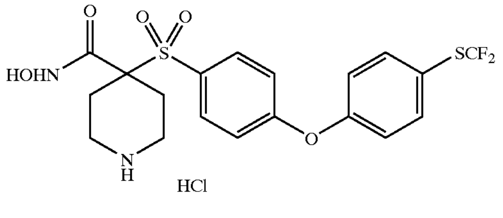

Part A: To a solution of the compound of example N-tert-butoxycarbonyl-ethyl 4-(4-fluorophenylsulfonyl)-4-piperidinecarboxylate, hydrochloride of Preparative Example II (1.50 g, 3.61 mmol) in N,N-dimethylformamide (10 mL) was added cesium carbonate (2.94 g, 9.03 mmol) and (4-trifluoromethylthio) phenol (1.05 g, 5.41 mmol) and the solution was heated to 100 degrees Celsius for 24 hours. The solution was partitioned between ethyl acetate and water and the organic layer was washed with water and dried over sodium sulfate. Filtration through silica gel (ethyl acetate) provided the phenoxyphenol compound as an oil (2.35 g, quantitative yield). MS(CI) $MH^+$ calculated for $C_{26}H_{30}NO_7S_2F_3$: 590, found 590.

Part B: To a solution of phenoxyphenol compound of part A (2.35 g, <3.61 mmol) in tetrahydrofuran (10 mL) and ethanol (10 mL) was added sodium hydroxide (1.44 g, 36.1 mmol) in water (5 mL). The solution was heated to sixty degrees Celsius for 20 hours. The solution was concentrated under a stream of nitrogen to remove the solvents and the residue was dissolved in water and acidified to pH=1 with 10% hydrochloric acid. The solution was extracted with ethyl acetate and washed with saturated sodium chloride and dried over magnesium sulfate. Concentration in vacuo provided the carboxylic acid as an oil (2.0 g, quantitative yield).

Part C: To a solution of the carboxylic acid of part B (2.0 g, <3.61 mmol) in N,N-dimethylformamide (10 mL) was added 1-hydroxybenzotriazole hydrate (586 mg, 4.33 mmol), 4-methylmorpholine (1.19 mL, 10.8 mmol) and O-tetrahydropyranyl hydroxylamine (634 mg, 5.41 mmol) and the solution was stirred for 30 minutes. The 1-[3-(dimethylamino)propyl]-3-ethylcarbodiimide hydrochloride (969 mg, 5.05 mmol) was added and the solution was stirred for seven days. The solution was partitioned between ethyl acetate and water and the organic layer was washed with water and saturated sodium chloride and dried over sodium sulfate. Chromatography (on silica, ethyl acetate/hexane) provided the protected hydroxamate as a clear, colorless oil (1.07 g, 45% yield). MS(CI) $MNa^+$ calculated for $C_{29}H_{35}N_2O_8S_2F_3$: 683, found 683.

Part D: To a solution of the protected hydroxamate of part C (1.05 g, 1.60 mmol) in 1,4-dioxane (10 mL) was added 4M hydrochloric acid in dioxane (10 mL) and the solution was stirred for 1.5 hours. The solution was diluted with ethyl ether and the resulting white precipitate was collected by vacuum filtration to provide the title compound as a white solid (330 mg, 40% yield). MS(CI) $MH^+$ calculated for $C_{19}H_{19}N_2O_5S_2F_3$: 477, found 477. HRMS calculated for $C_{19}H_{19}N_2O_5S_2F_3$: 477.0766, found 477.0766. Analytical calculation for $C_{19}H_{19}N_2O_5S_2HCl$: C, 44.49; H, 3.93; N, 5.46; Cl, 6.91. Found: C, 44.51; H, 3.90; N, 5.38; Cl, 6.95.

EXAMPLE 232

Preparation of 1-[4-[[1-Cyclopropyl-4-[(hydroxyamino)carbonyl]-4-piperidinyl]sulfonyl]phenyl]-N-methyl-N-(phenylmethyl)-4-piperidinecarboxamide, Monohydrochloride

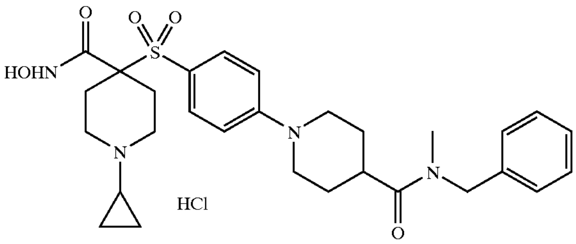

Part A: To a solution of ethyl N-cyclopropyl-4-(4-fluorophenylsulfonyl]-4-piperidinecarboxylate (Preparative Example VI, Part A) (2.0 g, 5.11 mmol) in dimethylacetamide (10 mL) was added methyl isonipectotate (1.03 mL, 7.66 mmol) and cesium carbonate (4.16 g, 12.78 mmol) and was heated to one hundred ten degrees Celsius for 18 hours. The solution was cooled to ambient temperature and partitioned between ethyl acetate and water. The organic layer was washed with water and saturated sodium chloride and dried over sodium sulfate. Concentration in vacuo provided the phenylamine as an oil (1.81 g, 74%). MS(CI) $MH^+$ calculated for $C_{24}H_{34}N_2O_6S$: 479, found 479.

Part B: To a solution of the phenylamine of part A (1.79 g, 3.74 mmol) in tetrahydrofuran (20 mL) was added potassium trimethylsilanoate (960 mg, 7.49 mmol) and the resulting solution was stirred for 18 hours at ambient temperature. The solution was concentrated in vacuo and the residue was dissolved into water. The solution was acidified with 3N hydrochloric acid to pH=3. The resulting precipitate was collected and washed with ethyl ether to provide the acid as a light yellow solid (1.09 g, 63%). MS(CI) $MH^+$ calculated for $C_{23}H_{32}N_2O_6S$: 465, found 465.

Part C: To a solution of the acid of part B (500 mg, 1.08 mmol) in dichloromethane (10 mL) was added 1-hydroxybenzotriazole hydrate (160 mg, 1.19 mmol), triethylamine (0.15 mL, 1.19 mmol) and N-benzylmethylamine (0.33 mL, 2.38 mmol). After thirty minutes the 1-[3-(dimethylamino)propyl]-3-ethylcarbodiimide hydrochloride was added and the solution was stirred for 20 hours at ambient temperature. The solution was diluted with ethyl acetate and washed with water and saturated sodium chloride and dried over sodium sulfate. Chromatography (on silica, ethyl acetate) provided the amide as a white solid (480 mg, 78%). MS(CI) $MH^+$ calculated for $C_{31}H_{41}N_3O_5S$: 568, found 568.

Part D: To a solution of the amide of part C (400 mg, 0.71 mmol) in ethanol (5 mL) and tetrahydrofuran (5 mL) was added sodium hydroxide (282 mg, 7.1 mmol) in water (3 mL). The solution was heated to sixty degrees Celsius for 24 hours. The solution was concentrated under a stream of nitrogen and the residue was diluted with water and acidified with 3N hydrochloric acid to pH=2. The solution was concentrated to provide the acid as a crude white solid which is used in the next step without further purification. MS(CI) $MH^+$ calculated for $C_{29}H_{37}N_5O_5S$: 540, found 540.

Part E: To a solution of the crude acid of part D (<0.71 mmol) in N,N-dimethylformamide (10 mL) was added 1-hydroxybenzotriazole hydrate (115 mg, 0.85 mmol), 4-methylmorpholine (0.39 mL) and O-tetrahydropyranyl hydroxylamine (124 mg, 1.06 mmol). After thirty minutes 1-[3-(dimethylamino)propyl]-3-ethylcarbodiimide hydrochloride (190 mg, 0.99 mmol) was added and the solution was stirred for 18 hours. The solution was partitioned between ethyl acetate and water and the organic layer was washed with water and saturated sodium chloride and dried over sodium sulfate. Chromatography (on silica, ethyl acetate) provided the protected hydroxamate as an oil (184 mg, 41%). MS(CI) $MH^+$ calculated for $C_{34}H_{46}N_4O_6S$: 639, found 639.

Part F: To a solution of the protected hydroxamate of part E (180 mg, 0.28 mmol) in dioxane (10 mL) was added 4M hydrochloric acid in dioxane (10 mL) and the solution was stirred for one hour. Trituration (ethyl ether) and vacuum filtration provided the title compound as a white solid (96.5 mg, 58%). MS(CI) $MH^+$ calculated for $C_{29}H_{38}N_4O_5S$: 555, found 555. HRMS calc. 555.2641, found 555.2644.

EXAMPLE 233

Preparation of 4-[[4-[4-[(3,5-Dimethyl-1-piperidinyl)carbonyl]-1-piperidinyl]-phenyl]sulfonyl]-N-hydroxy-1-(2-methoxyethyl)-4-piperidinecarboxamide, Monohydrochloride

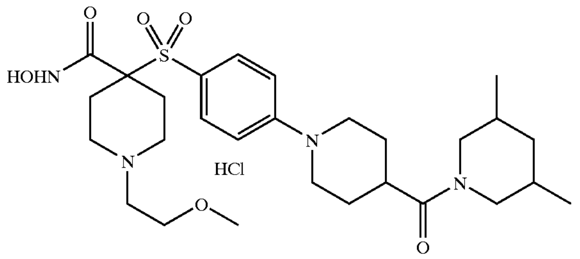

Part A: To a solution of isonipecotic acid (5.8 g, 44.9 mmol) in water (200 mL) was added sodium carbonate (4.62 g, 44.9 mmol) followed by the drop-wise addition of di-tert-butyl-dicarbonate (10.1 g, 46.3 mmol) in dioxane (40 mL). After four hours the solvent was concentrated in vacuo and the solution was extracted with ethyl ether. The aqueous layer was acidified with 3N hydrochloric acid to pH=2. The solution was extracted with ethyl ether and the organic layer was washed with saturated aqueous sodium chloride and dried over magnesium sulfate. Concentration in vacuo provided N-Boc-isonipecotic acid as a white solid (9.34 g, 90%).

Part B: To a solution of the N-Boc-isonipecotic acid of part A (1.0 g, 4.37 mmol) in dichloromethane (10 mL) was added 1-[3-(dimethylamino)propyl]-3-ethylcarbodiimide hydrochloride (853 mg, 4.45 mmol), 1-hydroxybenzotriazole hydrate (620 mg, 4.59 mmol) 3,5-dimethylpiperdine (0.67 mL, 5.03 mmol) and diisopropylethylamine (1.67 mL, 9.61 mmol) and was stirred for 21 hours. The solution was concentrated in vacuo. The residue was diluted with ethyl acetate and washed with 1M hydrochloric acid, saturated sodium bicarbonate and saturated aqueous sodium chloride and dried over sodium sulfate. Concentration in vacuo provided the amide as a clear colorless oil (1.21 g, 89%).

Part C: To a solution of the amide of part B (1.20 g, 3.84 mmol) in dichloromethane (5 mL) was added trifluoroacetic acid (5 mL) and the solution was stirred for 1 hour. Concentration in vacuo provided an oil which was added directly to a solution of the compound of Preparative Example VII, Part A (956 mg, 2.56 mmol) in dimethylacetamide (10 mL). Cesium carbonate (2.92 g, 8.96 mmol) was added and the solution was heated to one hundred degrees Celsius for 18 hours. The solution was partitioned between ethyl acetate and water and the organic layer was washed with water and saturated sodium chloride and dried over sodium sulfate. Concentration in vacuo provided the phenylamine as an oil (1.53 g, 68%). MS(CI) $MH^+$ calculated for $C_{30}H_{47}N_3O_6S$: 578, found 578.

Part D: To a solution of the phenylamine of part C (1.5 g, 2.6 mmol) in ethanol (9 mL) and tetrahydrofuran (9 mL) was added sodium hydroxide (1.02 g, 26 mmol) in water (5 mL) and the solution was heated to sixty degrees Celsius for 20 hours. The solution was concentrated and the residue was diluted with water and acidified to pH=3 with 3N hydrochloric acid. Vacuum filtration provided the acid as a beige solid (500 mg, 33%). MS(CI) $MH^+$ calculated for $C_{28}H_{43}N_3O_6S$: 550, found 550.

Part E: To a solution of the acid of part D (492 mg, 0.84 mmol) in N,N-dimethylformamide (10 mL) was added 1-hydroxybenzotriazole hydrate (136 mg, 1.01 mmol), 4-methylmorpholine (0.46 mL, 4.20 mmol), and O-tetrahydropyranyl hydroxylamine (147 mg, 1.26 mmol). After one hour 1-[3-(dimethylamino)propyl]-3-ethylcarbodiimide hydrochloride (225 mg, 1.18 mmol) was added and the solution was stirred for 72 hours at ambient temperature. The solution was partitioned between ethyl acetate and water. The organic layer was washed with water and saturated sodium chloride and dried over sodium sulfate. Concentration in vacuo provided the protected hydroxamate as an oil (524 mg, 96%). MS(CI) $MH^+$ calculated for $C_{33}H_{51}N_4O_7S$: 649, found 649.

Part F: To a solution of the protected hydroxamate of part E (514 mg, 0.79 mmol) in 1,4-dioxane (10 mL) was added 4M hydrochloric acid in dioxane (10 mL) and the solution was stirred for 1.5 hours. The solution was concentrated in vacuo and trituration (ethyl ether) provided the title compound as a white solid (360 mg, 76%). MS(CI) $MH^+$ calculated for $C_{28}H_{44}N_4O_6S$: 565, found 565. HRMS calculated for $C_{28}H_{44}N_4O_6S$: 565.3060, found 565.3070. Analytical calculation for $C_{28}H_{44}N_4O_6S2HCl:2H_2O$: C, 49.92; H, 7.48; N, 8.32; S, 4.76; Cl, 10.52. Found: C, 49.41; H, 7.55; N, 7.85; S, 4.53; Cl, 10.78.

EXAMPLE 234

Preparation of 4-[[4-[4-[(3,5-Dimethyl-1-piperidinyl)carbonyl]-1-piperidinyl]-phenyl]sulfonyl]-N-hydroxy-1-(2-methoxyethyl)-4-piperidinecarboxamide

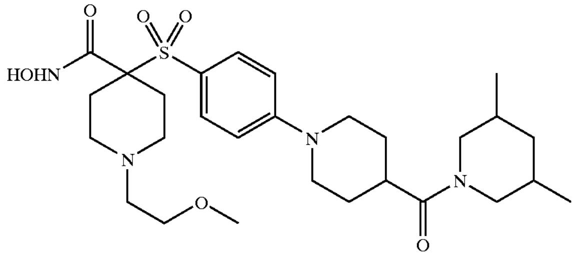

Part A: A solution of the hydroxamate of Example 233, part F (50 mg, 0.08 mmol) in water (2 mL) was neutralized with saturated sodium bicarbonate. The aqueous solution was extracted with ethyl acetate. Concentration in vacuo provided the hydroxamate free base as an orange solid (35 mg, 75%).

EXAMPLE 235

Preparation of 1-[4-[[4[(Hydroxyamino)carbonyl]-1-(2-methoxyethyl)-4-piperidinyl]sulfonyl]phenyl]-N-methyl-N-[2-(2-pyridinyl)ethyl]-4-piperidinecarboxamide, Dihydrochloride

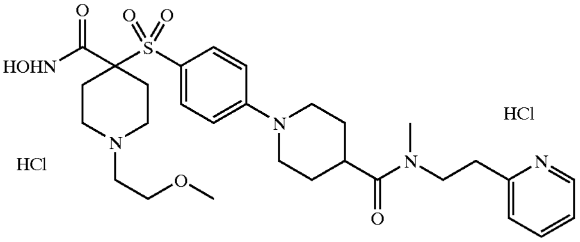

Part A: To a solution of the N-Boc-isonipecotic acid of Example 233, part A (1.0 g, 4.37 mmol) in dichloromethane (10 mL) was added 1-[3-(dimethylamino)propyl]-3-ethylcarbodiimide hydrochloride (853 mg, 4.45 mmol), 1-hydroxybenzotriazole hydrate (620 mg, 4.59 mmol), 2-(2-methylaminoethyl)pyridine (0.69 mL, 5.03 mmol) and diisopropylethylamine (1.67 mL, 9.61 mmol) and was stirred for 21 hours. The solution was concentrated in vacuo. The residue was diluted with ethyl acetate and washed with 1M hydrochloric acid, saturated sodium bicarbonate and saturated sodium chloride and dried over sodium sulfate. Concentration in vacuo provided the amide as a clear colorless oil (1.03 g, 68%). MS(CI) $MH^+$ calculated for $C_{19}H_{29}N_3O_3$: 348, found 348.

Part B: To a solution of the amide of part A (1.0 g, 2.88 mmol) in dichloromethane (5 mL) was added trifluoroacetic acid (5 mL) and the solution was stirred for 1 hour. Concentration in vacuo provided an oil which was added directly to a solution of the compound of Preparative Example VII, Part A (716 mg, 1.92 mmol) in dimethylacetamide (10 mL). Cesium carbonate (2.20 g, 6.72 mmol) was added and the solution was heated to one hundred degrees Celsius for 18 hours. The solution was partitioned between ethyl acetate and water and the organic layer was washed with water and saturated sodium chloride and dried over sodium sulfate. Concentration in vacuo provided the phenylamine as a yellow oil (1.20 g, quantitative yield). MS(CI) $MH^+$ calculated for $C_{31}H_{44}N_4O_6S$: 601, found 601.

Part C: To a solution of the phenylamine of part B (1.20 g, 2.00 mmol) in ethanol (8 mL) and tetrahydrofuran (8 mL) was added sodium hydroxide (800 mg, 20 mmol) in water (5 mL) and the solution was heated to sixty degrees Celsius for 20 hours. The solution was concentrated and the residue was diluted with water and acidified to pH=1 with 3N hydrochloric acid. Concentration in vacuo provided the crude acid as an oil. MS(CI) $MH^+$ calculated for $C_{29}H_{40}N_4O_6S$: 573, found 573.

Part D: To a solution of the acid of part C (<2.0 mmol) in N,N-dimethylformamide (10 mL) was added 1-hydroxybenzotriazole hydrate (324 mg, 2.04 mmol), 4-methylmorpholine (1.1 mL, 10.0 mmol), and O-tetrahydropyranyl hydroxylamine (351 mg, 3.00 mmol). After one hour 1-[3-(dimethylamino)propyl]-3-ethylcarbodiimide hydrochloride (536 mg, 2.80 mmol) was added and the solution was stirred for 18 hours at ambient temperature. The solution was partitioned between ethyl acetate and water. The organic layer was washed with water and saturated sodium chloride and dried over sodium sulfate. Reverse phase chromatography (on silica, acetonitrile/water) provided the protected hydroxamate as an oil (170 mg, 13% yield over two steps). MS(CI) $MH^+$ calculated for $C_{34}H_{49}N_5O_7S$: 672, found 672.

Part E: To a solution of the protected hydroxamate of part D (160 mg, 0.24 mmol) in dioxane (7 mL) was added 4M hydrochloric acid in dioxane (10 mL) and the solution was stirred for 30 minutes. The resulting solid was collected by vacuum filtration. Washing with ethyl ether provided the title compound as a white solid (90 mg, 57%). MS(CI) $MH^+$ calculated for $C_{29}H_{37}N_5O_6S$: 588, found 588. HRMS calculated for $C_{29}H_{37}N_5O_6S$: 558.2856, found 588.2857.

EXAMPLE 236

Preparation of N-Hydroxy-1-(2-methoxyethyl)-4-[[4-[4-[(phenylamino)carbonyl]-1-piperidinyl]phenyl]-sulfonyl]-4-piperidinecarboxamide Monohydrochloride)

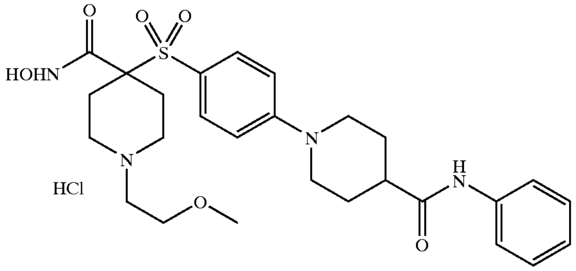

Part A: To a solution of the N-Boc-isonipecotic acid of Example 233, part A (1.0 g, 4.37 mmol) in dichloromethane (4 mL) was added 2-chloro-4,6-dimethoxy-1,3,5-triazine (752 mg, 4.28 mmol). The solution was cooled to zero degrees Celsius and 4-methylmorpholine (0.47 mL, 4.28 mmol) was added. After two hours aniline (0.39 mL, 4.28 mmol) was added and the solution was stirred for 20 hours at ambient temperature. The solution was concentrated in vacuo. The residue was diluted with ethyl acetate and washed with 1M hydrochloric acid, saturated sodium bicarbonate and saturated sodium chloride and dried over sodium sulfate. Concentration in vacuo provided the amide as a pink solid (1.48 g, quantitative yield).

Part B: To a solution of the amide of part A (1.48 g, 4.28 mmol) in dichloromethane (5 mL) was added trifluoroacetic (5 mL) and the solution was stirred for 1 hour. Concentration in vacuo provided an oil which was added directly to a solution of the compound of Preparative Example VII, Part A (1.06 mg, 2.85 mmol) in dimethylacetamide (10 mL). Cesium carbonate (3.25 g, 9.97 mmol) was added and the solution was heated to one hundred ten degrees Celsius for 18 hours. The solution was partitioned between ethyl acetate and water and the organic layer was washed with water and saturated sodium chloride and dried over sodium sulfate. Concentration in vacuo provided the phenylamine as a yellow oil (1.74 g, quantitative yield). MS(CI) $MH^+$ calculated for $C_{29}H_{39}N_3O_6S$: 558, found 558.

Part C: To a solution of the phenylamine of part B (1.74 g, 2.85 mmol) in ethanol (10 mL) and tetrahydrofuran (10 mL) was added sodium hydroxide (1.14 g, 28.5 mmol) in water (7 mL) and the solution was heated to sixty degrees Celsius for 20 hours. The solution was concentrated and the residue was diluted with water and acidified to pH=1 with 3N hydrochloric acid producing a solid. Vacuum filtration provided the acid as a beige solid (1.62 g, quantitative yield). MS(CI) $MH^+$ calculated for $C_{27}H_{35}N_3O_6S$: 530, found 530.

Part D: To a solution of the acid of part C (1.60 g, 2.83 mmol) in N,N-dimethylformamide (10 mL) was added 1-hydroxybenzotriazole hydrate (458 mg, 3.40 mmol), 4-methylmorpholine (1.56 mL, 14.2 mmol), and O-tetrahydropyranyl hydroxylamine (497 mg, 4.24 mmol). After one hour, 1-[3-(dimethylamino)propyl]-3-ethylcarbodiimide hydrochloride (759 mg, 3.96 mmol) was added and the solution was stirred for 18 hours at ambient temperature. The solution was partitioned between ethyl acetate and water. The organic layer was washed with water and saturated sodium chloride and dried over sodium sulfate. Chromatography (on silica, ethyl acetate/methanol) provided the protected hydroxamate as a yellow oil (790 mg, 44%). MS(CI) $MH^+$ calculated for $C_{32}H_{44}N_4O_7S$: 629, found 629.

Part E: To a solution of the protected hydroxamate of part D (780 mg, 1.24 mmol) in dioxane (10 mL) was added 4M hydrochloric acid in dioxane (10 mL) and the solution was stirred for two hours. The resulting solid was collected by vacuum filtration. Washing with ethyl ether provided the title compound as a white solid (580 mg, 80%). MS(CI) $MH^+$ calculated for $C_{27}H_{36}N_4O_6S$: 545, found 545. HRMS calculated for $C_{27}H_{36}N_4O_6S$: 545.2434, found 545.2429.

EXAMPLE 237

Preparation of N-Hydroxy-1-(2-methoxyethyl)-4-[[4-[4-[[(3-phenylpropyl)amino]carbonyl]-1-piperidinyl]-phenyl]sulfonyl]-4-piperidinecarboxamide, Monohydrochloride

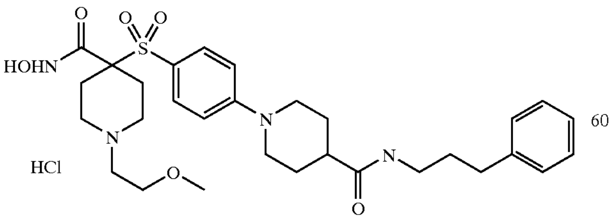

Part A: To a solution of the N-Boc-isonipecotic acid of Example 233, part A (1.0 g, 4.37 mmol) in dichloromethane (10 mL) was added 1-[3-(dimethylamino)propyl]-3-ethylcarbodiimide hydrochloride (853 mg, 4.45 mmol), 1-hydroxybenzotriazole hydrate (620 mg, 4.59 mmol), 3-phenyl-1-propylamine (0.72 mL, 5.03 mmol) and diisopropylethylamine (1.67 mL, 9.61 mmol) and was stirred for 18 hours. The solution was concentrated in vacuo. The residue was diluted with ethyl acetate and washed with 1M hydrochloric acid, saturated sodium bicarbonate and saturated sodium chloride and dried over sodium sulfate. Concentration in vacuo provided the amide as a yellow oil (1.4 g, 93%).

Part B: To a solution of the amide of part A (1.4 g, 4.05 mmol) in dioxane (10 mL) was added 4M hydrochloric acid in dioxane (10 mL) and the solution was stirred for 1 hour. The resulting solid was collected by vacuum filtration and washed with ethyl ether. The solid was added to a solution of the compound of Preparative Example VII, Part A (1.01 mg, 2.70 mmol) in dimethylacetamide (10 mL). Cesium carbonate (3.07 g, 9.45 mmol) was added and the solution was heated to one hundred degrees Celsius for 18 hours. The solution was partitioned between ethyl acetate and water and the organic layer was washed with water and saturated sodium chloride and dried over sodium sulfate. Concentration in vacuo provided the phenylamine as an orange oil (1.71 g, quantitative yield). MS(CI) $MH^+$ calculated for $C_{32}H_{45}N_3O_6S$: 600, found 600.

Part C: To a solution of the phenylamine of part B (1.70 g, 2.70 mmol) in ethanol (10 mL) and tetrahydrofuran (10 mL) was added sodium hydroxide (1.08 g, 27.0 mmol) in water (5 mL) and the solution was heated to sixty degrees Celsius for 20 hours. The solution was concentrated and the residue was diluted with water and acidified to pH=1 with 3N hydrochloric acid producing a solid. Vacuum filtration provided the acid as a white solid (1.15 g, 75%). MS(CI) $MH^+$ calculated for $C_{30}H_{41}N_3O_6S$: 572, found 572.

Part D: To a solution of the acid of part C (1.02 g, 1.68 mmol) in N,N-dimethylformamide (10 mL) was added 1-hydroxybenzotriazole hydrate (272 mg, 2.02 mmol), 4-methylmorpholine (0.92 mL, 8.4 mmol), and O-tetrahydropyranyl hydroxylamine (295 mg, 2.52 mmol). After one hour 1-[3-(dimethylamino)propyl]-3-ethylcarbodiimide hydrochloride (451 mg, 2.35 mmol) was added and the solution was stirred for 18 hours at ambient temperature. The solution was partitioned between ethyl acetate and water. The organic layer was washed with water and saturated sodium chloride and dried over sodium sulfate. Chromatography (on silica, ethyl acetate/methanol) provided the protected hydroxamate as an oil (490 mg, 41%). MS(CI) $MH^+$ calculated for $C_{35}H_{50}N_4O_7S$: 671, found 671.

Part E: To a solution of the protected hydroxamate of part D (480 mg, 0.72 mmol) in dioxane (10 mL) was added 4M hydrochloric acid in dioxane (10 mL) and the solution was stirred for one hour. The resulting solid was collected by vacuum filtration. Washing with ethyl ether provided the title compound as a white solid (400 mg, 90%). MS(CI) $MH^+$ calculated for $C_{30}H_{42}N_4O_6S$: 587, found 587. Analytical calculation for $C_{30}H_{42}N_4O_6S2HCl{:}2H_2O$: C, 51.79; H, 6.95; N, 8.05; S, 4.61; Cl, 10.19. Found: C, 51.34; H, 6.72; N, 7.82; S, 4.59; Cl, 10.92.

EXAMPLE 238

Preparation of rel-4-[[4-[4-[[(3R,5R)-3,5-Dimethyl-1-piperidinyl]carbonyl]-1-piperidinyl]phenyl]sulfonyl]-N-hydroxy-4-piperidinecarboxamide, Monohydrochloride

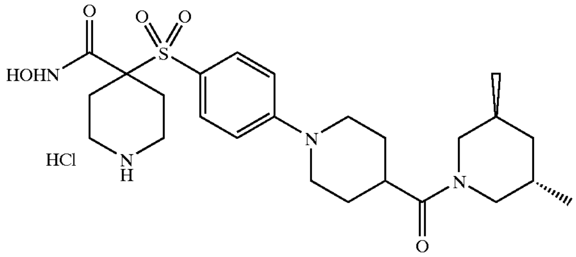

Part A: To a solution of the N-Boc-isonipecotic acid of Example 233, Part A (1.0 g, 4.37 mmol) in dichloromethane (10 mL) was added 1-[3-(dimethylamino)propyl]-3-ethylcarbodiimide hydrochloride (853 mg, 4.45 mmol), 1-hydroxybenzotriazole hydrate (620 mg, 4.59 mmol) 3,5-dimethylpiperdine (0.67 mL, 5.03 mmol) and diisopropylethylamine (1.67 mL, 9.61 mmol) and was stirred for 21 hours. The solution was concentrated in vacuo. The residue was diluted with ethyl acetate and washed with 1M hydrochloric acid, saturated sodium bicarbonate and saturated sodium chloride and dried over sodium sulfate. Concentration in vacuo provided the amide as a clear colorless oil (1.4 g, quantitative yield).

Part B: To a solution of the amide of part A (1.4 g, 4.49 mmol) in dioxane (10 mL) was added 4M hydrochloric acid in dioxane (10 mL) and the solution was stirred for 1 hour. Concentration in vacuo provided a solid that was added directly to a solution of the compound of Preparative Example II, Part D, (1.24 mg, 2.99 mmol) in dimethylacetamide (10 mL). Cesium carbonate (3.42 g, 10.5 mmol) was added and the solution was heated to one hundred degrees Celsius for 20 hours. The solution was partitioned between ethyl acetate and water and the organic layer was washed with water and saturated sodium chloride and dried over sodium sulfate. Concentration in vacuo provided the phenylamine as a yellow solid (1.90 g, quantitative yield). MS(CI) $MH^+$ calculated for $C_{32}H_{49}N_3O_7S$: 620, found 620.

Part C: To a solution of the phenylamine of part B (1.9 g, 3.0 mmol) in ethanol (10 mL) and tetrahydrofuran (10 mL) was added sodium hydroxide (1.2 g, 30 mmol) in water (5 mL) and the solution was heated to sixty degrees Celsius for 20 hours. The solution was concentrated and the residue was diluted with water and acidified to pH=1 with 3N hydrochloric acid. The solution was extracted with ethyl acetate and washed with 1M hydrochloric acid and saturated sodium chloride and dried over magnesium sulfate. Concentration in vacuo provided the acid as a yellow oil (1.9 g, quantitative yield). MS(CI) $MH^+$ calculated for $C_{30}H_{45}N_3O_7S$: 592, found 592.

Part D: To a solution of the acid of part C (1.87 g, 3.00 mmol) in N,N-dimethylformamide (10 mL) was added 1-hydroxybenzotriazole hydrate (486 mg, 3.6 mmol), 4-methylmorpholine (1.65 mL, 15 mmol), and O-tetrahydropyranyl hydroxylamine (526 mg, 4.5 mmol). After one hour 1-[3-(dimethylamino)propyl]-3-ethylcarbodiimide hydrochloride (805 mg, 4.2 mmol) was added and the solution was stirred for 18 hours at ambient temperature. The solution was partitioned between ethyl acetate and water. The organic layer was washed with water and saturated sodium chloride and dried over sodium sulfate. Chromatography (on silica, ethyl acetate/hexane) provided the protected hydroxamate as an oil (1.63 g, 79%).

Part E: To a solution of the protected hydroxamate of part D (1.61 g, 2.33 mmol) in dioxane (10 mL) was added 4M hydrochloric acid in dioxane (10 mL) and the solution was stirred for 45 minutes. The solution was concentrated in vacuo and trituration (ethyl ether) a white solid. Reverse phase chromatography (on silica, acetonitrile/water (hydrochloric acid)) produced fractions A, B, C and D. Concentration in vacuo of fraction A provided the title compound as a white solid (59 mg). MS(CI) $MH^+$ calculated for $C_{25}H_{38}N_4O_5S$: 507, found 507.

EXAMPLE 239

Preparation of rel-1,1-Dimethylethyl 4-[[4-[4-[[(3R,5R)-3,5-Dimethyl-1-piperidinyl]carbonyl]-1-piperidinyl]-phenyl]sulfonyl]-4-[(hydroxyamino)carbonyl]-1-piperidinecarboxylate

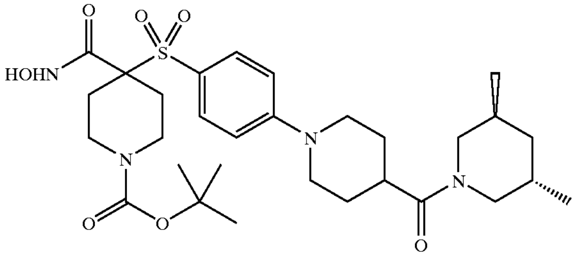

Part A: From the reverse phase chromatography of Example 238, Part E, fraction C was concentrated in vacuo to provide the title compound as a white solid (49 mg). MS(CI) $MH^+$ calculated for $C_{30}H_{46}N_4O_7S$: 607, found 607.

EXAMPLE 240

Preparation of rel-4-[[4-[4-[[(3R,5S)-3,5-Dimethyl-1-piperidinyl]carbonyl]-1-piperidinyl]phenyl]sulfonyl]-N-hydroxy-4-piperidinecarboxamide, Monohydrochloride

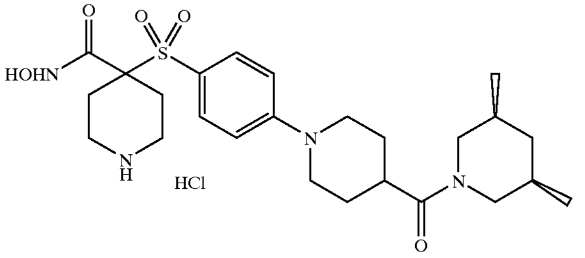

Part A: From the reverse phase chromatography of Example 238, Part E, fraction B was concentrated in vacuo to provide the title compound as a white solid (198 mg). MS(CI) $MH^+$ calculated for $C_{25}H_{38}N_4O_5S$: 507, found 507.

EXAMPLE 241

Preparation of rel-1,1-Dimethylethyl 4-[[4-[4-[[(3R, 5S)-3,5-Dimethyl-1-piperidinyl]carbonyl]-1-piperidinyl]-phenyl]sulfonyl]-4-[(hydroxyamino) carbonyl]-1-piperidinecarboxylate

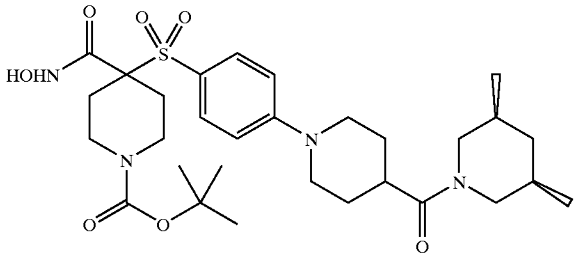

Part A: From the reverse phase chromatography of Example 238, Part E, fraction D was concentrated in vacuo to provide the title compound as a white solid (242 mg). MS(CI) $MH^+$ calculated for $C_{30}H_{46}N_4O_7S$: 607, found 607.

EXAMPLE 242

Preparation of 4-[[4-[4-[[(2,3-Dihydro-1H-inden-2-yl)amino]carbonyl]-1-piperidinyl]phenyl]sulfonyl]-N-hydroxy-1-(2-methoxyethyl)-4-piperidinecarboxamide, Monohydrochloride

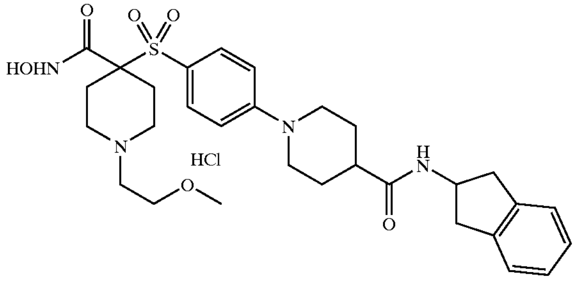

Part A: To a solution of the N-Boc-isonipecotic acid of Example 233, Part A (1.0 g, 4.37 mmol) in dichloromethane (10 mL) was added 1-[3-(dimethylamino)propyl]-3-ethylcarbodiimide hydrochloride (853 mg, 4.45 mmol), 1-hydroxybenzotriazole hydrate (620 mg, 4.59 mmol) 2-aminoindane hydrochloride (853 mg, 5.03 mmol) and diisopropylethylamine (1.67 mL, 9.61 mmol) and was stirred for 21 hours. The solution was concentrated in vacuo. The residue was diluted with ethyl acetate and washed with 1M hydrochloric acid, saturated sodium bicarbonate and saturated sodium chloride and dried over sodium sulfate. Concentration in vacuo provided the amide as a white solid (1.35 g, 90%).

Part B: To a solution of the amide of part A (1.35 g, 3.92 mmol) in 1,4-dioxane (10 mL) was added 4M hydrochloric acid in dioxane (10 mL) and the solution was stirred for 1 hour. Concentration in vacuo provided a solid which was added directly to a solution of the title compound of Preparative Example VII, Part A, (976 mg, 2.61 mmol) in dimethylacetamide (10 mL). Cesium carbonate (2.97 g, 9.14 mmol) was added and the solution was heated to one hundred degrees Celsius for 18 hours. The solution was partitioned between ethyl acetate and water and the organic layer was washed with water and saturated sodium chloride and dried over sodium sulfate. Concentration in vacuo provided the phenylamine as an orange oil (1.65 g, quantitative yield). MS(CI) MH+calculated for $C_{32}H_{43}N_3O_6S$: 598, found 598.

Part C: To a solution of the phenylamine of part B (1.60 g, 2.61 mmol) in ethanol (10 mL) and tetrahydrofuran (10 mL) was added sodium hydroxide (1.04 g, 26 mmol) in water (5 mL) and the solution was heated to sixty degrees Celsius for 18 hours. The solution was concentrated and the residue was diluted with water and acidified to pH=3 with 3N hydrochloric acid. Vacuum filtration provided the acid as a beige solid (1.06 g, 71%). MS(CI) $MH_+$ calculated for $C_{30}H_{39}N_3O_6S$: 570, found 570.

Part D: To a solution of the acid of part (1.0 g, 1.65 mmol) in N,N-dimethylformamide (10 mL) was added 1-hydroxybenzotriazole hydrate (267 mg, 1.98 mmol), 4-methylmorpholine (0.91 mL, 8.25 mmol), and O-tetrahydropyranyl hydroxylamine (289 mg, 2.48 mmol). After one hour 1-[3-(dimethylamino)propyl]-3-ethylcarbodiimide hydrochloride (443 mg, 2.31 mmol) was added and the solution was stirred for 18 hours at ambient temperature. The solution was partitioned between ethyl acetate and water. The organic layer was washed with water and saturated sodium chloride and dried over sodium sulfate. Chromatography (on silica, ethyl acetate, methanol) provided the protected hydroxamate as an oil (575 mg, 52%). MS(CI) $MH^+$ calculated for $C_{35}H_{48}N_4O_7S$: 669, found 669.

Part E: To a solution of the protected hydroxamate of part D (565 mg, 0.85 mmol) in dioxane (10 mL) was added 4M hydrochloric acid in dioxane (10 mL) and the solution was stirred for 1.5 hours. The solution was concentrated in vacuo and trituration (ethyl ether) provided the title compound as a white solid (450 mg, 86%). MS(CI) $MH^+$ calculated for $C_{30}H_{40}N_4O_6S$: 585, found 585. HRMS calculated for $C_{30}H_{40}N_4O_6S$: 585.2747, found 585.2776. Analytical calculation for $C_{30}H_{40}N_4O_6S2HCl{:}2H_2O$: C, 51.94; H, 6.68; N, 8.08; S, 4.62; Cl, 10.22. Found: C, 51.66; H, 6.25; N, 7.80; S, 4.73; Cl, 10.33.

EXAMPLE 243

Preparation of 1-Cyclopropyl-N-hydroxy-4-[[4-[4-[(phenylamino)carbonyl]-1-piperidinyl]phenyl] sulfonyl]-4-piperidinecarboxamide, Monohydrochloride

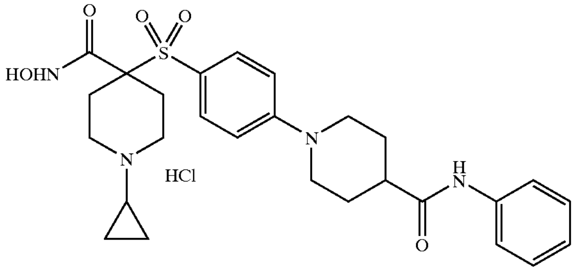

Part A: To a solution of the product of Example 232, Part B (562 mg, 1.12 mmol) in dichloromethane (3 mL) was added 2-chloro-4,6-dimethoxy-1,3,5-triazine (164 mg, 0.93 mmol) and 4-methylmorpholine (0.21 mL, 1.87 mmol). The solution was stirred for 45 minutes and aniline (0.085 mL, 0.93 mmol) was added. The solution was stirred for 72 hours. The solution was partitioned between ethyl acetate and water and the organic layer was washed with water and saturated sodium chloride and dried over sodium sulfate. Concentration in vacuo provided the amide as an oil (434 mg, 86%). MS(CI) MH+ calculated for $C_{29}H_{37}N_3O_5S$: 540, found 540.

Part B: To a solution of the amide of part A (425 mg, 0.79 mmol) in ethanol (5 mL) and tetrahydrofuran (5 mL) was added sodium hydroxide (315 mg, 7.89 mmol) in water (2 mL) and the solution was heated to sixty degrees Celsius for 18 hours. The solution was concentrated and the residue was diluted with water and acidified to pH=1 with 3N hydrochloric acid producing a solid. Vacuum filtration provided the acid as a beige solid (261 mg, 60%). MS(CI) MH+ calculated for $C_{27}H_{33}N_3O_5S$: 512, found 512.

Part C: To a solution of the acid of part B (245 mg, 0.45 mmol) in N,N-dimethylformamide (10 mL) was added 1-hydroxybenzotriazole hydrate (73 mg, 0.54 mmol), 4-methylmorpholine (0.25 mL, 2.25 mmol), and O-tetrahydropyranyl hydroxylamine (79 mg, 0.68 mmol). After one hour 1-[3-(dimethylamino)propyl]-3-ethylcarbodiimide hydrochloride (121 mg, 0.63 mmol) was added and the solution was stirred for 18 hours at ambient temperature. The solution was partitioned between ethyl acetate and water. The organic layer was washed with water and saturated sodium chloride and dried over sodium sulfate. Chromatography (on silica, ethyl acetate) provided the protected hydroxamate as a yellow oil (242 mg, 88%). MS(CI) MH+ calculated for $C_{32}H_{42}N_4O_6S$: 611, found 611.

Part D: To a solution of the protected hydroxamate of part C (235 mg, 0.38 mmol) in dioxane (5 mL) was added 4M hydrochloric acid in dioxane (10 mL) and the solution was stirred for two hours. The resulting solid was collected by vacuum filtration. Washing with ethyl ether provided the title compound as a white solid (114 mg, 53%). MS(CI) MH+ calculated for $C_{27}H_{34}N_4O_5S$: 527, found 527. HRMS calculated for $C_{27}H_{34}N_4O_5S$: 527.2328, found 527.2339.

EXAMPLE 244

Preparation of 1-[4-[[4-[(Hydroxyamino)carbonyl]-1-(2-methoxyethyl)-4-piperidinyl]-sulfonyl]phenyl]-N-methyl-N-phenyl-4-piperidinecarboxamide, Monohydrate

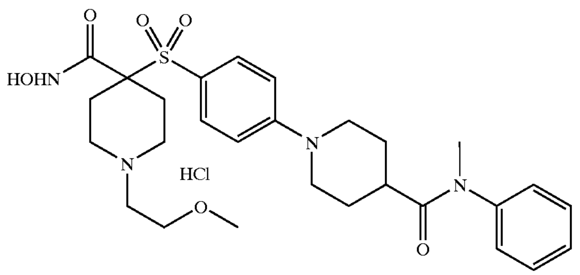

Part A: To a solution of the N-Boc-isonipecotic acid of Example 233, Part A (500 mg, 2.18 mmol) in dichloromethane (2 mL) was added 2-chloro-4,6-dimethoxy-1,3,5-triazine (319 mg, 1.82 mmol). The solution was cooled to zero degrees Celsius and 4-methylmorpholine (0.20 mL, 1.82 mmol) was added. After two hours, N-methylaniline (0.20 mL, 1.82 mmol) was added and the solution was stirred for 20 hours at ambient temperature. The solution was concentrated in vacuo. The residue was diluted with ethyl acetate and washed with 1M hydrochloric acid, saturated sodium bicarbonate and saturated sodium chloride and dried over sodium sulfate. Concentration in vacuo provided the amide as a pink solid (445 mg, 77%).

Part B: To a solution of the amide of part A (440 g, 1.38 mmol) in 1,4-dioxane (10 mL) was added 4M hydrochloric acid in dioxane (10 mL) and the solution was stirred for 1 hour. Concentration in vacuo provided an oil which was added directly to a solution of the compound of Preparative Example VII, Part A (344 mg, 0.92 mmol) in dimethylacetamide (10 mL). Cesium carbonate (1.05 g, 3.22 mmol) was added and the solution was heated to one hundred ten degrees Celsius for 18 hours. The solution was partitioned between ethyl acetate and water and the organic layer was washed with water and saturated sodium chloride and dried over sodium sulfate. Concentration in vacuo provided the phenylamine as a yellow oil (440 mg, 84%).

Part C: To a solution of the phenylamine of part B (440 mg, 0.77 mmol) in ethanol (7 mL) and tetrahydrofuran (7 mL) was added sodium hydroxide (308 mg, 7.7 mmol) in water (3 mL) and the solution was heated to sixty degrees Celsius for 20 hours. The solution was concentrated and the residue was diluted with water and acidified to pH=1 with 3N hydrochloric acid producing a solid. Vacuum filtration provided the acid as a yellow solid and carried on to the next step without additional purification.

Part D: To a solution of the acid of part C (<0.77 mmol) in N,N-dimethylformamide (10 mL) was added 1-hydroxybenzotriazole hydrate (125 mg, 0.92 mmol), 4-methylmorpholine (0.43 mL, 3.85 mmol), and O-tetrahydropyranyl hydroxylamine (135 mg, 1.16 mmol). After one hour, 1-[3-(dimethylamino)propyl]-3-ethylcarbodiimide hydrochloride (207 mg, 1.08 mmol) was added and the solution was stirred for 24 hours at ambient temperature. The solution was partitioned between ethyl acetate and water. The organic layer was washed with water and saturated sodium chloride and dried over sodium sulfate. Chromatography (on silica, ethyl acetate/methanol) provided the protected hydroxamate as a yellow oil (150 mg, 30%). MS(CI) MH+ calculated for $C_{33}H_{46}N_4O_7S$: 643, found 643.

Part E: To a solution of the protected hydroxamate of part D (150 mg, 0.23 mmol) in dioxane (2 mL) was added 4M hydrochloric acid in dioxane (3 mL) and the solution was stirred for two hours. The resulting solid was collected by vacuum filtration. Washing with ethyl ether provided the title compound as a yellow solid (75 mg, 55%). MS(CI) MH+ calculated for $C_{28}H_{38}N_4O_6S$: 559, found 559. HRMS calculated for $C_{28}H_{38}N_4O_6S$: 559.2590, found 559.2613.

EXAMPLE 245

Preparation of 1-Acetyl-N-hydroxy-4-[[4-[4-[(phenylamino)carbonyl]-1-piperidinyl]phenyl]sulfonyl]-4-piperidinecarboxamide

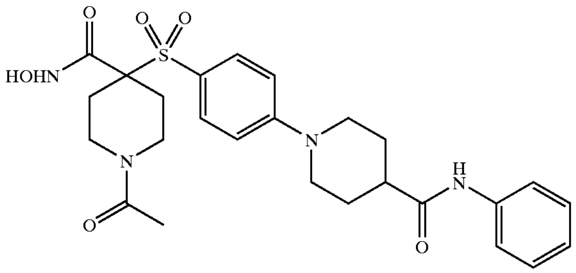

Part A: To a solution of the N-Boc-amide of Preparative Example III, Part B, (6.9 g, 11.4 mmol) in 1,4-dioxane (10 mL) was added 4M hydrochloric acid in dioxane (10 mL)

and the solution was stirred for 1 hour. Concentration in vacuo provided an oil which was added directly to a solution of the product of Preparative Example II, Part D (3.15 g, 7.6 mmol) in dimethylacetamide (30 mL). Cesium carbonate (8.65 g, 26.6 mmol) was added and the solution was heated to one hundred ten degrees Celsius for 18 hours. The solution was partitioned between ethyl acetate and water. The organic layer was washed with water and saturated sodium chloride and dried over sodium sulfate. Concentration in vacuo provided the phenylamine as a tan solid (3.92 g, 86%).

Part B: To a solution of the phenylamine of part A (3.90 g, 6.51 mmol) in methanol (20 mL) was added 4M hydrochloric acid in dioxane (10 mL) and the solution was stirred for 3 hours. Concentration in vacuo followed by trituration (ethyl ether) provided the amine hydrochloride salt as a yellow solid (3.25 g, 93%).

Part C: To a solution of the amine hydrochloride salt of part B (500 mg, 0.93 mmol) in dichloromethane (5 mL) was added triethylamine (0.40 mL, 2.79 mmol) followed by acetyl chloride (0.07 mL, 1.02 mmol). The solution was stirred for 3 hours. The solution was diluted with ethyl acetate and washed with 1M hydrochloric acid, saturated sodium bicarbonate and saturated sodium chloride and dried over sodium sulfate. Concentration in vacuo provided the acylated compound as an oil (390 mg, 77%). MS(CI) $MH^+$ calculated for $C_{28}H_{35}N_3O_6S$: 542, found 542.

Part D: To a solution of the acylated compound of part C (390 mg, 0.72 mmol) in ethanol (5 mL) and tetrahydrofuran (5 mL) was added sodium hydroxide (58 mg, 1.44 mmol) in water (1 mL) and the solution was heated to sixty degrees Celsius for 3 hours. The solution was concentrated and the residue was diluted with water and acidified to pH=1 with 3N hydrochloric acid. The solution was extracted with ethyl acetate and washed with water and saturated sodium chloride and dried over magnesium sulfate. Concentration in vacuo provided the acid as a white solid (137 mg, 37%). MS(CI) $MH^+$ calculated for $C_{26}H_{31}N_3O_6S$: 514, found 514.

Part E: To a solution of the acid of part D (137 mg, 0.27 mmol) in N,N-dimethylformamide (DMF) (10 mL) was added 1-hydroxybenzotriazole hydrate (44 mg, 0.32 mmol), 4-methylmorpholine (0.10 mL, 1.08 mmol), and O-tetrahydropyranyl hydroxylamine (47 mg, 0.41 mmol). After one hour 1-[3-(dimethylamino)propyl]-3-ethylcarbodiimide hydrochloride (72 mg, 0.38 mmol) was added and the solution was stirred for 24 hours at ambient temperature. The solution was partitioned between ethyl acetate and water. The organic layer was washed with water and saturated sodium chloride and dried over sodium sulfate. Chromatography (on silica, ethyl acetate/methanol) provided the protected hydroxamate as a white solid (140 mg, 85%). MS(CI) $MH^+$ calculated for $C_{31}H_{40}N_4O_7S$: 613, found 613.

Part F: To a solution of the protected hydroxamate of part E (130 mg, 0.21 mmol) in dioxane (2 mL) was added 4M hydrochloric acid in dioxane (3 mL) and the solution was stirred for two hours. The resulting solid was collected by vacuum filtration. Washing with ethyl ether provided the title compound as a yellow solid (51 mg, 48%). MS(CI) $MH^+$ calculated for $C_{26}H_{32}N_4O_6S$: 528, found 528.

EXAMPLE 246

Preparation of 4-[[4-[4-[(2,3-Dihydro-1H-indol-1-yl)carbonyl]-1-piperidinyl]-phenyl]sulfonyl]-N-hydroxy-1-(2-methoxyethyl)-4-piperidinecarboxamide, Monohydrate

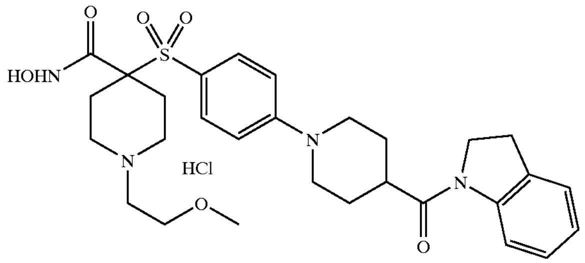

Part A: To a solution of the N-Boc-isonipecotic acid of Preparative Example I, Part B (750 mg, 3.27 mmol) in dichloromethane (3 mL) was added 2-chloro-4,6-dimethoxy-1,3,5-triazine (564 mg, 3.21 mmol). The solution was cooled to zero degrees Celsius and 4-methylmorpholine (0.35 mL, 3.21 mmol) was added. After two hours, indoline (0.36 mL, 3.21 mmol) was added and the solution was stirred for 22 hours at ambient temperature. The solution was concentrated in vacuo. The residue was diluted with ethyl acetate and washed with 1M hydrochloric acid, saturated sodium bicarbonate and saturated sodium chloride and dried over sodium sulfate. Concentration in vacuo provided the amide as a pink solid (940 mg, 89%).

Part B: To a solution of the amide of part A (935 g, 2.83 mmol) in 1,4-dioxane (10 mL) was added 4M hydrochloric acid in dioxane (10 mL) and the solution was stirred for 1 hour. Concentration in vacuo provided an oil which was added directly to a solution of the compound of Preparative Example VII, Part A, (705 mg, 1.89 mmol) in dimethylacetamide (10 mL). Cesium carbonate (2.15 g, 6.61 mmol) was added and the solution was heated to one hundred ten degrees Celsius for 18 hours. The solution was partitioned between ethyl acetate and water and the organic layer was washed with water and saturated sodium chloride and dried over sodium sulfate. Concentration in vacuo provided the phenylamine as an orange oil (893 mg, 81%). MS(CI) $MH^+$ calculated for $C_{31}H_{41}N_3O_6S$: 584, found 584.

Part C: To a solution of the phenylamine of part B (885 g, 1.52 mmol) in ethanol (10 mL) and tetrahydrofuran (10 mL) was added sodium hydroxide (607 mg, 15.2 mmol) in water (5 mL) and the solution was heated to sixty degrees Celsius for 20 hours. The solution was concentrated and the residue was diluted with water and acidified to pH=1 with 3N hydrochloric acid producing a solid. Vacuum filtration provided the acid as a beige solid (475 g, 53%). MS(CI) $MH^+$ calculated for $C_{29}H_{37}N_3O_6S$: 556, found 556.

Part D: To a solution of the acid of part C (465 g, 0.79 mmol) in N,N-dimethylformamide (10 mL) was added 1-hydroxybenzotriazole hydrate (128 mg, 0.95 mmol), 4-methylmorpholine (0.43 mL, 3.95 mmol), and O-tetrahydropyranyl hydroxylamine (139 mg, 1.18 mmol). After one hour, 1-[3-(dimethylamino)propyl]-3-ethylcarbodiimide hydrochloride (212 mg, 1.10 mmol) was added and the solution was stirred for 18 hours at ambient temperature. The solution was partitioned between ethyl acetate and water. The organic layer was washed with water and saturated sodium chloride and dried over sodium sulfate. Chromatography (on silica, ethyl acetate/methanol)

provided the protected hydroxamate as a yellow oil (305 mg, 60%). MS(CI) $MH^+$ calculated for $C_{34}H_{46}N_4O_7S$: 655, found 655.

Part E: To a solution of the protected hydroxamate of part D (300 mg, 0.46 mmol) in dioxane (5 mL) was added 4M hydrochloric acid in dioxane (5 mL) and the solution was stirred for two hours. The resulting solid was collected by vacuum filtration. Washing with ethyl ether provided the title compound as a white solid (260 mg, 94%). MS(CI) $MH^+$ calculated for $C_{29}H_{34}N_4O_6S$: 571, found 571.

EXAMPLE 247

Preparation of N-Hydroxy-1-(2-methoxyethyl)-4-[[4-[4-[[(phenylmethyl)amino]carbonyl]-1-piperidinyl]phenyl]-sulfonyl]-4-piperidinecarboxamide, Monohydrochloride

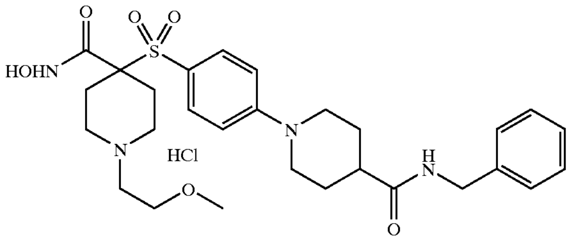

Part A: To a solution of the N-Boc-isonipecotic acid of Preparative Example I, Part B, (750 mg, 3.27 mmol) in dichloromethane (10 mL) was added 1-[3-(dimethylamino)propyl]-3-ethylcarbodiimide hydrochloride (640 mg, 3.34 mmol), 1-hydroxybenzotriazole hydrate (463 mg, 3.43 mmol) and diisopropylethylamine (1.25 mL, 7.19 mmol). After thirty minutes, benzylamine (0.41 mL, 3.76 mmol) was added and the solution was stirred for 22 hours at ambient temperature. The solution was concentrated in vacuo. The residue was diluted with ethyl acetate and washed with 1M hydrochloric acid, saturated sodium bicarbonate and saturated sodium chloride and dried over sodium sulfate. Concentration in vacuo provided the amide as an oil (320 mg, 31%).

Part B: To a solution of the amide of part A (320 g, 1.0 mmol) in 1,4-dioxane (10 mL) was added 4M hydrochloric acid in dioxane (10 mL) and the solution was stirred for 1 hour. Concentration in vacuo provided an oil which was added directly to a solution of the product of Preparative Example II, Part D, (288 mg, 0.77 mmol) in dimethylacetamide (10 mL). Cesium carbonate (878 g, 2.7 mmol) was added and the solution was heated to one hundred ten degrees Celsius for 18 hours. The solution was partitioned between ethyl acetate and water and the organic layer was washed with water and saturated sodium chloride and dried over sodium sulfate. Concentration in vacuo provided the phenylamine as an orange oil (367 mg, 83%). MS(CI) $MH^+$ calculated for $C_{30}H_{41}N_3O_6S$: 572, found 572.

Part C: To a solution of the phenylamine of part B (367 g, 0.64 mmol) in ethanol (5 mL) and tetrahydrofuran (5 mL) was added sodium hydroxide (257 mg, 6.4 mmol) in water (2 mL) and the solution was heated to sixty degrees Celsius for 20 hours. The solution was concentrated and the residue was diluted with water and acidified to pH=1 with 3N hydrochloric acid producing a solid. Vacuum filtration provided the acid as a beige solid (415 g, quantitative yield). MS(CI) $MH^+$ calculated for $C_{28}H_{37}N_3O_6S$: 544, found 544.

Part D: To a solution of the acid of part C (415 g, <0.64 mmol) in N,N-dimethylformamide (10 mL) was added 1-hydroxybenzotriazole hydrate (104 mg, 0.77 mmol), 4-methylmorpholine (0.35 mL, 3.20 mmol), and O-tetrahydropyranyl hydroxylamine (112 mg, 0.96 mmol). After one hour, 1-[3-(dimethylamino)propyl]-3-ethylcarbodiimide hydrochloride (172 mg, 0.90 mmol) was added and the solution was stirred for 18 hours at ambient temperature. The solution was partitioned between ethyl acetate and water. The organic layer was washed with water and saturated sodium chloride and dried over sodium sulfate. Chromatography (on silica, ethyl acetate/methanol) provided the protected hydroxamate as a yellow oil (9 mg, 2%). MS(CI) $MH^+$ calculated for $C_{33}H_{46}N_4O_7S$: 643, found 643.

Part E: To a solution of the protected hydroxamate of part D (9 mg, 0.014 mmol) in dioxane (1 mL) was added 4M hydrochloric acid in dioxane (1 mL) and the solution was stirred for two hours. The resulting solid was collected by vacuum filtration. Washing with ethyl ether provided the title compound as a white solid (2.5 mg, 30%). MS(CI) $MH^+$ calculated for $C_{28}H_{34}N_4O_6S$: 559, found 559.

EXAMPLE 248

Preparation of N-Hydroxy-1-(2-methoxyethyl)-4-[[4-[4-[[[4-(trifluoromethoxy)phenyl]amino]carbonyl]-1-piperidinyl]-phenyl]sulfonyl]-4-piperidinecarboxamide, Monohydrochloride

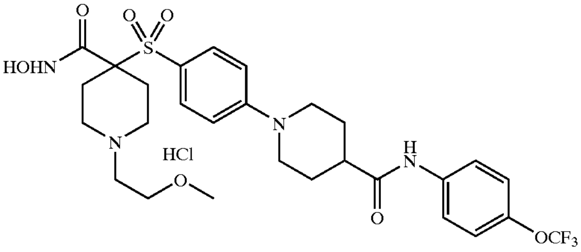

Part A: To a solution of the N-Boc-isonipecotic acid of Preparative Example I, Part B, (750 mg, 3.27 mmol) in dichloromethane (3 mL) was added 2-chloro-4,6-dimethoxy-1,3,5-triazine (564 mg, 3.21 mmol). The solution was cooled to zero degrees Celsius and 4-methylmorpholine (0.35 mL, 3.21 mmol) was added. After two hours, 4-(trifluoromethoxy)aniline (0.43 mL, 3.21 mmol) was added and the solution was stirred for 22 hours at ambient temperature. The solution was concentrated in vacuo. The residue was diluted with ethyl acetate and washed with 1M hydrochloric acid, saturated sodium bicarbonate and saturated sodium chloride and dried over sodium sulfate. Concentration in vacuo provided the amide as a pink solid (1.16 g, 93%).

Part B: To a solution of the amide of part A (1.16 g, 2.99 mmol) in 1,4-dioxane (10 mL) was added 4M hydrochloric acid in dioxane (10 mL) and the solution was stirred for 1 hour. Concentration in vacuo provided an oil which was added directly to a solution of the product of Preparative Example VII, Part A (743 mg, 1.99 mmol) in dimethylacetamide (10 mL). Cesium carbonate (2.26 g, 6.90 mmol) was added and the solution was heated to one hundred ten degrees Celsius for 18 hours. The solution was partitioned between ethyl acetate and water and the organic layer was washed with water and saturated sodium chloride and dried over sodium sulfate. Concentration in vacuo provided the phenylamine as an orange oil (1.38 g, quantitative yield). MS(CI) $MH^+$ calculated for $C_{30}H_{38}N_3O_7SF_3$: 642, found 642.

Part C: To a solution of the phenylamine of part B (1.38 g, 2.00 mmol) in ethanol (10 mL) and tetrahydrofuran (10 mL) was added sodium hydroxide (800 mg, 20 mmol) in water (5 mL), and the solution was heated to sixty degrees Celsius for 20 hours. The solution was concentrated and the residue was diluted with water and acidified to pH=1 with 3N hydrochloric acid producing a solid. Vacuum filtration provided the acid as a beige solid (536 g, 41%). MS(CI) $MH^+$ calculated for $C_{28}H_{34}N_3O_7SF_3$: 614, found 614.

Part D: To a solution of the acid of part C (536 g, 0.83 mmol) in N,N-dimethylformamide (10 mL) was added 1-hydroxybenzotriazole hydrate (134 mg, 0.99 mmol), 4-methylmorpholine (0.46 mL, 4.15 mmol), and O-tetrahydropyranyl hydroxylamine (145 mg, 1.24 mmol). After one hour 1-[3-(dimethylamino)propyl]-3-ethylcarbodiimide hydrochloride (223 mg, 1.16 mmol) was added and the solution was stirred for 18 hours at ambient temperature. The solution was partitioned between ethyl acetate and water. The organic layer was washed with water and saturated sodium chloride and dried over sodium sulfate. Chromatography (on silica, ethyl acetate/methanol) provided the protected hydroxamate as a yellow oil (287 mg, 48%). MS(CI) $MH^+$ calculated for $C_{33}H_{43}N_4O_8SF_3$: 713, found 713.

Part E: To a solution of the protected hydroxamate of part D (280 mg, 0.39 mmol) in dioxane (10 mL) was added 4M hydrochloric acid in dioxane (10 mL) and the solution was stirred for two hours. The resulting solid was collected by vacuum filtration. Washing with ethyl ether provided the title compound as a white solid (228 mg, 88%). MS(CI) $MH^+$ calculated for $C_{28}H_{35}N_4O_7SF_3$: 629, found 629.

EXAMPLE 249

Preparation of N-Hydroxy-1-(2-methoxyethyl)-4-[[4-[4-[[[3-(trifluoromethoxy)phenyl]amino]carbonyl]-1-piperidinyl]phenyl]sulfonyl]-4-piperidinecarboxamide, Monohydrochloride

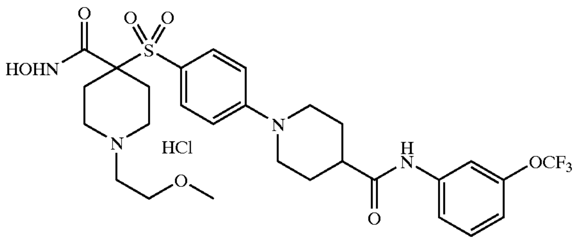

Part A: To a solution of the N-Boc-isonipecotic acid of Preparative Example I, Part B, (750 mg, 3.27 mmol) in dichloromethane (3 mL) was added 2-chloro-4,6-dimethoxy-1,3,5-triazine (564 mg, 3.21 mmol). The solution was cooled to zero degrees Celsius and 4-methylmorpholine (0.35 mL, 3.21 mmol) was added. After two hours 3-(trifluoromethoxy)aniline (0.43 mL, 3.21 mmol) was added and the solution was stirred for 22 hours at ambient temperature. The solution was concentrated in vacuo. The residue was diluted with ethyl acetate and washed with 1M hydrochloric acid, saturated sodium bicarbonate and saturated sodium chloride and dried over sodium sulfate. Concentration in vacuo provided the amide as a pink solid (1.20 g, 97%).

Part B: To a solution of the amide of part A (1.20 g, 3.10 mmol) in 1,4-dioxane (10 mL) was added 4M hydrochloric acid in dioxane (10 mL) and the solution was stirred for 1 hour. Concentration in vacuo provided an oil which was added directly to a solution of the product of Preparative Example VII, Part A, (770 mg, 2.06 mmol) in dimethylacetamide (10 mL). Cesium carbonate (2.34 g, 7.21 mmol) was added and the solution was heated to one hundred ten degrees Celsius for 18 hours. The solution was partitioned between ethyl acetate and water and the organic layer was washed with water and saturated sodium chloride and dried over sodium sulfate. Concentration in vacuo provided the phenylamine as an orange oil (1.72 g, quantitative yield). MS(CI) $MH^+$ calculated for $C_{30}H_{38}N_3O_7SF_3$: 642, found 642.

Part C: To a solution of the phenylamine of part B (1.72 g, <2.06 mmol) in ethanol (10 mL) and tetrahydrofuran (10 mL) was added sodium hydroxide (824 mg, 20.6 mmol) in water (5 mL) and the solution was heated to sixty degrees Celsius for 18 hours. The solution was concentrated and the residue was diluted with water and acidified to pH=1 with 3N hydrochloric acid. Concentration in vacuo provided the acid as a crude brown oil which was used in the next step without additional purification.

Part D: To a solution of the acid of part C (<2.06 mmol) in N,N-dimethylformamide (10 mL) was added 1-hydroxybenzotriazole hydrate (334 mg, 2.47 mmol), 4-methylmorpholine (1.13 mL, 10.3 mmol), and O-tetrahydropyranyl hydroxylamine (361 mg, 3.09 mmol). After one hour, 1-[3-(dimethylamino)propyl]-3-ethylcarbodiimide hydrochloride (553 mg, 2.88 mmol) was added and the solution was stirred for 18 hours at ambient temperature. The solution was partitioned between ethyl acetate and water. The organic layer was washed with water and saturated sodium chloride and dried over sodium sulfate. Chromatography (on silica, ethyl acetate/methanol) provided the protected hydroxamate as a yellow oil (64 mg, 4% for 2 steps). MS(CI) $MH^+$ calculated for $C_{33}H_{43}N_4O_8SF_3$: 713, found 713.

Part E: To a solution of the protected hydroxamate of part D (63 mg, 0.089 mmol) in dioxane (5 mL) was added 4M hydrochloric acid in dioxane (5 mL) and the solution was stirred for two hours. The resulting solid was collected by vacuum filtration. Washing with ethyl ether provided the title compound as a white solid (48 mg, 81%). MS(CI) $MH^+$ calculated for $C_{28}H_{35}N_4O_7SF_3$: 629, found 629.

EXAMPLE 250

Preparation of 1-(2-Ethoxyethyl)-N-hydroxy-4-[[4-[4-(trifluoromethoxy)phenoxy]phenyl]sulfonyl]-4-piperidinecarboxamide Monohydrochloride

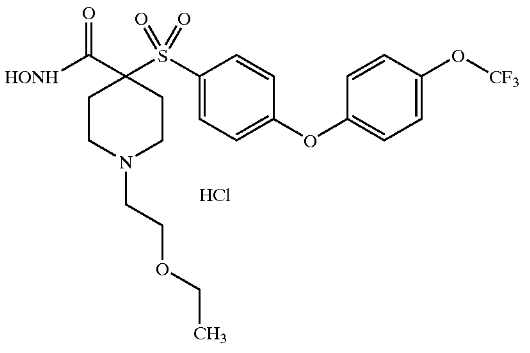

Part A: To a solution of the product of Preparative Example II, Part D, (1.0 g, 2.4 mmol) in dichloromethane (10 mL) was added trifluoroacetic acid (10 mL) and the solution was stirred at ambient temperature for 1 hour. Concentration in vacuo provided the amine trifluoroacetate salt as a light yellow gel. To the solution of the amine trifluoroacetate salt and potassium carbonate (0.99 g, 7.2 mmol) in N,N-dimethylformamide (5 mL) was added 2-bromoethyl ethyl ether (0.33 mL, 2.87 mmol) and the solution was stirred at ambient temperature for 36 hours. Then N,N-dimethylformamide was evaporated under high vacuum and the residue was diluted with ethyl acetate. The organic layer was washed with water and dried over magnesium sulfate. Concentration in vacuo provided the ethoxyl ethyl amine as a light yellow gel (0.68 g, 65.4%).

Part B: To a solution of ethoxyl ethyl amine (0.68 g, 1.56 mmol) of part A and powdered potassium carbonate (0.43 g, 3.1 mmol) in N,N-dimethylformamide (5 mL) was added 4-(trifluoromethoxy)phenol (0.4 mL, 3.08 mmol) at ambient temperature and the solution was heated to ninety degrees Celsius for 25 hours. The solution was concentrated under high vacuum and the residue was dissolved in ethyl acetate. The organic layer was washed with 1N sodium hydroxide, water and dried over magnesium sulfate. Chromatography on silica eluting with ethyl acetate/hexane provided the desired trifluoromethoxy phenoxyphenyl sulfone as a light yellow gel (1.0 g, quantitative).

Part C: To a solution of trifluoromethoxy phenoxyphenyl sulfone of Part B (1.0 g, 1.72 mmol) in ethanol (2 mL) and tetrahydrofuran (2 mL) was added sodium hydroxide (0.688 g, 17.2 mmol) in water (4 mL) at ambient temperature. The solution was then heated to sixty degrees Celsius for 18 hours. The solution was concentrated in vacuo and diluted with water. The aqueous layer was extracted with ether and acidified to pH=2. Vacuum filtration of the white precipitate provided the acid as a white solid (0.94 g, quantitative yield).

Part D: To a solution of the acid of part C (0.94 g, 1.86 mmol), N-methyl morpholine (0.61 mL, 5.55 mmol), 1-hydroxybenzotriazole (0.76 g, 5.59 mmol) and O-tetrahydropyranyl hydroxyl amine (0.33 g, 2.7 mmol) in N,N-dimethylformamide (40 mL) was added 1-[3-(dimethylamino)propyl]-3-ethylcarbodiimide hydrochloride (1.06 g, 5.59 mmol) and the solution was stirred at ambient temperature for 24 hours. The solution was concentrated under high vacuum and the residue was dissolved in ethyl acetate. The organic layer was washed with saturated aqueous Sodium bicarbonate, water and dried over magnesium sulfate. Concentration in vacuo and chromatography on silica eluting with ethyl acetate/hexane provided the tetrahydropyranyl amide as a white foam (0.74 g, 66.1%).

Part E: To a solution of 4N hydrochloric acid (3 mL, 12 mmol)) in dioxane was added a solution of the tetrahydropyranyl amide of part D (0.74 g, 1.2 mmol) in methanol (0.4 ml) and dioxane (1.2 mL) and was stirred at ambient temperature for 3 hours. Filtration of precipitation gave the title compound as white solid (0.217 g, 32.9%). Analytical calculation for $C_{22}H_{25}N_2O_7SF_3$.HCl.0.5$H_2O$: C, 46.85; H, 4.83; N, 4.97; S, 5.69. Found: C, 46.73; H, 4.57; N, 4.82; S, 5.77.

EXAMPLE 251

Preparation of N-Hydroxy-1-(2-methoxyethyl)-4-[[4-[4-(trifluoromethoxy)phenoxy]phenyl]sulfonyl]-4-piperidinecarboxamide Monomethanesulfonate (Salt)

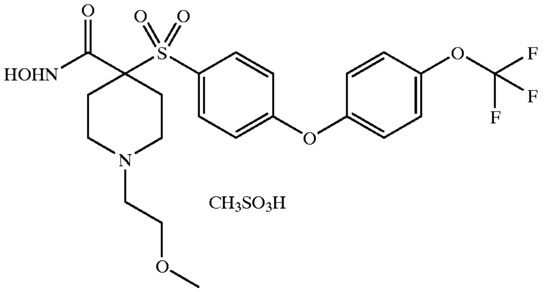

$CH_3SO_3H$

Part A: To the ethanol solution of the product of Preparative Example VII, Part D, (0.3 g, 0.5 mmol) was added methane sulfonic acid (0.042 mL, 0.65 mmol). After two hours stirring at room temperature the solution was cooled to zero degree Celsius. Filtration of the precipitate gave the title compound as a white crystalline solid (0.105 g, 35%). Analytical calculation for $C_{22}H_{25}N_2O_7SF_3$.$CH_4O_3S$.$H_2O$: C, 43.67; H, 4.94; N, 4.43. Found: C, 43.96; H, 4.62; N, 4.47.

EXAMPLE 252

Preparation of N-Hydroxy-1-(2-methoxyethyl)-4-[[4-[4-(trifluoromethoxy)phenoxy]phenyl]sulfonyl]-4-piperidinecarboxamide

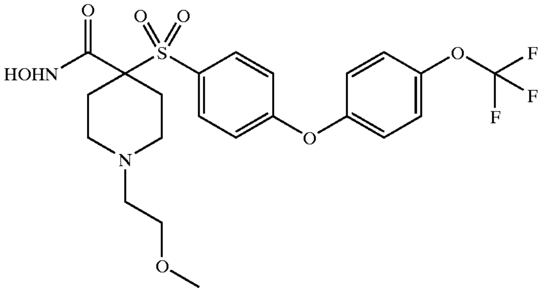

Part A: The title compound of Preparative Example VII (15 g, 27 mmol) was partitioned between ethyl acetate and saturated sodium bicarbonate solution. The aqueous layer was extracted with ethyl acetate. The combined organic layers were washed with saturated sodium bicarbonate solution, water, brine and dried over magnesium sulfate. Concentration in vacuo and recrystallization from hot toluene gave the title compound as white crystals (13.14 g, 93.9%). Analytical calculation for $C_{22}H_{25}N_2O_7SF_3$: C, 50.96; H, 4.86; N, 5.40; S, 6.18. Found: C, 51.33; H, 5.11; N, 5.29; S, 6.50.

EXAMPLE 253

Preparation of N-Hydroxy-1-(2-methoxyethyl)-4-[[4-[4-(trifluoromethoxy)phenoxy]phenyl]sulfonyl]-4-piperidinecarboxamide mono(4-Methylbenzenesulfonate) (Salt)

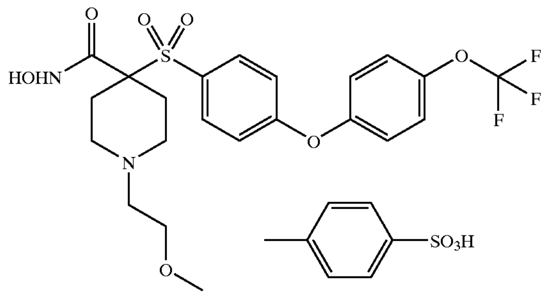

Part A: To the ethanol solution of Preparative Example VII (8 g, 13.32 mmol) was added p-toluenesulfonic acid (2.9 g, 15.24 mmol) and the solution was stirred at ambient temperature for 6 hours. Evaporation of the solvent and recrystallization from hot ethanol gave the title compound as white crystals (6.58 g, 71.8%). Analytical calculation for $C_{22}H_{25}N_2O_7SF_3.C_7H_8SO_3$: C, 50.43; H, 4.82; N, 4.06; S, 9.28. Found: C, 50.36; H, 4.95; N, 4.00; S, 9.47.

EXAMPLE 254

Preparation of N-Hydroxy-1-(2-methoxyethyl)-4-[[4-[4-(trifluoromethoxy)phenoxy]phenyl]sulfonyl]-4-piperidinecarboxamide Sulfate (2:1) (Salt)

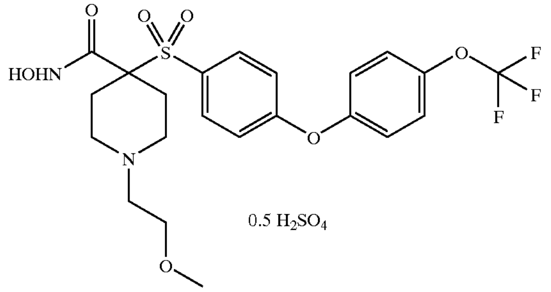

$0.5\ H_2SO_4$

Part A: To a solution of Preparative Example VII (0.35 g, 0.58 mmol) in ethanol (1.5 mL) was added sulfuric acid (17 ?L, 0.32 mmol) and the solution was stirred at ambient temperature for 6 hours. Evaporation of solvent and recrystallization from hot acetonitrile gave the title compound as a white powder (180 mg, 54.6%). Analytical calculation for $C_{22}H_{25}N_2O_7SF_3.0.7H_2SO_4$: C, 45.00; H, 4.53; N, 4.77; S, 9.28. Found: C, 44.77; H, 4.97; N, 4.41; S, 9.19.

EXAMPLE 255

Preparation of N-Hydroxy-1-(2-methoxyethyl)-4-[[4-[4-(trifluoromethoxy)phenoxy]phenyl]sulfonyl]-4-piperidinecarboxamide Phosphate (1:1) (Salt)

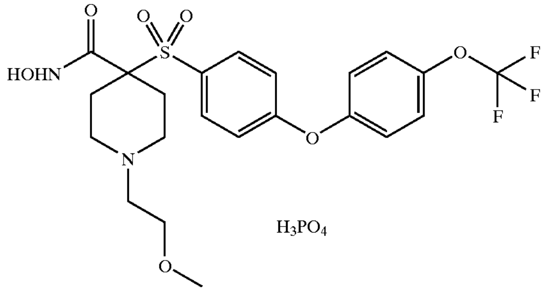

$H_3PO_4$

Part A: To the ethyl acetate solution (4 mL) of Example 252 (0.5 g, 0.9 mmol) was added concentrated phosphoric acid (85%, 0.1248 g, 1.08 mmol) and solution was stirred at ambient temperature for 2 hours. Evaporation of the solvent and recrystallization from hot ethanol gave the title compound as a white powder (0.4917 g, 82.7%). Analytical calculation for $C_{22}H_{25}N_2O_7SF_3.H_3PO_4.H_2O$: C, 41.64; H, 4.77; N, 4.42. Found: C, 41.14; H, 4.64; N, 4.25.

EXAMPLE 256

Preparation of N-Hydroxy-1-(2-methoxyethyl)-4-[[4-[4-(trifluoromethoxy)phenoxy]phenyl]sulfonyl]-4-piperidinecarboxamide Monoacetate (Salt)

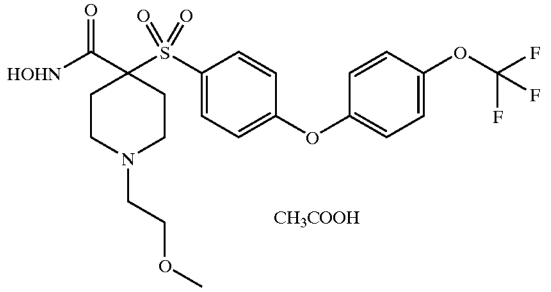

$CH_3COOH$

Part A: To a solution of Example 252 (0.5 g, 0.9 mmol) in ethyl acetate (5 mL) was added concentrated acetic acid (63.7 mg, 1.08 mmol) and solution was stirred at ambient temperature for 2 hours. Evaporation of the solvent and recrystallization from hot ethyl acetate gave the title compound as a white crystalline solid (0.4635 g, 83.0%). Analytical calculation for $C_{22}H_{25}N_2O_7SF_3.0.7C_2H_4O_2$: C, 50.14; H, 5.00; N, 5.00; S, 5.72. Found: C, 50.47; H, 5.09; N, 5.00; S, 6.13.

EXAMPLE 257

Preparation of N-Hydroxy-1-(2-methoxyethyl)-4-[[4-[4-(trifluoromethoxy)phenoxy]phenyl]sulfonyl]-4-piperidinecarboxamide 2-Hydroxy-1,2,3-propanetricarboxylate (3:1) (Salt)

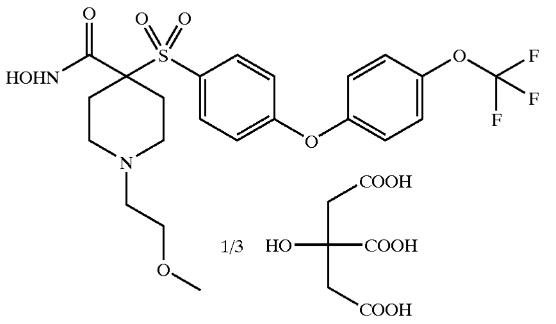

Part A: To a solution of Example 252 (0.3 g, 0.578 mmol) in ethyl acetate (5 mL) was added citric acid (41 mg, 0.21 mmol) and the solution was stirred at ambient temperature for 2 hours. Evaporation of the solvent and recrystallization from hot ethanol gave the title compound as a white crystalline solid (0.181 g, 53.7%). Analytical calculation for $C_{22}H_{25}N_2O_7SF_3$.(1/3)$C_6H_9O_7$.0.9$H_2O$: C, 48.34; H, 4.99; N, 4.70; S, 5.38. Found: C, 48.42; H, 4.99; N, 4.70; S, 5.38.

EXAMPLE 258

Preparation of N-Hydroxy-1-(2-methoxyethyl)-4-[[4-[4-(trifluoromethoxy)phenoxy]phenyl]sulfonyl]-4-piperidinecarboxamide Monobenzenesulfonate (Salt)

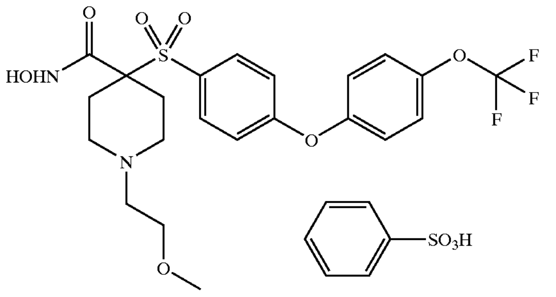

Part A: To a solution of Preparative Example VII, Part D (0.4 g, 0.66 mmol) in ethanol (2.5 mL) was added benzene sulfonic acid (0.11 g, 0.69 mmol) and the solution was stirred at ambient temperature for 3 hours. Evaporation of the solvent and recrystallization from hot ethanol at minus 20 degrees Celsius gave the title compound as white crystals (0.28 g, 64.3%). Analytical calculation for $C_{22}H_{25}N_2O_7SF_3$.$C_6H_6SO_3$.0.2$H_2O$: C, 49.44; H, 4.65; N, 4.12; S, 9.43. Found: C, 49.18; H, 4.67; N, 4.08; S, 9.75.

EXAMPLE 259

Preparation of N-Hydroxy-1-(2-methoxyethyl)-4-[[4-[4-(trifluoromethoxy)phenoxy]phenyl]sulfonyl]-4-piperidinecarboxamide (2R,3R)-2,3-Dihydroxybutanedioate (2:1) (Salt)

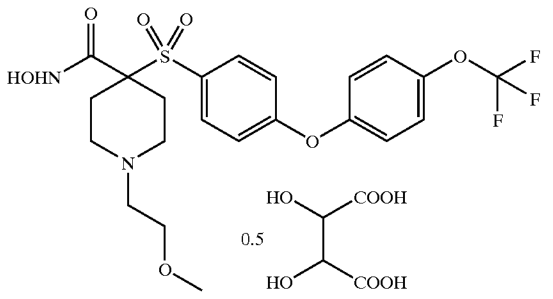

Part A: To a solution of Example 252 (0.3 g, 0.578 mmol) in ethyl acetate (5 mL) was added tartaric acid (48 mg, 0.3 mmol) and solution was stirred at ambient temperature for 2 hours. Evaporation of the solvent and recrystallization from hot ethanol at zero degrees Celsius gave the title compound as a white solid (0.2 g, 58.3%). Analytical calculation for $C_{22}H_{25}N_2O_7SF_3$.0.5$C_4H_6O_6$.1.25$H_2O$: C, 46.79; H, 4.99; N, 4.55; S, 5.20. Found: C, 47.17; H, 5.20; N, 4.07; S, 5.03

EXAMPLE 260

Preparation of N-Hydroxy-1-(2-methoxyethyl)-4-[[4-[4-(trifluoromethoxy)phenoxy]phenyl]sulfonyl]-4-piperidinecarboxamide Phosphate (3:1) (Salt)

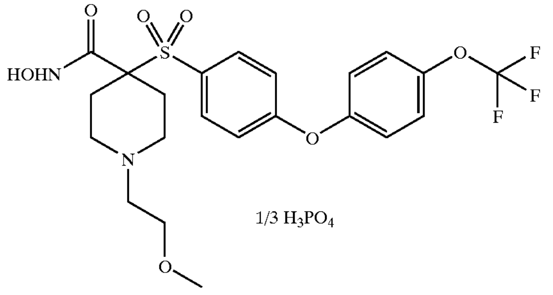

Part A: To a solution of Example 252 (0.5 g, 0.9 mmol) in ethyl acetate (5 mL) was added phosphoric acid (37 mg, 0.32 mmol) and solution was stirred at ambient temperature for 2 hours. Evaporation of the solvent and recrystallization from hot ethanol at zero degrees Celsius gave the title compound as a white solid (0.312 g, 59%). Analytical calculation for $C_{22}H_{25}N_2O_7SF_3$.0.33$H_3PO_4$.0.5$H_2O$: C, 47.18; H, 4.86; N, 5.00. Found: C, 47.15; H, 4.73; N, 4.90.

EXAMPLE 261

Preparation of N-Hydroxy-1-[2-(1H-imidazol-1-yl) ethyl]-4-[[4-[4-(trifluoromethoxy)phenoxy]phenyl] sulfonyl]-4-piperidinecarboxamide, Dihydrochloride

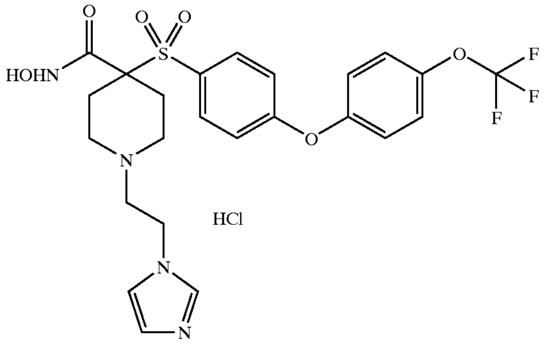

Part A: The aryl ether from Example 230, Part B (3.12 g, 5.2 mmol) was dissolved in absolute methanol (50 mL). Acetyl chloride (2.1 mL, 30 mmol) was added over 1 minute. The reaction was stirred for 4 hours, concentrated, azeotroped with chloroform/acetonitrile, and dried in vacuo, affording the desired hydroxyethyl compound as a white solid (2.75 g, 96%). The desired hydroxyethyl product was characterized by NMR spectroscopy.

Part B: To the dichloromethane solution of the hydroxyethyl compound of Part A (1 g, 1.9 mmol) was added thionyl chloride (3.8 mmol) and reaction solution was stirred at ambient temperature for 12 hours. Concentration in vacuo provided the chloride as a light yellow gel. To the solution of the chloride and potassium carbonate (0.54 g, 3.8 mmol) in N,N-dimethylformamide (5 mL) was added imidazole (0.4 g, 5.7 mmol) and solution was stirred at ambient temperature for 12 hours. Then N,N-dimethylformamide was evaporated under high vacuum and the residue was diluted with ethyl acetate. The organic layer was washed with water and dried over magnesium sulfate. Concentration in vacuo and chromatography on silica eluting with ethyl acetate/hexane provided the imidazole ethyl ester as a light yellow gel (0.82 g, 75.2%).

Part C: To a solution of imidazole ethyl ester of part A (0.82 g, 1.44 mmol) in ethanol (3 mL) and tetrahydrofuran (3 mL) was added sodium hydroxide (0.57 g, 14.4 mmol) in water (6 mL) at ambient temperature. The solution was then heated to sixty degrees Celsius for 18 hours. The solution was concentrated in vacuo and the residue was dissolved in acetonitrile. Concentrated hydrochloric acid was used to acidify the residue to pH=1 and concentration in vacuo gave the carboxylic acid as the product. To a solution of the carboxylic acid, N-methyl morpholine (0.62 mL, 5.7 mmol), 1-hydroxybenzotriazole (0.59 g, 4.3 mmol) and O-tetrahydropyranyl hydroxyl amine (0.34 g, 2.9 mmol) in N,N-dimethylformamide (30 mL) was added 1-[3-(dimethylamino)propyl]-3-ethylcarbodiimide hydrochloride (0.83 g, 5.7 mmol) and the solution was stirred at ambient temperature for 24 hours. The solution was concentrated under high vacuum and the residue was dissolved in ethyl acetate. The organic layer was washed with saturated aqueous Sodium bicarbonate, water and dried over magnesium sulfate. Concentration in vacuo and chromatography on silica eluting with ethyl acetate/hexane provided the tetrahydropyranyl amide as a white foam (0.27 g, 29.7%).

Part D: To a solution of 4N hydrochloric acid in dioxane (2 mL, 8 mmol)) was added a solution of the tetrahydropyranyl amide of part B (0.27 g, 0.45 mmol) in methanol (1 ml) and 1,4-dioxane (3 mL) and was stirred at ambient temperature for 3 hours. Evaporation of solvent and trituration with ethyl ether gave the title compound as a white solid (0.179 g, 67%). Analytical calculation for $C_{24}H_{25}N_4O_6SF_3.2HCl.1.25H_2O$: C, 44.35; H, 4.57; N, 8.62. Found: C, 44.57; H, 4.36; N, 7.95.

EXAMPLE 262

Preparation of N-Hydroxy-1-(2-methoxyethyl)-4-[[4-[4-(1H-1,2,4-triazol-1-yl)phenoxy]phenyl] sulfonyl]-4-piperidinecarboxamide Trihydrochloride

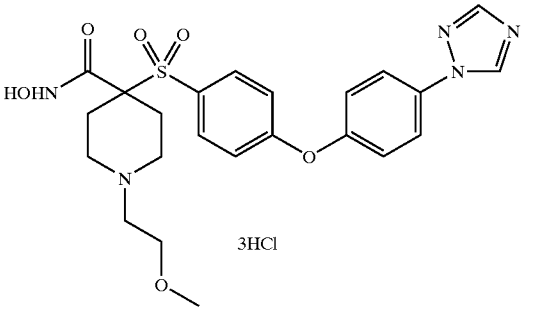

Part A: To a solution of the product of Preparative Example II, Part D, (1.5 g, 3.6 mmol) and powdered potassium carbonate (0.99 g, 7.2 mmol) in N,N-dimethylformamide (10 mL) was added 4-(1,2,4-triazole-1-yl)phenol (0.87 g, 5.4 mmol) at ambient temperature and the solution was heated to ninety degrees Celsius for 32 hours. Solution was concentrated under high vacuum and the residue was dissolved in ethyl acetate. The organic layer was washed with 1N sodium hydroxide, water and dried over magnesium sulfate. Chromatography on silica eluting with ethyl acetate/hexane provided the N-Boc diaryl ether as a light yellow gel (0.907 g, 44.5%).

Part B: To a solution of N-Boc diaryl ether of part A (0.907 g, 1.6 mmol) in dichloromethane (3 mL) was added trifluoroacetic acid (3 mL) and the solution was stirred at ambient temperature for 1 hour. Concentration in vacuo provided the amine trifluoroacetate salt as a light yellow gel. To the solution of the amine trifluoroacetate salt and potassium carbonate (0.44 g, 3.2 mmol) in N,N-dimethylformamide (5 mL) was added 2-bromoethyl methyl ether (0.36 mL, 3.8 mmol) and solution was stirred at ambient temperature for 36 hours. The N,N-dimethylformamide was evaporated under high vacuum and the residue was diluted with ethyl acetate. The organic layer was washed with water and dried over magnesium sulfate. Concentration in vacuo provided the methoxyl ethyl amine as a light yellow gel (0.82 g, 91%).

Part C: To a solution of the methoxyl ethyl amine of part B (0.80 g, 1.4 mmol) in ethanol (3 mL) and tetrahydrofuran (3 mL) was added sodium hydroxide (0.56 g, 14 mmol) in water (6 mL) at ambient temperature. The solution was then heated to sixty degrees Celsius for 18 hours. The solution was concentrated in vacuo and the residue was dissolved in acetonitrile. Concentrated hydrochloric acid was used to acidify the residue until the pH=1 and concentration in vacuo gave the carboxylic acid as product. To a solution of the carboxylic acid, N-methyl morpholine (0.92 mL, 8.4 mmol), 1-hydroxybenzotriazole (0.57 g, 4.3 mmol) and O-tetrahydropyranyl hydroxyl amine (0.34 g, 2.9 mmol) in N,N-dimethylformamide (30 mL) was added 1-[3-(dimethylamino)propyl]-3-ethylcarbodiimide hydrochloride (0.80 g, 4.2 mmol) and the solution was stirred at ambient temperature for 24 hours. The solution was concentrated under high vacuum and the residue was dissolved in ethyl acetate. The organic layer was washed with saturated aqueous sodium bicarbonate, water and dried over magnesium sulfate. Concentration in vacuo and chromatography on silica eluting with ethyl acetate/hexane provided the tetrahydropyranyl amide as a white foam (0.39 g, 47.6%).

Part D: To a solution of 4N hydrochloric acid in dioxane (1.6 mL, 6.4 mmol)) was added a solution of the tetrahydropyranyl amide of part C (0.39 g, 0.66 mmol) in methanol (2 ml) and dioxane (6 mL) and was stirred at ambient temperature for 3 hours. Evaporation of the solvent and trituration with ethyl ether gave the title compound as a white solid (0.34 g, 83%). ESI MS calculated for $C_{23}H_{27}N_5O_6S$: 501, found 501.

EXAMPLE 263

Preparation of 1-(2-Methoxyethyl)-4-[[4-[4-(trifluoromethoxy)phenoxy]phenyl]-sulfonyl]-4-piperidinecarboxamide Monohydrochloride

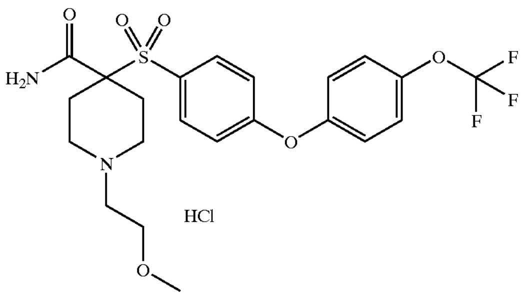

Part A: To a methanol solution of the product of Example 253 (1.0 g, 1.4 mmol) and 20% palladium on carbon (1.5 g) was added ammonium formate (2.4 g, 38 mmol) and reaction solution was heated to reflux for 72 hours. The reaction solution was filtered through Celite and the filtrate was concentrated in vacuo. The residue was dissolved in ethyl acetate and washed with saturated aqueous Sodium bicarbonate, water and dried over magnesium sulfate. Concentration in vacuo and chromatography on a C-18 reverse phase column eluting with acetonitrile/water with hydrochloric acid provided the title compound as a white powder (181 mg, 23.2%). Analytical calculation for $C_{22}H_{25}N_2O_6SF_3$.HCl: C, 49.03; H, 4.86; N, 5.20. Found: C, 48.80; H, 4.93; N, 5.29.

EXAMPLE 264

Preparation of N-Hydroxy-1-[3-(4-morpholinyl)propyl]-4-[[4-[4-(trifluoromethoxy)phenoxy]phenyl]sulfonyl]-4-piperidinecarboxamide Dihydrochloride

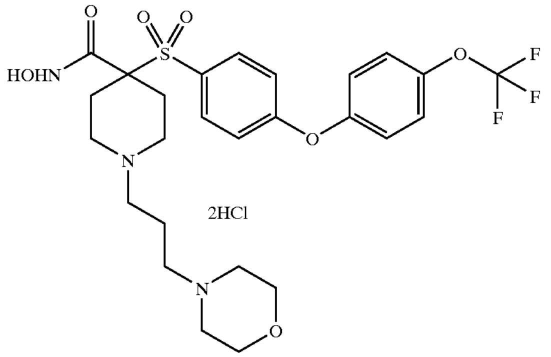

Part A: To a solution of the product of Preparative Example II, Part D, (15 g, 36 mmol) and powdered potassium carbonate (10 g, 72 mmol) in N,N-dimethylformamide (200 mL) was added 4-(trifluoromethoxy)phenol (19.3 mL, 72 mmol) at ambient temperature and the solution was heated to ninety degrees Celsius for 25 hours. The solution was concentrated under high vacuum and residue was dissolved in ethyl acetate. The organic layer was washed with 1N sodium hydroxide, water and dried over magnesium sulfate. Chromatography on silica eluting with ethyl acetate/hexane provided trifluoromethoxy phenoxyphenyl sulfone as a light yellow gel (20 g, quantitative).

Part B: To a solution of trifluoromethoxyl phenoxyphenyl sulfone (1.0 g, 1.75 mmol) of part A in dichloromethane (1 mL) was added trifluoroacetic acid (1 mL) and the solution was stirred at ambient temperature for 1 hour. Concentration in vacuo provided the amine trifluoroacetate salt as a light yellow gel. To the solution of the amine trifluoroacetate salt and potassium carbonate (0.48 g, 3.5 mmol) in N,N-dimethylformamide (10 mL) was added morpholino propyl chloride (0.68 g, 3.5 mmol) and solution was stirred at 40 degree Celsius for 36 hours. The N,N-dimethylformamide was evaporated under high vacuum and the residue was diluted with ethyl acetate. The organic layer was washed with water and dried over magnesium sulfate. Concentration in vacuo provided the morpholino propyl amine as a light yellow gel (1 g, quantitative yield).

Part C: To a solution of morpholino propyl amine of part B (1 g, 1.6 mmol) in ethanol (3 mL) and tetrahydrofuran (3 mL) was added sodium hydroxide (0.67 g, 16 mmol) in water (6 mL) at ambient temperature. The solution was then heated to sixty degrees Celsius for 18 hours. The solution was concentrated in vacuo and the residue was dissolved in acetonitrile. Concentrated hydrochloric acid was used to acidify the residue to pH=1 and concentration in vacuo gave the carboxylic acid as the product. To a solution of the carboxylic acid, N-methyl morpholine (0.18 mL, 4.8 mmol), 1-hydroxybenzotriazole (0.45 g, 3.2 mmol) and O-tetrahydropyranyl hydroxyl amine (0.3 g, 2.5 mmol) in N,N-dimethylformamide (30 mL) was added 1-[3-(dimethylamino)propyl]-3-ethylcarbodiimide hydrochloride (0.64 g, 3.2 mmol) and the solution was stirred at ambient temperature for 24 hours. The solution was concentrated under high vacuum and the residue was dissolved in ethyl acetate. The organic layer was washed with saturated aqueous Sodium bicarbonate, water and dried over magnesium sulfate. Concentration in vacuo and chromatography on silica eluting with ethyl acetate/hexane provided the tetrahydropyranyl amide as a white foam (0.56 g, 50%).

Part D: To a solution of 4N hydrogen chloride in dioxane (2 mL, 8 mmol)) was added a solution of the tetrahydropyranyl amide of part C (0.56 g, 0.83 mmol) in methanol (3 ml) and dioxane (8 mL) and was stirred at ambient temperature for 3 hours. Evaporation of solvent and tritration with ethyl ether gave the title compound as a white solid (0.476 g, 86.5%). Analytical calculation for $C_{26}H_{32}N_3O_7SF_3$.2HCl: C, 47.28; H, 5.19; N, 6.36; S, 4.85. Found: C, 46.86; H, 5.35; N, 6.29; S, 5.09.

EXAMPLE 265

Preparation of N-Hydroxy-1-(1H-imidazol-2-ylmethyl)-4-[[4-[4-(trifluoromethyl)phenoxy] phenyl]-sulfonyl]-4-piperidinecarboxamide Dihydrochloride

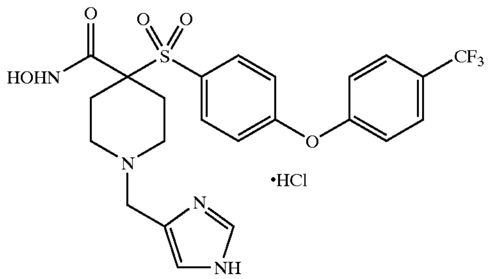

Part A: To a suspension of the hydrochloride salt from Preparative Example VIII, Part F, (0.988 g, 21.6 mmol) and 2-imidazolecarboxaldehyde (315 mg, 3.28 mmol) in methanol (5 mL) at room temperature was added borane-pyridine complex (0.41 mL, 3.28 mmol). After 18 hours the reaction was concentrated under a stream of nitrogen. Saturated aqueous sodium bicarbonate was then added and the mixture was extracted with ethyl acetate (3×). The combined organic extracts were washed with water and brine and dried over sodium sulfate. Concentration gave a residue which was purified on silica gel eluting with ammonia-saturated methanol/methylene chloride (3/97) to afford the desired 4(5)-imidazole derivative (1.04 g, 89.7%) as a yellow solid. MS $MH^+$ calculated for $C_{25}H_{26}N_3O_5SF_3$: 538, found 538.

Part B: A solution of sodium hydroxide (766 mg, 19.2 mmol) in water (5 mL) was added to a solution of the 4(5)-imidazole derivative of Part A (1.03 g, 1.92 mmol) in tetrahydrofuran (5 mL) and ethanol (5 mL) and the resulting solution was stirred at ambient temperature for 66 hours. The solution was concentrated in vacuo to afford a residue which was treated with 2 N aqueous hydrochloric acid (14.4 mL, 28.8 mmol). Concentration afforded the desired carboxylic acid as a yellow foam which was used directly without purification.

Part C: To a solution of the carboxylic acid of Part B in dimethylformamide (15 mL) was added sequentially N-methylmorpholine (1.16 g, 11.5 mmol), N-hydroxybenzotriazole (311 mg, 2.30 mmol), 1-(3-dimethylaminopropyl)-3-ethylcarbodiimide hydrochloride (478 mg, 2.50 mmol), and O-tetrahydropyranyl hydroxylamine (303 mg, 2.6 mmol). After 16 hours at ambient temperature the reaction was warmed to 51 degrees Celsius for 2 hours and then concentrated in vacuo. Water was added and the mixture was extracted sequentially with ethyl acetate and with methylene chloride. The combined organic extracts were washed with brine and dried over sodium sulfate. Concentration gave a residue which was chromatographed on silica gel eluting with ammonia-saturated methanol/methylene chloride (7/93) to afford the desired tetrahydropyranyl-protected hydroxamate (0.50 g, 43%) as an off-white foam. MS $MH^+$ calculated for $C_{28}H_{31}F_3N_4O_6S$: 609, found 609.

Part D: To a solution of tetrahydropyranyl-protected hydroxamate of part C (500 mg, 0.82 mmol) in methanol (1 mL) and 1,4-dioxane (5 mL) was added 4 N hydrogen chloride/dioxane (2.5 mL). After stirring at ambient temperature for 1 hours, the solution was concentrated in vacuo. Trituration with diethyl ether provided the title compound as a white solid (490 mg, quantitative yield). HRMS $MH^+$ calculated for $C_{23}H_{23}N_4SO_5F_3$: 525. Found: 525. MS $MH^+$ calculated for $C_{23}H_{23}F_3N_4O_5S$: 525, found 525.

EXAMPLE 266

Preparation of 1-Cyclopropyl-N-hydroxy-4-[[4-[4-(trifluoromethoxy)phenoxy]-phenyl]sulfonyl]-4-piperidinecarboxamide

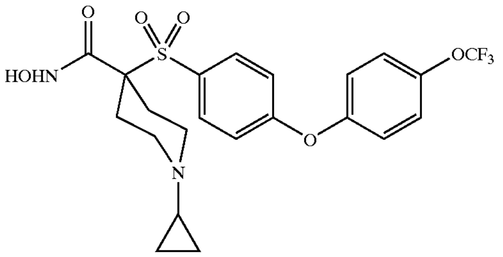

To a solution of the product of Preparative, Example IX (2.08 g, 4.0 mmol) in warm water (200 mL) was added sodium bicarbonate to pH=8 and the solution was stirred for 1 hour. The resulting white solid was isolated by filtration, washed with water and dried at 40° C. for 48 hours to afford the title compound as a white solid (1.82 g, 94%). Analytical calculation for $C_{22}H_{23}N_2SF_3O_5$:$H_2O$, 52.50; H, 5.01; N, 5.57; S, 6.38. Found: C, 52.24; H, 4.65; N, 5.46; S, 6.75.

EXAMPLE 267

Preparation of 1-Cyclopropyl-N-hydroxy-4-[[4-[4-(trifluoromethoxy)phenoxy]-phenyl]sulfonyl]-4-piperidinecarboxamide mono(4-Methylbenzenesulfonate) (Salt)

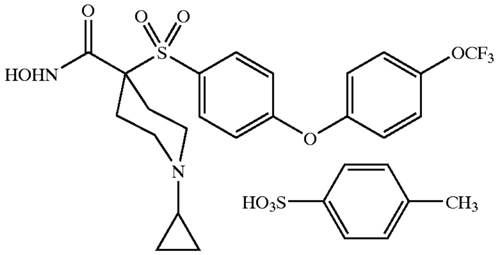

To a solution of the product of Example 266 (550 mg, 1.10 mmol) in ethanol (5 mL) was added p-toluenesulfonic acid (240 mg, 1.26 mmol) and the reaction was then stirred for 3.5 hour. The resulting white solid was isolated by filtration, washed with ethanol and dried at 40° C. for 48 hours to afford the title compound as a white solid (633 mg, 86%). Recrystallized from methanol/water afforded the title compound as analytically pure material. Analytical Calculation for $C_{29}H_{31}N_2S_2F_3O_9$: 51.78; H, 4.64; N, 4.16. Found: C, 51.44; H, 4.32; N, 4.18.

EXAMPLE 268

Preparation of 1-Cyclopropyl-N-hydroxy-4-[[4-[4-(trifluoromethoxy)phenoxy]-phenyl]sulfonyl]-4-piperidinecarboxamide Monomethanesulfonate (Salt)

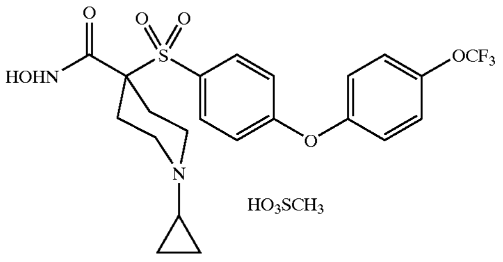

To a solution of the product of Example 266 (550 mg, 1.13 mmol) in ethanol (5 mL) was added methane sulfonic acid (82 μL) and the reaction was then stirred for 3.5 hours. Concentration in vacuo afforded the title compound as a solid (640 mg, 97%). Recrystallization from methanol afforded analytically pure title compound. Analytical Calculation for $C_{23}H_{27}N_2S_2F_3O_9$: 46.30; H, 4.56; N, 4.70, S, 10.75. Found: C, 46.10; H, 4.71; N, 4.65; S, 10.99.

EXAMPLE 269

Preparation of 1-Cyclopropyl-N-hydroxy-4-[[4-[4-(trifluoromethylphenoxy]-phenyl]sulfonyl]-4-piperidinecarboxamide

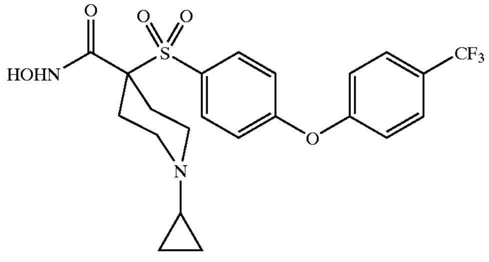

To a solution of the product of Preparative Example X (2.15 g, 4.0 mmol) in warm water (200 mL) was added sodium bicarbonate to pH=8. The solution was stirred for 1 hour. The resulting white solid was isolated by filtration, washed with water and dried at 40 degrees Celsius for 48 hours to afford the titled compound as a white solid (1.96 g, 98%). Analytical Calculation for $C_{22}H_{23}N_2SF_3O_5{:}2H_2O$: C, 51.26; H, 5.24; N, 5.44; S, 6.21. Found: C, 50.58; H, 4.72; N, 5.33; S, 6.04.

EXAMPLE 270

Preparation of 1-Cyclopropyl-N-hydroxy-4-[[4-[4-(trifluoromethylphenoxy]-phenyl]sulfonyl]-4-piperidinecarboxamide mono(4-Methylbenzenesulfonate) (Salt)

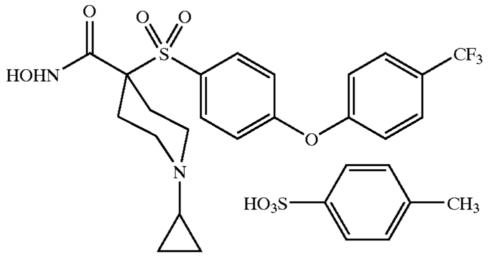

To a solution of the product of Example 269 (550 mg, 1.13 mmol) in ethanol (5 mL) was added p-toluenesulfonic acid (248 mg, 1.26 mmol) and the solution was stirred for 3.5 hours. The resulting white solid was isolated by filtration, washed with ethanol and dried at 40° C. for 48 hours to afford the title compound as a white solid (705 mg, 95%). Recrystallized from methanol afforded analytically pure material. Analytical Calculation for $C_{29}H_{31}N_2S_2F_3O_8$: C, 53.04; H, 4.76; N, 4.27; S, 9.77 Found: C, 52.94; H, 4.46; N, 4.30; S, 9.99.

EXAMPLE 271

Preparation of 1-Cyclopropyl-N-hydroxy-4-[[4-[4-(trifluoromethylphenoxy]-phenyl]sulfonyl]-4-piperidinecarboxamide Monomethanesulfonate (Salt)

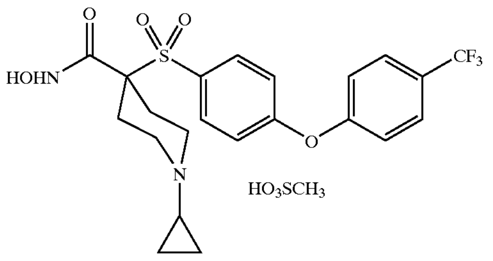

To a solution of the product of Example 269 (550 mg, 1.13 mmol) in ethanol (5 mL) was added methane sulfonic acid (79 μL) and the reaction was stirred for 3.5 hours. Concentration in vacuo gave the title compound as a solid (569 mg, 87%). Analytical Calculation for $C_{23}H_{27}N_2S_2F_3O_8$: C, 47.58; H, 4.69; N, 4.82. Found: C, 47.15; H, 4.18; N, 4.74.

EXAMPLE 272

Preparation of 1-Acetyl-N-hydroxy-4-[[4-[4-(trifluoromethoxy)phenoxy]-phenyl]sulfonyl]-4-piperidinecarboxamide

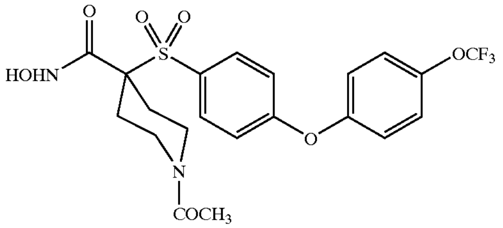

Part A: To a solution of the product of Preparative Example II, Part D (33.2 g, 80.0 mmol) in dimethylformamide (150 mL) was added cesium carbonate (65.2 g, 200 mmol) and 4-(trifluromethoxy)phenol (21.4 g, 120 mmol). The solution was mechanically stirred at sixty degrees Celsius for 24 hours. The solution was then diluted with water (1 L) and extracted with ethyl acetate. The organic layer was washed with water, saturated aqueous sodium chloride and dried over magnesium sulfate, then filtered and concentrated in vacuo. Chromatography on silica gel eluting with 20% ethyl acetate/hexane provided the desired diaryl sulfide as a white solid (45.0 g, quantitative yield).

Part B: To a solution of the diaryl sulfide from part A (24 g, 42.8 mmol) in ethanol (80 mL) and tetrahydrofuran (80 mL) was added a solution of NaOH (14.8 g, 370 mmol) in water (100 mL) and the solution was heated at sixty degrees Celsius for 18 hours. The solution was concentrated in vacuo and the aqueous residue was acidified to pH=5.0 and extracted with ethyl acetate. The organic extract was washed with saturated aqueous sodium chloride and dried over magnesium sulfate, then filtered and concentrated in vacuo to give the desired carboxylic acid as a white foam (23.0 g, quantitative yield).

Part C: To a solution of carboxylic acid of part B (22.8 g, 43.0 mmol) in ethyl acetate (400 mL) cooled to zero degrees Celsius was bubbled gaseous Hydrogen chloride for 20 minutes. The reaction was stirred at this temperature for 2.5 hours. The solution was then concentrated in vacuo to afford the desired hydrochloride salt as a white foam (21.0 g, quantitative yield).

Part D: To a solution of the hydrochloride salt of part C (17.0 g, 35.0 mmol) in acetone (125 mL) and water (125 mL) was added triethyl amine (24 mL, 175 mmol). The reaction was cooled to zero degrees Celsius and acetyl chloride (3.73 mL, 53.0 mmol) was added. The solution was then stirred at ambient temperature for 18 hours. Concentration in vacuo gave a residue which was acidified with aqueous hydrochloric acid to pH 1.0 and then extracted with ethyl acetate. The organic layer was washed with water, saturated aqueous sodium chloride and dried over magnesium sulfate, then filtered and concentrated in vacuo to give the desired methanesulfonamide as a white solid (17.0 g, quantitative yield).

Part E: To a solution of the methanesulfonamide of part D (14.4 g, 29.6 mmol) in dimethylformamide (250 mL) was added 1-hydroxybenzotriazole. (4.8 g, 35.5 mmol), N-methyl morpholine (12.3 mL, 88.8 mmol) and O-tetrahydropyranyl hydroxyl amine (5.2 g, 44.4 mmol) followed by 1-3-(dimethylamino)propyl]-3-ethyl carbodiimide hydrochloride (7.99 g, 41.4 mmol). The solution was stirred at ambient temperature for 18 hours. The solution was diluted with water (500 mL) and extracted with ethyl acetate. The organic layer was washed with saturated aqueous sodium chloride and dried over magnesium sulfate, then filtered and concentrated in vacuo. Chromatography on a C18 reverse phase column eluting with acetonitrile/water provided the desired tetrahydropyranyl-protected hydroxamate as a white solid (12.0 g, 71%).

Part F: To a solution of tetrahydropyranyl-protected hydroxamate of part E (12.0 g, 20.5 mmol) in dioxane (250 mL) and methanol (50 mL) was added 4 N hydrogen chloride/dioxane (51 mL). After stirring at ambient temperature for 3.5 hours the solution was concentrated in vacuo. Trituration with diethyl ether and filtration provided the title compound as a white solid (8.84 g, 85%). HRMS $MH^+$ calculated for $C_{21}H_{21}N_2SO_7F_3$: 503502.1021. Found 502.0979.

EXAMPLE 273

Preparation of N-Hydroxy-1-(methylsulfonyl)-4-[[4-[4-sulfonyl]-(trifluoromethoxy)phenoxy]phenyl]-4-piperidinecarboxamide

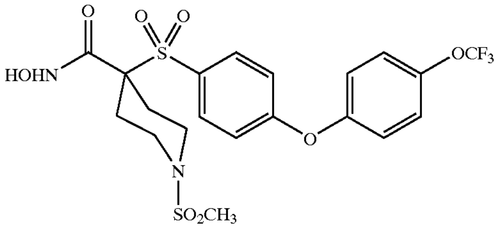

Part A: To a solution of the product of reparative Example II, Part D, (33.2 g, 80.0 mmol) in dimethylformamide (150 mL) was added cesium carbonate (65.2 gm, 200.0 mmol) and 4-(trifluromethoxy)phenol (21.4 g, 120 mmol). The solution was mechanically stirred at sixty degrees Celsius for 24 hours. The solution was then diluted with water (1 L) and extracted with ethyl acetate. The organic layer was washed with water, saturated aqueous sodium chloride and dried over magnesium sulfate, then filtered and concentrated in vacuo. Chromatography on silica gel eluting with 20% ethyl acetate/hexane provided the desired diaryl sulfide as a white solid (45.0 gm, quantitative yield).

Part B: To a solution of the diaryl sulfide from part A (21 g, 37.0 mmol) in ethanol (80 mL) and tetrahydrofuran (80 mL) was added a solution of NaOH (14.8 g, 370 mmol) in water (75 mL) and the solution was heated at sixty degrees Celsius for 18 hours. The solution was concentrated in vacuo and the aqueous residue was acidified to pH=5.0, and then extracted with ethyl acetate. The organic extract was washed with saturated aqueous sodium chloride and dried over magnesium sulfate, then filtered and concentrated in vacuo to give the desired carboxylic acid as a white foam (19.3 g, 97%)

Part C: To a solution of carboxylic acid of part B (19.3 g, 37.0 mmol) in ethyl acetate (400 mL) cooled to zero degrees Celsius was bubbled gaseous hydrogen chloride for 30 minutes. The reaction was stirred at this temperature for 2.5 hours. The solution was then concentrated in vacuo to afford the desired hydrochloride salt as a white foam (15.8 g, 93%).

Part D: To a solution of the hydrochloride salt of part C (15.8 g, 33.0 mmol) in acetone (100 mL) and water (100 mL) was added triethyl amine (23 mL, 164 mmol). The reaction was cooled to zero degrees Celsius and methanesulfonyl chloride (5.1 mL, 66.0 mmol) was added. The solution was stirred at ambient temperature for 18 hours. The reaction was concentrated in vacuo and acidified with aqueous hydrochloric acid to pH 1.0. The aqueous residue was extracted ethyl acetate. The organic extract was washed with water, saturated sodium chloride and dried over magnesium sulfate, then filtered and concentrated in vacuo to give the desired carboxylic acid methanesulfonamide as a white solid (17.6 gm, quantitative yield).

Part E: To a solution of the methanesulfonamide of part D (18 g, 35.0 mmol) in dimethylformamide (150 mL) was added 1-hydroxybenzotriazole (5.66 gm, 42.0 mmol), N-methyl morpholine (14.0 mL, 105.0 mmol) and O-tetrahydropyranyl hydroxyl amine (6.1 g, 52 mmol) followed by 1-3-(dimethylamino) propyl]-3-ethylcarbodiimide hydrochloride (9.4 gm, 49.0 mmol). The solution was stirred at ambient temperature for 18 hours. The solution was diluted with water (500 mL) and extracted with ethyl acetate. The organic extract was washed with saturated aqueous sodium chloride and dried over magnesium sulfate, then filtered and concentrated in vacuo. Chromatography on a C18 reverse phase column eluting with acetonitrile/water provided desired tetrahydropyranyl-protected hydroxamate as a white solid (8.17 g, 41%).

Part F: To a solution of tetrahydropyranyl-protected hydroxamate of part E (8.17 g, 13.0 mmol) in dioxane (100 mL) and methanol (100 mL) was added 4 N hydrogen chloride/dioxane (50 mL). After stirring at ambient temperature for 3.5 hours the solution was concentrated in vacuo. Trituration with diethyl ether provided the title compound as a white solid (6.83 g, 92%). MS $MH^+$ calculated for $C_{20}H_{21}NS_2O_8F$: 539. Found 539.

The following compounds were prepared by parallel synthesis (resin based synthesis, automated synthesis) procedures utilizing reactions such as acylation and nucleophilic displacement:

EXAMPLE 274

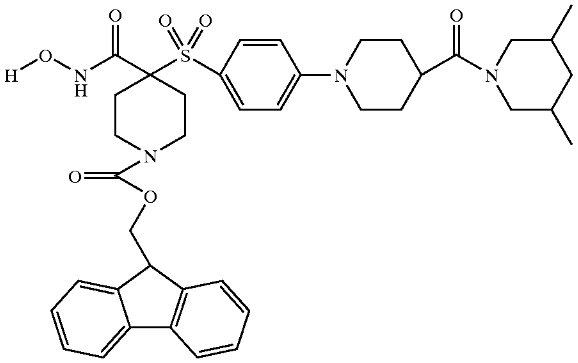

EXAMPLE 275

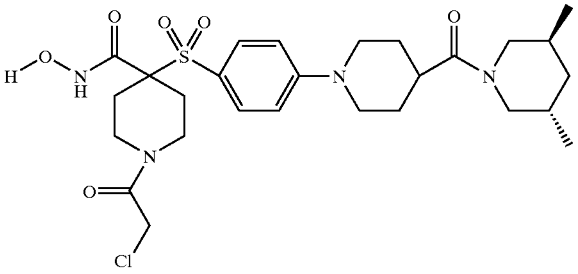

EXAMPLE 276

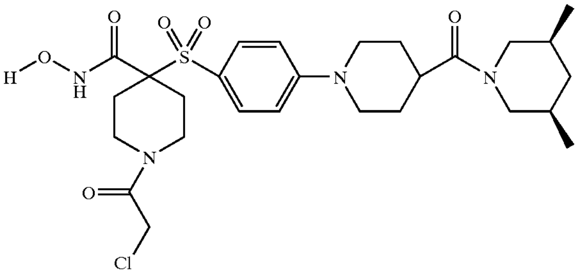

EXAMPLES: 277–315

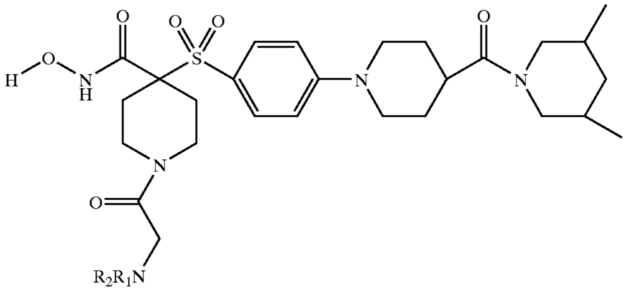

| Example | $R_1R_2NH$ | Amine | MS (ES) m/z |
|---|---|---|---|
| 277 | 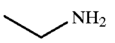 | Ethyl amine | 592 (M + H) |
| 278 | 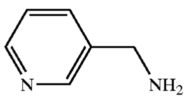 | 3-(Aminomethyl) pyridine | 655 (M + H) |

-continued
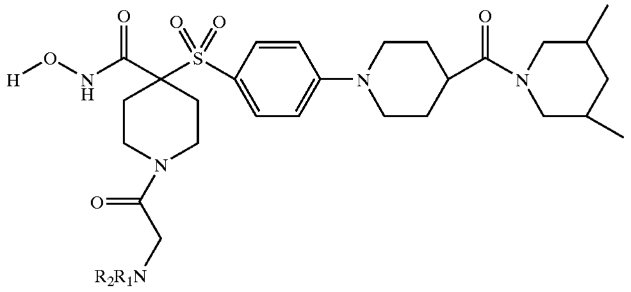
| Example | $R_1R_2NH$ | Amine | MS (ES) m/z |
|---|---|---|---|
| 279 | 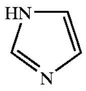 | Imidazole | 615 (M + H) |
| 280 | 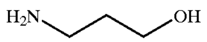 | 3-Amino-1-propanol | 622 (M + H) |
| 281 | 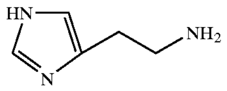 | Histamine | 658 (M + H) |
| 282 | 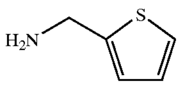 | 2-Thiophene methyl amine | 660 (M + H) |
| 283 | 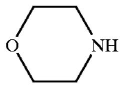 | Morpholine | 634 (M + H) |
| 284 | 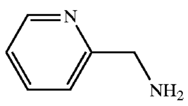 | 2-(Aminomethyl) pyridine | 655 (M + H) |
| 285 | 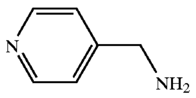 | 4-(Aminomethyl) pyridine | 655 (M + H) |
| 286 | 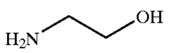 | Ethanolamine | 608 (M + H) |
| 287 | 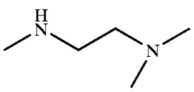 | N,N,N-Trimethyl ethylenediamine | 649 (M + H) |
| 288 | 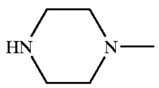 | 1-Methylpiperazine | 647 (M + H) |
| 289 | 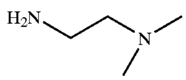 | N,N-Dimethyl ethylenediamine | 635 (M + H) |
| 290 | 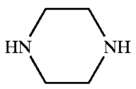 | Piperazine | 633 (M + H) |
| 291 | 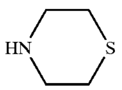 | Thiomorpholine | 650 (M + H) |

-continued

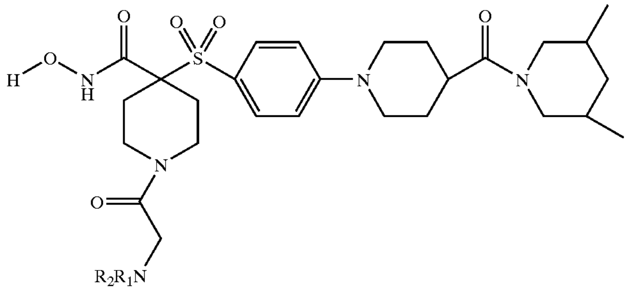

| Example | $R_1R_2NH$ | Amine | MS (ES) m/z |
|---|---|---|---|
| 292 | 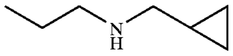 | N-Propylcyclopropne methylamine | 660 (M + H) |
| 293 | 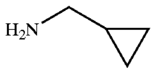 | (Aminomethyl) cyclopropane | 618 (M + H) |
| 294 | 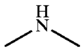 | Dimethylamine | 592 (M + H) |
| 295 | 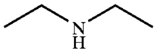 | Diethylamine | 620 (M + H) |
| 296 | 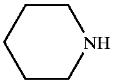 | Piperidine | 632 (M + H) |
| 297 | 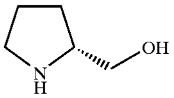 | (R)—(—)-2-Pyrrolidine methanol | 648 (M + H) |
| 298 | 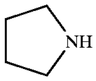 | Pyrrolidine | 618 (M + H) |
| 299 | 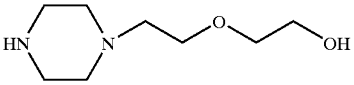 | 1-(2-(2-Hydroxyethoxy) ethyl)piperazine | 721 (M + H) |
| 300 | 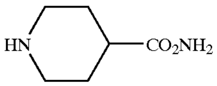 | Isonipecotamide | 675 (M + H) |
| 301 | 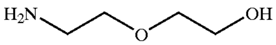 | 2-(2-Aminoethoxy) ethanol | 652 (M + H) |
| 302 | 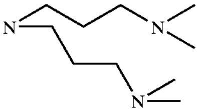 | 3,3'-Iminobis(N,N-dimethylpropylamine) | 734 (M + H) |
| 303 | 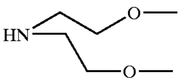 | Bis(2-Methoxy ethyl)amine | 680 (M + H) |
| 304 | 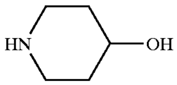 | 4-Hydroxy piperidine | 648 (M + H) |

-continued
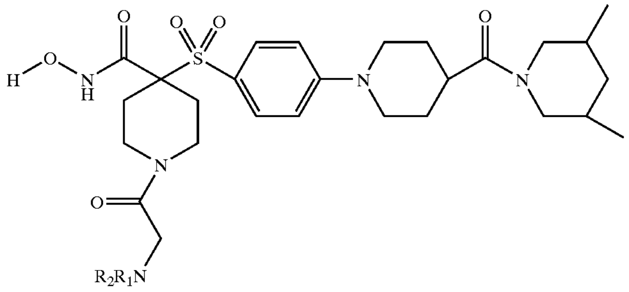
| Example | $R_1R_2NH$ | Amine | MS (ES) m/z |
|---|---|---|---|
| 305 | 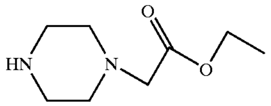 | N-(Carboethoxy methylpiperazine | 719 (M + H) |
| 306 | 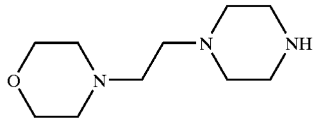 | 1-(2-Morpholinoethyl) piperazine | 746 (M + H) |
| 307 | 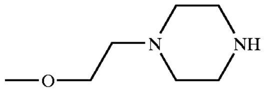 | 1-(2-Methoxyethyl) piperazine | 691 (M + H) |
| 308 | 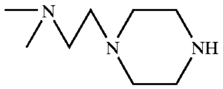 | 1-(2-Dimethylaminoethyl) piperazine | 704 (M + H) |
| 309 | 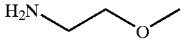 | 2-Methoxyethylamine | 622 (M + H) |
| 310 | 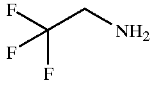 | 2,2,2-Trifluoroethyl amine | 646 (M + H) |
| 311 | 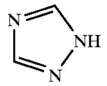 | 1,2,4-Triazole | 616 (M + H) |
| 312 | 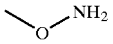 | Methoxyamine | 594 (M + H) |
| 313 | 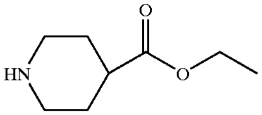 | Ethyl isonipecotate | 704 (M + H) |
| 314 | 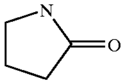 | 2-Pyrrolidinone | 632 (M + H) |
| 315 | 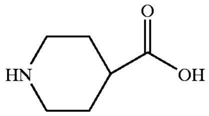 | Isonipecotic acid | 676 (M + H) |

EXAMPLES: 316–332
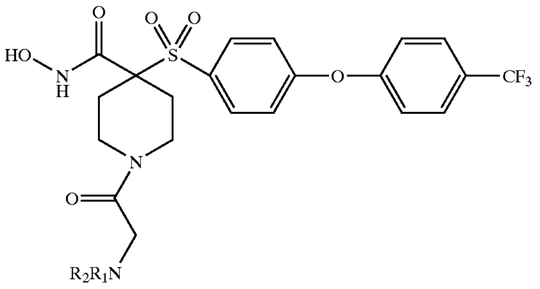
| Example | $R_1R_2NH$ | Amine | MS (ES) m/z |
|---|---|---|---|
| 316 | 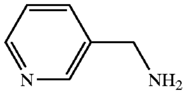 | 3-(Aminoethyl) pyridine | 593 (M + H) |
| 317 | 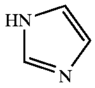 | Imidazole | 553 (M + H) |
| 318 | 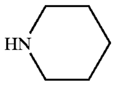 | Piperidine | 570 (M + H) |
| 319 | 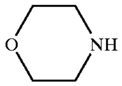 | Morpholine | 572 (M + H) |
| 320 | 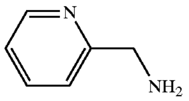 | 2-(Aminomethyl) pyridine | 593 (M + H) |
| 321 | 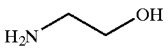 | Ethanolamine | 546 (M + H) |
| 322 | 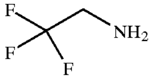 | 2,2,2-Trifluoro ethylamine | 584 (M + H) |
| 323 | 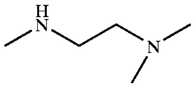 | N,N,N-Trimethyl ethylenediamine | 587 (M + H) |
| 324 | 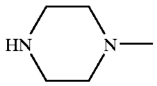 | 1-Methylpiperazine | 585 (M + H) |
| 325 | 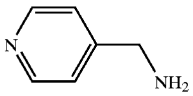 | 4-(Aminomethyl) pyridine | 593 (M + H) |
| 326 | 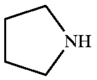 | Pyrrolidine | 556 (M + H) |
| 327 | 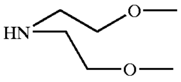 | Bis(2-Methoxy ethyl)amine | 618 (M + H) |

-continued
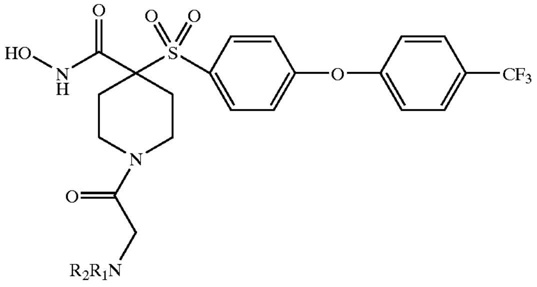
| Example | $R_1R_2NH$ | Amine | MS (ES) m/z |
|---|---|---|---|
| 328 | 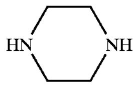 | Piperazine | 571 (M + H) |
| 329 | 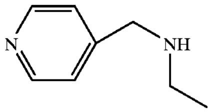 | 4-(Ethylamino methyl)pyridine | 621 (M + H) |
| 330 | 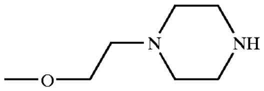 | 1-(2-Methoxy ethyl)pyridine | 629 (M + H) |
| 331 | 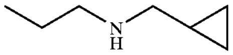 | N-Propylcyclopropane methylamine | 598 (M + H) |
| 332 | 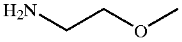 | 2-Methoxyethylamine | 560 (M + H) |
EXAMPLE: 333–347
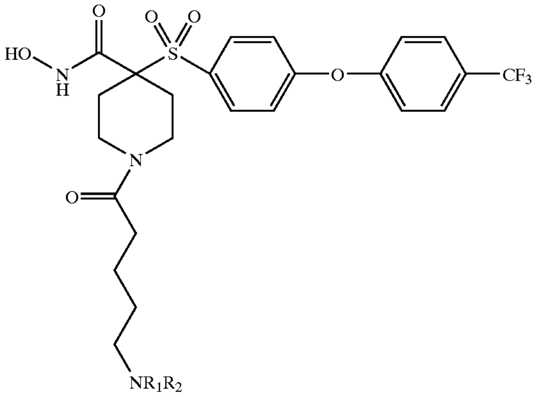
| Example | $R_1R_2NH$ | Amine | MS (ES) m/z |
|---|---|---|---|
| 333 | 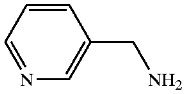 | 3-(Aminomethyl) pyridine | 635 (M + H) |
| 334 | 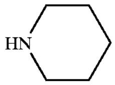 | Piperidine | 612 (M + H) |

-continued
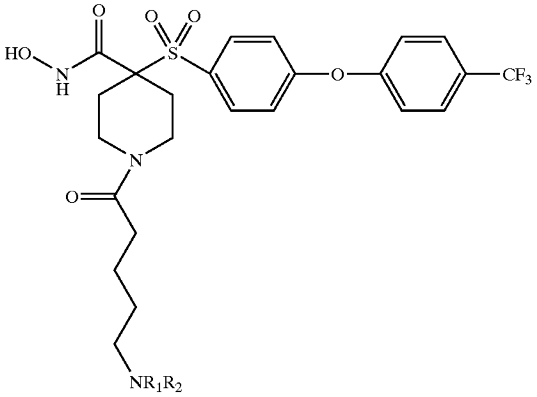
| Example | $R_1R_2NH$ | Amine | MS (ES) m/z |
| --- | --- | --- | --- |
| 335 | 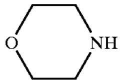 | Morpholine | 614 (M + H) |
| 336 | 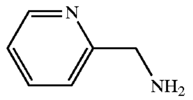 | 2-(Aminomethyl) pyridine | 635 (M + H) |
| 337 | 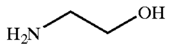 | Ethanolamine | 588 (M + H) |
| 338 | 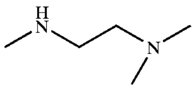 | N,N,N-Trimethyl ethylenediamine | 629 (M + H) |
| 339 | 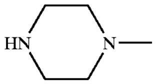 | 1-Methylpiperazine | 627 (M + H) |
| 340 | 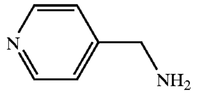 | 4-(Aminomethyl) pyridine | 636 (M + H) |
| 341 | 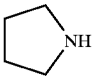 | Pyrrolidine | 598 (M + H) |
| 342 | 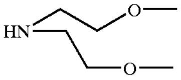 | Bis(2-Methoxy ethyl)amine | 660 (M + H) |
| 343 | 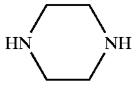 | Piperazine | 613 (M + H) |
| 344 | 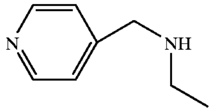 | 4-(Ethylamino methyl)pyridine | 663 (M + H) |
| 345 | 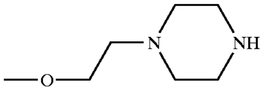 | 1-(2-Methoxy ethyl)pyridine | 671 (M + H) |

-continued

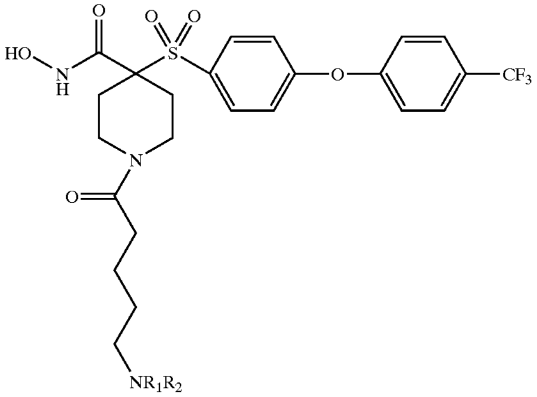

| Example | $R_1R_2NH$ | Amine | MS (ES) m/z |
|---|---|---|---|
| 346 | 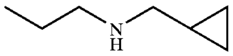 | N-Propylcyclopropane methylamine | 640 (M + H) |
| 347 | 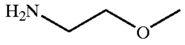 | 2-Methoxyethylamine | 602 (M + H) |

EXAMPLES 348–942

The following compounds were prepared in a manner similar to that used in the preceding examples. In the tables that follow, a generic structure is shown above the table with substituent groups being illustrated in the table along with available mass spectral data.

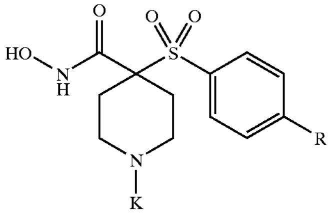

| Example | R | K | MS (ES) m/z |
|---|---|---|---|
| 348 | 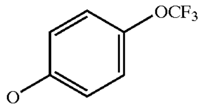 HCl | 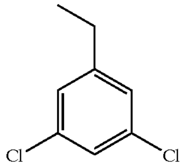 | |
| 349 | 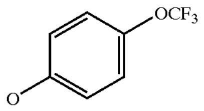 HCl | 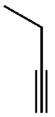 | 499.1131 |
| 350 | 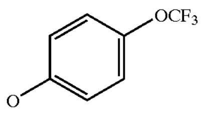 HCl | 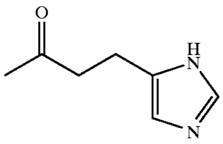 | 583 |

-continued
| | | | |
|---|---|---|---|
| 351 | 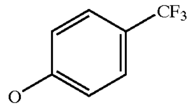 | 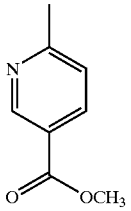 | 580.1366 |
| 352 | 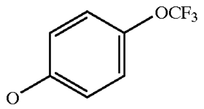 HCl | 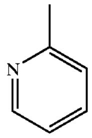 | 538.1282 |
| 353 | 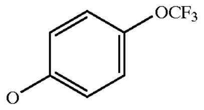 HCl | 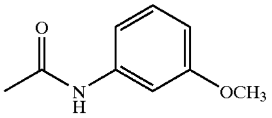 | 610 |
| 354 | 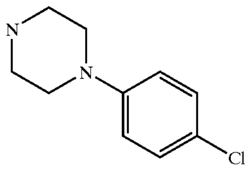 2HCl | 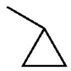 | |
| 355 | 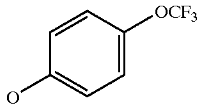 HCl | 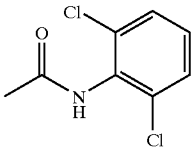 | 648 |
| 356 | 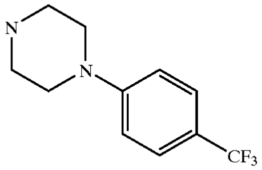 2HCl | 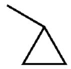 | |
| 357 | 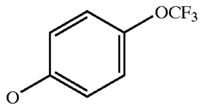 | 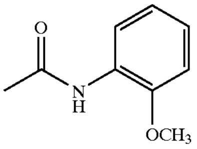 | 610 |
| 358 | 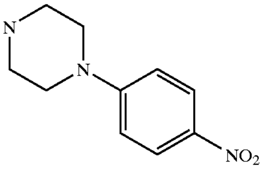 2HCl | 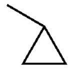 | |

-continued
| | | | |
|---|---|---|---|
| 359 | 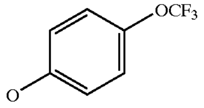 | 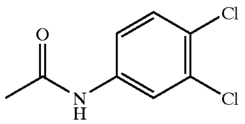 | 648 |
| 360 | 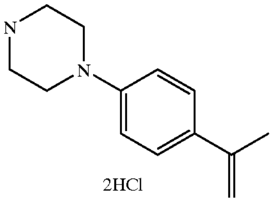 2HCl | 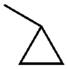 | |
| 361 | 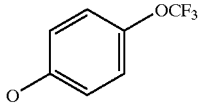 | 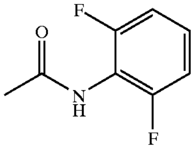 | 616 |
| 362 | 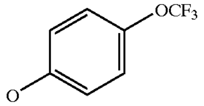 | 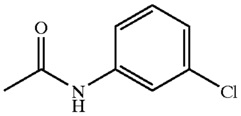 | 614 |
| 363 | 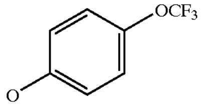 | 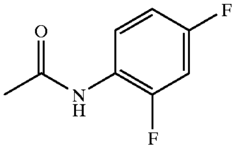 | 616 |
| 364 | 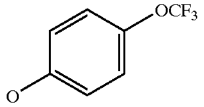 | 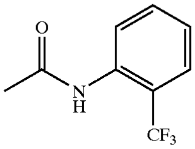 | 648 |
| 365 | 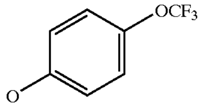 | 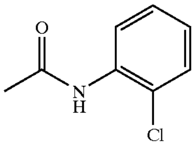 | 614 |
| 366 | 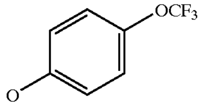 | 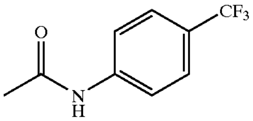 | 648 |
| 367 | 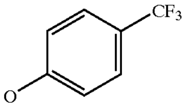 HCl | 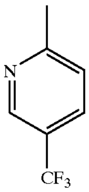 | |

-continued
| | | | |
|---|---|---|---|
| 368 | 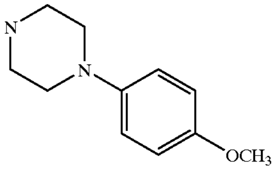<br>2HCl | 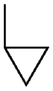 | |
| 369 | 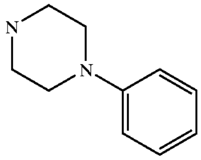<br>2HCl | 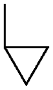 | |
| 370 | 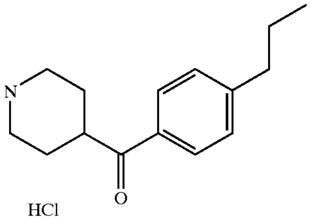<br>HCl | 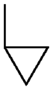 | |
| 371 | 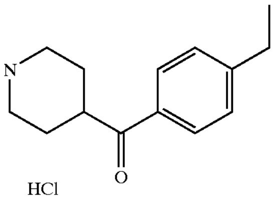<br>HCl | 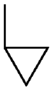 | |
| 372 | 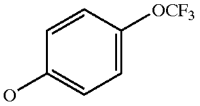 | 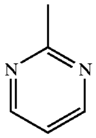 | 539.1201 |
| 373 | 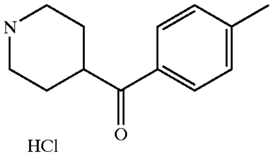<br>HCl | 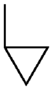 | |
| 374 | 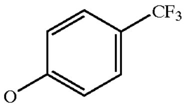 | 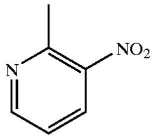 | 567.1120 |
| 375 | 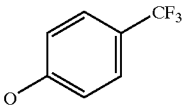 | 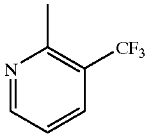 | 590.1174 |

-continued
| | | | |
|---|---|---|---|
| 376 | 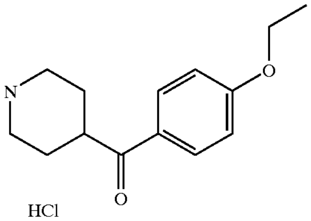 HCl | 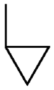 | |
| 378 | 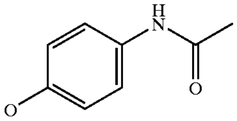 HCl | 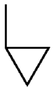 | 474.1567 |
| 379 | 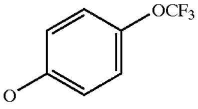 HCl | 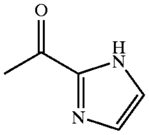 | 555 |
| 380 | 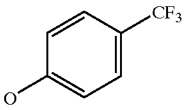 | 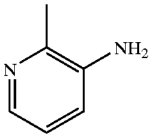 | 537.1412 |
| 381 | 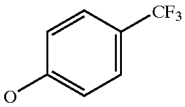 | 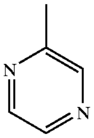 | 523 |
| 382 | 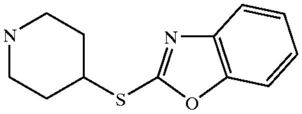 HCl | 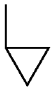 | |
| 383 | 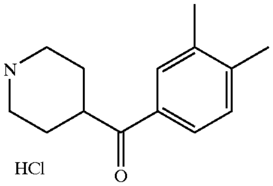 HCl | 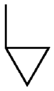 | |
| 384 | 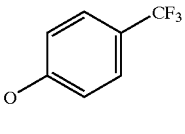 | 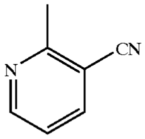 | 547.1279 |
| 385 | 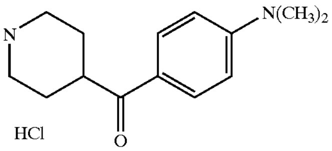 HCl | 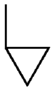 | |

-continued
| | | | |
|---|---|---|---|
| 386 | 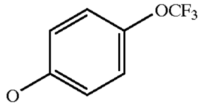 HCl | 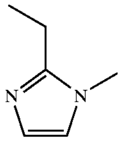 | 555.1516 |
| 387 | 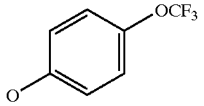 HCl | 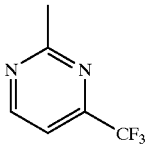 | 607.1061 |
| 388 | 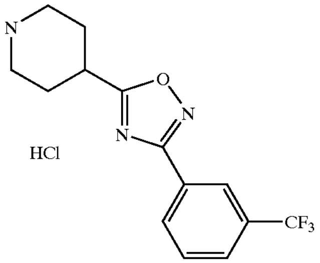 HCl | 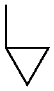 | |
| 389 | 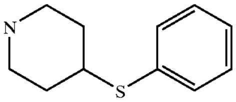 | 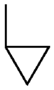 HCl | 516 |
| 390 | 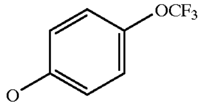 HCl | 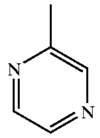 | 539 |
| 391 | 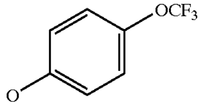 HCl | 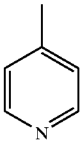 | 538.1272 |
| 392 | 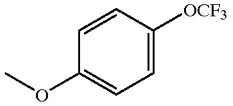 HCl | 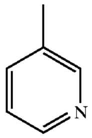 | 538.1252 |
| 393 | 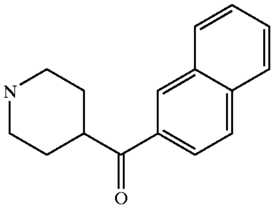 | 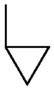 | |
| 394 | 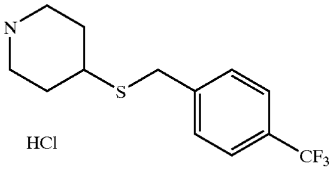 HCl | 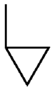 | |

-continued
| | | | |
|---|---|---|---|
| 395 | 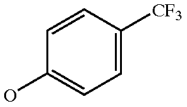 HCl | 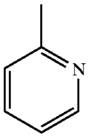 | 522.1351 |
| 396 | 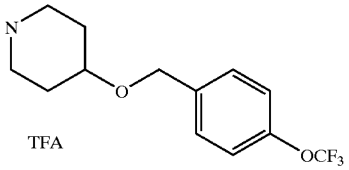 TFA | 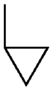 | 582.2245 |
| 397 | 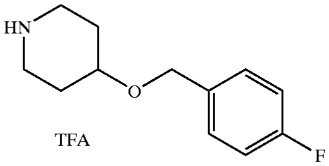 TFA | 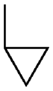 | 532.2280 |
| 398 | 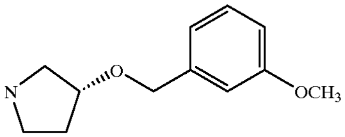 2HCl | 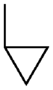 | |
| 399 | 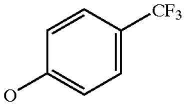 HCl | 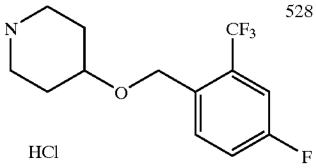 HCl | 528 |
| 400 | 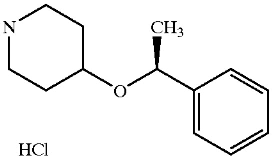 HCl | 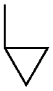 | |
| 401 | 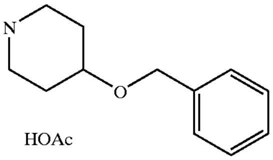 HOAc | 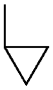 | 515.3344 |
| 402 | 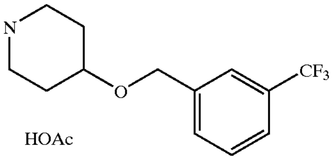 HOAc | 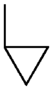 | 582.2266 |
| 403 | 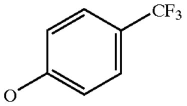 HCl | 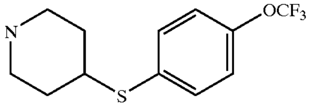 | |

-continued
| | | | |
|---|---|---|---|
| 404 | 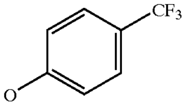 HCl | 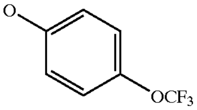 | 550 |
| 405 | 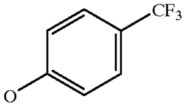 HCl | 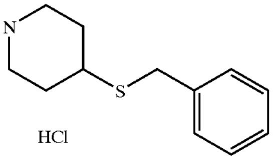 HCl | 550 |
| 406 | 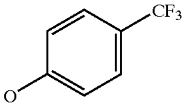 HCl | 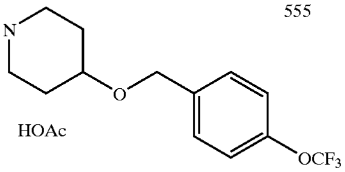 HOAc | 555 |
| 407 | 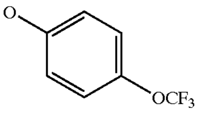 HCl | 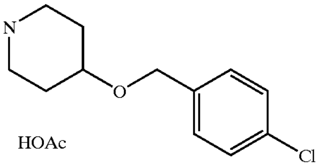 HOAc | |
| 408 | 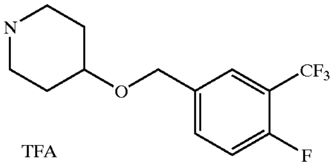 TFA | 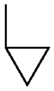 | 600.2162 |
| 409 | 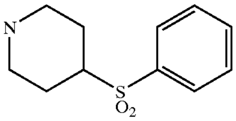 HCl | 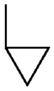 | 548 |
| 410 | 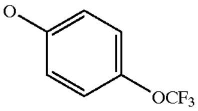 HCl | 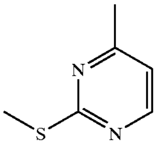 | |
| 411 | 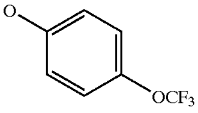 HCl | 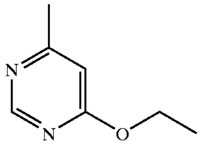 | |
| 412 | 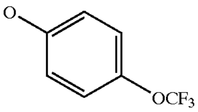 HCl | 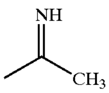 | 502 |

-continued
| | | | |
|---|---|---|---|
| 413 | 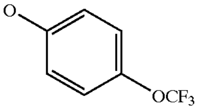 HCl | 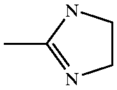 | 529 |
| 414 | 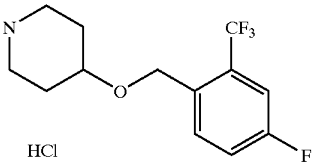 HCl | 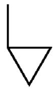 | 600.2141 |
| 415 | 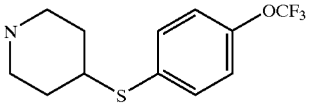 | 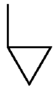 | 600 |
| 416 | 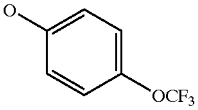 | 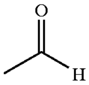 | 489 |
| 417 | 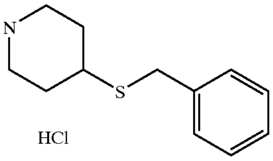 HCl | 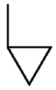 | 530 |
| 418 | 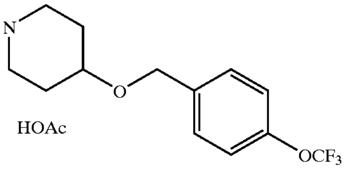 HOAc | 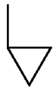 | 598.2200 |
| 419 | 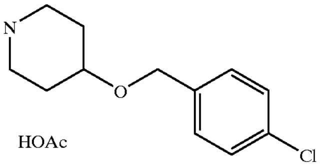 HOAc | 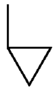 | 548.2013 |
| 420 | 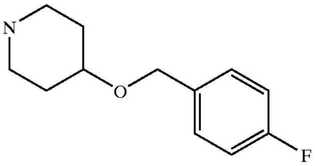 | 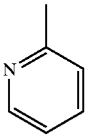 | 569.2259 |
| 421 | 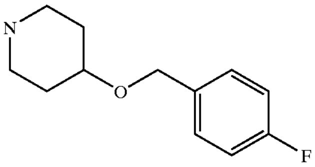 | 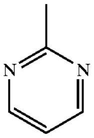 | 570.2186 |

-continued
| | | | |
|---|---|---|---|
| 422 | 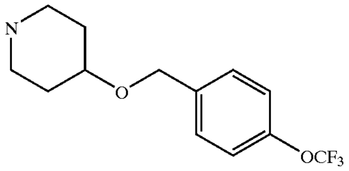 | 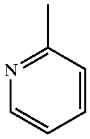 | 635.2185 |
| 423 | 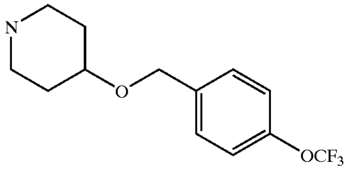 | 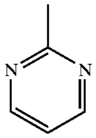 | 636.2104 |
| 424 | 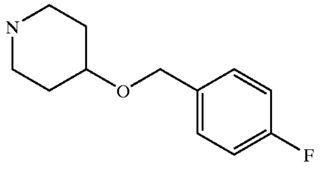 | 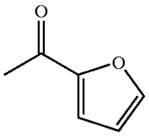 | 586.2059 |
| 425 | 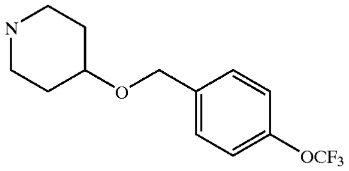 | 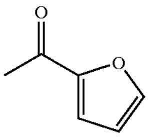 | 562.1957 |
| 426 | 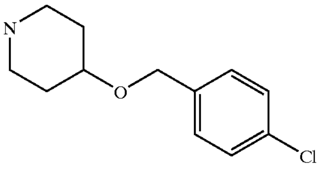 | 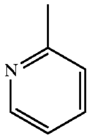 | 585.1968 |
| 427 | 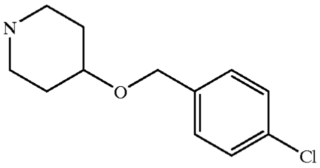 | 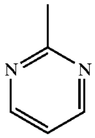 | 586.1936 |
| 428 | 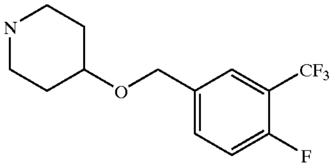 | 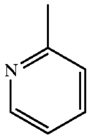 | 637.2137 |
| 429 | 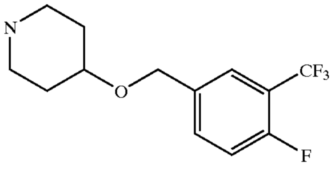 | 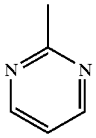 | 638.2072 |
| 430 | 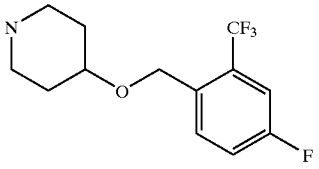 | 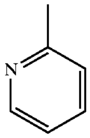 | 637.1246 |

-continued
| | | | |
|---|---|---|---|
| 431 | 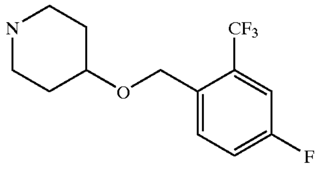 | 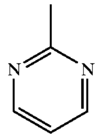 | 638.2075 |
| 432 | 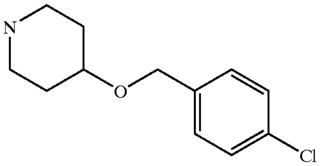 | 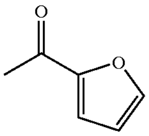 | 602.1731 |
| 433 | 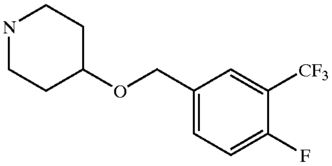 | 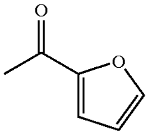 | 654.1921 |
| 434 | 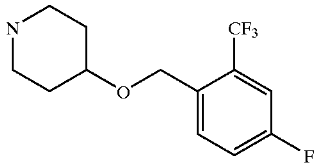 | 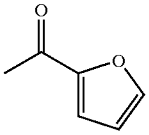 | 654.1932 |
| 435 | 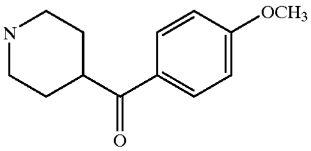 | 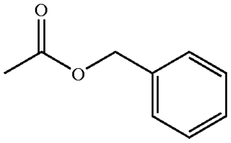 | 636 |
| 436 | 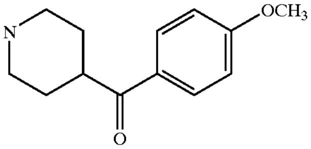 | 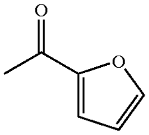 | 596 |
| 437 | 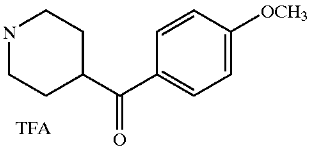 TFA | —H | 502 |
| 438 | 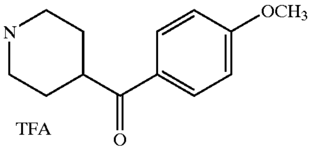 TFA | 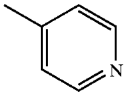 | 579 |
| 439 | 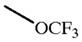 HCl | 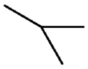 | 411.1211 |

-continued
| | | | |
|---|---|---|---|
| 440 | 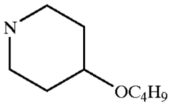 HCl | 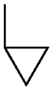 | 480 |
| 441 | 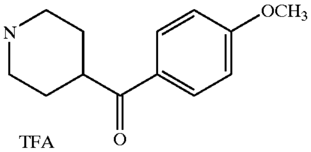 TFA | 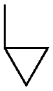 | 542 |
| 442 | 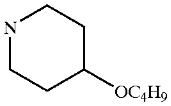 HCl | 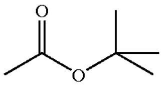 | 540 |
| 443 | 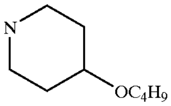 HCl | —H | 440 |
| 444 | 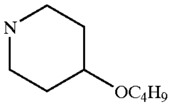 HCl | 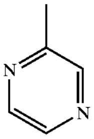 | 518 |
| 445 | 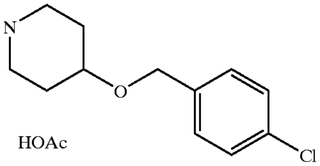 HOAc | 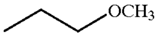 | 566 |
| 446 | 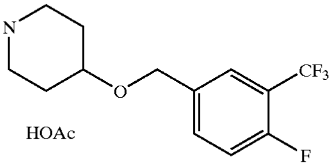 HOAc | 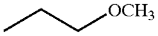 | 618 |
| 447 | 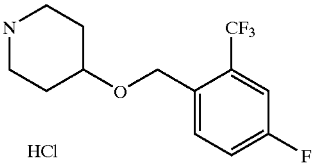 HCl | 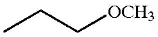 | 616 |
| 448 | 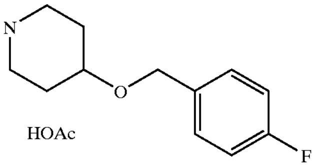 HOAc | 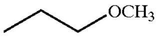 | 550.2387 |

-continued
| | | | |
|---|---|---|---|
| 449 | 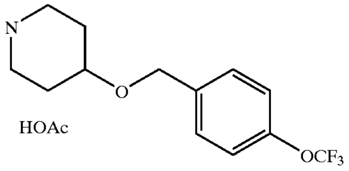 HOAc | 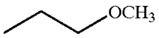 | 616 |
| 450 | 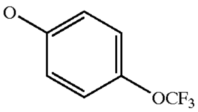 HCl | 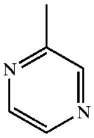 | |
| 451 | 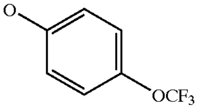 HCl | 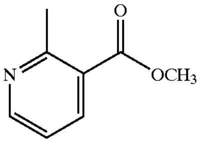 | 580.1370 |
| 452 | 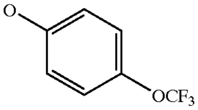 | 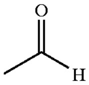 | |
| 453 | 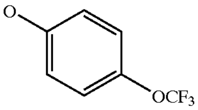 HCl | 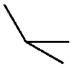 | |
| 454 | 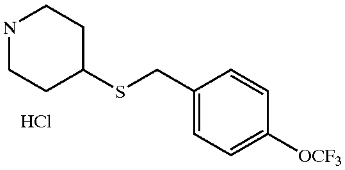 HCl | 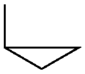 | 614 |
| 455 | 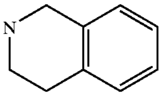 2HCl | 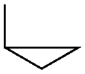 | 456 |
| 456 | 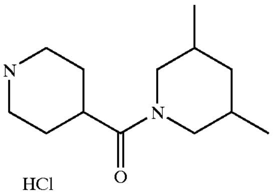 HCl | 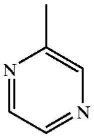 | 585 |
| 457 | 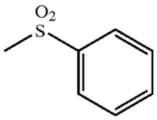 HCl | 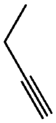 | 463 |

-continued
| | | | |
|---|---|---|---|
| 458 | 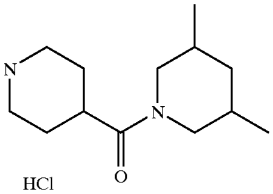 HCl | 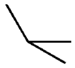 | 549 |
| 459 | 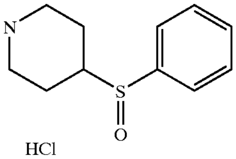 HCl | 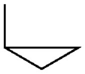 | 532 |
| 460 | 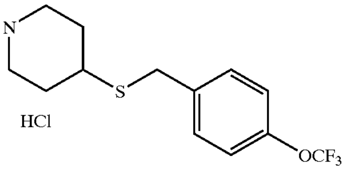 HCl | —H | 574 |
| 461 | 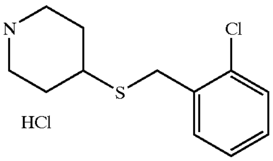 HCl | 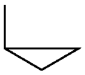 | 564 |
| 462 | 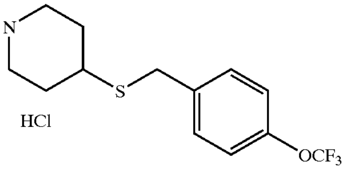 HCl | 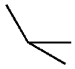 | 616 |
| 463 | 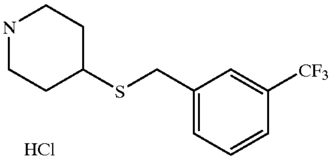 HCl | 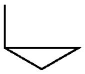 | 598 |
| 464 | 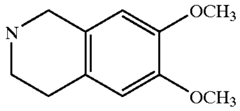 2HCl | 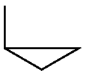 | 514 |
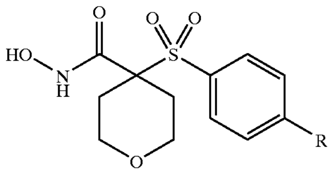
| Example | R | MS (ES) m/z |
|---|---|---|
| 465 | 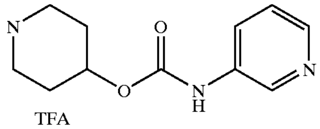 TFA | 505.1746 |

-continued
| | | |
|---|---|---|
| 466 | 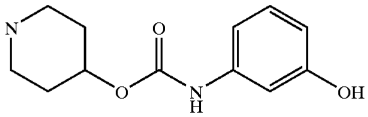 | 551 (+Na) |
| 467 | 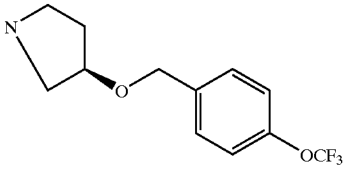 | |
| 468 | 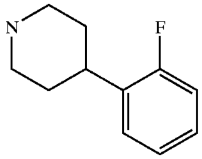 | 463.1704 |
| 469 | 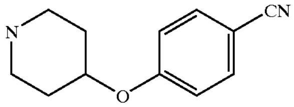 | 486 |
| 470 | 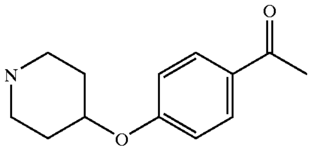 | 503 |
| 471 | 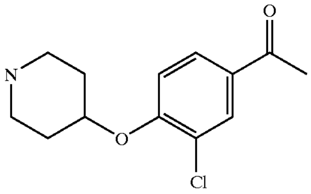 | 537 |
| 472 | 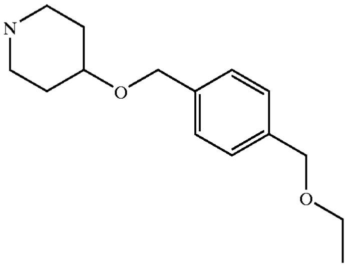 | 533.2348 |
| 473 | 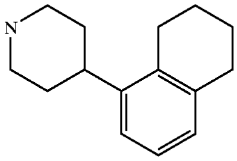 | 499.2304 |
| 474 | 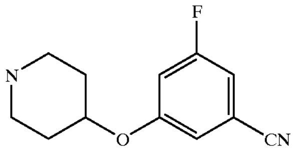 | 504 |

-continued
| | | |
|---|---|---|
| 475 | 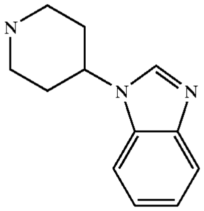 | |
| 476 | 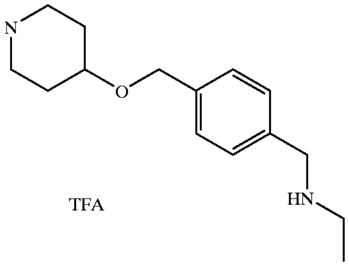 TFA | 532.2522 |
| 477 | 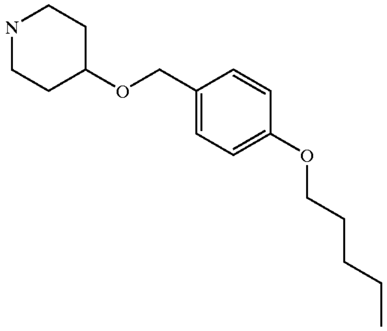 | |
| 478 | 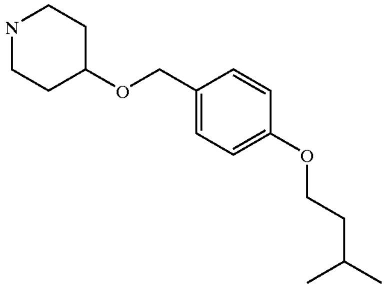 | |
| 479 | 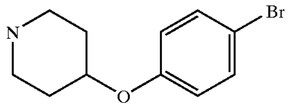 | 539.0842 |
| 480 | 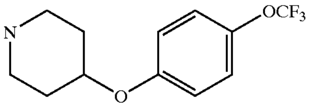 | 545.1595 |
| 481 | 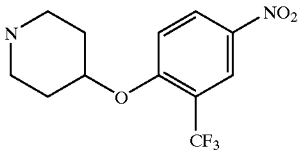 | 574.1483 |

-continued
| | | |
|---|---|---|
| 482 | 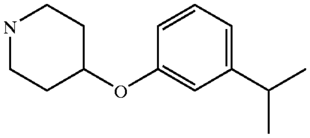 | 503.2238 |
| 483 | 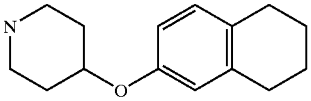 | 515.2234 |
| 484 | 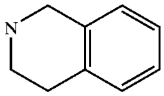 | 417 |
| 485 | 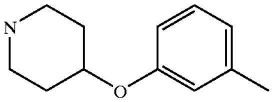 | 475.1910 |
| 486 | 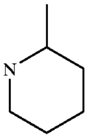 | 383 |
| 487 | 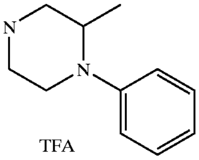 TFA | 460 |
| 488 | 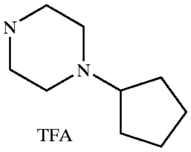 TFA | 438 |
| 489 | 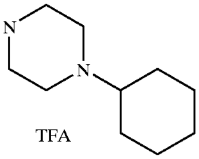 TFA | 452 |
| 490 | 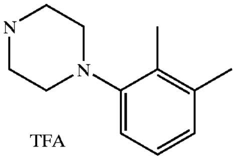 TFA | 474 |
| 491 | 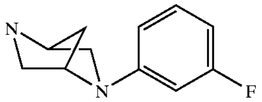 | 476 |
| 492 | 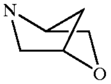 | 383 |

-continued
| | | |
|---|---|---|
| 493 | 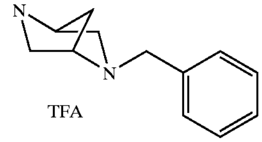 TFA | 472 |
| 494 | 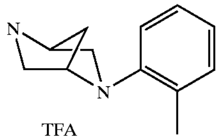 TFA | 472 |
| 495 | 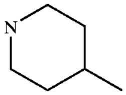 | 383 |
| 496 | 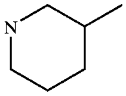 | 383 |
| 497 | 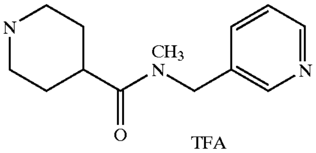 TFA | 517 |
| 498 | 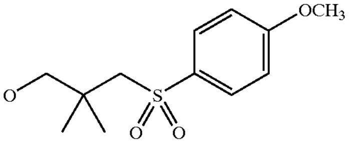 | |
| 499 | 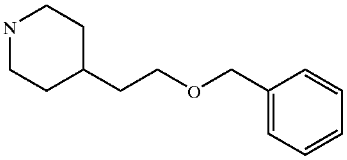 | 503 |
| 500 | 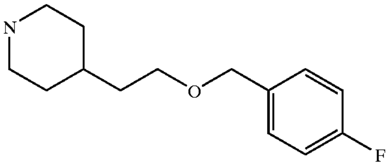 | 521 |
| 501 | 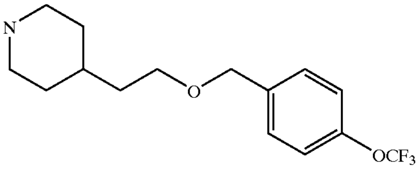 | 571 |
| 502 | 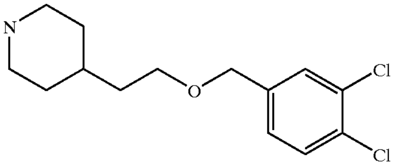 | 571 |

-continued
| | | |
|---|---|---|
| 503 | 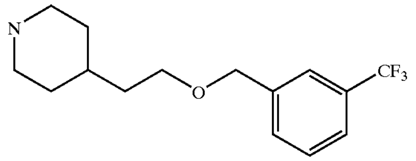 | 571 |
| 504 | 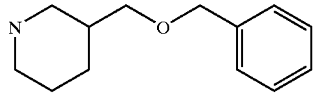 | 489.2059 |
| 505 | 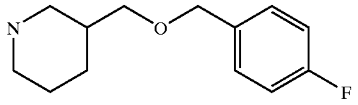 | 507.1987 |
| 506 | 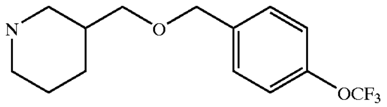 | 557 |
| 507 | 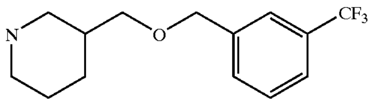 | 557 |
| 508 | 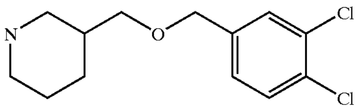 | 557 |
| 509 | 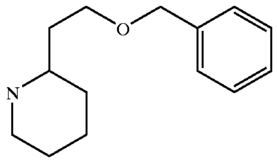 | 503.2226 |
| 510 | 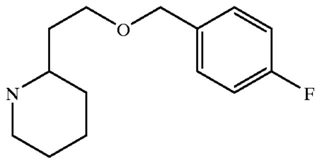 | 521.2122 |
| 511 | 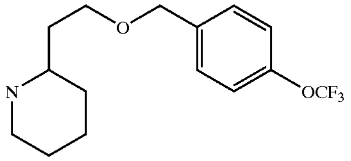 | 571.2056 |
| 512 | 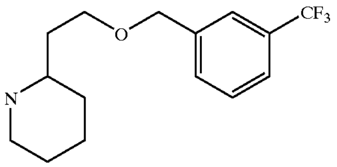 | 571.2054 |
| 513 | 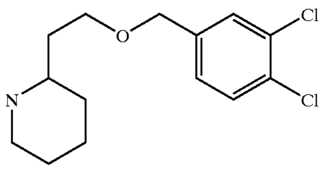 | 571.1464 |

-continued
| | | |
|---|---|---|
| 514 | 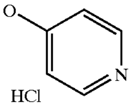 | 379.0964 |
| 515 | 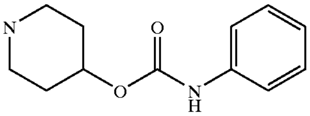 | 504.1831 |
| 516 | 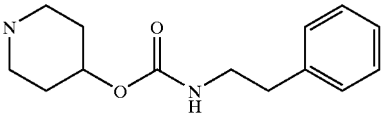 | 532.2105 |
| 517 | 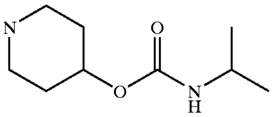 | 470.1935 |
| 518 | 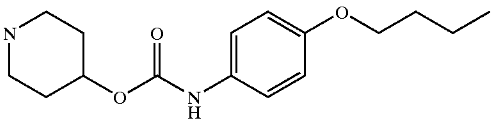 | 576.2355 |
| 519 | 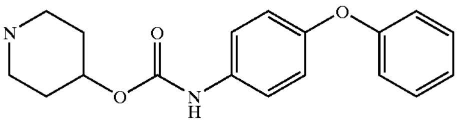 | 596.2033 |
| 520 | 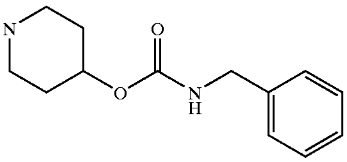 | 518.1945 |
| 521 | 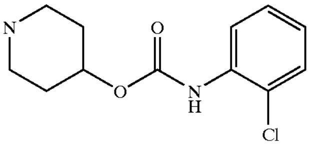 | 538.1372 |
| 522 | 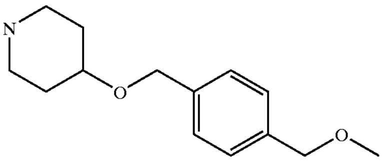 | 519 |
| 523 | 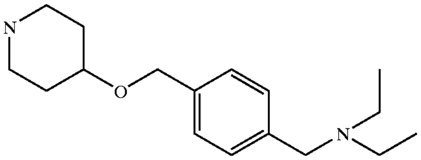 | 560 |
| 524 | 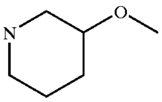 | 399 |

-continued
| | | |
|---|---|---|
| 525 | 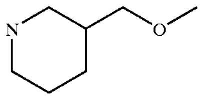 | 413 |
| 526 | 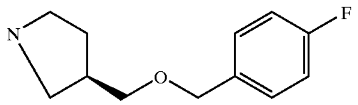 | 493 |
| 527 | 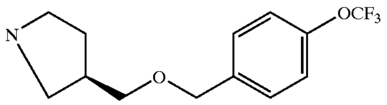 | 581 |
| 528 | 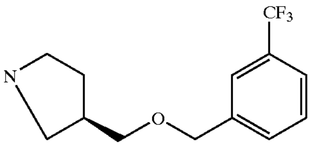 | 343.1742 |
| 529 | 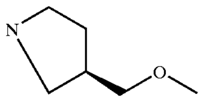 | 399.1597 |
| 530 | 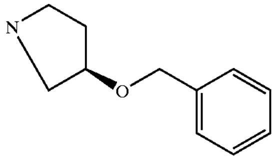 | 483 |
| 531 | 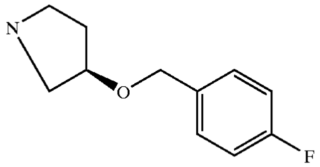 | 501 |
| 532 | 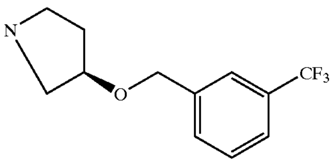 | 551 |
| 533 | 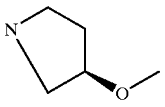 | 407 |
| 534 | 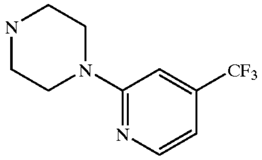 | 515 |

-continued
| | | |
|---|---|---|
| 535 | 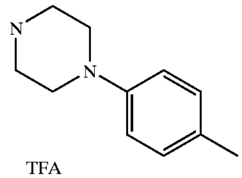 TFA | 460 |
| 536 | 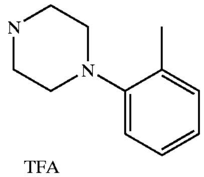 TFA | 460 |
| 537 | 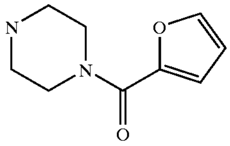 | 464 |
| 538 | 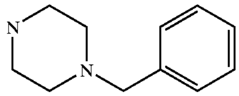 | 460 |
| 539 | 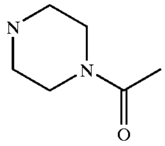 | 412 |
| 540 | 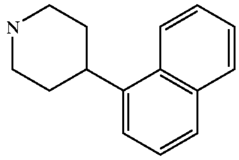 | 495.4984 |
| 541 | 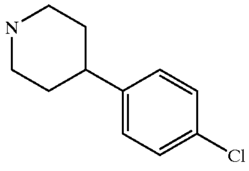 | 479.1416 |
| 542 | 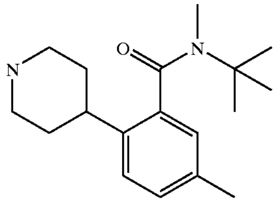 | 572.2800 |

-continued
| | | |
|---|---|---|
| 543 | 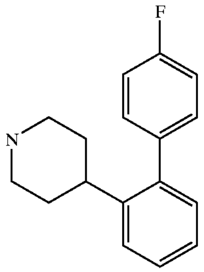 | 539.2017 |
| 544 | 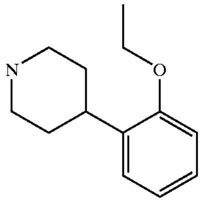 | 489.2049 |
| 545 | 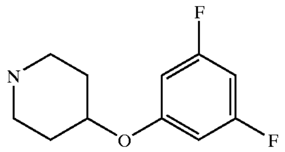 | 497 |
| 546 | 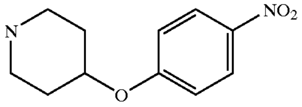 | 506 |
| 547 | 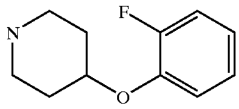 | 479 |
| 548 | 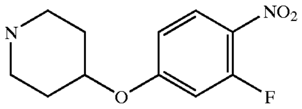 | 524 |
| 549 | 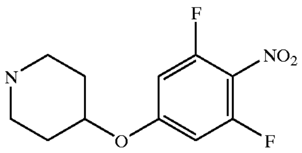 | 542 |
| 550 | 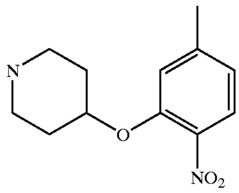 | 520 |
| 551 | 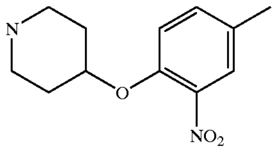 | 520 |

-continued
| | | |
|---|---|---|
| 552 | 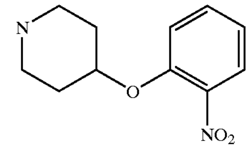 | 506 |
| 553 | 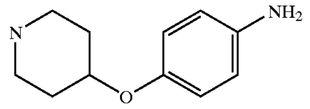 | 476 |
| 554 | 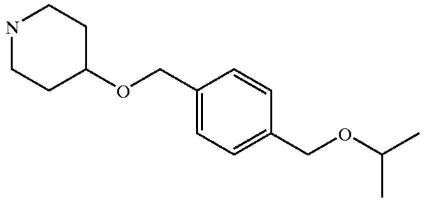 | 547.2525 |
| 555 | 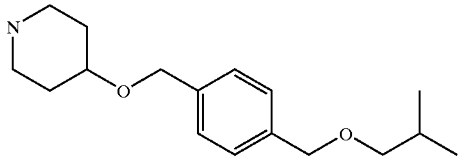 | 561.2692 |
| 556 | 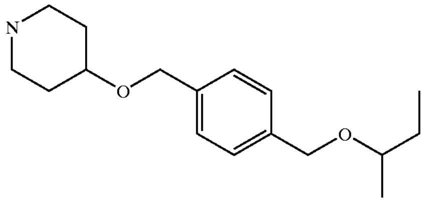 | 561.2679 |
| 557 | 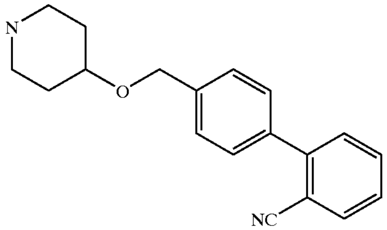 | 576.2184 |
| 558 | 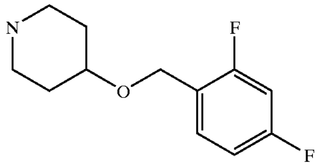 | 511.1755 |
| 559 | 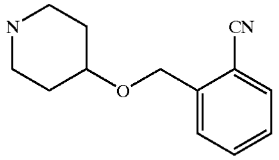 | 500.1830 |

-continued
| | | |
|---|---|---|
| 560 | 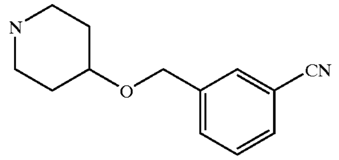 | 500.1888 |
| 561 | 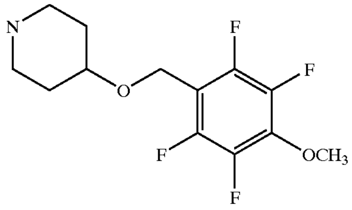 | 577.1650 |
| 562 | 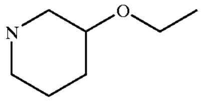 | 413.1750 |
| 563 | 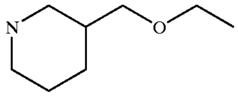 | 427.1903 |
| 564 | 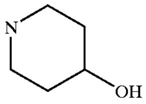 | 385.1457 |
| 565 | 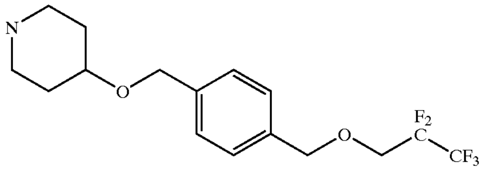 | 637.2067 |
| 566 | 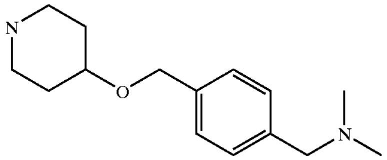 | 532.2448 |
| 567 | 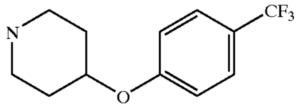 | 529.1631 |
| 568 | 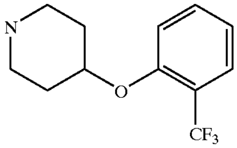 | 529.1603 |
| 569 | 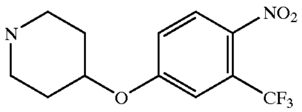 | 574.1478 |

-continued
| | | |
|---|---|---|
| 570 | 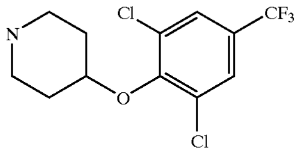 | 597.0849 |
| 571 | 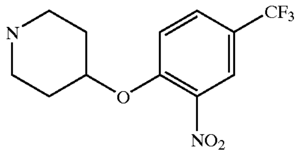 | 574.1473 |
| 572 | 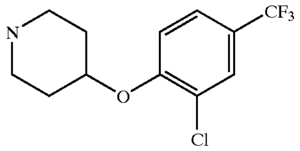 | 513.1228 |
| 573 | 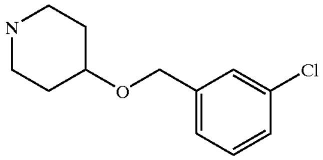 | 509.1536 |
| 574 | 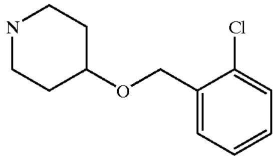 | 509.1529 |
| 575 | 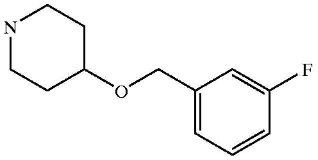 | 493.1803 |
| 576 | 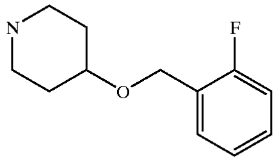 | 493.1838 |
| 577 | 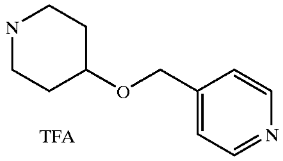 TFA | 476.1847 |
| 578 | 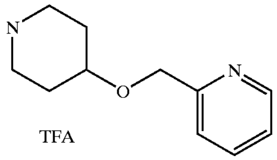 TFA | 476.1865 |

-continued
| | | |
|---|---|---|
| 579 | 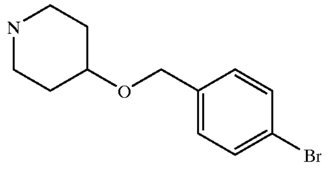 | 553.1057 |
| 580 | 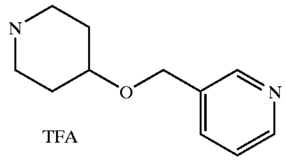 TFA | 476.1879 |
| 581 | 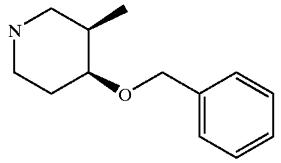 | 489.2076 |
| 582 | 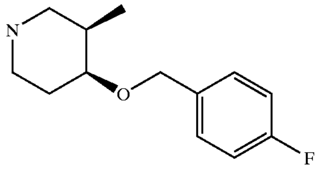 | 507.2016 |
| 583 | 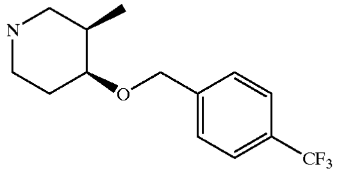 | |
| 584 | 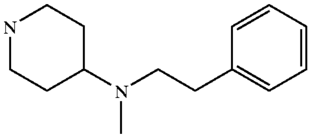 | |
| 585 | 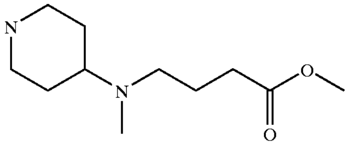 | 415.1559 |
| 586 | 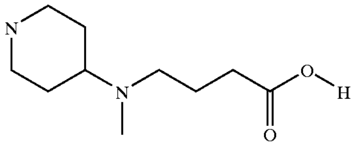 | 401.1399 |
| 587 | 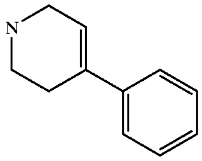 | 443 |

-continued
588 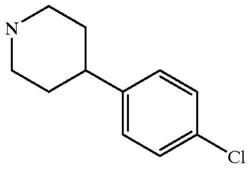 477
589 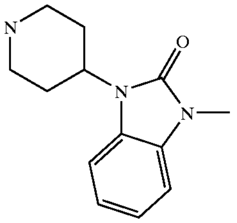 515
590 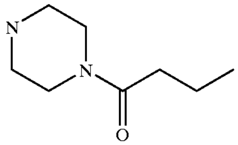 438
591 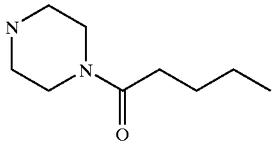 452
592 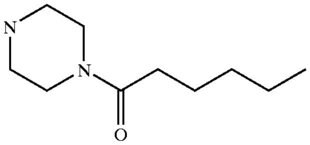 466
593 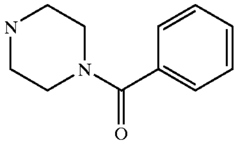 472
594 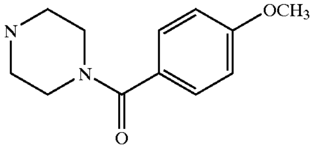 502
595 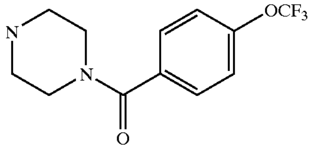 556
596 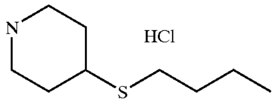 457

-continued
597 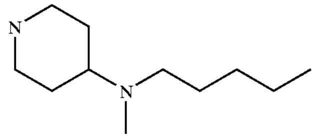
598 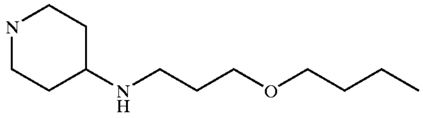 415.1911
599 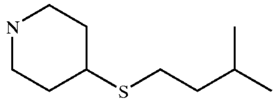 471
600 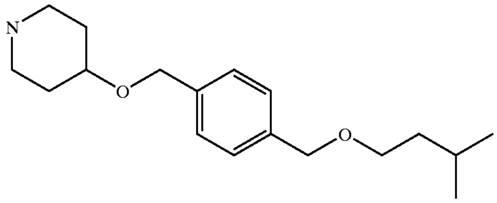 575.2777
601 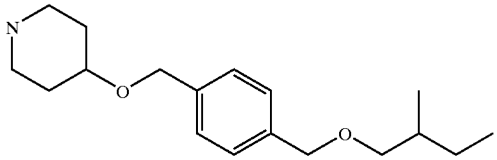 575
602 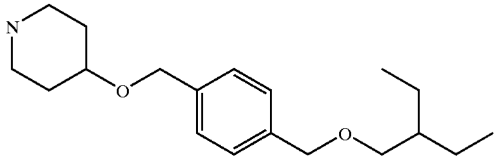 589.2947
603 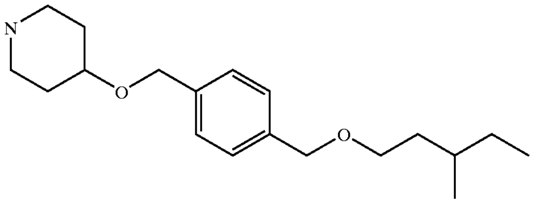 589.2914
604 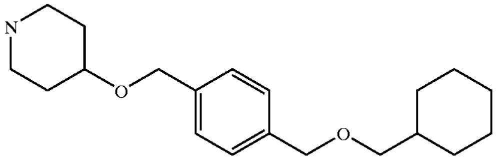 601.2936
605 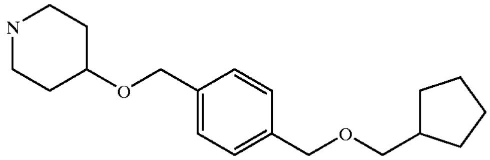 587.2808

-continued
| | | |
|---|---|---|
| 606 | 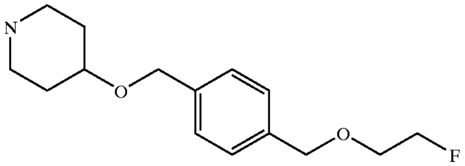 | 551.2225 |
| 607 | 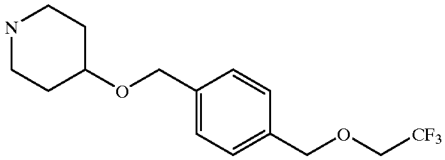 | 587.2048 |
| 608 | 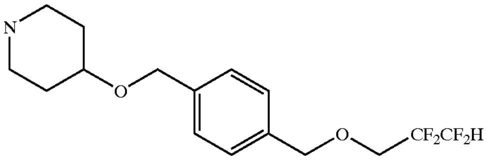 | 619.2098 |
| 609 | 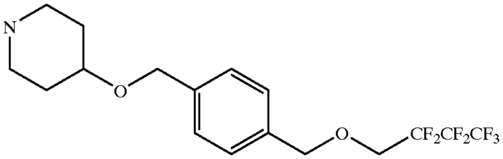 | 687.1978 |
| 610 | 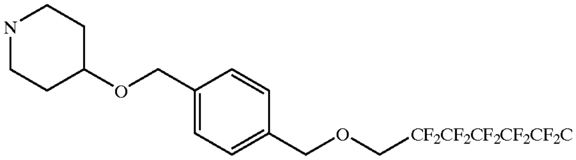 | 857.2070 |
| 611 | 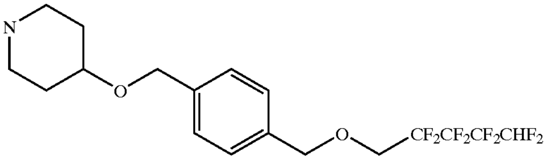 | 719.2024 |
| 612 | 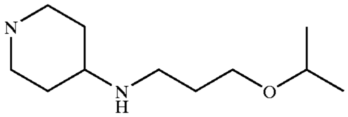 | 401.1746 |
| 613 | 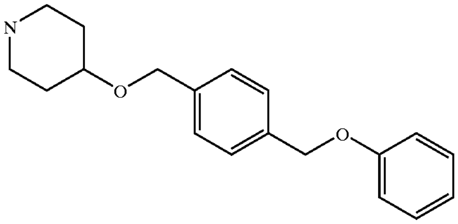 | 581.2323 |
| 614 | 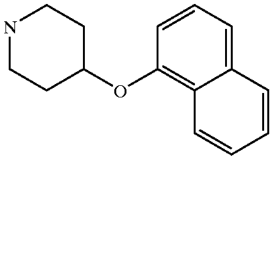 | 511.1900 |

-continued
| | | |
|---|---|---|
| 615 | 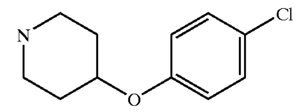 | 495.1368 |
| 616 | 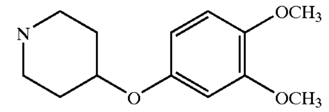 | 521.1980 |
| 617 | 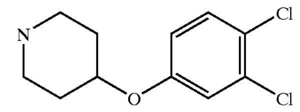 | 529.0962 |
| 618 | 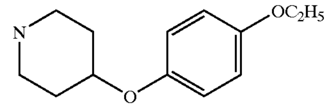 | 505.2031 |
| 619 | 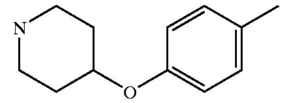 | 475.1898 |
| 620 | 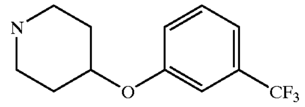 | 529.1604 |
| 621 | 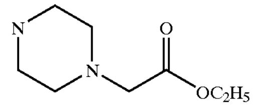 | 456.1761 |
| 622 | 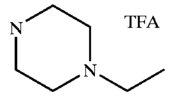 | 398.1751 |
| 623 | 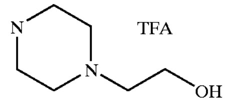 | 414.1690 |
| 624 | 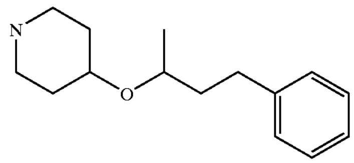 | 434.1651 |
| 629 | 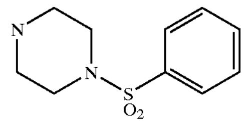 | 510 |
| 634 | 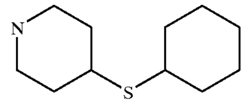 | 483.1992 |

-continued
| | | |
|---|---|---|
| 635 | 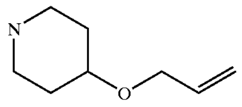 | 425 |
| 636 | 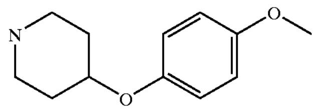 | 507.1910 |
| 637 | 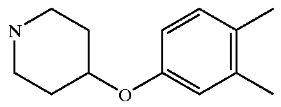 | 489.2064 |
| 638 | 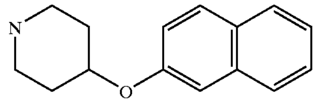 | 511.1910 |
| 639 | 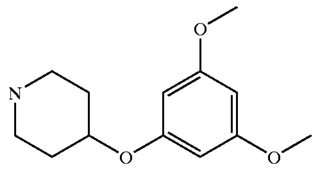 | 521.1962 |
| 640 | 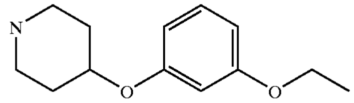 | 505.2006 |
| 641 | 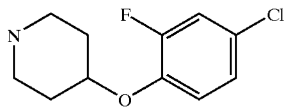 | 513.1277 |
| 642 | 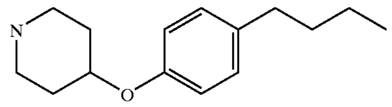 | 517.2410 |
| 643 | 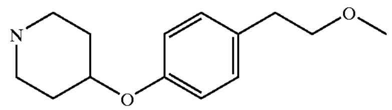 | 519.2190 |
| 644 | 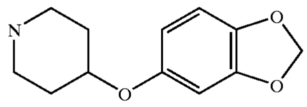 | 505 |
| 645 | 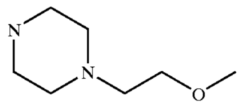 TFA | 428.1821 |

-continued
| | | |
|---|---|---|
| 646 | 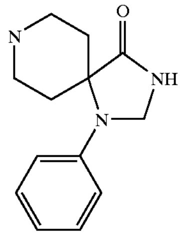 | 428 |
| 647 | 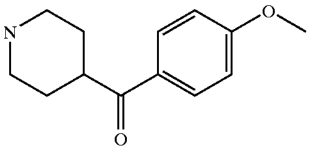 | 503 |
| 648 | 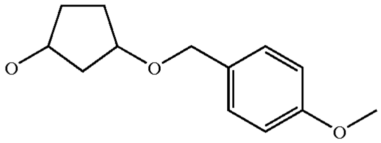 | 506.1830 |
| 649 | 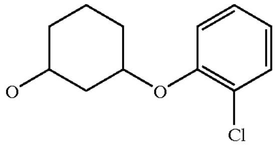 | 524 |
| 650 | 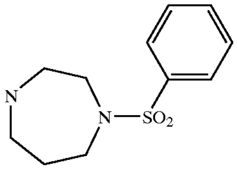 | 524.1531 |
| 651 | 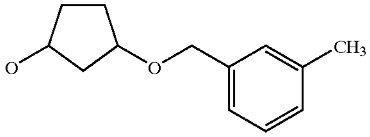<br>Isomer 2 (minor) | 490.1912 |
| 652 | 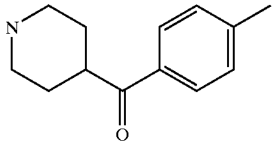 | 487 |
| 653 | 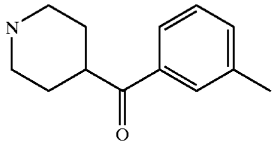 | 487 |
| 654 | 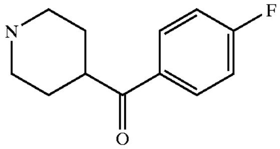 | 491 |

-continued
| | | |
|---|---|---|
| 655 | 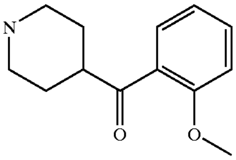 | 503 |
| 656 | 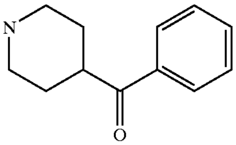 | 473 |
| 658 | 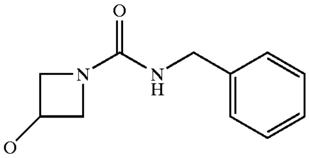 | |
| 659 | 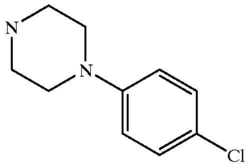 | |
| 665 | 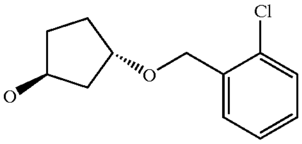 | 510.1353 |
| 666 | 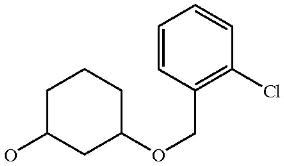 | 541.1815 |
| 667 | 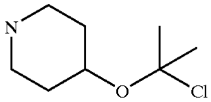 | 475 |
| 668 | 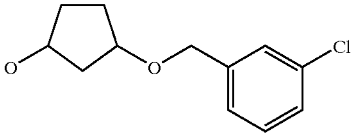<br>Isomer 1 | 510.1366 |
| 669 | 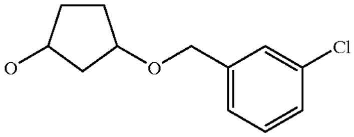<br>Isomer 2 | 510.1358 |
| 670 | 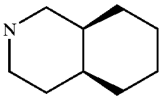 | |

-continued
| | | |
|---|---|---|
| 671 | 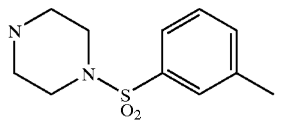 | 524 |
| 672 | 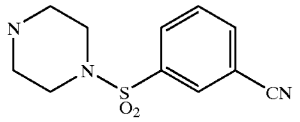 | 535 |
| 673 | 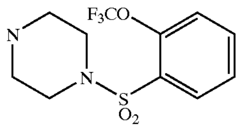 | 594 |
| 674 | 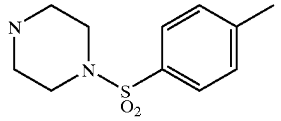 | 524 |
| 675 | 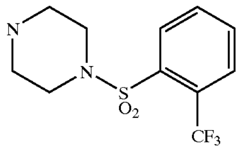 | 578 |
| 676 | 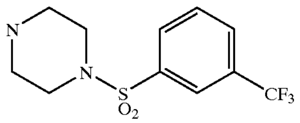 | 578 |
| 677 | 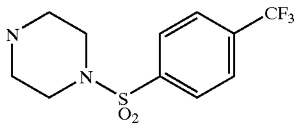 | 578 |
| 678 | 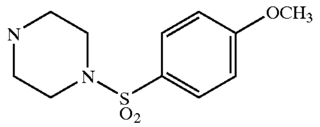 | 540 |
| 679 | 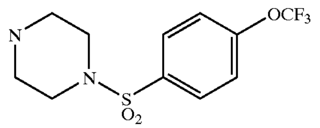 | 594 |
| 680 | 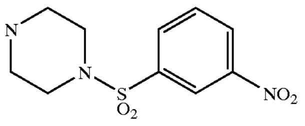 | 555 |
| 681 | 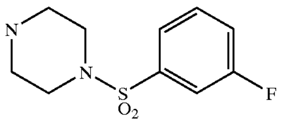 | 528 |

-continued
| | | |
|---|---|---|
| 682 | 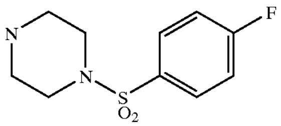 | 528 |
| 683 | 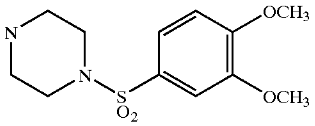 | 570 |
| 684 | 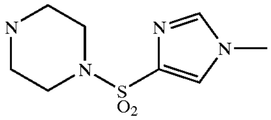 | 514 |
| 685 | 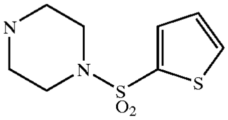 | 516 |
| 686 | 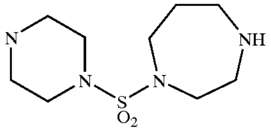 TFA | 384.1593 |
| 688 | 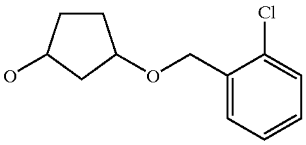 | 527.1658 (M + NH4) |
| 690 | 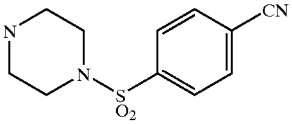 | 535 |
| 691 | 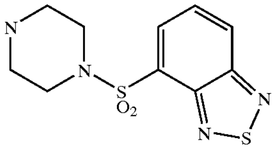 | 568 |
| 692 | 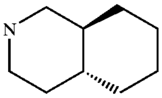 | 423.1946 |
| 693 | 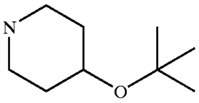 | 441.2080 |
| 694 | 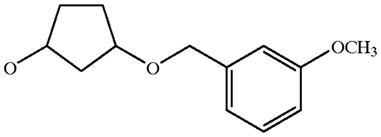 | 506.1857 |

-continued
| | | |
|---|---|---|
| 695 | 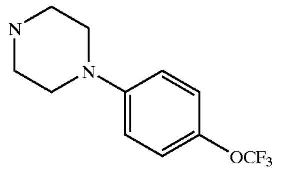 | 530.1565 |
| 696 | 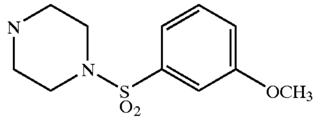 | 540 |
| 697 | 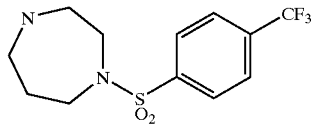 | 592.1401 |
| 698 | 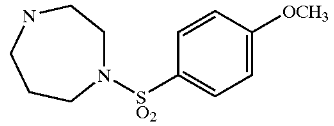 | 554.1659 |
| 699 | 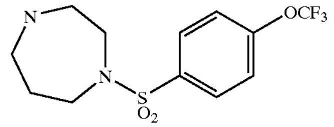 | 608.1355 |
| 706 | 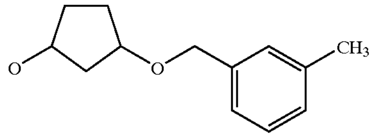 Isomer 1 (major) | 490.1929 |
| 707 | 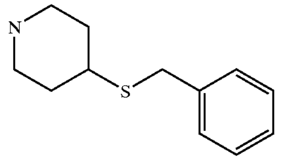 | 491 |
| 708 | 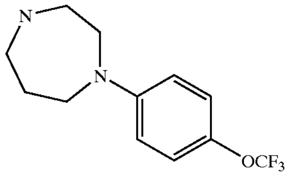 | |
| 714 | 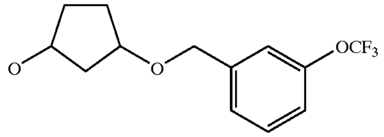 | 560.1568 |
| 720 | 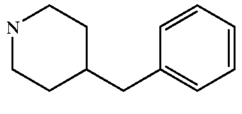 | 459.1987 |

-continued
| | | |
|---|---|---|
| 721 | 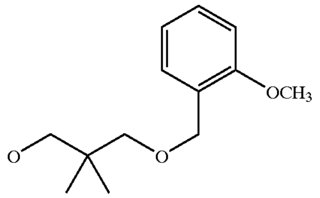 | 508.2019 |
| 722 | 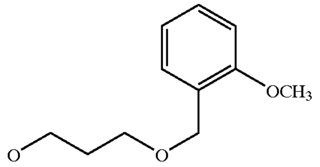 | 480.1700 |
| 723 | 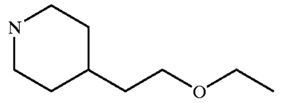 HCl | 441.2053 |
| 724 | 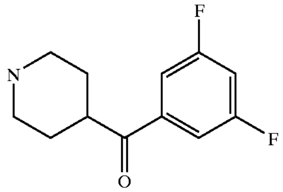 | 509 |
| 725 | 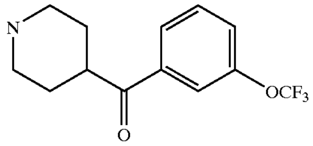 | 557 |
| 726 | 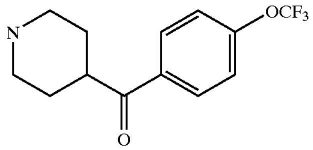 | 557 |
| 727 | 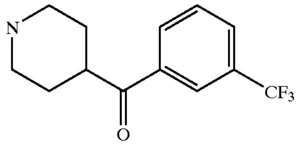 | 541 |
| 728 | 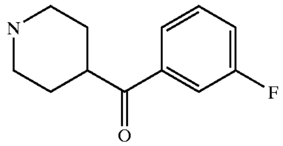 | 491 |
| 729 | 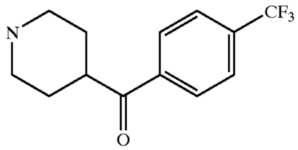 | 541 |

-continued
| | | |
|---|---|---|
| 730 | 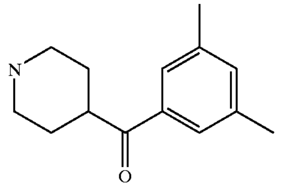 | 501 |
| 731 | 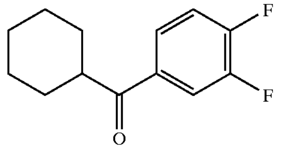 | 509 |
| 732 | 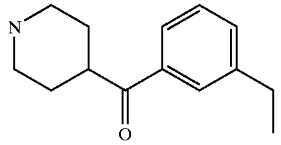 | 501 |
| 733 | 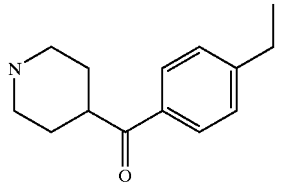 | 501 |
| 734 | 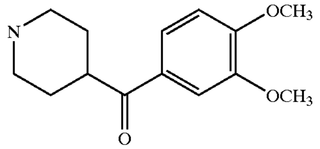 | 517 |
| 735 | 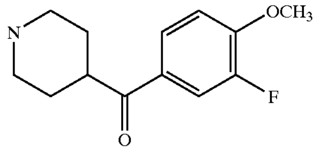 | 521 |
| 736 | 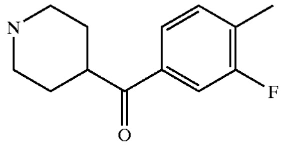 | 505 |
| 737 | 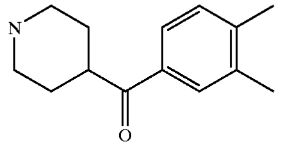 | 501 |
| 738 | 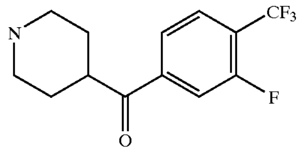 | 559 |

-continued
740
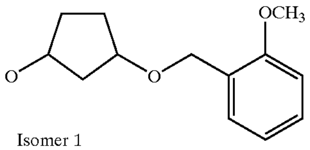
Isomer 1
741
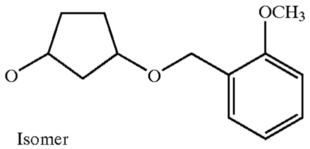
Isomer
752 572
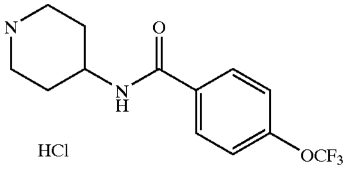
HCl
755 467
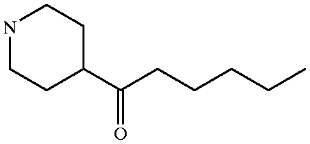
756 453
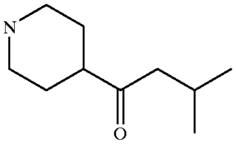
757 453
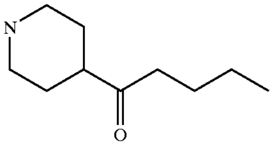
758 451
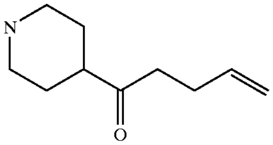
759 451
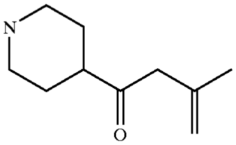
760 488
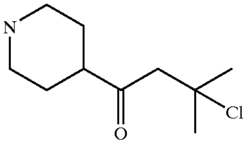
761 451
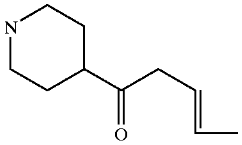

-continued
| | | |
|---|---|---|
| 781 | 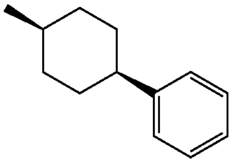 | 444 |
| 782 | 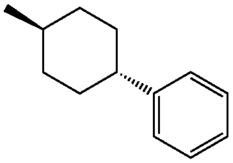 | 444 |
| 784 | 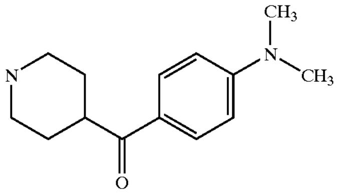 | |
| 786 | 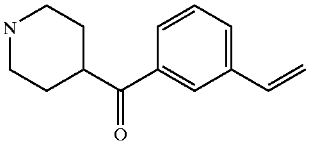 | 499 |
| 787 | 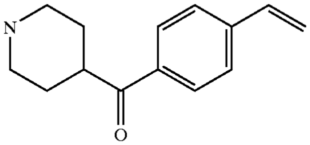 | 499 |
| 788 | 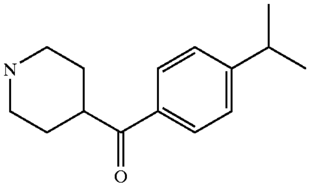 | 515 |
| 789 | 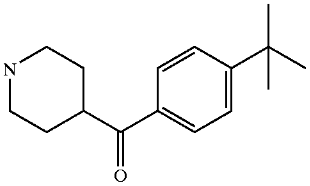 | 529 |
| 790 | 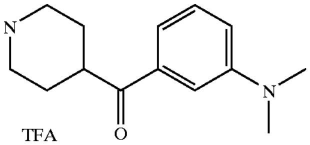 TFA | 516 |
| 791 | 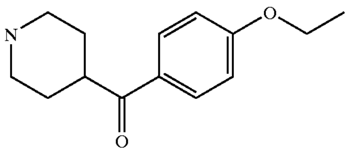 | 517 |

-continued
793
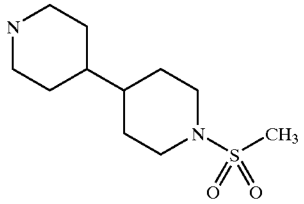
794
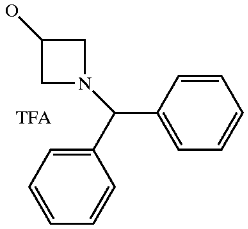
796 517
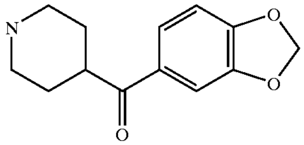
797
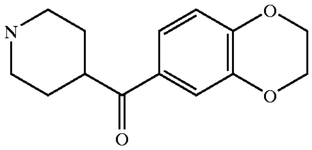
798
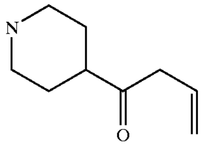
799
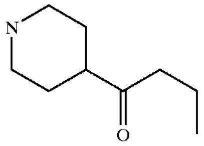
802
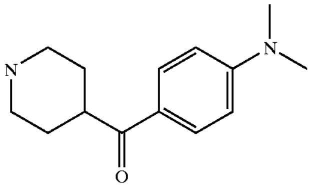
807
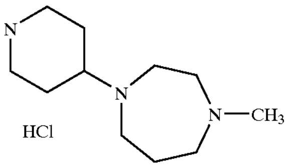

-continued
811
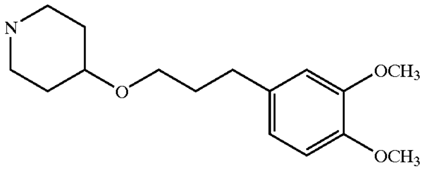
815
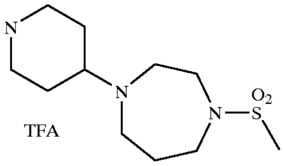
TFA
816
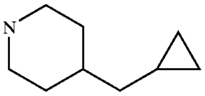
822
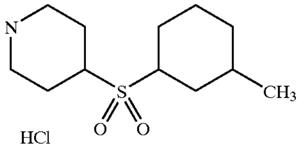
HCl
823
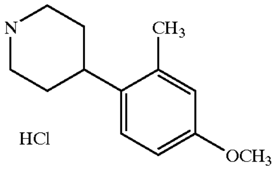
HCl
825
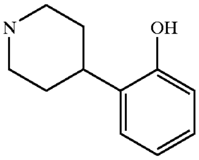
826
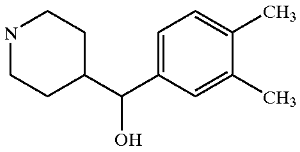
827
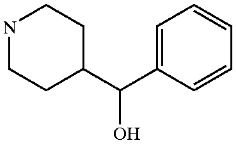
828
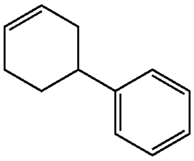

-continued
829
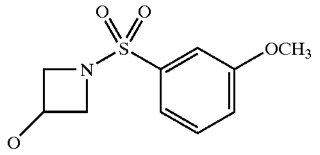
830
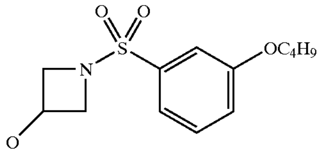
831
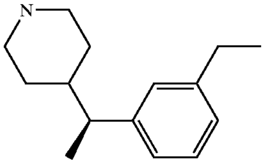
832
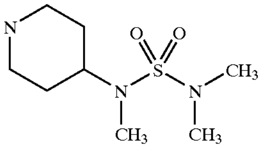
833
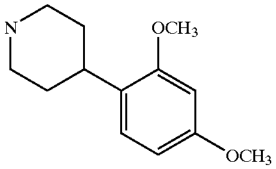
834
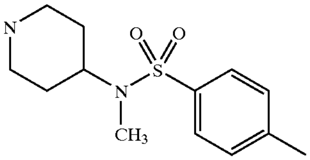
835
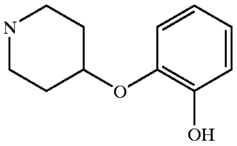
836
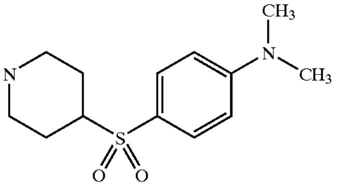
838
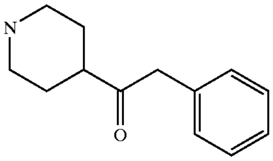

-continued
841
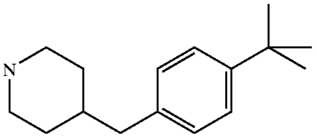
842
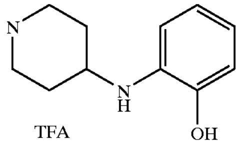
844
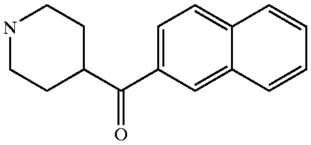
845
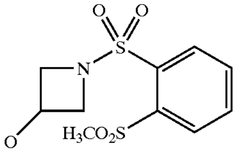
846
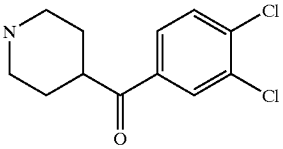
847
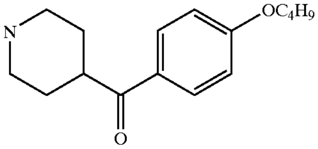
848
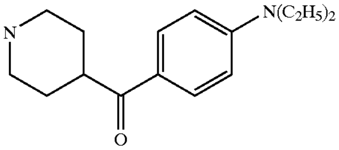
850
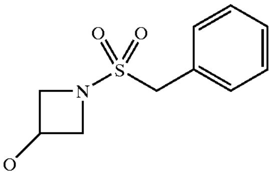
851
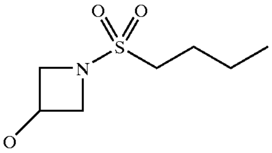

-continued
852
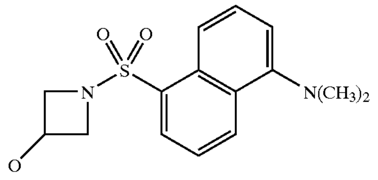
853
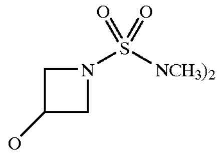
854
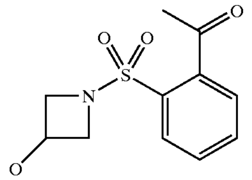
856
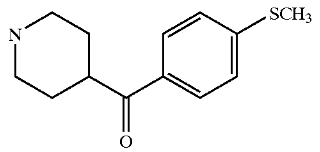
857
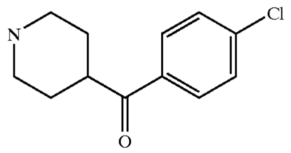
858
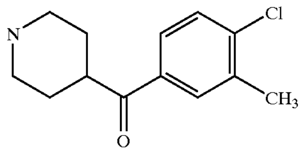
859
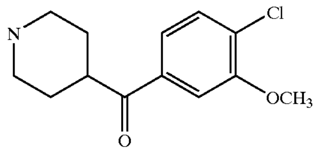
860
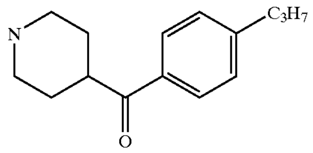
861
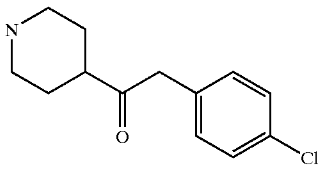

-continued
862
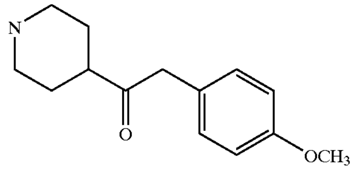
863
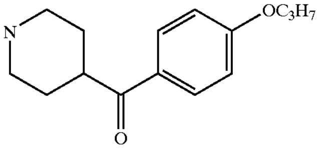
864
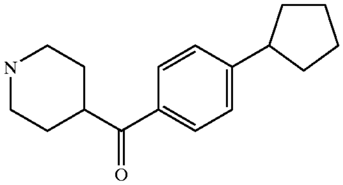
867
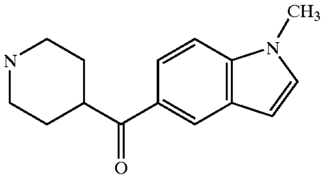
868
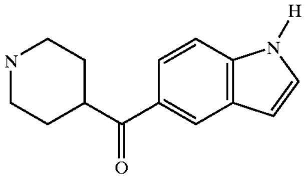
869
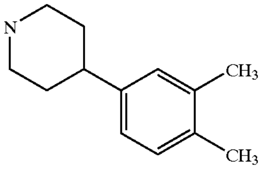
872
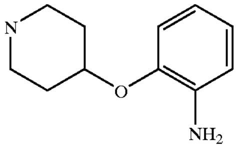
873
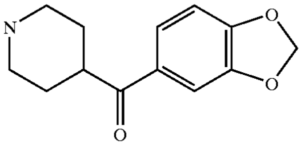
877
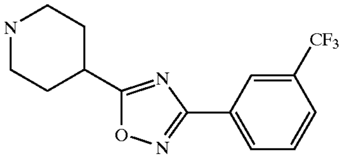

-continued
878
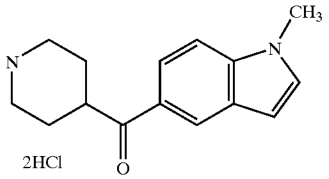
2HCl
881
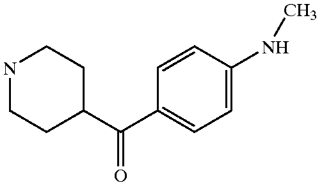
882
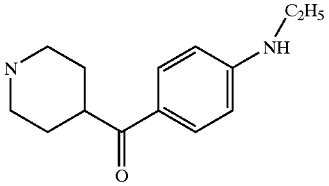
883
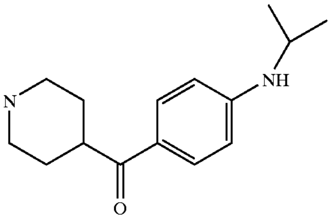
884
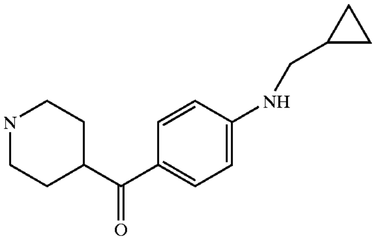
885
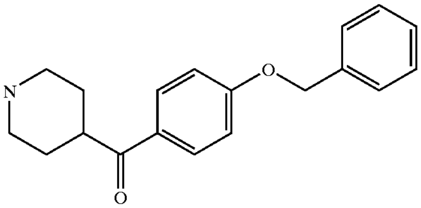
886
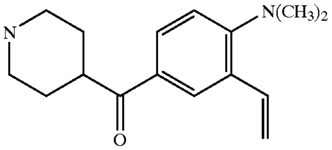
887
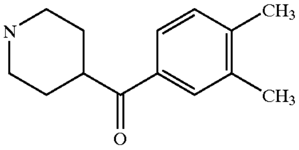

-continued
888 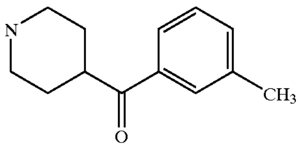
889 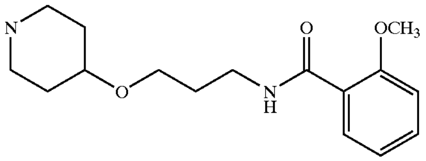
890 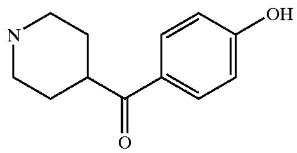
891 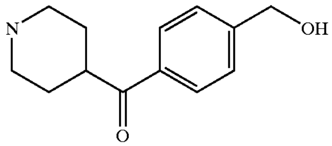
892 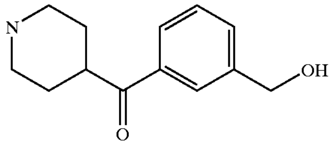
893 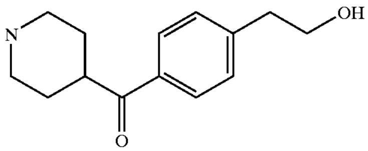
894 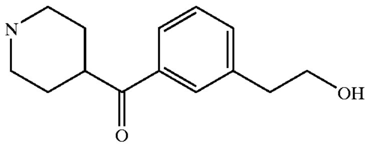
895 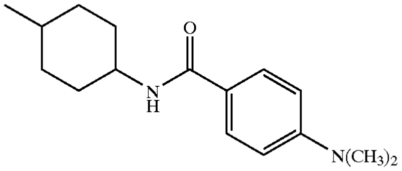
899 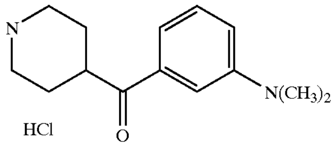
HCl -continued
901
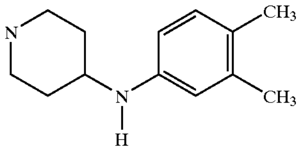
902
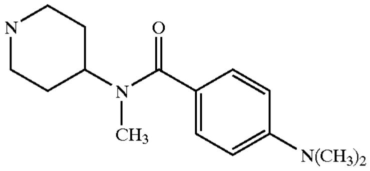
905
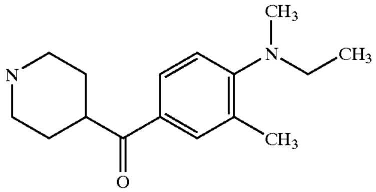
906
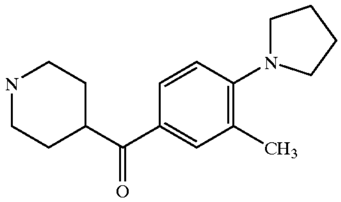
909
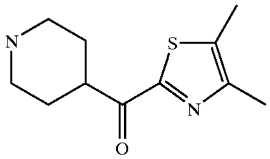
910
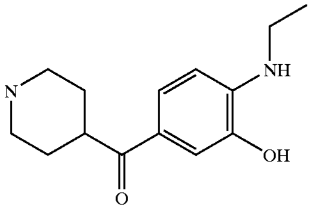
911
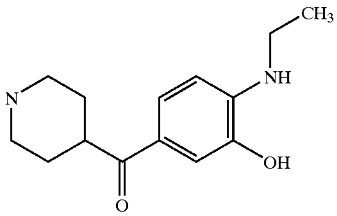
912
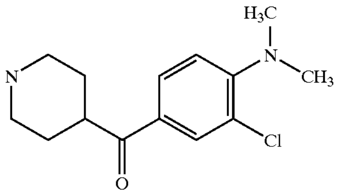

-continued
913
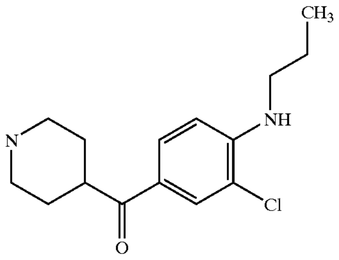
914
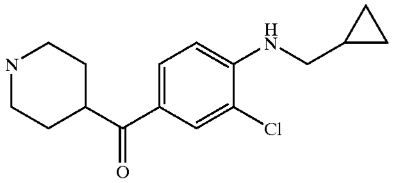
915
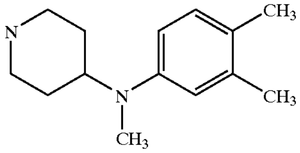
916
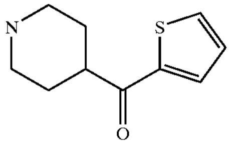
920
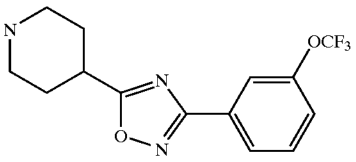
921
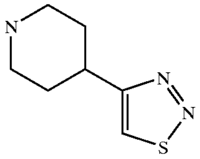
922
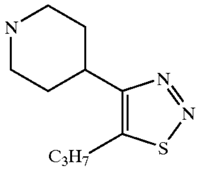
924
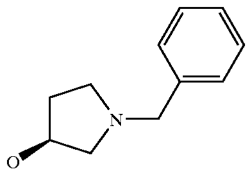

-continued
| | |
|---|---|
| 926 | 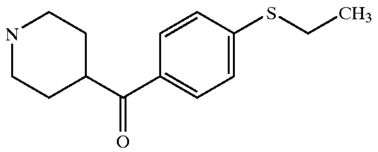 |
| 931 | 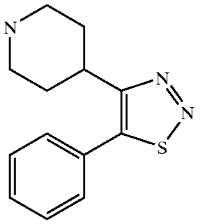 |
| 932 | 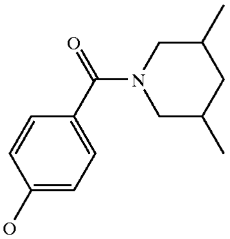 |
| 939 | 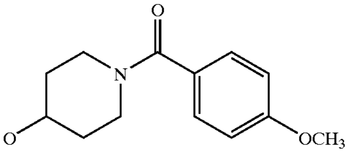 |
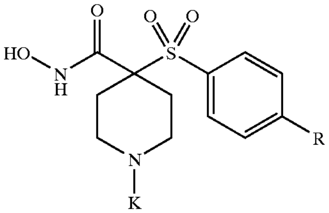
| Example | R | K | MS |
|---|---|---|---|
| 940 | 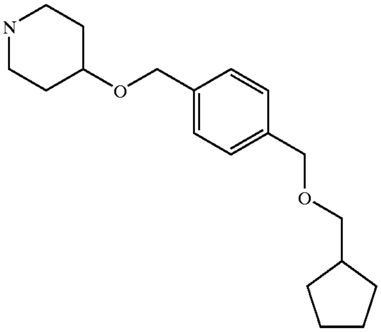 | 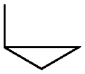 HCl | |

-continued

941

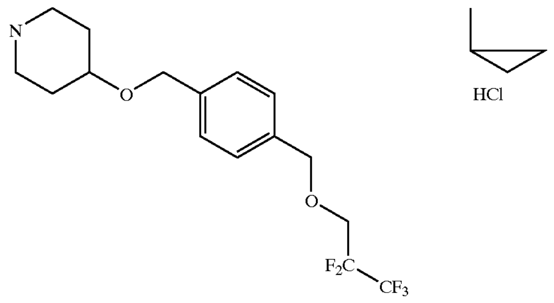

942

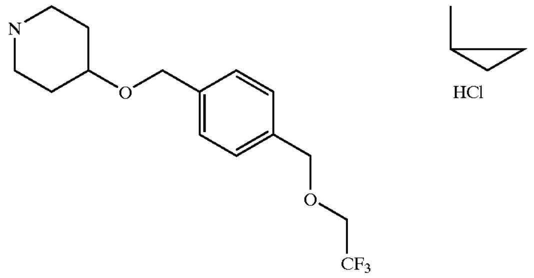

EXAMPLE 943

In Vitro Metalloprotease Inhibition

The compounds prepared in the manner described in the Examples above were assayed for activity by an in vitro assay. Following the procedures of Knight et al., *FEBS Lett.* 296(3):263 (1992). Briefly, 4-aminophenylmercuric acetate (APMA) or trypsin-activated MMPs were incubated with various concentrations of the inhibitor compound at room temperature for 5 minutes.

More specifically, recombinant human MMP-13, MMP-1, MMP-2 and MMP-9 enzymes were prepared in laboratories of the assignee following usual laboratory procedures. MMP-13-from a full length cDNA clone was expressed as a proenzyme using a baculovirus as discussed in V. A. Luckow, Insect Cell Expression Technology, pages 183–218, in *Protein Engineering: Principles and Practice*, J. L. Cleland et al eds., Wiley-Liss, Inc., (1996). See, also, Luckow et al., *J. Virol.*, 67:4566–4579 (1993); O'Reilly et al., *Baculovirus Expression Vectors: A Laboratory Manual*, W.H. Freeman and Company, New York, (1992); and King et al., *The Baculovirus Expression System: A Laboratory Guide*, Chapman & Hall, London (1992) for further details on use of baculovirus expression systems. The expressed enzyme was purified first over a heparin agarose column and then over a chelating zinc chloride column. The proenzyme was activated by APMA for use in the assay.

MMP-1 expressed in transfected HT-1080 cells was provided by Dr. Harold Welgus of Washington University, St. Louis, Mo. The enzyme was also activated using APMA and was then purified over a hydroxamic acid column. Dr. Welgus also provided transfected HT-1080 cells that expressed MMP-9. Transfected cells that expressed MMP-2 were provided by Dr. Gregory Goldberg, also of Washington University. Studies carried out using MMP-2 in the presence of 0.02% 2-mercaptoethanol are shown in the table below with an asterisk. Studies with MMP-7 were carried out at pH 7.5 in the presence of 0.02% 2-mercaptoethanol using conditions otherwise similar to those used for the other enzymes. The enzyme was obtaind from a hMMP-7-expressing *E. coli* clone that was a gift of Dr. Steven Shapiro of Washington University, St. Louis, Mo. Further specifics for preparation and use of these enzymes can be found in the scientific literature describing these enzymes. See, for example, *Enzyme Nomenclature*, Academic Press, San Diego, Calif. (1992) and the citations therein, and Frije et al., *J. Biol. Chem.*, 26(24): 16766–16773 (1994). The enzyme substrate is a methoxycoumarin-containing polypeptide having the following sequence:

MCA-ProLeuGlyLeuDpaAlaArgNH$_2$, wherein MCA is methoxycoumarin and Dpa is 3-(2,4-dinitrophenyl)-L-2,3-diaminopropionyl alanine. This substrate is commercially available from Baychem as product M-1895.

The buffer used for assays contained 100 mM Tris-HCl, 100 mM NaCl, 10 mM $CaCl_2$ and 0.05 percent polyethyleneglycol (23) lauryl ether at a pH value of 7.5. Assays were carried out at room temperature, and dimethyl sulfoxide (DMSO) at a final concentration of 1 percent was used to dissolve inhibitor compound.

The assayed inhibitor compound in DMSO/buffer solution was compared to an equal amount of DMSO/buffer with no inhibitor as control using Microfluor White Plates (Dynatech). The inhibitor or control solution was maintained in the plate for 10 minutes and the substrate was added to provide a final concentration of 4 $\mu$M.

In the absence of inhibitor activity, a fluorogenic peptide was cleaved at the gly-leu peptide bond, separating the highly fluorogenic peptide from a 2,4-dinitrophenyl quencher, resulting in an increase of fluorescence intensity (excitation at 328 nm/emission at 415 nm). Inhibition was measured as a reduction in fluorescent intensity as a function of inhibitor concentration, using a Perkin Elmer L550 plate reader. The $IC_{50}$ values were calculated from those values. The results are set forth in the Inhibition Table A, below, reported in terms of $IC_{50}$ to three significant figures, where appropriate.

-continued

Inhibition Table A (nM)

| Example Number | MMP-13 $IC_{50}$ (nM) | MMP-2 $IC_{50}$ (nM) | MMP-1 $IC_{50}$ (nM) |
|---|---|---|---|
| 1 | 22.7 | 8.5 | >10,000 |
| 2 | 5,500 | 6,000 | >10,000 |
| 8 | 15.6 | 2,900 | >10,000 |
| 9 | 15.6 | 2,900 | >10,000 |
| 10 | 18.1 | >10,000 | >10,000 |
| 11 | 18.0 | 4,500 | >10,000 |
| 12 | 50.0 | 2,500 | >10,000 |
| 13 | 12.2 | 5,600 | >10,000 |
| 14 | 40.0 | 6,000 | >10,000 |
| 15 | 37.0 | 2,700 | >10,000 |
| 16 | 6.70 | 1,400 | >10,000 |
| 17 | 31.6 | 3,500 | >10,000 |
| 18 | 45.0 | >10,000 | >10,000 |
| 19 | 28.0 | 5,500 | >10,000 |
| 20 | 42.5 | 4,800 | >10,000 |
| 21 | 70.0 | 7,000 | >10,000 |
| 22 | >10,000 | >10,000 | >10,000 |
| 23 | 90.0 | 10,000 | >10,000 |
| 24 | 23.5 | 4,500 | >10,000 |
| 25 | 6.00 | 1,600 | >10,000 |
| 26 | 10.7 | 3,600 | >10,000 |
| 27 | 6.40 | 1,600 | >10,000 |
| 28 | 6.70 | 700 | >10,000 |
| 29 | 4.00 | 445 | >10,000 |
| 32 | 10.0 | 800 | >10,000 |
| 33 | 20.0 | 4,500 | >10,000 |
| 34 | 18.1 | >10,000 | >10,000 |
| 35 | 30.0 | 9,000 | >10,000 |
| 36 | 15.8 | 2,100 | >10,000 |
| 37 | 30.0 | 1,750 | >10,000 |
| 38 | 67.4 | 6,000 | 67.4 |
| 39 | 19.3 | 3,700 | >10,000 |
| 40 | 26.8 | 900 | >10,000 |
| 41 | 70.0 | 5,400 | >10,000 |
| 42 | 82.5 | >10,000 | >10,000 |
| 43 | 17.9 | 5,000 | >10,000 |
| 44 | 19.0 | 1,050 | >10,000 |
| 45 | 360 | 5,000 | >10,000 |
| 46 | 80.0 | 5,700 | >10,000 |
| 47 | 11.4 | 6,000 | >10,000 |
| 48 | 27.0 | 3,200 | >10,000 |
| 49 | 20.0 | 6,500 | >10,000 |
| 51 | 370 | 7,000 | >10,000 |
| 52 | 90.0 | 1,900 | >10,000 |
| 53 | 28.9 | 1,400 | >10,000 |
| 54 | 40.0 | 5,700 | >10,000 |
| 55 | 10.0 | >10,000 | >10,000 |
| 56 | 55.0 | 3,500 | >10,000 |
| 57 | 80.0 | 2,700 | >10,000 |
| 58 | 22.0 | 4,000 | >10,000 |
| 59 | 4.00 | 530 | >10,000 |
| 60 | 13.9 | 3,700 | >10,000 |
| 61 | 7.00 | 1,500 | >10,000 |
| 62 | 14.0 | 690 | >10,000 |
| 63 | 20.0 | 2,900 | >10,000 |
| 64 | 19.3 | 770 | >10,000 |
| 65 | 5.00 | 195 | >10,000 |
| 66 | 8.00 | 240 | >10,000 |
| 68 | 13.0 | 1,800 | >10,000 |
| 69 | 18.1 | 3,500 | >10,000 |
| 70 | 10.6 | 700 | >10,000 |
| 71 | 7.70 | 270 | >10,000 |
| 72 | 13.0 | 800 | >10,000 |
| 73 | 15.4 | 2,000 | >10,000 |
| 74 | 9.00 | 80.0 | >10,000 |
| 75 | 11.5 | 500 | >10,000 |
| 76 | 9.00 | 250 | >10,000 |
| 77 | 75.0 | 3,400 | >10,000 |
| 78 | 11.7 | 730 | >10,000 |
| 79 | 20.0 | 2,000 | >10,000 |
| 80 | 4.10 | 562 | >10,000 |
| 81 | 60.0 | 158 | >10,000 |
| 82 | 6.70 | 490 | >10,000 |
| 83 | 2.70 | 21.1 | 3,100 |
| 84 | 28.6 | 1,400 | >10,000 |
| 85 | 130 | 370 | >10,000 |
| 86 | 0.6 | 12.1 | >10,000 |
| 87 | 4.00 | 15.5 | >10,000 |
| 88 | 9.00 | 40.0 | >10,000 |
| 91 | 0.3 | <0.1 | >10,000 |
| 92 | 0.8 | 0.1 | >10,000 |
| 95 | 0.3 | <0.1 | 3,600 |
| 96 | 0.4 | 0.1 | 7,300 |
| 97 | 0.6 | <0.1 | >10,000 |
| 98 | 1.70 | 0.2 | >10,000 |
| 99 | 1.00 | <0.1 | >10,000 |
| 100 | 0.5 | <0.1 | 6,000 |
| 101 | 1.10 | 0.8 | >10,000 |
| 102 | 0.6 | 0.2 | >10,000 |
| 103 | 1.80 | 0.3 | >10,000 |
| 104 | 0.25 | 0.2 | 10,000 |
| 105 | 1.10 | 0.3 | 10,000 |
| 106 | 0.2 | 0.15 | >10,000 |
| 106 | 0.1 | <0.1 | 8,200 |
| 108 | 0.2 | <0.1 | 5,000 |
| 109 | 0.3 | <0.1 | >10,000 |
| 110 | 0.6 | 0.2 | >10,000 |
| 111 | 0.8 | 0.15 | >10,000 |
| 112 | 0.5 | <0.1 | >10,000 |
| 113 | 0.3 | <0.1 | >10,000 |
| 114 | 0.4 | <0.1 | >10,000 |
| 115 | 0.1 | <0.1 | >10,000 |
| 116 | 0.3 | <0.1 | >10,000 |
| 117 | 0.2 | 0.1 | >10,000 |
| 118 | 0.2 | <0.1 | >10,000 |
| 119 | 0.3 | 0.3 | >10,000 |
| 120 | 0.4 | 0.1 | >10,000 |
| 121 | 0.2 | 0.1 | 5,000 |
| 122 | 0.2 | <0.1 | 3,000 |
| 123 | 0.7 | <0.1 | >10,000 |
| 124 | <0.1 | <0.1 | >10,000 |
| 125 | 0.4 | <0.1 | >10,000 |
| 126 | 0.7 | <0.1 | >10,000 |
| 127 | 2.90 | 0.2 | >10,000 |
| 128 | 0.1 | <0.1 | 3,400 |
| 129 | 37.2 | 3.00 | >10,000 |
| 130 | 0.5 | 0.3 | 1,600 |
| 131 | 0.2 | <0.1 | 8,000 |
| 132 | 0.5 | <0.1 | >10,000 |
| 133 | 1.40 | 0.3 | >10,000 |
| 134 | 1.80 | 0.3 | >10,000 |
| 135 | 0.6 | 0.3 | 10,000 |
| 136 | 0.9 | <0.1 | >10,000 |
| 137 | 0.8 | 0.1 | 10,000 |
| 138 | 3.90 | 0.25 | >10,000 |
| 140 | 11.4 | 0.8 | >10,000 |
| 141 | 20.0 | 9.00 | >10,000 |
| 142 | 12.6 | 10.0 | >10,000 |
| 143 | 22.0 | 14.5 | >10,000 |
| 144 | 0.4 | 0.2 | 10,000 |
| 145 | 0.4 | 0.2 | 3,700 |
| 146 | 0.2 | 0.3 | 3,000 |
| 147 | 0.4 | 0.2 | 7,700 |
| 148 | 2.50 | 3.70 | >10,000 |
| 149 | 15.8 | 13.8 | 480 |
| 150 | 175 | 175 | >10,000 |
| 151 | 270 | 290 | >10,000 |
| 152 | 2.00 | 59.0 | >10,000 |
| 153 | 50.0 | 5,000 | >10,000 |
| 154 | 18.0 | 3,700 | >10,000 |
| 155 | 130 | 240 | >10,000 |
| 156 | 2.20 | 0.45 | >10,000 |
| 157 | 0.5 | 0.2 | >10,000 |
| 160 | 300 | 90.0 | >10,000 |
| 161 | 32.6 | 900 | >10,000 |
| 162 | 27.8 | 7,000 | >10,000 |
| 163 | 44.5 | 2,500 | >10,000 |
| 164 | 3.50 | 440 | >10,000 |

-continued

| Inhibition Table A (nM) | | | |
|---|---|---|---|
| Example Number | MMP-13 $IC_{50}$ (nM) | MMP-2 $IC_{50}$ (nM) | MMP-1 $IC_{50}$ (nM) |
| 165 | 3.00 | 48.5 | >10,000 |
| 166 | 32.7 | 240 | >10,000 |
| 168 | 50.0 | 285 | >10,000 |
| 169 | 20.0 | 175 | >10,000 |
| 170 | 2.40 | 200 | >10,000 |
| 171 | 5.40 | 186 | >10,000 |
| 172 | 3.80 | 160 | >10,000 |
| 173 | 6.70 | 330 | 3,400 |
| 174 | 23.5 | 800 | >10,000 |
| 175 | 2.50 | 290 | >10,000 |
| 176 | 4.00 | 250 | >10,000 |
| 177 | 8.80 | 520 | 10,000 |
| 178 | 18.1 | 325 | >10,000 |
| 179 | 20.6 | 170 | >10,000 |
| 180 | 1.10 | 41.8 | >10,000 |
| 181 | 190 | 2,300 | >10,000 |
| 183 | 300 | 1,500 | >10,000 |
| 184 | 480 | 1,500 | >10,000 |
| 185 | 2.20 | 32.6 | >10,000 |
| 187 | 10.0 | 600 | >10,000 |
| 188 | 7.0 | 235 | >10,000 |
| 189 | 7.00 | 235 | >10,000 |
| 190 | 4.70 | 136 | >10,000 |
| 191 | 3.50 | 25.1 | >10,000 |
| 193 | 3.50 | 0.15 | >10,000 |
| 194 | 0.3 | <0.1 | >7,300 |
| 195 | 1.00 | 0.2 | >10,000 |
| 196 | 1.60 | <0.1 | >10,000 |
| 197 | 2.70 | <0.1 | >10,000 |
| 198 | 0.375 | 0.25 | 7,300 |
| 199 | 0.2 | <0.1 | 3,000 |
| 200 | 0.2 | <0.1 | 3,000 |
| 201 | 0.3 | 0.2 | >10,000 |
| 202 | 0.4 | 0.2 | >10,000 |
| 207 | 28.8 | 900 | >10,000 |
| 208 | 110 | 1,000 | >10,000 |
| 209 | 50.0 | 130 | >10,000 |
| 210 | 5.40 | 4.50 | 4,000 |
| 211 | 11.4 | 1,200 | >10,000 |
| 212 | 160 | 240 | >10,000 |
| 213 | 1,400 | 2,700 | >10,000 |
| 214 | 4,900 | 3,500 | >10,000 |
| 224 | <0.1 | <0.1 | 4,500 |
| 225 | 180 | 41.8 | >10,000 |
| 227 | 28.8 | 21.7 | >10,000 |
| 228 | 2,448 | 2,000 | >10,000 |
| 229 | 0.18 | 0.1 | >10,000 |
| 231 | 0.2 | 0.1 | >10,000 |
| 233 | 43.5 | 2,050 | >10,000 |
| 235 | 235 | 5,300 | >10,000 |
| 236 | 9.00 | 400 | >10,000 |
| 237 | 13.0 | 1,900 | >10,000 |
| 238 | 80.0 | 10,000 | >10,000 |
| 239 | 9.00 | 8,300 | >10,000 |
| 240 | 76.9 | 10,000 | >10,000 |
| 241 | 4.80 | >10,000 | >10,000 |
| 242 | 42.5 | 1,500 | >10,000 |
| 243 | 11.3 | 420 | >10,000 |
| 244 | 67.4 | 4,400 | >10,000 |
| 245 | 20.0 | 800 | >10,000 |
| 246 | 32.7 | 2,700 | >10,000 |
| 247 | 34.5 | 1,600 | >10,000 |
| 248 | 2.29 | 270 | >10,000 |
| 249 | 13.0 | 235 | >10,000 |
| 251 | <0.1 | <0.1 | 5,840 |
| 252 | <0.1 | <0.1 | 3,933.33 |
| 253 | <0.1, 0.15 | 3,400 | <0.1 |
| 256 | 0.2 | 0.1 | 3,200 |
| 257 | 0.2 | 0.1 | 4,100 |
| 258 | 0.2 | 0.1 | >10,000 |
| 260 | 0.1 | <0.1 | 5,300 |
| 261 | <0.1 | <0.1 | 3,700 |
| 262 | 1.50 | 0.9 | >10,000 |
| 264 | 0.2 | <0.1 | 4,500 |
| 265 | 0.2 | 1.30, <0.1 | >10,000 |
| 266 | 0.1 | <0.1 | 5,500 |
| 267 | 0.2 | 0.15 | 10,000 |
| 268 | <0.1, 0.2 | 4,000 | <0.1 |
| 269 | 0.2 | <0.1 | >10,000 |
| 270 | 1.00 | 1.00 | >10,000 |
| 271 | 0.3 | 0.17 | >10,000 |
| 272 | 0.2 | 0.1 | 3,600 |
| 273 | 0.3 | 0.1 | >10,000 |
| 274 | 160 | >10,000 | >10,000 |
| 275 | 70.0 | >10,000 | >10,000 |
| 276 | 37.3 | >10,000 | >10,000 |
| 277 | 70.0 | >10,000 | >10,000 |
| 278 | 19.3 | >10,000 | >10,000 |
| 279 | 20.0 | 7,300 | >10,000 |
| 280 | 90.0 | >10,000 | >10,000 |
| 281 | 105 | >10,000 | >10,000 |
| 282 | 14.8 | 9,000 | >10,000 |
| 283 | 13.8 | >10,000 | >10,000 |
| 284 | 130 | >10,000 | >10,000 |
| 285 | 19.3 | 9,000 | >10,000 |
| 286 | 60.0 | >10,000 | >10,000 |
| 287 | 150 | >10,000 | >10,000 |
| 288 | 35.0 | >10,000 | >10,000 |
| 289 | 50.0 | >10,000 | >10,000 |
| 290 | 50.0 | >10,000 | >10,000 |
| 292 | 100 | >10,000 | >10,000 |
| 293 | 63.1 | >10,000 | >10,000 |
| 294 | 59.1 | >10,000 | >1,000 |
| 295 | 50.0 | >10,000 | >10,000 |
| 296 | 50.0 | >10,000 | >10,000 |
| 297 | 34.9 | >10,000 | >10,000 |
| 298 | 40.0 | >10,000 | >10,000 |
| 299 | 30.6 | 9,000 | >10,000 |
| 300 | 37.3 | >10,000 | >10,000 |
| 301 | 90.0 | >10,000 | >10,000 |
| 302 | 175 | >10,000 | >10,000 |
| 303 | 115 | >10,000 | >10,000 |
| 304 | 30.6 | 7,000 | >10,000 |
| 305 | 28.6 | >10,000 | >10,000 |
| 306 | 60.0 | >10,000 | >10,000 |
| 307 | 40.0 | >10,000 | >10,000 |
| 308 | 40.0 | 10,000 | >10,000 |
| 309 | 48.5 | >10,000 | >10,000 |
| 310 | 60.0 | 10,000 | >10,000 |
| 311 | 120 | >10,000 | >10,000 |
| 312 | 200 | >10,000 | >10,000 |
| 313 | 77.0 | >10,000 | >10,000 |
| 314 | 65.0 | >10,000 | >10,000 |
| 315 | 420 | >10,000 | >10,000 |
| 316 | 0.4 | 0.2 | >10,000 |
| 317 | 1.40 | 0.4 | >10,000 |
| 318 | 0.3 | 0.1 | >10,000 |
| 319 | 0.5 | 0.2 | >10,000 |
| 320 | 12.1 | 4.00 | >10,000 |
| 321 | 0.5 | 0.3 | >10,000 |
| 322 | 0.3 | 0.3 | >10,000 |
| 323 | 1.30 | 0.4 | >10,000 |
| 324 | 0.7 | 0.4 | >10,000 |
| 325 | 0.9 | 0.2 | >10,000 |
| 326 | 0.6 | 0.45 | >10,000 |
| 327 | 0.9 | 0.3 | >10,000 |
| 328 | 0.35 | 0.4 | >10,000 |
| 329 | 0.9 | 0.4 | >10,000 |
| 330 | 0.5 | 0.7 | >10,000 |
| 331 | 0.7 | 0.2 | >10,000 |
| 332 | 2.10 | 0.4 | >10,000 |
| 333 | 0.8 | 0.2 | >10,000 |
| 334 | 0.7 | 0.3 | >10,000 |
| 335 | 0.9 | 0.15 | >10,000 |
| 336 | 1.00 | <0.1 | >10,000 |

-continued

| Inhibition Table A (nM) | | | |
|---|---|---|---|
| Example Number | MMP-13 $IC_{50}$ (nM) | MMP-2 $IC_{50}$ (nM) | MMP-1 $IC_{50}$ (nM) |
| 337 | 2.70 | 0.2 | >10,000 |
| 338 | 1.90 | 0.2 | >10,000 |
| 339 | 1.00 | 0.3 | >10,000 |
| 340 | 0.3 | <0.1 | >10,000 |
| 341 | 0.6 | 0.2 | >10,000 |
| 342 | 4.00 | 0.3 | >10,000 |
| 343 | 1.70 | 0.8 | >10,000 |
| 344 | 2.90 | 0.65 | >10,000 |
| 346 | 1.20 | 0.2 | >10,000 |
| 347 | 3.00 | 0.7 | >10,000 |
| 348 | 16.5 | 0.8 | >10,000 |
| 349 | 0.2 | <0.1 | 2600 |
| 350 | 0.1 | <0.1 | 6000 |
| 351 | — | — | — |
| 352 | 1.4 | 0.3 | >10,000 |
| 353 | 0.3 | <0.1 | >10,000 |
| 354 | 1.6 | 15.4 | |
| 355 | 0.4 | <0.1 | 7000 |
| 356 | 2.4 | 32.6 | |
| 357 | 0.3 | 0.1 | >10,000 |
| 358 | — | — | — |
| 359 | 34.9 | 12.2 | >10,000 |
| 360 | 10.0 | 5.6 | |
| 361 | 0.5 | <0.1 | 5000 |
| 362 | 2.7 | <0.1 | >10,000 |
| 363 | 0.4 | 0.2 | 8800 |
| 364 | 1.0 | 0.2 | >10,000 |
| 365 | 0.3 | 0.1 | >10,000 |
| 366 | 13.0 | 2.5 | >10,000 |
| 367 | — | — | — |
| 368 | 0.5 | 7.0 | |
| 369 | 3.3 | 5.4 | |
| 370 | | | |
| 371 | 11.1 | 400 | |
| 372 | — | — | — |
| 373 | 3.0 | 80.0 | |
| 374 | 3.3 | 4.0 | >10,000 |
| 375 | 16.9 | 15.6 | >10,000 |
| 376 | 5.5 | 230 | |
| 378 | 1.7 | 0.3 | 200 |
| 379 | 0.3 | 0.1 | >10,000 |
| 380 | — | — | — |
| 381 | — | — | — |
| 382 | 11.4 | 260 | |
| 383 | 3.0 | 700 | >10,000 |
| 384 | — | — | — |
| 385 | — | — | — |
| 386 | 0.4 | 0.2 | 2100 |
| 387 | — | — | — |
| 388 | 50.0 | 430 | |
| 389 | 1.7 | 16.1 | >10,000 |
| 390 | — | — | — |
| 391 | 0.1 | <0.1 | 5400 |
| 392 | 0.2 | 0.1 | >10,000 |
| 393 | 4.5 | 427 | >10,000 |
| 394 | 0.5 | 8.0 | |
| 395 | 0.9 | 0.5 | >10,000 |
| 396 | 4.8 | 330 | >10,000 |
| 397 | 4.4 | 70.0 | >10,000 |
| 398 | 7.0 | 70.0 | >10,000 |
| 399 | 1.2 | 0.3 | >10,000 |
| 400 | 23.5 | 520 | |
| 401 | 16.9 | 195 | >10,000 |
| 402 | 15.8 | 340 | >10,000 |
| 403 | 55.3 | 4.0 | >10,000 |
| 404 | 0.5 | 0.25 | >10,000 |
| 405 | | | |
| 406 | | | |
| 407 | 1.2 | 0.1 | >10,000 |
| 408 | 25.1 | 800 | >10,000 |
| 409 | 22.4 | 275 | >10,000 |
| 410 | 0.6 | 0.25 | >10,000 |
| 411 | 0.2 | <0.1 | >10,000 |
| 412 | 0.4 | 0.2 | 6400 |

-continued

| Inhibition Table A (nM) | | | |
|---|---|---|---|
| Example Number | MMP-13 $IC_{50}$ (nM) | MMP-2 $IC_{50}$ (nM) | MMP-1 $IC_{50}$ (nM) |
| 413 | 1.1 | 0.3 | 8000 |
| 414 | 50.5 | 1500 | >10,000 |
| 415 | 50.4 | 246 | >10,000 |
| 416 | 0.4 | 0.2 | 3000 |
| 417 | 0.7 | 4.5 | >10,000 |
| 418 | 7.0 | 1400 | >10,000 |
| 419 | 4.2 | 400 | >10,000 |
| 420 | — | — | — |
| 421 | — | — | — |
| 422 | — | — | — |
| 423 | — | — | — |
| 424 | 5.5 | 80.0 | >10,000 |
| 425 | 20.0 | 1000 | >10,000 |
| 426 | — | — | — |
| 427 | — | — | — |
| 428 | — | — | — |
| 429 | — | — | — |
| 430 | — | — | — |
| 431 | — | — | — |
| 432 | 13.9 | 100 | >10,000 |
| 433 | 450 | 3500 | >10,000 |
| 434 | 190 | 3700 | >10,000 |
| 435 | 5.9 | 1500 | >10,000 |
| 436 | 1.8 | 330 | >10,000 |
| 437 | 18.1 | 800 | >10,000 |
| 438 | 1.4 | 160 | >10,000 |
| 439 | 1070 | 1600 | >10,000 |
| 440 | 26.8 | 240 | >10,000 |
| 441 | 6.0 | 420 | >10,000 |
| 442 | 10.0 | 211 | >10,000 |
| 443 | 90.0 | 2200 | >10,000 |
| 444 | — | — | — |
| 445 | 90.0 | 1200 | >10,000 |
| 446 | 270 | 7000 | >10,000 |
| 447 | 23.9 | 155 | >10,000 |
| 448 | 2.4 | 540 | >10,000 |
| 449 | — | — | — |
| 450 | — | — | — |
| 451 | 0.3 | 0.1 | 3700 |
| 452 | <0.1 | <0.1 | |
| 453 | 0.4 | 35.0 | >10,000 |
| 454 | 2.1 | 100 | >10,000 |
| 455 | 6.3 | 26.8 | >10,000 |
| 456 | — | — | — |
| 457 | 1800 | 2700 | >10,000 |
| 458 | 210 | 2100 | >10,000 |
| 459 | 136 | 3100 | >10,000 |
| 460 | 4.0 | 200 | >10,000 |
| 461 | 20.0 | 145 | >10,000 |
| 462 | 2.9 | 80.0 | >10,000 |
| 463 | 16.9 | 210 | >10,000 |
| 464 | 120 | 400 | >10,000 |
| 465 | 80 | 370 | >10,000 |
| 466 | 9.4 | 60 | >10,000 |
| 467 | 27.0 | 140 | >10,000 |
| 468 | — | — | — |
| 469 | 0.8 | 12.0 | >10,000 |
| 470 | 140 | 2000 | >10,000 |
| 471 | 2400 | >10,000 | >10,000 |
| 472 | 4.0 | 200 | >10,000 |
| 473 | 160 | 3300 | >10,000 |
| 474 | 12.1 | 300 | >10,000 |
| 475 | 27.1 | 500 | >10,000 |
| 476 | 25.4 | 140 | >10,000 |
| 477 | 11.3 | 160 | >10,000 |
| 478 | 16.4 | 306 | >10,000 |
| 479 | 5.0 | 60.0 | >10,000 |
| 480 | 18.6 | 155 | >10,000 |
| 481 | 50.0 | 1400 | >10,000 |
| 482 | 6.0 | 4.0 | >10,000 |
| 483 | 32.6 | 10.6 | >10,000 |
| 484 | 240 | 100 | >10,000 |
| 485 | 8.0 | 4.2 | >10,000 |
| 486 | 5400 | 4000 | >10,000 |

-continued

| Inhibition Table A (nM) | | | |
|---|---|---|---|
| Example Number | MMP-13 $IC_{50}$ (nM) | MMP-2 $IC_{50}$ (nM) | MMP-1 $IC_{50}$ (nM) |
| 487 | 140 | 800 | >10,000 |
| 488 | 140 | 370 | >10,000 |
| 489 | 770 | 1900 | >10,000 |
| 490 | 61.0 | 3000 | >10,000 |
| 491 | >10,000 | >10,000 | >10,000 |
| 492 | 6100 | >10,000 | >10,000 |
| 493 | >10,000 | >10,000 | >10,000 |
| 494 | 650 | 3300 | >10,000 |
| 495 | 14.5 | 21.1 | >10,000 |
| 496 | 30.7 | 200 | >10,000 |
| 497 | 50.0 | 8000 | >10,000 |
| 499 | 0.9 | 19.3 | >10,000 |
| 500 | 3.0 | 22.0 | >10,000 |
| 501 | 2.5 | 180 | >10,000 |
| 502 | 14.0 | 63 | >10,000 |
| 503 | 10.0 | 50.0 | >10,000 |
| 504 | 6.3 | 220 | >10,000 |
| 505 | 14.0 | 72.0 | >10,000 |
| 506 | 5.0 | 400 | >10,000 |
| 507 | 15.8 | 210 | >10,000 |
| 508 | 19.3 | 210 | >10,000 |
| 509 | 520 | >10,000 | >10,000 |
| 510 | 7700 | >10,000 | >10,000 |
| 511 | 9000 | 6000 | >10,000 |
| 512 | 7700 | >10,000 | >10,000 |
| 513 | 7700 | >10,000 | >10,000 |
| 514 | 1.0 | 0.6 | 5,000 |
| 515 | 8.0 | 27.0 | >10,000 |
| 516 | 14.8 | 300 | >10,000 |
| 517 | 14.0 | 1100 | >10,000 |
| 518 | 11.4 | 350 | >10,000 |
| 519 | 45.4 | 1300 | >10,000 |
| 520 | 22.5 | 250 | >10,000 |
| 521 | 3.5 | 50.0 | >10,000 |
| 522 | 2.4 | 94.0 | >10,000 |
| 523 | 2.4 | 190 | >10,000 |
| 524 | 2700 | 6400 | >10,000 |
| 525 | 290 | 700 | >10,000 |
| 526 | >10,000 | >10,000 | >10,000 |
| 527 | 6700 | 9000 | >10,000 |
| 528 | 7700 | >10,000 | >10,000 |
| 529 | 8800 | >10,000 | >10,000 |
| 530 | 20.0 | 60.7 | >10,000 |
| 531 | 13.0 | 10.0 | >10,000 |
| 532 | 10.0 | 150 | >10,000 |
| 533 | 60.0 | 150 | >10,000 |
| 534 | 30.0 | 480 | >10,000 |
| 535 | 1.9 | 35.0 | >10,000 |
| 536 | 7.7 | 88.0 | >10,000 |
| 537 | 70.0 | 55.0 | 5200 |
| 538 | 80.0 | 370 | >10,000 |
| 539 | 270 | 350 | >10,000 |
| 540 | 11.4 | 500 | >10,000 |
| 541 | 0.7 | 2.0 | >10,000 |
| 542 | — | — | — |
| 543 | 33.7 | 5400 | >10,000 |
| 544 | 35.0 | 3100 | >10,000 |
| 545 | 7.7 | 120 | >10,000 |
| 546 | 2.7 | 18.6 | >10,000 |
| 547 | 5.0 | 64.7 | >10,000 |
| 548 | 40.0 | 800 | >10,000 |
| 549 | 55.3 | 2900 | >10,000 |
| 550 | 20.0 | 2000 | >10,000 |
| 551 | 9.0 | 140 | >10,000 |
| 552 | 12.8 | 140 | >10,000 |
| 553 | 12.8 | 50.0 | >10,000 |
| 554 | 3.7 | 140 | >10,000 |
| 555 | 3.7 | 220 | >10,000 |
| 556 | 4.5 | 170 | >10,000 |
| 557 | 16.9 | 200 | >10,000 |
| 558 | 4.5 | 66.4 | >10,000 |
| 559 | 7.2 | 80.0 | >10,000 |
| 560 | 4.5 | 306 | >10,000 |
| 561 | 6.0 | 500 | >10,000 |

-continued

| Inhibition Table A (nM) | | | |
|---|---|---|---|
| Example Number | MMP-13 $IC_{50}$ (nM) | MMP-2 $IC_{50}$ (nM) | MMP-1 $IC_{50}$ (nM) |
| 562 | 1200 | 6300 | >10,000 |
| 563 | 70.0 | 235 | >10,000 |
| 564 | 150 | 550 | >10,000 |
| 565 | 5.5 | 700 | >10,000 |
| 566 | 15.8 | 57.1 | >10,000 |
| 567 | 5.0 | 87.7 | >10,000 |
| 568 | 120 | 4600 | >10,000 |
| 569 | 16.9 | 87.7 | >10,000 |
| 570 | 290 | >10,000 | >10,000 |
| 571 | 28.6 | 140 | >10,000 |
| 572 | 37.2 | 3000 | >10,000 |
| 573 | 11.4 | 235 | >10,000 |
| 574 | 10.6 | 220 | >10,000 |
| 575 | 10.7 | 110 | >10,000 |
| 576 | 8.8 | 78.0 | >10,000 |
| 577 | 107 | 2200 | >10,000 |
| 578 | 160 | 2000 | >10,000 |
| 579 | 2.7 | 100 | >10,000 |
| 580 | 37.2 | 700 | >10,000 |
| 581 | 27.0 | 480 | >10,000 |
| 582 | 30.0 | 1800 | >10,000 |
| 583 | 70.0 | 4700 | >10,000 |
| 584 | 2700 | 3500 | >10,000 |
| 585 | 1400 | 3500 | >10,000 |
| 586 | >10,000 | >10,000 | >10,000 |
| 587 | 1.8 | 1.0 | >10,000 |
| 588 | — | — | — |
| 589 | 70.0 | >10,000 | >10,000 |
| 590 | 121 | 80.0 | >10,000 |
| 591 | 70.0 | 730 | >10,000 |
| 592 | 57.0 | 690 | >10,000 |
| 593 | 420 | 650 | >10,000 |
| 594 | 570 | 650 | >10,000 |
| 595 | 270 | 425 | >10,000 |
| 596 | 1.1 | 10.6 | >10,000 |
| 597 | 670 | 700 | >10,000 |
| 598 | 25.4 | 145 | >10,000 |
| 600 | 9.0 | 600 | >10,000 |
| 601 | 9.0 | 1300 | >10,000 |
| 602 | 70.0 | 3000 | >10,000 |
| 603 | 15.8 | 2300 | >10,000 |
| 604 | 20.0 | 2500 | >10,000 |
| 605 | 10.6 | 2000 | >10,000 |
| 606 | 3.0 | 77.0 | >10,000 |
| 607 | 2.9 | 220 | >10,000 |
| 608 | 3.0 | 250 | >10,000 |
| 609 | 30.6 | 2800 | >10,000 |
| 610 | 425 | 1300 | >10,000 |
| 611 | 139 | 1800 | >10,000 |
| 612 | 290 | 2200 | >10,000 |
| 613 | 8.0 | 30.7 | >10,000 |
| 614 | 22.0 | 25.4 | >10,000 |
| 615 | 3.1 | 11.0 | >10,000 |
| 616 | 4.0 | 3.7 | >10,000 |
| 617 | 7.0 | 5.7 | >10,000 |
| 618 | — | — | — |
| 619 | 4.3 | 5.7 | >10,000 |
| 620 | 27.8 | 225 | >10,000 |
| 621 | 120 | 1500 | >10,000 |
| 622 | 500 | 1600 | >10,000 |
| 623 | 350 | 1400 | >10,000 |
| 624 | 120 | 940 | >10,000 |
| 634 | 4.4 | 60.7 | >10,000 |
| 635 | 13.9 | 260 | >10,000 |
| 636 | 3.0 | 8.0 | >10,000 |
| 637 | 3.8 | 22 | >10,000 |
| 638 | — | — | — |
| 639 | 1.5 | 1.5 | 9400 |
| 640 | 4.2 | 15.8 | >10,000 |
| 641 | 4.0 | 13.7 | >10,000 |
| 642 | 2.2 | 1.1 | >10,000 |
| 643 | 1.8 | 1.2 | 6000 |
| 644 | 1.6 | 3.3 | 8800 |
| 645 | 370 | 1200 | >10,000 |

-continued

| Inhibition Table A (nM) | | | |
|---|---|---|---|
| Example Number | MMP-13 $IC_{50}$ (nM) | MMP-2 $IC_{50}$ (nM) | MMP-1 $IC_{50}$ (nM) |
| 646 | — | 7800 | >10,000 |
| 647 | 6.0 | 160 | >10,000 |
| 648 | 25.8 | 110 | >10,000 |
| 649 | 130 | 1400 | >10,000 |
| 650 | 14.7 | 1200 | >10,000 |
| 651 | 13.7 | 60 | >10,000 |
| 652 | 0.4 | 82.0 | >10,000 |
| 653 | 0.8 | 160 | >10,000 |
| 654 | 3.2 | 35.0 | >10,000 |
| 655 | 37.3 | 1400 | >10,000 |
| 656 | 3.1 | 120 | >10,000 |
| 658 | 12.2 | 1000 | >10,000 |
| 659 | 1.0 | 3.7 | >10,000 |
| 665 | 2.3 | 29.2 | >10,000 |
| 666 | 48.4 | 330 | >10,000 |
| 667 | 30 | 135 | >10,000 |
| 668 | 2.0 | 25.8 | >10,000 |
| 669 | 4.3 | 22.7 | >10,000 |
| 670 | | | |
| 671 | 6.0 | 130 | >10,000 |
| 672 | 6.7 | 60 | >10,000 |
| 673 | 14.8 | 455 | >10,000 |
| 674 | 8.0 | 110 | >10,000 |
| 675 | 13.0 | 88 | 6000 |
| 676 | 7.7 | 90 | >10,000 |
| 677 | 7.0 | 34.7 | >10,000 |
| 678 | 5.0 | 50 | >10,000 |
| 679 | | | |
| 680 | | | |
| 681 | | | |
| 682 | | | |
| 683 | 11.3 | 290 | >10,000 |
| 684 | 60 | 1450 | >10,000 |
| 685 | 3.0 | 34.7 | >10,000 |
| 686 | 4200 | 3700 | >10,000 |
| 688 | 17.6 | 110 | >10,000 |
| 690 | 7.3 | 41.8 | >10,000 |
| 691 | 10.0 | 130 | >10,000 |
| 692 | 10.0 | 22.7 | >10,000 |
| 693 | 210 | 1900 | >10,000 |
| 694 | 3.1 | 23.2 | >10,000 |
| 695 | 2.0 | 22.7 | >10,000 |
| 696 | 10.0 | 140 | >10,000 |
| 697 | 18.1 | 1500 | >10,000 |
| 698 | 16.9 | 700 | >10,000 |
| 699 | 50.0 | 455 | >10,000 |
| 705 | 44.5 | 1100 | >10,000 |
| 706 | 4.3 | 40 | >10,000 |
| 707 | 2.3 | 9.0 | >10,000 |
| 708 | 114 | 3000 | >10,000 |
| 714 | 28.8 | 420 | >10,000 |
| 720 | 4.5 | 36.9 | >10,000 |
| 724 | 28.6 | 300 | >10,000 |
| 725 | 25.1 | 210 | >10,000 |
| 726 | 15.8 | 250 | >10,000 |
| 727 | 34.9 | 240 | >10,000 |
| 728 | 9.4 | 106 | >10,000 |
| 729 | 14.8 | 240 | >10,000 |
| 730 | 37 | 3000 | >10,000 |
| 731 | 1.9 | 35 | >10,000 |
| 732 | 3.1 | 590 | >10,000 |
| 733 | 1.6 | 270 | >10,000 |
| 734 | 6.0 | 3300 | >10,000 |
| 735 | 9.0 | 800 | >10,000 |
| 736 | 0.9 | 145 | >10,000 |
| 737 | 3.0 | 1280 | >10,000 |
| 738 | 22.0 | 270 | >10,000 |
| 740 | 61 | 175 | >10,000 |
| 741 | 50 | 125 | >10,000 |
| 752 | 14.8 | 271 | >10,000 |
| 755 | 2.2 | 20 | >10,000 |
| 756 | 7.0 | 28.8 | >10,000 |
| 757 | 3.3 | 28.8 | >10,000 |
| 758 | 5.0 | 34.7 | >10,000 |

-continued

| Inhibition Table A (nM) | | | |
|---|---|---|---|
| Example Number | MMP-13 $IC_{50}$ (nM) | MMP-2 $IC_{50}$ (nM) | MMP-1 $IC_{50}$ (nM) |
| 759 | 3.0 | 60.8 | >10,000 |
| 760 | 6.0 | 25.4 | >10,000 |
| 761 | 5.0 | 41.8 | >10,000 |
| 769 | 5.0 | 0.7 | >10,000 |
| 770 | 270 | 485 | >10,000 |
| 771 | 500 | 10,000 | >10,000 |
| 772 | 350 | 4200 | >10,000 |
| 773 | 6.0 | 2.7 | >10,000 |
| 774 | — | — | — |
| 775 | 120 | 270 | >10,000 |
| 776 | 3.0 | 10.0 | >10,000 |
| 777 | 2.5 | 6.5 | >10,000 |
| 778 | 3.3 | 12 | >10,000 |
| 779 | 40 | 210 | >10,000 |
| 780 | 17.5 | 80 | >10,000 |
| 781 | 800 | 5100 | >10,000 |
| 782 | 21.1 | 100 | >10,000 |
| 784 | 6.0 | 4500 | >10,000 |
| 786 | 3.7 | 700 | >10,000 |
| 787 | 1.2 | 175 | >10,000 |
| 788 | 3.0 | 445 | >10,000 |
| 789 | 12.2 | 3700 | >10,000 |
| 790 | 4.5 | 700 | >10,000 |
| 791 | 2.0 | 700 | >10,000 |
| 793 | 4.0 | 23.5 | >10,000 |
| 794 | 1500 | 2900 | >10,000 |
| 796 | 5.7 | 130 | >10,000 |
| 797 | 4.0 | 175 | >10,000 |
| 798 | 20.0 | 210 | >10,000 |
| 799 | 10.6 | 43.5 | >10,000 |
| 802 | 2.3 | 10,000 | >10,000 |
| 807 | 200 | 1400 | >10,000 |
| 811 | 14.8 | 110 | >10,000 |
| 815 | 140 | 1400 | >10,000 |
| 816 | 1200 | >10,000 | >10,000 |
| 820 | 29.0 | 1400 | >10,000 |
| 821 | 4.0 | 10.0 | >10,000 |
| 822 | 10.0 | 210 | >10,000 |
| 823 | 7.0 | 505 | >10,000 |
| 825 | 11.3 | 70.0 | >10,000 |
| 826 | 40.0 | 650 | ND |
| 827 | 10.0 | 540 | >10,000 |
| 828 | 1.5 | 12.8 | ND |
| 829 | 6.0 | 22.0 | ND |
| 830 | 17.9 | 2100 | >10,000 |
| 831 | 2.3 | 170 | >10,000 |
| 832 | 18.1 | 2000 | >10,000 |
| 833 | 11.0 | 1750 | >10,000 |
| 834 | 150 | 780 | ND |
| 835 | 6.0 | 20.0 | >10,000 |
| 836 | 135 | 4200 | ND |
| 838 | 3.0 | 70.0 | >10,000 |
| 841 | 285 | 1900 | ND |
| 842 | 5.5 | 45.4 | >10,000 |
| 844 | 5.0 | 4700 | >10,000 |
| 845 | 28.6 | 2000 | ND |
| 846 | 4.5 | 186 | >10,000 |
| 847 | 20.0 | 1800 | ND |
| 848 | — | — | ND |
| 850 | 4.5 | 150 | >10,000 |
| 851 | 3.7 | 42.5 | ND |
| 852 | 25.0 | 3000 | ND |
| 853 | 15.8 | 120 | ND |
| 854 | 40.0 | 3300 | ND |
| 856 | 1.2 | 250 | ND |
| 857 | 1.3 | 120 | ND |
| 858 | 3.7 | 600 | >10,000 |
| 859 | 5.5 | 440 | ND |
| 860 | 2.7 | 1500 | >10,000 |
| 861 | 2.0 | 34.9 | ND |
| 862 | 1.7 | 40.0 | ND |
| 863 | — | — | ND |
| 864 | — | — | ND |
| 867 | 16.5 | 10,000 | >10,000 |

-continued

| Inhibition Table A (nM) | | | |
|---|---|---|---|
| Example Number | MMP-13 $IC_{50}$ (nM) | MMP-2 $IC_{50}$ (nM) | MMP-1 $IC_{50}$ (nM) |
| 868 | — | — | ND |
| 869 | 2.0 | 76.9 | ND |
| 870 | 305 | 6000 | ND |

EXAMPLE 944

In Vivo Angiogenesis Assay

The study of angiogenesis depends on a and reproducible model for the stimulation and inhibition of a neovascular response. The corneal micropocket assay provides such a model of angionesis in the cornea of a mouse. See, *A Model of Angiogenesis in the Mouse Cornea*; Kenyon, B M, et al., Investigative Ophthalmology & Visual Science, July 1996, Vol. 37, No. 8.

In this assay, uniformly sized Hydron pellets containing bFGF and sucralfate were prepared and surgically implanted into the stroma mouse cornea adjacent to the temporal limbus. The pellets were formed by making a suspension of 20 $\mu$L sterile saline containing 10 $\mu$g recombinant bFGF, 10 mg of sucralfate and 10 $\mu$L of 12 percent Hydron in ethanol. The slurry was then deposited on a 10×10 mm piece of sterile nylon mesh. After drying, the nylon fibers of the mesh were separated to release the pellets.

The corneal pocket is made by anesthetizing a 7 week old C57B/6 female mouse, then proptosing the eye with a jeweler's forceps. Using a dissecting microscope, a central, intrastromal linear keratotomy of approximately 0.6 mm in length is performed with a #15 surgical blade, parallel to the insertion of the lateral rectus muscle. Using a modified cataract knife, a lamellar micropocket is dissected toward the temporal limbus. The pocket is extended to within 1.0 mm of the temporal limbus. A single pellet was placed on the corneal surface at the base of the pocket with a jeweler's forceps. The pellet was then advanced to the temporal end of the pocket. Antibiotic ointment was then applied to the eye.

Mice were dosed on a daily basis for the duration of the assay. Dosing of the animals was based on bioavailability and overall potency of the compound, an exemplary dose was 10 or 50 mg/kg (mpk) bid, po. Neovascularization of the corneal stroma begins at about day three and was permitted to continue under the influence of the assayed compound until day five. At day five, the degree of angiogenic inhibition was scored by viewing the neovascular progression with a slit lamp microscope.

The mice were anesthetized and the studied eye was once again proptosed. The maximum vessel length of neovascularization, extending from the limbal vascular plexus toward the pellet was measured. In addition, the contiguous circumferential zone of neovascularization was measured as clock hours, where 30 degrees of arc equals one clock hour. The area of angiogenesis was calculated as follows.

$$\text{area} = \frac{(0.4 \times \text{clock hours} \times 3.14 \times \text{vessel length (in mm)})}{2}$$

Five to six mice were utilized for each compound in each study. The studied mice were thereafter compared to control mice and the difference in the area of neovascularization was recorded as an averaged value. Each group of mice so studied constitutes an "n" value of one, so that "n" values greater than one represent multiple studies whose averaged result is provided in the table. A contemplated compound typically exhibits about 25 to about 75 percent inhibition, whereas the vehicle control exhibits zero percent inhibition.

EXAMPLE 350

In Vivo PC-3 Tumor Reduction

PC-3 human pancreatic cancer cells (ATCC CRL 1435) were grown to 90% confluence in F12/MEM (Gibco) containing 7% FBS (Gibco). Cells were mechanically harvested using a rubber scraper, and then washed twice with cold medium. The resulting cells were resuspended in cold medium with 30% matrigel (Collaborative Research) and the cell-containing medium was maintained on ice until used.

Balb/c nu/nu mice at 7–9 weeks of age were anesthetized with avertin [2,2,2-tribromethanol/t-amyl alcohol (1 g/1 mL) diluted 1:60 into phosphate-buffered sline] and 3–5×$10^6$ of the above cells in 0.2 mL of medium were injected into the left flank of each mouse. Cells were injected in the morning, whereas dosing with an inhibitor began at 6 PM. The animals were gavaged BID from day zero (cell injection day) to day 25–30, at which time the animals were euthanized and tumors weighed.

Compounds were dosed at 10 mg/mL in 0.5% methylcellulose/0.1% polysorbate 80 to provide a 50 mg/kg (mpk) dose twice each day, or diluted to provide a 10 mg/kg (mpk) dose twice each day. Tumor measurements began on day 7 and continued every third or fourth day until completion of the study. Groups of ten mice were used in each study and nine to ten survived. Each group of mice so studied constitutes an "n" value of one, so that "n" values greater than one represent multiple studies whose averaged result is provided in the table.

EXAMPLE 945

Tumor Necrosis Factor Assays

Cell Culture.

The cells used in the assay are the human moncytic line U-937 (ATCC CRL-1593). The cells are grown in RPMI w/10% FCS and PSG supplement (R-10) and are not permitted to overgrow. The assay is carried out as follows:

1. Count, then harvest cells by centrifugation. Resuspend the pellet in R-10 supplement to a concentration of 1.540×$10^6$ cells/mL.

2. Add test compound in 65 uL R-10 to the appropriate wells of a 96-well flat bottom tissue culture plate. The initial dilution from a DMSO stock (100 mM compound) provides a 400 uM solution, from which five additional three-fold serial dilutions are made. Each dilution of 65 ul (in triplicate) yields final compound test concentrations of 100 $\mu$M, 33.3 $\mu$M, 11.1 $\mu$M, 3.7 $\mu$M, 1.2 $\mu$M and 0.4 $\mu$M.

3. The counted, washed and resuspended cells (200,000 cells/well) in 130 $\mu$L are added to the wells.

4. Incubation is for 45 minutes to one hour at 37° C. in 5% CO2 in a water saturated container.

5. R-10 (65 uL) containing 160 ng/mL PMA (Sigma) is added to each well.

6. The test system is incubated at 37° C. in 5% CO2 overnight (18–20 hours) under 100% humidity.

7. Supernatant, 150 $\mu$L, is carefully removed from each well for use in the ELISA assay.

8. For toxicity, a 50 μL aliquot of working solution containg 5 mL R-10, 5 mL MTS solution [CellTiter 96 AQueous One Solution Cell Proliferation Assay Cat.#G358/0,1 (Promega Biotech)] and 250 ul PMS solution are added to each well containing the remaining supernatant and cells and the cells incubated at 37° C. in 5% CO2 until the color develops. The system is excited at 570 nm and read at 630 nm.

TNF Receptor II ELISA Assay

1. Plate 100 μL/well 2 ug/mL mouse anti-human TNFrII antibody (R&D Systems #MAB226) in 1×PBS (pH 7.1, Gibco) on NUNC-Immuno Maxisorb plate. Incubate the plate at 4° C. overnight (about 18–20 hours).

2. Wash the plate with PBS-Tween (1×PBS w/ 0.05% Tween).

3. Add 200 μL 5% BSA in PBS and block at 37° C. in a water saturated atmosphere for 2 hours.

4. Wash the plate with PBS-Tween.

5. Add sample and controls (100 ul of each) to each well. The standards are 0, 50, 100, 200, 300 and 500 pg recombinant human TNFrII (R&D Systems #226-B2) in 100 μL 0.5% BSA in PBS. The assay is linear to between 400–500 pg of standard.

6. Incubate at 37° C. in a saturated atmosphere for 1.5 hours.

7. Wash the plate with PBS-Tween.

8. Add 100 μL goat anti-human TNFrII polyclonal (1.5 μg/mL R&D Systems #AB226-PB in 0.5% BSA in PBS).

9. Incubate at 37° C. in a saturated atmosphere for 1 hour.

10. Wash the plate with PBS-Tween.

11. Add 100 μL anti-goat IgG-peroxidase (1:50,000 in 0.5% BSA in PBS, Sigma #A5420).

11. Incubate at 37° C. in a saturated atmosphere for 1 hour.

12. Wash the plate with PBS-Tween.

13. Add 10 μL KPL TMB developer, develop at room temperature (usually about 10 minutes), then terminate with phosphoric acid and excite at 450 nm and read at 570 nm.

TNFα ELISA Assay

Coat Immulon® 2 plates with 0.1 mL/well of 1 ug/mL Genzyme mAb in 0.1 M NaHCO3 pH 8.0 buffer overnight (about 18–20 hours) at 4° C., wrapped tightly in Saran® wrap.

Flick out coating solution and block plates with 0.3 mL/well blocking buffer overnight at 4° C., wrapped in Saran® wrap.

Wash wells thoroughly 4× with wash buffer and completely remove all wash buffer. Add 0.1 mL/well of either samples or rhTNFα standards. Dilute samples if necessary in appropriate diluant (e.g. tissue culture medium). Dilute standard in same diluant. Standards and samples should be in triplicates.

Incubate at 37° C. for 1 hour in humified container.

Wash plates as above. Add 0.1 mL/well of 1:200 dilution of Genzyme rabbit anti-hTNF.

Repeat incubation.

Repeat wash. Add 0.1 mL/well of 1 μg/mL Jackson goat anti-rabbit IgG (H+L)-peroxidase.

Incubate at 37° C. for 30 minutes.

Repeat wash. Add 0.1 mL/well of peroxide-ABTS solution.

Incubate at room temperature for 5–20 minutes.

Read OD at 405 nm.

12 Reagents are:

Genzyme mouse anti-human TNF? monoclonal (Cat.# 80-3399-01)

Genzyme rabbit anti-human TNF? polyclonal (Cat.#IP-300)

Genzyme recombinant human TNF? (Cat.#TNF-H).

Jackson Immunoresearch peroxide-conjugated goat anti-rabbit IgG (H+L) (Cat.#111-035-144).

Kirkegaard/Perry peroxide ABTS solution (Cat#50-66-01).

Immulon 2 96-well microtiter plates.

Blocking solution is 1 mg/mL gelatin in PBS with 1× thimerasol.

Wash buffer is 0.5 mL Tween® 20 in 1 liter of PBS.

From the foregoing, it will be:observed that numerous modifications and variations can be effectuated without departing from the true spirit and scope of the novel concepts of the present invention. It is to be understood that no limitation with respect to the specific example presented is intended or should be inferred. The disclosure is intended to cover by the appended claims all such modifications as fall within the scope of the claims.

What is claimed:

1. A process for treating osteoarthritis in a mammal, wherein:

the process comprises administering a compound or a pharmaceutically acceptable salt thereof in an effective amount to the mammal;

the compound or salt is characterizeable in that the compound or salt exhibits inhibitory activity against one or more of MMP-2, MMP-9 and MMP-13, while exhibiting substantially less inhibitory activity against MMP-1;

the compound corresponds in structure to formula B-1:

B-1;

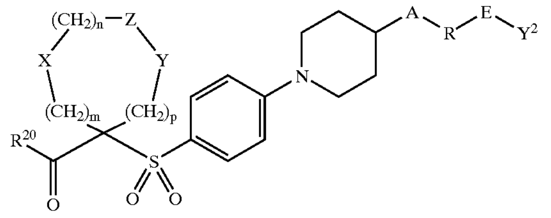

$R^{20}$ is —NH—O—$R^{14}$;

$R^{14}$ is selected from the group consisting of hydrido, a pharmaceutically acceptable cation, and $C(W)R^{25}$;

W is selected from the group consisting of O and S;

$R^{25}$ is selected from the group consisting of $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl, and amino $C_1$–$C_6$-alkyl, wherein:

the amino $C_1$–$C_6$-alkyl nitrogen is optionally substituted with:

up to two substituents independently selected from the group consisting of $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and $C_1$–$C_6$-alkanoyl, or two substituents such that the two substituents and amino nitrogen form a 5- to 8-membered heterocyclo or heteroaryl ring;

m is selected from the group consisting of zero, 1 and 2;

n is selected from the group consisting of zero, 1 and 2;

p is selected from the group consisting of zero, 1 and 2;

the sum of m+n+p is 2;

Z is $NR^6$, and X and Y are $CR^8R^9$ and $CR^{10}R^{11}$;

$R^6$ is selected from the group consisting of hydrido, formyl, sulfonic-$C_1$–$C_6$-alkyl, $C_1$–$C_6$-alkoxycarbonyl-$C_1$–$C_6$-alkyl, hydroxycarbonyl-$C_1$–$C_6$-alkyl, $C_1$–$C_6$-alkylcarbonyl-$C_1$–$C_6$-alkyl, $R^8R^9$-aminocarbonyl-$C_1$–$C_6$-alkyl, $C_1$–$C_6$-alkoxycarbonyl-$C_1$–$C_6$-alkylcarbonyl, hydroxycarbonyl-$C_1$–$C_6$-alkylcarbonyl, $C_1$–$C_6$-alkylcarbonyl-$C_1$–$C_6$-alkylcarbonyl, $C_1$–$C_6$-alkoxycarbonylcarbonyl, hydroxycarbonylcarbonyl, $C_1$–$C_6$-alkylcarbonylcarbonyl, $R^8R^9$-aminocarbonylcarbonyl, $C_1$–$C_6$-alkanoyl, aryl-$C_1$–$C_6$-alkyl, aroyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, heteroarycarbonyl, heterocyclocarbonyl, $C_3$–$C_8$-heterocycloalkyl, $C_3$–$C_8$-heterocycloalkylcarbonyl, aryl, $C_5$–$C_6$-heterocyclo, $C_5$–$C_6$-heteroaryl, $C_3$–$C_8$-cycloalkyl-$C_1$–$C_6$-alkyl, aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, arylsulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycaxbonyl-$C_1$–$C_6$-alkyl, aminocarbonyl, $C_1$–$C_6$-alkyl($R^8N$)iminocarbonyl, aryl($R^8N$)iminocarbonyl, $C_5$–$C_6$-heterocyclo($R^8N$)iminocarbonyl, arylthio-$C_1$–$C_6$-alkyl, $C_1$–$C_6$-alkylthio-$C_1$–$C_6$-alkyl, arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—($R^8$)iminomethyl, $NR^8R^9$—$C_1$–$C_5$-alkoxycarboyl, hydroxy-$C_1$–$C_5$-alkyl, $R^8R^9$-aminocarbonyl, $R^8R^9$-aminocarbonyl-$C_1$–$C_6$-alkylcarbonyl, hydroxyaminocarbonyl, $R^8R^9$-aminosulfonyl, $R^8R^9$-aminosulfon-$C_1$–$C_6$-alkyl, $R^8R^9$-amino-$C_1$–$C_6$-alkylsulfonyl, and $R^8R^9$-amino-$C_1$–$C_6$-alkyl;

as to $R^8$:

$R^8$ is selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^8$ and $R^9$ and the carbon to which they are bonded form carbonyl, or $R^8$ and $R^9$ or $R^8$ and $R^{10}$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur;

as to $R^9$:

$R^9$ is selected from the group consisting of hydrido, hydroxy, $C_1$–$C_6$-alkyl $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, hetoroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^8$ and $R^9$ and the carbon to which they are bonded form carbonyl, or $R^8$ and $R^9$ and the atoms to which they are bonded form a 5- to 8-membered carbocyclic ring, or a 5 to 8-membered heterocyclic or heteroaryl ring containing one or two heteroatoms independently selected from the group consisting of nitrogen, oxygen, and sulfur;

as to $R^{10}$:

$R^{10}$ is selected from the group consisting of hydrido, hydroxy, $C_1$–$C_6$-alkyl, $C_1$–$_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarboylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^{10}$ and $R^{11}$ and the carbon to which they are bonded form carbonyl, or $R^{10}$ and $R^{11}$ or $R^8$ and $R^{10}$ and the atoms to which they are bonded form a 5- to 8-membered carbocyclic ring or a 5- to 8-membered heterocyclic or heteroaryl ring containing one or two heteroatoms independently selected from the group consisting of nitrogen, oxygen, and sulfur;

as to $R^{11}$:

$R^{11}$ is selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkythio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkonoyl, or $R^{10}$ and $R^{11}$ and the carbon to which they are bonded form carbonyl or $R^{10}$ and $R^{11}$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur;

only one of $R^8$ and $R^9$ or $R^{10}$ and $R^{11}$ may be hydroxy, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkanoylamino, and alkoxycarbonyl;

R is other than alkyl or alkoxyalkyl when A is —O— or —S—;

R is other than methyl or phenyl when A is a bond;

E is selected from the group consisting of:

(1) —CO($R^{19}$)—;
(2) —($R^{19}$)CO—;
(3) —CONH—;
(4) —HNCO—;
(5) —CO—;
(6) —$SO_2$—$R^{19}$—;
(7) —$R^{19}$—$SO_2$—;
(8) —$SO_2$—;
(9) —NH—$SO_2$—;
(10) —$SO_2$—NH—;
(11) —S—;
(12) —NH—CO—O—;
(13) —O—CO—NH—; and
(14) a bond;

$R_{19}$ is selected from the group consisting of heterocycloalkyl and cycloalkyl; and $Y^2$ is selected from the group consisting of hydrido, alkyl, alkoxy, haloalkyl, aryl, aralkyl, cycloalkyl, heteroaryl, hydroxy, aryloxy, aralkoxy, heteroaryloxy, heteroaralkyl, perfluoroalkoxy, perfluoroalkylthio, trifluoromethylalkyl, alkenyl, heterocycloalkyl, cycloalkyl, trifluoromethyl, alkoxycarbonyl, and aminoalkyl, wherein:

the aryl, heteroaryl, aralkyl, or heterocycloalkyl is optionally substituted with up to two substituents independently selected from the group consisting of alkyl, alkanoyl, halo, nitro, aralkyl, aryl, alkoxy, trifluoroalkyl, trifluoroalkoxy, and amino, wherein:

the amino nitrogen is optionally substituted with up to two substituents independently selected from the group consisting of alkyl and aralkyl.

2. The process according to claim 1, wherein the compound corresponds in structure to formula B-2:

B-2.

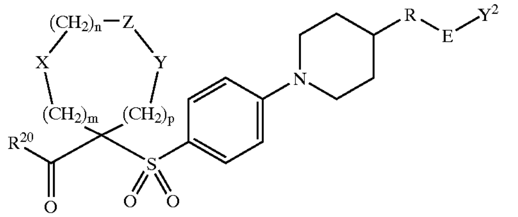

3. The process according to claim 1, wherein the compound or salt is administered a plurality of times.

4. A process for treating osteoarthritis in a mammal, wherein:

the process comprises administering a compound or a pharmaceutically acceptable salt thereof in an effective amount to the mammal;

the compound or salt is characterizeable in that the compound or salt exhibits inhibitory activity against one or more of MMP-2, MMP-9 and MMP-13, while exhibiting substantially less inhibitory activity against MMP-1;

the compound corresponds in structure to formula VIC:

VIC:

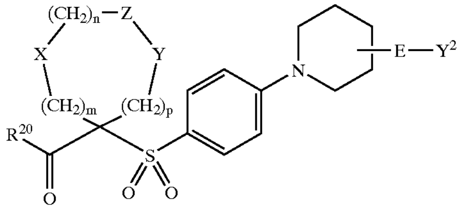

$R^{20}$ is —NH—O—$R^{14}$;

$R^{14}$ is selected from the group consisting of hydrido, a pharmaceutically acceptable cation, and C(W)$R^{25}$;

W is selected from the group consisting of O and S;

$R^{25}$ is selected from the group consisting of $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl, and amino $C_1$–$C_6$-alkyl, wherein:

the amino $C_1$–$C_6$-alkyl nitrogen is optionally substituted with:

up to two substituents independently selected from the group consisting of $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and $C_1$–$C_6$-alkanoyl, or two substituents such that the two substituents and amino nitrogen form a 5- to 8-membered heterocyclo or heteroaryl ring;

m is selected from the group consisting of zero, 1 and 2;

n is selected from the group consisting of zero, 1 and 2;

p is selected from the group consisting of zero, 1 and 2;

the sum of m+n+p is 2;

Z is $NR^6$, and X and Y and Z are $CR^8R^9$ and $CR^{10}R^{11}$;

$R^6$ is selected from the group consisting of hydrido, formyl, sulfonic-$C_1$–$C_6$-alkyl, $C_1$–$C_6$-alkoxycarbonyl-$C_1$–$C_6$-alkyl, hydroxycarbonyl-$C_1$–$C_6$-alkyl, $C_1$–$C_6$-alkylcarbonyl-$C_1$–$C_6$-alkyl, $R^8R^9$-aminocarbonyl-$C_1$–$C_6$-alkyl, $C_1$–$C_6$-alkoxycarbonyl-$C_1$–$C_6$-alkylcarbonyl, hydroxycarbonyl-$C_1$–$C_6$-alkylcarbonyl, $C_1$–$C_6$-alkylcarbonyl-$C_1$–$C_6$-alkylcarbonyl, $C_1$–$C_6$-alkoxycarbonylcarbonyl, hydroxycarbonylcarbonyl, $C_1$–$C_6$-alkylcarbonylcarbonyl, $R^8R^9$-aminocarbonylcarbonyl, $C_1$–$C_6$-alkanoyl, aryl-$C_1$–$C_6$-alkyl, aroyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, heteroarycarbonyl, heterocyclocarbonyl, $C_3$–$C_8$-heterocycloalkyl, $C_3$–$C_8$-heterocycloalkylcarbonyl, aryl, $C_5$–$C_6$-heterocyclo, $C_5$–$C_6$-heteroaryl, $C_3$–$C_8$-cycloalkyl-$C_1$–$C_6$-alkyl, aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, arylsulfonyl $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyl($R^8$N)iminocarbonyl, aryl($R^8$N)iminocarbonyl, $C_5$–$C_6$-heterocyclo($R^8$N)iminocarbonyl, arylthio-$C_1$–$C_6$-alkyl, $C_1$–$C_6$-alkylthio-$C_1$–$C_6$-alkyl, arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—($R^8$)iminomethyl, $NR^8R^9$—$C_1$–$C_5$-alkylcarbonyl, hydroxy-$C_1$–$C_5$-alkyl, $R^8R^9$-aminocarbonyl, $R^8R^9$-aminocarbonyl-$C_1$–$C_6$-alkylcarbonyl, hydroxyaminocarbonyl, $R^8R^9$-aminosulfonyl, $R^8R^9$-aminosulfon-$C_1$–$C_6$-alkyl, $R^8R^9$-amino-$C_1$–$C_6$-alkylsulfonyl, and $R^8R^9$-amino-$C_1$–$C_6$-alkyl;

as to $R^8$:

$R^8$ is selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^8$ and $R^9$ and the carbon to which they are bonded form carbonyl, or $R^8$ and $R^9$ or $R^8$ and $R^{10}$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur;

as to $R^9$:

$R^9$ is selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkythio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^8$ and $R^9$ and the carbon to which they are bonded form carbonyl, or $R^8$ and $R^9$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur;

as to $R^{10}$:

$R^{10}$ is selected from the group consisting of hydrido, hydroxy, $C_1$–$C_6$-alkyl, $C_1$–$C_6$-alkanoyl, aroyl, aryl ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-carbonyl, or $R^{10}$ and $R^{11}$ and the carbon to which they are bonded form carbonyl, or $R^{10}$ and $R^{11}$ or $R^8$ and $R^{10}$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur;

as to $R^{11}$:

$R^{11}$ is selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkythio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^{10}$ and $R^{11}$ and the carbon to which they are bonded form carbonyl or $R^{10}$ and $R^{11}$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur;

only one of $R^8$ and $R^9$ or $R^{10}$ and $R^{11}$ may be hydroxy;

E is selected from the group consisting of:

(1) —CO($R^{19}$)—;
(2) —($R^{19}$)CO—;
(3) —CONH—;
(4) —HNCO—;
(5) —CO—;
(6) —$SO_2$—$R^{19}$—;
(7) —$R^{19}$—$SO_2$—;
(8) —$SO_2$—;
(9) —NH—$SO_2$—;
(10) —$SO_2$—NH—;
(11) —S—;
(12) —NH—CO—O—;
(13) —O—CO—NH—;
(14) a bond;

$R^{19}$ is selected from the group consisting of heterocycloalkyl and cycloalkyl;

$Y^2$ is selected from the group consisting of hydrido, alkyl, alkoxy, haloalkyl, aryl, aralkyl, cycloalkyl, heteroaryl, hydroxy, aryloxy, aralkoxy, heteroaryloxy, heteroaralkyl, perfluoroalkoxy, perfluoroalkylthio, trifluoromethylalkyl, alkenyl, heterocycloalkyl, cycloalkyl, trifluoromethyl, alkoxycarbonyl, and aminoalkyl, wherein:

the aryl, heteroaryl, aralkyl, or heterocycloalkyl is optionally substituted with up to two substituents independently selected from the group consisting of alkyl, alkanoyl, halo, nitro, aralkyl, aryl, alkoxy, trifluoroalkyl, trifluoroalkoxy, and amino, wherein:

the amino nitrogen is optionally substituted with up to two substituents independently selected from the group consisting of alkyl and aralkyl;

$Y^2$ is other than optionally-substituted piperazinyl when E is —C(O)—; and $Y^2$ is other than hydrido, methyl, or optionally-substituted phenyl when E is a bond.

5. The process according to claim 4, wherein the compound corresponds in structure to formula IX:

IX.

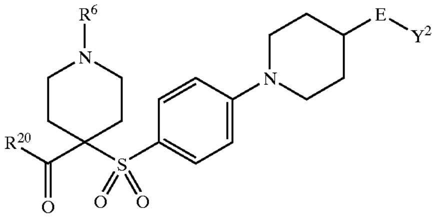

6. The process according to claim 4, wherein the compound or salt is administered a plurality of times.

7. The process according to claim 4, wherein the compound corresponds in structure to formula VIC-1:

VIC-1.

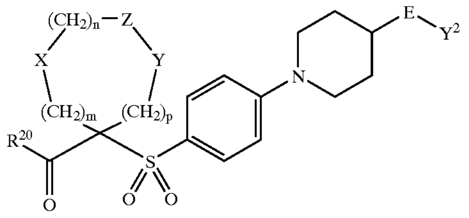

8. The process according to claim 4, wherein the compound corresponds in structure to formula VIC-2:

VIC-2.

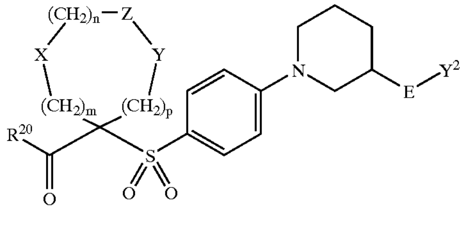

9. The process according to claim 4, wherein the compound corresponds in structure to formula IX-1:

IX-1.

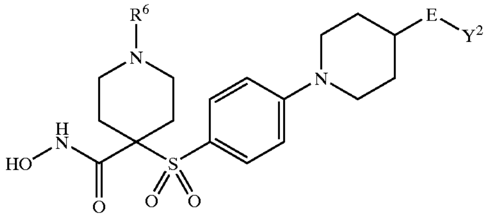

10. The process according to claim 4, wherein the compound corresponds in structure to formula IX-2:

IX-2.

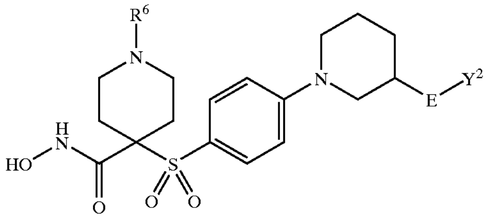

11. A compound or a pharmaceutically acceptable salt thereof, wherein:

the compound corresponds in structure to formula B:

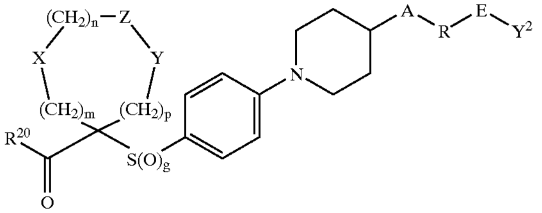

$R^{20}$ is selected from the group consisting of —O—$R^{21}$, —NH—O—$R^{22}$, —NH—O—$R^{14}$, and —$NR^{26}R^{27}$;

$R^{21}$ is selected from the group consisting of hydrido, $C_1$–$C_6$-alkyl, aryl, ar-$C_1$–$C_6$-alkyl, and a pharmaceutically acceptable cation;

$R^{22}$ is a selectively removable protecting group;

$R^{14}$ is selected from the group consisting of hydrido, a pharmaceutically acceptable cation; and $C(W)R^{25}$;

W is selected from the group consisting of O and S;

$R^{25}$ is selected from the group consisting of $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl, and amino $C_1$–$C_6$-alkyl, wherein:

the amino $C_1$–$C_6$-alkyl nitrogen is optionally substituted with:

up to two substituents independently selected from the group consisting of $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and $C_1$–$C_6$-alkanoyl, or two substituents such that the two substituents and the amino nitrogen form a 5- to 8-membered heterocyclo or heteroaryl ring;

as to $R^{26}$ and $R_{27}$:

$R^{26}$ and $R^{27}$ are independently selected from the group consisting of hydrido, $C_1$–$C_6$-alkyl, amino $C_1$–$C_6$-alkyl, hydroxy $C_1$–$C_6$-alkyl, aryl, and ar-$C_1$–$C_6$-alkyl, or $R^{26}$ and $R^{27}$ and the nitrogen to which $R^{26}$ and $R^{27}$ are both bonded form a 5- to 8-membered ring containing zero or one additional heteroatom optionally selected from the group consisting of oxygen, nitrogen, and sulfur;

g is selected from the group consisting of zero, 1, and 2;

m is selected from the group consisting of zero, 1, and 2;

n is selected from the group consisting of zero, 1, and 2;

p is selected from the group consisting of zero, 1, and 2;

the sum of m+n+p is 2;

Z is $NR^6$, and X and Y are $CR^8R^9$ and $CR^{10}R^{11}$;

$R^6$ is selected from the group consisting of hydrido, formyl, sulfonic-$C_1$–$C_6$-alkyl, $C_1$–$C_6$-alkoxycarbonyl-$C_1$–$C_6$-alkyl, hydroxycarbonyl-$C_1$–$C_6$-alkyl, $C_1$–$C_6$-alkylcarbonyl-$C_1$–$C_6$-alkyl, $R^8R^9$-aminocarbonyl-$C_1$–$C_6$-alkyl, $C_1$–$C_6$-alkoxycarbonyl-$C_1$–$C_6$-alkylcarbonyl, hydroxycarbonyl-$C_1$–$C_6$-alkylcarbonyl, $C_1$–$C_6$-alkylcarbonyl-$C_1$–$C_6$-alkylcarbonyl, $C_1$–$C_6$-alkoxycarbonylcarbonyl, hydroxycarbonylcarbonyl, $C_1$–$C_6$-alkylcarbonylcarbonyl, $R^8R^9$-aminocarbonylcarbonyl, $C_1$–$C_6$-alkanoyl, aryl-$C_1$–$C_6$-alkyl, aroyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, heteroarycarbonyl, heterocyclocarbonyl, $C_3$–$C_8$-heterocycloalkyl, $C_3$–$C_8$-heterocycloalkylcarbonyl, aryl, $C_5$–$C_6$-heterocyclo, $C_5$–$C_6$-heteroaryl, $C_3$–$C_8$-cycloalkyl-$C_1$–$C_6$-alkyl, aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, arylsulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyl($R^8$N)iminocarbonyl, aryl($R^8$N)iminocarbonyl, $C_5$–$C_6$-heterocyclo($R^8$N)iminocarbonyl, arylthio-$C_1$–$C_6$-alkyl, $C_1$–$C_6$-alkylthio-$C_1$–$C_6$-alkyl, arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—($R^8$)iminomethyl, $NR^8R^9$—$C_1$–$C_5$-alkylcarbonyl, hydroxy-$C_1$–$C_5$-alkyl, $R^8R^9$-aminocarbonyl, $R^8R^9$-aminocarbonyl-$C_1$–$C_6$-alkylcarbonyl, hydroxyaminocarbonyl, $R^8R^9$-aminosulfonyl, $R^8R^9$-aminosulfon-$C_1$–$C_6$-alkyl, $R^8R^9$-amino-$C_1$–$C_6$-alkylsulfonyl, and $R^8R^9$-amino-$C_1$–$C_6$-alkyl;

as to $R_8$:

$R^8$ is selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl- $C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^8$ and $R^9$ and the carbon to which they are bonded form carbonyl, or $R^8$ and $R^9$ or $R^8$ and $R^{10}$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur;

as to $R^9$:

$R^9$ is selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocyloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^8$ and $R^9$ and the carbon to which they are bonded form carbonyl, or $R^8$ and $R^9$ and the atoms to which they are bonded form a 5- to 8-membered carbocyclic ring, or a 5- to 9-membered heterocyclic or heteroaryl ring containing one or two heteroatoms independently selected from the group consisting of nitrogen, oxygen, and sulfur;

as to $R_{10}$:

$R^{10}$ is selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl and $C_1$–$C_6$-alkanoyl, or $R^{10}$ and $R^{11}$ and the carbon to which they are bonded form carbonyl, or $^{10}$ and $R^{11}$ or $R^8$ and $R^{10}$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur:

as to $R^{11}$:

$R^{11}$ is selected from the group consisting of hydrido, hydroxy-$C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloakyl, and $C_1$–$C_6$-alkanoyl, or $R^{10}$ and $R^{11}$ and the carbon to which they are bonded form carbonyl or $R^{10}$ and $R^{11}$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur;

only one of $R^8$ and $R^9$ or $R^{10}$ and $R^{11}$ may be hydroxy;

A is selected from the group consisting of:

(1) —O—;
(2) —S—;
(3) —$NR^{17}$—;
(4) —CO—$N(R^{17})$—;
(5) —$N(R^{17})$—CO—;
(6) —CO—O—;
(7) —O—CO—;
(8) —O—CO—O—;
(9) —HC═CH—;
(10) —NH—CO—NH—;
(11) —C≡C—;
(12) —NH—CO—O—;

(13) —O—CO—NH—;
(14) —N=N—;
(15) —NH—NH—;
(16) —CS—N($R^{18}$)—;
(17) —N($R^{18}$)—CS—; and
(18) a bond;

$R^{17}$ is selected from the group consisting of hydrogen, $C_1$–$C_4$-alkyl, and phenyl;

$R^{18}$ is selected from the group consisting of hydrogen, $C_1$–$C_4$-alkyl, and phenyl;

R is selected from the group consisting of alkyl, alkoxyalkyl, aryl, heteroaryl, cycloalkyl, heterocycloalkyl, aralkyl, heteroaralkyl, heterocycloalkylalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, and heterocycloalkylthioalkyl, wherein:

the aryl, heteroaryl, cycloalkyl, or heterocycloalkyl is optionally substituted with up to two substituents independently selected from the group consisting of halo, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkanoylamino, and alkoxycarbonyl;

R is other than alkyl or alkoxyalkyl when A is —O— or —S—;

R is other than methyl or phenyl when A is a bond;

E is selected from the group consisting of:
(1) —CO($R^{19}$)—;
(2) —($R^{19}$)CO—;
(3) —CONH—;
(4) —HNCO—;
(5) —CO—;
(6) —$SO_2$—$R^{19}$—;
(7) —$R^{19}$—$SO_2$—;
(8) —$SO_2$—;
(9) —NH—$SO_2$—;
(10) —$SO_2$—NH—;
(11) —S—;
(12) —NH—CO—O—;
(13) —O—CO—NH—; and
(14) a bond;

$R^{19}$ is selected from the group consisting of heterocycloalkyl and cycloalkyl; and $Y^2$ is selected from the group consisting of hydrido, alkyl, alkoxy, haloalkyl, aryl, aralkyl, cycloalkyl, heteroaryl, hydroxy, aryloxy, aralkoxy, heteroaryloxy, heteroaralkyl, perfluoroalkoxy, perfluoroalkylthio, trifluoromethylalkyl, alkenyl, heterocycloalkyl, cycloalkyl, trifluoromethyl, alkoxycarbonyl, and aminoalkyl, wherein:

the aryl, heteroaryl, aralkyl, or heterocycloalkyl is optionally substituted with up to two substituents independently selected from the group consisting of alkyl, alkanoyl, halo, nitro, aralkyl, aryl, alkoxy, trifluoroalkyl, trifluoroalkoxy, and amino, wherein:

the amino nitrogen is optionally substituted with up to two substituents independently selected from the group consisting of alkyl and aralkyl.

12. The compound or salt according to claim 11, wherein A is selected from the group consisting of —O— and —S—.

13. The compound or salt according to claim 11, wherein A is a bond.

14. The compound or salt according to claim 11, wherein R is selected from the group consisting of aryl, heteroaryl, cycloalkyl, and heterocycloalkyl.

15. The compound or salt according to claim 11, wherein $R^{14}$ is hydrido.

16. The compound or salt according to claim 11, wherein:

W is O; and $R^{15}$ is selected from the group consisting of $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, and aryloxy.

17. The compound or salt according to claim 14, wherein the compound corresponds in structure to formula B-A:

B-A.

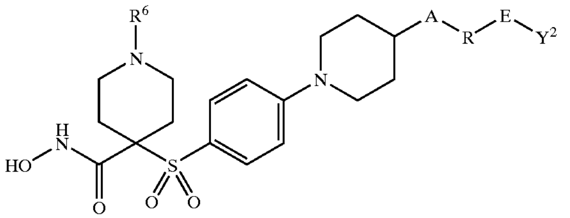

18. The compound or salt according to claim 11, wherein $R^{20}$ is —NH—O—$R^{22}$.

19. The compound or salt according to claim 11 wherein $R^{20}$ is —NH—O—$R^{14}$.

20. A compound or a pharmaceutically acceptable salt thereof, wherein:

the compound corresponds in structure to formula B-A:

B-A

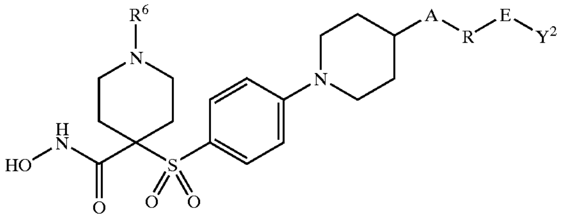

$R^6$ is selected from the group consisting of hydrido, formyl, sulfonic-$C_1$–$C_6$-alkyl, $C_1$–$C_6$-alkoxycarbonyl-$C_1$–$C_6$-alkyl, hydroxycarbonyl-$C_1$–$C_6$-alkyl, $C_1$–$C_6$-alkylcarbonyl-$C_1$–$C_6$-alkyl, $R^8R^9$-aminocarbonyl-$C_1$–$C_6$-alkyl, $C_1$–$C_6$-alkoxycarbonyl-$C_1$–$C_6$-alkylcarbonyl, hydroxycarbonyl-$C_1$–$C_6$-alkylcarbonyl, $C_1$–$C_6$-alkylcarbonyl-$C_1$–$C_6$-alkylcarbonyl, $C_1$–$C_6$-alkoxycarbonylcarbonyl, hydroxycarbonylcarbonyl, $C_1$–$C_6$-alkylcarbonylcarbonyl, $R^8R^9$-aminocarbonylcarbonyl, $C_1$–$C_6$-alkanoyl, aryl-$C_1$–$C_6$-alkyl, aroyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, heteroarylcarbonyl, heterocyclocarbonyl, $C_3$–$C_8$-heterocycloalkyl, $C_3$–$C_8$-heterocycloalkylcarbonyl, aryl, $C_5$–$C_6$-heterocyclo, $C_5$–$C_6$-heteroaryl, $C_3$–$C_8$-cycloalkyl-$C_1$–$C_6$-alkyl, aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, arylsulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyl($R^8$N)iminiocarbonyl, aryl($R^8$N)iminocarbonyl, $C_5$–$C_6$-heterocyclo($R^8$N)iminocarbonyl, arylthio-$C_1$–$C_6$-alkyl, $C_1$–$C_6$-alkylthio-$C_1$–$C_6$-alkyl, arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—($R^8$)iminomethyl, $NR^8R^9$—$C_1$–$C_5$-alkylcarbonyl, hydroxy-$C_1$–$C_5$-alkyl, $R^8R^9$-aminocarbonyl, $R^8R^9$-aminocarbonyl-$C_1$–$C_6$-alkylcarbonyl, hydroxyaminocarbonyl, $R^8R^9$-aminosulfonyl, $R^8R^9$-aminosulfon-$C_1$–$C_6$-alkyl, $R^8R^9$-amino-$C_1$–$C_6$-alkylsulfonyl, and $R^8R^9$-amino-$C_1$–$C_6$-alkyl;

as to $R^8$ and $R^9$:

$R^8$ and $R^9$ are independently selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^8$ and $R^9$ and the carbon to which they are bonded form carbonyl, or $R^8$ and $R^9$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur;

only one of $R^8$ and $R^9$ may be hydroxy;

A is selected from the group consisting of:

(1) —O—;
(2) —S—;
(3) —$NR^{17}$—;
(4) —CO—N($R^{17}$);
(5) —N($R^{17}$)—CO—;
(6) —CO—O—;
(7) —O—CO—;
(8) —O—CO—O—;
(9) —HC═CH—;
(10) —NH—CO—NH—;
(11) —C≡C—;
(12) —NH—CO—O—;
(13) —O—CO—NH—;
(14) —N═N—;
(15) —NH—NH—;
(16) —CS—N($R^{18}$);
(17) —N($R^{18}$); and
(18) a bond;

$R^{17}$ is selected from the group consisting of hydrogen, $C_1$–$C_4$-alkyl, and phenyl;

$R^{18}$ is selected from the group consisting of hydrogen, $C_1$–$C_4$-alkyl, and phenyl;

R is selected from the group consisting of alkyl, alkoxyalkyl, aryl, heteroaryl, cycloalkyl, heterocycloalkyl, aralkyl, heteroaralkyl, heterocycloalkylalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, and heterocycloalkylthioalkyl, wherein:

the aryl, heteroaryl, cycloalkyl, or heterocycloalkyl is optionally substituted with up to two substituents independently selected from the group consisting of halo, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkanoylamino, and alkoxycarbonyl;

R is other than alkyl or alkoxyalkyl when A is —O— or —S—;

R is other than methyl or phenyl when A is a bond;

E is selected from the group consisting of:

(1) —CO($R^{19}$)—;
(2) —($R^{19}$)CO—;
(3) —CONH—;
(4) —HNCO—;
(5) —CO—;
(6) —$SO_2$—$R^{19}$—;
(7) —$R^{19}$—$SO_2$—;
(8) —$SO_2$—;
(9) —NH—$SO_2$—;
(10) —$SO_2$—NH—;
(11) —S—;
(12) —NH—CO—O—;
(13) —O—CO—NH—; and
(14) a bond;

$R^{19}$ is selected from the group consisting of heterocycloalkyl and cycloalkyl; and $Y^2$ is selected from the group consisting of hydrido, alkyl, alkoxy, haloalkyl, aryl, aralkyl, cycloalkyl, heteroaryl, hydroxy, aryloxy, aralkoxy, heteroaryloxy, heteroaralkyl, perfluoroalkoxy, perfluoroalkylthio, trifluoromethylalkyl, alkenyl, heterocycloalkyl, cycloalkyl, trifluoromethyl, alkoxycarbonyl, and aminoalkyl, wherein:

the aryl, heteroaryl, aralkyl, or heterocycloalkyl is optionally substituted with up to two substituents independently selected from the group consisting of alkyl, alkanoyl, halo, nitro, aralkyl, aryl, alkoxy, trifluoroalkyl, trifluoroalkoxy, and amino, wherein:

the amino nitrogen is optionally substituted with up to two substituents independently selected from the group consisting of alkyl and aralkyl.

21. The compound or salt according to claim 20, wherein $R^6$ is selected from the group consisting of $C_3$–$C_6$-cycloalkyl, $C_1$–$C_6$-alkyl, $C_3$–$C_6$-alkenyl, $C_3$–$C_6$-alkynyl, $C_1$–$C_6$-alkoxy-$C_1$–$C_6$-alkyl, amino-$C_1$–$C_6$-alkyl, aminosulfonyl, heteroaryl-$C_1$–$C_6$-alkyl, aryloxycarbonyl, and $C_1$–$C_6$-alkoxycarbonyl.

22. The compound or salt according to claim 20, wherein A is a bond.

23. The compound or salt according to claim 20, wherein the compound corresponds in structure to the following formula:

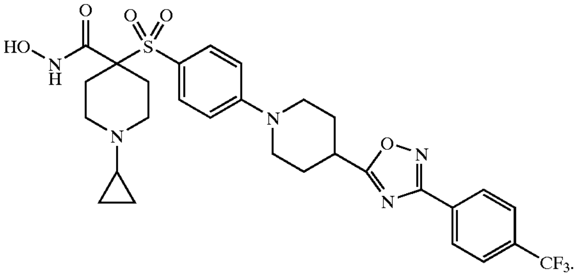

24. A compound or a pharmaceutically acceptable salt thereof, wherein:

the compound corresponds in structure to formula B-3A:

B-3A,

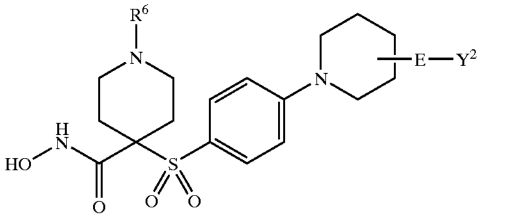

$R^6$ is selected from the group consisting of hydrido, formyl, sulfonic-$C_1$–$C_6$-alkyl, $C_1$–$C_6$-alkoxycarbonyl-$C_1$–$C_6$-alkyl, hydroxycarbonyl-$C_1$–$C_6$-alkyl, $C_1$–$C_6$-alkylcarbonyl-$C_1$–$C_6$-alkyl, $R^8R^9$-aminocarbonyl-$C_1$–$C_6$-alkyl, $C_1$–$C_6$-alkoxycarbonyl-$C_1$–$C_6$-alkylcarbonyl, hydroxycarbonyl-$C_1$–$C_6$-alkylcarbonyl, $C_1$–$C_6$-alkylcarbonyl-$C_1$–$C_6$-alkylcarbonyl, $C_1$–$C_6$-alkoxycarbonylcarbonyl, hydroxycarbonylcarbonyl, $C_1$–$C_6$-alkylcarbonylcarbonyl, $R^8R^9$-aminocarbonylcarbonyl, $C_1$–$C_6$-alkanoyl, aryl-$C_1$–$C_6$-alkyl, aroyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, heteroarycarbonyl, heterocyclocarbonyl, $C_3$–$C_8$-heterocycloalkyl, $C_3$–$C_8$-heterocycloalkylcarbonyl, aryl, $C_5$–$C_6$-heterocyclo, $C_5$–$C_6$-heteroaryl, $C_3$–$C_8$-cycloalkyl-$C_1$–$C_6$-alkyl, aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, arylsulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyl($R^8$N)iminocarbonyl, aryl($R^8$N)iminocarbonyl, $C_5$–$C_6$-heterocyclo($R^8$N)iminocarbonyl, arylthio-$C_1$–$C_6$-alkyl, $C_1$–$C_6$-alkylthio-$C_1$–$C_6$-alkyl, arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—($R^8$)iminomethyl, $NR^8R^9$—$C_1$–$C_5$-alkylcarbonyl, hydroxy-$C_1$–$C_5$-alkyl, $R^8R^9$-aminocarbonyl, $R^8R^9$-aminocarbonyl-$C_1$–$C_6$-alkylcarbonyl, hydroxyaminocarbonyl, $R^8R^9$-aminosulfonyl, $R^8R^9$-aminosulfon-$C_1$–$C_6$-alkyl, $R^8R^9$-amino-$C_1$–$C_6$-alkylsulfonyl, and $R^8R^9$-amino-$C_1$–$C_6$-alkyl;

as to $R^8$ and $R^9$:

$R^8$ and $R^9$ are independently selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^8$ and $R^9$ and the carbon to which they are bonded form carbonyl, or $R^8$ and $R^9$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur; wherein:

one or more carbons of the heterocyclic ring optionally are substituted with a substituent independently selected from the group consisting of alkyl, hydroxy, carboxy, and aminocarbonyl, and if the heterocyclic ring is piperazine, one of the piperazine nitrogens optionally is substituted with a substituent selected from the group consisting of alkyl, hydroxyalkoxyalkyl, alkoxycarbonylalkyl, alkoxyalkyl, and N,N-alkylaminoalkyl;

only one of $R^8$ and $R^9$ may be hydroxy;

E is selected from the group consisting of:

(1) —CO($R_{19}$)—;
(2) —($R^{19}$)CO—;
(3) —CONH—;
(4) —HNCO—,
(5) —CO—;
(6) —$SO_2$—$R^{19}$—;
(7) —$R^{19}$—$SO_2$—;
(8) —$SO_2$—;
(9) —NH—$SO_2$—;
(10) —$SO_2$—NH—;
(11) —S—;
(12) —NH—CO—O—,

(13) —O—CO—NH—; and

(14) a bond;

$R^{19}$ is selected from the group consisting of heterocycloalkyl and cycloalkyl;

$Y^2$ is selected from the group consisting of hydrido, alkyl, alkoxy, haloalkyl, aryl, aralkyl, cycloalkyl, heteroaryl, hydroxy, aryloxy, aralkoxy, heteroaryloxy, heteroaralkyl, perfluoroalkoxy, perfluoroalkylthio, trifluoromethylalkyl, alkenyl heterocycloalkyl, cycloalkyl, trifluoromethyl, alkoxycarbonyl, and aminoalkyl, wherein:

the aryl, heteroaryl, aralkyl, or heterocycloalkyl is optionally substituted with up to two substituents independently selected from the group consisting of alkyl, alkanoyl, halo, nitro, aralkyl, aryl, alkoxy, trifluoroalkyl, trifluoroalkoxy, and amino, wherein:

the amino nitrogen is optionally substituted with up to two substituents independently selected from the group consisting of alkyl and aralkyl;

$Y^2$ is other than optionally-substituted piperazinyl when E is —C(O)—; and $Y_2$ is other than hydrido, methyl, or optionally-substituted phenyl when E is a bond.

25. The compound or salt according to claim 24, wherein the compound corresponds in structure to formula IX-1:

IX-1.

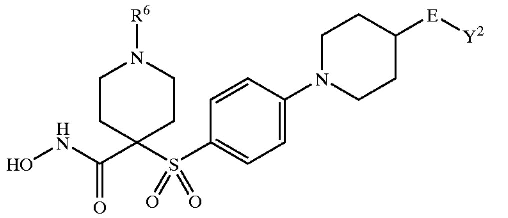

26. The compound or salt according to claim 24, wherein the compound corresponds in structure to formula IX-2:

IX-2.

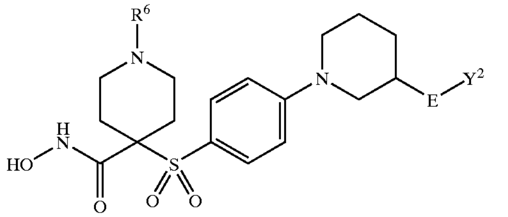

27. The compound or salt according to claim 24, wherein $R^6$ is selected from the group consisting of $C_3$–$C_6$-cycloalkyl, $C_1$–$C_6$-alkyl, $C_3$–$C_6$-alkenyl, $C_3$–$C_6$-alkyl, $C_1$–$C_6$-alkoxy-$C_1$–$C_6$-alkyl, amino-$C_1$–$C_6$-alkyl, aminosulfonyl, heteroaryl-$C_1$–$C_6$-alkyl, aryloxycarbonyl, and $C_1$–$C_6$-alkoxycarbonyl.

28. A pharmaceutical composition that comprises a compound or salt according to claim 11 dissolved or dispersed in a pharmaceutically acceptable carrier.

29. A pharmaceutical composition that comprises a compound according to claim 20 dissolved or dispersed in a pharmaceutically acceptable carrier.

30. A pharmaceutical composition that comprises a compound according to claim 24 dissolved or dispersed in a pharmaceutically acceptable carrier.

31. A pharmaceutical composition that comprises a compound according to claim 22 dissolved or dispersed in a pharmaceutically acceptable carrier.

32. A process for treating a pathological condition in a mammal, wherein:

the process comprises administering a compound or a pharmaceutically acceptable salt thereof in an effective amount to the mammal;

the condition is treatable by inhibiting matrix metalloprotease activity;

the compound or salt is characterizeable in that the compound or salt exhibits inhibitory activity against one or more of MMP-2, MMP-9, and MMP-13, while exhibiting substantially less inhibitory activity against MMP-1;

the compound corresponds in structure to formula B-1:

B-1;

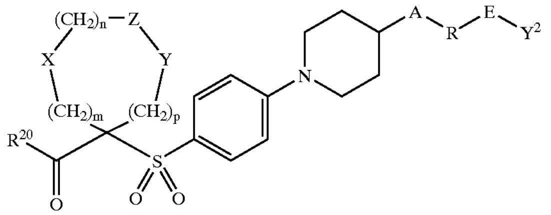

$R^{20}$ is —NH—O—$R^{14}$;

$R^{14}$ is selected from the group consisting of hydrido, a pharmaceutically acceptable cation, and $C(W)R^{25}$;

W is selected from the group consisting of O and S;

$R^{25}$ is selected from the group consisting of $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl, and amino $C_1$–$C_6$-alkyl, wherein:

the amino $C_1$–$C_6$-alkyl nitrogen is optionally substituted with:

up to two substituents independently selected from the group consisting of $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and $C_1$–$C_6$-alkanoyl, or two substituents such that the two substituents and amino nitrogen form a 5- to 8-membered heterocyclo or heteroaryl ring;

m is selected from the group consisting of zero, 1 and 2;

n is selected from the group consisting of zero, 1 and 2;

p is selected from the group consisting of zero, 1 and 2;

the sum of m+n+p is 2;

Z is $NR^6$, and X and Y are $CR^8R^9$ and $CR^{10}R^{11}$;

$R^6$ is selected from the group consisting of hydrido, formyl, sulfonic-$C_1$–$C_6$-alkyl, $C_1$–$C_6$-alkoxycarbonyl-$C_1$–$C_6$-alkyl, hydroxycarbonyl-$C_1$–$C_6$-alkyl, $C_1$–$C_6$-alkylcarbonyl-$C_1$–$C_6$-alkyl, $R^8R^9$-aminocarbonyl-$C_1$–$C_6$-alkyl, $C_1$–$C_6$-alkoxycarbonyl-$C_1$–$C_6$-alkylcarbonyl, hydroxycarbonyl-$C_1$–$C_6$-alkylcarbonyl, $C_1$–$C_6$-alkylcarbonyl-$C_1$–$C_6$-alkylcarbonyl, $C_1$–$C_6$-alkoxycarbonylcarbonyl, hydroxycarbonylcarbonyl, $C_1$–$C_6$-alkylcarbonylcarbonyl, $R^8R^9$-aminocarbonylcarbonyl, $C_1$–$C_6$-alkanoyl, aryl-$C_1$–$C_6$-alkyl, aroyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$- alkoxy-$C_1$–$C_6$-alkyl, $C_3$–$C_6$-cycloalkyl, heteroarycarbonyl, heterocyclocarbonyl, $C_3$–$C_8$-heterocycloalkyl, $C_3$–$C_8$-heterocycloalkylcarbonyl, aryl, $C_5$–$C_6$-heterocyclo, $C_5$–$C_6$-heteroaryl, $C_3$–$C_8$-cycloalkyl-$C_1$–$C_6$-alkyl, aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, arylsulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyl($R^8$N)iminocarbonyl, aryl($R^8$N)iminocarbonyl, $C_5$–$C_6$-heterocyclo($R^8$N)iminocarbonyl, arylthio-$C_1$–$C_6$-alkyl, $C_1$–$C_6$-alkylthio-$C_1$–$C_6$-alkyl, arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—($R^8$)iminomethyl, $NR^8R^9$—$C_1$–$C_5$-alkylcarbonyl, hydroxy-$C_1$–$C_5$-alkyl, $R^8R^9$-aminocarbonyl, $R^8R^9$-aminocarbonyl-$C_1$–$C_6$-alkylcarbonyl, hydroxyaminocarbonyl, $R^8R^9$-aminosulfonyl, $R^8R^9$-aminosulfon-$C_1$–$C_6$-alkyl, $R^8R^9$-amino-$C_1$–$C_6$-alkylsulfonyl, and $R^8R^9$-amino-$C_1$–$C_6$-alkyl;

as to $R^8$:

$R^8$ is selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^8$ and $R^9$ and the carbon to which they arc bonded form carbonyl, or $R^8$ and $R^9$ or $R^8$ and $R^{10}$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur;

as to $R^9$:

$R^9$ is selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_6$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^8$ and $R^9$ and the carbon to which they are bonded form carbonyl or $R^8$ and $R^9$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur;

as to $R^{10}$:

$R^{10}$ is selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_{2-C6}$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^{10}$ and $R^{11}$ and the carbon to which they are bonded form carbonyl, or $R^{10}$ and $R^{11}$ or $R^8$ and $R^{10}$ and the atoms to which they re bonded form a 5- to 8-membered carbocyclic ring, or a 5- to 8-membered heterocyclic or heteroaryl ring containing one or two heteroatoms independently selected from the group consisting of nitrogen, oxygen, and sulfur;

as to $R^{11}$:

$R^{11}$ is selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_2$–$C_6$-alkyl, $C_1$–$C_6$-alkythio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl- $C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^{10}$ and $R^{11}$ and the carbon to which they are bonded form carbonyl, or $R^{10}$ and $R^{11}$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur;

only one of $R^8$ and $R^9$ or $R^{10}$ and $R^{11}$ may be hydroxy;

A is selected from the group consisting of:

(1) —O—;
(2) —S—;
(3) —$NR^{17}$;
(4) —CO—N($R^{17}$)—;
(5) —N($R^{17}$)—CO—;
(6) —CO—O—;
(7) —O—CO—;
(8) —O—CO—O—;
(9) —HC═CH—;
(10) —NH—CO—NH—;
(11) —C≡C—;
(12) —NH—CO—O—;
(13) —O—CO—NH—;
(14) —N═N—;
(15) —NH—NH—;
(16) —CS—N($R^{18}$)—;
(17) —N($R^{18}$)—CS—; and
(18) a bond;

$R^{17}$ is selected from the group consisting of hydrogen, $C_1$–$C_4$-alkyl, and phenyl;

$R^{18}$ is selected from the group consisting of hydrogen, $C_1$–$C_4$-alkyl, and phenyl;

R is selected from the group consisting of alkyl, alkoxyalkyl, aryl, heteroaryl, cycloalkyl, heterocycloalkyl, aralkyl, heteroaralkyl, heterocycloalkylalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, and heterocycloalkylthioalkyl, wherein:

the aryl, heteroaryl, cycloalkyl, or heterocycloalkyl is optionally substituted with up to two substituents independently selected from the group consisting of halo, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkanoylamino, and alkoxycarbonyl; and R is other than alkyl or alkoxyalkyl when A is —O— or —S—;

R is other than methyl or phenyl when A is a bond;

E is selected from the group consisting of:

(1) —CO($R^{19}$)—;
(2) —($R^{19}$)CO—;
(3) —CONH—;
(4) —HNCO—;
(5) —CO—;
(6) —$SO_2$—$R^{19}$—;
(7) —$R^{19}$—$SO_2$—;
(8) —$SO_2$—;
(9) —NH—$SO_2$—;
(10) —$SO_2$—NH—;
(11) —S—;
(12) —NH—CO—O—;
(13) —O—CO—NH—; and
(14) a bond;

$R^{19}$ is selected from the group consisting of heterocycloalkyl and cycloalkyl; and $Y^2$ is selected from the group consisting of hydrido, alkyl, alkoxy, haloalkyl, aryl, aralkyl, cycloalkyl, heteroaryl, hydroxy, aryloxy, aralkoxy, heteroaryloxy, heteroaralkyl, perfluoroalkoxy, perfluoroalkylthio, trifluoromethylalkyl, alkenyl, heterocycloalkyl, cycloalkyl, trifluoromethyl, alkoxycarbonyl, and aminoalkyl, wherein:

the aryl, heteroaryl, aralkyl, or heterocycloalkyl is optionally substituted with up to two substituents independently selected from the group consisting of alkyl, alkanoyl, halo, nitro, aralkyl, aryl, alkoxy, trifluoroalkyl, trifluoroalkoxy, and amino, wherein:

the amino nitrogen is optionally substituted with up to two substituents independently selected from the group consisting of alkyl and aralkyl.

33. The process according to claim 32, wherein the compound corresponds in structure to formula B-2:

B-2.

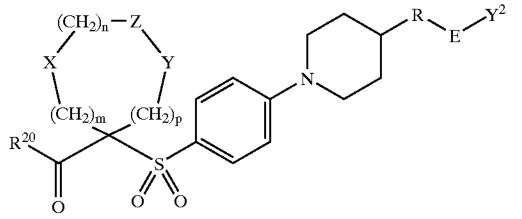

34. The process according to claim 32, wherein the compound or salt is administered a plurality of times.

35. A process for treating a pathological condition the process comprises administering a compound or a pharmaceutically acceptable salt thereof in an effective amount to the mammal;

the condition is treatable by inhibiting matrix metalloprotease activity;

the compound or salt is characterizeable in that the compound or salt exhibits inhibitory activity against one or more of MMP-2, MMP-9 and MMP-13, while exhibiting substantially less inhibitory activity against MMP-1;

the compound corresponds in structure to formula VIC;

VIC,

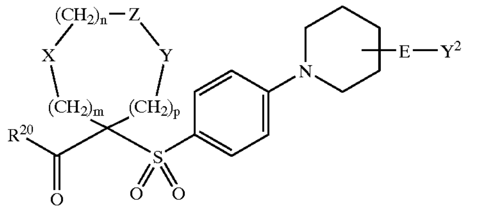

$R^{20}$ is —NH—O—$R^{14}$;

$R^{14}$ is selected from the group consisting of hydrido, a pharmaceutically acceptable cation, and C(W)$R^{25}$;

W is selected from the group consisting of O and S;

$R^{25}$ is selected from the group consisting of $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl, and amino $C_1$–$C_6$-alkyl, wherein:

the amino $C_1$–$C_6$-alkyl nitrogen is optionally substituted with:

up to two substituents independently selected from the group consisting of $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and $C_1$–$C_6$-alkanoyl, or two substituents such that the two substituents and amino nitrogen form a 5- to 8-membered heterocyclo or heteroaryl ring;

m is selected from the group consisting of zero, 1 and 2;

n is selected from the group consisting of zero, 1 and 2;

p is selected from the group consisting of zero, 1 and 2;

the sum of n+n+p is 2;

Z is $NR^6$, and X and Y and Z are $CR^8R^9$ and $CR^{10}R^{11}$;

$R^6$ is selected from the group consisting of hydrido, formyl, sulfonic-$C_1$–$C_6$-alkyl, $C_1$–$C_6$-alkoxycarbonyl-$C_1$–$C_6$-alkyl, hydroxycarbonyl-$C_1$–$C_6$-alkyl, $C_1$–$C_6$-alkylcarbonyl-$C_1$–$C_6$-alkyl, $R^8R^9$-aminocarbonyl-$C_1$–$C_6$-alkyl, $C_1$–$C_6$-alkylcarbonyl-$C_1$–$C_6$-alkyl, $C_1$–$C_6$-alkoxycarbonyl-$C_1$–$C_6$-alkylcarbonyl, hydroxycarbonyl-$C_1$–$C_6$-alkylcarbonyl, $C_1$–$C_6$-alkylcarbonyl-$C_1$–$C_6$-alkylcarbonyl, $C_1$–$C_6$-alkoxycarbonylcarbonyl, hydroxycarbonylcarbonyl, $C_1$–$C_6$-alkylcarbonylcarbonyl, $R^8R^9$-amino- carbonylcarbonyl, $C_1$–$C_6$-alkanoyl, aryl-$C_1$–$C_6$-alkyl, aroyl, bis ($C_1$–$C_6$-alkoxy-$C_1$–$C_6$-alkyl)-$C_1$–$C_6$-alkyl $C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, heteroarycarbonyl, heterocyclocarbonyl, $C_3$–$C_8$-heterocycloalkyl, $C_3$–$C_8$-heterocycloalkylcarbonyl, aryl, $C_5$–$C_6$-heterocyclo, $C_5$–$C_6$-heteroaryl, $C_3$–$C_8$-cycloalkyl-$C_1$–$C_6$-alkyl, aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, arylsulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyl($R^8$N)iminocarbonyl, aryl($R^8$N)iminocarbonyl, $C_5$–$C_6$-heterocyclo($R^8$N) iminocarbonyl, arylthio-$C_1$–$C_6$-alkyl, $C_1$–$C_6$-alkylthio-$C_1$–$C_6$-alkyl, arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—($R^8$) iminomethyl, $NR^8R^9$—$C_1$–$C_5$-alkylcarbonyl, hydroxy-$C_1$–$C_5$-alkyl, $R^8R^9$-aminocarbonyl, $R^8R^9$-aminocarbonyl-$C_1$–$C_6$-alkylcarbonyl, hydroxyaminocarbonyl, $R^8R^9$-aminosulfonyl, $R^8R^9$-aminosulfon-$C_1$–$C_6$-alkyl, $R^8R^9$-amino-$C_1$–$C_6$-alkylsulfonyl, and $R^8R^9$-amino-$C_1$–$C_6$-alkyl;

as to $R^8$:

$R^8$ is selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^8$ and $R^9$ and the carbon to which they are bonded form carbonyl, or $R^8$ and $R^9$ or $R^8$ and $R^{10}$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur;

as to $R^9$:

$R^9$ is selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, $C_1$–$C_6$-alkyl, cycloalkyl, and $C_1$–$C_6$-alkanoyl, or $R^8$ and $R^9$ and the carbon to which they are bonded form carbonyl, or $R^8$ and $R^9$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur;

as to $R^{10}$:

$R^{10}$ is selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^{10}$ and $R^{11}$ and the carbon to which they are bonded form carbonyl, or $R^{10}$ and $R^{11}$ or $R^8$ and $R^{10}$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur;

as to $R^{11}$:

$R_{11}$ is selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^{10}$ and $R^{11}$ and the carbon to which they are bonded form carbonyl, or $R^{10}$ and $R^{11}$ and the atoms to which they are bonded form a 5- to 8-membered carbocyclic ring, or a 5- to 8-membered heterocyclic or heteroaryl ring containing one or two heteroatoms independently selected from the group consisting of nitrogen, oxygen, and sulfur;

only one of $R^8$ and $R^9$ or $R^{10}$ and $R^{11}$ may be hydroxy;

E is selected from the group consisting of:

(1) —CO($R^{19}$)—;
(2) —($R^{19}$)CO—;
(3) —CONH—;
(4) —HNCO—;
(5) —CO—;
(6) —$SO_2$—$R_{19}$—;
(7) —$R^{19}$—$SO_2$—;
(8) —$SO_2$—;
(9) —NH—$SO_2$—;
(10) —$SO_2$—NH—;
(11) —S—;
(12) —NH—CO—O—;
(13) —O—CO—NH—; and
(14) a bond;

$R^{19}$ is selected from the group consisting of heterocycloalkyl and cycloalkyl;

$Y^2$ is selected from the group consisting of hydrido, alkyl, alkoxy, haloalkyl, aryl, aralkyl, cycloalkyl, heteroaryl, hydroxy, aryloxy, aralkoxy, heteroaryloxy, heteroaralkyl, perfluoroalkoxy, perfluoroalkylthio, trifluoromethylalkyl, alkenyl, heterocycloalkyl, cycloalkyl, trifluoromethyl, alkoxycarbonyl, and aminoalkyl, wherein:

the aryl, heteroaryl, aralkyl, or heterocycloalkyl is optionally substituted with up to two substituents independently selected from the group consisting of alkyl, alkanoyl, halo, nitro, aralkyl, aryl, alkoxy, trifluoroalkyl, trifluoroalkoxy, and amino, wherein:

the amino nitrogen is optionally substituted with up to two substituents independently selected from the group consisting of alkyl and aralkyl;

$Y^2$ is other than optionally-substituted piperazinyl when E is —C(O)—; and $Y^2$ is other than hydrido, methyl, or optionally-substituted phenyl when E is a bond.

36. The process according to claim 35, wherein the compound corresponds in structure to formula VIC-1:

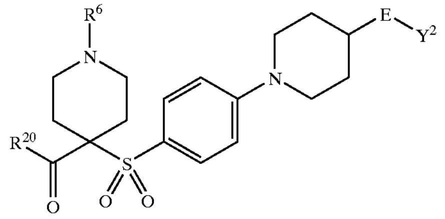

IX.

37. The process according to claim 35, wherein the compound or salt is administered a plurality of times.

38. The process according to claim 35, wherein the compound corresponds in structure to formula VIC-1:

VIC-1.

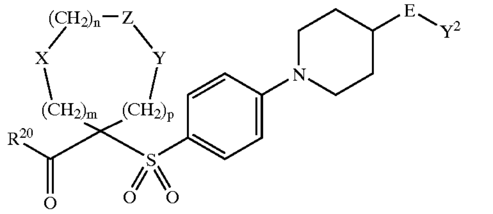

39. The process according to claim 35, wherein the compound corresponds in structure to formula VIC-2:

VIC-2.

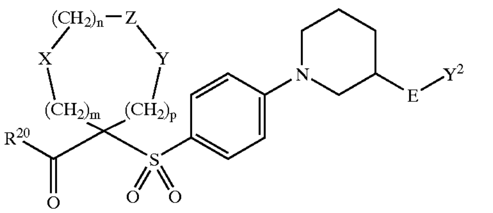

40. The process according to claim 35, wherein the compound corresponds in structure to formula IX-1:

IX-1.

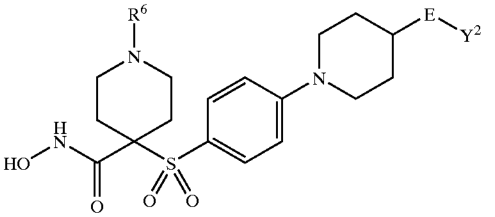

41. The process according to claim 35, wherein the compound corresponds in structure to formula IX-2:

IX-2.

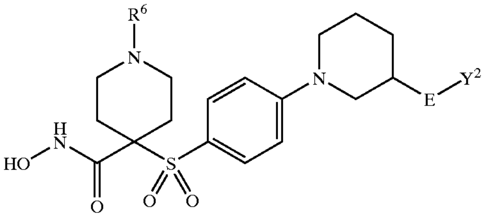

42. A process for treating a pathological condition in a mammal, wherein:

the process comprises administering a compound or a pharmaceutically acceptable salt thereof in an effective amount to the mammal;

the condition is treatable by inhibiting matrix metalloprotease activity;

the compound or salt is characterizeable in that the compound or salt exhibits inhibitory activity against one or more of MMP-2, MMP-9 and MMP-13, while exhibiting substantially less inhibitory activity against MMP-1;

the compound corresponds in structure to formula B-3A:

B-3A,

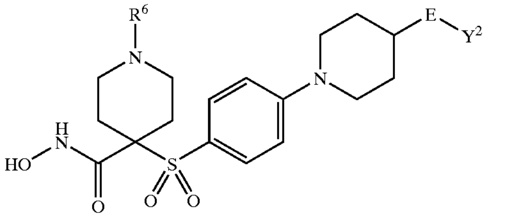

$R^6$ is selected from the group consisting of hydrido, formyl, sulfonic-$C_1$–$C_6$-alkyl, $C_1$–$C_6$-alkoxycarbonyl-$C_1$–$C_6$-alkyl, hydroxycarbonyl-$C_1$–$C_6$-alkyl, $C_1$–$C_6$-alkylcarbonyl-$C_1$–$C_6$-alkyl, $R^8R^9$-aminocarbonyl-$C_1$–$C_6$-alkyl, $C_1$–$C_6$-alkoxycarbonyl-$C_1$–$C_6$-alkylcarbonyl, hydroxycarbonyl-$C_1$–$C_6$-alkylcarbonyl, $C_1$–$C_6$-alkylcarbonyl-$C_1$–$C_6$-alkylcarbonyl, $C_1$–$C_6$-alkoxycarbonylcarbonyl, hydroxycarbonylcarbonyl, $C_1$–$C_6$-alkylcarbonylcarbonyl, $R^8R^9$-aminocarbonylcarbonyl, $C_1$–$C_6$-alkanoyl, aryl-$C_1$–$C_6$-alkyl, aroyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, heteroarylcarbonyl, heterocyclocarbonyl, $C_3$–$C_8$-heterocycloalkyl, $C_3$–$C_8$-heterocycloalkylcarbonyl, aryl, $C_5$–$C_6$-heterocyclo, $C_5$–$C_6$-heteroaryl, $C_3$–$C_8$-cycloalkyl-$C_1$–$C_6$-alkyl, aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, arylsulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyl($R^8$N)iminocarbonyl, aryl($R^8$N)iminiocarbonyl, $C_5$–$C_6$-heterocyclo($R^8$N)iminocarbonyl, arylthio-$C_1$–$C_6$-alkyl, $C_1$–$C_6$-alkylthio-$C_1$–$C_6$-alkyl, arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—($R^8$)iminomethyl, $NR^8R_9$—$C_1$–$C_5$-alkylcarbonyl, hydroxy-$C_1$–$C_5$-alkyl, $R^8R^9$-aminocarbonyl, $R^8R^9$-aminocarbonyl-$C_1$–$C_6$-alkylcarbonyl, hydroxyaminocarbonyl, $R^8R^9$-aminosulfonyl, $R^8R^9$-aminosulfon-$C_1$–$C_6$-alkyl, $R^8R^9$-amino-$C_1$–$C_6$-alkylsulfonyl, and $R^8R^9$-amino-$C_1$–$C_6$-alkyl;

as to $R^8$ and $R^9$:

$R^8$ and $R^9$ are independently selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, hetoroar-$C_1$–$C_6$-alkyl, $C_2$–$C_6$-alkyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonyl-$C_1$–$C_6$-alkyl, and amino-$C_1$–$C_6$-alkyl wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^8$ and $R^9$ and the carbon to which they are bonded form carbonyl, or $R^8$ and $R^9$ together with the atoms to which they are bonded form a 5- to 8-membered carbocyclic ring, or a 5- to 8-membered heterocyclic or heteroaryl ring containing one or two heteroatom is independently selected from the group consisting of nitrogen, oxygen, and sulfur, wherein:

one or more carbons of the heterocyclic ring optionally is substituted with substituent(s) independently selected from the group consisting of alkyl, hydroxy, carboxy, and aminocarbonyl, and if the heterocyclic ring is piperazine, one of the piperazine nitrogens optionally is substituted with a substituent selected from the group consisting of alkyl, hydroxyalkoxyalkyl, alkoxycarbonylalkyl, alkoxyalkyl, and N,N-alkylaminoalkyl;

only one of $R^8$ and $R^9$ may be hydroxy;

E is selected from the group consisting of:

(1) —CO($R^{19}$)—;

(2) —($R^{19}$)CO—;

(3) —CONH—;

(4) —HNCO—;

(5) —CO—;

(6) —$SO_2$—$R^{19}$—;

(7) —$R^{19}$—$SO_2$—;

(8) —$SO_2$—;

(9) —NH—$SO_2$—;

(10) —$SO_2$—NH—;

(11) —S—;

(12) —NH—CO—O—;

(13) —O—CO—NH—; and

(14) a bond;

$R^{19}$ is selected from the group consisting of heterocycloalkyl and cycloalkyl;

$Y^2$ is selected from the group consisting of hydrido, alkyl, alkoxy, haloalkyl, aryl, aralkyl, cycloalkyl, heteroaryl, hydroxy, aryloxy, aralkoxy, heteroaryloxy, heteroaralkyl, perfluoroalkoxy, perfluoroalkylthio, trifluoromethylalkyl, alkenyl, heterocycloalkyl, cycloalkyl, trifluoromethyl, alkoxycarbonyl, and aminoalkyl, wherein:

the aryl, heteroaryl, aralkyl, or heterocycloalkyl is optionally substituted with up to two substituents independently selected from the group consisting of alkyl, alkanoyl, halo, nitro, aralkyl, aryl, alkoxy, trifluoroalkyl, trifluoroalkoxy, and amino, wherein:

the amino nitrogen is optionally substituted with up to two substituents independently selected from the group consisting of alkyl and aralkyl;

$Y^2$ is other than optionally-substituted piperazinyl when E is —C(O)—; and $Y_2$ is other than hydrido, methyl, or optionally-substituted phenyl when E is a bond.

43. The process according to claim 24, wherein:

as to $R^8$ and $R^9$:

$R^8$ and $R^9$ are independently selected from the group consisting of hydrido, hydroxy, $C_1$–$C_6$-alkyl, $C_1$–$C_6$-alkanoyl, aroyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any of the thio substituents, the sulfone of any of the thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl wherein:

the aminoalkyl nitrogen is optionally substituted with up to two substituents independently selected from the group consisting of $C_1$–$C_6$-alkyl, ar-$C_1$–$C_6$-alkyl, cycloalkyl, and $C_1$–$C_6$-alkanoyl, or $R^8$ and $R^9$ and the carbon to which they are bonded form carbonyl, or $R^8$ and $R^9$ together with the atoms to which they are bonded form a 5- to 8-membered carbocyclic ring, or a 5- to 8-membered heterocyclic or heteroaryl ring containing up to two heteroatoms independently selected from the group consisting of nitrogen, oxygen, and sulfur; and only one of $R^8$ and $R^9$ may be hydroxy.

44. The process according to claim 24, wherein $R^8$ and $R^9$ and the atoms to which they are bonded form a 6-membered heterocyclic ring containing one or two nitrogens, wherein:

one or more carbons of the heterocyclic ring optionally are substituted with a substituent independently selected from the group consisting of alkyl, hydroxy, carboxy, and aminocarbonyl, and if the heterocyclic ring is piperazine, one of the piperazine nitrogens optionally is substituted with a substituent selected from the group consisting of alkyl, hydroxyalkoxyalkyl, alkoxycarbonylalkyl, alkoxyalkyl, and N,N-alkylaminoalkyl.

* * * * *

UNITED STATES PATENT AND TRADEMARK OFFICE

CERTIFICATE OF CORRECTION

PATENT NO. : 6,750,228 B1
DATED : June 15, 2004
INVENTOR(S) : Thomas E. Barta et al.

It is certified that error appears in the above-identified patent and that said Letters Patent is hereby corrected as shown below:

Column 773,
Line 19, replace "heteroarylthio-$C_1$-$C_6$-alkyl the" with -- heteroarylthio-$C_1$-$C_6$-alkyl, the --; and
Line 38, replace "may be hydroxy," with -- may be hydroxy; --; and
Between lines 38 and 39, insert -- A is selected from the group consisting of;

(1) -O-;

(2) -S-;

(3) -$NR^{17}$-;

(4) -CO-N($R^{17}$)-;

(5) -N($R^{17}$)-CO-;

(6) -CO-O-;

(7) -O-CO-;

(8) -O-CO-O-;

(9) -HC=CH-;

(10) -NH-CO-NH-;

(11) -C≡C-;

(12) -NH-CO-O-;

(13) -O-CO-NH-;

(14) -N=N-;

(15) -NH-NH-;

(16) -CS-N($R^{18}$)-;

(17) -N($R^{18}$)-CS-; and

(18) a bond;

$R^{17}$ is selected from the group consisting of hydrogen, $C_1$-$C_4$-alkyl, and phenyl;

$R^{18}$ is selected from the group consisting of hydrogen, $C_1$-$C_4$-alkyl, and phenyl;

R is selected from the group consisting of alkyl, alkoxyalkyl, aryl, heteroaryl, cycloalkyl, heterocycloalkyl, aralkyl, heteroaralkyl, heterocycloalkylalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, and heterocycloalkylthioalkyl, wherein:

UNITED STATES PATENT AND TRADEMARK OFFICE

CERTIFICATE OF CORRECTION

PATENT NO. : 6,750,228 B1
DATED : June 15, 2004
INVENTOR(S) : Thomas E. Barta et al.

It is certified that error appears in the above-identified patent and that said Letters Patent is hereby corrected as shown below:

Column 773 (cont'd), the aryl, heteroaryl, cycloalkyl, or heterocycloalkyl is optionally substituted with up to two substituents independently selected from the group consisting of halo, alkyl, perfluoroalkyl, perfluoroalkoxy, perfluoroalkylthio, trifluoromethylalkyl, amino,".

Column 775,
Line 8, delete "and Z"; and
Line 30, replace "arylsulfonyl $C_1$-$C_6$-alkylsulfonyl" with -- arylsulfonyl, $C_1$-$C_6$-alkylsulfonyl --; and Column 776,
Line 54, delete "$C_1$-$C_6$-alkyl, thiol-$C_1$,$C_6$-alkyl,"; and
Line 58, insert -- $C_1$-$C_6$-alkoxy-$C_1$-$C_6$-alkoxy-$C_1$-$C_6$-alkyl, hydroxy-$C_1$-$C_6$-alkyl, -- before "hydroxycarbonyl-$C_1$-$C_6$-alkyl"; and Column 777,
Line 5, replace "carbonyl" with -- alkanoyl --.

Column 786,
Line 3, replace "-N($R^{18}$)" with -- -N($R^{18}$)-CS- --.

Column 788,
Line 56, replace "-CO($R_{19}$)-" with -- -CO($R^{19}$) --.

Column 789,
Line 53, replace "$C_3$–$C_6$-alkyl" with -- $C_3$–$C_6$-alkynyl --.

Column 791,
Line 63, replace "$C_2$-$_6$-alkenyl" with -- $C_2$-$C_6$-alkenyl --; and
Lines 65-66, replace "heterocycloalkyl-$C_1$-$C_6$-alkyl" with -- heterocycloalkyl-$C_1$-$C_6$-alkyl, $C_1$-$C_6$-alkoxy-$C_1$-$C_6$-alkyl, aralkoxy-$C_1$-$C_6$-alkyl --; and Column 792,
Line 16, replace "carbonyl or" with -- carbonyl, or --.

UNITED STATES PATENT AND TRADEMARK OFFICE

CERTIFICATE OF CORRECTION

PATENT NO. : 6,750,228 B1
DATED : June 15, 2004
INVENTOR(S) : Thomas E. Barta et al.

It is certified that error appears in the above-identified patent and that said Letters Patent is hereby corrected as shown below:

<u>Column 795,</u>
Line 39, delete "and Z"; and
Lines 44-45, delete "$C_1$-$C_6$-alkycarbonyl-$C_1$-$C_6$-alkyl; ; and
Lines 51-53, replace "bis($C_1$-$C_6$-alkoxy-$C_1$-$C_6$-alkyl)-$C_1$-$C_6$-alkyl $C_1$-$C_6$-alkyl" with -- bis ($C_1$-$C_6$-alkoxy-$C_1$-$C_6$-alkyl)-$C_1$-$C_6$-alkyl, $C_1$-$C_6$-alkyl --; and <u>Column 797,</u>
Line 2, replace "$C_1$–$C_6$-alkyl" with -- ar-$C_1$–$C_6$-alkyl --; and <u>Column 798,</u>
Line 19, replace "-$SO_2$-$R_{19}$-" with -- -$SO_2$-$R^{19}$- --.
Line 52, replace "VIC-1" with -- IX --.

<u>Column 800,</u>
Line 57, replace "$C_2$-$C_6$-alkyl" with -- $C_2$-$C_6$-alkynyl --; and <u>Column 801,</u>
Line 4, replace "alkoxycarbonyl-$C_1$-$C_6$-alkyl" with -- alkoxycarbonylamino-$C_1$-$C_6$-alkyl --.

<u>Column 802,</u>
Lines 9 and 44, replace "process" with -- compound or salt --.

Signed and Sealed this

Nineteenth Day of April, 2005

JON W. DUDAS
*Director of the United States Patent and Trademark Office*